US010138492B2

(12) United States Patent
Nadzan et al.

(10) Patent No.: US 10,138,492 B2
(45) Date of Patent: Nov. 27, 2018

(54) NUCLEOTIDE SEQUENCES AND CORRESPONDING POLYPEPTIDES CONFERRING IMPROVED NITROGEN USE EFFICIENCY CHARACTERISTICS IN PLANTS

(71) Applicant: CERES, INC., Thousand Oaks, CA (US)

(72) Inventors: Gregory Nadzan, Woodland Hills, CA (US); Richard Schneeberger, Carlsbad, CA (US); Han Suk Kim, Pinole, CA (US); David Van-Dinh Dang, Oak Park, CA (US); Kenneth A. Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 15/838,142

(22) Filed: Dec. 11, 2017

(65) Prior Publication Data

US 2018/0112229 A1 Apr. 26, 2018

Related U.S. Application Data

(62) Division of application No. 14/164,064, filed on Jan. 24, 2014, now Pat. No. 9,879,275, which is a division of application No. 12/918,609, filed as application No. PCT/US2009/034638 on Feb. 20, 2009.

(60) Provisional application No. 61/030,152, filed on Feb. 20, 2008.

(51) Int. Cl.
*C12N 15/82* (2006.01)
*C07K 14/415* (2006.01)
*C12Q 1/6895* (2018.01)

(52) U.S. Cl.
CPC ........ *C12N 15/8271* (2013.01); *C07K 14/415* (2013.01); *C12N 15/8261* (2013.01); *C12Q 1/6895* (2013.01); *Y02A 40/146* (2018.01); *Y10T 436/143333* (2015.01)

(58) Field of Classification Search
None
See application file for complete search history.

(56) References Cited

U.S. PATENT DOCUMENTS

| | | | |
|---|---|---|---|
| 4,885,357 A | 12/1989 | Larkins et al. | |
| 6,084,153 A | 4/2000 | Good et al. | |
| 2004/0214272 A1 | 10/2004 | La Rosa et al. | |
| 2006/0123505 A1 | 6/2006 | Kikuchi et al. | |
| 2006/0195934 A1* | 8/2006 | Apuya ............... | C12N 15/8216 800/278 |

FOREIGN PATENT DOCUMENTS

| | | | |
|---|---|---|---|
| EP | 1 431 392 | | 6/2004 |
| EP | 1 586 645 | A2 | 10/2005 |
| WO | WO 2002/016655 | A2 | 2/2002 |
| WO | WO 2005/047516 | A2 | 5/2005 |

OTHER PUBLICATIONS

Itagaki et al 1999 (Genbank AB017565.1).*
Yanagisawa et al 2004 (PNAS 101:20, p. 7833-7838).*
Bi Y. et al., "Global transcription profiling reveals differential responses to chronic nitrogen stress and putative nitrogen regulatory components in *Arabidopsis*", BMC Genomics, 8, paper 281, Aug. 16, 2007.
Canadian Official Action dated Jul. 27, 2011 issued in Canadian Application No. 2,715,397.
Chinese Office Action dated Sep. 12, 2012 issued in Chinese Application 200980113796.9.
Fuentes et al. 2001 Journal of Experimental Botany 52:328 p. 1071-1088.
Gardiner, J. et al., "Anchoring 9371 Maize Expressed Sequence Tagged Unigenes to the Bacterial Artificial Chromosome Contig map by Two-Dimensional Overgo Hybridization," Plant Physiology, Apr. 2004, vol. 134, pp. 1317-1326.
Kosarev, P. et al., "Evaluation and classification of RING-finger domains encoded by the *Arabidopsis* genome", Genome Biology, 2002, vol. 3, No. 4, pp. 1-12.
NCBI database sequence accession No. BAC42722, GI: 26451240, Feb. 14, 2004.
NCBI GenBank: AAM62627.1, Jan. 27, 2006.
NCBI GenBank: BAB09087.1, Feb. 14, 2004.
NCBI GenBank: BAD44406.1, Sep. 9, 2004.
Ogawa, D. et al., "High-level overexpression of the *Arabidopsis* HsfA2 gene confers not only increased themotolerance but also salt/osmotic stress tolerance and enhanced callus growth", Journal of Experimental Botany, 2007, vol. 58, No. 12, pp. 3373-3383.
Supplementary European Search Report; EP Application No. 09712553.8, dated Jul. 25, 2011.
Yokotani, N. et al., "Expression of rice heat stress transcription factor OsHsfA2e enhances tolerance to environmental stresses in transgenic *Arabidopsis*", Planta: International Journal of Plant Biology, 2008, vol.
Guerois et al., "Predicting Changes in the Stability of Proteins and Protein Complexes: A Study of More Than 1000 Mutations," J. Mol. Biol. 320:369-387, 2002.
Kumar et al., "Predicting the effects of coding non-synonymous variants on protein function using the SIFT algorithm," Nature Protocols 4(8):1073-1082, 2009.
Ng et al., "Predicting the Effects of Amino Acid Substitutions on Protein Function," Annu. Rev. Genom. Hum. Genet. 7:61-80, 2006.
Reva et al., "Predicting the functional impact of protein mutations: application to cancer genomics," Nucleic Acids Research 39(17):e118, 2011.
Friedberg (2006 Briefings in Bioinformatics 7:3 p. 225-242).
Guo et al. (PNAS (2004) 101: 9205-9210).

* cited by examiner

*Primary Examiner* — Matthew R Keogh
(74) *Attorney, Agent, or Firm* — Dentons US LLP

(57) ABSTRACT

Methods and materials for modulating low-nitrogen tolerance levels in plants are disclosed. For example, nucleic acids encoding low nitrogen tolerance-modulating polypeptides are disclosed as well as methods for using such nucleic acids to transform plant cells. Also disclosed are plants having increased low-nitrogen tolerance levels and plant products produced from plants having increased low-nitrogen tolerance levels.

15 Claims, 165 Drawing Sheets

Specification includes a Sequence Listing.

Figure 1 (continued)

```
SEQ_ID_NO_21  L---------  ----PPGPNP  WPIIGNLPHM  -GPKPHQTLA  AMVTT---YG   61
SEQ_ID_NO_36  L---------  ----PPGPKP  WPIVGNLPHL  -GPVPHHSIA  ALAKT---YG   60
SEQ_ID_NO_47  L---------  ----PPGPSP  WPIVGNLPHM  -GPVPHHALA  ALALK---HG   63
SEQ_ID_NO_4   ----------  ----IPGPKG  WPIIGSLMDM  SVGLPHRKLE  SLARL-HGAK  113
SEQ_ID_NO_46  ----------  ----------  ----------  ----------  ----------    0
SEQ_ID_NO_39  IAAA------  ----IPGPRG  LPVLGSMSLM  -AGLAHRKLA  AAAGGSPARR  108
SEQ_ID_NO_40  IAAA------  ----IPGPRG  LPVLGSMSLM  -AGLAHRKLA  AAAGGSPARR  110
SEQ_ID_NO_27  IGEAR-----  ----IPGPRG  FPVIGSMGLM  -TGLAHRKLA  AAAAGNVRRR  108
SEQ_ID_NO_29  IVRAA-----  ----IPGPRG  LPVVGSMGLM  -TGLAHRKLS  AAAERQASRR  105
SEQ_ID_NO_38  IGAA------  ----IPGPRG  LPVLGSMGLM  -TGLAHRKLA  AAAGK--ARR  101
SEQ_ID_NO_3   V---------  ----IPGPRG  LPFVGSMSLM  SNTLAHRCIA  ATAEK-FRAE  101
SEQ_ID_NO_25  SSTKPSTTTS  SSIFIPGPKG  YPLFGSMNLM  SSSLAHHRIA  STAKT-CKAT  119
SEQ_ID_NO_22  I---------  ----IPGPKG  FPLIGSMGLM  -TSLAHHRIA  AAAAT-CRAK   96
SEQ_ID_NO_6   TINKP-----  ----IPGPRG  LPLIGSMNMV  ANSLAHHLIA  TIAKT-CKAK  103
SEQ_ID_NO_10  ISNP------  ----IPGPRG  FPITGSMKLM  -TSLAHHKIA  AAADA-CKAR  101

SEQ_ID_NO_21  PILHLRLGFA  DVVVAASKSV  AEQFLKVHDA  NFASRPPNSG  AKHMAYNYQD  111
SEQ_ID_NO_36  PLMHLRMGFV  DVVVAASASV  AAQFLKTHDA  NFSNRPPNSG  AKHIAYNYQD  110
SEQ_ID_NO_47  PLMHLQLGFV  DVIVAASASV  AEQFLKVHDA  NFSSRPPNSG  AKYIAYNYQD  113
SEQ_ID_NO_4   QLMSFSLGCT  PAVITSDPEV  ARELL--TSP  HFANRPLKQS  AQQLLFG-RA  160
SEQ_ID_NO_46  --MAFSVGLT  RFIVSSHPKT  AKEIL--SSP  AFADRPIKES  AYELLFN-RA   45
SEQ_ID_NO_39  RLMALSLGET  RVVVTADPGV  ARELL--ASA  AFADRPVKES  AYGMLFH-RA  155
SEQ_ID_NO_40  RLMALSLGET  RVVVTADPGV  ARELL--ASA  AFADRPVKES  AYGMLFH-RA  157
SEQ_ID_NO_27  RLMSFSMGET  RVVVTADPDV  ARELL--ASP  AFADRPVKES  AYGLMFH-RA  155
SEQ_ID_NO_29  RLMAFSLGET  RVVVTADLDV  ARELL--ASA  AFADRPVKES  AYGLLFH-RA  152
SEQ_ID_NO_38  RLMAFSLGET  RVVVTADPDV  ARELL--ASA  TFADRPVKES  AYGLLFH-RA  148
SEQ_ID_NO_3   RLMAFSLGET  RVIVTCNPDV  AKEIL--NSP  VFADRPVKES  AYSLMFN-RA  148
SEQ_ID_NO_25  RLMAFSLGDT  RAMVTCNPDV  AKEIL--HSS  VFADRPIKES  AYSLMFN-RA  166
SEQ_ID_NO_22  RLMAFSLGDT  RVIVTCHPDV  AKEIL--NSS  VFADRPVKES  AYSLMFN-RA  143
SEQ_ID_NO_6   RLMAFSLGDT  RVIVTCNPEV  AKEIL--NSS  VFADRPVKES  AYSLMFN-RA  150
SEQ_ID_NO_10  RLMAFSLGDT  RVIVTCNPDV  AKEIL--NSS  VFADRPVKES  AYSLMFN-RA  148
```

Figure 1 (continued)

```
SEQ_ID_NO_21   LVFAPYGQRW RMLRKISSVH LFSAKALEDF KHVRQEEVGT LMRE--LARA   159
SEQ_ID_NO_36   LVFAPYGPRW RMLRKICSVH LFSGQALDDF RHIRQEEVLA LMRA--LARE   158
SEQ_ID_NO_47   LVFAPYGPRW RLLRKISYVH MFSSKALDDF RHIRQDEVAR LIRN--LSNS   161
SEQ_ID_NO_4    IGFAPNGGYW RLLRRIASAH LFAPRRIAAH EAGRQADVVA MLDD--IQKE   208
SEQ_ID_NO_46   MGFAPFGDYW RNLRRISSTY LFSPRRVSSF EKQRSEIGEG MVRD--MKRM   93
SEQ_ID_NO_39   IGFAPYGTYW RALRRVASTH LFSPRQVSAS AAQRAVIARQ MVEAMRSAAA   205
SEQ_ID_NO_40   IGFAPYGTYW RALRRVASTH LFSPRQVSAS AAQRAVIARQ MVEAMRSAAA   207
SEQ_ID_NO_27   IGFAPYGAYW RTLRRVSSSH LFSPRQVAAS AAQRAVIAHQ MVDA--MRPV   203
SEQ_ID_NO_29   IGFAPHGAYW RALRRVASAH LFSPRQIAAS AAQRAAIARQ MVDA--TTTA   200
SEQ_ID_NO_38   IGFAPHGAYW RALRRVASAH LFSPRQIAAS AAQRAVIARQ MVDAMMMEQG   198
SEQ_ID_NO_3    IGFAPYGVYW QTLRKIASNH LFSPKQIKRS ETQRSVIANQ IVKC--LTKQ   196
SEQ_ID_NO_25   IGFAPYGVYW RTLRKISTNH LFSPMQIKSS GPQRSEIATQ MIDL--FRNR   214
SEQ_ID_NO_22   IGFASYGVYW RSLRRIASNH LFCPRQIKAS ELQRSQIAAQ MVHI--LNNK   191
SEQ_ID_NO_6    IGFAPYGVYW RELRRIAATH LFCPKQIKNS EEQRRFIADE MVNL--FGRH   198
SEQ_ID_NO_10   IGFAPYGVYW RTLRKIASTH LFCPKQIKAA ESQRLQIASQ MVST--FNDR   196

SEQ_ID_NO_21   NTKP---VNL GQLVNMCVLN ALGREMIGRR LFGAD----- ADHKAEEFRS   201
SEQ_ID_NO_36   GQTP---VKL GQLLNVCTTN ALGRVMLGRR VFGDGSGG-- EDPKADEFKE   203
SEQ_ID_NO_47   GSKA---ANL GQMLNVCTTN ALARVMLGRR VFNEGNGGCE CDPRADEFKS   208
SEQ_ID_NO_4    YHSK-GVVRV RRHLQGAALN NIMGSVFGRR FDMSH----- ENEEVKKLRE   252
SEQ_ID_NO_46   MERN-GVVEV RRMLHYGSLN NIMLTVFGKK FDF------- AKDEGLELEL   135
SEQ_ID_NO_39   AAAG-GGVAA RPFLKRASLH NVMWSVFGRK YELAAP---- ESEETAELRS   250
SEQ_ID_NO_40   AAAG-GGVAA RPFLKRASLH NVMWSVFGRK YELAAP---- ESEETAELRS   252
SEQ_ID_NO_27   GGAGVKHVEA RRFLKRASLH NVMWSVFGRR YELDEA---- GSGEAAELKS   249
SEQ_ID_NO_29   AAHA-PVVVA RRFLKRASLH NVMWSVFGRR YDLMA----- DSREAEELKA   244
SEQ_ID_NO_38   AAAP-GVVTA RRFLKRASLH SVMWSVFGRR YELLQAAD-- GGEEAAELQS   245
SEQ_ID_NO_3    SNTK-GLCFA RDLIKTASLN NMMCSVFGKE YELEE----- EHEEVSELRE   240
SEQ_ID_NO_25   HLHG-GFC-V RDVLKKASLN NMMCSVFGQR FKIDE----- VNERMMELSG   257
SEQ_ID_NO_22   RHRS---LRV RQVLKKASLS NMMCSVFGQE YKLHD----- PNSGMEDLGI   233
SEQ_ID_NO_6    GHER--SFIV REVVKRASLN NMMVSIFGRK YKLDC----- DNNEVDELRG   241
SEQ_ID_NO_10   EKSS---FSV REVLKRASLN NMMCSVFGRE YKLDS----- FNNEVEELRA   238
```

Figure 1 (continued)

| | | | | | | |
|---|---|---|---|---|---|---|
| SEQ_ID_NO_21 | MVTEMMALAG | VFNIGDFVPA | LDCLDLQGVA | GKMKRLHKRF | DAFLSSILEE | 251 |
| SEQ_ID_NO_36 | MVVELMVLAG | VFNIGDFVPA | LEWLDLQGVA | SKMKKLHARF | DAFLGAIVEE | 253 |
| SEQ_ID_NO_47 | MVVELMVLAG | VFNIGDFVPS | LEWLDIQGVQ | SKMKKLHKRF | DSFLTSIIED | 258 |
| SEQ_ID_NO_4 | MVDEGFQLLG | AFNWADHLPW | LRPLDPLRIH | ARCARLVPRV | TTFVSNIIEQ | 302 |
| SEQ_ID_NO_46 | ILKEGYELLG | IFNWGDHLPL | LGWLDLQGVR | RRCRTLVAKV | NVFVKKIIDE | 185 |
| SEQ_ID_NO_39 | MVDEGYDLLG | QLNWSDHLPW | LAPFDLQKTR | SRCSSLVPRV | NRFVTRIIDE | 300 |
| SEQ_ID_NO_40 | MVDEGYDLLG | QLNWSDHLPW | LAPFDLKKTR | SRCSSLVPRV | NRFVTRIIDE | 302 |
| SEQ_ID_NO_27 | LVDEGYDLLG | QLNWSDHLPW | LARFDLQKIR | SRCSALVPRV | NRFVGRIIDE | 299 |
| SEQ_ID_NO_29 | LVDEGYDLLG | QLNWSDHLPW | LARFDLQKTR | ARCCALVPRV | NRFVGNIIGE | 294 |
| SEQ_ID_NO_38 | LVDQGYDLLG | QLNWSDHLPW | LARFDLQRTR | ARCAALVPRV | NRFVGRIIDE | 295 |
| SEQ_ID_NO_3 | LVEEGYDLLG | TLNWTDHLPW | LSEFDPQRIR | SRCSNLVPKV | NRFVNRIISD | 290 |
| SEQ_ID_NO_25 | LVEQGYDLLG | GLNWGDHLPF | LKDFDVQKIR | FSCSELVPKV | NRFVGSIISD | 307 |
| SEQ_ID_NO_22 | LVDQGYDLLG | LFNWADHLPF | LAHFDAQNIR | FRCSNLVPMV | NRFVGTIIAE | 283 |
| SEQ_ID_NO_6 | LVDEGYDLLG | TLNWSDHLPW | LAQFDPQNIR | VRCSNLVPKV | NGFVGGIIAQ | 291 |
| SEQ_ID_NO_10 | LVEEGYDLLG | TLNWSDHLPW | LADFDPQKIR | FRCSNLVPKV | NRFVSRIIAE | 288 |

| | | | | | | |
|---|---|---|---|---|---|---|
| SEQ_ID_NO_21 | HEAMK----N | GQDQKHTDML | STLISLK--- | --GTDFDGEG | GTLTDTEIKA | 292 |
| SEQ_ID_NO_36 | HKISG----S | AGSERHVDLL | STLISLKDNA | DGEGG----- | -KLTDVEIKA | 293 |
| SEQ_ID_NO_47 | HMVSK----- | --SEKHNDLL | STLLSLKEKV | DEDGD----- | -KLNDTEIKA | 295 |
| SEQ_ID_NO_4 | HRREE---QR | RESGDQCDFV | DVLLSLQ--- | --GED----- | -KLDEEDMIA | 338 |
| SEQ_ID_NO_46 | HKRRA-NGVG | IDEGEGEDFV | DVLLGLE--- | --EKD----- | -RLSESDMVA | 223 |
| SEQ_ID_NO_39 | HRARL----S | LAVDAAVDFT | DVLLSLH--- | --GGD----- | -KLSDADMVA | 335 |
| SEQ_ID_NO_40 | HRARL----S | LAVDAAVDFT | DVLLSLH--- | --GGD----- | -KLSDADMVA | 337 |
| SEQ_ID_NO_27 | HRAAL----N | DDDDAVVDFT | DVLLSLQ--- | --GSD----- | -KLSDADMIA | 334 |
| SEQ_ID_NO_29 | HRARL---GR | GGDTAVMDFT | DVLLSLQ--- | --GDD----- | -KLSDADMIA | 330 |
| SEQ_ID_NO_38 | HRAARLHLGG | DGAAAVVDFT | DVLLSLQ--- | --GSD----- | -RLSDADMIA | 334 |
| SEQ_ID_NO_3 | HREQT----- | --RDSPSDFV | DVLLSLD--- | --GPD----- | -KLSDPDIIA | 322 |
| SEQ_ID_NO_25 | HRADK----- | --NQTNKDFV | HVLLSLQ--- | --EPD----- | -KLSDSDMIA | 339 |
| SEQ_ID_NO_22 | HRASK----- | --TETNRDFV | DVLLSLP--- | --EPD----- | -QLSDSDMIA | 315 |
| SEQ_ID_NO_6 | HRART----- | --NEEARDLV | DVLLSLQ--- | --GAD----- | -KLSDSDMIA | 323 |
| SEQ_ID_NO_10 | HRALT----- | --RSENPDFV | DVLLSLQ--- | --GHD----- | -KLSDSDMIA | 320 |

Figure 1 (continued)

| | | | | | | |
|---|---|---|---|---|---|---|
| SEQ_ID_NO_21 | LLLNMFTAGT | DTSASTVDWA | IAELIRHPEI | MRKAQEELDS | VV-GRGRPIN | 341 |
| SEQ_ID_NO_36 | LLLNLFTAGT | DTSSSTVEWA | IAELIRHPEM | MAQAQQELDA | VV-GRGRLVT | 342 |
| SEQ_ID_NO_47 | LLLNMFTAGT | DTSSSTTEWA | IAELIKNPKL | MIRIQNELDT | VV-GRDRLVT | 344 |
| SEQ_ID_NO_4 | VLWEMIFRGT | DTTALLTEWT | MAELVLHPEA | QKKAQAELDA | VV-GHDRSVK | 387 |
| SEQ_ID_NO_46 | VLWEMIFRGT | DTVAILLEWT | LARMVLHPDI | QSKAQVEIDS | VV-DSSRPVL | 272 |
| SEQ_ID_NO_39 | VLWEMIFRGT | DTVAVLIEWV | AARLVLHQDV | QARVHDELDR | VV-GSDRAVT | 384 |
| SEQ_ID_NO_40 | VLWEMIFRGT | DTVAVLIEWV | AARLVLHQDV | QARVHDELDR | VV-GSDRAVT | 386 |
| SEQ_ID_NO_27 | VLWEMIFRGT | DTVAVVIEWV | LARLMLHQDV | QARVHEELDR | VV-GPNRAVT | 383 |
| SEQ_ID_NO_29 | VLWEMIFRGT | DTVAVLIEWV | LARLVLHQDV | QSKVQEELDR | VV-GLGQAVT | 379 |
| SEQ_ID_NO_38 | VLWEMIFRGT | DTVAVLMEWV | LARLVLHQDV | QRRVQEELDR | VV-GPGRAVT | 383 |
| SEQ_ID_NO_3 | VLWEMIFRGT | DTVAVLIEWI | LARMVLHPDI | QSTVHNELDQ | IV-GRSRAVE | 371 |
| SEQ_ID_NO_25 | VLWEMIFRGT | DTVAVLIEWI | LARLVIHPDV | QKKVQTELDE | VASGESCAIT | 389 |
| SEQ_ID_NO_22 | VLWEMIFRGT | DTVAVLIEWI | LARMALHPHV | QSKVQEELDA | VV-GKARAVA | 364 |
| SEQ_ID_NO_6 | VLWEMIFRGT | DTVAVLIEWI | LARIVVHPDV | QSRVHDELDK | VV-GKSKAVY | 372 |
| SEQ_ID_NO_10 | VLWEMIFRGT | DTVAVLIEWI | LARMVLHPDV | QSKVHDELYK | VV-GRSRAVA | 369 |

| | | | | | | |
|---|---|---|---|---|---|---|
| SEQ_ID_NO_21 | ESDLSQLPYL | QAVIKENFRL | HPPTP-LSLP | HIASESCEI- | NGYHIPKGST | 389 |
| SEQ_ID_NO_36 | DLDLPKLTYL | QAIVKETFRL | HPSTP-LSLP | RMAAESCEI- | NGYHIPKNAT | 390 |
| SEQ_ID_NO_47 | EQDLTHLPYL | EAVIKETFRL | HPSTP-LSLP | RVATNSCEI- | FNYHIPKGAT | 392 |
| SEQ_ID_NO_4 | DSDIPKLPYI | QAVVKEALRM | HPPGPLLSWA | RLSTEDVNMG | DGMCVPAGTT | 437 |
| SEQ_ID_NO_46 | DSDIQRLPYL | QSIVKETLRM | HPPGPLLSWA | RLAIHDVPV- | DGHMIPAGTT | 321 |
| SEQ_ID_NO_39 | ESDASKLVYL | QAVIKEVLRL | HPPGPLLSWA | RLATSDVHV- | GGFLIPSGTT | 433 |
| SEQ_ID_NO_40 | ESDASKLVYL | QAVIKEVLRL | HPPGPLLSWA | RLATSDVHV- | GGFLIPSGTT | 435 |
| SEQ_ID_NO_27 | ESDAASLVFL | QAVVKEVLRL | HPPGPLLSWA | RLATSDVHV- | DGLHVPAGTT | 432 |
| SEQ_ID_NO_29 | ESDTASLPYL | QAVIKEVLRL | HPPGPLLSWA | RLATSDVYV- | SGYLVPAGTT | 428 |
| SEQ_ID_NO_38 | EPDGASLAYL | HAVIREVLRL | HPPGPLLSWA | RLATSDVHV- | GGYLVPAGTT | 432 |
| SEQ_ID_NO_3 | ESDVVSLVYL | TAVVKEVLRL | HPPGPLLSWA | RLAITDTII- | DGRRVPAGTT | 420 |
| SEQ_ID_NO_25 | EEDVAAMVYL | PAVIKEVLRL | HPPGPLLSWA | RLAITDTTI- | DGYHVPAGTT | 438 |
| SEQ_ID_NO_22 | EDDVAVMTYL | PAVVKEVLRL | HPPGPLLSWA | RLSINDTTI- | DGYHVPAGTT | 413 |
| SEQ_ID_NO_6 | ESDVMNLTYL | MAVIKEVLRL | HPPGPLLSWA | RLAITDTTV- | DGYHVPKGTM | 421 |
| SEQ_ID_NO_10 | ESDITAMVYL | QAVVKEVLRL | HPPGPLLSWA | RLAITDTTI- | DGYHVPKGTT | 418 |

Figure 1 (continued)

```
SEQ_ID_NO_21   LLTNIWAIAR DPDQWSDPLT FRPERFLPGG EKA-G----- VDVKGNDFEL 433
SEQ_ID_NO_36   LLVNVWAIAR DPEVWEEPLE FRPNRFLPGG ERP-N----- ADVRGNDFEV 434
SEQ_ID_NO_47   LLVNVWAISR DPKEWTNPLE FKPERFLPGG EKF-D----- VDIRGNDFEV 436
SEQ_ID_NO_4    AMVNMWSITH DPNIWESPYE FRPERFVVFE GGE-E----- VDVRGNDLRL 481
SEQ_ID_NO_46   AMVNMWAITH DECNWAEPNK FNPDRFIDED ---------- VNILGSDLRL 361
SEQ_ID_NO_39   AMVNMWAITH DPAVWPDPNE FKPERFVAGP SSDQA---AE FPIMGSDLRL 480
SEQ_ID_NO_40   AMVNMWAITH DPAVWPDPNE FKPERFVAGP SSDQA---TE FPIMGSDLRL 482
SEQ_ID_NO_27   AMVNMWAITH DPTVWVKPAE FKPERFLGGS SSDHAAAGAE FSVTGSDLRL 482
SEQ_ID_NO_29   AMVNMWAITH DPSLWPEPME FRPERFMGPA AED------- VPIMGSDLRL 471
SEQ_ID_NO_38   AMVNMWAITH DPAVWPDPAE FKPERFAAGS PGDEA----- FPVMGSDLRL 477
SEQ_ID_NO_3    AMVNMWAIAH DPHVWENPLE FKPERFVAKE GEV-E----- FSVLGSDLRL 464
SEQ_ID_NO_25   AMVNMWAISR DPDVWRNPLE FNPERFVSEG AE-------- FSVLGSDLRL 480
SEQ_ID_NO_22   AMVNTWAICR DPHVWKDPLE FMPERFVTAG GDA-E----- FSILGSDPRL 457
SEQ_ID_NO_6    AVVNMWAIAR DPQEWADPTE FVPDRFVAKT GEV-E----- FSVLGSDLRL 465
SEQ_ID_NO_10   AMVNMWAISR DPEFWEDPLE FMPERFVVTK EDVLE----- FSVLGSDLRL 463

SEQ_ID_NO_21   IPFGAGRRIC AGLSLGLRTI QLLTATLVHG FEWELAGGVT -PEKLNMEET 482
SEQ_ID_NO_36   IPFGAGRRIC AGMSLGLRMV HLLTATLVHA FNWELPEGQV -AEKLNMDEA 483
SEQ_ID_NO_47   IPFGAGRRIC AGMSLGLRMV QLLTATLAHA YDWELENGLS -PEKLNMDEA 485
SEQ_ID_NO_4    APFGAGRRVC PGKALGLATV NLWVAKLLHH FEWL-PHAE- --HPVDLSEV 527
SEQ_ID_NO_46   APFGSGKRVC PGKTMALAAV HLWLAQLLKS FKLL-PSR-- --NGVDLSEC 406
SEQ_ID_NO_39   APFGSGRRSC PGKSLAIATV GFWVATLLHE FDWLPLSDK- -SRGVDLSEV 528
SEQ_ID_NO_40   APFGSGRRSC PGKSLAIATV GFWVATLLHE FDWLPLSDK- -SRGVDLSEV 530
SEQ_ID_NO_27   APFGSGRRSC PGKSLAIATV GFWVATLLHE FEWTPPSSDG -SGGVDLSEV 531
SEQ_ID_NO_29   APFGSGRRSC PGKSLAVATV GFWVATLLYE FKWLPPSDEP RGGGVDLSEV 521
SEQ_ID_NO_38   APFGSGRRVC PGKSLAMATV AFWVATLLHE FEWLPASSDE PPRGVDLSEV 527
SEQ_ID_NO_3    APFGSGRRVC PGKNLGLTTV TFWTATLLHE FEWLTPSDE- --KTVGLSEK 511
SEQ_ID_NO_25   APFGSGRRSC PGKNLGLATV TFWVAKLLHE FEWL-PLDE- -VNGVDLTEV 527
SEQ_ID_NO_22   APFGSGRRAC PGKTLGMATV NFWVASLLHE FEWV-PSDE- --KGVDLTEV 503
SEQ_ID_NO_6    APFGSGRRTC PGKNLGLTTV SFWVATLLHE FEWL-PSDQ- --NSVDLSEV 511
SEQ_ID_NO_10   APFGSGRRTC PGKTLGITTV TFWVASLLHE YEWV-PGEE- --NNVDLSEV 509
```

Figure 1 (continued)

```
SEQ_ID_NO_21    YGI TLQRAVP  LVVHPKLRLD  MSAYGLGSA     511
SEQ_ID_NO_36    YGLTLQRAAP   LMVHPRPRLS  PQVFGK---     509
SEQ_ID_NO_47    YGLTLQRAVP   ILAHPRPRLS  PHLYL----     510
SEQ_ID_NO_4     LKLSCEMARP   LHCVPVTRVP  FAKFSD---     553
SEQ_ID_NO_46    LKMSLEMKNP   LVCVAVPRFE  ---------     426
SEQ_ID_NO_39    LKLSCEMATP   LEARLRPRRK  VMSV-----     552
SEQ_ID_NO_40    LKLSCEMATP   LEARLRPRRK  V--------     551
SEQ_ID_NO_27    LRLSCEMAAP   LEARLRPRRA  V--------     552
SEQ_ID_NO_29    LRLSCEMAAP   LEARVVPRHA  VC-------     543
SEQ_ID_NO_38    LRLSCEMAAP   LEARLVPRRA  V--------     548
SEQ_ID_NO_3     LRLSCEMANP   LAAKLRPRRS  FSV------     534
SEQ_ID_NO_25    LRLSCEMANP   LTVQVRPRR-  ---------     546
SEQ_ID_NO_22    LKLSSEMANP   LTVKVRPRRG  ---------     523
SEQ_ID_NO_6     LKLSCEMANP   LKVRIRPRRK  LT-------     533
SEQ_ID_NO_10    LRLSCEMANP   LTVKVRPRRS  SQSPLY---     535
```

Figure 2

| | | | | | | |
|---|---|---|---|---|---|---|
| SEQ_ID_NO_67 | - - - - - - - - - - | MQLQPAVAN- | - - - - - - - - - P | NTPSGAA- - - | - - - - - - - - - - | 17 |
| SEQ_ID_NO_65 | MDTSHWPQGI | GLVKAVEPS- | - - - - - KPVPT | ERKPRPQ- - - | - - - - KEQ- - - | 34 |
| SEQ_ID_NO_63 | MGMDSSSGQQ | QQMSNQSLES | MLTCSKGE-Q | DKKPKPP- - - | - - - - QPE- - - | 39 |
| SEQ_ID_NO_73 | - - - - - MDQQQ | QEMSSQTLES | MLVCTKPDQD | QKKPRPA- - - | - - - - EQQ- - - | 35 |
| SEQ_ID_NO_69 | - - - - - - MQEE | PGRRPVPPF- | - - - - - AGVDL | RRPKGYP- - - | -VAVAKEERP | 34 |
| SEQ_ID_NO_70 | - - - - - - - MQE | AGRRPAPQF- | - - - - - AGVDL | RRPKGYPAAA | QLTPAAEEAA | 37 |
| SEQ_ID_NO_71 | - - - - - - - MQE | AGRRPAPQF- | - - - - - AGVDL | RRPKGYPAAA | QLTPAAEEAA | 37 |
| SEQ_ID_NO_64 | - - - - - MPSSD | SGESRRSIK- | - - - - - - - - - P | QNRPGAP- - - | - - APEQE- - - | 27 |
| SEQ_ID_NO_75 | - - - - - - - MEA | GQVPDGRAL- | - - - - - MAAVT | TTGGGGR- - - | - - - - EPE- - - | 27 |
| SEQ_ID_NO_51 | - - - - - - - MQD | - - - - PTGFH- | - - - - - - - - - Q | MKAPAFQ- - - | - - - - EQEQQ- | 21 |
| SEQ_ID_NO_53 | - - - - - - - MQD | - - - - PSTAF- | - - - - - - - - - H | TIKPQFP- - - | - - - - EQE- - - | 19 |
| SEQ_ID_NO_60 | - - - - - - - MQD | - - - - P-TLF- | - - - - - - - - - Q | PMKPHFP- - - | - - - - EQE- - - | 18 |
| SEQ_ID_NO_58 | - - - - - - - MQE | DLTSAAAYYH | HQSMIMTAKQ | QQQPELP- - - | - - - - EQE- - - | 33 |
| SEQ_ID_NO_49 | - - - - - - - MQD | - - - - PAAYY- | -QTMMAKQQQ | QQQPQFA- - - | - - - - EQE- - - | 27 |

| | | | | | | |
|---|---|---|---|---|---|---|
| SEQ_ID_NO_67 | - - - REQCPRC | ASHDTKFCYY | NNYNTSQPRH | FCRACRRYWT | LGGSLRNVPI | 64 |
| SEQ_ID_NO_65 | - - - AINCPRC | NSTNTKFCYY | NNYSLSQPRY | FCKTCRRYWT | EGGSLRNVPV | 81 |
| SEQ_ID_NO_63 | - - - ALKCPRC | DSNNTKFCYY | NNYSLSQPRY | FCKSCRRYWT | KGGTLRNVPV | 86 |
| SEQ_ID_NO_73 | - - - PQKCPRC | DSANTKFCYY | NNYSLTQPRY | FCKSCRRYWT | KGGTLRNVPV | 82 |
| SEQ_ID_NO_69 | APGGDPCPRC | GSRDTKFCYY | NNYNTSQPRH | LCKSCRRYWT | KGGSLRNVPV | 84 |
| SEQ_ID_NO_70 | AGVGDPCPRC | ESRDTKFCYY | NNYNTSQPRH | FCKSCRRYWT | KGGSLRNVPV | 87 |
| SEQ_ID_NO_71 | AGVGDPCPRC | ESRDTKFCYY | NNYNTSQPRH | FCKSCRRYWT | KGGSLRNVPV | 87 |
| SEQ_ID_NO_64 | - - - NLPCPRC | DSTNTKFCYY | NNYNYSQPRH | LCKACRRYWT | HGGTLRDIPV | 74 |
| SEQ_ID_NO_75 | - - - GLPCPRC | ESVNTKFCYY | NNYNLSQPRY | FCKTCRRYWT | RGGALRNVPV | 74 |
| SEQ_ID_NO_51 | - - - QLKCPRC | DSTNTKFCYY | NNYNLSQPRH | FCKNCRRYWT | KGGALRNIPV | 68 |
| SEQ_ID_NO_53 | - - - QLKCPRC | DSNNTKFCYY | NNYNLSQPRH | FCKNCKRYWT | KGGALRNIPV | 66 |
| SEQ_ID_NO_60 | - - - QLKCPRC | DSTNTKFCYY | NNYNLSQPRH | FCKNCRRYWT | KGGALRNIPV | 65 |
| SEQ_ID_NO_58 | - - - QLNCPRC | ASPNTKFCYY | NNYNLSQPRH | FCKNCRRYWT | KGGSLRNIPV | 80 |
| SEQ_ID_NO_49 | - - - QLKCPRC | DSPNTKFCYY | NNYNLSQPRH | FCKSCRRYWT | KGGALRNVPV | 74 |

Figure 2 (continued)

```
SEQ_ID_NO_67   GGSTRKRLRP APQQTMRRPP VHFGAP---P PPPMPA---- ----------   97
SEQ_ID_NO_65   GGGSRKNKRS SSSSNNSSSS ---TSS---S YKKIPDLT-- ----------  113
SEQ_ID_NO_63   GGGCRKNKRS SSASSKRSQD ----QPFQTN PNPLTCFPSL SYDSNDLTLA  132
SEQ_ID_NO_73   GGGCRKNKKL SSTTSAKRSS QDNISPNISN PIPSYDSSTD LSLAFARLQK  132
SEQ_ID_NO_69   GGGTRKSSSS SSSSSAAAAA ----TTTTTS TSPGAAPK-- -ATKRSKNSK  127
SEQ_ID_NO_70   GGGSRKSSTS SSSSSSAAAA ----SS---S SSPSSPAK-- -SPKRSKNSK  127
SEQ_ID_NO_71   GGGSRKSSTS SSSAAAAAAS -----S---S SSPSSPAK-- -SPKRSKNSK  126
SEQ_ID_NO_64   GGGTRKNAKR SRTHHVAVTS ----SS---S SSAVT----- ----------  102
SEQ_ID_NO_75   GGNTRKATPA TGRRKRSTPA -----P---V NVTVPAP--- ----------  103
SEQ_ID_NO_51   GGGTRKGTKR SSSSTNKPKR ----QP---N PSPDPTPNQK -IPDPSPPPP  110
SEQ_ID_NO_53   GGGSRKNTKR SSNTKRANPD -----P---N PDPVKPTR-- ----------   96
SEQ_ID_NO_60   GGGSRKNTKR SSSSNNNTKR ---------- ASPSPPVS-- ----------   93
SEQ_ID_NO_58   GGGTRKNSSK RSSVGSSSSA ----PS---S SSPKSKTV-- ----------  111
SEQ_ID_NO_49   GGGSRKNATK RSTSSSSSAS ----SP---S NSSQNKKT-- ----------  105

SEQ_ID_NO_67   -QSHSQQAPQ GGLLSSLFAF GAAPLFEGRV GF-----D-- LGLGLPGLSQ  139
SEQ_ID_NO_65   -IPTSSQNPK IINEPHDLNL AFNPSATSNF SNISEFMA-- LPLMNPNSTT  160
SEQ_ID_NO_63   LARLQKGHLG FDHEHDFSIL GNQTNTSCGI LNN------- HGMNHSSNNQ  175
SEQ_ID_NO_73   QTNAHLEIDQ EHDNNNMSMM YNTGNNCTST TFLDALRGG- FLENAPNHPG  181
SEQ_ID_NO_69   RRRVAPAPDP AAPGTDASTA DVASTAPSTV ---------- AASEKPSATE  167
SEQ_ID_NO_70   RRRVSPPPPQ PAP------- APPPPTTADA ---------- ADVAAPTAPE  160
SEQ_ID_NO_71   RRRVSPPPPQ PVP------- APPPPTTADA ---------- ADVAAPTAPE  159
SEQ_ID_NO_64   -SAPEQNYP- ---------- SMTPIQGGSF PY-------- GGVDGEGKQN  132
SEQ_ID_NO_75   -ATASPPPPP ALHGGSLLRP YGGGGGSGLL SFAAPALASP LAAADPDRRL  152
SEQ_ID_NO_51   KSSSSSMFPQ QIVLNSGAQN SDSDIDSTRM -Y-----L-- LPVDHQDGKM  152
SEQ_ID_NO_53   -RVADSSSSS ATSSTSGQQL AGNGNQDPTR VY-------- GVEADPDRKI  137
SEQ_ID_NO_60   -SAPAPEPDP TRI------- ---------- ---------- GPTPVVG---  112
SEQ_ID_NO_58   -AVSDQESRT TGN------- SGQEMDPTRM LY-----G-- LPVGDPS---  143
SEQ_ID_NO_49   -KNPDPDPDP RNS------- QKPDLDPTRM LY-----G-- FPLGDQDVKG  140
```

Figure 2 (continued)

```
SEQ_ID_NO_67   ----SGGGAA AMWAPEFSPA PTVAQVGGNG MFHGGAQIMG QL   222
SEQ_ID_NO_65   D------EQN RGQAAESHGF WNG------- MLGGGS---- --   262
SEQ_ID_NO_63   -------LGR AGWNGLTSSW GHGL------ LNSPLM---- --   289
SEQ_ID_NO_73   STN----KQS WNGFGGSSNW HGL------- INSPLM---- --   299
SEQ_ID_NO_69   -------PPY WGWGTSVFAD TDPA------ LFLNLP---- --   245
SEQ_ID_NO_70   ---------G PYWPTGVFAD TDPS------ LFLNLP---- --   231
SEQ_ID_NO_71   ---------G PYWPTGVFAD TDPS------ LFLNLP---- --   230
SEQ_ID_NO_64   EGGE---TGF VGGGGDCFSW PGLA------ ISTPGNGLK- --   234
SEQ_ID_NO_75   -------PEG MVW---SMGW PDLS------ I--------- --   228
SEQ_ID_NO_51   V---QGGRDT SCWSGDSNGW PDLS------ IYTPGSSLRR --   252
SEQ_ID_NO_53   -------LQG GEWGNSNNGW PGLA------ IYTPGSSFQ- --   235
SEQ_ID_NO_60   LQN----GDS SCW-NGTSGW SHLA------ IFTPGSSFQ- --   211
SEQ_ID_NO_58   -------LGS GIRRNDDAAL TDLA------ MNRVEKN--- --   200
SEQ_ID_NO_49   -------RRT EPGNNNNNPW TDLA------ MNRAEKN--- --   204
```

Figure 3 (continued)

```
SEQ_ID_NO_88   RAFYNDRFPV FAEYSTALFG YDMVLPINTG AEGVETALKL ARKWGYDKKK   155
SEQ_ID_NO_95   NVFYTTPQVE LAKRLVEVSF ADRAFFASTG TEANEAAIKF SRK--FQRVA   183
SEQ_ID_NO_90   NVGYTVPQVE LAKRLVEASF ADRAFFANSG TEANEAAIKF ARK--YQRVA   175
SEQ_ID_NO_93   NVQYTVPQVA LAKRLVEASF ADRVFFANTG TEANEAAIKF ARK--FQRVA   183
SEQ_ID_NO_80   NAYYSIPQ-- ---------- ---------- ---------- ----------   130
SEQ_ID_NO_87   NIFHTIPQVE LAKRLVASSF ADRVFFANSG TEANEAAIKF ARK--YQRHT   183
SEQ_ID_NO_77   NVYYTIPQIE LAKRLVASSF ADRVFFCNSG TEANEAAIKF SRK--FQRFT   178
SEQ_ID_NO_92   NVYYTIPQIE LAKRLVASSF ADRVFFCNSG TEANEAAIKF SRK--FQRFT   169
SEQ_ID_NO_78   NVFYSIPQVE LAKRLVASSF ADRVFFSNSG TEANEAAIKF ARK--FQRFT   169
SEQ_ID_NO_82   NVFYSVPQVE LAKRLVACSF ADRVFFTNSG TEANEAAIKF ARK--YQRFT   170

SEQ_ID_NO_88   IPNDEAL--- IVSCCGCFNG RTLGVISMSC DNEATRGFGP LIPGHLKVDF   202
SEQ_ID_NO_95   HPDSDDPPME FLAFSSSFHG RTMGAVALTS KSQYREPFAP VMPGVTFVDY   233
SEQ_ID_NO_90   HPNGDAP-TE FMSFTNCFHG RTIGSLALTS KVQYREPFEP VMPGSTFVEY   224
SEQ_ID_NO_93   RPDGDAP-TE FMSFTNCFHG RTMGSLALTS KVQYREPFAP VMPGATFAEY   232
SEQ_ID_NO_80   ---------- ---------- ---------- ---------- ----------   130
SEQ_ID_NO_87   TSNGKVPATE FIAFSNCFHG RTLGALALTS KVQYRMPFEP VMPGVTFLEY   233
SEQ_ID_NO_77   HPEDKEVATG FIAFTNSFHG RTLGALALTS KEQYRTPFEP IMPGVTFLEY   228
SEQ_ID_NO_92   HPEDKEVATS FIAFTNSFHG RTLGALALTS KEQYRTPFEP IMPGVTFLEY   219
SEQ_ID_NO_78   RPDEKQPATE FVSFSNSFHG RTMGSLALTS KENYRSPFEP VMPGVTFLEY   219
SEQ_ID_NO_82   NPEKQQA-TE FISFSNSFHG RTMGALALTS KEQYRFPFEP VMPGVNFLEY   219

SEQ_ID_NO_88   GDAEALEKIL KEKGDAIAAF ILEPIQGEAG VKIPPDGYLK AVRDLCSKYN   252
SEQ_ID_NO_95   GDLEAAKKFI --QSGRVAAV FVEPVQGEGG IHSATQEFLQ GLREACDEAG   281
SEQ_ID_NO_90   GNLEEAKKVI --QSGKIAAV FVEPVQGEGG IHSATNEFLQ GLRDACDEAG   272
SEQ_ID_NO_93   GNLEEAKKVI --QSGKIAAV FVEPVQGEGG IHSATKEFLQ GLRDACDEAG   280
SEQ_ID_NO_80   ---------- ---------- ---------- ---------- ----------   130
SEQ_ID_NO_87   GNAQAAVELI --KQGKIAAV FVEPIQGEGG IYSATKEFLQ SLRNACDETG   281
SEQ_ID_NO_77   GNIQAATDLI --RSGKIAAV FVEPIQGEGG IYSATKEFLQ SLRSACDAAG   276
SEQ_ID_NO_92   GNTQAATDLI --RSGKIAAV FVEPIQGEGG VYSATKEFLQ SLRSACDAAG   267
SEQ_ID_NO_78   GNIEAATQLI --QRRKIAAV FVEPIQGEGG VYSATKEFLY ALRKACDDSG   267
SEQ_ID_NO_82   GDVQAATELI --KSGRIAAV FVEPIQGEGG IYSATKEFLQ SLRSACDDAG   267
```

Figure 3 (continued)

```
SEQ_ID_NO_88   VLMIADEIQT GLARTGKMLA CEWEEVRPDV VVLGKALGGG IIPVSAVLAD   302
SEQ_ID_NO_95   ALLVFDEVQC GFGRTGYLWA HEAYGVEPDI MTLAKPLANG -IPIGVVLVK   330
SEQ_ID_NO_90   ALLVFDEVQC GLGRTGYLWA HEVYGVLPDI MTLAKPLANG -LPIGVALVT   321
SEQ_ID_NO_93   ALLVFDEVQC GLGRTGYLWA YEAYGVLPDI MTLAKPLAGG -LPIGVVLVT   329
SEQ_ID_NO_80   -------VQC GLGRTGYLWA HEAYGVFPDM MTLAKPLAGG -LPIGATLVS   172
SEQ_ID_NO_87   ALLVFDEVQC GLGRSGFLWA HEAYGVFPDM MTLAKPLAGG -LPIGALLVT   330
SEQ_ID_NO_77   SLLVFDEVQC GLGRTGLMWA YEAFGVTPDI MTVAKPLAGG -LPIGAVLVT   325
SEQ_ID_NO_92   SLLVFDEVQC GLGRTGNLWA YEAFGVTPDI MTVAKPLAGG -LPIGAVLVT   316
SEQ_ID_NO_78   TLLVFDEVQC GLGRTGYLWA HEIYDVFPDI MTLAKPLAGG -LPIGAVLVT   316
SEQ_ID_NO_82   SLLVFDEVQC GLGRTGYLWA HEAYGVVPDI MTLAKPLAGG -LPIGAALVS   316

SEQ_ID_NO_88   KEVMLCIKPG QHGSTFGGNP LASAVAIASL EVIKEERLAE RSTKLGGELL   352
SEQ_ID_NO_95   EKVAAAINYG DHGTTFGGGP LACQTAITVF DKIMKPGFLA EVSKKGENFK   380
SEQ_ID_NO_90   EKVAAAIHYG DHGTTFGGGP FVCHAALATL DKIQKPGFLA EVTKKGEYFK   371
SEQ_ID_NO_93   EKVASAINFG DHGTTFGGGP LVCQAALTTL DKIQKPGFLA EVAKKGENFK   379
SEQ_ID_NO_80   ERVASAIAHG DHGSTFAGSP FVCSAAICVF NKISNPSFLS SVLKKGDYMK   222
SEQ_ID_NO_87   ERVASAINYG DHGSTFAGSP LVCSAALAVL DKISKPDFLS SVSKKGLYFK   380
SEQ_ID_NO_77   EKVAETINYG DHGSTFAGSP LVCSAAIAVM DKVSKPSFLS SVSNKGRYFR   375
SEQ_ID_NO_92   EKVAETIKYG DHGSTFAGNP LVCSAAIAVF DKVSKSSFLA SVSSKGLYFK   366
SEQ_ID_NO_78   ERVASAITYG DHGTTFAGGP LVCKAALTVL DKILRPGFLA SVSKKGHYFK   366
SEQ_ID_NO_82   EKVAAAIKYG DHGSTFAGGP LVCNAAIAVL DKISKPGFLA SVSEKGQYFK   366

SEQ_ID_NO_88   GLLEKIQKQY PDHVKEVRGR GLFIGVELNS ESLSPVSFFE LSEKLKDRGV   402
SEQ_ID_NO_95   QLLRTKLSGN P-HVKEVRGV GLLVGIELD- -----VPAGP LVDACLDAGV   423
SEQ_ID_NO_90   QLLKTKLGGN P-HVKEIRGA GLIVGIELD- -----VPAGP LVDACLDAGV   414
SEQ_ID_NO_93   QLLSTKLSGN A-HVKEIRGI GLIVGIELD- -----VPAGP LVDACLDRGV   422
SEQ_ID_NO_80   ELLNQKLGGN P-HVKEIRGW GLMIGIELD- -----VSASP LVDACRNSGL   265
SEQ_ID_NO_87   ELLREKLGEN R-HVKEIRGV GLIIGIDLD- -----VPASP LVDACRSSGL   423
SEQ_ID_NO_77   DLLVKKLGGN S-YVKEVRGE GLIIGVELD- -----VPASS LVDACRDSGL   418
SEQ_ID_NO_92   DLLVKKLGGN L-HVKEVRGE GLIIGVELD- -----VPAGP LVDACRDSGL   409
SEQ_ID_NO_78   EMLINKLGGN S-HVREVRGV GLIVGIELD- -----VSASP LVNACLNSGL   409
SEQ_ID_NO_82   ELLIHKLGGN S-HVREVRGL GLIIGIELD- -----VSASP LVDACRDSSL   409
```

Figure 3 (continued)

```
SEQ_ID_NO_88    LAKST-HDTI IRFTPPLCIS ADEIQQGSKA LADVLEIDLP MLKKMKPKDA    451
SEQ_ID_NO_95    IVLTAGKGNV VRLVPPLIIS EKELEHA--- -ADVIRDCLP VLDVAAA---    466
SEQ_ID_NO_90    FLLTAGKGNV VRLVPALIVS EKELEQA--- -AEVIRECLP ALEASTS---    457
SEQ_ID_NO_93    IVLTAGKGNV VRLVPPLIIS EKELEQA--- -AEVIRDCLP ALDASTS---    465
SEQ_ID_NO_80    LVLTAGKGNV VRLVPPLIIS EEELKHA--- -AEILHECLP ALDNSN----    307
SEQ_ID_NO_87    LVLTAGKGNV VRLVPPLIIT EKELEQA--- -AGILCQTLP VLDN------    463
SEQ_ID_NO_77    LILTAGKGNV VRIVPPLVIS EEEIERA--- -VEIMAQNLT ALD-------    457
SEQ_ID_NO_92    LILTAGKGNV VRIVPPLIIS EEEIERA--- -VEIIFHDLT ALD-------    448
SEQ_ID_NO_78    LVLTAGKGNV VRIVPPLIIT EQELEKA--- -AEILLQCLP ALDRHG----    451
SEQ_ID_NO_82    LILTAGKGNV VRLVPPLIIS EQELERA--- -AEIILECLP ALDKTS----    451

SEQ_ID_NO_88    APPAGPSACD RCGRVVYG    469
SEQ_ID_NO_95    ---------- --------    466
SEQ_ID_NO_90    ---------- --------    457
SEQ_ID_NO_93    ---------- --------    465
SEQ_ID_NO_80    ---------- --------    307
SEQ_ID_NO_87    ---------- --------    463
SEQ_ID_NO_77    ---------- --------    457
SEQ_ID_NO_92    ---------- --------    448
SEQ_ID_NO_78    ---------- --------    451
SEQ_ID_NO_82    ---------- --------    451
```

SEQ_ID_NO_101 34
SEQ_ID_NO_102 35
SEQ_ID_NO_150 38
SEQ_ID_NO_118 32
SEQ_ID_NO_145 31
SEQ_ID_NO_149 33
SEQ_ID_NO_144 22
SEQ_ID_NO_125 42
SEQ_ID_NO_137 34
SEQ_ID_NO_146 35
SEQ_ID_NO_147 35
SEQ_ID_NO_119 42
SEQ_ID_NO_100 39
SEQ_ID_NO_113 36
SEQ_ID_NO_104 37
SEQ_ID_NO_108 37
SEQ_ID_NO_116 43
SEQ_ID_NO_117 44
SEQ_ID_NO_122 41
SEQ_ID_NO_120 39
SEQ_ID_NO_101 84
SEQ_ID_NO_102 79
SEQ_ID_NO_150 82
SEQ_ID_NO_118 76
SEQ_ID_NO_145 71
SEQ_ID_NO_149 74
SEQ_ID_NO_144 63
SEQ_ID_NO_125 86
SEQ_ID_NO_137 75
SEQ_ID_NO_146 79
SEQ_ID_NO_147 79
SEQ_ID_NO_119 86
SEQ_ID_NO_100 87
SEQ_ID_NO_113 79
SEQ_ID_NO_104 81
SEQ_ID_NO_108 83
SEQ_ID_NO_116 87
SEQ_ID_NO_117 63
SEQ_ID_NO_122 84
SEQ_ID_NO_120 81

Figure 4 (continued)

| | | |
|---|---|---|
| SEQ_ID_NO_101 | KKFIENKYGK DIHDKNFAKT LSQVVKTFVK GGKLVKVKGS FKLSE----- | 129 |
| SEQ_ID_NO_102 | AKFLGDKY-K ADLPPNFKKQ LNVQLKNLTK SGKLTKVKAS YKLTA----- | 123 |
| SEQ_ID_NO_150 | AKFLSEKY-K SDLPPVFKKK LNVQLRNLTN SGKLTKVKGS YKLAE----- | 126 |
| SEQ_ID_NO_118 | NKFVEDKH-K Q-LPSNFRKL LLFHLKKLVA SGKLVKVKNS FKLPS----- | 119 |
| SEQ_ID_NO_145 | SKFVENKH-K AHLPANFKKL LLVQLRKLTA AGKLTKVKNS YKISA----- | 115 |
| SEQ_ID_NO_149 | AKFVEDKH-K SHLPANFKKL LLVQLQKLTA AGKLTKVKNS YKISA----- | 118 |
| SEQ_ID_NO_144 | GKFIEDKH-K AHLPSNFRKI LFLQLKKLAA AGKLTKVKSS YKLST----- | 107 |
| SEQ_ID_NO_125 | AKFVEDKH-K AHLPANFRKI LSVQLKKLVA SGKLTKVKAS YKLSA----- | 130 |
| SEQ_ID_NO_137 | AKFVEDKH-K DKLPPNFRKL LLGQLKKLVA AGKLTKVKNS YKLPA----- | 119 |
| SEQ_ID_NO_146 | GKFLEDKH-K DHLPSNFRKQ LLVQIKKLVA AGKLTKVKNS YKLPP----- | 123 |
| SEQ_ID_NO_147 | GKFLEDKH-K DHLPSNFRKQ LLVQIKKLVA AGKLTKVKNS YKLPP----- | 123 |
| SEQ_ID_NO_119 | QKFLEAKH-K D-LPAVFRKM LSNNLKKLVA AGKLVKVKAS YKLPS----- | 129 |
| SEQ_ID_NO_100 | QKFIEEKH-K S-LPPTFRKL LLVNLKRLVA SEKLVKVKAS FKIPS---A- | 131 |
| SEQ_ID_NO_113 | QKFIEEKQ-K S-LPPTFRKL LLVNLRRLVA SGKLVKVKAS FKIPS----- | 122 |
| SEQ_ID_NO_104 | AKFIEEKQ-K N-LPGNFKKL LLVHLKKLVA AGKLVKVKAS YKLPS---A- | 125 |
| SEQ_ID_NO_108 | TKFLEEKH-K Q-LPSNFKKL LLFHLKKLVL SDKIVKVKGS FKLPS----- | 126 |
| SEQ_ID_NO_116 | AKFIEEKH-K N-LPANFKKI LLVQIKKLVA SGKLVKVKGS YKLPA---KS | 132 |
| SEQ_ID_NO_117 | AKFIEEKH-K Q-LPSNFKKL LLVQIRKLVA SGKLVKVKAS YKLPA----- | 126 |
| SEQ_ID_NO_122 | TKFIEDKQ-K N-LPSNFRKL LLVQLKKLVA SGKLVKVKSS YKLPA--AR- | 129 |
| SEQ_ID_NO_120 | TKFIEEKQ-K S-LPSNFKKL LLTQLKKFVA SEKLVKVKNS YKLPSGSKP- | 128 |

| | | |
|---|---|---|
| SEQ_ID_NO_101 | ---ALKAKAK KSTPKK-AKA DG----EAKP KK-SE-AKPK ----KAEAVK | 165 |
| SEQ_ID_NO_102 | -----PKAPA APKPKK-EKK TVAKKKAPKP KV-PA-AKPK -APAAKAAKP | 164 |
| SEQ_ID_NO_150 | ----KEKKAD APKPKT-EKK PA----AKKP KA-PA-AKAP --AKAPSKAS | 163 |
| SEQ_ID_NO_118 | -------ARA APAPAL-AKK PT----IPKP KV-------- --AAKPKTAK | 147 |
| SEQ_ID_NO_145 | ----KPTTAT KPKKTS-AKS TT----VAKP KS-AA-AKPK --STAAKVKK | 152 |
| SEQ_ID_NO_149 | ----KPTPAA KPKSA----- ------AVKP KS-AA-TKLK --SAAKKVKK | 149 |
| SEQ_ID_NO_144 | ---IVHAAPA EPKS------ ------AAGP KK-PA-AVQT --KLKAKAKP | 138 |
| SEQ_ID_NO_125 | -------AAA KPKP------ ------AAKK KPAAK-KKAP --AKKTATKT | 158 |
| SEQ_ID_NO_137 | ----RAPAAA KPKPKS-KTA ------VKKP KA-------- --GAKKPKAA | 148 |
| SEQ_ID_NO_146 | ---TRAPAAA KPKAKP-AAA A-----KPKP KPKAA-AKPK --AAAKPKAK | 161 |
| SEQ_ID_NO_147 | ---TRAPAAA KPKAKP-AAA A-----KPKP KPKAA-AKPK --AAAKPKAK | 161 |
| SEQ_ID_NO_119 | -AKSSAPAKK KPAAAP-AKK KA----AAAP AKKKT-AAAP --KKKAAAAP | 170 |
| SEQ_ID_NO_100 | -RSAATPKPA APVKKK-ATV VA----KPKG KV-AA-AVAP --AKAKAAAK | 171 |
| SEQ_ID_NO_113 | --AAKPAATT KPVNKK-PAA A-----VTKP KG-----KAP --AKAKPAAK | 157 |
| SEQ_ID_NO_104 | -RSSKTATAA SAPAKK-KTA TT----KSKS KP--A-SKPK --EGKSTKAT | 164 |
| SEQ_ID_NO_108 | ---AKSSAPA KPAAASPAKK KTATAAKPKA KSKPAYSKAK ETKSAKSTAK | 173 |
| SEQ_ID_NO_116 | AAPAKKPAAA KPKPKPKAKA PVAKAPAAKS KAKAA-PAKA KAKAKAKAAP | 181 |
| SEQ_ID_NO_117 | -KSSAAKPAK KPAAAK-SKA KPKAKAATKS KAKPA-AKAK --PAAKAKPA | 171 |
| SEQ_ID_NO_122 | -SAAPKAAAT APAKKK-PGA KPKAT-KAKP KPKPK-TVAP --KAKTATKP | 173 |
| SEQ_ID_NO_120 | -AAAAVPAKK KPAAAK-SKP AAKPKAAVKP KAKPA-AKAK --PAAKAKPA | 173 |

Figure 4 (continued)

```
SEQ_ID_NO_101   KTKAPKEKVE RPKKEKKEKV EKKKATPKAE KPKK----AA TPKSAGKKK-   210
SEQ_ID_NO_102   KAAKKAAPAK PAAPAPP--- ------KKEE KPAA-AA-PK KAAPAAKPKK   203
SEQ_ID_NO_150   KPAAPKKAEK PVAPKK---A AAPKKAAKPA APKAAAPKAK KPAAAAKP--   208
SEQ_ID_NO_118   IGAKPKAKAK VAAKTKA--T TKTVA----- ---------- KKIPAAKPKA   180
SEQ_ID_NO_145   A--------- ---------A VKPKPKSAAV KPKAEPA-AP KPKAVSKPKA   183
SEQ_ID_NO_149   AAVKPKPKSA ---------A VKPKAPAVNM KSKP--A-AL KPNTVTKSKT   187
SEQ_ID_NO_144   AAAASKTKAK IATTAKA--K SKHVASTVKP KPKA--A-AA KPRVAPKRKS   183
SEQ_ID_NO_125   KAKAPAKKA- ---------A AKPKA-KAPA KPKA----AA KPKAAAKPKA   193
SEQ_ID_NO_137   TKPKPKAKAK SPAKAKP--A AKPKA-AAKP KPAA-----A KPKAAAKPKA   190
SEQ_ID_NO_146   APAKSKAAAK PKAAAKP--A AKPKAAAKPK SPAK--P-AA KPKAAPKAKA   206
SEQ_ID_NO_147   APAKSKAAAK PKAAAKP--A AKPKAAAKPK SPAK--P-AA KPKAAPKAKA   206
SEQ_ID_NO_119   KKKAPVAKAK PAAKPKAKAV VKPKA-KAAV KPKA-KP-AA KPAAKAKPA-   216
SEQ_ID_NO_100   GTKKPAAKVV AKAKV----T AKPKAKVTAA KPKS-----K SVAAVSKTKA   212
SEQ_ID_NO_113   GAKKPAAAAK PKAKT----T ATTKA-AAKP KPKT-----K SVAAVSKTKA   197
SEQ_ID_NO_104   PKAKAKTKTT SKAKSKP--A AKPKA---TS KAKAAPA-KT KAVASVKPKT   208
SEQ_ID_NO_108   SPAKSKAAAK PKAKPKAA-A AKPKV-TAKA KPKA-AP-AK AKTSVAKPKA   219
SEQ_ID_NO_116   AKAKPAAKAK PAAKAKP--A AKAKP-VAKA KPKAKAP-VA KANAVPVA--   225
SEQ_ID_NO_117   AKAKPAAKAK PAAKAKP--A AKAKPAAKPV KTAAAKP-AA KAKPAAKPKA   218
SEQ_ID_NO_122   KAKQRQVKAK LVAKAKP--A VKPKA----- -----AA-VA MPKAAEKPK-   209
SEQ_ID_NO_120   AKAKPAAKAK PAAKAKP--A AKAKP-VAKA KPKA-AA-AA KPKAAVKPKA   218

SEQ_ID_NO_101   -ATPKPKAAP ---------- ---------K SPAKKDAKPK KATPSKKAAP   240
SEQ_ID_NO_102   -PAAKPKKAA ---------- ---------- ---TPKKPAP KPKPAKKAAT   229
SEQ_ID_NO_150   -AAPKRSST- ---------- ---------- ---RTAAKPA APKAAKKPTP   233
SEQ_ID_NO_118   KTAGKPKTVA ---------- ---------A KPAKVAKTAA VASPGKKKAV   211
SEQ_ID_NO_145   -VAPKPKTAG ---------- ---------- -PAKKAKTSA KPSPSKKAAP   211
SEQ_ID_NO_149   -VALKGKTAG ---------- ---------- RPAKAAKTSV KAAPGKKAAP   216
SEQ_ID_NO_144   PVKPKPKPKP ---------- ---------- RPTRAAKTAA KDSPGKKAAK   213
SEQ_ID_NO_125   KAAAKPKAAA ---------- ------KPKG RPAKAAKTSA KDAPGKKAPA   227
SEQ_ID_NO_137   KPAAKAKPKA -------VAA KPKPAAKKAG RPAKAAKTSA KDTPGKKAAP   233
SEQ_ID_NO_146   KPAAKPKAKA APKPKAAVVT KTKATSAPAR RPAKAAKTSA KDTPSKKAAP   256
SEQ_ID_NO_147   KPAAKPKAKA APKPKAAAVT KTKATSAPAR RPAKAAKTSA KDTPSKKAAP   256
SEQ_ID_NO_119   -AKAKPAAKP ---------- KAK------A KPAKVARTST RTTPGKKAPA   249
SEQ_ID_NO_100   -VAAKPKAKE ---------- ---------- RPAKASRTST RTSPGKKVAA   241
SEQ_ID_NO_113   -VAAKPKAKE ---------- ---------- RPVKASRTST RTSPGKKAAA   226
SEQ_ID_NO_104   TAATKPKAAA ---------- KPK------D KPVKASRTST RTSPGKRAAA   242
SEQ_ID_NO_108   -APAKPKAKE ---------- ---------- RPAKASRTST RTSPGKKAAA   248
SEQ_ID_NO_116   -AKAKPAAKA ---------- KPAAKAKPAA RPAKASRTST RTSPGKRAAA   264
SEQ_ID_NO_117   AAKAKPAAKA ---------- KPAAKAKPAA KPAKAARTST RTSPAAAAAA   258
SEQ_ID_NO_122   -TPVKTKAAA ---------- KP--KAK--E KPAKVARTAT RSTPSRKAAP   244
SEQ_ID_NO_120   -APAKTKAAV ---------- KPNLKAK--T TTAKVAKTAT RTTPSRKAAP   255
```

Figure 5

```
SEQ_ID_NO_164   MENM------ KMNNDERFA- ------QKGV PVHSQVMKIK QESEKIVDWS   37
SEQ_ID_NO_158   MENN------ SSNDDSRGRN GDGDHGYVGF PIHSQVIKIR QEFDKIKHPS   44
SEQ_ID_NO_154   MEQKKISSSS SSNNNAVIRD EDE---YKGV PIHSQVMKIK QEFEKIKHPS   47
SEQ_ID_NO_152   MENK------ TDNGN----- ------EDGP IIHSQVEKIK KEFEKIRQPS   33
SEQ_ID_NO_162   MENK------ TNNGN----- ------EDG- PKHSQVVKIK REFEKISQPS   32

SEQ_ID_NO_164   PGKPEIRSVL REIS-RQISR SPLGISGQPI SVGES   71
SEQ_ID_NO_158   LQQLEVRGVV KCRINRQRSR SPLGLAERPI SVGN-   78
SEQ_ID_NO_154   LQQPDMRRVL REIT-RQRSR SPLGLAERPI SVGNS   81
SEQ_ID_NO_152   LQQPEMRRVL SEIKRRQRSR SPLGLGERSI SVGN-   67
SEQ_ID_NO_162   LKQPEMRRVL SEITRRQRSR SPLGLGERSL SVGH-   66
```

Figure 6

| SEQ_ID_NO_184 | | | | | | 3 |
|---|---|---|---|---|---|---|
| SEQ_ID_NO_168 | | | | MG | LSL PTQVLQG | LLGEFHRRL | 22 |
| SEQ_ID_NO_177 | | | | MS | YPRRTL H-- | ---------- | 10 |
| SEQ_ID_NO_181 | | | | ME | TPLRMPHMST | CSNVAPAP-- | 20 |
| SEQ_ID_NO_182 | | | | MG | MSPHDQHEHE | PDHAHRSP-- | 20 |
| SEQ_ID_NO_183 | | | | MA | MSPHDQHEHE | PDHAHRSP-- | 20 |
| SEQ_ID_NO_170 | | | | MA | PAPLEAEAAA | ANSHLSP--- | 20 |
| SEQ_ID_NO_166 | | | | MR | VAEAA----- | ---------- | 9 |
| SEQ_ID_NO_174 | MWMMI SQEGQ | RSNPII YHNN | I HLLCEVDQK | MR | REKASVIVLK | IQTKHPNPES | 50 |

| SEQ_ID_NO_184 | --SSLP---- | GPSEGMLCVI | -------- | TALSISFKG | IVRSVLHVLG | 40 |
|---|---|---|---|---|---|---|
| SEQ_ID_NO_168 | LLTPL----- | PPSSELHHNS | SDLYTRNNSF | DANIVMVLSV | LLCALICSLG | 70 |
| SEQ_ID_NO_177 | TPFSGHPS-- | GPSCPLDGAT | A---LDGSNF | DANVVMILAV | LLCALICALG | 55 |
| SEQ_ID_NO_181 | APEAPRAP-- | PSSPL----- | ------LVN- | DYDVVVILAA | MLCALVCALG | 53 |
| SEQ_ID_NO_182 | SNGT------ | AATSTIATNR | WGPYSGAGDF | ASNMAVILAA | LLAALALALA | 64 |
| SEQ_ID_NO_183 | SNGT------ | AATSTIATNR | WGPYSGAGDF | ASNMAVILAA | LLAALALALA | 64 |
| SEQ_ID_NO_170 | --PFLHSRAP | SCDPQVHSCK | MKPYSNSNDF | GANTAMILII | LLCALICALV | 68 |
| SEQ_ID_NO_166 | -SPLSSFAA- | TPTCNSHTCR | MKPYSNSSEF | TANASVLLIL | VISALICALS | 56 |
| SEQ_ID_NO_174 | FKTSLEPISP | PLSPHSLCIR | --------L | QANASVLLIL | FVSALICGLS | 99 |

| SEQ_ID_NO_184 | RLSQSSSSP | SSVTIASSEIP | ASEPFDFRVS | HPESFLEEFR | NKTPTLRYES | 90 |
|---|---|---|---|---|---|---|
| SEQ_ID_NO_168 | LNSIRCALR | CSSLIASESG | ATTSSRLANK | GVKRKAL--- | KTFPTVNYS- | 116 |
| SEQ_ID_NO_177 | LNSIVRCALR | CSSRVVGPE | PNQVTRLVQS | GLRKAL---- | RAMPVLVYS- | 101 |
| SEQ_ID_NO_181 | LNSMLQCEVR | CTRRAVADPV | GWVAHRRASA | GLKREDV--- | VALPVVEYS- | 99 |
| SEQ_ID_NO_182 | LNAAVRYLLR | RHRRAROOPA | AAAAAEDPE | KPPVQEADPP | PPPPALVYSA | 114 |
| SEQ_ID_NO_183 | LNAAVRYLLR | RHRRAROOPA | AAAAAEDPE | KPPVQEADPP | PPPPALVYSA | 114 |
| SEQ_ID_NO_170 | -NTAIRMFLR | SNNNSSDRL | GELEEQRKPK | --DEADMATLL | VLATTQVYS- | 115 |
| SEQ_ID_NO_166 | LYAAIRCFLR | --PT------ | LETEDDHKPD | --PEAAASST | PTIPTLVYS- | 95 |
| SEQ_ID_NO_174 | LCAAIRCFLR | PN-------- | QTDDNEHKPD | --PEEDVSSI | VPTIPTLVYS- | 139 |

| SEQ_ID_NO_184 | LCRCKKHEDN | ECSVCLSKFE | EDSEINKLK- | GHL------- | FHKTCLEKW- | 132 |
|---|---|---|---|---|---|---|
| SEQ_ID_NO_168 | ADLKLPGLDS | ECLCLSDFT | AGDRVRLLPK | NHG------- | FHVRCIDKW- | 159 |
| SEQ_ID_NO_177 | PGLRINAANP | TCAICLSDFE | AGEHVRVLPV | NHG------- | FHVRCIDRW- | 141 |
| SEQ_ID_NO_181 | -ASPPAAAAA | GCAICLSDFA | DGERMRVLPV | GHR------- | FHVCIDRW- | 163 |
| SEQ_ID_NO_182 | AGTKLAGALA | ECAICLAEFV | DGDTVRVMPC | WCQEIPLESG | LRFAQIKVYQ | 156 |
| SEQ_ID_NO_183 | AGTKLAGALA | ECAICLAEFV | DGDTVRVMPV | GHG------- | FHARCIERW- | 158 |
| SEQ_ID_NO_170 | AGMKLGVEA | DCAICLSEFV | EGEGIRVLGR | QHG------- | FHVLCIEKW- | 138 |
| SEQ_ID_NO_166 | SDLELAGAEA | ECAICLSEFE | QGESIQVLEK | QHG------- | FHVKCIHKW- | 182 |
| SEQ_ID_NO_174 | SDLELAGAQA | ECAICLSEFE | PIGESIHVLEK | HHG------- | FHIKCIHKW- | 182 |

Figure 6 (continued)

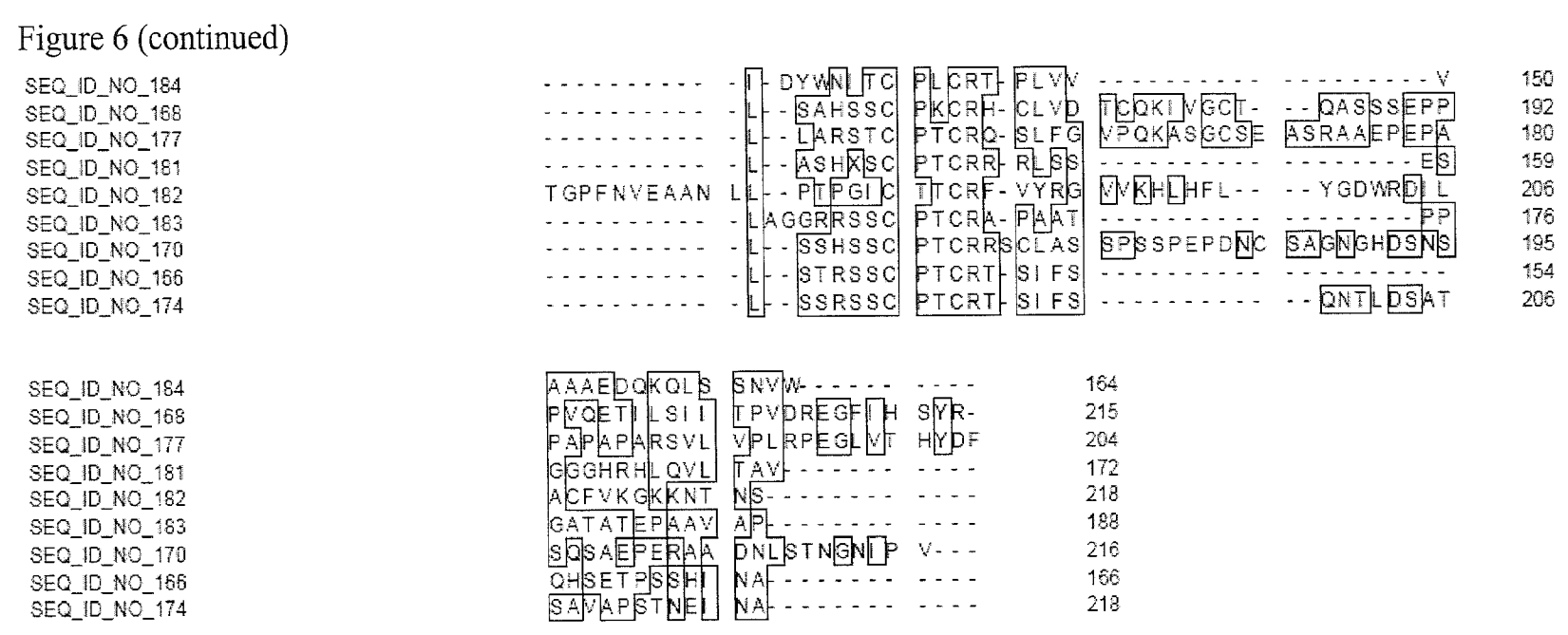

```
SEQ_ID_NO_184  ---------- -I-DYWNLTC PLCRT-PLVV ---------- ---------V  150
SEQ_ID_NO_168  ---------- -L--SAHSSC PKCRH-CLVD TCQKIVGCT- --QASSSEPP  192
SEQ_ID_NO_177  ---------- -L--LARSTC PTCRQ-SLFG VPQKASGCSE ASRAAEPEPA  180
SEQ_ID_NO_181  ---------- -L--ASHXSC PTCRR-RLSS ---------- --------ES  159
SEQ_ID_NO_182  TGPFNVEAAN LL--PTPGIC TTCRF-VYRG VVKHLHFL-- --YGDWRDLL  206
SEQ_ID_NO_183  ---------- -LAGGRRSSC PTCRA-PAAT ---------- --------PP  176
SEQ_ID_NO_170  ---------- -L--SSHSSC PTCRRSCLAS SPSSPEPDNC SAGNGHDSNS  195
SEQ_ID_NO_166  ---------- -L--STRSSC PTCRT-SIFS ---------- ----------  154
SEQ_ID_NO_174  ---------- -L--SSRSSC PTCRT-SIFS ---------- --QNTLDSAT  206

SEQ_ID_NO_184  AAAEDQKQLS SNVW------ ----  164
SEQ_ID_NO_168  PVQETILSII TPVDREGFIH SYR-  215
SEQ_ID_NO_177  PAPAPARSVL VPLRPEGLVT HYDF  204
SEQ_ID_NO_181  GGGHRHLQVL TAV------- ----  172
SEQ_ID_NO_182  ACFVKGKKNT NS-------- ----  218
SEQ_ID_NO_183  GATATEPAAV AP-------- ----  188
SEQ_ID_NO_170  SQSAEPERAA DNLSTNGNIP V---  216
SEQ_ID_NO_166  QHSETPSSHI NA-------- ----  166
SEQ_ID_NO_174  SAVAPSTNEI NA-------- ----  218
```

Figure 7

```
SEQ_ID_NO_194   MLKSKKSCREE MRSSSIAYK- YHCLTNGGTP EAVAAPSPTN PQLPVMLRSY   49
SEQ_ID_NO_199   -MAAADYDRA YRPYAPSSAA DYDRPYRNE- ---------- ------IVPY   32
SEQ_ID_NO_204   -MAAADADYE YRAYG-APA- DHDRPYHG-- ---------- RE----VVPY   31
SEQ_ID_NO_186   ---MANYYE- -PPAS-GNRR DAVKGYNS-- -G-------- ---------SF   25
SEQ_ID_NO_201   ---MD--RS- -KSYA-GGR- MQIEPYYD-- -G----GGAR PD----FRSY   30
SEQ_ID_NO_203   ---MDDFRS- -RSFN-DGK- MQLEVYGGRR SGAVPAPPVL HD----YRSY   39
SEQ_ID_NO_188   ---MEHFRS- -KSCR-EGR- IEMEGYDEDK AA----PTNM QD----LRSY   35
SEQ_ID_NO_196   ---MEEFRS- -KSYG-DGR- MQIEAYRG-- -------ANI QD----LRCY   30
SEQ_ID_NO_197   ---MEDYNKQ IRPYG-NSQM MQMEGYYG-- -A----TNPN YD----LRSY   35
SEQ_ID_NO_193   ---MEDYNRQ -RAYG-DTG- MQIQPYHG-- -G----GPGT GD----FRXY   33

SEQ_ID_NO_194   S--------- TSTYS----- ---------- ----PHKNPT TVRDNPNS-K   70
SEQ_ID_NO_199   G--------- DRRIDLVVKP PPP------- ----TRSPPP PLPVTKSG--   60
SEQ_ID_NO_204   G--------- DRRIDVVVKP PGTTTTTT-- ----TRSPPP PLPVTKVG-G   65
SEQ_ID_NO_186   D--------- DSSGDQSQ-- ---------- ----TNDYQL KIKKSKSVPN   50
SEQ_ID_NO_201   SYSAGGSGMG TSSYAYQYEY S--------- ----GAGAGE EMKRSKS---   64
SEQ_ID_NO_203   S--------- -ASYFYTYD- ---------- ----GSGVGY GDFKGKPDHG   64
SEQ_ID_NO_188   S--------- -VSYAVSVQP N--------- ----QSGKEG KMKKGKSN--   60
SEQ_ID_NO_196   S--------- -ASYASSVHP TTTTTTTTQT QMGGNNNNEA KFKKGKST--   68
SEQ_ID_NO_197   S--------- DFSYAQTQRG ---------- ----PNNKDL KLKKGKSI-S   61
SEQ_ID_NO_193   S--------- -TSYA----- ---------- ----TENNIX NIKKEKSI--   52

SEQ_ID_NO_194   SNGKVKKGL- --KEAEIQRK KRVAAYNVYG VEGKVKGSIR KNFKWEKETC   117
SEQ_ID_NO_199   GGGGIGSAWC F-SDPEVKRR RRVASYKAYS VEGKVKASFR RGFRWIKDKC   109
SEQ_ID_NO_204   GGGGMGSAWC F-SDPEMKRR RRVASYKAYS VEGKVKSSLR RGFRWIKAKC   114
SEQ_ID_NO_186   ADRAASRSWS F-SDPESRRK RRVAGYKVYS VEQKMKGSIR KSFKWFKD--   97
SEQ_ID_NO_201   -----KRRWL ALADPDMERK RRVAAYKAYG VEGKMKGSFR KSFKWIKDRY   109
SEQ_ID_NO_203   SSASNKGGRV F-KDPEFQRK RRVASYKAYA VEGKVKGSLR RSLRWFKDKY   113
SEQ_ID_NO_188   -LESSSKSWS F-NDPELQRK RRVANYKVYA IEGKMKGSLR KSFRWIKDTC   108
SEQ_ID_NO_196   -NGSTSKSWS F-SDPELQRK KRVASYKVYA VEGKLKGSLR KSFKWLKDRC   116
SEQ_ID_NO_197   SRSSISKSWS FGDDPEFQRK KRVASYKMYS VEGKVKGSFR KSFKWLKNRY   111
SEQ_ID_NO_193   ---ARSKSWG I-TDPELQRK KRVASYKMYS VEGKVKGSFR KSFRWLKQRY   98
```

Figure 7 (continued)

| | | | | | |
|---|---|---|---|---|---|
| SEQ_ID_NO_194 | SNAVNGLW- - | - - - - - - - - - - | - - - - - - - - - - | - | 125 |
| SEQ_ID_NO_199 | TGFI HG- - - - | - - - - - - - - - - | - - - - - - - - - - | - | 115 |
| SEQ_ID_NO_204 | SELI HGWYGS | LLLPLSFSLD | DFIITSKQAL | S | 145 |
| SEQ_ID_NO_186 | - - - I I GI S- - | - - - - - - - - - - | - - - - - - - - - - | - | 102 |
| SEQ_ID_NO_201 | LNLVYGWS- - | - - - - - - - - - - | - - - - - - - - - - | - | 117 |
| SEQ_ID_NO_203 | TRAVYGWW- - | - - - - - - - - - - | - - - - - - - - - - | - | 121 |
| SEQ_ID_NO_188 | TQVVYGWR- - | - - - - - - - - - - | - - - - - - - - - - | - | 116 |
| SEQ_ID_NO_196 | NRVVYG- - - - | - - - - - - - - - - | - - - - - - - - - - | - | 122 |
| SEQ_ID_NO_197 | WHVVYSLW- - | - - - - - - - - - - | - - - - - - - - - - | - | 119 |
| SEQ_ID_NO_193 | TQVVYGWW- - | - - - - - - - - - - | - - - - - - - - - - | - | 106 |

Figure 8

```
SEQ_ID_NO_216    MGKGEAWWNG QRIGRYWPTY VASDASCTDS CNYRGPYSAS KCRKNCEKPS    50
SEQ_ID_NO_208    ---------- ---------- -----METLQ CRHQHVFIL- ---------L    15
SEQ_ID_NO_214    ---------- ---------- ----MDTTHS CRRG--YIL- ---------L    14

SEQ_ID_NO_216    QTLYHVPRSW LKPSGNILVL FEERGGDPTQ ISIVTKQTES LCAHVSDSHP    100
SEQ_ID_NO_208    LVLFHS--SL FVLASKIDVS DDARGIRIDG ---GQKRFLT NSPQHGKEHA    60
SEQ_ID_NO_214    LVLSYS--SV FGLASNMSIS NDTSGNKTDS FFESQSTSTE WGTDMGDKYI    62

SEQ_ID_NO_216    PPVDLWNSET ESGRKVGPVL SLTCPHDNQV ISSIKFASYG TPLGTCGNFY    150
SEQ_ID_NO_208    -------ACT NEEPDLGPLT RISCNEPEYV LTKINFADYG NPTGTCGHFR    103
SEQ_ID_NO_214    -------MCT ESNMEIPWM- -ISCKKSKEV FTRINFADYG NPSGKCEHYR    103

SEQ_ID_NO_216    HGRCSSNKAL SIVQKACIGS SSCSVGVSSD TFGDP-CRGM AKSLAVEATC    199
SEQ_ID_NO_208    RDNCGARATM RIVKKNCLGK EKCHLLVTDE MFGPSKCKGA PM-LAVETTC    152
SEQ_ID_NO_214    HGNCGAKTTM EVAKKNCLGK HQCVFKVSDE MFGTSHCKKE AK-FFVQLTC    152

SEQ_ID_NO_216    A--    200
SEQ_ID_NO_208    TIA    155
SEQ_ID_NO_214    TKA    155
```

Figure 9 (continued)

```
SEQ_ID_NO_218    ---------- ---------S VVYLIAVMLG MTGDIN-IW 158
SEQ_ID_NO_225    ---------- ---------S VVYLIAVMLG MAGNININIW 143
SEQ_ID_NO_227    ---------- ---------A ILATIAVILG VTKGAE-DW 156
SEQ_ID_NO_220    ---------- ---------A VLATIAIILG VTKGID-D- 153
SEQ_ID_NO_222    VEHECHIEIR CLLHNLCVKA ILATIAIILG ATKGAD-EW 180
SEQ_ID_NO_231    ---------- ---------A SLAAIAILLG VTRGEE-IW 185
SEQ_ID_NO_230    ---------- ---------A VIAAIVIPLG LTKGAH-VW 189
SEQ_ID_NO_229    ---------- ---------F LLIQCNLTVY FTSGI---- 174
SEQ_ID_NO_1052   ---------- ---------A VVAAVAILLG VTKGTH-VW 174
```

Figure 10

```
SEQ_ID_NO_244   MEYQRTNNLS LAFQFFRKAF EMCDSDPLLF NEYGVLRYRQ G-NYEEAVEN  49
SEQ_ID_NO_234   MEYMRTHSYK LADQFFMQAK AICPSDPLVY NELGVVAYHM K-EYGKAVRW  49
SEQ_ID_NO_236   MEYMRTHSYK LAEQFFMQAK TICPSDPLVY NELGVVAYNM K-EYNKAVLW  49
SEQ_ID_NO_241   MQYVRMHNFK LAEQFFTQAK SICPSDPLIH NELGVVAYNM KEEYQKAVSY  50
SEQ_ID_NO_242   MQYLRMHNFK LAEQFFTQAK SICPSDPLIY NEMGVVAYNM K-EYQKAVQW  49

SEQ_ID_NO_244   FERALDLAPK PVGSRWESLI VNLAQAFRKI GRYDEAIATF QSALLISPRN  99
SEQ_ID_NO_234   FEKTLAHIPS ALTESWEPTV VNLAHAYRKL RKDREAISYY ERALTLSTKS  99
SEQ_ID_NO_236   FEKTLKHIPS -LSQLWEPTV INLAHAYRKL KIYHEAISCY ERALALSTRS  98
SEQ_ID_NO_241   YAKALTFPTK SLS-----AF AGLAYTYHLM DDFEAAINYY HKALWLKPDD  95
SEQ_ID_NO_242   FELTLEHTSS SLNEMWEPTL VNLGHALRKL KKYQKAISYY EKALTFQTKS  99

SEQ_ID_NO_244   ASTYAALAFT YQMKSRCSEP VSLGLAIEYY HKALSLRADD AFSQHHLELA  149
SEQ_ID_NO_234   LSTYSGLAYT YHLQGNFS-- ----AAISYY HKALWLKPDD QFCTEMLNVA  143
SEQ_ID_NO_236   LSTYAGLAYT YHLQDNFT-- ----AAITCY HKALWLKPDD QFCTEMLSLA  142
SEQ_ID_NO_241   QFCTDMLTYA LESICQIT-- ---------- ---------- ---------A  114
SEQ_ID_NO_242   LSAFAGLAYT YHLMAMYH-- ----V----- HRA------- ----EVLQIL  127

SEQ_ID_NO_244   LIDQSAITIP RHQQVEWDTM FPKVEDINAV TPTFGIASSP QGGILFPTPS  199
SEQ_ID_NO_234   LMDE------ ---------- ---------- ---------- ----------  147
SEQ_ID_NO_236   LVDE------ ---------- ---------- ---------- ----------  146
SEQ_ID_NO_241   RRKP------ ---------- ---------- ---------- ----------  118
SEQ_ID_NO_242   TKEP------ ---------- ---------- ---------- ----------  131

SEQ_ID_NO_244   PHSFQGTPTF GQTPFSARVD RMDESVDMDQ SVDMDESE  237
SEQ_ID_NO_234   ---------- CQNGVDSKV- ---------- -----ELC  159
SEQ_ID_NO_236   ---------- GRRGIDPKI- ---------- -----EFR  158
SEQ_ID_NO_241   ---------- GRGLLTATGG ---------- -----VTC  131
SEQ_ID_NO_242   ---------- GR-------- ---------- --------  133
```

Figure 11 (continued)

```
SEQ_ID_NO_268   HACTFDFKKS  DREKI AKENP  LI VAPK TKF    224
SEQ_ID_NO_298   HACDFDFKAA  GREKI AKNNP  LVVAAK NKI     193
SEQ_ID_NO_260   HECSFDFKEV  GRGAI AKANP  VVKADKVQRI     175
SEQ_ID_NO_249   TCLCF-----  ----------  ----------     137
SEQ_ID_NO_255   HDCEFDFKSL  GKEQI AKANP  VVKGEKLQRI     159
SEQ_ID_NO_265   HGCGFDFKGM  GREEI KKANP  VVKGEKLNKI     170
SEQ_ID_NO_262   HACGFDFKAV  GREEI ARANP  VI KGEKLRRI    164
SEQ_ID_NO_251   HGCTFDFKKV  GREEI ARANP  LVKAEKLEKI     161
SEQ_ID_NO_246   HGCTFDFKSA  GREEI AKANP  LVI AAKLQKI    161
SEQ_ID_NO_274   HGCTFDFKSA  GREEI AKANP  LVVAAKLQKI     160
SEQ_ID_NO_248   HDCSFDYKAA  GRESI ARQNP  VVKAAK IRL     170
SEQ_ID_NO_279   HQCTFDYKKV  AREQI AKQNP  VVMAEK NKI     163
SEQ_ID_NO_296   HECTFDYKKV  AREQI AKQNP  VVI AEK NKI    159
SEQ_ID_NO_270   HNCSFDYHVA  AQEAI AKANP  VVKADKLDKI     166
SEQ_ID_NO_287   HDCPFDYRSA  AQDAI AKANP  VVKAEKLDKL     173
SEQ_ID_NO_277   HDCPYDYHTA  ARDVI AKANP  VVKADKLEKI     173
SEQ_ID_NO_286   HDCQFDYRTA  ARDAI AKANP  VVKAEKLDKI     171
SEQ_ID_NO_290   HDCQFDYRTA  ARDAI AKANP  VVKAEKLDKI     171
```

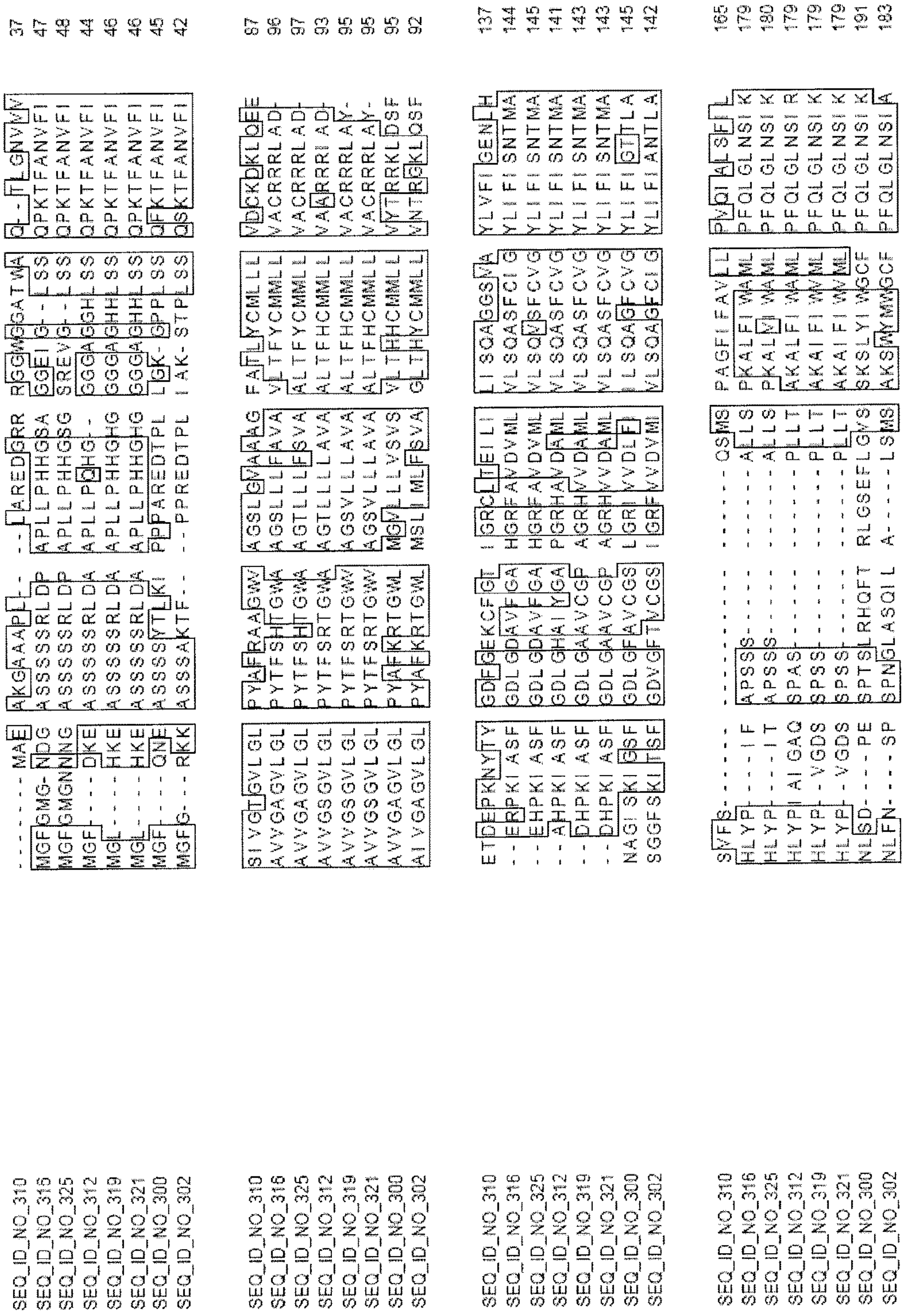

Figure 12

| | | | | | | |
|---|---|---|---|---|---|---|
| SEQ_ID_NO_310 | - - - - - - | - - - - - - | - - - - - - | - - MAE | AKGAAAPL - | - - - - - - AREDGRR | RGGWGGATWA | QL - TLGNVW | 37 |
| SEQ_ID_NO_316 | MGFGMG- | NDG | ASSSSSRLDP | APLLPHHGSA | GGEIG - - LSS | QPKTFANVFI | 47 |
| SEQ_ID_NO_325 | MGFGMGN | NNG | ASSSSSRLDP | APLLPHHGSG | SREVG - - LSS | QPKTFANVFI | 48 |
| SEQ_ID_NO_312 | MGFL - - - | DKE | ASSSSSRLDA | APLLPQHG - | GGGAGHHLSS | QPKTFANVFI | 44 |
| SEQ_ID_NO_319 | MGL - - - - | HKE | ASSSSSRLDA | APLLPHHGHG | GGGAGHHLSS | QPKTFANVFI | 46 |
| SEQ_ID_NO_321 | MGFL - - - | HKE | ASSSSSRLDA | APLLPHHGHG | GGGAGHHLSS | QFKTFANVFI | 46 |
| SEQ_ID_NO_300 | MGFL - - - | QNE | ASSSSSVTLKI | PPAREDTPL | LGK- GPPLSS | QSKTFANVFI | 45 |
| SEQ_ID_NO_302 | MGFG - - - | RKK | ASSSAKTF - - | - PPREDTPL | IAK- STPLSS | QSKTFANVFI | 42 |

| SEQ_ID_NO_310 | SIVGTGVLGL | PYAFRAAGWV | AGSLGVAAAG | FATLYCMLL | VDCKDKLQEE | 87 |
| SEQ_ID_NO_316 | AVVGAGVLGL | PYTFSHTGWA | AGSLLLLFSVA | VLTFYCMMLL | VACRRRLAD- | 96 |
| SEQ_ID_NO_325 | AVVGAGVLGL | PYTFSHTGWA | AGTLLLLFSVA | ALTFYCMMLL | VACRRRLAD- | 97 |
| SEQ_ID_NO_312 | AVVGSGVLGL | PYTFSRTGWA | AGTLLLLAVA | ALTFHCMMLL | VAARRRIAD- | 93 |
| SEQ_ID_NO_319 | AVVGSGVLGL | PYTFSRTGWV | AGSVLLLAVA | ALTFHCMMLL | VACRRRLAY- | 95 |
| SEQ_ID_NO_321 | AVVGSGVLGL | PYTFSRTGWV | AGSVLLLAVA | ALTFHCMMLL | VACRRRLAY- | 95 |
| SEQ_ID_NO_300 | AVVGAGVLGL | PYAFKRTGWL | MGVLLLVSVS | VLTHCMMLL | VYTRRKLDSF | 95 |
| SEQ_ID_NO_302 | AIVGAGVLGL | PYAFKRTGWL | MSLIMLFSVA | GLTHYCMMLL | VNTRGKLQSF | 92 |

| SEQ_ID_NO_310 | ETDEPKNYTY | GDFGEKCFGI | IGRCLTEIL | LISQAGGSVA | YLVFIGENH | 137 |
| SEQ_ID_NO_316 | - ERPKIASF | GDLGDAVFGA | HGRFAVDVML | VLSQASFCIG | YLIFISNTMA | 144 |
| SEQ_ID_NO_325 | EHPKIASF | GDLGDAVFGA | HGRFAVDVML | VLSQSFCVG | YLIFISNTMA | 145 |
| SEQ_ID_NO_312 | - AHPKIASF | GDLGHAIYGA | PGRHAVDAML | VLSQASFCVG | YLIFISNTMA | 141 |
| SEQ_ID_NO_319 | DHPKIASF | GDLGAAVCGP | AGRHVVDAML | VLSQASFCVG | YLIFISNTMA | 143 |
| SEQ_ID_NO_321 | DHPKIASF | GDLGFAVCGS | LGRIVVDLE | VLSQAGFCVG | YLIFIGTTLA | 143 |
| SEQ_ID_NO_300 | NAGISKIGSF | GDVGFTVCGS | IGRFVVDVMI | VLSQAGFCIG | YLIFIANTLA | 145 |
| SEQ_ID_NO_302 | SGGFSKITSF | | | | | 142 |

| SEQ_ID_NO_310 | SVFS - - - | - - - - - - | - - - QSMS | PAGFIFAVL | PVQIALSFI | 165 |
| SEQ_ID_NO_316 | HLYPI - - IF | APSSS- - - | - ALLS | PKALFIWAML | PFQLGLNSIK | 179 |
| SEQ_ID_NO_325 | HLYPI - - IT | APSSS- - - | - ALLS | PKALVIWAML | PFQLGLNSIK | 180 |
| SEQ_ID_NO_312 | HLYPIAIGAQ | SPAS - - - | - PLLT | AKAIFIWAML | PFQLGLNSIR | 179 |
| SEQ_ID_NO_319 | HLYPI - VGDS | SPSS - - - | - PLLT | AKAIFIWVML | PFQLGLNSIK | 179 |
| SEQ_ID_NO_321 | HLYPI - VGDS | SPSS - - - | - PLLT | AKAIFIWVML | PFQLGLNSIK | 179 |
| SEQ_ID_NO_300 | NLSD- - - PE | SPTSLRHQFT | RLGSEFLGVS | SKSLYIWGCF | PFQLGLNSIK | 191 |
| SEQ_ID_NO_302 | NLFN - - - SP | SPNGLASQIL | A- - - - - | AKSMYMXMGCF | PFQLGLNSIA | 183 |

Figure 12 (continued)

```
SEQ_ID_NO_310   SLSSLSPFSI FADVCNVLAA AVVIRKDLQL IDHPFANRSA FNGVLAIPFA   215
SEQ_ID_NO_316   TLTLLAPLSI FADVVDLGAM GVVLGQDVAA WLAMPPPVVA FGGPAALLYG   229
SEQ_ID_NO_325   TLTLLAPLSI FADVVDLGAM GVVLGQDVAA WVAKPVPVAA FGGPAALLYG   230
SEQ_ID_NO_312   TLTLLAPLSI FADVVDLGAM GVVLGQDASV WLADRPPVFA FAGPAQLLYG   229
SEQ_ID_NO_319   TLTLLAPLSI FADVVDLGAM GVVLGQDVST WLANKPPVFA SAGPTEILYG   229
SEQ_ID_NO_321   TLTLLAPLSI FADVVDLGAM GVVLGQDVST WLANKPPVFA SAGPTEILYG   229
SEQ_ID_NO_300   TLTHLAPLSI FADIVDLGAM AVVIVEDSMI ILKQRPDVVA FGGMSLFLYG   241
SEQ_ID_NO_302   TLTHLAPLSI FADVVDLAAM GVVIVKDVFI MMENRAEVRA FGGLSVFFYG   233

SEQ_ID_NO_310   FGVAVFCFEG FSMTLALESS MAERRKFRWW LSQAVVGILV VYACFGVCGY   265
SEQ_ID_NO_316   LGVSVYAFEG VGMVLPLEAE AANKRKFGVT LGLSMAFIAV MYGLFGVMGY   279
SEQ_ID_NO_325   LGVSVYAFEG VGMVLPLEAE AANKKKFGVT LGLSMAFIAV MYGLFGVMGY   280
SEQ_ID_NO_312   LGVAVYAFEG IGMVLPLEAE AADKRRFGAT LALSMAFIAV MYGLFGAMGY   279
SEQ_ID_NO_319   LGVAVYAFEG IGMVLPLEAE AADKRKFGGT LALSMAFIAV MYGLFGAMGY   279
SEQ_ID_NO_321   LGVAVYAFEG IGMVLPLEAE AADKRKFGGT LALSMAFIAV MYGLFGAMGY   279
SEQ_ID_NO_300   MGVAVYSFEG VGMVLPLESE MKDKDKFGKV LALGMGFISL IYIAFGILGY   291
SEQ_ID_NO_302   MGVAVYAFEG IGMVLPIESE MREREKFGRI LGLSMGLISV IYGAFGVLGY   283

SEQ_ID_NO_310   LAYGEATKDI ITLNLPNSMS SAAVKVGLCI ALAFTFPVMM HPIHEIVETR   315
SEQ_ID_NO_316   VAFGDATRDI ITTNLGAGWL SAAVQLGLCI NLFFTMPVMM NPVYEVAERL   329
SEQ_ID_NO_325   VAFGDATRDI ITTNLGAGWL SAAVQLGLCI NLFFTMPVMM NPVYEVAERL   330
SEQ_ID_NO_312   LAFGAATRDI ITTNLGTGWL SVLVQLGLCI NLFFTMPVMM NPVYEVAERL   329
SEQ_ID_NO_319   LAFGAATRDI ITTNLGTGWL SVAVQLGLCI NLFFTMPVMM NPVYEVAERL   329
SEQ_ID_NO_321   LAFGAATRDI ITTNLGTGWL SVTVQLGLCI NLFFTMPVMM NPVYEVAERL   329
SEQ_ID_NO_300   LAFGEDTMDI ITANLGAGLV STVVQLGLCI NLFFTFPLMM NPVFEIVERR   341
SEQ_ID_NO_302   FAFGNDTQDI ITANLGPGLI SLLVQLGLCI NLFFTFPLMM NPVYEILERR   333

SEQ_ID_NO_310   LRSSGCFQKL SHGVPGAEWL GLHSSRLIMV TILTVMASCI PAFGSFVSFV   365
SEQ_ID_NO_316   L--------- -HGKRYCWWL -----RWLLV VVVGLAAMYV PNFTDFLALV   364
SEQ_ID_NO_325   L--------- -HGKRYCWWL -----RWLLV IVVGLAAMYV PNFTDFLALV   365
SEQ_ID_NO_312   L--------- -CGKRYAWWL -----RWILV VLVGLLAMLV PNFADFLSLV   364
SEQ_ID_NO_319   L--------- -CRKRYAWWL -----RWLLV MVVGLMAMLV PNFADFLSLV   364
SEQ_ID_NO_321   L--------- -CRKRYAWWL -----RWLLV MVVGLMAMLV PNFADFLSLV   364
SEQ_ID_NO_300   F--------- -SRGMYSAWL -----RWVLV LAVTLVALFV PNFADFLSLV   376
SEQ_ID_NO_302   F--------- -WGGRYCLWL -----RWVSV LLVTLVALMV PNFADFMSLV   368
```

Figure 12 (continued)

```
SEQ_ID_NO_310    GCTVCALLSF VLPTFFHLNI VGSSMSLWRR VLDYGFLLFG LGFAGYGLFT    415
SEQ_ID_NO_316    GSSVCVLLGF VLPASFHLKV FGAEMAWPGV LSDALLVVLG LALAVFGTYT    414
SEQ_ID_NO_325    GSSVCVLLGF VLPASFHLKV FGGEMEWPGV VSDVLLVVIG LSLAVFGTYT    415
SEQ_ID_NO_312    GSSVCVVLGF VLPAVFHLKV FGTEIGWAGL VADVAIIVTG IALAVSGTWT    414
SEQ_ID_NO_319    GSSVCVLLGF VLPAAFHLKV FGAEVGWPGL AGDVAVIVVG TALAVSGTWT    414
SEQ_ID_NO_321    GSSVCVLLGF VLPAAFHLKV FGAEVGWPGL AGDVAVIVVG TALAVSGTWT    414
SEQ_ID_NO_300    GSSTCCVLGF VLPALFHLLV FKEEMGWLQW SSDTAIVVLG VVLAVSGTWS    426
SEQ_ID_NO_302    GSSVCCGLGF VLPALFHLLV FKEEMSWKGW SIDVGIVALG LVLAVSGTWY    418

SEQ_ID_NO_310    ALSSH----- -    420
SEQ_ID_NO_316    SLLQIFHSSS A    425
SEQ_ID_NO_325    SLLQIFHSSS A    426
SEQ_ID_NO_312    SLVQIFSSSD L    425
SEQ_ID_NO_319    SLAQIFSSSD V    425
SEQ_ID_NO_321    SLAQIFSSSD V    425
SEQ_ID_NO_300    SLSEIFSVKV -    436
SEQ_ID_NO_302    ALMEIFAVKV -    428
```

Figure 13 (continued)

```
SEQ_ID_NO_366    PGWLPIIGH- -LHLIK-NPL HRTLYDCSQK LGSIFSVWFG --SRLVVVVS   84
SEQ_ID_NO_348    PGWLPVIGH- -AHLMK-NLL HRTLYDFSQK LGPIFSIRFG --SRLVVVVS   84
SEQ_ID_NO_365    PGWLPVIGH- -VHLMK-NLL HRTLYDFSQK LGPIFSLRFG --TRLVVVVS   84
SEQ_ID_NO_346    -RGWPVIGA- -LPLLG-AMP HVSLAKMAKK YGAIMYLKVG --TCGMVVAS   81
SEQ_ID_NO_2546   -PALPFIGH- -LHILG-SLW HQSFQKLALR YGPFMLIHAG --ASTSYVVS   91
SEQ_ID_NO_332    ---------- ---------- ---------- ---------- ----------    0
SEQ_ID_NO_338    -PSLPIIGH- -LHHLLSLFM HRSLQKLSSK YGPLLYLHVF --NVPILLVS   88
SEQ_ID_NO_341    -PSIPLLGH- -LHHLT-PSL YKSLYTLSSK HGPLLLLRLG PSRRLLLLVS   78
SEQ_ID_NO_2549   -PALPIIGHL RLHFLS-SSI YKSFHSLSTQ YGPLLYLHFG --ASRCLLVS   90
SEQ_ID_NO_2544   KPRLPLIGH- -LHLLKDQLL HHSLIDLSKR YGPLYSLYFG --SMPTVVAS   84
SEQ_ID_NO_2541   KPRLPFIGH- -LHLLKDKLL HYALIDLSKK HGPLFSLYFG --SMPTVVAS   84
SEQ_ID_NO_358    KPRLPFIGH- -LHLLKDKLL HYALIDLSKK HGPLFSLYFG --SMPTVVAS   84
SEQ_ID_NO_360    KPRLPFIGH- -LHLLKDKLL HYALIDLSKK HGPLFSLYFG --SMPTVVAS   84
SEQ_ID_NO_339    KPRLPFVGH- -LHLLDHPLL HQSLIRLGER YGPLYSLYFG --SMPTIVAS   85
SEQ_ID_NO_2550   KPRLPFVGH- -LHLLDQPLL HHSLIKLGER YGPLYSLYFG --SMPTVVAS   84
SEQ_ID_NO_2543   PISFPILGH- -APYLR-SLL HKSLYKLSNR YGPLMHIMLG --SQHVVVAS   82
SEQ_ID_NO_2551   PISLPLIGH- -APYLR-SLL HQALYKLSTR YGPLMHVLIG --SQHVIVAS   82
SEQ_ID_NO_2548   -LALPVLGH- -FHLLA-PLP HQALHRLASR HGPLLYLRLG --SMPAIAAC   91
SEQ_ID_NO_353    -FGLPILGH- -LHLLA-PLP HQALHRLAAR HGPLLFLRLG --SVPCVAAC   88
SEQ_ID_NO_354    -FGLPILGH- -LHLLA-PLP HQALHRLAAR HGPLLFLRLG --SVPCVAAC   89
SEQ_ID_NO_334    -LALPIIGH- -LHLLA-PIP HQALHKLSTR YGPLIHLFLG --SVPCVVAS   82
SEQ_ID_NO_356    FFRLPIIGH- -MHMLG-PLL HQSFHNLSHR YGPLFSLNFG --SVLCVVAS   81
SEQ_ID_NO_349    -PALPIIGH- -LHHLG-PLI HHSFHDLSTR YGPLIHLRLG --SVPCVVAS   86
SEQ_ID_NO_351    -PSFPIIGH- -LHHLG-PLI HQSFHALSTR YGSLIHLRLG --SVPCVVVS   81
SEQ_ID_NO_2553   -PSLPIIGH- -LHHLG-PLI HQSFHNLSTR YGPLIHLRLG --SVPCVVAS   85
SEQ_ID_NO_364    -FPLPIIGH- -LHLLG-PRL HQTFHDLSQR YGPLMQLRLG --SIRCVIAA   76
SEQ_ID_NO_347    -LALPLIGH- -LHLLG-PKL HHTFHQFSQR YGPLIQLYLG --SVPCVVAS   76
SEQ_ID_NO_359    -LSLPIIGH- -LHLLG-PRL HHTFHEFSLK YGPLIQLKLG --SIPCVVAS   78
```

Figure 13 (continued)

```
SEQ_ID_NO_366   SSSLVEECFT KYD- IVLANR PDLHLDLRSL GASTILSVIGA PYGDHWRNLR 133
SEQ_ID_NO_348   SSSLVEECFT KYD- IVLANR PQASVDRRSL GFSTTSVIGA  PYGDHWRNLR 133
SEQ_ID_NO_365   SSSLVEECFT KYD- IVLANR PQPSVDRRSL GFSTTSVIGA  PYGDHWRNLR 133
SEQ_ID_NO_346   TPDAAKAFLK TLD- LNFSNR PPNAGATH-L AYGAQDMVFA  HYGPRWKLLR 129
SEQ_ID_NO_2546  NGAIAKEVFK TND- INFANR PEFGSSEY-Q IYNDTMFSIM  DYNKLWIFLK 139
SEQ_ID_NO_332   ---------- ---- ------ ---------- ----------  ---------- 0
SEQ_ID_NO_338   SPSIAYEIFR TQD- VNVSSR DFPTNEGS-L LFGSFGFGTA  PYGEYWKFMK 136
SEQ_ID_NO_341   SAAVATDVFK THD- LAFSSR PAFAFAER-L PFGTSGFVTA  PYGPYWRFMK 126
SEQ_ID_NO_2549  SAAMAAEIFK TND- LAFASR PRLAFADK-L PYGTSSFITA  EYGDYWRFMK 138
SEQ_ID_NO_2544  TPELFKLFLQ THEAASFNTR FQTSAIKR-L TYDNS-VAMV  PFGPYWKFIR 132
SEQ_ID_NO_2541  TPELFKLFLQ THEATSFNTR FQTSAIRR-L TYDSS-VAMV  PFGPYWKFVR 132
SEQ_ID_NO_358   TPELFKLFLQ THEATSFNTR FQTSAIRR-L TYDSS-VAMV  PIGPYWKFVR 132
SEQ_ID_NO_360   TPELFKLFLQ THEATSFNTR FQTSAIRR-L TYDSS-VAMV  PFGPYWKFVR 132
SEQ_ID_NO_339   TPDLFKLFLQ THEAVSFNTR FQTSAIRR-L TYDNS-VAMV  PFAPYWKFIR 133
SEQ_ID_NO_2550  TPELFKLFLQ THEASSFNTR FQTSAIRR-L TYDNS-VAMV  PFAPYWKFIR 132
SEQ_ID_NO_2543  TAESAKQILK TCE- ESFTNR PIMIASEN-L TYGAADYFFI  PYGNYWRFLK 130
SEQ_ID_NO_2551  SAEMAKQILK TYE- ESFCNR PIMIASEN-L TYGAADYFFI  PYGTYWRFLK 130
SEQ_ID_NO_2548  SPDAAREVLK THE- AAFLDR AMPTAVHR-L MYGGQDFIFS  AYGPYWRFMK 139
SEQ_ID_NO_353   SPDAAREVLK THE- AAFLDR PKPAAVHR-L TYGGQDFSFS  AYGPYWRFMK 136
SEQ_ID_NO_354   SPDAAREVLK THE- AAFLDR PKPAAVHR-L TYGGQDFSFS  AYGPYWRFMK 137
SEQ_ID_NO_334   TPETAKEFLK THE- NSFCDR PKSTAVDF-L TYGSADFSFA  PYGPYWKFMK 130
SEQ_ID_NO_356   TPHFAKQLLQ TNE- LAFNCR IESTAVKK-L TYESS-LAFA  PYGDYWRFIK 128
SEQ_ID_NO_349   TPDLARDFLK TNE- LAFSSR KHSLAIDH-V TYGVS-FAFA  PYGPYWKFIK 133
SEQ_ID_NO_351   TPDLAKDFLK TNE- LAFSSR KHSLAIDH-I TYGVA-FAFA  PYGTYWKFIK 128
SEQ_ID_NO_2553  TPDLARDFLK TNE- LAFSSR KHSLAIDH-I TYGVA-FAFA  PYGPYWKFIK 132
SEQ_ID_NO_364   SPELAKECLK THE- LVFSSR KHSTAIDI-V TYDSS-FAFS  PYGPYWKFIK 123
SEQ_ID_NO_347   TPELAREFLK THE- LDFSSR KHSTAIDI-V TYDSS-FAFA  PYGPYWKFIK 123
SEQ_ID_NO_359   TPELAREFLK TNE- LAFSSR KHSTAIDI-V TYDSS-FAFS  PYGPYWKYIK 125
```

Figure 13 (continued)

| | | | | | | | |
|---|---|---|---|---|---|---|---|
| SEQ_ID_NO_366 | RGERQNTMVG | HLLSL--- | QE | SQPDYYTDEI | ITGLIISLII | AGTDASVVTT | 313 |
| SEQ_ID_NO_348 | RGERQNTMVD | HLLSL--- | QE | SQPEYYTDEI | ITGLIVALII | AGTDASVVTT | 313 |
| SEQ_ID_NO_365 | RGERQNTMVD | HLLSL--- | QE | SQPEYYTDEI | ITGLIVALII | AGTDASVVTT | 313 |
| SEQ_ID_NO_346 | ERKGKPDFLD | CVMENRD- | NS | EGE-RLSTTN | IKALLLNLFT | AGTDTSSSAI | 310 |
| SEQ_ID_NO_2546 | GGKERRDMMD | ILLEIAD- | DE | NAEMKLTRNG | IKGLFLDLFL | GGTDTTSVAL | 321 |
| SEQ_ID_NO_332 | EHHQGTDMMD | KLLEVYG- | DE | KAEYKITRDH | IKSLFVDLFF | AGTDTSTHAI | 135 |
| SEQ_ID_NO_338 | EHHQGTDMMD | KLLEVYG- | DE | KAEYKITRDH | IKSLFVDLFF | AGTDTWTHAI | 314 |
| SEQ_ID_NO_341 | GDQSERDLMD | ILLDVYH- | DA | HAEFKITMAH | IKAFFMDLFI | AGTHTSAEAT | 311 |
| SEQ_ID_NO_2549 | GKREDKDLMD | VLLEVYQ- | DD | KAGMKLTRTH | IKAFILDLFM | AGTNTSAESM | 317 |
| SEQ_ID_NO_2544 | EGEQSGIFLD | TLLEFAE- | DE | TMEIKITKEQ | IKGLVVDFFS | AGTDSTAVAT | 313 |
| SEQ_ID_NO_2541 | EGEVSGVFLD | TLLEFAE- | DE | TMEIKITKDH | IKGLVVDFFS | AGTDSTPVAT | 313 |
| SEQ_ID_NO_358 | EGEVSGVFLD | TLLEFAE- | DE | TTEIKITKDH | IKGLVVDFFS | AGTDSTAVAT | 313 |
| SEQ_ID_NO_360 | EGEVSGVFLD | TLLEFAE- | DE | TMEIKITKDH | IKGLVVDFFS | AGTDSTAEAT | 313 |
| SEQ_ID_NO_339 | EGEQSVVFLD | TLLDFAE- | DE | TMEIKITKEQ | IKGLVVDFFS | AGTDSTAVAT | 316 |
| SEQ_ID_NO_2550 | EGEQSVVFLD | TLLEFAE- | DE | TMEIKITKEQ | IKGLVVDFFS | AGTDSTAVAT | 315 |
| SEQ_ID_NO_2543 | GSDRKKDLFD | ILLNLIEA | DD | GAESKLTRQS | AKAFALDMFI | AGTNGPASVL | 316 |
| SEQ_ID_NO_2551 | ESDRKKDLFD | ILLNLIE- | AD | GADNKLTRES | AKAFALDMFI | AGTNGPASVL | 317 |
| SEQ_ID_NO_2548 | GEGAKKDLLD | MLFDMHE- | DE | AAEMRLTRDN | IKAFMLDIFG | AGTDTTAITL | 333 |
| SEQ_ID_NO_353 | GEDDEKDLLD | MLFDMHE- | DE | AAEMRLTRDN | IKAFMLDIFA | AGTDTTTITL | 325 |
| SEQ_ID_NO_354 | GEDDEKDLLD | MLFDMHE- | DE | AAEMRLTRDN | IKAFMLDIFA | AGTDTTTITL | 326 |
| SEQ_ID_NO_334 | EGDPVKDLLD | ILLDISE- | DD | SSEMKLTREN | IKAFILDIFA | AGTDTSAVTM | 317 |
| SEQ_ID_NO_356 | SGDGIRDFLD | ILLDCTE- | DE | NSEIKIQRVH | IKALIMDFFT | AGTDTTAIST | 313 |
| SEQ_ID_NO_349 | DG-KGKDFLD | ILLDVLE- | DE | NAEIKITRDH | IKALILDFFT | AATDTTAISI | 318 |
| SEQ_ID_NO_351 | DG-EGKDFLD | MLLDVLE- | DG | KAEIKITRDH | IKALILDFLT | AGTDTTAIAI | 313 |
| SEQ_ID_NO_2553 | DDVKGTDFLD | MLLDVLE- | DG | KAEIKITRDH | IKALILDFFT | AATDTTAIAV | 318 |
| SEQ_ID_NO_364 | GGGEAKDFLD | MFLDIME- | SG | KAEVKFTREH | LKALILDFFT | AGTDTTAIVC | 310 |
| SEQ_ID_NO_347 | GGGEVKDFLD | MLLDVME- | SE | KSEVEFTREH | LKALILDFFT | AGTDTTAITT | 310 |
| SEQ_ID_NO_359 | NNEEAKDFLD | MLLDVME- | SG | DTEVKFTREH | LKALILDFFT | AGTDTTAIAT | 315 |

Figure 13 (continued)

| | | | | | | |
|---|---|---|---|---|---|---|
| SEQ_ID_NO_366 | EWAMSLLLNH | PKVLEKARQE | MDTLVGHERM | VEEDDLPKLR | YLHYIILETL | 363 |
| SEQ_ID_NO_348 | EWAMSLLLNH | PKVLEKARKE | LDTLVGHERM | VDEHDLPKLR | YLHCIVLETL | 363 |
| SEQ_ID_NO_365 | EWAMSLILNH | PQVLEKARKE | LDTLVGHERM | VDEHDLPKLR | YLHCIVLETL | 363 |
| SEQ_ID_NO_346 | EWALAEMMKN | PAILKKAQGE | MDQVIGNNRR | LLESDIPNLP | YLRAICKETF | 360 |
| SEQ_ID_NO_2546 | QWGIAEVLNH | PKALKKLQEE | IDRVVGPNRL | VDDSDIPNLP | YLQAVVKETL | 371 |
| SEQ_ID_NO_332 | QWIMAEIINN | SYILERLREE | IDSVVGKTRL | IQETDLPNLP | CLQATVKEGL | 185 |
| SEQ_ID_NO_338 | QWIMAEIINN | SYILERLREE | IDSVVGKTRL | IQETDLPNLP | CLQATVKEGL | 364 |
| SEQ_ID_NO_341 | QWAMAELLNH | PEAFQKVRKE | IELVTGNVRL | VDESDITNLP | YLQAVVKETL | 361 |
| SEQ_ID_NO_2549 | QWTIAELINH | PDVFKKVREE | IDLAVGRTRL | VEESDIPNLP | YLQAVVKETL | 367 |
| SEQ_ID_NO_2544 | EWALAELINN | PRVLQKAREE | VYSVVGKDRL | VDEVDTQNLP | YIRAIVKETF | 363 |
| SEQ_ID_NO_2541 | EWALAELINN | PKVLEKAREE | VYSVVGKDRL | VDEVDTPNLP | YIGAIVKETF | 363 |
| SEQ_ID_NO_358 | EWALAELINN | PKVLEKAREE | VYSVVGKDRL | VDEVDTQNLP | YIRAIVKETF | 363 |
| SEQ_ID_NO_360 | EWALAELINN | PKVLEKAREE | VYSVVGKDRL | VDEVDTQNLP | YIRAIVKETF | 363 |
| SEQ_ID_NO_339 | DWCLSELINN | PRVMKKAREE | VDSVVGKDRL | VDESDIQNLP | YIRAVVKETF | 366 |
| SEQ_ID_NO_2550 | DWALSELINN | PRVLKKAREE | VESVVGKDRL | VDEADIQNLP | YIRAIVKETF | 365 |
| SEQ_ID_NO_2543 | EWALAELIRN | PHVFKKAREE | IDSTVGKERL | FKESDIPNLP | YLQAVVKETL | 366 |
| SEQ_ID_NO_2551 | EWSLAELIRN | PQVFKKAREE | IDSVVGKERL | VKESDIPNLP | YLQAVVKETL | 367 |
| SEQ_ID_NO_2548 | EWALSELINN | PDILRRAQAE | LDAIVGASRL | ADESDIPRLP | YLQAIAKETL | 383 |
| SEQ_ID_NO_353 | EWALSELINN | PPVLRKLQAE | LDAVVGGARL | ADESDIPSLP | YLQAVAKETL | 375 |
| SEQ_ID_NO_354 | EWALSELINN | PPVLRKLQAE | LDAVVGGARL | ADESDIPSLP | YLQAVAKETL | 376 |
| SEQ_ID_NO_334 | EWALAELINN | PNILERAREE | IDSVVGQSRL | VQESDIANLP | YVQAILKETL | 367 |
| SEQ_ID_NO_356 | EWALVELVKK | PSVLQKVREE | IDNVVGKDRL | VEESDCPNLP | YLQAILKETF | 363 |
| SEQ_ID_NO_349 | EWTLVELTNN | PKVLENARKE | IAEVVGDERL | VQESDIPNLP | YIQAIIKETL | 368 |
| SEQ_ID_NO_351 | EWALVELINN | PNALEKARQE | IDQVIGDERL | VQESDTPNLP | YIQAIIKEAL | 363 |
| SEQ_ID_NO_2553 | EWTMVELINN | PKVLEKAKKE | VDNVIGNSRL | VQESDAPNLP | YIQAIIKETL | 368 |
| SEQ_ID_NO_364 | EWAIAEVINN | PNVLKKAQEE | IANIVGFDRI | LQESDAPNLP | YLQALIKETF | 360 |
| SEQ_ID_NO_347 | EWAIAELISN | PNVLKKAQEE | MDKVIGSQRL | LQESDAPNLP | YLNAIIKETF | 360 |
| SEQ_ID_NO_359 | EWAIAELINN | PNVLKKAQEE | ISRIIGTKRI | VQESDAPDLP | YLQAIIKETF | 365 |

Figure 13 (continued)

| | | | | | | | |
|---|---|---|---|---|---|---|---|
| SEQ_ID_NO_366 | RLFPSVPTLV | PHEPSEDCN | GGYNVPKGTM | --VNAWAIHR | DPKVW- | DDPM | 412 |
| SEQ_ID_NO_348 | RLFPSVPTLV | PHEPSEDCKI | GGYNVPKGTM | VLVNAWAIHR | DPKVW- | DDPL | 412 |
| SEQ_ID_NO_365 | RLFPSVPTLV | PHEPSEDCKI | GGYNVPKGTM | ILVNAWAIHR | DPKVW- | DDPL | 412 |
| SEQ_ID_NO_346 | RKHPSTPLNL | PRISNEPCIV | DGYYIPKNTR | LSVNIWAIGR | DPEVW- | ENPL | 409 |
| SEQ_ID_NO_2545 | RVHPSLP-LI | FRKCREDCVV | NGYTIPKNSR | LVLNIYAINR | DPNEW- | RDAD | 419 |
| SEQ_ID_NO_332 | RLHPPVP-IV | LRTFKEGCTI | GGFYVPEKTT | LVVHGYAMMR | DPEYW- | EDPQ | 233 |
| SEQ_ID_NO_338 | RLHPPVP-LV | LRTFKEGCTI | GGFYVPEKTT | LVVNGYAMMR | DPEYW- | EDPQ | 412 |
| SEQ_ID_NO_341 | RLYPPAP-IT | TRECRQHCKI | NEFDVPPKTA | VAINLYAIMR | DPDSW- | DNPN | 409 |
| SEQ_ID_NO_2549 | RLHPPAP-VA | TRECRKNCKI | GGFNIPEKTA | VAINLYAIMR | DPEIW- | DDPT | 415 |
| SEQ_ID_NO_2544 | RMHPPLP-VV | KRKCVEECEI | EGCVIPEGAL | ILFNVWAVGR | DPKYW- | DRPS | 411 |
| SEQ_ID_NO_2541 | RMHPPLP-VV | KRKCTEECEI | NGYVIPEGAL | ILFNVWQVGR | DPKYW- | DRPS | 411 |
| SEQ_ID_NO_358 | RMHPPLP-VV | KRKCTEECEI | NGYVIPEGAL | ILFNVWQVGR | DPKYW- | DRPS | 411 |
| SEQ_ID_NO_360 | RMHPPLP-VV | KRKCTEECEI | NGYVIPEGAL | ILFNVWQVGR | DPKYW- | DRPS | 411 |
| SEQ_ID_NO_339 | RMHPPLP-VV | KRKCTEECEI | NGYVIPEGAL | VLFNVWAVGR | DPKYW- | DRPL | 414 |
| SEQ_ID_NO_2550 | RMHPPLP-VV | KRKCVQECEL | NGYVIPEGAL | ILFNVWAVQR | DPKYW- | EGPS | 413 |
| SEQ_ID_NO_2543 | RMHPPTP-IF | AREATRSCQV | DGYDVPAFSK | IFINAWAIGR | DPNYW- | DNPL | 414 |
| SEQ_ID_NO_2551 | RMHPPTP-IF | AREAIRGCQV | DGYDIPANSK | IFINAWAIGR | DPKYW- | DNPQ | 415 |
| SEQ_ID_NO_2548 | RLHPAFP-LV | VRRSTEPCKV | SGYDVPAGST | VFVNVWAIGR | DPACWA | PDPL | 432 |
| SEQ_ID_NO_353 | RLHPTGP-LV | VRRSLERATV | AGYDVPAGAT | VFVNVWAIGR | DAAWW- | PEPT | 423 |
| SEQ_ID_NO_354 | RLHPTGP-LV | VRRSLERATV | AGYDVPAGAT | VFVNVWAIGR | DAAWW- | PEPT | 424 |
| SEQ_ID_NO_334 | RLHPTGP-II | LRESSESCTI | NGYEIPARTR | LFVNVWAINR | DPNYW- | ENPL | 415 |
| SEQ_ID_NO_356 | RLHPPVP-MV | TRRCVAECTV | ENYVIPEDSL | LFVNVWSIGR | NPKFW- | DNPL | 411 |
| SEQ_ID_NO_349 | RMHPPIP-MV | IRKSIDNVTV | QGYDIRAGTM | LFVNIWSIGR | NPLYW- | ESPL | 416 |
| SEQ_ID_NO_351 | RLHPPIP-ML | IRKSTENVIV | QGYDIPAGTL | LFVNIWSIGR | NPQCW- | ETPL | 411 |
| SEQ_ID_NO_2553 | RLHPPIP-ML | IRKSIEKVTV | QGYEIPAGTM | LFVNIWSIGR | NAQYW- | ESPL | 416 |
| SEQ_ID_NO_364 | RLHPPIP-ML | ARKSISDCVI | DGYMIPANTL | LFVNLWSMGR | NPKIW- | DYPT | 408 |
| SEQ_ID_NO_347 | RLHPPIP-ML | TRKSISDVVV | NGYTIPAKTL | LFVNLWSMGR | NPNYW- | ENPM | 408 |
| SEQ_ID_NO_359 | RLHPPIP-ML | SRKSTSDCTV | NGYKIQAKSL | LFVNIWSIGR | NPNYW- | ESPM | 413 |

Figure 13 (continued)

```
SEQ_ID_NO_366   SFKPDRFET   ----------  --------LE  VETHKLLPFG  MGRRGCPGAG  443
SEQ_ID_NO_348   SFKPDRFEI   ----------  --------ME  VETHKLLPFG  MGRRACPGAG  443
SEQ_ID_NO_365   SFKPDRFET   ----------  --------ME  VETHKLLPFG  MGRRACPGAG  443
SEQ_ID_NO_346   EFYPERFLS   ---GRNSKI   -D------PR  GNDFELIPFG  AGRRICAGTR  447
SEQ_ID_NO_2546  EFIPERYLVN  SGGGEENQLA  IEPDELEAMK  GQNFCYVPFG  GGRRGCPGAG  469
SEQ_ID_NO_332   EFKPERFLAS  SRSSQND---  -E------IR  DELLKYLPFG  NGRRACPGAN  273
SEQ_ID_NO_338   EFKPERFLAS  SRSSQND---  -E------IR  DELLKYLPFG  NGRRACPGAN  452
SEQ_ID_NO_341   EFCPERFLQE  QDHEDLSD--  -D------GK  RMKFNFVPFG  GGRRGCPGTA  450
SEQ_ID_NO_2549  EFRPERFLVP  SKEQVDLD--  -Q------TK  GQNFNFVPFG  GGRRGCPGTL  456
SEQ_ID_NO_2544  EFRPERFLEN  GGEGAVGPI   -D------LR  GQHFQLLPFG  SGRRMCPGVN  453
SEQ_ID_NO_2541  EFRPERFLET  GAEGEAGPL   -D------LR  GQHFQLLPFG  SGRRMCPGVN  453
SEQ_ID_NO_358   EFRPERFLET  GAEGEARPL   -D------LR  GQHFQLLPFG  SGRRMCPGVN  453
SEQ_ID_NO_360   EFRPERFLET  GAEGEARPL   -D------LR  GQHFQLLPFG  SGRRMCPGVN  453
SEQ_ID_NO_339   EFRPERFLEN  AGEGDAGSI   -D------LR  GQHFQLLPFG  SGRRMCPGVN  456
SEQ_ID_NO_2550  EFRPERFLT-  -AEGGATSI   -D------LR  GQNFELLPFG  SGRRMCPGVN  453
SEQ_ID_NO_2543  VFNPERFLQ-  SDDPSKSKI   -D------VR  GQYYQLLPFG  SGRRSCPGSS  455
SEQ_ID_NO_2551  VYBPERFLI-  TDEPGKSKI   -D------VR  GQYYQLLPFG  SGRRSCPGSS  456
SEQ_ID_NO_2548  AFRPERFLE-  GGEGRGDSAG  LD------VR  GQHFHLLPFG  SGRRICPGAS  475
SEQ_ID_NO_353   AFRPERFVS-  GGGGGGTAA   -D------VR  GQHFHLLPFG  SGRRICPGAS  464
SEQ_ID_NO_354   AFRPERFVS-  GGGGGGTAA   -D------VR  GQHFHLLPFG  SGRRICPGAS  465
SEQ_ID_NO_334   EFEPERFLC-  AGENGKSQL   -D------VR  GQHFHFLPFG  SGRRGCPGTT  456
SEQ_ID_NO_356   EFRPERFLK-  LEGDSSGWV   -D------VR  GSHFQLLPFG  SGRRMCPGVS  452
SEQ_ID_NO_349   EFKPHRFLD-  ---GHARNL   -D------VK  GQCFQLLPFG  TGRRGCPGIS  454
SEQ_ID_NO_351   EFKPHRFLD-  -GGDLKSSL   -D------IK  GHNFQLLPFG  TGRRGCPGVN  451
SEQ_ID_NO_2553  EFEPDRFFE-  -GDFLKSSL   -D------IK  GQSFQLLPFG  TGRRGCPGIN  456
SEQ_ID_NO_364   AFQPERFLE-  ---KEKAAI   -D------VK  GQHFELLPFG  TGRRGCPGML  446
SEQ_ID_NO_347   EFRPERFLEK  GTGSI-----  -D------VK  GQHFELLPFG  TGRRGCPGML  446
SEQ_ID_NO_359   EFRPERFLEK  GRESI-----  -D------VK  GQHFELLPFG  TGRRGCPGML  451
```

Figure 13 (continued)

| | | | | |
|---|---|---|---|---|
| SEQ_ID_NO_366 | ATTLEAMCKP | RHVMEKVLRQ | VSNV | 507 |
| SEQ_ID_NO_348 | AKTLEAMCKP | RHVMEKVLRQ | VSNV | 506 |
| SEQ_ID_NO_365 | AKTLEAMCKP | RHIMERVLRQ | VSNV | 506 |
| SEQ_ID_NO_346 | AVPLEAMVTP | RLPLDVYAPL | A- | 508 |
| SEQ_ID_NO_2546 | VHPLICYPVV | R-----VNPL | EIAN | 527 |
| SEQ_ID_NO_332 | AHPLNCTLVP | RTLIPVTSTV | QIPSS | 337 |
| SEQ_ID_NO_338 | AHPLNCTLVP | RTLIPVTSTV | QIPSS | 516 |
| SEQ_ID_NO_341 | VHPLICVPVV | H-----FIPY | D | 509 |
| SEQ_ID_NO_2549 | LHPLKCHPIV | H-----FNPF | EG | 515 |
| SEQ_ID_NO_2544 | KHNLVCLPLA | K--FTLAAKL | LSP | 522 |
| SEQ_ID_NO_2541 | AHSLVCVPLA | R--IGVASKL | LS | 521 |
| SEQ_ID_NO_358 | AHSLVCVPLA | R--IGVASKL | LS | 521 |
| SEQ_ID_NO_360 | AHSLVCVPLA | R--IGVASKL | LS | 521 |
| SEQ_ID_NO_339 | AHNLVCVPLA | R--PGAAAKL | LSS | 525 |
| SEQ_ID_NO_2550 | AHNLMCVPLA | R--TNVTSEL | LSS | 522 |
| SEQ_ID_NO_2543 | AKPLKCKPVP | H-----FVPF | SSA | 514 |
| SEQ_ID_NO_2551 | AKPLKCKPVP | R-----FVPF | SA | 514 |
| SEQ_ID_NO_2548 | KRPLVCTVKA | R-----LHPV | PVPTAAAADN GVDGTLHCA | 548 |
| SEQ_ID_NO_353 | KRPLVCTVSP | R-----IHPL | PAAASASLT | 527 |
| SEQ_ID_NO_354 | KRPLVCTVSP | R-----IHPL | PAAASASLT | 528 |
| SEQ_ID_NO_334 | AHPLICVPVA | R-----LNPF | PSF | 511 |
| SEQ_ID_NO_356 | AHNLVCVPVD | RTSGGGPLKI | IEC | 523 |
| SEQ_ID_NO_349 | AVDLEFVPLM | R--QNCPNIF | VSA | 514 |
| SEQ_ID_NO_351 | AVDFVCVPLE | R---GNTLKI | LGSN | 511 |
| SEQ_ID_NO_2553 | AVDFVCVPSM | R--ENCPKVF | ---- | 513 |
| SEQ_ID_NO_364 | ETDLFCRVVP | R-----VDPL | VVSTQ | 506 |
| SEQ_ID_NO_347 | ANDLVCQLVP | R-----IDPV | VVSGP | 506 |
| SEQ_ID_NO_359 | AFDLVCRLYP | R-----VDPA | TLSGA | 512 |

Figure 14

```
SEQ_ID_NO_475  ---------- --MSS----- ---------- --------RL ------ YVGN  9
SEQ_ID_NO_436  MAFCNKLGNL LRQGATQS-- ------SHAP VSSMLNYLRH MSSSKL FIGG 42
SEQ_ID_NO_420  MAFLSKVGKI FRQTSAHVTA SNSMLQSI-- --------RC MSSSKI FVGG 40
SEQ_ID_NO_473  ---------- --MAASDV-- ------EF-- --------RC ------ FVGG 14
SEQ_ID_NO_369  ---------- --MAGGE--- ------EF-- --------RC ------ FVGG 13
SEQ_ID_NO_371  ---------- --MASADV-- ------EF-- --------RC ------ FVGG 14
SEQ_ID_NO_372  ---------- --MASADV-- ------EF-- --------RC ------ FVGG 14
SEQ_ID_NO_373  ---------- ----MAEV-- ------EY-- --------RC ------ FVGG 12
SEQ_ID_NO_456  ---------- ----MADV-- ------EY-- --------RC ------ FVGG 12
SEQ_ID_NO_507  ---------- ----MADV-- ------EY-- --------RC ------ FVGG 12
SEQ_ID_NO_455  ---------- --MAAADV-- ------EY-- --------RC ------ FVGG 14
SEQ_ID_NO_477  ---------- --MAAADV-- ------EY-- --------RC ------ FVGG 14
SEQ_ID_NO_465  ---------- --MAASDV-- ------EY-- --------RC ------ FVGG 14
SEQ_ID_NO_488  ---------- --MAAPDV-- ------EY-- --------RC ------ FVGG 14
SEQ_ID_NO_494  ---------- --MAAPDV-- ------EY-- --------RC ------ FVGG 14
SEQ_ID_NO_374  ---------- ---MDAEV-- ------EY-- --------RC ------ FVGG 13
SEQ_ID_NO_441  ---------- ----MAEV-- ------EY-- --------RC ------ FVGG 12
SEQ_ID_NO_444  ---------- --MASADV-- ------EY-- --------RC ------ FVGG 14
SEQ_ID_NO_451  ---------- ----MGDV-- ------EY-- --------RC ------ FVGG 12
SEQ_ID_NO_505  ---------- ----MAEV-- ------EY-- --------RC ------ FVGG 12
SEQ_ID_NO_474  ---------- ----MAEV-- ------EY-- --------RC ------ FVGG 12
SEQ_ID_NO_447  ---------- ----MAEV-- ------EY-- --------SC ------ FVGG 12
SEQ_ID_NO_450  ---------- ---MAAEV-- ------EY-- --------SC ------ FVGG 13
SEQ_ID_NO_434  ---------- --MGSSDV-- ------EY-- --------RC ------ FVGG 14
SEQ_ID_NO_437  ---------- --MAAADI-- ------EY-- --------RC ------ FVGG 14
SEQ_ID_NO_438  ---------- ---MSADI-- ------EY-- --------RC ------ FVGG 13
SEQ_ID_NO_454  ---------- --MAE----- ------EY-- --------RC ------ FVGG 11
SEQ_ID_NO_392  ---------- ---MSAEV-- ------EY-- --------RC ------ FVGG 13
SEQ_ID_NO_425  ---------- --MASAEV-- ------EF-- --------RC ------ FVGG 14
SEQ_ID_NO_504  ---------- --MASAEI-- ------EF-- --------RC ------ FVGG 14
SEQ_ID_NO_366  ---------- --MASGDV-- ------EY-- --------RC ------ FVGG 14
SEQ_ID_NO_422  ---------- --MASPDV-- ------EY-- --------RC ------ FVGG 14
SEQ_ID_NO_506  ---------- --MASADV-- ------EF-- --------RC ------ FVGG 14
SEQ_ID_NO_433  ---------- --M--ADV-- ------ED-- --------RC ------ FVGG 12
SEQ_ID_NO_376  ---------- --MASADV-- ------EY-- --------RC ------ FVGG 14
SEQ_ID_NO_440  ---------- --MASADV-- ------EY-- --------RC ------ FVGG 14
```

Figure 14 (continued)

| | | | | | | |
|---|---|---|---|---|---|---|
| SEQ_ID_NO_475 | LSWNAKEEDL | RTYFGKFGEV | EEASIALDRE | SGRSRGFGFV | TLPADVA-KD | 58 |
| SEQ_ID_NO_436 | LSYGVDDQSL | KDAFASYGEV | VEARVITDRD | TGRSRGFGFV | NFTSDESATS | 92 |
| SEQ_ID_NO_420 | ISYSTDEFGL | REAFSKYGEV | VDAKIIVDRE | TGRSRGFAFV | TFTSTEEASN | 90 |
| SEQ_ID_NO_473 | LAWATDDASL | ERAFSTYGDI | VESKIINDRE | TGRSRGFGFV | TFRDEQSMRD | 64 |
| SEQ_ID_NO_369 | LAWATTDGRL | EGAFRPFGEV | VQSKVISDRE | TGRSRGFGFV | TFADENSMNA | 63 |
| SEQ_ID_NO_371 | LAWSTDDRSL | QEAFSPYGEV | VESKIISDRE | TGRSRGFGFV | TFNDEQSMRD | 64 |
| SEQ_ID_NO_372 | LSWSTDDRSL | KDAFTAFGEV | MDSKVVSDRE | TGRSRGFGFV | TFMDEQSMRD | 64 |
| SEQ_ID_NO_373 | LSWGTDDRSL | AEAFNKFGEV | TDSKIINDRE | TGRSRGFGFV | TFANEQSMRD | 62 |
| SEQ_ID_NO_458 | LAWATDDQSL | QNAFSKYGDV | IDSKIITDRE | TGRSRGFGFV | TFASDEAMRQ | 62 |
| SEQ_ID_NO_507 | LRWATDDQSL | QNAFSKYGDV | IDSKIITDRE | TGRSRGFGFV | TFASDEAMRQ | 62 |
| SEQ_ID_NO_455 | LAWATNNETL | EQAFANFGQV | IDSKVITDRE | TGRSRGFGFV | TFSSEQSMLD | 64 |
| SEQ_ID_NO_477 | LAWATDNASL | QQAFASYGDV | LDSKVITDRE | TGRSRGFGFV | TFSSEQSMLD | 64 |
| SEQ_ID_NO_465 | LAWATDDHSL | HNAFSTYGEV | LESKIILDRE | TDRSRGFGFV | TFSTEEAMRN | 64 |
| SEQ_ID_NO_488 | LAWATDDRSL | EAAFSTYGEI | LDSKIINDRE | TGRSRGFGFV | TFSSEQSMRD | 64 |
| SEQ_ID_NO_494 | LAWATDDRSL | EAAFSTYGEI | LDSKIINDRE | TGRSRGFGFV | TFSSEQSMRD | 64 |
| SEQ_ID_NO_374 | LAWATDDQSL | ERAFSNYGQV | LESKIINDRE | TGRSRGFGFV | TFSSEQAMRD | 63 |
| SEQ_ID_NO_441 | LAWATNDESL | EQAFSQFGDI | TDSKIINDRE | TGRSRGFGFV | TFKDEKSMRD | 62 |
| SEQ_ID_NO_444 | LAWATTDQSL | SEAFSQYGEI | LESKIINDRE | TGRSRGFGFV | TFKDEQSMRD | 64 |
| SEQ_ID_NO_451 | LAWATTDNTL | SEAFSQYGEV | VESKIINDRE | TGRSRGFGFV | TFKDEQAMRD | 62 |
| SEQ_ID_NO_505 | LAWATTDQTL | GDAFSQFGEI | LDSKIINDRE | TGRSRGFGFV | TFKDEKAMRD | 62 |
| SEQ_ID_NO_474 | LAWATTDQTL | GDAFSQYGEI | LDSKIINDRE | TGRSRGFGFV | TFKDEQAMRD | 62 |
| SEQ_ID_NO_447 | LAWATTDRTL | ADAFGTYGEV | LDSKIINDRE | TGRSRGFGFV | TFKDEKQMRD | 62 |
| SEQ_ID_NO_450 | LAWATTDRTL | SDAFSTYGEV | VDSKIINDRE | TGRSRGFGFV | TFKDEKSMKE | 63 |
| SEQ_ID_NO_434 | LAWATDSQAL | EQAFSKFGEI | TDSKVINDRE | TGRSRGFGFV | TFAEEKSMRD | 64 |
| SEQ_ID_NO_437 | LAWATSDKAL | EEAFSAYGEV | LESKIINDRE | TGRSRGFGFV | TFNNEKSMRD | 64 |
| SEQ_ID_NO_438 | LAWATTDQSL | QEAFSPYGEI | LDSKIINDRE | TGRSRGFGFV | TFNNEKSMRD | 63 |
| SEQ_ID_NO_454 | LAWATNDQSL | EQAFSQFGEI | TDCKIINDRE | TGRSRGFGFV | TFSSSESMKN | 61 |
| SEQ_ID_NO_392 | LAWATTDQVL | QEAFSQYGEI | IDSKIINDRE | TGRSRGFGFV | TFGNEKAMRD | 63 |
| SEQ_ID_NO_425 | LAWATDHDAL | EKAFSQFGEI | VESKVINDRE | TGRSRGFGFV | TFATEQAMRD | 64 |
| SEQ_ID_NO_504 | LAWATDNDAL | ERAFSPFGEI | IESKIINDRE | TGRSRGFGFV | TFSNEKAMRD | 64 |
| SEQ_ID_NO_368 | LAWATDDRAL | ETAFAQYGDV | IDSKIINDRE | TGRSRGFGFV | TFKDEKAMKD | 64 |
| SEQ_ID_NO_422 | LAWATDDRAL | ETAFSQYGEV | LDSKIINDRE | TGRSRGFGFV | TFKDEKSMKD | 64 |
| SEQ_ID_NO_506 | LAWATTDSSL | HEAFSAYGDI | LESKIINDRE | TGRSRGFGFV | TFRDEKSMRD | 64 |
| SEQ_ID_NO_433 | LAWATDNDAL | EKAFSQYGEI | VDSKIINDRE | TGRSRGFGFV | TFANEKSMND | 62 |
| SEQ_ID_NO_376 | LAWATDDRAL | EEAFSVYGEI | VESKIINDRE | SGRSRGFGFV | TFRDEKSMRD | 64 |
| SEQ_ID_NO_440 | LAWATDDHAL | EQAFSQYGEV | VESKIINDRE | TGRSRGFGFV | TFSNEKSMND | 64 |

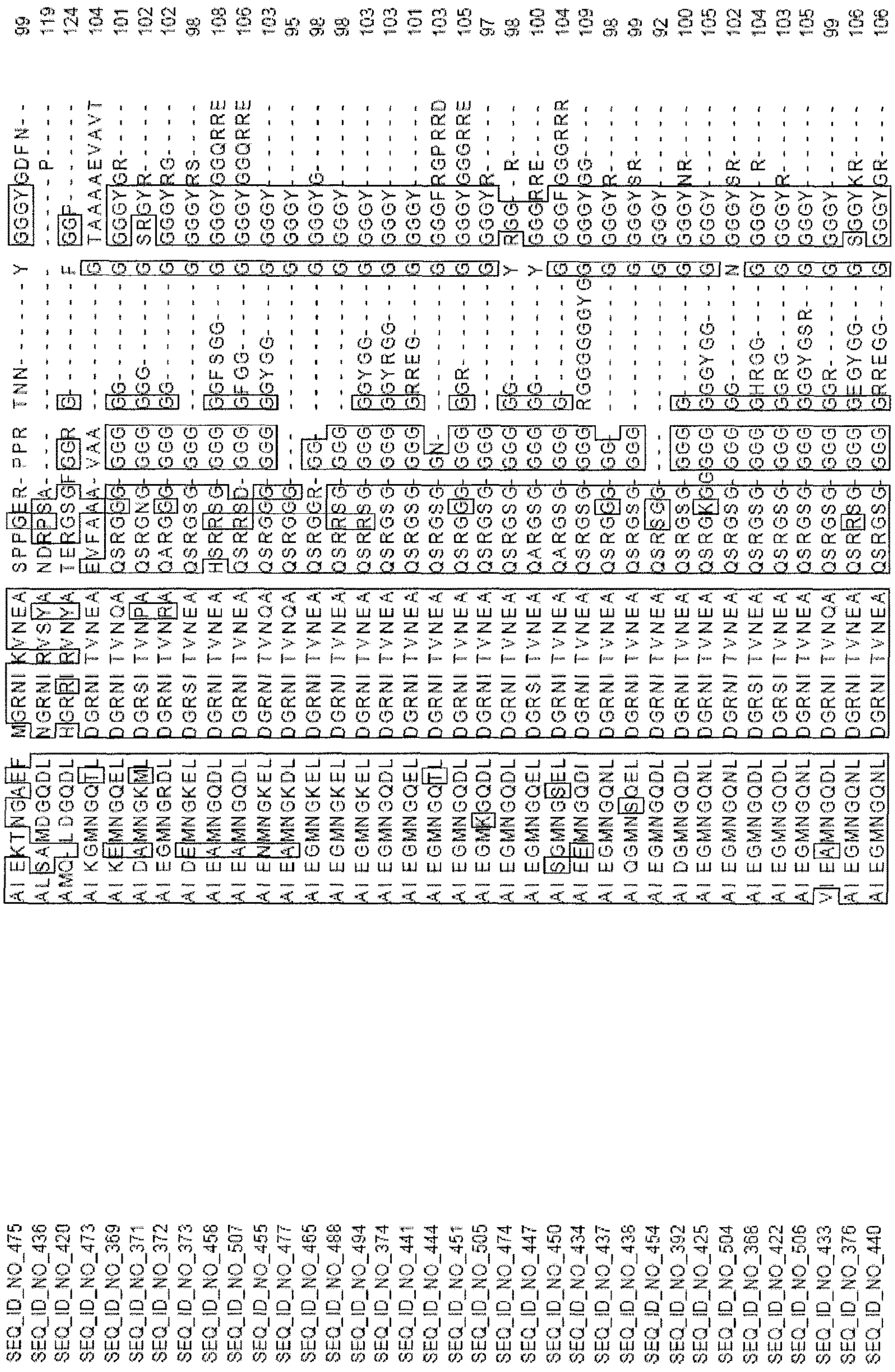

Figure 14 (continued)

| SEQ ID | Sequence | Length |
|---|---|---|
| SEQ_ID_NO_475 | AIEKTNGAEF MGRNI KVNEA SPPGER-PPR TNN------ Y GGGYGDFN- | 99 |
| SEQ_ID_NO_436 | ALSAMQLDGQDL NGRNI RVSYA NDRPSA------- ---------- ---P----- | 119 |
| SEQ_ID_NO_420 | AMQLDGQDL HGREI RWNYA IERGSGF GGR -G------- -F- GGP------ | 124 |
| SEQ_ID_NO_473 | AIKGMNGQT- DGRNI TVNEA EVFAAA-VAA -G-------- -G- TAAAEVAVT | 104 |
| SEQ_ID_NO_369 | AIKEMNGQEL DGRSI TVNPA QSRGNG-GGG GG-------- -G- GGGYR---- | 101 |
| SEQ_ID_NO_371 | AIDAMNGKM- DGRNI TVNEA QSRGNG-GGG GG-------- -G- SRGYR---- | 102 |
| SEQ_ID_NO_372 | AIDEMNGRDL DGRSI TVNEA QARGGG-GGG GG-------- -G- GGGYRG--- | 102 |
| SEQ_ID_NO_373 | AIEMNGKEL DGRSI TVNEA QSRGSG-GGG GG-------- -G- GGGYRS--- | 98 |
| SEQ_ID_NO_458 | AIEAMNGQDL DGRNI TVNEA HSRRSD-GGL GGFSGG---- -G- GGGYGGQRRE | 108 |
| SEQ_ID_NO_507 | AIENMNGQEL DGRNI TVNEA QSRGGG-GGG GFGG------ -G- GGGYGGQRRE | 106 |
| SEQ_ID_NO_455 | AIEAMNGKDL DGRNI TVNEA QSRGGR-GGG GGYGG----- -G- GGGYRS--- | 103 |
| SEQ_ID_NO_477 | AIEGMNGKEL DGRNI TVNEA QSRRS-GGGL -GGYGG---- -G- GGGY----- | 95 |
| SEQ_ID_NO_485 | AIEGMNGKEL DGRNI TVNEA QSRGSG-GGG GG-------- -G- GGGY----- | 98 |
| SEQ_ID_NO_488 | AIEGMNGQEL DGRNI TVNEA QSRGSG-GGG GGYGG----- -G- GGGY----- | 98 |
| SEQ_ID_NO_494 | AIEGMNGKEL DGRNI TVNEA QSRGSG-GGG GGYRGG---- -G- GGGY----- | 103 |
| SEQ_ID_NO_374 | AIEGMNGQEL DGRNI TVNEA QSRGSG-GGG GRREG----- -G- GGGY----- | 103 |
| SEQ_ID_NO_441 | AIEGMNGQEL DGRNI TVNEA QSRGSG-GGG GN-------- -G- GGGYR---- | 101 |
| SEQ_ID_NO_444 | AIEGMNGQDL DGRNI TVNEA QSRGSG-GGG GGR------- -G- GGGFRGPRRD | 103 |
| SEQ_ID_NO_451 | AIEGMGGQDL DGRNI TVNEA QSRGSG-GGG GG-------- -Y- GGGYGGGRRE | 105 |
| SEQ_ID_NO_505 | AIEGMEMNGQDL DGRSI TVNEA QARGSG-GGG GG-------- -Y- GGGFR--- | 97 |
| SEQ_ID_NO_474 | AIEEMNGQDI DGRNI TVNEA QSRGSG-GGG GG-------- -G- RGG----R- | 98 |
| SEQ_ID_NO_447 | AIEGMNGQEL DGRNI TVNEA QSRGSG-GGG -G-------- -G- GGGRRE--- | 100 |
| SEQ_ID_NO_450 | AISGMNGSEL DGRNI TVNEA QSRRS-GGGL RGGGGGGGYGG G- GGGFGGGRRR | 104 |
| SEQ_ID_NO_434 | AIEEMNGQDI DGRSI TVNEA QSRGSG-KGG GGYGG----- -G- GGGYGG--- | 109 |
| SEQ_ID_NO_437 | AIOGMNGSQEL DGRSI TVNEA QSRGSG-GGG -G-------- -G- GGGYSR--- | 98 |
| SEQ_ID_NO_438 | AIEGMNGQEL DGRNI TVNQA QSRGSG-GGG GHRGG----- -G- GGGY----- | 99 |
| SEQ_ID_NO_454 | VIEAMNGQEL DGRNI TVNEA QSRGSG-GGG GGRG------ -G- GGGYNR--- | 92 |
| SEQ_ID_NO_392 | AIDGMNGQDL DGRNI TVNEA QSRGSG-GGG -G-------- -G- GGGY----- | 100 |
| SEQ_ID_NO_425 | AIEGMNGQNL DGRNI TVNEA QSRGSG-GGG GGGYGSR--- -G- GGGYR---- | 105 |
| SEQ_ID_NO_504 | AIEGMNGQNL DGRNI TVNEA QSRGSG-GGG GG-------- -G- GGGYR---- | 102 |
| SEQ_ID_NO_368 | AIEGMNGQEL DGRNI TVNEA QSRGSG-GGG GG-------- -G- GGGY-R--- | 104 |
| SEQ_ID_NO_422 | AIEAMNGQDL DGRNI TVNEA QSRGSG-GGG GG-------- -G- GGGYR---- | 103 |
| SEQ_ID_NO_506 | AIEGMNGQNL DGRNI TVNEA QSRGSG-GGG GG-------- -N- GGGYR---- | 105 |
| SEQ_ID_NO_433 | AIEGMNGQNL DGRNI TVNEA QSRGSG-GGG GG-------- -G- GGGY----- | 99 |
| SEQ_ID_NO_376 | AIEAMNGQNL DGRNI TVNEA QSRGSG-GGG GEGYGG---- -G- SIGGYKR-- | 106 |
| SEQ_ID_NO_440 | AIEGMNGQNL DGRNI TVNEA QSRGSG-GGG GRREGG---- -G- GGGYGR--- | 106 |

Figure 14 (continued)

```
SEQ_ID_NO_475   RGNFG--GQG ------GYGD NRFGNDNFGG SYGGRGGYRG -PRGPSAEEN 169
SEQ_ID_NO_436   SNRGG--GGG ---------- ---------- ---------- ---------- 142
SEQ_ID_NO_420   GGYGA--PGG ------GYGX ---WWWL-RR RCWWLRC--- ---------- 174
SEQ_ID_NO_473   MGTGG----- ---------- --------AK AVVRLPR--- ---------- 134
SEQ_ID_NO_369   SGYGG--SRG G-----GYG- --------GG GGGGYGG-R -GG------- 148
SEQ_ID_NO_371   GGYGG--GGG ------GYG- --------GG GGSRYGG--- -GG------- 147
SEQ_ID_NO_372   SGGGGYSGGG RERSERGYGG GSRN----GG GYGGYSG-GG -GGGSRYGGG 171
SEQ_ID_NO_373   GGYGG--GSG G-----GYGG ---RRE--GG GGGGYGG-G -GGGGYRG-- 155
SEQ_ID_NO_458   GGYGG--GGG ------GYGG SRGGS---GG GGGGYGGSRG -G-------- 163
SEQ_ID_NO_507   GGYGSRDGGG G-----GY-- --------GG GGGGYGG-S RGG------- 153
SEQ_ID_NO_455   GGYGGREGGG ------GYGG --------GG GYGGNRG--- ---------- 160
SEQ_ID_NO_477   GGYGG--GGG GGRREGGYG- --------GG GYGSRG---- ---------- 150
SEQ_ID_NO_465   GGYGG--GGG ------GYGG --------GN RGGGYGN--- ---------- 149
SEQ_ID_NO_488   GGYGGGRGGG G-----GYG- --------GS RGGGYGG--- ---------- 155
SEQ_ID_NO_494   GGRGG--GGG ------GYG- --------GS RGGGYGG--- ---------- 145
SEQ_ID_NO_374   GGYGG--GGG ------GYGG --------GR REGGYGG-G -GGDRYARG- 160
SEQ_ID_NO_441   GGYGG--GGG ------GYGG RR------EG GDGGYGG--- ---------- 150
SEQ_ID_NO_444   GGYGG--GDR ------GYG- --------GG GGGGSRYSRG -GG------- 156
SEQ_ID_NO_451   GGYSG--GGG ------GYGG GRREGGY-GG GGGGYGGGDR YSDRSSRGGG 168
SEQ_ID_NO_505   GGYGG--GGG G-----GYGG --------GR REGGYGG--- ---------- 148
SEQ_ID_NO_474   GGYGG--GGG -------YGG --------GR REGGYGG--- ---------- 148
SEQ_ID_NO_447   GGYGG--GRR ---------- --------EG GGGGYGG--- ---------- 139
SEQ_ID_NO_450   RREGG--GGG ------GYGG GRRE----GG GGGGYGG--- ---------- 153
SEQ_ID_NO_434   GGYGG--GRD R-----GYGG --------GG GDRGYGG-GG -GGDRYSRGG 180
SEQ_ID_NO_437   GGYGG--GGG ------GYG- --------GG RDRGYGGGGD -GGSRYSRGG 156
SEQ_ID_NO_438   GGYGG--GRD Q-----GYGG --------GG GGSRYSR--G -GG------- 156
SEQ_ID_NO_454   -------GGG ---------- ---------- ---------- ---------- 99
SEQ_ID_NO_392   YGSGG--GGG ------GYG- --------GG RDRGYGD--- --GGSRYSSR 160
SEQ_ID_NO_425   GGYGG--GGG GYGGGGGYGG --------GG RDRGYGG-D -GGSRYSRGG 172
SEQ_ID_NO_504   GGYGS--GGG ------GYGG G-------GR REGGYGGGEG -GGARYSRGS 168
SEQ_ID_NO_368   -GRRE--GGG ------GYG- --------GG EGGGYGG-S -GG------- 144
SEQ_ID_NO_422   GGYSSRGGGG G-----GYGG GGRRD---GG EGGGYGG-S -GG------- 162
SEQ_ID_NO_506   GGYGGRREGG YSRDG-GYG- --------GD GGSRYSR--S -GA------- 159
SEQ_ID_NO_433   ---------- ---------- ---------- ---------- ---------- 103
SEQ_ID_NO_376   GGYGG--GGG ------GYG- --------GG GGGGY----- ---------- 159
SEQ_ID_NO_440   GGYGG--GRE QR----GYGD --------SG GGSRYSR--- ---------- 157
```

Figure 14 (continued)

| | | | | | |
|---|---|---|---|---|---|
| SEQ_ID_NO_475 | NSNNYGGY-- | ---------- | ---------- | ------ | 177 |
| SEQ_ID_NO_436 | ----GGGW-- | ---------- | ---------- | ------ | 146 |
| SEQ_ID_NO_420 | --SSWWLWRR | WLQCSRWWLR | RWLILWWKCC | WWRLWR | 208 |
| SEQ_ID_NO_473 | ----SEGWAS | ---------- | ---------- | ------ | 140 |
| SEQ_ID_NO_369 | --PSSGNWRN | DRQPEY---- | ---------- | ------ | 162 |
| SEQ_ID_NO_371 | --SEGGSWRR | ---------- | ---------- | ------ | 155 |
| SEQ_ID_NO_372 | GVSDDGGWRS | ---------- | ---------- | ------ | 181 |
| SEQ_ID_NO_373 | --NSDGNWRN | ---------- | ---------- | ------ | 163 |
| SEQ_ID_NO_458 | --SGGGNWRE | ---------- | ---------- | ------ | 171 |
| SEQ_ID_NO_507 | --SGGGNWRE | ---------- | ---------- | ------ | 161 |
| SEQ_ID_NO_455 | --DSGGNWRN | ---------- | ---------- | ------ | 168 |
| SEQ_ID_NO_477 | --DSGGNWRN | ---------- | ---------- | ------ | 158 |
| SEQ_ID_NO_465 | ---SDGNWRN | ---------- | ---------- | ------ | 156 |
| SEQ_ID_NO_488 | --DSGGNWRN | ---------- | ---------- | ------ | 163 |
| SEQ_ID_NO_494 | --DSGGNWRN | ---------- | ---------- | ------ | 153 |
| SEQ_ID_NO_374 | --NSDSDWRN | ---------- | ---------- | ------ | 168 |
| SEQ_ID_NO_441 | ----GGGGSR | W--------- | ---------- | ------ | 157 |
| SEQ_ID_NO_444 | --ASDGNWRN | ---------- | ---------- | ------ | 164 |
| SEQ_ID_NO_451 | GGSSDGNWRN | ---------- | ---------- | ------ | 178 |
| SEQ_ID_NO_505 | --GSEG---- | ---------- | ---------- | ------ | 152 |
| SEQ_ID_NO_474 | --GSEGNWRN | ---------- | ---------- | ------ | 156 |
| SEQ_ID_NO_447 | --GGYGGGGR | Y--------- | ---------- | ------ | 148 |
| SEQ_ID_NO_450 | --GGYGGGDR | Y--------- | ---------- | ------ | 162 |
| SEQ_ID_NO_434 | GADSGGNWRD | ---------- | ---------- | ------ | 190 |
| SEQ_ID_NO_437 | G-ASEGNWRS | ---------- | ---------- | ------ | 165 |
| SEQ_ID_NO_438 | --ESDGNWKN | ---------- | ---------- | ------ | 164 |
| SEQ_ID_NO_454 | --DSGGNWRN | ---------- | ---------- | ------ | 107 |
| SEQ_ID_NO_392 | GESEGGSWRS | ---------- | ---------- | ------ | 170 |
| SEQ_ID_NO_425 | GGSDGGSWRN | ---------- | ---------- | ------ | 182 |
| SEQ_ID_NO_504 | GGSEGGSWRS | ---------- | ---------- | ------ | 178 |
| SEQ_ID_NO_368 | ----GGGW-- | ---------- | ---------- | ------ | 148 |
| SEQ_ID_NO_422 | ----GGGW-- | ---------- | ---------- | ------ | 166 |
| SEQ_ID_NO_506 | --SDGGSWRN | ---------- | ---------- | ------ | 167 |
| SEQ_ID_NO_433 | ----GG---- | ---------- | ---------- | ------ | 105 |
| SEQ_ID_NO_376 | ----GG---- | ---------- | ---------- | ------ | 161 |
| SEQ_ID_NO_440 | -DSDGGNWRS | ---------- | ---------- | ------ | 166 |

Figure 15

```
SEQ_ID_NO_527   ---MAGISVI VVVVVAFLHI LAFVLAIGAE MRRST----- ----------   32
SEQ_ID_NO_529   MGDVGRSSIL VHILVIALCL AAFGFAIAAE RRRST----- ----------   35
SEQ_ID_NO_530   MGDTERSSIL VHILVIALCL TAFGFAIAAE RRRSTVKSTY LRYILNFVFE   50
SEQ_ID_NO_531   MGDTERSSIL VHILVIALCL TAFGFAIAAE RRRST----- ----------   35
SEQ_ID_NO_510   MGE-GKASTL VFILVVALSL VAFGFSIAAE RRRS------ ----------   34
SEQ_ID_NO_525   MGE-GKGSTL VFILVIALCL VAFGFSIAAE RRRS------ ----------   34
SEQ_ID_NO_521   MAE-GRGSTL VHLLVVVLCL VAFGFAIAAE RRRSV----- ----------   34
SEQ_ID_NO_513   MGE-GKGSTL VHLLVVVLSL VAFGFAIAAE RRRSV----- ----------   34
SEQ_ID_NO_517   MEE-GKGSTL VHLLVVVLSL VAFGFAIAAE RRRS------ ----------   33
SEQ_ID_NO_511   -----MASKL LLIAVFVLDL IAFGLAVAAE QRRST----- ----------   30
SEQ_ID_NO_523   -----MASIL VQVSALLLNL LAFGLAVAAE QRRSK----- ----------   30

SEQ_ID_NO_527   ---------- ---GKVVPDE YDERTFCAYD SDASTAYGLS AFGLLLLSQA   69
SEQ_ID_NO_529   ---------- ---GSIVTDS S-NTTFCVYD SDIATGYGVG AFLFLLSGHS   71
SEQ_ID_NO_530   FMDGVFFTIY IVQGSIVTDS F-NSTFCVYD SDIATGYGVG AFLFLLSGQS   99
SEQ_ID_NO_531   ---------- ---GSIVTDS F-NSTFCVYD SDIATGYGVG AFLFLLSGQS   71
SEQ_ID_NO_510   ---------- ---GKSIQDP ITNTTFCVYD SDVATGYGVG AFLFLLSSES   71
SEQ_ID_NO_525   ---------- ---GKSIQDP ITNATYCVYS SDVATGYGVG AFLFLLSSES   71
SEQ_ID_NO_521   ---------- ---GTMHKIE GTNETFCSYS SDVATGYGVG AFLFLLSXES   71
SEQ_ID_NO_513   ---------- ---GTVVKDD ITNSTYCVYN SDVATGYGVG AFLFLLSGES   71
SEQ_ID_NO_517   ---------- ---------- ---------- ------YGVG AFLFLLSSES   47
SEQ_ID_NO_511   ---------- ---AKIVQDS EVNYNYCVYD SYISTGYGVG AFLFLMVSQA   67
SEQ_ID_NO_523   ---------- ---ATVTPDL AKEYDYCVYD SDVATGYGVG ALLLLVAAQA   67

SEQ_ID_NO_527   VMSAATRCLC FGRGLSAGGP RTCAIASFVV SWISFLVAEV CLLAGSARNA   119
SEQ_ID_NO_529   LLMGLTKCMC FGAPLAPGGS RAWSIIYFAS SWVTFAIAEA CLIAGATKNA   121
SEQ_ID_NO_530   LLMVVTKCMC FGKPLAPGGS RAWSIIYFAS SWVTFMIAES CLIAGATKNA   149
SEQ_ID_NO_531   LLMVVTKCMC FGKPLAPGGS RAWSIIYFAS SWVTFMIAES CLIAGATKNA   121
SEQ_ID_NO_510   LLMSVTKCMC FGRPLAPGSD RAWSIIYFIS SWMTFLVAEA CVIAGATKNA   121
SEQ_ID_NO_525   LLMGVTKCMC FGRPLSPGSD RAWSIIYFIS SWMTFLVAEA CLIAGATKNA   121
SEQ_ID_NO_521   LXMGVTKCMC FGRPLTPGVN RAXSIXYFLS SWVTFXVAEA CLIAGATKNA   121
SEQ_ID_NO_513   LLMGVTKCMC FGRPLAPGSD RAWSIIYFVS SWLTFLVAEA CLIAGATRNA   121
SEQ_ID_NO_517   LLMGLTKCMC FGRSLAPGGD RAWAIIYFVS SWATFLVAEG CLIAGAKKNA   97
SEQ_ID_NO_511   LIMAASKCFC CGKGLNPSGS RAWAVILFIV CWLFFLIAEL CLLAGSVRNA   117
SEQ_ID_NO_523   VVMLASRCFC CGRGLKPGGS RACALMLFLF SWLTFLVAAA CLLAGSVRNA   117
```

Figure 15 (continued)

```
SEQ_ID_NO_527   YHTKYVGYYA KKDLSSCTAL RKGVFAAGAT FVLLSMISSL LYYWSYSKA-   168
SEQ_ID_NO_529   YHTKYRDMVY AGNW-TCQSL RKGVFIAGAV FVVFTMILDV YFYMYYAKA-   169
SEQ_ID_NO_530   YHTRYRHMVY VGSW-TCESL RKGVFIAGAV FVVFTMILNV YFYMYYTKS-   197
SEQ_ID_NO_531   YHTRYRHMVY VGSW-TCESL RKGVFIAGAV FVVFTMILNV YFYMYYTKS-   169
SEQ_ID_NO_510   YHTKY---LS SQTF-SCASL RKGIFIAGAV FIVATMVLNV YYYMYFTKSV   167
SEQ_ID_NO_525   YHTKY---LS AQAF-SCESL RKGIFIAGAV FTVATMILNV YYYFHFTKFV   167
SEQ_ID_NO_521   YHTKYRGMIY AHNF-SCEAL RKGXFIAGAV FVVATMILNV YYYMYFTKAM   170
SEQ_ID_NO_513   YHTKYRGMIY AQNF-SCETL RKGVFIAGAV FVVATMILNV YYYMYFAKAT   170
SEQ_ID_NO_517   YHTKYRGMIY AQNF-TCETL RKGVFIAGAV FVVATMILNV YYYMYFSKAT   146
SEQ_ID_NO_511   YHTKYRTIFS EQPP-SCETV RKGVFGAGAA FIFLNAIVNK FYYICYSSA-   165
SEQ_ID_NO_523   YHTRYRGIFN GDPL-SCETL RKGVFAAGAA FTFFTALLSE FYYISYSKS-   165

SEQ_ID_NO_527   -DMGGWVKHQ NEGGVGMAEF GPEKRGLGNT NG   199
SEQ_ID_NO_529   TSQAAKKISK TTPSVGMTGY A--------- --   190
SEQ_ID_NO_530   TSQAAKKINK TTPNVGMTGY A--------- --   218
SEQ_ID_NO_531   TSQAAKKLNK TTPNVGMTGY A--------- --   190
SEQ_ID_NO_510   SSPPAHKANR SSSNIGMAGY A--------- --   188
SEQ_ID_NO_525   FFPPTHKANR SGSNIGMAGY A--------- --   188
SEQ_ID_NO_521   TXPVXHKANR VSSTVGMAGY A--------- --   191
SEQ_ID_NO_513   TTMPAHKANR TNSTVGMTGY A--------- --   191
SEQ_ID_NO_517   ASKAAHKTNR TSS-VGMTGN P--------- --   166
SEQ_ID_NO_511   -RDKSFQAYG GETGVGMGTY K--------- --   185
SEQ_ID_NO_523   -RDAAGGAPY GGSSIGMGPY T--------- --   185
```

Figure 16 (continued)

```
SEQ_ID_NO_546   SNVN------ QNGVDNSKNS NDSDKVVADD VVTAGAGYV- ---------S   109
SEQ_ID_NO_542   SFPT------ ---SSSSPTS SFSSSRLTID DRASIGYLSD GL--------   86
SEQ_ID_NO_547   GVVH------ DSPGDTPDHP A-VGGGSADG YASEDFVAG- ----------   91
SEQ_ID_NO_533   RYHHRKGLIV DEAAAAATSP ANRDSHSSGS SEKKPNPGTS GIS------S   115
SEQ_ID_NO_539   NYAS------ DETTSSNKD- FHGSSKATSS DKRSNCNYGS GFSGLGLDST   113
SEQ_ID_NO_535   CYKG------ EEPSSSAKDY FHGPSMAPNS DRRSNSGYGN GFSGLTLDST   114
SEQ_ID_NO_538   NYEG------ EEAASSTKD- LHGLSGTMTT VKKLNCGYGS GFVGLGHESS   112
SEQ_ID_NO_553   RYAG------ EESAAPPDGA GAAAAASKDG GHRRDERKGG G--------G   123
SEQ_ID_NO_550   VYAG------ DGDEGGSGGG AGGSGGGGGG GGKKSGGGG- ---------G   118
SEQ_ID_NO_552   AYAA------ ---------- -DGAAEEGGG GGKKGSGGG- ---------G   104
SEQ_ID_NO_536   GYDL------ ----ASSFSF EFVDDRNFDV YRRKSSVG-- ----------   113
SEQ_ID_NO_543   GYSS------ ---SDAFTLE WFNNNQGYDG FRHYYTPGG- ----------   119
SEQ_ID_NO_548   GYST------ ----SSPFTL EWGSGHGFDG FKQSYGTGG- ----------   115

SEQ_ID_NO_546   ADDAVQHQ-- STGGRERKRG IPWTEEEHKL FLLGLQKVGK GDWRGISRNF   157
SEQ_ID_NO_542   ---------- IVRTQERKKG VPWTEEEHRK FLVGLEKLGK GDWRGISRNY   126
SEQ_ID_NO_547   ---------- SSSSRERKKG VPWTEEEHRM FLLGLQKLGK GDWRGIARNY   131
SEQ_ID_NO_533   SNGGRSGG-- SRAEQERRKG IPWTEEEHRL FLLGLDKFGK GDWRSISRNF   163
SEQ_ID_NO_539   THSSGKGGLS RSSEQERRKG IPWTEEEHRL FLLGLDKFGK GDWRSISRNF   163
SEQ_ID_NO_535   GHGGKQS--- SRSDQERRKG IPWTEEEHRL FLLGLDKFGK GDWRSISRNF   161
SEQ_ID_NO_538   GHGGKGA--- SRSEQERKKG IPWTEEEHRL FLLGLDKFGK GDWRSISRNF   159
SEQ_ID_NO_553   GYDGGKSC-- SKAEQERRKG IPWTEEEHRL FLLGLDKFGK GDWRSISRNF   171
SEQ_ID_NO_550   GHGEKGSS-- KSAEQERRKG IAWTEDEHRL FLLGLEKYGK GDWRSISRNF   166
SEQ_ID_NO_552   THGDKRSA-- KSAEQERRKG IAWTEDEHRL FLLGLEKYGK GDWRSISRNF   152
SEQ_ID_NO_536   ---------- RGSEHERKKG VPWTEEEHKQ FLRGLLKYGK GDWRNISRNF   153
SEQ_ID_NO_543   ----KRTTAA RSSEQERKKG VPWTEEEHRQ FLMGLQKYGK GDWRNISRNF   165
SEQ_ID_NO_548   ----RKSSSG RPSEQERKKG VPWTEEEHKL FLMGLKKYGK GDWRNISRNF   161
```

Figure 16 (continued)

```
SEQ_ID_NO_546   VKTRTPTQVA SHAQKYYLRK NNLNRRRRRS SLFDITTDSV PGGLPMDDVK   207
SEQ_ID_NO_542   VTTRTPTQVA SHAQKYFIRL ATLNKKKRRS SLFDMVGSGK TN-KTVD---   172
SEQ_ID_NO_547   VISRTPTQVA SHAQKYFIRQ SNMSRRKRRS SLFDIVADES GDTPMVSR--   179
SEQ_ID_NO_533   VISRTPTQVA SHAQKYFIRL NSMNRDRRRS SIHDITTVNN QA--------   205
SEQ_ID_NO_539   VISRTPTQVA SHAQKYFIRL NSMNRDRRRS SIHDITSVNN GD--------   205
SEQ_ID_NO_535   VISRTPTQVA SHAQKYFIRL NSMNRDRRRS SIHDITSVNN GD--------   203
SEQ_ID_NO_538   VISRTPTQVA SHAQKYFIRL NSMNRDRRRS SIHDITSLNN GD--------   201
SEQ_ID_NO_553   VISRTPTQVA SHAQKYFIRL NSMNRDRRRS SIHDITSVTA GDQV------   215
SEQ_ID_NO_550   VISRTPTQVA SHAQKYFIRL NSMNRERRRS SIHDITSVN- GE--------   207
SEQ_ID_NO_552   VISRTPTQVA SHAQKYFIRL NSMNRERRRS SIHDITSVNN GD--------   194
SEQ_ID_NO_536   VNSKTPTQVA SHAQKYFMRQ LSGGKDKRRP SIHDITTVNL TE--------   195
SEQ_ID_NO_543   VTTRTPTQVA SHAQKYFIRQ STGGKDERRS SIHDITTVNL PDTKS-----   210
SEQ_ID_NO_548   VITRTPTQVA SHAQKYFIRQ LSGGKDKRRA SIHDITTVNL SDNQTPS---   208

SEQ_ID_NO_546   NHQDKSVPKV LQHSQVPHAE KPNMNGYTIA PFPLAVGPIL LPVQVHNPME   257
SEQ_ID_NO_542   ---------- ------PNNS SKSKSGDSVC RHDHEVEKDA TLSL---LIN   203
SEQ_ID_NO_547   ---------- ------DFLA DDPAQAEMQS ----NNLLPP TPAVDEECES   209
SEQ_ID_NO_533   ---------- ------PAVT GGGQQPQVVK ----HRPAQP QPQP---Q--   230
SEQ_ID_NO_539   ---------- ------VASS QAPITGLHSS -----TISSN TMGV------   228
SEQ_ID_NO_535   ---------- -------TSH QAPITGQQAN --------TN SPGA---AVM   225
SEQ_ID_NO_538   ---------- ------VSSH QAPITGQQAN ----TSPAGP APAM------   225
SEQ_ID_NO_553   ---------- ------AAQQ GAPITGHQAT ----GNPAAA ALGP---PGM   242
SEQ_ID_NO_550   ---------- ------ASAA QGPITG---- ----TNGQAA VPGK---S--   228
SEQ_ID_NO_552   ---------- ------PSTA QGPITGQ--- ----TNGQAA NPGK---P--   216
SEQ_ID_NO_536   ---------- ------PTAS ENEKLSSMDQ ---FSKLPSL QKSP---CYQ   223
SEQ_ID_NO_543   ---------- ------PSPD EKKSSPDHST TSLQSQPQQK MVGM---A--   239
SEQ_ID_NO_548   ---------- ------PDNK KPPSSPDHSM ----AQQQTS STSI---H--   233
```

Figure 16 (continued)

```
SEQ_ID_NO_546    NKAFHWGDHQ L-QNGPGMLL RTVPFIPVAN S--------- -----SSAIR    292
SEQ_ID_NO_542    SLQQQTKSDD Y-DMQKIEDD SEEAEHKDVP D--------- -----WLHPL    238
SEQ_ID_NO_547    MGSAASANSI DGEHALPIPE SSQYQHPLVY PAYVAPFYPM PYPCWPGYTA    259
SEQ_ID_NO_533    PQPQQHHPPT --MAGLGMYG GAPVGQPIIA P--------- -----PDHMG    264
SEQ_ID_NO_539    GQSLKHRVQG HIPPGLGMYG T-PVGHPVAA P--------- -----PGHMA    263
SEQ_ID_NO_535    GQSVKHRAQP H-LPGLGMYG A-PVGRPIAA A--------- -----PGHIG    259
SEQ_ID_NO_538    GPPVKHRTQA H-MPGLAMYG P-PLGHPVAP P--------- -----PGHMA    259
SEQ_ID_NO_553    KHHHHHHPGG A-PPPMPMYS AAPMGHPVA- ---------- ------GHMV    274
SEQ_ID_NO_550    PKQSPHQPGN L-PPGVDAFG T-TIGQPVGG P--------- -----LV---    259
SEQ_ID_NO_552    SKQSP-QPAN T-PPGVDAYG T-TIGQPVGG P--------- -----LV---    246
SEQ_ID_NO_536    KLLFDWNRSS --NGGLLGLG S-NYGDRLMS F--------- -----PSGIA    256
SEQ_ID_NO_543    KGLIDWKPQN EGGGAAGVFS Q-ANGNLLMA P--------- -----LCGI-    273
SEQ_ID_NO_548    KLPFQWDQTS N-ETIMGFAS SGHHGNMFQS N--------- -----PFGM-    267

SEQ_ID_NO_546    DLNLN-QRV- ----EGEPSS P--------- --------LS LKLSLSSSDN    319
SEQ_ID_NO_542    TKSLN-MTLV I-PNSSNVAP P--------- --------DL ELTLAGSKSN    269
SEQ_ID_NO_547    EPAIAETHEV LKPIAVHSKS PINVDELVGM SKLSLGESIG DAAKPPSLSL    309
SEQ_ID_NO_533    -SAVG-TPVM LPPPMGTHHH H--------- --------HH HHLGVAPYAV    295
SEQ_ID_NO_539    -SAVG-TPVM LPPGPHPHPH P--------- --------HH HAHPHPPYVL    294
SEQ_ID_NO_535    -SAVG-TPVM L-PPAHHPHS P--------- ---------- -----PPYIV    282
SEQ_ID_NO_538    -SAVG-TPVM LPPPGHHPH- ---------- ---------- -----PPYVV    281
SEQ_ID_NO_553    PAAVG-TPVV F-PPGH---- ---------- ---------- -----APYVV    293
SEQ_ID_NO_550    -SAVG-TPVT L-PVAAPPHM G--------- --------YA MHAPVPGTVV    289
SEQ_ID_NO_552    -SAVG-TPVT L-PVSAPPHL A--------- --------YG MRAPVPGAVV    276
SEQ_ID_NO_536    ANGLK-N--- --EQDQELNS A--------- --------YY GTYSKPHKSI    283
SEQ_ID_NO_543    -SSYG-QRL- --QEQNLLRG T--------- --------LP GYQFAPYNLI    301
SEQ_ID_NO_548    -NSYG-FKM- --QGQQMQRG G--------- --------FC DTYLGSQNMA    295
```

Figure 16 (continued)

| | | | | | |
|---|---|---|---|---|---|
| SEQ_ID_NO_546 | SQSSSTRHST | GFQAMAATSF | SKGGDSIISV | A-- | 350 |
| SEQ_ID_NO_542 | NMEQDKTSSS | SFLIGPISVT | ---------- | --- | 289 |
| SEQ_ID_NO_547 | KLVEGSSRQS | AFHANPSSGS | SGMNSSHNPI | HAV | 342 |
| SEQ_ID_NO_533 | PA-------- | -YPVPPLPQQ | HPAPSTMH-- | --- | 314 |
| SEQ_ID_NO_539 | PLA------- | -YPMAPPTMH | Q--------- | --- | 307 |
| SEQ_ID_NO_535 | PVA------- | -YPMAPPPMH | Q--------- | --- | 295 |
| SEQ_ID_NO_538 | PVA------- | -YPTAPPKTA | ---------- | --- | 293 |
| SEQ_ID_NO_553 | PVG------- | -YPAPPAKMH | Q--------- | --- | 306 |
| SEQ_ID_NO_550 | PRAPM----- | -YPMPPPPSR | ---------- | --- | 303 |
| SEQ_ID_NO_552 | PGAPVNIAPM | PYPMPPPPSH | G--------- | --- | 297 |
| SEQ_ID_NO_536 | ---------- | -FQFEPSRYQ | IYG------- | --- | 295 |
| SEQ_ID_NO_543 | ---------- | -FQMQPMQRQ | ---------- | --- | 310 |
| SEQ_ID_NO_548 | ---------- | -FQMQSGLHF | PNA------- | --- | 307 |

Figure 17 (continued)

```
SEQ_ID_NO_559   GWCPTVGTGG HISGGGFGMM SRKYGLAADN VVDAILIDAN GAILDRQAMG   213
SEQ_ID_NO_586   GYCPTVGSGG HISGGGFGMM SRKYGLAADN VIDALIVDAN GAVLDRSSMG   209
SEQ_ID_NO_591   GYCPTGGSGG HIAPGGFGMM SRKYGLAADN VVDALLVDAN GVVLDRESMG   210
SEQ_ID_NO_581   GSCPTMGVGG HLSGGGFGSL ARKYGLSADN VLDAVVVDAD GRLVNRSTMG   229
SEQ_ID_NO_588   GVCPTVGVGG HLGGGGFGTL MRRYGLAADN VLDAVLVDAD GRLLNRTTMG   224
SEQ_ID_NO_589   GVCPTIGVGG HFSGGGFGML LRKFGLASDN VLDVKVVDAN GKVQDRKSMG   223
SEQ_ID_NO_590   GVCPTIGVGG HFSGGGFGML LRKFGLASDN VLDVKVVDAN GKVQDRKSMG   228
SEQ_ID_NO_584   GVCPTIGVGG NFAGGGFGML LRKYGIAAEN VIDVKLVDAN GKLHDKKSMG   222
SEQ_ID_NO_583   GVCATIGVGG HFSGGGFGML LRKYGTAGDN VIDAKVVDAN GTLLDRKSMG   227
SEQ_ID_NO_585   GVCTTIGVGG HFSGGGFGML LRKYGTAADN VIDAKVVDAQ GRLLDRKAMG   224
SEQ_ID_NO_560   GYCPTVGVGG HFSGGGYGAL MRNYGLAADN IIDAHLVNVD GKVLDRKSMG   223
SEQ_ID_NO_577   GVCYSVGAGG HISGGGYGFL MRKYGLAADN VIDAHIIDVN GNLLDRKAMG   218
SEQ_ID_NO_569   GVCPTVGVGG HLSGAGYGTL IRKYGLSVDH VVDAKLVDVN GKILDRKTMG   221
SEQ_ID_NO_575   GACPTVGVGG HLSGGGYGNM IRKYGLSVDH VVDAKIVDVK GRILDKESMG   225
SEQ_ID_NO_576   GVCETLGAGG HFSGGGYGNL MRKFGLSVDN IIDAKMVDVK GNILDRKSMG   216
SEQ_ID_NO_578   GVCPTVGVGG HFSGGGYGNL MRKYGLSVDN IVDAQIIDVN GKLLDRKSMG   228
SEQ_ID_NO_579   GVCPTVGVGG HFSGGGYGNL MGKYGLSVDN IVDAQLIDVN GKLLNRKSMG   227
SEQ_ID_NO_558   GICPGLGAGG HFSGGGYGNM MRKYGLSIDN IIDAKIVDAK GKVLDRSSMG   224
SEQ_ID_NO_571   GVCPTLGVGG HFSGGGYGNM MRKYGLSVDN IVDAQIIDVR GRILDRKSMG   216

SEQ_ID_NO_559   EDVFWAIRGG GGGVWGAIYA WKIKLLPVPE KVTVFRVTKN VAIDE--ATS   261
SEQ_ID_NO_586   EDVFWAIRGG GGGVWGAIYA WKLQLLPVPK QVTVFKLMKN FDNIE-EASK   258
SEQ_ID_NO_591   EDVFWAIRGG GGGVWGAVYA WKLQLVPVPK NVTIFRLMKH SEVED--ASK   258
SEQ_ID_NO_581   EDHFWALCGG GGESFGVVLS WKVRLVPVPE TVTVFSIVRS RSQS---AVE   276
SEQ_ID_NO_588   EDLFWAIRGG GGESFGVVLS WKLRLVPVPE TVTVFTVRRS RNQS---ASE   271
SEQ_ID_NO_589   EDYLWAVRGG GGSSFGIVVS WKLRLLPVPA TVTVIQMPKM VNEG---AVD   270
SEQ_ID_NO_590   EDYLWAVRGG GGSSFGIVVS WKLRLLPVPA TVTVIQMPKM VNEG---AVD   275
SEQ_ID_NO_584   DDHFWAVRGG GGESFGIVVA WQVKLLPVPP TVTIFKISKT VSEG---AVD   269
SEQ_ID_NO_583   EDYFWAIRGG GGESFGIMVS WQVQLVPVPP KVTVFQIHRG VKDG---AID   274
SEQ_ID_NO_585   EDHFWAIRGG GGESFGIVAS WQVKLLPVPP KVTVFQVHKG IKEG---AID   271
SEQ_ID_NO_560   EDLFWAIRGG GGENFGIIAA WKIKLVVVPS KATIFSVKKN MEIHG--LVK   271
SEQ_ID_NO_577   EDLFWAIRGG GGASFGVIVS WKIKLVPVPS TVTVFNVERI LEEN---ATE   265
SEQ_ID_NO_569   EDLFWAIRGG GAASFGVVLS YKIKLVPVPE TVTVFRIERL LTEN---ATD   268
SEQ_ID_NO_575   EDLFWAIRGG GGASFGVILS YTVKLVPVPE NVTVFQIDKT LEEN---ATD   272
SEQ_ID_NO_576   EDLFWAIRGG GGASFGVILS WKLQLVPVTP QVLVFDVKRN VSEG---ATD   263
SEQ_ID_NO_578   EDLFWAITGG GGVSFGVVLA YKIKLVRVPE VVTVFTIERR EEQN---LST   275
SEQ_ID_NO_579   EDLFWAITGG GGVSFGVVVA YKIKLVRVPT TVTVFNVQRT SEQN---LST   274
SEQ_ID_NO_558   EDLFWALRGG GAASFCVVLA WKIKLVPVPA KVTVFNIETF GNTGSVNTTE   274
SEQ_ID_NO_571   EDLFWAIRGG GAASFGVILS WKIKLVPVPE IVTVFSVDRT LEEG---VSD   263
```

Figure 17 (continued)

```
SEQ_ID_NO_559   LLHKWQFV-A EELEEDFTLS VLGGADEK-- -------QVW LTMLGFHFGL   301
SEQ_ID_NO_586   MLHKWQVV-A PALEDDFTLS VLAGADTN-- -------GIW FSFLGLYLGP   298
SEQ_ID_NO_591   LLHKWQLV-A PKLEDDFSLA VLAGTNKDS- -------SIW LTFLGLYLGP   299
SEQ_ID_NO_581   LITKWQEM-A PASPQELYLR VLVL------ -------NQQ ANFQALFLGR   312
SEQ_ID_NO_588   LITKWQEI-A PALPRDLILR VVVQ------ -------GRH AQFEALFLGR   307
SEQ_ID_NO_589   LLTKWQSL-A PTFPEDLMIR VMAQ------ -------AQK AVFEGLYLGT   306
SEQ_ID_NO_590   LLTKWQSL-A PTFPEDLMIR VMAQ------ -------AQK AVFEGLYLGT   311
SEQ_ID_NO_584   IINKWQVV-A PQLPADLMIR IIAQ------ -------GPK ATFEAMYLGT   305
SEQ_ID_NO_583   LINKWQQV-A PSLPDDLMIR IMAM------ -------EQD AMFEALYLGT   310
SEQ_ID_NO_585   LVTKWQTV-A PALPDDLMIR IMAM------ -------GQG AMFEALYLGT   307
SEQ_ID_NO_560   LFNKWQNI-A YKYDKDLMLT THFRTRNITD NHGKNKTTVH GYFSSIFLGG   320
SEQ_ID_NO_577   IIEKWQLV-A NKLDERIFLR MDLARANSS- QHGKL--ALQ ANFVAMFQGG   311
SEQ_ID_NO_569   ITFKWQTI-A PTTDENLFMR MLLQPVTRN- --KKK--TAR ISVIALYLGD   312
SEQ_ID_NO_575   LVVQWQKV-A PHTDDRLYLR LVLQPVSSNF VKGKK--TIR ASVEALFLGE   319
SEQ_ID_NO_576   IVYKWQLI-A PKLHKDLFIR AQPNVVQIG- QEGKK--VVQ ISFIGQFLGK   309
SEQ_ID_NO_578   IAERWVQV-A DKLDRDLFLR MTFSVINDT- NGG-K--TVR AIFPTLYLGN   320
SEQ_ID_NO_579   IAHRWIQV-A DKLDNDLFLR MTFNVINNT- NGE-K--TIR GLFPTLYLGN   319
SEQ_ID_NO_558   LVAKWQEI-A DKIDNDLFIR LTLGSSNK-- -------TVK ASFMGMYLGN   314
SEQ_ID_NO_571   LAWKWQQIAA DKLDNDLFIR LMLQPVNGT- QEGKK--TIQ ASFVAMFLGR   310

SEQ_ID_NO_559   KTVAKSTFDL LFPELGLVEE DYLEMSWGES FAYLAGLE-- -----TVSQL   344
SEQ_ID_NO_586   KELAISSVDQ NFPELNLVME DCKEMSWVES FAHLAGLN-- -----SVEEM   341
SEQ_ID_NO_591   KELASSSMHK KFPELNLLLE DCMEMSWVEA TAELAGLK-- -----SVSEL   342
SEQ_ID_NO_581   CGGLHRLMQD RFPELGMTEQ DCEEVSWVQS TAFFGFSTTS V----PPEQL   358
SEQ_ID_NO_588   CSRVLEHMRA HFPELGVARA DCEEISWIQS TVYFAFYSSS K----PPELL   353
SEQ_ID_NO_589   CDALLPLVTS RFPELGVNRS HCNEMSWVQS IAFIHLGKNA T-----VKDI   351
SEQ_ID_NO_590   CDALLPLVTS RFPELGVNRS HCNEMSWVQS IAFIHLGKNA T-----VKDI   356
SEQ_ID_NO_584   CKTLTPLMSS KFPELGMNPS HCNEMSWIQS IPFVHLGHRD A----LEDDL   351
SEQ_ID_NO_583   CKDLLPLMAS RFPELGVKQE DCNEMPWIQS VAFIPMGKSA T-----VMDL   355
SEQ_ID_NO_585   CKDLVLLMTA RFPELGMNAT HCKEMTWIES VPYIPMGPKG T-----VRDL   352
SEQ_ID_NO_560   VDSLVDLMNK SFPELGIKKT DCKELSWIDT TIFYSGVVNY NTANFKKEIL   370
SEQ_ID_NO_577   VEELIPLMQK NFPELGLKRK DCTETSWIGS AVFTNGALIG SSGHEAPEVL   361
SEQ_ID_NO_569   SDSLVSLLQK DFPELSIGKS NCNETTWIDS VLWWANFNLG T----PPTAL   358
SEQ_ID_NO_575   ADELVKLLGQ EFPLLGLKKE LCHEMRWIDS VVWWANYNDG S----SVNAL   365
SEQ_ID_NO_576   IERLLTLMNK EFPELGLNKS DCFSMPWINS TLFWYGEPIG T----PLEVL   355
SEQ_ID_NO_578   SRNLVTLLNK DFPELGLQES DCTEMSWVES VLYYTGFPSG T----PTTAL   366
SEQ_ID_NO_579   STALVALLNK DFPELGVEIS DCIEMSWIES VLFYTNFPIG T----PTTAL   365
SEQ_ID_NO_558   SSNLLEIMNA KFPELGLIKR ECIEMKWIES VLFWLGIPPG TA---PTTSM   361
SEQ_ID_NO_571   AERLLSVMNE SFPELGLQAK DCAEMRWIES VLSWVGMPKG T----PLEVL   356
```

Figure 17 (continued)

| | | | | | | |
|---|---|---|---|---|---|---|
| SEQ_ID_NO_559 | NNRFLKFDER | AFKTKVDLTK | EPLPSKAFYG | LL-ERLSK-- | EPNGFIALNG | 391 |
| SEQ_ID_NO_586 | NNRFLKYDDR | AFKTKVDFVK | EPIPLEGIKG | AL-TMLTK-- | ELRGFMAFNG | 388 |
| SEQ_ID_NO_591 | KDRFLRYDDR | AFKTKVDFPK | EAIPLEGIQG | AL-EILKK-- | EQRGFMVMNG | 389 |
| SEQ_ID_NO_581 | LNR-SSNPSY | YLKAKSDHVQ | EPIPRDVWES | IWTTWLEK-- | PEAALLMLDP | 405 |
| SEQ_ID_NO_588 | LDR-IGETGR | YVKAKSDYVQ | EPIPRHAWES | TW-SWLEK-- | PEAGLLILDP | 399 |
| SEQ_ID_NO_589 | LNR-TSSIRA | FGKYKSDYVT | QPLSKATWDT | IYKDWFSK-- | PGSGIMIMDP | 398 |
| SEQ_ID_NO_590 | LNR-TSSIRA | FGKYKSDYVT | QPLSKATWDT | IYKDWFSK-- | PGSGIMIMDP | 403 |
| SEQ_ID_NO_584 | LNR-NNSFKP | FAEYKSDYVY | QPFPKTVWEQ | ILNTWLVK-- | PGAGIMIFDP | 398 |
| SEQ_ID_NO_583 | LNR-TSNIKA | FGKYKSDYVK | DPIPRDVWEK | IY-TWLAK-- | PGAGVMIMDP | 401 |
| SEQ_ID_NO_585 | LNR-TSNIKA | FGKYKSDYVL | EPIPKSDWEK | IF-TWLVK-- | PGAGVMIMDP | 398 |
| SEQ_ID_NO_560 | LDR-SAGKKT | AFSIKLDYVK | KLIPETAMVK | IL-EKLYEEE | VGVGMYVLYP | 418 |
| SEQ_ID_NO_577 | LNR-TQIRSG | KYKGKSDYVR | KPIPVDGLRG | LW-RWLNDDK | VQYSQLQFAP | 409 |
| SEQ_ID_NO_569 | LDR-DLNDAG | FLKRKSDYVQ | TPIPKSGLES | LW-QKMIE-- | LGKVGMVFNA | 404 |
| SEQ_ID_NO_575 | LDR-NHYSVH | SNKRKSDYVQ | TPISKDGFTW | IW-KKMIE-- | LGKVSIVFNP | 411 |
| SEQ_ID_NO_576 | LDEPKDPQPL | YQKNKSDYVK | KPIPREALES | IW-KLMIE-- | GENFLMQWNP | 402 |
| SEQ_ID_NO_578 | LSR-TPQRLN | PFKIKSDYVQ | NPISKRQFEF | IF-ERMKE-- | LENQMLAFNP | 412 |
| SEQ_ID_NO_579 | LSR-TPQRLN | PFKIKSDYVK | NTISKQGFES | IF-ERMKE-- | LENQMLAFNP | 411 |
| SEQ_ID_NO_558 | RNR-IPQKQI | YLKRKSDYVQ | KPISRTGLES | IF-KIMTE-- | NENVTMAFNP | 407 |
| SEQ_ID_NO_571 | LDR-IPKGVS | YLKRKSDYVK | EPISKEGLES | IW-KVMTE-- | VGEVAMLWNP | 402 |

| | | | | | | |
|---|---|---|---|---|---|---|
| SEQ_ID_NO_559 | FGGQMSKISS | DFTPFPHRSG | TRLMVEYIVA | WNQSEQKKKT | EFLDWLEKVY | 441 |
| SEQ_ID_NO_586 | QGGLMSRISS | DSTPFPHRKG | TLMMMEYIVA | WDRDEDAKSY | EFIGWLHGFY | 438 |
| SEQ_ID_NO_591 | QGGMMDRIST | DASPFPHRSG | TLSMVEYIVA | WDKHEDLHSN | EFIHWLHQLF | 439 |
| SEQ_ID_NO_581 | YGGVMSSIPP | SETPFPHRQG | NLYQLQYYSF | WYENGTAAAE | KRMSWVRGLY | 455 |
| SEQ_ID_NO_588 | YGGRMASISP | SATPFPHRKG | NLYNLQYYSF | WFENGTAAME | KRMNWVRGLY | 449 |
| SEQ_ID_NO_589 | YGATISKPGE | ADTPFPHRKG | MLYNIQYITF | WFGEGAPAEA | -PIKWIRDFY | 447 |
| SEQ_ID_NO_590 | YGATISKPGE | ADTPFPHRKG | MLYNIQYITF | WFGEGAPAEA | -PIKWIRDFY | 452 |
| SEQ_ID_NO_584 | YGATISATPE | SATPFPHRKG | VLFNIQYVNY | WFAPGAAAA- | -PLSWSKDIY | 446 |
| SEQ_ID_NO_583 | YGARISSIPQ | DATPFPHRQG | VLFNIQYVSY | WFGEGDGAA- | -PTQWSRDMY | 449 |
| SEQ_ID_NO_585 | YGGGIASVPE | SATPFPRRSG | VLFNIQYVVY | WFGEGAAAL- | -PTQWTRDIY | 446 |
| SEQ_ID_NO_560 | YGGLMDEISE | SAIPFPHRAG | IMYELWYTAT | WEKQEDNEK- | -HINWVRSVY | 466 |
| SEQ_ID_NO_577 | YGGKMDNISE | SEIPFAHRSG | YIFHIHYVVV | WQEEGDEATQ | RHVNWIRRLY | 459 |
| SEQ_ID_NO_569 | YGGRMDQIKP | DETPFPHRAG | NLYKIQYSVN | WDQPGSEADK | NFTTQAKLLH | 454 |
| SEQ_ID_NO_575 | YGGKMNEVPS | DATPFPHRAG | NLYKIQYTVS | WQEPGAAVEK | SFLSQIRVLH | 461 |
| SEQ_ID_NO_576 | YGGRMEEILP | SETPFSHRAG | NLFLIQYLNI | WSNESSEVSE | RHVNFSRSFF | 452 |
| SEQ_ID_NO_578 | YGGRMSEISE | FAKPFPHRSG | NIAKIQYEVN | WEDLSDEAEN | RYLNFTRLMY | 462 |
| SEQ_ID_NO_579 | YGGRMSEISE | FAKPFPHRSG | NIAKIQYEVN | WDELGVEAAN | RYLNFTRVMY | 461 |
| SEQ_ID_NO_558 | YGGRMSEIPS | TETAFPHRAG | NMFKIQYAAN | WFVPGEAVAK | DCLSQTERLF | 457 |
| SEQ_ID_NO_571 | YGGKMSEISE | TETAFPHRAG | NIFKIQYSVN | WKQEGIDTTN | HYVNLTRTLF | 452 |

Figure 17 (continued)

```
SEQ_ID_NO_559   EFMKPFVSKN PRLGYVNHID LDLGGIDW-- -GNKTVVNN- AIEISRS-WG   486
SEQ_ID_NO_586   NYMGQFLPSD PRIAYVNHVD LDLGRLDW-- -TNSTIASN- AIEIART-WG   483
SEQ_ID_NO_591   DYMGKFVSNN PRVGYVNHVD LDLGRIDW-- -VNKTISSGR AIEIART-WG   485
SEQ_ID_NO_581   KEMEPYVSKN PRAVYVNYRD LDLGTNELD- -GDVT----- SYEKARVSWG   498
SEQ_ID_NO_588   REMEPYVSKN PRTGYVNYRD LDLGTNELE- -GNVT----- SYAKARI-WG   491
SEQ_ID_NO_589   AFMEPYVTKN PRQAYVNYRD LDLGVNAVEA GANVS----- CYQVGKV-WG   491
SEQ_ID_NO_590   AFMEPYVTKN PRQAYVNYRD LDLGVNAVEA GANVS----- CYQVGKV-WG   496
SEQ_ID_NO_584   NYMEPYVSKN PRQAYANYRD IDLGRNEVV- -NDVS----- TYASGKV-WG   488
SEQ_ID_NO_583   AFMEPYVSKN PRQAYANYRD LDLGVNEVV- -GDVS----- TYDSGRV-WG   491
SEQ_ID_NO_585   DFMTPYVSKN PRQAYVNYRD LDLGVNQVV- -GNVS----- TYASGKV-WG   488
SEQ_ID_NO_560   NFTTPYVSQN PRLAYLNYRD LDLGKTNP-- -ESPN----- NYTQARI-WG   507
SEQ_ID_NO_577   KYMEPYVSNS PRAAYVNYRD LDIGVNN--- -NGYT----- SYHQASI-WG   499
SEQ_ID_NO_569   DFMTPFVSKN PRSAYFNYRD IDVG--S--- -TKKW----- SYEEGKV-YG   492
SEQ_ID_NO_575   NYMTPFVSKN PRSAYFNYRD LDIGINS--- -HGKD----- NFEDGKV-YG   501
SEQ_ID_NO_576   EFMTPYVSTS PREAFLNYRD ADIGANHP-- -SNVT----- RFDIAKT-YG   493
SEQ_ID_NO_578   DYMTPFVSKN PREAFLNYRD LDIGINS--- -HGRN----- AYTEGMV-YG   502
SEQ_ID_NO_579   DYMTPFVSKN PREAFLNYRD LDIGVNS--- -HGKN----- AYGEGMV-YG   501
SEQ_ID_NO_558   EAMSPYVSKN PREAFLNYRD VDIGK----- -SLNS----- TYEEGKV-YG   495
SEQ_ID_NO_571   EAMTPYVSKN PREAFLNYRD IDIGSIGS-- -HGNG----- TFQEASV-YG   493

SEQ_ID_NO_559   ESYFLS-NYE RLIRAKTLID PNNVFNHPQS IPPMANFDYL EKTLGSDGGE   535
SEQ_ID_NO_586   EKYFLS-NYE RLVRAKTLID PKNVFHHPQS IPPMPQDDLR PNGIWRTEEM   532
SEQ_ID_NO_591   EKYFMS-NYD RLVRAKTMID PKNVFNHPQS IPPLLEIMLD NVKENDVIYK   534
SEQ_ID_NO_581   DKYFKG-NFK RLAAVKTMVD PHDFFRNEQS IPPLPTAKMM IDSI------   541
SEQ_ID_NO_588   EKYFRG-NFE RLAAVKAMVD PDDFFRNEQS IPPLPAAKGW SSI-------   533
SEQ_ID_NO_589   EKYFKG-NFE RLARTKAKVD PTDFFRNEQS IPPLLA---- ----------   526
SEQ_ID_NO_590   EKYFKG-NFE RLARTKAKVD PTDFFRNEQS IPPLLA---- ----------   531
SEQ_ID_NO_584   QKYFKG-NFE RLAITKGKVD PTDYFRNEQS IPPLIKKY-- ----------   525
SEQ_ID_NO_583   EKYYNG-NFE RLARTKAKVD PCDYFRNEQS IPPLLK---- ----------   526
SEQ_ID_NO_585   EKYFKG-NFE RLARTKGKID PEDYFRNEQS IPPLL----- ----------   522
SEQ_ID_NO_560   EKYFGK-NFN RLVKVKTKAD PNNFFRNEQS IPPLPPHHH- ----------   545
SEQ_ID_NO_577   LKYFSN-NFK RLATVKTKVD PHNFFRNEQS IPTLSKE--- ----------   535
SEQ_ID_NO_569   ESYFNG-NYE RLVDVKTAVD ANNFFRNEQS IPPRSSKI-- ----------   529
SEQ_ID_NO_575   IKYFNK-NFE RLVKVKSAID PENFFWNEQS IPTYPRSNA- ----------   539
SEQ_ID_NO_576   SKFFKG-NFE RLVSVKTKVD PQNFFRYEQS IPTRSL---- ----------   528
SEQ_ID_NO_578   HKYFKETNYK RLVSVKTKVD PDNFFRNEQS IPTLSS---- ----------   538
SEQ_ID_NO_579   HKYFKETNYK RLTMVKTRVD PSNFFRNEQS IPTLSSSWK- ----------   540
SEQ_ID_NO_558   FKYFKD-NFE KLVKIKSRVD PDNFFRYEQS IPVLSSH--- ----------   531
SEQ_ID_NO_571   HKYFKD-NFD RLVQIKTRVD PDNFFGYEQS IPTQSSSYRP DLCAWQQPRK   542
```

Figure 17 (continued)

| | | | | | | |
|---|---|---|---|---|---|---|
| SEQ_ID_NO_559 | VVI------- | ---------- | ---------- | ---------- | ---------- | 538 |
| SEQ_ID_NO_586 | FFLE------ | ---------- | ---------- | ---------- | ---------- | 536 |
| SEQ_ID_NO_591 | L--------- | ---------- | ---------- | ---------- | ---------- | 535 |
| SEQ_ID_NO_581 | ---------- | ---------- | ---------- | ---------- | ---------- | 541 |
| SEQ_ID_NO_588 | ---------- | ---------- | ---------- | ---------- | ---------- | 533 |
| SEQ_ID_NO_589 | ---------- | ---------- | ---------- | ---------- | ---------- | 526 |
| SEQ_ID_NO_590 | ---------- | ---------- | ---------- | ---------- | ---------- | 531 |
| SEQ_ID_NO_584 | ---------- | ---------- | ---------- | ---------- | ---------- | 525 |
| SEQ_ID_NO_583 | ---------- | ---------- | ---------- | ---------- | ---------- | 526 |
| SEQ_ID_NO_585 | ---------- | ---------- | ---------- | ---------- | ---------- | 522 |
| SEQ_ID_NO_560 | ---------- | ---------- | ---------- | ---------- | ---------- | 545 |
| SEQ_ID_NO_577 | ---------- | ---------- | ---------- | ---------- | ---------- | 535 |
| SEQ_ID_NO_569 | ---------- | ---------- | ---------- | ---------- | ---------- | 529 |
| SEQ_ID_NO_575 | ---------- | ---------- | ---------- | ---------- | ---------- | 539 |
| SEQ_ID_NO_576 | ---------- | ---------- | ---------- | ---------- | ---------- | 528 |
| SEQ_ID_NO_578 | ---------- | ---------- | ---------- | ---------- | ---------- | 538 |
| SEQ_ID_NO_579 | ---------- | ---------- | ---------- | ---------- | ---------- | 540 |
| SEQ_ID_NO_558 | ---------- | ---------- | ---------- | ---------- | ---------- | 531 |
| SEQ_ID_NO_571 | RTLGARTSER | AWQQHQAADT | WRRAVMPYGL | GKLARLAKHP | KRRFTGPPAW | 592 |

| | | | | | | |
|---|---|---|---|---|---|---|
| SEQ_ID_NO_559 | ---------- | ---------- | ---------- | ---------- | ---------- | 538 |
| SEQ_ID_NO_586 | ---------- | ---------- | ---------- | ---------- | ---------- | 536 |
| SEQ_ID_NO_591 | ---------- | ---------- | ---------- | ---------- | ---------- | 535 |
| SEQ_ID_NO_581 | ---------- | ---------- | ---------- | ---------- | ---------- | 541 |
| SEQ_ID_NO_588 | ---------- | ---------- | ---------- | ---------- | ---------- | 533 |
| SEQ_ID_NO_589 | ---------- | ---------- | ---------- | ---------- | ---------- | 526 |
| SEQ_ID_NO_590 | ---------- | ---------- | ---------- | ---------- | ---------- | 531 |
| SEQ_ID_NO_584 | ---------- | ---------- | ---------- | ---------- | ---------- | 525 |
| SEQ_ID_NO_583 | ---------- | ---------- | ---------- | ---------- | ---------- | 526 |
| SEQ_ID_NO_585 | ---------- | ---------- | ---------- | ---------- | ---------- | 522 |
| SEQ_ID_NO_560 | ---------- | ---------- | ---------- | ---------- | ---------- | 545 |
| SEQ_ID_NO_577 | ---------- | ---------- | ---------- | ---------- | ---------- | 535 |
| SEQ_ID_NO_569 | ---------- | ---------- | ---------- | ---------- | ---------- | 529 |
| SEQ_ID_NO_575 | ---------- | ---------- | ---------- | ---------- | ---------- | 539 |
| SEQ_ID_NO_576 | ---------- | ---------- | ---------- | ---------- | ---------- | 528 |
| SEQ_ID_NO_578 | ---------- | ---------- | ---------- | ---------- | ---------- | 538 |
| SEQ_ID_NO_579 | ---------- | ---------- | ---------- | ---------- | ---------- | 540 |
| SEQ_ID_NO_558 | ---------- | ---------- | ---------- | ---------- | ---------- | 531 |
| SEQ_ID_NO_571 | VCRHVLWVQT | PTSGSAATRA | WGMCPALLTL | QTWALGADSH | ARVNCDPHLS | 642 |

Figure 17 (continued)

| | | | | | | |
|---|---|---|---|---|---|---|
| SEQ_ID_NO_559 | ---------- | ---------- | ---------- | ---------- | ---------- | 538 |
| SEQ_ID_NO_586 | ---------- | ---------- | ---------- | ---------- | ---------- | 536 |
| SEQ_ID_NO_591 | ---------- | ---------- | ---------- | ---------- | ---------- | 535 |
| SEQ_ID_NO_581 | ---------- | ---------- | ---------- | ---------- | ---------- | 541 |
| SEQ_ID_NO_588 | ---------- | ---------- | ---------- | ---------- | ---------- | 533 |
| SEQ_ID_NO_589 | ---------- | ---------- | ---------- | ---------- | ---------- | 526 |
| SEQ_ID_NO_590 | ---------- | ---------- | ---------- | ---------- | ---------- | 531 |
| SEQ_ID_NO_584 | ---------- | ---------- | ---------- | ---------- | ---------- | 525 |
| SEQ_ID_NO_583 | ---------- | ---------- | ---------- | ---------- | ---------- | 526 |
| SEQ_ID_NO_585 | ---------- | ---------- | ---------- | ---------- | ---------- | 522 |
| SEQ_ID_NO_560 | ---------- | ---------- | ---------- | ---------- | ---------- | 545 |
| SEQ_ID_NO_577 | ---------- | ---------- | ---------- | ---------- | ---------- | 535 |
| SEQ_ID_NO_569 | ---------- | ---------- | ---------- | ---------- | ---------- | 529 |
| SEQ_ID_NO_575 | ---------- | ---------- | ---------- | ---------- | ---------- | 539 |
| SEQ_ID_NO_576 | ---------- | ---------- | ---------- | ---------- | ---------- | 528 |
| SEQ_ID_NO_578 | ---------- | ---------- | ---------- | ---------- | ---------- | 538 |
| SEQ_ID_NO_579 | ---------- | ---------- | ---------- | ---------- | ---------- | 540 |
| SEQ_ID_NO_558 | ---------- | ---------- | ---------- | ---------- | ---------- | 531 |
| SEQ_ID_NO_571 | RTQEEYIKLG | PAQQDPFKLG | SALEGPKIAR | LDPLALALVA | LMGPVLSKTH | 692 |

| | | | |
|---|---|---|---|
| SEQ_ID_NO_559 | ---------- | - | 538 |
| SEQ_ID_NO_586 | ---------- | - | 536 |
| SEQ_ID_NO_591 | ---------- | - | 535 |
| SEQ_ID_NO_581 | ---------- | - | 541 |
| SEQ_ID_NO_588 | ---------- | - | 533 |
| SEQ_ID_NO_589 | ---------- | - | 526 |
| SEQ_ID_NO_590 | ---------- | - | 531 |
| SEQ_ID_NO_584 | ---------- | - | 525 |
| SEQ_ID_NO_583 | ---------- | - | 526 |
| SEQ_ID_NO_585 | ---------- | - | 522 |
| SEQ_ID_NO_560 | ---------- | - | 545 |
| SEQ_ID_NO_577 | ---------- | - | 535 |
| SEQ_ID_NO_569 | ---------- | - | 529 |
| SEQ_ID_NO_575 | ---------- | - | 539 |
| SEQ_ID_NO_576 | ---------- | - | 528 |
| SEQ_ID_NO_578 | ---------- | - | 538 |
| SEQ_ID_NO_579 | ---------- | - | 540 |
| SEQ_ID_NO_558 | ---------- | - | 531 |
| SEQ_ID_NO_571 | QRSLKKKISL | M | 703 |

Figure 18

```
SEQ_ID_NO_603   MAAAT--SSS AVAVSTPQGV AERRGIPAAS FVEDVETYLR QAGLEVNSAL  48
SEQ_ID_NO_605   MAAAA----- --SASTPQGV AERRGIPAAA FVEDVEAYLR QAGLDVNSAL  43
SEQ_ID_NO_610   MAAAAASSSS SSAAATPQGV TERRGIPAAS FVEDVETYLR QAGLDVNSGL  50
SEQ_ID_NO_593   MSSSS----- --PSGSGSDL TERRGIPAAK FIQDVETYLS QSGLDPNSAL  43
SEQ_ID_NO_595   MASSS---S TAVATATETT TERRGIPGAQ FVEDVETYLN QSGLDVNSAL  46
SEQ_ID_NO_599   MASSS----- -----SESAV SERRGIPGAQ FVEDVQTYLT QSGLDVGSAL  40

SEQ_ID_NO_603   AFLQERLQQY KMVEMKLLAQ QRELQAKIPD IEKCLDIVAT LKAKKALGEA  98
SEQ_ID_NO_605   AFLQERLQQY KIVEMKLLAQ QRDLQAKIPD IEKCLDIVST LQAKKDLGEA  93
SEQ_ID_NO_610   AFLQERLQQY KIVEMKLLAQ QRDLQAKIPD IEKCLDIVAT LQAKKALGEA  100
SEQ_ID_NO_593   AFHQERLQQY KVVEMKLLAQ QRDLQAKIPD IEKCLEVVAT LEAKKGTGEA  93
SEQ_ID_NO_595   SFLQERLQQY KLVEMKLLAQ QRDLQAKIPD IEKCLDVVAT LQAKKGTGEP  96
SEQ_ID_NO_599   AFLQERLQQY KVVEMKLLAQ QRDLQAKIPD IEKCLDVVAT LKAKKGTGEE  90

SEQ_ID_NO_603   LIADFELSEG IYSRAKIEDS DSVCLWLGAN VMLEYSCDEA NELLKSNLEN  148
SEQ_ID_NO_605   LIADFELSEG IYSCAKIEDT DSVCLWLGAN VMLEYSCDEA NALLKKNLEN  143
SEQ_ID_NO_610   LTADFELSEG IYSRAKIEDT DSVCLWLGAN VMLEYSCDEA NALLKKNLEN  150
SEQ_ID_NO_593   LLADFEVSEG IYSRACIEDT DSVCLWLGAN VMLEYSCEEA SALLKNNLEN  143
SEQ_ID_NO_595   LIADFEVSEG IYSQARIEDA ESVCLWLGAN VMLEYSCEEA NDLLQKNLDN  146
SEQ_ID_NO_599   LIADFEVSEG IYSRARIEET NSVCLWLGAN VMLEYSLEEA TGLLQKNLDN  140

SEQ_ID_NO_603   ARASLEVLVG DLHFLRDQQT ITQVTIARIF NWDVHQ-RRS KQ----SVM  192
SEQ_ID_NO_605   AKASLEVLVA DLQFLRDQQT ITQVTIARVF NWDVHH-RRS KQ-----AV  186
SEQ_ID_NO_610   AKASLEVLVA DLQFLRDQQT ITQVTIARVF NWDVHQ-RRS KQ-----AI  193
SEQ_ID_NO_593   AKASLEVLVA DLQFLRDQVT VTQVTIARVY NWDVHQ-RRV KQVTPTAIAV  192
SEQ_ID_NO_595   AKASLEVLVA DLLFLRDQVT ITQVTIARVY NWDVHQKRRM RE--AVTAE  193
SEQ_ID_NO_599   ARASLEVLIA DLQFLRDQVT ITQVTIARVY NWDVHQ-RRV QQ--AVATT  186

SEQ_ID_NO_603   KET  195
SEQ_ID_NO_605   KEP  189
SEQ_ID_NO_610   KET  196
SEQ_ID_NO_593   ADS  195
SEQ_ID_NO_595   KDS  196
SEQ_ID_NO_599   AQD  189
```

Figure 19

```
SEQ_ID_NO_622    ----MAFSNA LRSAAKLVAS SESSLSNSVS RGFHSTGMKR M-GGGHGHDE   45
SEQ_ID_NO_613    ----MALSTS IRSVSKIISS SEASVSRSVT RSFHSTGVKK MSGGGHGGYD   46
SEQ_ID_NO_620    ----MALNTG IRSISKIIAF SEASVSRSVS RSFHSTGAKK M-SGGHGHDE   45
SEQ_ID_NO_626    ----MALNTG IRSVSRLIAS SESSVSRSVS RSFHSTGAKK M-SGGHGHDE   45
SEQ_ID_NO_643    ----MAAAAA --------AA GEEE--GEAS RGFHATGVKR M--GGHGHDE   34
SEQ_ID_NO_644    MATATALNRG LRSGIRLLAT GAEA-SKTDS RGFHATGVKR M--GGHGHDE   47
SEQ_ID_NO_624    --MATALNRG LRSGIRLLAT GAEA-SKPAS RGFHATGVKR M--SGHGHDE   45
SEQ_ID_NO_638    --MATALNRG LRSGIRLLAA GAEA-SKPAS RGFHATGVKR M--GGHGHDE   45
SEQ_ID_NO_634    ----MALSRG IRSGLKLLSH SEAALPRSVT HEFHATSMKR M--GGHGHDE   44
SEQ_ID_NO_615    ----MAMIRG IGSGIKLLTS SEAALFRSVT REFHATGMKR M--GGHGHDE   44

SEQ_ID_NO_622    PYYLHAKHMY NLDRMKHQGL KMSLAVFTAF SIGVAVPVYA VIFQQKKTAS   95
SEQ_ID_NO_613    EYYLHAKHMY NLDRMKYQAL KMSLGVFTAF SIGVGVPIFA VVFQQRKTQS   96
SEQ_ID_NO_620    PYYLHAKHMY NLDRMKYQGL KMSLGVFTAF SIGVGVPIFA VVFQQRKTAS   95
SEQ_ID_NO_626    PYYLHAKHMY NLDRMKFQGL KMSLAVFTAF SIGVGVPIFA VVFQQRKTAS   95
SEQ_ID_NO_643    PYYLHAKHMY NLHRMKHQKP KVYLSVLGAV GIGIAVPVYA VVFQQKKTAS   84
SEQ_ID_NO_644    PYYLHAKHMY NLHRMKHQKP KVYLSVLGAV GIGIAVPVYA VVFQQKKTAS   97
SEQ_ID_NO_624    PYYLHAKHMY NLHRMKHQKL TAWTSVLGAV SIGIGVPVFA VVFQQKKTSS   95
SEQ_ID_NO_638    PYYLHAKHMY NLHRMKHQGL KVTLSVLGAV SIGVGVPVYA VIFQQKKTAS   95
SEQ_ID_NO_634    PFYIHAKHMY NLDRMKHQKL KVTLGVLSAF SIGVVVPIYA VIFQQKKAAS   94
SEQ_ID_NO_615    PYYLHAKHMY NLDQMKHQKL KVALSVWSAF GIGMAVPVYA VMFQQKKAAS   94

SEQ_ID_NO_622    S   96
SEQ_ID_NO_613    G   97
SEQ_ID_NO_620    G   96
SEQ_ID_NO_626    G   96
SEQ_ID_NO_643    G   85
SEQ_ID_NO_644    G   98
SEQ_ID_NO_624    G   96
SEQ_ID_NO_638    G   96
SEQ_ID_NO_634    G   95
SEQ_ID_NO_615    A   95
```

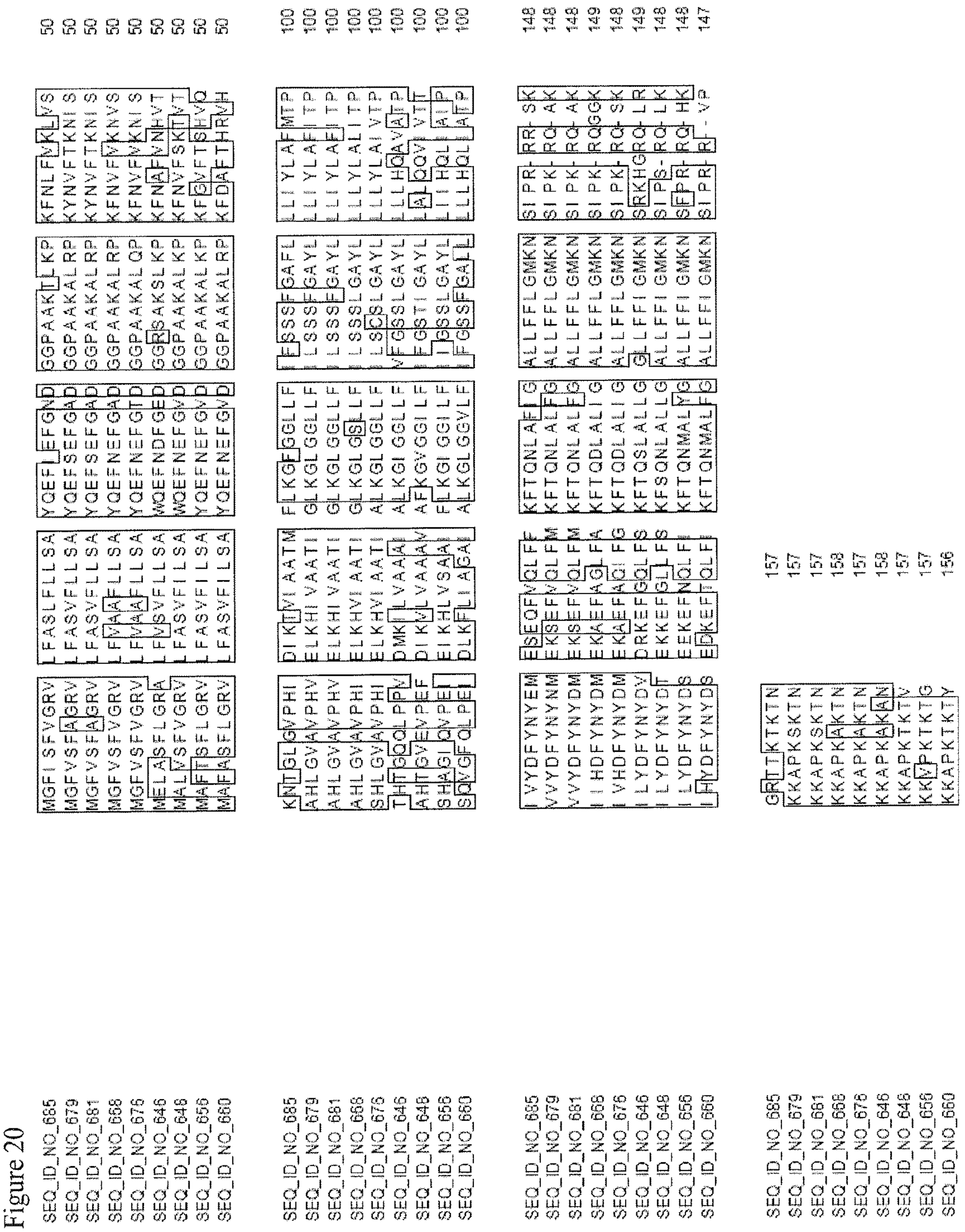

Figure 20

| | | | | | | |
|---|---|---|---|---|---|---|
| SEQ_ID_NO_685 | MGFI SFVGRV | LFASLFLLSA | YQEFLEFGND | GGPAAKILKP | KFNLFVKLVS | 50 |
| SEQ_ID_NO_679 | MGFVSFAGRV | LFASVFLLSA | YQEFSEFGAD | GGPAAKALRP | KYNVFTKNIS | 50 |
| SEQ_ID_NO_681 | MGFVSFAGRV | LFASVFLLSA | YQEFSEFGAD | GGPAAKALRP | KYNVFTKNIS | 50 |
| SEQ_ID_NO_658 | MGFVSFVGRV | LFVAAFLLSA | YQEFNEFGTD | GGPAAKALQP | KFNVFVKNVS | 50 |
| SEQ_ID_NO_676 | MGFVSFVGRV | LFVAAFLLSA | YQEFNDFGED | GGRSAKSLKP | KFNAFVKNIS | 50 |
| SEQ_ID_NO_646 | MELASFLGRA | LFVSVFLLSA | MQEFNEFGVD | GGPAAKALKP | KFNVFSKTVT | 50 |
| SEQ_ID_NO_648 | MALVSFVGRV | LFASVFILSA | YQEFNEFGVD | GGPAAKALKP | KFDVFTSHVQ | 50 |
| SEQ_ID_NO_656 | MAFTSFLGRV | LFASVFILSA | YQEFNEFGVD | GGPAAKALKP | KFDAFTHRVH | 50 |
| SEQ_ID_NO_660 | MAFASFLGRV | LFASVFILSA | YQEFNEFGVD | GGPAAKALRP | KFDAFTHRVH | 50 |

| | | | | | | |
|---|---|---|---|---|---|---|
| SEQ_ID_NO_685 | KNTGLGVPHI | DIKTVIAATM | FLKGFGGLLF | LSSSFGAFL | LLIYLAFMTP | 100 |
| SEQ_ID_NO_679 | AHLGVAVPHV | ELKHIVAATI | GLKGLGGLLF | LSSSFGAYL | LLIYLAFITP | 100 |
| SEQ_ID_NO_681 | AHLGVAVPHV | ELKHIVAATI | GLKGLGGLLF | LSSSEGAYL | LLIYLAFITP | 100 |
| SEQ_ID_NO_658 | SHLGVAVPHI | ELKHVIAATI | GLKGLGSLLF | LSCSLGAYL | LLIYLALITP | 100 |
| SEQ_ID_NO_676 | THTGQLPPV | DMKLVAAAV | ALKGIGGLLF | VFGSTIGAYL | LLHQAVATP | 100 |
| SEQ_ID_NO_646 | AHTGVEVPEF | DIKVLVAAAV | AFKGVGGILF | FGSSLGAYL | ALQQVVIT | 100 |
| SEQ_ID_NO_648 | SHAGIQVPEI | EIKHLVSAIA | FLKGIGGILF | GSSLGAYL | LIIHQLAIP | 100 |
| SEQ_ID_NO_656 | SQVGFQLPEI | DLKFLIAGAL | ALKGLGGVLF | FGSSFGALL | LLLHQLATP | 100 |
| SEQ_ID_NO_660 | | | | | | 100 |

| | | | | | | |
|---|---|---|---|---|---|---|
| SEQ_ID_NO_685 | IVYDFYNYEM | ESEQFNQLFF | KFTQNLALFG | ALLFFLGMKN | SIPRRR-SK | 148 |
| SEQ_ID_NO_679 | VVYDFYNYNM | EKSEFVQLFM | KFTQNLALFG | ALLFFLGMKN | SIPKRQ-AK | 148 |
| SEQ_ID_NO_681 | VVYDFYNYNM | EKSEFVQLFM | KFTQNLALFG | ALLFFLGMKN | SIPKRQ-AK | 148 |
| SEQ_ID_NO_658 | IHDFYNYDM | EKAEFAGLFA | KFTQDLALIG | ALLFFLGMKN | SIPKRQ-AK | 148 |
| SEQ_ID_NO_676 | VHDFYNYDM | EKAEFAGLFG | KFTQDLALIG | ALLFFLGMKN | SIPKRQGGK | 149 |
| SEQ_ID_NO_646 | LYDFYNYDV | DRKEFGQLFS | KFTQSLALLG | ALLFFIGMKN | SIPKRQ-SK | 148 |
| SEQ_ID_NO_648 | LYDFYNYDT | EKKEFGLLFS | KFSQNLALLG | GLLFFIGMKN | SRKHGRQ-LR | 149 |
| SEQ_ID_NO_656 | LYDFYNYDS | EEKEFNQLF | KFTQNMALFG | ALLFFIGMKN | SIPSRQ-LK | 148 |
| SEQ_ID_NO_660 | HYDFYNYDS | EDKEFTQLF | KFTQNMALFG | ALLFFIGMKN | SIPRRQ-HK | 148 |
| | | | | | SIPRR--VP | 147 |

| | | |
|---|---|---|
| SEQ_ID_NO_685 | GRITKTN | 157 |
| SEQ_ID_NO_679 | KKAPKSKTN | 157 |
| SEQ_ID_NO_681 | KKAPKSKTN | 157 |
| SEQ_ID_NO_658 | KKAPKAKTN | 158 |
| SEQ_ID_NO_676 | KKAPKAKTN | 157 |
| SEQ_ID_NO_646 | KKAPKAKAN | 158 |
| SEQ_ID_NO_648 | KKAPKTKTV | 157 |
| SEQ_ID_NO_656 | KKVPKTKTG | 157 |
| SEQ_ID_NO_660 | KKAPKTKTY | 156 |

Figure 21

```
SEQ_ID_NO_708  MDEIMNKMGS YWLGQRANKE MSSAGDDIES LSTSVGDGAK WLVNKLKGKM  50
SEQ_ID_NO_728  MDQIFNKVGS YWLGQKANKE FNSVGDDINS MGSSIGDGTK WLVNKLKGKM  50
SEQ_ID_NO_718  MDQILNKVGS YWINKRANKE ISSVGDDLNS LSSSIEGGAK WLVNKLKGKM  50
SEQ_ID_NO_687  MDQIFNKVGS YWLGQKANKQ FDSVGNDLNS VSTSIEGGTK WLVNKIKGKM  50
SEQ_ID_NO_699  MDQVFXKVGS YWLGQKANKQ FDSVGKDVSS LSTSIEGGTK WLVNKFKGTM  50
SEQ_ID_NO_689  MDQILNKVGS YWLGQKANKE IDSVGDDLNS LSTSIEGGAK WLVNKIKGKM  50
SEQ_ID_NO_691  MDAVLNKVGS YWLGQKASKE FNSVGDDINS LSTSIEGGTK WLVNKLKGKM  50
SEQ_ID_NO_703  MDQIFNKVGS YWFNQKASSQ LNSVGDDINS MTNSIXGGTK WLVNKIKGKM  50
SEQ_ID_NO_706  MDQVFNKVGS YWFNQKASKE LNSVGDEINS LSNSIEGGTK WLVNKVKGKM  50
SEQ_ID_NO_721  MDQIMGKVGG YWFKQNAGKE INNIGDDINS ISSSIGDGAK WMVNKIKGKM  50
SEQ_ID_NO_712  MDQVLNKVGS YWFSKRASKE IDSIGDDLNS VSSSIGGGAK WMVNKIKGKL  50
SEQ_ID_NO_724  MDQVLNKVGS YWFSKRASKE IDSIGDDISS ISTSIGTGAK WMVNKIKGKM  50

SEQ_ID_NO_708  QKPLAELLQE HDLPAGLFPR EATNYEFEPE TRRLTVHIPA VCEVGYRDGS  100
SEQ_ID_NO_728  QKPLPELLKD YDLAVGIFPR DATHYEFDER QGKLTVYVPQ ICEVGYKDSS  100
SEQ_ID_NO_718  QKSLPELLRE YDMPIGLFPQ DATHYEFNEE TGKLTVFIPS ICEVGYRDSS  100
SEQ_ID_NO_687  QKPLPELLKE YDLPIGIFPG DATNYEFDEE TKKLTVLIPS ICEVGYKDSS  100
SEQ_ID_NO_699  QKPLAELLKD YDLPVGIFPR DATNYEFDEQ TKKLTVLIPS VCEVGYKDSS  100
SEQ_ID_NO_689  QKPLPELLRE YNLPIGIFPR DATNYEFNEE TGKLTVFIPA ICEVGYKDSS  100
SEQ_ID_NO_691  QKPLPDLLKE YDLPIGIFPR DATNYEFNEE TRKLTVFIPS ICEVGYKDSS  100
SEQ_ID_NO_703  QKALPELLKE YDLPIGIFPR DATNYEFNEE TGKLVVYIPQ VCEVGYKDSS  100
SEQ_ID_NO_706  QKPLPELLKE YDLPIGIFPR DATNYEFNEE TGKLEVFIPQ VCEVGYKDSS  100
SEQ_ID_NO_721  QKPLPEFLKE YDLPVGLFPQ DATNYEFNEE TKKLTVYISS VCEVGYKDSS  100
SEQ_ID_NO_712  QKALPDLLKE YDMPAGLFPR DITNYEFNEE TKKLTVYIPS ACDVGYKDSS  100
SEQ_ID_NO_724  QKALPDLLKE YDMPAGLFPR DATNYEFNEE TKKLTVYIPS ACDVGYKDSS  100

SEQ_ID_NO_708  ELRFDTTVTG TLDKGSLTGV EGLKAKVLVW ARVTAVKADA AKVYFAVGIK  150
SEQ_ID_NO_728  VLRFFATVTG YLEKGKLADI EGLKTKIIIW VKVTAITSEG SKLHFTAGVK  150
SEQ_ID_NO_718  VLRFLNIVTG YLEKGKLVDI EGIKTKVLIW SKVTRISTEG SKIHFTIGVK  150
SEQ_ID_NO_687  VLKFTTTVTG HLEKGKLTDV EGIKTKVMIW VKVTSISTDA SKVYFTAGMK  150
SEQ_ID_NO_699  VLKFTTTVTG RLEKGKLGDL EGMKTKVMIW VKVTSISADS SKVYFTAGVK  150
SEQ_ID_NO_689  F-----CASS PL-------- ---------- ---------- ----------  107
SEQ_ID_NO_691  VVRFLTTVTG YLEKGKIADI EGMKTKVMIW VKVTCIASTG SKLNFTAGMK  150
SEQ_ID_NO_703  VLRFXTTVTG YLEKGKLADI EGMKTKVLIW VKVTTILSXG XKXYVTAGKK  150
SEQ_ID_NO_706  VLRFFTTVTG YLEKGKLADI EGMKTKVIIW VKVTTIFSEG SKLYVTAGMK  150
SEQ_ID_NO_721  VLRFSTTVTG YLENGKLSEV EGLKTKILIW TKVTAVRTEA TKVHFAAGMN  150
SEQ_ID_NO_712  VVRFFTCVTG YLEKGKLSDI EGMKTKVLVW TKVTSIKTEG SKVHFTAGMK  150
SEQ_ID_NO_724  VLRFFTCVTG YLEKGKLSDI EGLKTKVLVW TKVTAIKTEG SKVHFTAGVK  150
```

Figure 21 (continued)

```
SEQ_ID_NO_708    KSRSREAYEV  VRGAI TVDEF    170
SEQ_ID_NO_728    KTRSREAYQV  LRDGVLVDKF     170
SEQ_ID_NO_718    KTRSRDAYQV  LRAGI TVDKF    170
SEQ_ID_NO_687    KSRSRDAYEV  QRNGLRVDKF     170
SEQ_ID_NO_699    KSRNRDAYEV  LRDGVRADKF     170
SEQ_ID_NO_689    ----------  ----------     107
SEQ_ID_NO_691    KTRDRGAYEV  LRDGVGI DKF    170
SEQ_ID_NO_703    KTRSREAYEV  TRXGVCI DKF    170
SEQ_ID_NO_706    KTRSREAYDV  TRDGVPVDKF     170
SEQ_ID_NO_721    KARNRDAYEV  VRDGVGI DKF    170
SEQ_ID_NO_712    KTRSRDAYEV  VRDGI I I DKF  170
SEQ_ID_NO_724    KTRSRDAYEV  VRDGI PI DKF   170
```

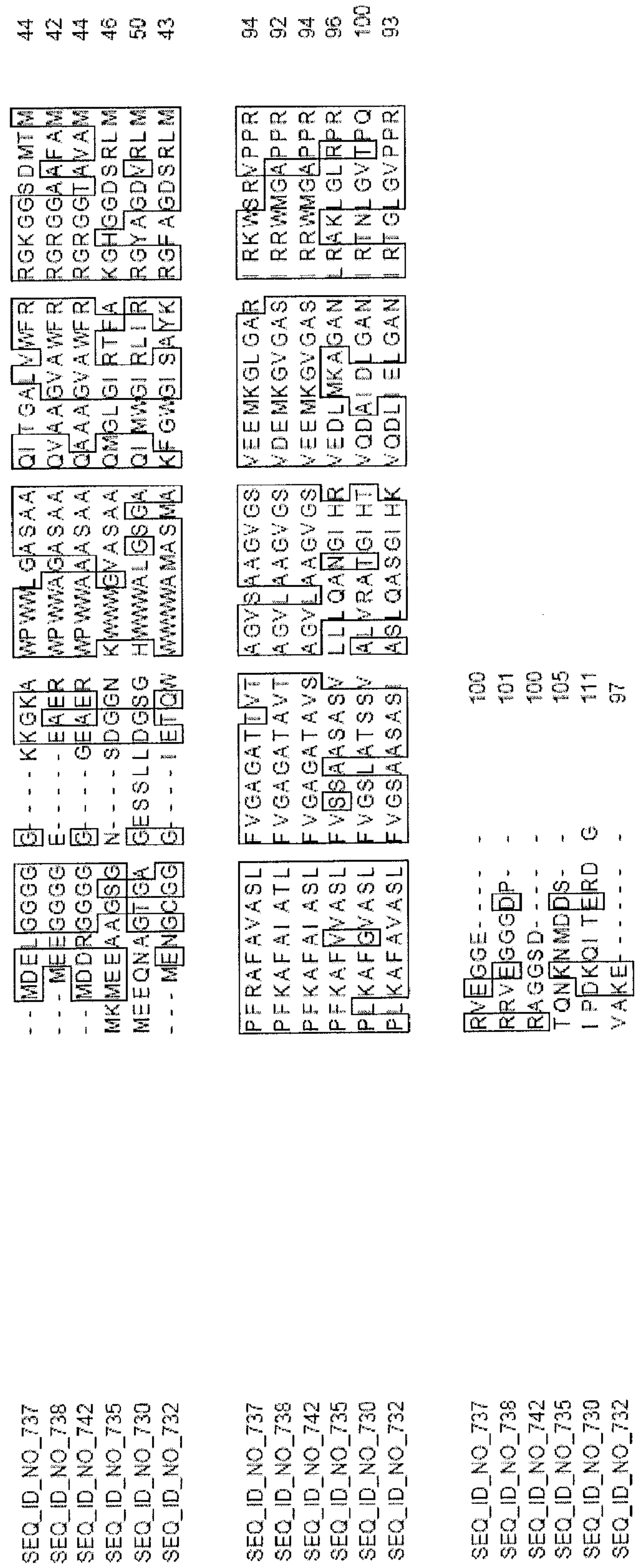

Figure 22

| SEQ_ID_NO_737 | --MDEL GGGG G----- KKGKA MPVWL GASAA QITGAL VWFR RGKGGSDMTM | 44 |
|---|---|---|
| SEQ_ID_NO_738 | ---ME EGGGG E----- EAER MPVWWAGASAA QVAAGVAWFR RGRGGAAFAM | 42 |
| SEQ_ID_NO_742 | MDDRGGGG G----- GEAER MPVWWAAASAA QAAAGVAWFR RGRGGIAVAM | 44 |
| SEQ_ID_NO_735 | MKMEEAAGSG N----- SDGGN KWWWWGVASAA QMGLGI RTFA KGHGGDSRLM | 46 |
| SEQ_ID_NO_730 | MEEQNAGTGA GESSLLDGSG HWWWALGSGA QIMWGI RLIR RGYAGDVRLM | 50 |
| SEQ_ID_NO_732 | ---MENGCGG G----- IETQW WWWWAMASMA KFGWGI SAYK RGFAGDSRLM | 43 |

| SEQ_ID_NO_737 | PFRAFAVASL FVGAGATLVT AGVSAAGVGS VEEMKGLGAR RKWSRVPPR | 94 |
|---|---|---|
| SEQ_ID_NO_738 | PFKAFAIATL FVGAGATAVT AGVLAAGVGS VDEMKGVGAS RRVWMGAPPR | 92 |
| SEQ_ID_NO_742 | PFKAFAIASL FVGAGATAVS AGVLAAGVGS VEEMKGVGAS RRVWMGAPPR | 94 |
| SEQ_ID_NO_735 | PFKAFVVASL FVSSASASW LLLQANGI HK VEDLMKAGAN LRAKLGLRPR | 96 |
| SEQ_ID_NO_730 | PLKAFGVASL FVGSLATSSV ALVRATGI HT VQDAI DLGAN RTNLGVTPQ | 100 |
| SEQ_ID_NO_732 | PLKAFAVASL FVGSAASAS ASLQASGI HK VQDLI ELGAN RTGLGVPPR | 93 |

| SEQ_ID_NO_737 | RVEGGE----- | 100 |
|---|---|---|
| SEQ_ID_NO_738 | RRVEGGGDP--- | 101 |
| SEQ_ID_NO_742 | RAGGSD------ | 100 |
| SEQ_ID_NO_735 | TQNKNMDDS--- | 105 |
| SEQ_ID_NO_730 | IPDKQITERD G | 111 |
| SEQ_ID_NO_732 | VAKE-------- | 97 |

Figure 23

```
SEQ_ID_NO_765   MSPMSNPSFD HSY---E--L PLRRNLLLLL DLLGRLRFIA EVLLDRLGVA   45
SEQ_ID_NO_763   MMLSSAYSTP AADELGGPPP LPPPPGADVS VIVGALTGVL LGLFLFL---   47
SEQ_ID_NO_758   ------MGFP VGY--PE--V SVPNIFLYTL SLLSFLRSLT ISFLSLLHLS   40
SEQ_ID_NO_761   ------MGFP VGY--SE--L LLPRLLLQVL LLLGHLHRFL LWAFHAVGLG   40
SEQ_ID_NO_762   ------MGFP VGY--SE--L LLPRLLLQVL LLLGHLHRFL LWAFHAVGLG   40
SEQ_ID_NO_755   ------MGFY AEDPLSG--L TIGQAIYEVA LMIAVLRWVL CLIFRVI---   39
SEQ_ID_NO_748   ------MGFF VEE--SG--L IVTHLLYKAA LVLAVLRWAL AWALRFK---   37
SEQ_ID_NO_746   ------MTFF IED--TS--L IISHVLYKTA LIITVLRWIF AWILRYR---   37
SEQ_ID_NO_751   ------MTFF IED--TS--L IISHVLYKTA LIITVLRWIF AWILRYR---   37
SEQ_ID_NO_753   ------MSFF IQD--SG--L IVTQLLYQMA VFITLLRWIF SWILRYR---   37
SEQ_ID_NO_760   ------MSFF IED--SG--L IVTQLLYQMA VLITLLRWIF TWILRYR---   37

SEQ_ID_NO_765   SW------QG EVHLPGQLWG WGGEHASDAT LEHFLEARLW ETGTRSPLTT   89
SEQ_ID_NO_763   ---------- --IYAKHCRQ RGRGGARGAA GGLGLGFRAS STCDRCRSGV   85
SEQ_ID_NO_758   DL-------- ---------- ---------L DTDFSTTTLP DSHIHRPTLS   63
SEQ_ID_NO_761   DLIDNPPGLA ATEQDMMLQG RGGGMAEGWA SSSALQHRRP EFRAIPPM--   88
SEQ_ID_NO_762   DLIDNPPGLA ATEQDLMLQG RGGGMAEGWA SSSALQHRRP EFRAIPPM--   88
SEQ_ID_NO_755   ---------- ---------- ---------- NDRRTTQSDE TPTPEPCSQM   59
SEQ_ID_NO_748   ---------- ---------- ---------N RTHLASPSND SLRRSHPVPS   58
SEQ_ID_NO_746   ---------- ---------- ---------- SRSSSSSSSS SQSSSSPSIS   57
SEQ_ID_NO_751   ---------- ---------- ---------- --SRSSSSSS SQSSSSPSIS   55
SEQ_ID_NO_753   ---------- ---------- ---------- -------SKS RTSSAPPV-S   49
SEQ_ID_NO_760   ---------- ---------- ---------- ----SRSTSS SSSSTPPI-S   52

SEQ_ID_NO_765   TRYRRRRVAL AQPADGKLAA EGDAEGAA-- AVCAICVAGL ESGDLETVVE   137
SEQ_ID_NO_763   SLSVVDALPV VRFGD---MG GAAAAAQP-- -ECAVCLGTF DPAADELLRV   129
SEQ_ID_NO_758   AILIRQFLPI ITFND---LA EGDSSPPV-- -GCAVCLNEF --AGEEEIRC   105
SEQ_ID_NO_761   --AIEEALPV VRFDE---LV ASAPAAVCGG GDCAVCLSGI --CGRDEVRR   131
SEQ_ID_NO_762   --AIEEALPV VRFDE---LV ASAPAAVCGG GDCAVCLSGI --CGRDEVRR   131
SEQ_ID_NO_755   TRDKDSILLL TTFGE---IK ERLPETE--- ETCAVCLSQL --SVEDEVRE   101
SEQ_ID_NO_748   SQQIRDGLIL TTFGD---VT ERMPLGVC-- DTCAVCLSQL --RDQDEVRE   100
SEQ_ID_NO_746   SQTIKESLAV FAFRD---AV ERSPAAIN-- DMCAVCLGDL --EDEDEIRE   100
SEQ_ID_NO_751   SQTIKESLAV SAFRD---AV ERSPAAIN-- DMCAVCLGDL --EDEDEIRE   98
SEQ_ID_NO_753   SQAIKESLSV TTFHD---AL ERXPELIS-- DTCAVCLGDL --EDGDEVRE   92
SEQ_ID_NO_760   SQTIKESLAV TTFRD---AA DRSPELIS-- DTCAVCLGDL --EDGDEVRE   95
```

Figure 23 (continued)

```
SEQ_ID_NO_765   LCSCSHAFHD ACIDAWVRSG D--------- -DDAATCPLC RAPCCPRRG-   176
SEQ_ID_NO_763   LPKCRHAFHA DCVDTWLEA- ---------- ---HSTCPVC RRRVGKEDA-   164
SEQ_ID_NO_758   MANCRHMFHR TCVDRWIDHD ---------- ---QKTCPLC RTHFVPYHK-   141
SEQ_ID_NO_761   LSNCRHVFHR GCLDRWMAHE ---------- ---QRTCPLC RAPLIPDELL   168
SEQ_ID_NO_762   LSNCRHVFHR GCLDRWMAHE ---------- ---QRTCPLC RAPLIPDELL   168
SEQ_ID_NO_755   LMNCYHVFHR ECIDRWLEHE HE-------- -NHSATCPIC RAPLLSSSC-   141
SEQ_ID_NO_748   LRNCCHVFHR DCIDRWVDHD HEHD------ -ENHNTCPLC RAPLLTTSQ-   142
SEQ_ID_NO_746   LRNCTHVFHR DCIDRWLDYE CCGGDD---- -DNHRTCPLC RTPLLPSFT-   144
SEQ_ID_NO_751   LRNCTHVFHR DCIDRWLDYE CCGGDD---- -DNHRTCPLC RTPLLPSFT-   142
SEQ_ID_NO_753   LRNCSHVFHR ECIDRWLDYE CCGGDGNEGE EDNHRTCPLC RTPLLAADT-   141
SEQ_ID_NO_760   LRNCSHVFHR ECIDRWLDYE CCGGDDNDGE EDNHRTCPLC RTPLLAANT-   144

SEQ_ID_NO_765   ---------- ---------- TTTGGEQSLS R----VLKGV CVSVP   197
SEQ_ID_NO_763   ---------- -----FAVIP ELEAADADWY PAREAEMQIV VRRPA   194
SEQ_ID_NO_758   -----MEDYN QRLWNDAASE DDIDDDVSLF SHRHDYYYIA NASL-   180
SEQ_ID_NO_761   PAASGLPDPS DYDLSYYPSP LPLAPTPTLL RPHELLLNGL GGFQ-   212
SEQ_ID_NO_762   PAASGLPDPS DYDLSYYPSP LPLAPTPTLL RPHELLLNGL GGFQ-   212
SEQ_ID_NO_755   ---------- ----HHSSAT CLPPPQPSWA VERLLYLFGD DLLPC   172
SEQ_ID_NO_748   ---------- --------SL ARTRAEPSWA VERILYLFGD DLVM-   168
SEQ_ID_NO_746   ---------- ---------D YSTVTQTSWA VERLLYLFGD DLLP-   169
SEQ_ID_NO_751   ---------- ---------D YSTVTQTSWA VERLLYLFGD DLLP-   167
SEQ_ID_NO_753   ---------- -----SSCGD WPVKTEPSWA VERLLYLFGD DLLV-   170
SEQ_ID_NO_760   ---------- -----SSCAD WPVKNEPSWA VERLLYLFGD DLLV-   173
```

Figure 24

```
SEQ_ID_NO_779   MVLESIL-SS S--KSPSF-- ------RRQF AKHELGSWST LLKRHRFLLF   39
SEQ_ID_NO_783   MVLDSILSSS PCLKSPSF-- ------SRQF ARHELGSWST LVKRHCFLLS   42
SEQ_ID_NO_769   MVLDGLV-SS PSRRQQCL-- ------KKQW --DELGSWST LIQRHQYLLT   39
SEQ_ID_NO_777   MVLDGIV-SS PLRRHQSL-- ------KKQW --EDLGSCST VVNRHRYLLT   39
SEQ_ID_NO_773   MVLDSMI-TS PHRRSPSF-- ------RKPF PRDELGSWST LLRRHRFLLT   41
SEQ_ID_NO_771   MVLDGIV-SS PLRRSAST-- ------RRQS SRDEFGSWST LVERHRFLLT   41
SEQ_ID_NO_789   MVLDSL--SS PHRRSQNTVF LASPSKKQQS GFNEPGSWST IYERHRFLLT   48
SEQ_ID_NO_785   MVLDSL--SS PHRRSQNTFF VSSA-KKPQS SRDD--SWSA LVERHRFLLT   45
SEQ_ID_NO_790   MVLDSL--SS PHRRSQNTFF LSSP-KKLQS SKDDVGSWSA LVERHRFLLT   47

SEQ_ID_NO_779   ALALLTVLCT IYLYFAVTFA AN--DSCSGL NGPLKDSCHM EHVKASVAKS   87
SEQ_ID_NO_783   ALALLTVLCT IYLYFAVTFA AN--DSCSGL SGSLRDSCHM EHVMDSEAKS   90
SEQ_ID_NO_769   ALALLAFLCT VYLYFAVTLG ARH-SSCYGL TGKDKAMCQL -QLVQALSKG   87
SEQ_ID_NO_777   ALLLLGFLCT VYLYFAVTLD ARHNSSCYGL AGKEKAMC-- ----QAISKG   83
SEQ_ID_NO_773   AFALLAFLCT IYLYFAVTLG AT--ESCSGL TGTKKTLCRL ELAKDSVGNG   89
SEQ_ID_NO_771   ALGLLAFLCT IYLYFAVTLG AT--DTCSGL KGTEKATCNL QHVSSTLSHG   89
SEQ_ID_NO_789   MLALLAFLCT IYLYFAVTLG AT--GSCSGM SGAEKALC-- -QAKSSLHKG   93
SEQ_ID_NO_785   TLLVLAFLCT VYLYFAVTLG AS--DACTGL TGAERIEC-- -QARSVLQHG   90
SEQ_ID_NO_790   TLVVLVFLCT IYLYFAVTLG AP--DACSGL AGTEKAVC-- -RAKSALRHG   92

SEQ_ID_NO_779   KLKGLRHF   95
SEQ_ID_NO_783   KLKGLRHL   98
SEQ_ID_NO_769   KLK---FF   92
SEQ_ID_NO_777   KLK---LF   88
SEQ_ID_NO_773   KLK---FF   94
SEQ_ID_NO_771   KLK---FL   94
SEQ_ID_NO_789   KLK---FF   98
SEQ_ID_NO_785   KLK---FR   95
SEQ_ID_NO_790   KLK---FF   97
```

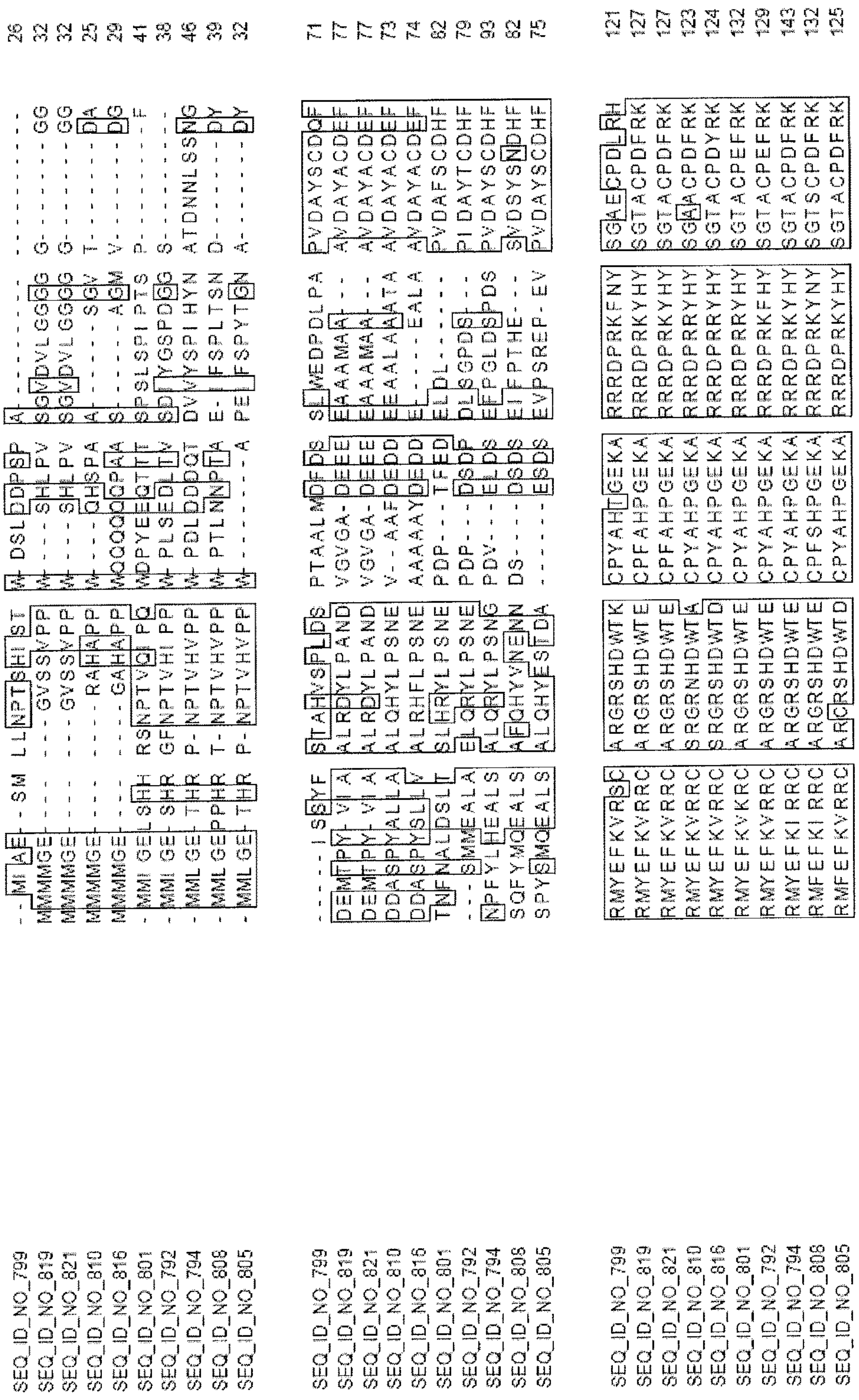

Figure 25

| SEQ_ID_NO_799 | - - M I - A E - S M - - - - - L L N P T S H I S T - - - - - - - - - - - - - W - D S L D D P S P - - - - - - - - - - - - - - - - - - - - - - - - - - - - A - - - - - - - - - - - - - - | 26 |
| SEQ_ID_NO_819 | M M M M G E - - - - - - - - - - - G V S S V P P - - - - - - - - - - - - - W - - - S H L P V - - - - - - - - S G V D V L G G G G - - - - - - - - - G - - - - - - - | 32 |
| SEQ_ID_NO_821 | M M M M G E - - - - - - - - - - - G V S S V P P - - - - - - - - - - - - - W - - - S H L P V - - - - - - - - S G V D V L G G G G - - - - - - - - - G - - - - - - - | 32 |
| SEQ_ID_NO_810 | M M M M G E - - - - - - - - - - - - R A H A P P - - - - - - - - - - - - - W - - - Q H S P A - - - - - - - - A - - - - - - - - - - - - - - - - - T - - - - - - - | 25 |
| SEQ_ID_NO_816 | M M M M G E - - - - - - - - - - - - G A H A M P - - - - - - - - - - - - - W - - - - - - - - - - - - - - - - S G V - - - - - - - - - - - - - - - - V - - - - - - - | 29 |
| SEQ_ID_NO_801 | M M I G E L S H H - - R S N P T V Q I P Q - - - W - D P Y E E Q T T T - - - - - - - S P S L S P I P T S - - - - - - - - A G M - - - - - - - - - - - P - - - - - - - | 41 |
| SEQ_ID_NO_792 | M M I G E L S H R - - G F N P T V H I P P - - - W - P L S E D L I V - - - - - - - - - - - - - - - - - - - - S D I Y G S P D G G - - - - - - - - - S - - - - - - - | 38 |
| SEQ_ID_NO_794 | M M L G E L T H R - - P - N P T V H V P P - - - W - P D L D D D Q T - - - - - - - - - - - - - - - - - - - - D V V Y S P I H Y N - - A T D N N L S S N G - - - - - - - | 46 |
| SEQ_ID_NO_808 | M M L G E P P H R - - T - N P T V H V P P - - - W - P T L N N P T A - - - - - - - E - I F S P L T S N - - - - - - - - D - - - - - - - - - - - - - - - - - - - - | 39 |
| SEQ_ID_NO_805 | M M L G E L T H R - - P - N P T V H V P P - - - W - - - - - - - - - - - - - - - - A - - P E L F S P Y T G N - - - - - - - - D Y - - - - - - - | 32 |

| SEQ_ID_NO_799 | - - - - - - I S S Y F - - S T A H V S P L D S - - - - - - - - - - P T A A L M D F D S - - - - - - - - - S L W E D P D L P A - - - - P V D A Y S C D D F | 71 |
| SEQ_ID_NO_819 | D E M T P Y L - - V I - A - - - A L R D Y L P A N D - - - - - - - - - - V G V G A - D E E E - - - - - - - - - - E A A A M A A - - - - - - - A V D A Y A C D E F | 77 |
| SEQ_ID_NO_821 | D E M T P Y L - - V I - A - - - A L R D Y L P A N D - - - - - - - - - - V G V G A - D E E E - - - - - - - - - - E A A A M A A - - - - - - - A V D A Y A C D E F | 77 |
| SEQ_ID_NO_810 | D D A S P Y A L L A - - - A L Q H Y L P S N E - - - - - - - - - - V - - A A F D E D D - - - - - - - - - - E E A A L A A A T A - - - - - - A V D A Y A C D E F | 73 |
| SEQ_ID_NO_816 | D D A S P Y S L I V - - - A L R H F L P S N E - - - - - - - - - - A A A A Y D E D D - - - - - - - - - - E L - - - - E A L A - - - - - - - - A V D A F S C D H F | 74 |
| SEQ_ID_NO_801 | T N F N A L D S L T - - - S L H R Y L P S N E - - - - - - - - - - P D P - - - T F E D - - - - - - - - - - E L D L - - - - - - - - - - - - - P I D A Y T C D H F | 82 |
| SEQ_ID_NO_792 | - - - S M M E A L A - - - E L Q R Y L P S N E - - - - - - - - - - P D P - - - D S D P - - - - - - - - - - D L S G P D S - - - - - - - - - P V D A Y S C D H F | 79 |
| SEQ_ID_NO_794 | N P F Y L H E A L S - - - A L Q R Y L P S N G - - - - - - - - - - P D V - - - E L D S - - - - - - - - - - E E F G L D S P D S - - - - - - - P V D A Y S C D H F | 93 |
| SEQ_ID_NO_808 | S Q F Y M Q E A L S - - - A F Q H Y V N E N N - - - - - - - - - - D S - - - - - D S D S - - - - - - - - - - E I F P T H E - - - - - - - - - S V D S Y S N D H F | 82 |
| SEQ_ID_NO_805 | S P Y S M Q E A L S - - - A L Q H Y E S T D A - - - - - - - - - - - - - - - - E S D S - - - - - - - - - - E V P S R E P - E V - - - - - - - P V D A Y S C D H F | 75 |

| SEQ_ID_NO_799 | R M Y E F K V R S C - - A R G R S H D W T K - - - C P Y A H T G E K A - - - R R R D P R K F N Y - - - S G A E C P D L R H | 121 |
| SEQ_ID_NO_819 | R M Y E F K V R R C - - A R G R S H D W T E - - - C P F A H P G E K A - - - R R R D P R K Y H Y - - - S G T A C P D F R K | 127 |
| SEQ_ID_NO_821 | R M Y E F K V R R C - - A R G R S H D W T E - - - C P F A H P G E K A - - - R R R D P R K Y H Y - - - S G T A C P D F R K | 127 |
| SEQ_ID_NO_810 | R M Y E F K V R R C - - A R G R S H D W T A - - - C P Y A H P G E K A - - - R R R D P R R Y H Y - - - S G A C P D F R K | 123 |
| SEQ_ID_NO_816 | R M Y E F K V R R C - - S R G R N H D W T E - - - C P Y A H P G E K A - - - R R R D P R R Y H Y - - - S G T A C P D F R K | 124 |
| SEQ_ID_NO_801 | R M Y E F K V R R C - - A R G R S H D W T D - - - C P Y A H P G E K A - - - R R R D P R R Y H Y - - - S G T A C P D Y R K | 132 |
| SEQ_ID_NO_792 | R M Y E F K V K R C - - A R G R S H D W T E - - - C P Y A H P G E K A - - - R R R D P R K F H Y - - - S G T A C P E F R K | 129 |
| SEQ_ID_NO_794 | R M Y E F K V R R C - - A R G R S H D W T E - - - C P Y A H P G E K A - - - R R R D P R K Y H Y - - - S G T A C P E F R K | 143 |
| SEQ_ID_NO_808 | R M F E F K I R R C - - A R G R S H D W T E - - - C P F S H P G E K A - - - R R R D P R K Y N Y - - - S G T S C P D F R K | 132 |
| SEQ_ID_NO_805 | R M F E F K V R R C - - A R C R S H D W T D - - - C P Y A H P G E K A - - - R R R D P R K Y H Y - - - S G T A C P D F R K | 125 |

Figure 25 (continued)

```
SEQ_ID_NO_799   GCCKKGDACE YAHGTFELWL HPDRYRTQPC RDGTGCRRRV CFFAHTSEQL   171
SEQ_ID_NO_819   GGCKRGDACE YAHGVFECWL HPARYRTQPC KDGTACRRRV CFFAHTPDQL   177
SEQ_ID_NO_821   GGCKRGDACE YAHGVFECWL HPARYRTQPC KDGTACRRRV CFFAHTPDQL   177
SEQ_ID_NO_810   GGCKRGDACE LAHGVFECWL HPSRYRTQPC KDGTGCRRRV CFFAHTPDQL   173
SEQ_ID_NO_816   GGCKRGDACE FAHGVFECWL HPSRYRTQPC KDGTACRRRV CFFAHTPDXL   174
SEQ_ID_NO_801   GGCKKGDACE FAHGVFECWL HPARYRTQPC KDGPACRRRV CFFAHTPEQL   182
SEQ_ID_NO_792   GCCKRGDACE FSHGVFECWL HPARYRTQPC KDGGNCRRRV CFFAHSPDQI   179
SEQ_ID_NO_794   GNCRKGDSCE FAHGVFECWL HPARYRTQPC KDGSGCRRRV CFFAHTPDQL   193
SEQ_ID_NO_808   GSCKKGDSCE FAHGVFECWL HPSRYRTQPC KDGTSCRRPV CFFAHTTEQL   182
SEQ_ID_NO_805   GSCKKGDACE YAHGVFECWL HPARYRTQPC KDGTSCRRRV CFFAHTPDQL   175

SEQ_ID_NO_799   RI-PGKQSVR SPRAREM--- ---------- ---------- ---AIPAVSS   194
SEQ_ID_NO_819   RVLPAQQS-- SPRSVAS--S PLAESYD-GS PLRRQAFESY LTKTI-MSSS   221
SEQ_ID_NO_821   RVLPAQQS-- SPRSVAS--S PLAESYD-GS PLRRQAFESY LTKTI-MSSS   221
SEQ_ID_NO_810   RVPPPRQS-- SPRGAAAA-S PLAESYD-GS PLRRQAFESY LTKSGIVSSP   219
SEQ_ID_NO_816   RVLPPQQSSA SPRGAGAAPS PLAESYD-GS PLRRQAFESY LTKTGIMSSS   223
SEQ_ID_NO_801   RLLPQQ---- SPKGNGSGSG LGSGEYDFGS PV-IHPFDSY MTKAGIFVSS   227
SEQ_ID_NO_792   RVLPNQ---- SPDR------ --VDSFDVLS PTIRRAFQ-- ------FSIS   209
SEQ_ID_NO_794   RLVSS----- ---------- --TDTYD-GS P--------- CGKTLTFWSS   216
SEQ_ID_NO_808   RAPTQQ---- SPRSVPS--- --VDSYD-GS PL-RLAFESS CVKTLQFMSS   221
SEQ_ID_NO_805   RVLPQQ---- SPRS------ --ADSYD-GS PL-RHAFESS CAKSHPFVAS   211

SEQ_ID_NO_799   PTSILLSPSS -------DSP PLSPISP--V ISGG------ ESLSRLVALM   229
SEQ_ID_NO_819   PTSTLMSPPK SPPS---ESP PLSPDGAA-A IRRGSMPGVG SPVNDVLASF   267
SEQ_ID_NO_821   PTSTLMSPPK SPPS---ESP PLSPDGAA-A IRRGSMPGVG SPVNDVLASF   267
SEQ_ID_NO_810   PTSTLVSPPR SPPS---ESP PMSPDAAA-A LRRGSMPGVG SPVNEVLASM   265
SEQ_ID_NO_816   PTSTLVSPPR SPPS---ESP PMSPDAAAGA LRRGSMPGVG SPVNEVVASL   270
SEQ_ID_NO_801   PTSILTSPPV SPPS---DSP PMSPGSP--Q VIGGSGPGSL NSMSALLASM   272
SEQ_ID_NO_792   PSSN--SPPV SPRG------ --DSDSSCSL LSRSLGSNLG ---NDVVASL   246
SEQ_ID_NO_794   PGSS--SPPV SPRAESCSSP PVSPMAQ--S LSRSLGSASI NEM---VTSL   259
SEQ_ID_NO_808   PGSV--SPPV -------ESP PMSPMTR--S LGRSVGS--- SSVNEMVASL   257
SEQ_ID_NO_805   PGSA--SSPV -------ESP PMSPMT---- ---------- VSVNEMVASL   238
```

Figure 25 (continued)

```
SEQ_ID_NO_799   HSLRLDELK- ---------- ---------- ---------- TNPGVSSF--   246
SEQ_ID_NO_819   RQLRLNKVK- -SSPSGGWSY PSSS------ AVYGSPKAA- --TGLYSLPT   306
SEQ_ID_NO_821   RQLRLNKVK- -SSPSGGWSY PSSS------ AVYGSPKAA- --TGLYSLPT   306
SEQ_ID_NO_810   RQLRLGGGS- PRSAPSGGSF LGGG------ YPFGSPKSP- --AGLYSLPS   305
SEQ_ID_NO_816   RQLRLGGGGS PRSAPSGGSF LVG------- YPFGSPKSP- --AALYSLPS   310
SEQ_ID_NO_801   RGLQVGKAK- MGSPVGSWGV QSG------- FRFGSPRGSS LRPGFCSLPS   314
SEQ_ID_NO_792   RNLQLNKVK- -SSLSSSYNN QIGGYG---- SGFGSPRGSV LGPGFRSLPT   290
SEQ_ID_NO_794   RNLQLGKGK- ------SWKT QVGCCSPSSP SSFGSPRAAM IRPGFCSLPS   302
SEQ_ID_NO_808   RNLQLGTMK- --SLPSSWNV QMGS------ PRFGSPRGPV IRPGFCSLPS   298
SEQ_ID_NO_805   RNLQLGKVK- --SLPSSWNV -MGS------ SGFGSPRGPM IRPGFFSLPT   278

SEQ_ID_NO_799   SPNL------ -RRSSGAAF- -DLWDRG--N EEEPAMERVE SGRNLRAQMY   285
SEQ_ID_NO_819   TPLASTATVT TASSFMPNL- -EPLDLGLIG DEEPV-QRVE SGRALREKVF   353
SEQ_ID_NO_821   TPLASTATVT TASSFMPNL- -EPLDLGLIG DEEPV-QRVE SGRALREKVF   353
SEQ_ID_NO_810   TPTRPSPVTV TTASGATVLT VERLNLGLIG DEEPVMERVE SGRALREKVF   355
SEQ_ID_NO_816   TPTRPAAVTV TTPSGATVMT VERLNLGLIG DEEPVMERVE SGRALREMVF   360
SEQ_ID_NO_801   TPTR----TM ASRSGLSQL- -DIWGDGVTC EEEPAMERVE SGRDLRAKIY   358
SEQ_ID_NO_792   TPTRP----- ------GFM- -NIWENG--L EEEPAMERVE SGRELRAQLF   325
SEQ_ID_NO_794   TPTR----NL -TRPGISYP- -DSWDKA--C EEEPVMERVE SGRDLRAKMF   343
SEQ_ID_NO_808   TPTQ-----V PSRGRVNHF- -DLWDQS--C EEEPVMERVE SGRDIRVKMF   339
SEQ_ID_NO_805   TPTQ-----A PTRGGVNYF- -DQWDQS-CC EEEPVMERVE SGRSIRARMF   320

SEQ_ID_NO_799   AKLMRENSVD RVRPMISA-- ---------- GSLN------ ----------   307
SEQ_ID_NO_819   ERLSRDGAIY GDATAFATAG -----VGLDV DWVSDLIN-- ----------   386
SEQ_ID_NO_821   ERLSRDGAIS GDATAFATAG -----VGLDV DWVSDLIN-- ----------   386
SEQ_ID_NO_810   ERLSKEATVP SDTAASANVE GAA--PAPDV GWVSDLIN-- ----------   391
SEQ_ID_NO_816   ERLSKEATVP NDAAASANAE GAAPAAAPDV GWVSDLIN-- ----------   398
SEQ_ID_NO_801   AKLSKENSVD RDRGDSGVSG -------PDV GWVSELVK-- ----------   389
SEQ_ID_NO_792   EKLSKENCMG RIEPDPDQGA G----DTPDV GWVSDLVM-- ----------   359
SEQ_ID_NO_794   EKLSKENSLE RVNPDQSSGG -------PDL NWVSDLGKQA MGIIVMVDIV   386
SEQ_ID_NO_808   EKLSKENSFN GSGMGSGSGL GEVV-EDPDV GWVSELVSPF LGD-------   381
SEQ_ID_NO_805   EKLSKENHLD GSGSGSSQIG ------VPDV GWVSELVSR- ----------   353
```

Figure 25 (continued)

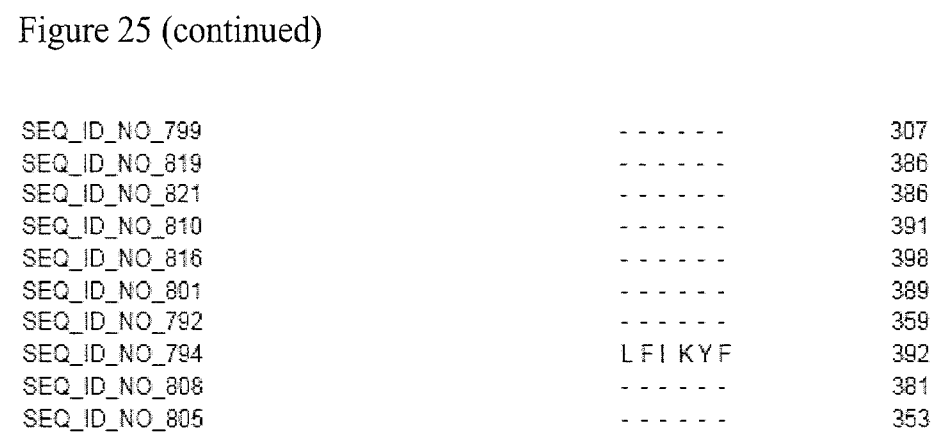

| | | |
|---|---|---|
| SEQ_ID_NO_799 | - - - - - - | 307 |
| SEQ_ID_NO_819 | - - - - - - | 386 |
| SEQ_ID_NO_821 | - - - - - - | 386 |
| SEQ_ID_NO_810 | - - - - - - | 391 |
| SEQ_ID_NO_816 | - - - - - - | 398 |
| SEQ_ID_NO_801 | - - - - - - | 389 |
| SEQ_ID_NO_792 | - - - - - - | 359 |
| SEQ_ID_NO_794 | L F I K Y F | 392 |
| SEQ_ID_NO_808 | - - - - - - | 381 |
| SEQ_ID_NO_805 | - - - - - - | 353 |

Figure 26

```
SEQ_ID_NO_1708   MA-PPLSSWP WASLGIYKYF LLGPLVWKVA QEWAE--QGG AP--LGSRWL   45
SEQ_ID_NO_826    MA-APLSSWP WTSLGDYKYA LLGPLAWKVV QEWREQGQGA LPLVLGSWWL   49
SEQ_ID_NO_1713   MA-PPLSSWP WASLGQYKYV LFGALVWKVV QEWRE--QGG LP--LGSWWL   45
SEQ_ID_NO_824    MAPPPLSSWP WASLGQYKYV LLGPLVWKVL QEWRE--QAG LP--LGSWWL   48

SEQ_ID_NO_1708   HLLLLFSARG LTYQFWFSYS NMLFLTRRRR VVPDGVDFRQ VDHEWDW---   92
SEQ_ID_NO_826    HLLLLFVVRG LTYQFWFTYG NMLFFTRRRR VVADGVDFRQ IDAEWDW---   96
SEQ_ID_NO_1713   HLLVLFAVRG LTYQFWFTYG NMLFFTRRRR VVADGVDFRQ IDAEWDW---   92
SEQ_ID_NO_824    HLLLLFAARG LTYQFWFSYG NMLFFTRRRR VVADGVDFRQ IDAEWDWKKI   96

SEQ_ID_NO_1708   ---------- ---------- ---------- ---------   92
SEQ_ID_NO_826    ---------- ---------- ---------- ---------   96
SEQ_ID_NO_1713   ---------- ---------- ---------- ---------   92
SEQ_ID_NO_824    LWIPPPNNQP WSPSDTGNAQ AHLAGIGRLF FLRLVPAFG   135
```

Figure 27

```
SEQ_ID_NO_828    ---MGRKP-- DAVAKSYHSG GGGAAASS-- ---------- --PRAARKAS   31
SEQ_ID_NO_845    ---MGRKP-- DPSKPHY--- GGGAS----- ---------- --PRAARRTQ   25
SEQ_ID_NO_847    ---MGRKP-- DPSKPHY--- GGGAS----- ---------- --PRAARRTQ   25
SEQ_ID_NO_832    -MLSLLSE-- KPNLALYNQS NGKHYQYHQN IYNDWRWWRS SATQQHRRKV   47
SEQ_ID_NO_837    --MGVVAEVW RSSVRLLTNS PQLNGGSHKS ALWKWRFF-- --SAQPKRTV   44
SEQ_ID_NO_840    --MKRRKQ-- RSHEKLFLVL QIILHTLIF- ---------- --KRRRRIHH   33
SEQ_ID_NO_842    ---MVLPR-- RRGGHNHH-- ---------- ---------- --PCPRRAVL   21
SEQ_ID_NO_844    ---MGSRR-- RRHHHHHG-- ---------- ---------- --PWLVPAVA   21
SEQ_ID_NO_839    MFMAPRRGLL DGGEDRYGLM SFGTKDI--- ---------- --FTMRRKIR   35
SEQ_ID_NO_850    ---MSEAEKF IYHRKLWEVK GISVGESKAE KLRSY----- --LVSRSRMK   40

SEQ_ID_NO_828    PSP------- VFLGTALFVL GFVSLFTGHV VTDADW---- ARIRSRWRPK   70
SEQ_ID_NO_845    PSP------- VFLGTALFVL GFVSLFTGHI VTDADW---- SRIRSRWRSK   64
SEQ_ID_NO_847    PSP------- VFLGTALFVL GFVSLFTGHI VTDADW---- SRIRSRWRSK   64
SEQ_ID_NO_832    PWS------- LVCGLMLFGL GLVSLFTGHV ASDLEW---- YSQRLVKRSL   86
SEQ_ID_NO_837    MWT------- WVCGFMLFSL GVISLFTGHV VSHLEW---- YSQQLSKRSL   83
SEQ_ID_NO_840    LLP------- LLAALTGGIL FFFVLFSPPL TSQHH----- HLINPIWFNN   71
SEQ_ID_NO_842    PAA------- ALLLL--FLL AAVTLLYVSP PPLSDHPALA YSRRRSPHAL   62
SEQ_ID_NO_844    PAA------- AAFAAAGLLL VVVAFHCFLS PPLGDGGGGA RVVRRPNPPF   64
SEQ_ID_NO_839    YWQKQFKQRH LFGGLMVLLL MCVITKFILM NMFSDQ---- LDLDTAIPSN   81
SEQ_ID_NO_850    LWM------- IRAVTILLLW SCVV----HL MALGEFWG-- PRLLKGWPSC   77

SEQ_ID_NO_828    -----QHRNY EP-------- ---------D IWESKYSSMY YGCSERSASF   99
SEQ_ID_NO_845    -----QVRNN EP-------- ---------N IWKSRYSNLY YGCSRRSVNF   93
SEQ_ID_NO_847    -----QVRNN EP-------- ---------N IWKSRYSNLY YGCSRRSVNF   93
SEQ_ID_NO_832    FYSRLEGRRR EA-------- ---------D IWKSKYSNLF YGCSERGRNF  120
SEQ_ID_NO_837    ----LDMSRR EP-------- ---------D VWKSKYSKFF YGCSERGRNF  113
SEQ_ID_NO_840    GTELQMNLQK EH----VFRV PMGGGSLSGD IWTSKQSILY HGCSNSSYKF  117
SEQ_ID_NO_842    LNSSGGGSLV EPGRREISRV PKGGWSATDG LWGSKLASKF YGCSNSSSKF  112
SEQ_ID_NO_844    LLKKPAEVAR SVIGAVDFTV PSGGSKHGQE LWESKATGNF FGCSNATKHF  114
SEQ_ID_NO_839    VVQDEPSPNN WP-------- -------TLE IWKHPNSDNY FNCMGRAK--  114
SEQ_ID_NO_850    ---------- ---------- --------FN HHDLPVAAET ASLPMKIA--   97
```

Figure 27 (continued)

```
SEQ_ID_NO_828    RSAVPENSST GYLLIATSGG LNQQRIGITD AVVVAMILNA TLVVPELDHH  149
SEQ_ID_NO_845    RSAVPENSST GYLLIGTSGG LNQQRIGITD AVVVARILNA TLVVPELDHH  143
SEQ_ID_NO_847    RSAVPENSST GYLLIGTSGG LNQQRIGITD AVVVARILNA TLVVPELDHH  143
SEQ_ID_NO_832    PPAVRERASN GYLLIAASGG LNQQRTGITD AVVVARILNA TLVVPELDHH  170
SEQ_ID_NO_837    LPAVQEQSSN GYLLIAASGG LNQQRTGITD AVVVARILNA TLVVPELDHH  163
SEQ_ID_NO_840    PSADVNTHPN RYLMIATSGG LNQQRTGIVD AVVAAHILNA VLVVPKLDQK  167
SEQ_ID_NO_842    LDSGVMTHPD RYLMIVTSGG LNQQRTGIID AVVAARILNA TLVVPKLDQT  162
SEQ_ID_NO_844    ADAKAVTKLD RYLMIATSGG LNQQRTGIID AVVAARILNA TLVIPKLDEE  164
SEQ_ID_NO_839    KDIRQGNNTN GYLLVHANGG LNQMKTGISD MVAIAKIMNA TLVFPTLDHN  164
SEQ_ID_NO_850    LPPKRVYKNN GYLMVSCNGG LNQMRAAICD MVTIARYMNV TLIVPELDKT  147

SEQ_ID_NO_828    SFWKDDSDFS DIFDVEWFIS HLSKDVTIVK RIPYEVMLSM DKLPWTMRAP  199
SEQ_ID_NO_845    SFWKDDSDFS DIFDVDWFIS YLSKDVTIVK RIPYEVMMSM DKLPWTMRAP  193
SEQ_ID_NO_847    SFWKDDSDFS DIFDVDWFIS YLSKDVTIVK RIPYEVMMSM DKLPWTMRAP  193
SEQ_ID_NO_832    SYWKDDSDFV NIFDVDWFIS YLAKDVTIVK RVPDKVMRSM EKPPYTMRVP  220
SEQ_ID_NO_837    SYWKDDSDFS DIFDVNWFIS SLAKDVTIVK RVPDRVMRAM EKPPYTTRVP  213
SEQ_ID_NO_840    SYWKDSSNFS EIFDVDRFIS HLSKDVKIIR DIPR--IGDK VITPYTTRVP  215
SEQ_ID_NO_842    SFWKDASDFA EIFNADWFIS FLSKDVRIVK ELPK--IGGK LWAPHRMRVP  210
SEQ_ID_NO_844    SFWNDASDFA QIFDVDSFIY SLSNDVKVIR QLPD--MNGK KLSPYKMRIP  212
SEQ_ID_NO_839    SFWTDPSDFK EIFNWKNFVE VLNEDVQVVE SLPPELAAIK P----ALKAP  210
SEQ_ID_NO_850    SFWSDPSEFQ DIFDVDHFIT SLRDEVRILK ELPPRLKRRF ELGMYYSFPP  197

SEQ_ID_NO_828    RK-SVPEFYI DEVLPILMRR RALQLTKFDY RLTSD-LDED LQKLRCRVNF  247
SEQ_ID_NO_845    RK-SMPDFYI DEVLPILMRR RALQLTKFDY RLTNE-LDEE LQKLRCRVNF  241
SEQ_ID_NO_847    RK-SMPDFYI DEVLPILMRR RALQLTKFDY RLTNE-LDEE LQKLRCRVNF  241
SEQ_ID_NO_832    RK-SPPEYYL DQVLPILLRR RVVQLTKFDY RLASN-LDEE LQKLRCRANY  268
SEQ_ID_NO_837    RK-STLEYYL DQVLPILTRR HVLQLTKFDY RLAND-LDED MQKLRCRVNY  261
SEQ_ID_NO_840    RK-CNAKCYQ TRILPILKKK HAVQLTKFDY RLSNR-LDID MQKLRCRVNF  263
SEQ_ID_NO_842    RK-CTQRCYL NRVLPALVKK HVVRLTKFDY RLANR-LDSD LQKLRCRVNY  258
SEQ_ID_NO_844    RK-CTPKCYE NRVLPALLKK HVVQLTKFDY RVSNR-LETD LQKLRCRVNY  260
SEQ_ID_NO_839    VSWSKASYYR TDMLQLLKKH KVIKFTHTDS RLVNNGLASS IQRVRCRAMY  260
SEQ_ID_NO_850    ISWSDISYYS NQILPLVKKY KVVHLNKTDT RLANNGLSLD IQKLRCRVNF  247
```

Figure 27 (continued)

```
SEQ_ID_NO_828   HALKFTSSIH AMGQKLVQKL RLMNTRYVAI HLRFEPDMLA FSGCYYGGGE   297
SEQ_ID_NO_845   HALRFTNSIQ TLGEKLVRKL RSMSSRYVAV HLRFEPDMLA FSGCYYGGGD   291
SEQ_ID_NO_847   HALRFTNSIQ TLGEKLVRKL RSMSSRYVAV HLRFEPDMLA FSGCYYGGGD   291
SEQ_ID_NO_832   HALRFTKPIQ EIGERLVTKM RKMAKRYIAI HLRFEPDMLA FSGCYFGGGE   318
SEQ_ID_NO_837   HALRFTKRIQ SVGMKVVKRM RKMAKRFIAV HLRFEPDMLA FSGCDFGGGE   311
SEQ_ID_NO_840   HALKFTDPIL EMGRKLVERI RMKSKHFVAL HLRFEPDMLA FSGCYYGGGD   313
SEQ_ID_NO_842   HALRFTDPIQ EMGEKIIQRV RERSTYFIAL HLRFEPDMLA FSGCYYGGGE   308
SEQ_ID_NO_844   HALQFTDPIL RMGELLVQRM KEKSGRFIAL HLRFEPDMLA FSGCYYGGGD   310
SEQ_ID_NO_839   EALRFAVPIE ELGKKLVNRL RENNTPYIAL HLRYEKDMLA FTGCSHNLTK   310
SEQ_ID_NO_850   NALRFTPQIE ELGRRVVRIL REK-GPFLVL HLRYEMDMLA FSGCSHGCNP   296

SEQ_ID_NO_828   KERKELGEIR ---KRWDTLP ELSAEDERSR GKCPLTPHEV GLMLRALGFG   344
SEQ_ID_NO_845   KERRELGEIR ---KRWDTLP ELSAEDERSR GKCPLTPQEI GLMLRALGFS   338
SEQ_ID_NO_847   KERRELGEIR ---KRWDTLP ELSAEDERSR GKCPLTPQEI GLMLRALGFS   338
SEQ_ID_NO_832   KERFELGEIR ---KRWATLP DLSPDGERER GKCPLTPHEV GLMLRALGFA   365
SEQ_ID_NO_837   KERAELAEIR ---KRWDTLP DLDPLEERKR GKCPLTPHEV GLMLRALGFT   358
SEQ_ID_NO_840   KETKELGKIR ---KRWKTLH ATNPDKERRH GKCPLTPEEI GLMLRALGFG   360
SEQ_ID_NO_842   KEKRELGVIR ---KRWKTLH ASNPEKERRH GRCPLTPEEV GLMLRALGYR   355
SEQ_ID_NO_844   IERRELGEIR ---KRWKTLH ASNPDRERRH GKCPLTPEEV GLMLRALGFG   357
SEQ_ID_NO_839   EETQELKKMR YSVKHWKE-K EIDSKSKRLK GSCPMTFREV AVFLEALGYP   359
SEQ_ID_NO_850   DEEEELTRMR YAYPWWKE-K VINSELKRKD GLCPLTFEET ALALNALGID   345

SEQ_ID_NO_828   NDTLLYVASG EIYGGDSTLQ PLRGLFPNFY TKEKLAG-DD LNPFLPFSSR   393
SEQ_ID_NO_845   NDTYLYVASG EIYGGEETLQ PLRDLFPNYY TKEMLAG-ND LKLFLPFSSR   387
SEQ_ID_NO_847   NDTYLYVASG EIYGGEETLQ PLRDLFPNYY TKEMLAG-ND LKPFLPFSSR   387
SEQ_ID_NO_832   NDTYLYVASG EIYGGEETLR PLRELFPNFY TKEMLAL-EE LKSFFPFSSR   414
SEQ_ID_NO_837   NDTYIYVASG EIYGGEKTLK PLRELFPNFY TKEMLAN-DE LKPLLPYSSR   407
SEQ_ID_NO_840   NDVHIYVASG EIYGGEETLA PLKALFPNFY SKETIASKEE LAPFSSFSSR   410
SEQ_ID_NO_842   KNVHIYVASG DIYGGAKTLA PLKALFPNLH TKETVTSKDE LAPFSKYSSR   405
SEQ_ID_NO_844   KDVHLYVASG DVYGGEETLA PLKALFPNFH SKETLASKEE LAPFLPYSSR   407
SEQ_ID_NO_839   VDTKIYVAAG VIYGSEG-MK PLQKKFPNLL WHSSLATKEE LQPFEGHLNQ   408
SEQ_ID_NO_850   RNVQIYIAAG EIYGGERRMK ALAEAFPNVV RKETLLEPSD LKFFQNHSSQ   395
```

Figure 27 (continued)

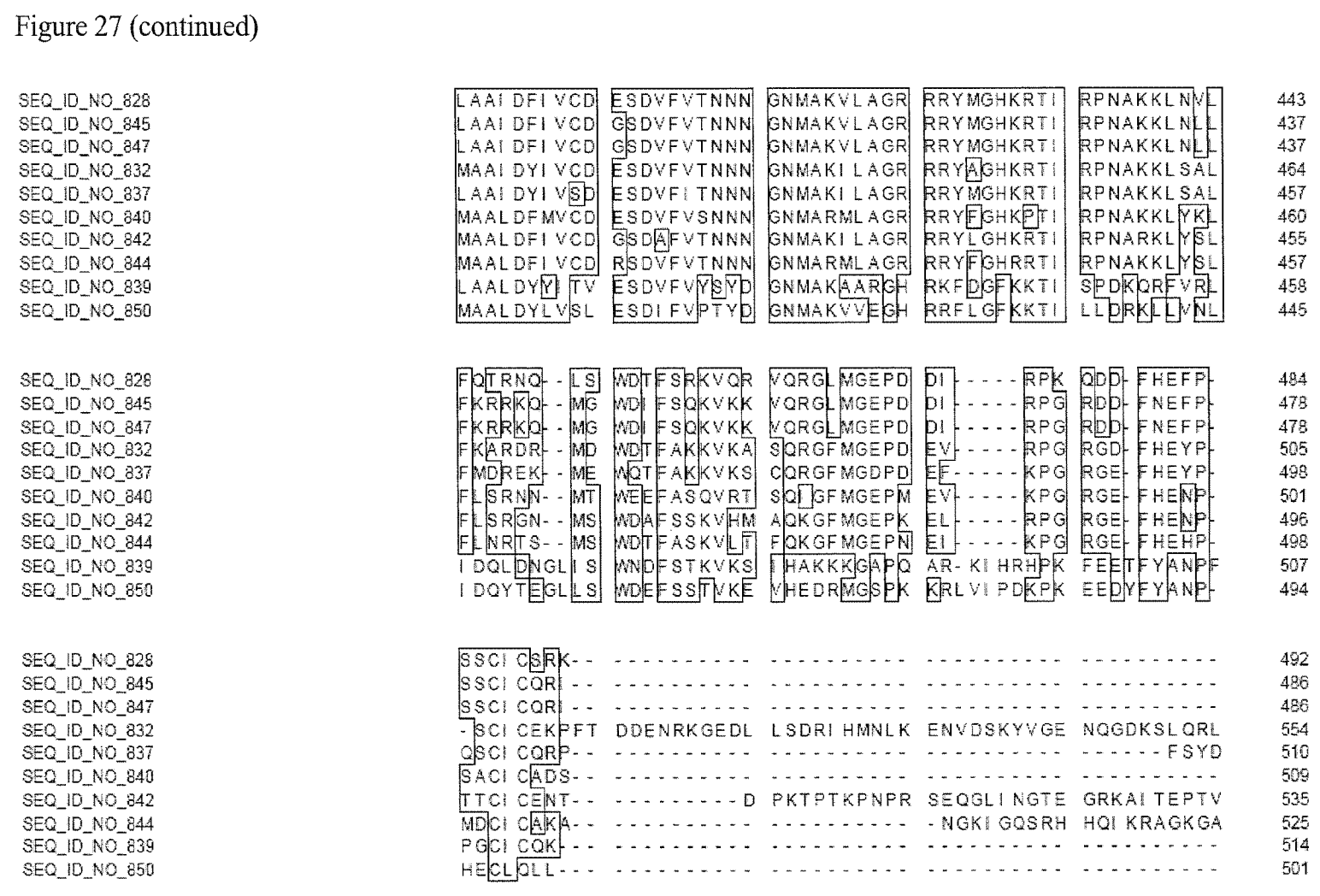

```
SEQ_ID_NO_828  LAAIDFIVCD ESDVFVTNNN GNMAKVLAGR RRYMGHKRTI RPNAKKLNVL 443
SEQ_ID_NO_845  LAAIDFIVCD GSDVFVTNNN GNMAKVLAGR RRYMGHKRTI RPNAKKLNLL 437
SEQ_ID_NO_847  LAAIDFIVCD GSDVFVTNNN GNMAKVLAGR RRYMGHKRTI RPNAKKLNLL 437
SEQ_ID_NO_832  MAAIDYIVCD ESDVFVTNNN GNMAKILAGR RRYAGHKRTI RPNAKKLSAL 464
SEQ_ID_NO_837  LAAIDYIVSD ESDVFITNNN GNMAKILAGR RRYMGHKRTI RPNAKKLSAL 457
SEQ_ID_NO_840  MAALDFMVCD ESDVFVSNNN GNMARMLAGR RRYFGHKPTI RPNAKKLYKL 460
SEQ_ID_NO_842  MAALDFIVCD GSDAFVTNNN GNMAKILAGR RRYLGHKRTI RPNARKLYSL 455
SEQ_ID_NO_844  MAALDFIVCD RSDVFVTNNN GNMARMLAGR RRYFGHRRTI RPNAKKLYSL 457
SEQ_ID_NO_839  LAALDYYITV ESDVFVYSYD GNMAKAARGH RKFDGFKKTI SPDKQRFVRL 458
SEQ_ID_NO_850  MAALDYLVSL ESDIFVPTYD GNMAKVVEGH RRFLGFKKTI LLDRKLLVNL 445

SEQ_ID_NO_828  FQTRNQ--LS WDTFSRKVQR VQRGLMGEPD DI-----RPK QDD-FHEFP- 484
SEQ_ID_NO_845  FKRRKQ--MG WDIFSQKVKK VQRGLMGEPD DI-----RPG RDD-FNEFP- 478
SEQ_ID_NO_847  FKRRKQ--MG WDIFSQKVKK VQRGLMGEPD DI-----RPG RDD-FNEFP- 478
SEQ_ID_NO_832  FKARDR--MD WDTFAKKVKA SQRGFMGEPD EV-----RPG RGD-FHEYP- 505
SEQ_ID_NO_837  FMDREK--ME WQTFAKKVKS CQRGFMGDPD EF-----KPG RGE-FHEYP- 498
SEQ_ID_NO_840  FLSRNN--MT WEEFASQVRT SQIGFMGEPM EV-----KPG RGE-FHENP- 501
SEQ_ID_NO_842  FLSRGN--MS WDAFSSKVHM AQKGFMGEPK EL-----RPG RGE-FHENP- 496
SEQ_ID_NO_844  FLNRTS--MS WDTFASKVLT FQKGFMGEPN EI-----KPG RGE-FHEHP- 498
SEQ_ID_NO_839  IDQLDNGLIS WNDFSTKVKS IHAKKKGAPQ AR-KIHRHPK FEETFYANPF 507
SEQ_ID_NO_850  IDQYTEGLLS WDEFSSTVKE VHEDRMGSPK KRLVIPDKPK EEDYFYANP- 494

SEQ_ID_NO_828  SSCICSRK-- ---------- ---------- ---------- ---------- 492
SEQ_ID_NO_845  SSCICQR--- ---------- ---------- ---------- ---------- 486
SEQ_ID_NO_847  SSCICQR--- ---------- ---------- ---------- ---------- 486
SEQ_ID_NO_832  -SCICEKPFT DDENRKGEDL LSDRIHMNLK ENVDSKYVGE NQGDKSLQRL 554
SEQ_ID_NO_837  QSCICQRP-- ---------- ---------- ---------- ------FSYD 510
SEQ_ID_NO_840  SACICADS-- ---------- ---------- ---------- ---------- 509
SEQ_ID_NO_842  TTCICENT-- ---------D PKTPTKPNPR SEQGLINGTE GRKAITEPTV 535
SEQ_ID_NO_844  MDCICAKA-- ---------- ---------- -NGKIGQSRH HQIKRAGKGA 525
SEQ_ID_NO_839  PGCICQK--- ---------- ---------- ---------- ---------- 514
SEQ_ID_NO_850  HECLQLL--- ---------- ---------- ---------- ---------- 501
```

Figure 27 (continued)

| | | | | | | |
|---|---|---|---|---|---|---|
| SEQ_ID_NO_828 | ---------- | ---------- | ---------- | ---------- | ---------- | 492 |
| SEQ_ID_NO_845 | ---------- | ---------- | ---------- | ---------- | ---------- | 486 |
| SEQ_ID_NO_847 | ---------- | ---------- | ---------- | ---------- | ---------- | 486 |
| SEQ_ID_NO_832 | KKRSIEEPIS | LRENKDVTVI | GSANELGLCT | GDRYVKVNGT | CLVASTKSDL | 604 |
| SEQ_ID_NO_837 | KTSTDDEEED | MSEENHNSTS | PGHVHLSS-- | ---------- | ---------- | 538 |
| SEQ_ID_NO_840 | DANDREDASL | FGTHSIISEI | DTGSSTNSAR | RDMVEVTDGQ | ASEEEQEWS- | 558 |
| SEQ_ID_NO_842 | ANHTNEELVG | SSAEEDDASV | EKEDDTSAEK | EDDTSEEKEE | IADPEAEDDA | 585 |
| SEQ_ID_NO_844 | ENHSSDGDLD | WRDLDYGEHT | PLGRDSSNES | ESDDIRVGGS | ---------- | 565 |
| SEQ_ID_NO_839 | ---------- | ---------- | ---------- | ---------- | ---------- | 514 |
| SEQ_ID_NO_850 | ---------- | ---------- | ---------- | ---------- | ---------- | 501 |

| | | | | |
|---|---|---|---|---|
| SEQ_ID_NO_828 | --------PG | NISATT---- | - | 500 |
| SEQ_ID_NO_845 | --------PV | NRSVTARAEN | L | 499 |
| SEQ_ID_NO_847 | --------PV | NRSVTARAEN | L | 499 |
| SEQ_ID_NO_832 | LCHHVLSFST | PFLDETGSGM | L | 625 |
| SEQ_ID_NO_837 | --------AD | NERDEVFPD- | - | 549 |
| SEQ_ID_NO_840 | --------DT | EYMETELEI- | - | 569 |
| SEQ_ID_NO_842 | LVRP----DD | PELEEVLSD- | - | 600 |
| SEQ_ID_NO_844 | --------DI | PELEDMMSD- | - | 576 |
| SEQ_ID_NO_839 | --------PT | HLMAETNHES | L | 527 |
| SEQ_ID_NO_850 | --------DE | PLRTTRLSMF | L | 514 |

Figure 28

```
SEQ_ID_NO_876   ----MGPVVL TQLATGLSML AGAALVKSVM DQN--TMMGP GSD---RF--  39
SEQ_ID_NO_855   ----MSPIVI TQLATGISVL AGAVFIKSVM DQK------P MAG---QF--  35
SEQ_ID_NO_862   ----MGPIVL TQLATGLSVL AGAVLVKSVM DQK------P MAG-------  33
SEQ_ID_NO_858   ----MVPIVL TQMATGLGVL AGAVFVKSVM DQK------P MAG---PF--  35
SEQ_ID_NO_856   ----MFPAVL TQVATGLSVL AGAVLVKSVM DQK------P MAG---PF--  35
SEQ_ID_NO_885   MVVVVAPIAV A--SAGLGML AGVAMASRSS NSSSSSGRTS SPAALLRWGA  48
SEQ_ID_NO_868   ---MVSPVVI A--SAGLGML AGVALASRGT GDG-----LP ASS---RWDA  37
SEQ_ID_NO_886   ---MVGPIVI A--SAGLGML AGVAMANRTM GGGGDGRQLP AAS---RWDA  42
SEQ_ID_NO_870   ---MVAPVVI A--SAGLGML AGVAMANRSL GNG-----LP AAS---RWDA  37
SEQ_ID_NO_878   ---MVAPVVI T--SAGLGML AGLAMANRSL GDG-----LP AAS---RWDA  37

SEQ_ID_NO_876   ----PRCSRC NGTGRVSC-L CNRWSD--GD -RGCRTCAGS GRMVCSSCGG  81
SEQ_ID_NO_855   ----PRCPTC NGTGRVTC-F CSRWSD--GD -VGCRRCSGS GRAACSNCGG  77
SEQ_ID_NO_862   ----PLCPSC NGTGRVAC-L CSRWSD--GD -AGCRACSGS GRMACSSCGG  75
SEQ_ID_NO_858   ----QRCPTC NGTGRVSC-I CSRWSD--GD -VGCRTCSGS GRRACSSCGG  77
SEQ_ID_NO_856   ----QRCPTC NGTGRITC-I CTRWSD--GD -IGCRTCAGS GRMACSSCGG  77
SEQ_ID_NO_885   PEPAPRCAAC GGTGREECRL CARWSDARGD CSGCRACAGT RRAPCRSCGG  98
SEQ_ID_NO_868   R---PRCSTC SGTGREEC-L CSRWSD--GD -VGCGTCSGS GRKRCRSCGG  80
SEQ_ID_NO_886   R---PRCATC GGSGRVDC-L CNRWSD--GD -SGCRTCAGS GRMPCRSCGG  85
SEQ_ID_NO_870   R---PRCATC GGSGRVEC-I CNRWSD--GD -SGCRTCAGS GRMPCRSCGG  80
SEQ_ID_NO_878   R---PRCATC GGSGRVEC-L CNRWSD--GD -SGCRTCAGS GRMPCRSCGG  80

SEQ_ID_NO_876   TGTGRPLPVQ ISVR------ ---PPNQS-- ---Y-  101
SEQ_ID_NO_855   SGTGRPLPAQ ITVQ------ ---PPNRP-- ---Y-  97
SEQ_ID_NO_862   TGTGRPIPVQ ISMR------ ---SPNRP-- ---PS  96
SEQ_ID_NO_858   SGTGRPIPVQ LIVR------ ---QPTNR-- ---SF  98
SEQ_ID_NO_856   SGTGRPIPVQ ISVR------ ---QPTNR-- ---NS  98
SEQ_ID_NO_885   SGTGRRAPVR VSSS------ ---APPSR-- -----  117
SEQ_ID_NO_868   SGTGRPLPAR LIVQ------ EQKLPTAPGR RGDYN  109
SEQ_ID_NO_886   SGTGRPLPAR LLARGHHHHH NPPPSSAPGR GGDYS  120
SEQ_ID_NO_870   SGTGRPLPAR LTVQ----HQ KPPPPPPPG- ---YN  107
SEQ_ID_NO_878   SGTGRPLPAR LTVQ----HH K--PPPPAG- ---YN  105
```

Figure 29 (continued)

| | | | | | | |
|---|---|---|---|---|---|---|
| SEQ_ID_NO_907 | FGSETFLPAA | AATELLLGLE | STNRPFFVVL | NFPKGTDTEA | ELAKCTPPGF | 327 |
| SEQ_ID_NO_912 | FGSETFLPTA | AATELLLGLE | ATGQPFVAVL | NFPRSVDAEA | EVKKCMAPGF | 335 |
| SEQ_ID_NO_911 | FGSETFLLHA | AATELLLGLE | ATALPFLAVL | NFPKGTDAEA | ELRKLTPPGL | 344 |
| SEQ_ID_NO_898 | FGSETFLSDY | QIKELASGLE | LTGLPFILVL | NFPSNLSAKA | ELERALPKGY | 325 |
| SEQ_ID_NO_913 | FGSETFLTDD | QIRELALGLE | LTGLPFFLVL | NFPANVDKSA | ELKRTLPDGF | 316 |
| SEQ_ID_NO_901 | FGSETFLTDD | QVKELALGLE | QTGLPFFLVL | NFPANVDVSA | ELNRALPEGF | 329 |
| SEQ_ID_NO_915 | FGSETFLKDD | QIKELALGLE | QTGLPFFLVL | NFPANVDASA | ELNRGLPEGF | 327 |
| SEQ_ID_NO_904 | FGSECTLRKE | QFQELLWGLE | LTGMPFFAAL | KAPFGTDS-- | -IEAAIPEEL | 320 |
| SEQ_ID_NO_905 | FGSECTLRKD | KFQELLWGLE | LTGMPFFAAL | KPPFETES-- | -VEAAIPEEL | 320 |
| SEQ_ID_NO_908 | FGSECTLRKD | KFQELLWGLE | LTGMPFFAAL | KPPFEAES-- | -IEAAIPEEL | 320 |
| SEQ_ID_NO_891 | LGSQIVLEKD | QFQELCLGME | LTGLPFLIAV | KPPRGSST-- | -VEEGLPEGF | 304 |
| SEQ_ID_NO_893 | FGSQLILEKE | QLQELVLGFE | STGLPFLVVL | KPPVGSST-- | -IEEALPEGF | 323 |

| | | | | | | |
|---|---|---|---|---|---|---|
| SEQ_ID_NO_907 | AERTKGRGVV | HTGWVQQQHI | LRHRGVGCFV | NHAGLSSVVE | GLVAGCRLVL | 377 |
| SEQ_ID_NO_912 | EERVKGRGVV | HSGWVQQQHI | LRHRSVGCYV | NHAGFSSVVE | GLVAGCRLVL | 385 |
| SEQ_ID_NO_911 | EERVKGRGIL | HTGWVQQQHI | LRHRSVGCFV | NHSGLSSVVE | GLIAGCRLVL | 394 |
| SEQ_ID_NO_898 | LERVKNRGVV | HSGWFQQQLV | LKHSSVGCYV | CHGGFSSVIE | AMVNECQLVL | 375 |
| SEQ_ID_NO_913 | LERVKDKGIV | HSGWVQQRHI | LAHDSVGCYV | FHAGYGSVIE | GLVNDCQLVM | 366 |
| SEQ_ID_NO_901 | LERVKDKGII | HSGWVQQQNI | LAHSSVGCYV | CHAGFSSVIE | ALVNDCQVVM | 379 |
| SEQ_ID_NO_915 | RERVKEKGVI | HSGWVQQQHI | LAHTSVGCYV | CHAGFSSVIE | AFMNDCQVVM | 377 |
| SEQ_ID_NO_904 | REKIHGKGIV | HGGWVQQQLF | LQHPSVGCFV | SHCGWASLSE | ALVNDCQIVL | 370 |
| SEQ_ID_NO_905 | KEKIQGRGIV | HGEWVQQQLF | LQHPSVGCFV | SHCGWASLSE | ALVNDCQIVL | 370 |
| SEQ_ID_NO_908 | KEKIQGRGIV | HGEWVQQQLF | LQHPSVGCFV | SHCGWASLSE | ALVNDCQIVL | 370 |
| SEQ_ID_NO_891 | QERVKGRGVV | WGGWVQQPLI | LDHPSIGCFV | NHCGPGTIWE | CLMTDCQMVL | 354 |
| SEQ_ID_NO_893 | EERVKGRGVV | WGGWVQQLEI | LDHPSIGCFV | NTCGFGSMWE | SLMSDCQIVL | 373 |

| | | | | | | |
|---|---|---|---|---|---|---|
| SEQ_ID_NO_907 | LPMKGDQYLN | AALFARDLRV | GAEVARRDSD | GWFGRGDVSD | AVDTAMAD-- | 425 |
| SEQ_ID_NO_912 | LPMKSDQFFN | AALLARELRV | GTEVARRDGD | GWFGHDAVRD | AVNAAVAD-- | 433 |
| SEQ_ID_NO_911 | LPMKGDQYLN | AALFARELRV | GTEVARRARD | GWFGREDVRD | ALAAAFAG-- | 442 |
| SEQ_ID_NO_898 | LPFKGDQFFN | SKLIANDLKA | GVEVNRSDED | GFFHKEDILE | ALKTVMLEDN | 425 |
| SEQ_ID_NO_913 | LPMKVDQFTN | SKVIALELKA | GVEVNRRDED | GYFGKDDVFE | AVESVMMDTE | 416 |
| SEQ_ID_NO_901 | LPQKGDQILN | AKLVSGDMEA | GVEINRRDED | GYFGKEDIKE | AVEKVMVDVE | 429 |
| SEQ_ID_NO_915 | LPQKGDQLLN | AKLVSGDMKA | GVEVNRRDED | GYFSKDDIEE | AVEKVMVE-- | 425 |
| SEQ_ID_NO_904 | LPQVGDQIIN | ARIMSVSLKV | GVEVEKGEED | GVFSRESVCK | AVKAVM-DEK | 419 |
| SEQ_ID_NO_905 | LPQVGDQIIN | ARIMSVSLKV | GVEVEKGEED | GVFSRESVCK | AVKAVM-DEK | 419 |
| SEQ_ID_NO_908 | LPQVGDQIIN | ARIMSVSLKV | GVEVEKGEED | GVFSRESVCK | AVKAVM-DEK | 419 |
| SEQ_ID_NO_891 | LPFLGDQVLF | TRLMTEEFKV | SVEVSR-EKT | GWFSKESLSD | AIKSVM-DKD | 402 |
| SEQ_ID_NO_893 | VPHLGDQILN | TRLMAEELKV | AVEVER-DEK | GWFTKENLSN | AIKCVM-DKD | 421 |

Figure 29 (continued)

```
SEQ_ID_NO_907   ---GWEGQG- -IKWRDFLMD DAVQKRLADD FVRDFKKFVR A---   461
SEQ_ID_NO_912   ---AGGGDDD ERKWREFLTD DAVQRRFVEE FVRELRKLVL ----   470
SEQ_ID_NO_911   ---GEDGGGE EKKWREFLMD DAVQRRFVRE FVAGLRRLKG ----   479
SEQ_ID_NO_898   KEQGKQIREN HMQWSKFLSN KEIQNKFITD LVAQLKSMA- ----   464
SEQ_ID_NO_913   NEPAKSIREN HRKLKEFLQN DEIQKKYIAD FVENLKAL-- ----   454
SEQ_ID_NO_901   KDPGKLIREN QKKWKEFLLN KDIQSKYIGN LVNEMTAMAK VSTT   473
SEQ_ID_NO_915   ----KVIREN QKKWKEFLLN KDTHSKFVED LVHDMMAMAK LSTT   465
SEQ_ID_NO_904   SEIGREVRGN HDKLRGFLLN ADLDSKYMDS FNQKLQDLLG ----   459
SEQ_ID_NO_905   SEIGREVRGN HDKLRGFLMN ADLDSKYMDS FNQKLQDLLG ----   459
SEQ_ID_NO_908   SEIGREVRGN HDKLRGFLLN ADLDSKYMDS FNQKLQDLLG ----   459
SEQ_ID_NO_891   SDLGKLVRSN HAKLKETLGS HGLLTGYVDK FVEELQEYLI ----   442
SEQ_ID_NO_893   SEVGSMIKKN HTEWRKLLRS EGFMSSYFDK FFQNMQELVD HK--   463
```

Figure 30 (continued)

| | | |
|---|---|---|
| SEQ_ID_NO_935 | - - - | 132 |
| SEQ_ID_NO_917 | L K A | 201 |
| SEQ_ID_NO_925 | - - - | 131 |
| SEQ_ID_NO_940 | - - - | 130 |
| SEQ_ID_NO_937 | - - - | 134 |
| SEQ_ID_NO_921 | - - - | 131 |
| SEQ_ID_NO_919 | - - - | 129 |
| SEQ_ID_NO_923 | - - - | 130 |

Figure 31

```
SEQ_ID_NO_947    MGIKFSQGPS NTTIHNRS-- -HQDGEDQRN ETATKLNHDK PQNQSS--SF  45
SEQ_ID_NO_972    MGSL-GPSTI SSMNMAKAAS VVGGKTGVVA VADQQKEVPP KTMNCSSYAF  49
SEQ_ID_NO_967    MGSL-GPAVV VSASAAKM-- ---AGGGQQP STERKETSSA FGGGCCGGGF  44
SEQ_ID_NO_964    MGSLLGPTVT VNVSMTKPDA AAAGGGQQPP --ERKEGGGR CGVLGC--GF  46
SEQ_ID_NO_944    MGSL-GPTVS LSI-MARP-- ----GGQQPA EMERKKDSGV FFGGGC--GF  40
SEQ_ID_NO_946    ---MSGVSCP SSVSSAMP-- -----KDLRP NGYNQHQASK RGTCSC---F  37
SEQ_ID_NO_962    MGSISQPVAN LSLAASAQ-- ---------- --AKQQQRDL H----C---F  29
SEQ_ID_NO_950    MESVTTRPSP NVVGVANS-- ---------- ---------K HGVEWCG-HF  28

SEQ_ID_NO_947    QIPLHYPKYT KSDYEKMPEW QLDRLLREYG LPVIGDSYEK RKFAIGAFLW  95
SEQ_ID_NO_972    QMPLHYPRYK KADYESMPEW RVDCLLREYG LPADGDLDSK RKFAMGAFLW  99
SEQ_ID_NO_967    QMPLHYPRYK KADYEAMPEW RVDCLLREYG LPVDGGVEEK RRFAMGAFLW  94
SEQ_ID_NO_964    RMPLHYPRYK KEDYEGMPEW RVDSLLREYG LPADGDLDSK RRFAMGAFLW  96
SEQ_ID_NO_944    RMPLHYPRYK KADYESMPEW RVDCLLREYG LPADGDVDSK RRFAMGAFLW  90
SEQ_ID_NO_946    QMPLHYPRYK KSDYETMPEW RLDCLLKEYG LPAIGDANQK RKFAMGAFLW  87
SEQ_ID_NO_962    RMPLHYPRYT RADYESMPEW KLDCLLREYG LPVTGDVDHK RSFAMGAFLW  79
SEQ_ID_NO_950    QMPLHYPRYT QADYEAMPEW RLDCLLKEYG LPIFGDVESK RKFAMGAFLW  78

SEQ_ID_NO_947    SSENEH  101
SEQ_ID_NO_972    PDQY--  103
SEQ_ID_NO_967    PDQY--  98
SEQ_ID_NO_964    PDQY--  100
SEQ_ID_NO_944    PDQY--  94
SEQ_ID_NO_946    PSENE-  92
SEQ_ID_NO_962    PAH---  82
SEQ_ID_NO_950    IK----  80
```

Figure 32

```
SEQ_ID_NO_976    ------MALH LNTVIDLTVD NYWLFRIPPI TIDFLNKLPQ QSEAPTPASA  44
SEQ_ID_NO_980    MAPSTIYQYH MRQDFSTNVD SN---NSTAP TTDAIIIHLQ FSHVLELCYP  47
SEQ_ID_NO_978    ---------- ---------- ---------- MARLLFRLLQ ETNSPTPATP  20

SEQ_ID_NO_976    VTAQLTRRFT CSTGDF--VL YRQPQRVEEM VTAAGLPLEC APSVAEFISL  92
SEQ_ID_NO_980    ETIQIPLNTT NESHLFPRQL FSSHVNRESI VKEILSSMGC SSDFIESAAP  97
SEQ_ID_NO_978    SP-------- --------AL YSDLV---VV IAALLCALIC VLGLLAVS--  49

SEQ_ID_NO_976    SVRSNSYRK- ---------- --PVVMTVEV GAPVDEDEDE DEEL------  123
SEQ_ID_NO_980    DISSFALDMV TNPCNASSSE VLTMVLAIHV TTPYDEREEI DRALSESLMQ  147
SEQ_ID_NO_978    --RCVWLRRI ANR------- ---------- SATNSDQPPA NKGLKKKVLK  80

SEQ_ID_NO_976    ---------- ---------- -PPGAVFEEC AICYKEYLVG GATSVKLACS  152
SEQ_ID_NO_980    EASRFKPASK SCIDGLKRMS LEGSCSMKEC MVCLEEFLMG SEV-VCLPCG  196
SEQ_ID_NO_978    SLPKLTYSPD S--------- -PPAEKFAEC AICLMEFAAG DELRVLSQCG  120

SEQ_ID_NO_976    HTFHRKCLDR WTAVNRTCPY CRAPVPVEQD YWDDEDACDN GESESDDIPS  202
SEQ_ID_NO_980    HIFHGDCIVR WLETSHLCPL CRFAMP---- ---------- ----------  222
SEQ_ID_NO_978    HGFHVSCIDT WLGSHSSCPS CRQILV---- ---------- GIARCQKCGG  156

SEQ_ID_NO_976    EEGDDEESEY DDIPSEGGDD EETEHDDIPS EEGDDWESEY EDVPNEEDDG  252
SEQ_ID_NO_980    ---------- ---------- ---------- ---------- ----------  222
SEQ_ID_NO_978    LPGSSSSGPE PDTRIKQDDP NSNNNDNXSX LN-------- ----------  188

SEQ_ID_NO_976    SSPAPDGSSQ EITAASPEFV SSVRDLSLSC LRLD  286
SEQ_ID_NO_980    ---------- ---------- ---------- ----  222
SEQ_ID_NO_978    ---------- ---------- ---------- ----  188
```

Figure 33

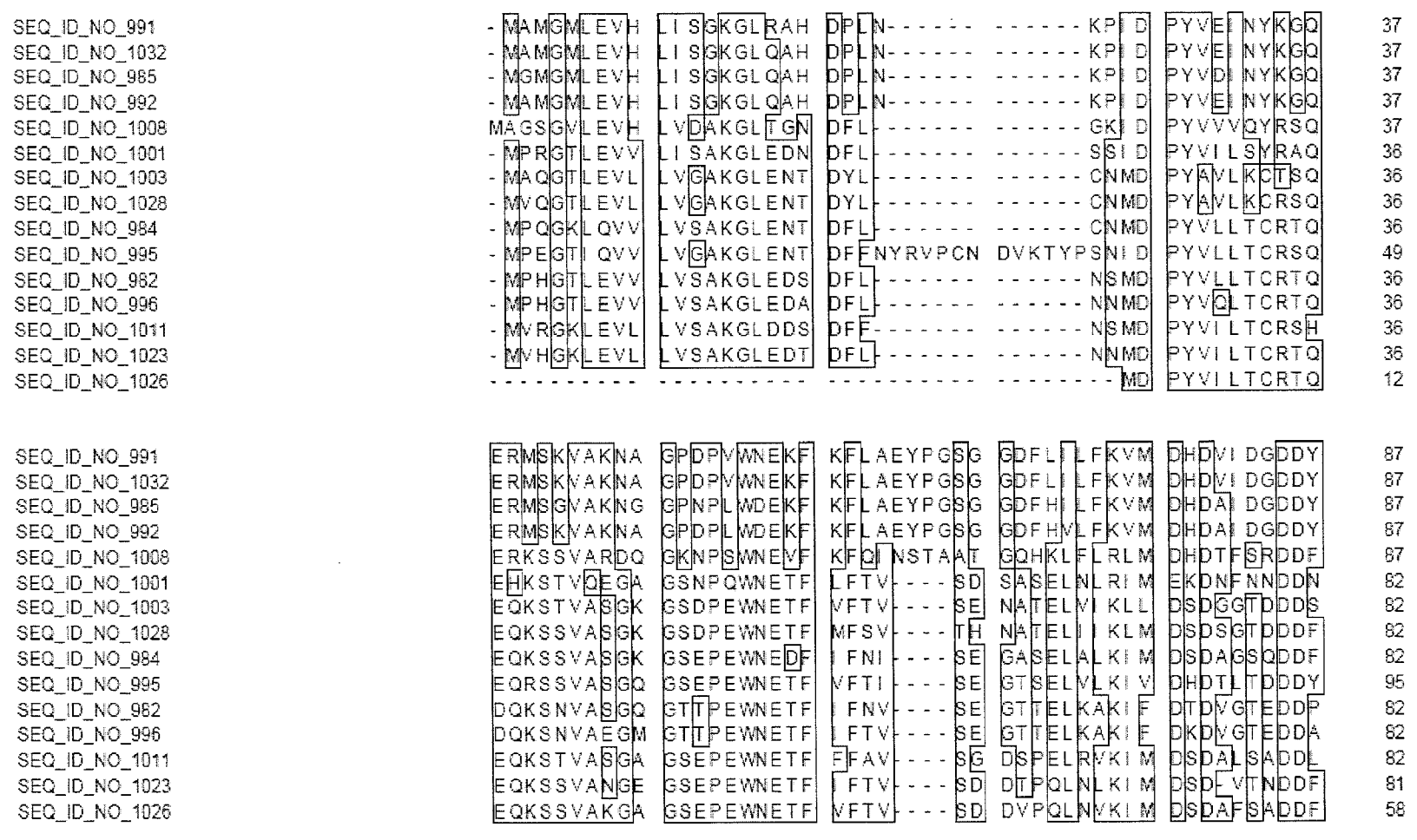

```
SEQ_ID_NO_991    -MAMGMLEVH LISGKGLRAH DPLN------ ------KPID PYVEINYKGQ 37
SEQ_ID_NO_1032   -MAMGMLEVH LISGKGLQAH DPLN------ ------KPID PYVEINYKGQ 37
SEQ_ID_NO_985    -MGMGMLEVH LISGKGLQAH DPLN------ ------KPID PYVDINYKGQ 37
SEQ_ID_NO_992    -MAMGMLEVH LISGKGLQAH DPLN------ ------KPID PYVEINYKGQ 37
SEQ_ID_NO_1008   MAGSGVLEVH LVDAKGLTGN DFL------- ------GKID PYVVVQYRSQ 37
SEQ_ID_NO_1001   -MPRGTLEVV LISAKGLEDN DFL------- ------SSID PYVILSYRAQ 36
SEQ_ID_NO_1003   -MAQGTLEVL LVGAKGLENT DYL------- ------CNMD PYAVLKCTSQ 36
SEQ_ID_NO_1028   -MVQGTLEVL LVGAKGLENT DYL------- ------CNMD PYAVLKCRSQ 36
SEQ_ID_NO_984    -MPQGKLQVV LVSAKGLENT DFL------- ------CNMD PYVLLTCRTQ 36
SEQ_ID_NO_995    -MPEGTIQVV LVGAKGLENT DFFNYRVPCN DVKTYPSNID PYVLLTCRSQ 49
SEQ_ID_NO_982    -MPHGTLEVV LVSAKGLEDS DFL------- ------NSMD PYVLLTCRTQ 36
SEQ_ID_NO_996    -MPHGTLEVV LVSAKGLEDA DFL------- ------NNMD PYVQLTCRTQ 36
SEQ_ID_NO_1011   -MVRGKLEVL LVSAKGLDDS DFF------- ------NSMD PYVILTCRSH 36
SEQ_ID_NO_1023   -MVHGKLEVL LVSAKGLEDT DFL------- ------NNMD PYVILTCRTQ 36
SEQ_ID_NO_1026   ---------- ---------- ---------- --------MD PYVILTCRTQ 12

SEQ_ID_NO_991    ERMSKVAKNA GPDPVWNEKF KFLAEYPGSG GDFLILFKVM DHDVIDGDDY 87
SEQ_ID_NO_1032   ERMSKVAKNA GPDPVWNEKF KFLAEYPGSG GDFLILFKVM DHDVIDGDDY 87
SEQ_ID_NO_985    ERMSGVAKNG GPNPLWDEKF KFLAEYPGSG GDFHILFKVM DHDAIDGDDY 87
SEQ_ID_NO_992    ERMSKVAKNA GPDPLWDEKF KFLAEYPGSG GDFHVLFKVM DHDAIDGDDY 87
SEQ_ID_NO_1008   ERKSSVARDQ GKNPSWNEVF KFQINSTAAT GQHKLFLRLM DHDTFSRDDF 87
SEQ_ID_NO_1001   EHKSTVQEGA GSNPQWNETF LFTV----SD SASELNLRIM EKDNFNNDDN 82
SEQ_ID_NO_1003   EQKSTVASGK GSDPEWNETF VFTV----SE NATELVIKLL DSDGGTDDDS 82
SEQ_ID_NO_1028   EQKSSVASGK GSDPEWNETF MFSV----TH NATELIIKLM DSDSGTDDDF 82
SEQ_ID_NO_984    EQKSSVASGK GSEPEWNEDF IFNI----SE GASELALKIM DSDAGSQDDF 82
SEQ_ID_NO_995    EQRSSVASGQ GSEPEWNETF VFTI----SE GTSELVLKIV DHDTLTDDDY 95
SEQ_ID_NO_982    DQKSNVASGQ GTTPEWNETF IFNV----SE GTTELKAKIF DTDVGTEDDP 82
SEQ_ID_NO_996    DQKSNVAEGM GTTPEWNETF IFTV----SE GTTELKAKIF DKDVGTEDDA 82
SEQ_ID_NO_1011   EQKSTVASGA GSEPEWNETF FFAV----SG DSPELRVKIM DSDALSADDL 82
SEQ_ID_NO_1023   EQKSSVANGE GSEPEWNETF IFTV----SD DTPQLNLKIM DSD-VTNDDF 81
SEQ_ID_NO_1026   EQKSSVAKGA GSEPEWNETF VFTV----SD DVPQLNVKIM DSDAFSADDF 58
```

Figure 33 (continued)

```
SEQ_ID_NO_991    IGDVSIDVKD LLVEGVRKGW SELPPRMYQV IAHKLYFKGE IEVGVSFKRQ 137
SEQ_ID_NO_1032   IGDVSIDVKD LLVEGVRKGW SELPPRMYQV IAHKLYFKGE IEVGVSFKRQ 137
SEQ_ID_NO_985    IGDVKIDVKD LLAEGVRKGW SEIPPRMYHV LAHKIHFKGE IEVGVSFKLQ 137
SEQ_ID_NO_992    IGDVKIDVKD LLAEGVRKGW SEIRPRMYHV LAHKIHFKGE IEVGVSFKLQ 137
SEQ_ID_NO_1008   LGEATINVTD LISLGMEHGT WEMSESKHRV VLADKTYHGE IRVSLTFTAS 137
SEQ_ID_NO_1001   LGEAIIPLEA VFEEG----- -SLAENAYKL V-KEQEYCGE IKVALTFTPE 125
SEQ_ID_NO_1003   VGEATIPLDG VYTEG----- -SIPPTVYNV V-KDEEYRGE IKIGLTFTPE 125
SEQ_ID_NO_1028   VGEATISLEA IYTEG----- -SIPPTVYNV V-KEEEYRGE IKVGLTFTPE 125
SEQ_ID_NO_984    VEEVAIPLEP VFIER----- -NIPLTPYTV V-KDGEYRGE IKFGLTFTPE 125
SEQ_ID_NO_995    LGKASIPLEP LFIEG----- -NLPTTAYNV V-KDEEYRGE IRVGLSFTPE 138
SEQ_ID_NO_982    LGEATIPLEA VFLEG----- -DIPPAAYNV V-KDEEFKGE IWIALSFKPS 125
SEQ_ID_NO_996    VGEATIPLEP VFVEG----- -SIPPTAYNV V-KDEEYKGE IWVALSFKPS 125
SEQ_ID_NO_1011   VGEACIPLEA VLQEG----- -SLPPAVHRV V-KDEEYRGE IKIALTFTPA 125
SEQ_ID_NO_1023   VGEASIPLEA VFQEG----- -SLPPTVHPV V-KEEKYCGE IKLALTFTPA 124
SEQ_ID_NO_1026   VGEANIPLEP VFLEG----- -SLPPAVHRV V-KEEKYCGE IKVALTFTPA 101

SEQ_ID_NO_991    ---------- ---------- ---------- ---------- ---------- 137
SEQ_ID_NO_1032   ---------- ---------- ---------- ---------- ---------- 137
SEQ_ID_NO_985    ---------- ---------- ---------- ---------- --GGGGCGGC 145
SEQ_ID_NO_992    ---------- ---------- ---------- ---------- --GGGGCAGC 145
SEQ_ID_NO_1008   ---------- ---------- ---------- ---------- AKAQDHAEQV 147
SEQ_ID_NO_1001   ---------- ---------- ---------- ---------- --RNDEEETC 133
SEQ_ID_NO_1003   --E------- ---------- ---------- ---------A RDEDQPEENY 137
SEQ_ID_NO_1028   --D------- ---------- ---------- ---------D RDRGLSEEDI 137
SEQ_ID_NO_984    ERE------- ---------- ---------- ---------S RDFEV-EESF 138
SEQ_ID_NO_995    RRT------- ---------- ---------- ---------S RTFDAGEESY 152
SEQ_ID_NO_982    --E------- ---------- ---------- ---------N RSRGFEEESY 137
SEQ_ID_NO_996    --E------- ---------- ---------- ---------N RSRGMDEESY 137
SEQ_ID_NO_1011   ---------- ---------- ---------- ---------- -EENEEEESY 134
SEQ_ID_NO_1023   -VE------- ---------- ---------- ---------T RRPDNEEGTY 137
SEQ_ID_NO_1026   AVKTLTSVSC NIDGVVAIVS EHLVGVCDAN VLDTRISSGN SPSSQPRERG 151
```

Figure 33 (continued)

| | | |
|---|---|---|
| SEQ_ID_NO_991 | - G - - - - - - - - - - | 138 |
| SEQ_ID_NO_1032 | - G - - - - - - - - - - | 138 |
| SEQ_ID_NO_985 | N P W E N - - - - - - - | 150 |
| SEQ_ID_NO_992 | Y P W E N - - - - - - - | 150 |
| SEQ_ID_NO_1008 | G G W A H S F R Q - - - | 156 |
| SEQ_ID_NO_1001 | G G W K E S T R D F - - | 143 |
| SEQ_ID_NO_1003 | G G W N Q S S - - - - - | 144 |
| SEQ_ID_NO_1028 | G G W K Q S S - - - - - | 144 |
| SEQ_ID_NO_984 | G G W K Q S S Y T D - - | 148 |
| SEQ_ID_NO_995 | G G W K E S A Y T D - - | 162 |
| SEQ_ID_NO_982 | G G W K N S E A S Y - - | 147 |
| SEQ_ID_NO_996 | G G W K N S E A S Y - - | 147 |
| SEQ_ID_NO_1011 | G G W N Q S T - - - - - | 141 |
| SEQ_ID_NO_1023 | S S W - N - - - - - - - | 141 |
| SEQ_ID_NO_1026 | G G L Q Q L E L I A C Y | 163 |

Figure 34 (continued)

```
SEQ_ID_NO_1058  SYGAPKVTKD GVTVAKSIEF KDKVKNVGAS LVKQVANATN DVAGDGTTCA  123
SEQ_ID_NO_1077  KYGAPKIVND GVTVAREVEL EDPVKNIGAK LVRQAAAKTN DLAGDGTTTS  146
SEQ_ID_NO_1078  KYGAPKIVND GVTVAREVEL EDPVENIGAK LVRQAAAKTN DLAGDGTTTS  146
SEQ_ID_NO_1075  -SGKLKVIND GVTIARSIEL SDAIENAGAM LIQEVASKMN DLAGDGTSTA  129
SEQ_ID_NO_1095  KFGMPQVIND GVTIARAIEL PDPVENAGAQ LIKEVAGRTN DSAGDGTTTA  117
SEQ_ID_NO_1055  KFGVPQVIND GVSIRRAIEL KDPVENAGAQ LIKEVAGRTN DAAGDGTTTA  125
SEQ_ID_NO_1080  -FGSPKVVND GVTIARAIEL ADPMENAGAA LIREVASKTN DSAGDGTTTA  138
SEQ_ID_NO_1086  -FGSPKVVND GVTIARAIEL ADPMENAGAA LIREVASKTN DSAGDGTTTA  132
SEQ_ID_NO_1085  -FGTPKVVND GVTIARAIEL ADPMENAGAS LIREVASKTN DSAGDGTTTA  133
SEQ_ID_NO_1097  -FGTPKVVND GVTIARAIEL ADPMENAGAA LIREVASKTN DSAGDGTTTA  135
SEQ_ID_NO_1054  -YGNPKVVND GVTIARAIEL YDPMENAGAA LIREVASKTN DSAGDGTTTA  121
SEQ_ID_NO_1088  -YGSPKVVND GVTIARAIEL YDPMENAGAA LIREVASKTN DSAGDGTTTA  127
SEQ_ID_NO_1068  -FGSPKVVND GVTIARAIEL PNAMENAGAA LIREVASKTN DSAGDGTTTA  136
SEQ_ID_NO_1072  -FGSPKVVND GVTIARAIEL PDAMENAGAA LIREVASKTN DSAGDGTTTA  135
SEQ_ID_NO_1057  -FGSPKVVND GVTIARAIEL PNAMENAGAA LIREVASKTN DSAGDGTTTA  136
SEQ_ID_NO_1061  -FGSPKVVND GVTIARAIEL PDPMENAGAA LIREVASKTN DSAGDGTTTA  136
SEQ_ID_NO_1076  -FGSPKVVND GVTIARAIEL PDPMENAGAA LIREVASKTN DSAGDGTTTA  137
SEQ_ID_NO_1092  -FGSPKVVND GVTIARAIEL PDPMENAGAA LIREVASKTN DSAGDGTTTA  138
SEQ_ID_NO_1074  -FGSPKVVND GVTIARAIEL PDPMENAGAA LIREVASKTN DSAGDGTTTA  134
SEQ_ID_NO_1063  -FGSPKVVND GVTIARAIEL PDAMENAGAA LIREVASKTN DSAGDGTTTA  134

SEQ_ID_NO_1058  TILTRAIETE GCKSVAAGMN AMDLRRGISM AVDSVVTNLK SRARMISTSE  173
SEQ_ID_NO_1077  VVLAQGLIAE GVKVVAAGAN PVLITRGIEK TAKALVAELK NMSKEVEDS-  195
SEQ_ID_NO_1078  VVLAQGLIAE GVKVVAAGAN PVLITRGIEK TAKALVAELK NMSKEVEDS-  195
SEQ_ID_NO_1075  IILARAMIKS GLSAVAFGAN PISLKKGMEK TVKDLVKFLK KRSIPVEGRD  179
SEQ_ID_NO_1095  SVLAREMIKY GLQSVAAGAN PVTVKRGMDK TSEFCRKKLD ELTIPVRNAA  167
SEQ_ID_NO_1055  SVLAREMIHY GLQSVTAGAN PIAVKRGLDK TAEYLVAKLK EHAKPVKGRD  175
SEQ_ID_NO_1080  SVLAREIIKL GLLSVTSGAN PVSIKKGIDK TVQSLVEELE KKSRPVKGSG  188
SEQ_ID_NO_1086  SVLAREIIKL GLLSVTSGAN PVSIKKGIDK TVHSLVEELE KKSRPVKGSG  182
SEQ_ID_NO_1085  SVLAREIIKL GMLSVTSGAN PVSIKKGIDK TVQKLVEELE KKSRPVKGGG  183
SEQ_ID_NO_1097  SVLAREIIKL GMLSITSGAN PVSVKKGIDK TVQKLVEELE KKSRPVKGSG  185
SEQ_ID_NO_1054  CVLAREIIKL GLLSVTSGAN PVSLKKGIDK TVQGLIQELE NKSRPIKGGG  171
SEQ_ID_NO_1088  SVLAREIIKL GLLSVTSGAN PVSLKKGIDK TVHGLIEELE KKARPVKGSG  177
SEQ_ID_NO_1068  SILAREIIKH GLLSVTSGAN PVSLKRGIDK TVQGLIEELQ KKARPVKGRD  186
SEQ_ID_NO_1072  SVLAREIIKH GLLSVTSGAN PVSLKRGIDK TVQALIEELE KRSRPVKGGR  185
SEQ_ID_NO_1057  SVLAREIIKL GLLTVTSGAN PVSVXRGIDK TVQSLIEELE KKARPVKGRD  186
SEQ_ID_NO_1061  SVLAREIIKL GLLSVTSGAN PVSIKRGIDK TVQGLVEELE KKARPVKGRD  186
SEQ_ID_NO_1076  SILAREIIKL GLLNVTSGAN PVSIKKGIDK TVAALVEELE KLARPVKGGD  187
SEQ_ID_NO_1092  SILAREIIKL GLLSVTSGAN PVSIKKGIDK TVAGLIEELE KLARPVKGGD  188
SEQ_ID_NO_1074  SVLAREIIKL GLLSVTSGAN PVSLKRGIDK TVQGLVEELE KKARPVKGGD  184
SEQ_ID_NO_1063  SVLAREIIKL GLLSVTSGAN PVSLKRGIDK TVQGLVEELE KRARPVKGGD  184
```

Figure 34 (continued)

```
SEQ_ID_NO_1058   EIAQVGTISA NGEREIGELI AKAMEKVGKE GVITISDGKT LFNELEVVEG   223
SEQ_ID_NO_1077   ELPDVAAVSA GNNLEVGSMI AEPMSTVGRK GVVTLEEGKS AENSLRVVEG   245
SEQ_ID_NO_1078   ELADVAAVSA GNNLEVGSMI AEAMSKVGRK GVVTLEEGKS AENSLRVVEG   245
SEQ_ID_NO_1075   HIKAVASISA GNDEYVGNLI AEAIEKIGFD GVITIESSRS SETSVVIEEG   229
SEQ_ID_NO_1095   DIRAVASISA GNNEEIGNMI AEAIEKVGPD GVLSIETGSG LETVVEVEEG   217
SEQ_ID_NO_1055   DIKNVASISA GNDNAIGEMI ADALDKVGSN GVLSIETSNS TETVVEVQEG   225
SEQ_ID_NO_1080   DIKAIAAISA GNDDFIGTMI AEAINKVGPD GVLSIESSSS FETTVEVEEG   238
SEQ_ID_NO_1086   DIKAVAAISA GNDDFVGTMI AEAIDKVGPD GVLSIESSSS FETTVEVEEG   232
SEQ_ID_NO_1085   DIKAVAAISA GNDEFVGTMI AEAIDKVGPD GVLSIESSSS FETTVEVEEG   233
SEQ_ID_NO_1097   DIKAVAAISA GNDEFVGTMI AEAIDKVGPD GVLSIESSSS FETTVEVEEG   235
SEQ_ID_NO_1054   DIKAVASISA GNDEFIGSMI AEAIDKVGPD GVLSIESSSS FETTVEVEEG   221
SEQ_ID_NO_1088   DIKAVASISA GNDELIGSMI ADAIDKVGPD GVLSIESSSS FETTVDVEEG   227
SEQ_ID_NO_1068   DIRAVASISA GNDDLIGSMI ADAIDKVGPD GVLSIESSSS FETTVEVEEG   236
SEQ_ID_NO_1072   DIKAVATISA GNDELIGAMI ADAIDKVGPD GVSPIESSSS FETTVEVEEG   235
SEQ_ID_NO_1057   DIKAVASISA GNDDLIGTMV ADAIDKVGPD GVLSIESSSS FETTVDVEEG   236
SEQ_ID_NO_1061   DIKAVASISA GNDELIGTMI ADAIDKVGPD GVLSIESSSS FETVVEVEEG   236
SEQ_ID_NO_1076   DIKAVATISA GNDELIGKMI AEAIDKVGPD GVLSIESSNS FETTVEVEEG   237
SEQ_ID_NO_1092   DIKAVASISA GNDELIGKMI AEAIDKVGPD GVLSIESSSS FETTVEVEEG   238
SEQ_ID_NO_1074   DIKAVASISA GNDELIGQMI AEAIDKVGPD GVLSIESSSS FETTVEVEEG   234
SEQ_ID_NO_1083   DIKAVASISA GNDELIGKMI AEAIDKVGPD GVLSIESSSS FETTVEVEEG   234

SEQ_ID_NO_1058   MKLDRGYISP YFITNQKNQK CELDDPLILI HEKKISSINS VVKVLELALK   273
SEQ_ID_NO_1077   MQFDRGYFAP YFVTDSEKMS VEYDNCKLLL VDKKITNAKD LVNVLKDAIR   295
SEQ_ID_NO_1078   MQFDRGYVSP YFVTDSEKMS VEYENCKLLL VDKKITNARD LVNVLEDAIR   295
SEQ_ID_NO_1075   MKIDRGYMSP HFITNQEKSI VEFDNAKVLV TDQKISSVRE IVPLLEKAMQ   279
SEQ_ID_NO_1095   MEIDRGYISP QFVNDNERLM VEYEGCRILI TDEKIEQVQM LVPLLEEVSQ   267
SEQ_ID_NO_1055   MEIDRGYISP QFVTNQERLL VEYDNCRVLV TDQKIDAIRD IIPILEQVTR   275
SEQ_ID_NO_1080   MEIDRGYISP QFVTNSEKSV VEFENARVLV TDQKISSIKE ILPLLEQTTQ   288
SEQ_ID_NO_1086   MEIDRGYISP QFVTNPEKSL VEFENARILV TDQKISSIKE IIPLLEQTTQ   282
SEQ_ID_NO_1085   MELDRGYISP QFVTNPEKST VEFENARILV TDQKISSIKE ILPLLEQTTQ   283
SEQ_ID_NO_1097   MELDRGYISP QFVTNPEKST VEFENARILV TDQKISSIKE IIPLLEQTTQ   285
SEQ_ID_NO_1054   MEIDRGYISP QFVTNLEKSI VEFENCKVLI TDQKITSIKE ILPILEKTTQ   271
SEQ_ID_NO_1088   MEIDRGYISP QFVTNLEKSI VEFENAKVLI TDQKITSIKE ILPILEKTTQ   277
SEQ_ID_NO_1068   MEIDRGYISP QFVTNPEKLL AEFENARVLI TDQKITAIKD IIPILEKTTQ   286
SEQ_ID_NO_1072   MEIDRGYISP QFVTNPEKLL VEFENARVLI TDQKITAIKD IIPILEKTTQ   285
SEQ_ID_NO_1057   MEIDRGYISP QFVTNPEKLI CEFENARVLV TDQKITAIKD IIPLLEKTTQ   286
SEQ_ID_NO_1061   MEIDRGYISP QFVTNPEKLI CEFENARVLI TDQKITAIKD IIPLLEKTTQ   286
SEQ_ID_NO_1076   MEIDRGYISP QFVTNPEKSI VEFENARVLI TDQKISAIKD IIPLLEKTTQ   287
SEQ_ID_NO_1092   MEIDRGYISP QFVTNLEKSI VEFENARVLI TDQKISAIKD IIPLLEKTTQ   288
SEQ_ID_NO_1074   MEIDRGYISP QFVTNPEKLI VEFENARVLI TDQKISAIKD IIPLLEKTTQ   284
SEQ_ID_NO_1083   IEIDRGYISS -FVTNLEKSI VEFENARVLV TDQKISAIKD IIPLLEKTTQ   283
```

Figure 34 (continued)

```
SEQ_ID_NO_1058   RQ-RPLLIVS EDVESDALAT LILNKLRAGI KVCAIKAPGF GENRKAGLHD   322
SEQ_ID_NO_1077   NG-SPTLIIA ENIDQEALAT LVVNKLRGAL KVAALKAPGF GERKSQYLDD   344
SEQ_ID_NO_1078   NG-YPILIIA EDIEQEALAT LVVNKLRGAL KVAALKAPGF GERKSQYLDD   344
SEQ_ID_NO_1075   LS-APLLIIA EDVTAQVLET LIVNKMQGLL RVAAVKCPGL GDGKKALLQD   328
SEQ_ID_NO_1095   AGSPPLLIIA EDITGEALAT LVVNKMRGVL KVAAIKAPGF GERRKALLQD   317
SEQ_ID_NO_1055   LN-APLLIIA EDVSGEALAT LVVNKLRGVL NVCAIKAPGF GERRKSLLQD   324
SEQ_ID_NO_1080   LR-APLLIIA EDVSGEALAT LVVNKLRGIL NVAAIKAPGF GERRKALLQD   337
SEQ_ID_NO_1086   LR-APLLIIA EDVAGEALAT LVVNKLRGIL NVAAIKAPGF GERRKALLQD   331
SEQ_ID_NO_1085   LR-APLLIIA EDVSGEALAT LVVNKLRGIL NVAAIKAPGF GERRKALLQD   332
SEQ_ID_NO_1097   LR-APLLIIA EDVSGEALAT LVVNKLRGIL NVAAIKAPGF GERRKALLQD   334
SEQ_ID_NO_1054   LR-APLFIIA EDITGEALAT LVVNKLRGIL NVAAIKAPSF GERRKAVLQD   320
SEQ_ID_NO_1088   LR-APLFIIA EDITGEALAT LVVNKLRGIL NVAAIKAPSF GERRKAVLQD   326
SEQ_ID_NO_1068   LR-APLLIIA EDVTGEALAT LVVNKLRGVL NVVAVKAPGF GERRKAMLQD   335
SEQ_ID_NO_1072   LR-APLLIIA EDVTGEALAT LVVNKLRGVL NVVAVKAPGF GERRKAMLQD   334
SEQ_ID_NO_1057   LR-APLLIIA EDVTGEALAT LVVNKLRGIL NVAAIKAPSF GERRKAVLQD   335
SEQ_ID_NO_1061   LR-APLLIIA EDVTGEALAT LVVNKLRGVL NVAAIKAPGF GERRKAMLQD   335
SEQ_ID_NO_1076   LR-APLLIIS EDITGEALAT LVVNKLRGIL NVAAIKAPGF GERRKALLQD   336
SEQ_ID_NO_1092   LR-APLFIIA EDITGEALAT LVVNKLRGIL NVAAIKAPGF GERRKALLQD   337
SEQ_ID_NO_1074   LR-APLLIIA EDVTGEALAT LVVNKLRGIL NVAAIKAPGF GERRKALLQD   333
SEQ_ID_NO_1083   LR-APLLIIA EDVTGEALAT LVVNKLRGIL NVAAIKAPSF GERRKAVLQD   332

SEQ_ID_NO_1058   LAVLTGGQLI TEELGMNLEK VDLDMLGSCK KITISKDDTV ILDGAGDKKS   372
SEQ_ID_NO_1077   IATLTGGTVI REELGLTLDK ADKEVLGHAA KVVLTKDATT IVGDGSTQEA   394
SEQ_ID_NO_1078   IATLTGGTVI REELGLTLDK ADKEVLGHAA KVVLTKDATT IVGDGSTQEA   394
SEQ_ID_NO_1075   IALMTGADFL CGDLGLTLEG TTSDQLGSAL KVKITSNATT IFADPNTKAE   378
SEQ_ID_NO_1095   IAIVTGAQYI AKDLGLSVQR ATMDSLGYAR KVSIAQTTTT LIADGASKED   367
SEQ_ID_NO_1055   IAIVTGAEFL AKDLGMKVEQ AVVEQLGVAR KVTVANNTTT LIADAASKDE   374
SEQ_ID_NO_1080   IAIVTGAEFQ AKDLGQLIEQ TTVEQLGIAR KVTISGSSTT IIADVATKDE   387
SEQ_ID_NO_1086   IAIVTGAEFQ AKDLGLLVES TTVEQLGIAR KVTISQSSTT IIADVATKDE   381
SEQ_ID_NO_1085   IAIVTGAEYQ SKDLGLLVEK TTVEQLGIAR KVTISSSSTT IIADAASKDD   382
SEQ_ID_NO_1097   IAIVTGAEYQ SKDLGLLVEN TTVEQLGIAR KVTISSSSTT IIADAASKDD   384
SEQ_ID_NO_1054   IAIVTGAEFL AKDLGLLVEN ATEEQLGTAR KVTIHQTTTT LIADAASKDE   370
SEQ_ID_NO_1088   IAIVTGAEFL AKDLGLLVEN ATEEQLGTAR KVTIHQTTTT LIADAASKDE   376
SEQ_ID_NO_1068   IAILTGAEYL AMDMSLLVEN ATIDQLGIAR KVTISKDSTT LIADAASKDE   385
SEQ_ID_NO_1072   IAILTEPS-T ALDMGLLVEN TTIDQLGIAR KVTISKDSTT LIADAASKAE   383
SEQ_ID_NO_1057   IAILTGAEFQ ANDLGLLIEN TSVEQLGIAR KVIITKDSTQ IIADAASKDE   385
SEQ_ID_NO_1061   IAILTGAEFQ ASDLGLSIEN TSIEQLGLAR KVTISKDSTT IIADAASKDE   385
SEQ_ID_NO_1076   IAILTGAEFQ ASDLGLLVEN TTIEQLGLAR KVTISKDSTT IIADAASKDE   386
SEQ_ID_NO_1092   IAILTGAEYQ ASDLGLLVEN TSIEQLGLAR KVTISKDSTT IIADAASKDE   387
SEQ_ID_NO_1074   IAILTGAEFQ ASDLGLLVEN TSVEQLGLAR KITISKDSTT VIADAATKDE   383
SEQ_ID_NO_1083   IAILTGAEFQ ASDLGLLVEN TSIEQLGLAR KVTISKDSTT IIADAASKDE   382
```

Figure 34 (continued)

```
SEQ_ID_NO_1058   IEERCEQIRS AIELSTSDYD KEKLQERLAK LSGGVAVLKI GGASEAEVGE   422
SEQ_ID_NO_1077   VNKRVAQIKN LIEAADQDYE KEKLNERIAK LSGGVAVIQV GAQTETELKE   444
SEQ_ID_NO_1078   VNKRVAQIKN LIEAADQDYE KEKLNERIAK LSGGVAVIQV GAQTETELKE   444
SEQ_ID_NO_1075   IQARILQIKK DLIETDNANH SRKLSERIAK LTGGIAVIKV GAHTELELED   428
SEQ_ID_NO_1095   IDMRVAQLKQ ELAETDSVYD TEKLSERIAK LAGGVAVIKV GAATETEMEE   417
SEQ_ID_NO_1055   IEMRIAQLKK ELAETDSVYD TEKLSERIAK LSGGVAVIKV GAATEAELED   424
SEQ_ID_NO_1080   IQARIAQLKR ELSQTDSTYD SEKLAERIAK LSGGVAVIKV GAATETELED   437
SEQ_ID_NO_1086   IQARIAQLKR ELSQTDSAYD SEKLAERIAK LSGGVAVIKV GAATETELED   431
SEQ_ID_NO_1085   IQARIAQLKR ELSQTDSTYD SEKLAERIAK LSGGVAVIKV GASTEAELED   432
SEQ_ID_NO_1097   IQARIAQLKR ELSQTDSAYD SEKLAERIAK LSGGVAVIKV GASTEAELED   434
SEQ_ID_NO_1054   IQARIAQLKK ELAETDSVYD TEKLAERIAK LAGGVAVIKV GAATETELED   420
SEQ_ID_NO_1088   IQARVAQLKK ELSETDSIYD TEKLAERIAK LSGGVAVIKV GAATETELED   426
SEQ_ID_NO_1068   LQARIAQLKK ELFETDSVYD SEKLAERIAK LSGGVAVIKV GAATETELED   435
SEQ_ID_NO_1072   LQARISQLKK ESFETDSVYD SEKLAERIAK LSGGVAVIKV GAATETELED   433
SEQ_ID_NO_1057   IQARVQQLKK ELAETDSVYD TEKLAERIAK LSGGVAVIKV GAATETELED   435
SEQ_ID_NO_1061   LQARIAQLKK ELSETDSVYD SEKLAERIAK LSGGVAVIKV GAATETELED   435
SEQ_ID_NO_1076   LQSRVAQLKK ELSETDSIYD SEKLAERIAK LSGGVAVIKV GAATETELED   436
SEQ_ID_NO_1092   LQSRVAQLKK ELSETDSVYD SEKLAERIAK LSGGVAVIKV GAATETELED   437
SEQ_ID_NO_1074   LQARVAQLKK ELSQTDSVYD TEKLAERIAK LSGGVAVIKV GAATETELED   433
SEQ_ID_NO_1083   LQARVAQLKK ELAETDAVYD SVKLAERITK LSGGVAVIKV GAATETELED   432

SEQ_ID_NO_1058   KKDRVTDALN ATKAAVEEGI VPGGGVALLY ASKELDKL-- STANFDQKIG   470
SEQ_ID_NO_1077   KKLRVEDALN ATKAAVERGI VVGGGCTLLR LAAKVDAIKG TLANDEEKVG   494
SEQ_ID_NO_1078   KKLRVEDALN ATKAAVEEGI VVGGGCTLLR LAAKVDAIKG TLANDEEKVG   494
SEQ_ID_NO_1075   RKLRIEDAKN ATFAAINEGL VPGGGATYVH LLDLIPAIKN SMEDLDEQIG   478
SEQ_ID_NO_1095   RKLRIEDAKN ATFAAVEEGI VPGGGAALVH LSKMIDEFIP TLTSAEERLG   467
SEQ_ID_NO_1055   RKLRIEDAKN ATFAAVEEGI VPGGGAALLH LSELVPAFKE TLTDAEEKLG   474
SEQ_ID_NO_1080   RKLRIEDAKN ATFAAIEEGI VPGGGAAYVH LSTFVPAIKE KLDDPEERLG   487
SEQ_ID_NO_1086   RKLRIEDAKN ATFAAIEEGI VPGGGAAYVH LSKFVPAIKE KLDDPEERLG   481
SEQ_ID_NO_1085   RKLRIENAKN ATFAAIEEGI VPGGGAAYVH LSTFVPAIKE KLDDPEERLG   482
SEQ_ID_NO_1097   RKLRIEDAKN ATFAAIEEGI VPGGGAAYVH LSTFVPAIKE TLDDPEERLG   484
SEQ_ID_NO_1054   RQLRIEDAKN ATFAAIEEGI VPGGGAAYVH LSTVVPKIKE AIEDPDERLG   470
SEQ_ID_NO_1088   RQLRIEDAKN ATFAAIEEGI VPGGGTAYVH LSTTVPAIKE TIEDHDERLG   476
SEQ_ID_NO_1068   RKLRIEDAKN ATFAAIEEGI VPGGGAALVH LSTVIPAIKE TFEDADERLG   485
SEQ_ID_NO_1072   RKLRIEDAKN ATFAAIEEGI VPGGGATLVH LSTVIPAIKE TFEDADVRLG   483
SEQ_ID_NO_1057   RKLRIEDAKN ATFAAIEEGI VPGGGAALVH LSTCVPAIKD KLEDPEERIG   485
SEQ_ID_NO_1061   RKLRIEDAKN ATFAAIEEGI VPGGGAALVH LSTCVPAIKD KIEDADERLG   485
SEQ_ID_NO_1076   RKLRIEDAKN ATFAAIEEGI VPGGGTALVH LSGYVPAIKE KLEDADERLG   486
SEQ_ID_NO_1092   RKLRIEDAKN ATFAAIEEGI VPGGGTALVH LSAYVPAIKE KLEDADERLG   487
SEQ_ID_NO_1074   RKLRIEDAKN ATFAAIEEGI VPGGGTALVH LSTHVPAIKD KLEDADERLG   483
SEQ_ID_NO_1083   RKLRIEDAKN ATF AIEVGI VL-VDTALLH LSTHVPAIKD KLEDADERLG   480
```

Figure 34 (continued)

```
SEQ_ID_NO_1058  VQIIQNALKT PVHTIASNAG VEGAVVVGKL LEQDNPDLGY DAAKGEYVDM 520
SEQ_ID_NO_1077  ADIVQRALSY PLKLIAKNAG VNGSVVSEKV LSSDDPKFGY NAATGNYEDL 544
SEQ_ID_NO_1078  ADIVKRALSY PLKLIAKNAG VNGSVVSEKV LSSDDPKFGY NAATGNYEDL 544
SEQ_ID_NO_1075  ADIVAKALVE PAKSIAANAG VDGDVVVEKT RTFD-WRIGY NAMTGTYEDL 527
SEQ_ID_NO_1095  AEIVQKALLA PCRLIGNNAG VEGDVIVQHV MEGD-FNYGY DAMVGEYGDL 516
SEQ_ID_NO_1055  ADIVMKSLRA PCRLIADNAG VEGEVIVQRL LGKP-FEVGY NAMLDKVENL 523
SEQ_ID_NO_1080  ADIIQKALVA PASLIAHNAG VEGEVIVEKI KDSE-WEFGY NAMTDKHENL 536
SEQ_ID_NO_1086  ADIIQKALVA PAALIAHNAG VEGEVIVEKI KESE-WEVGY NAMADRHENL 530
SEQ_ID_NO_1085  ADIIQKALVA PAALIAHNAG VEGEVIVDKI KESE-WEYGY NAMADKHENL 531
SEQ_ID_NO_1097  ADIIQKALVA PAALIAHNAG VEGEVIVDKI RESE-WEFGY NAMADKHENL 533
SEQ_ID_NO_1054  ADIIQKALVA PASLIAHNAG VEGEVVVEKI KDSD-WEVGY NAMTDKYENL 519
SEQ_ID_NO_1088  ADIIQKALVA PASLIAHNAG VEGEVVVEKI KDGE-WEVGY NAMNDKYENL 525
SEQ_ID_NO_1068  ADIVQKALLS PAALIAQNAG VEGEVVVEKI MFSD-WENGY NAMTDTYENL 534
SEQ_ID_NO_1072  ADIVQKALVA Q-SLIAQNAG IEGEVVVEKI MFSE-WELGY NAMTDTYENL 531
SEQ_ID_NO_1057  ADIVQKALVA PASLIAQNAG MEGEVVVEKV KNSE-WEIGY NAMTDTYENL 534
SEQ_ID_NO_1061  ADIVQKALVS PASLIAQNAG IEGEVVVEKL KASE-WEIGY NAMTDKYENL 534
SEQ_ID_NO_1076  ADIVQKALVA PAALIAQNAG IEGEVVVEKI KNGE-WEVGY NAMTDTYENL 535
SEQ_ID_NO_1092  ADIVQKALVA PASLIAQNAG IEGEVVVEKI RNGE-WEVGY NAMTDTYENL 536
SEQ_ID_NO_1074  ADIVQKALIA PAALIAQNAG IEGEVVVEKI KSGE-WEVGY NAMADRYENL 532
SEQ_ID_NO_1083  ADIVQKALIA PASLIAQNAG IEGEVVVEKV KNGE-WEVGY NAMTDRYENL 529

SEQ_ID_NO_1058  -IKAGIIDPL KVIRTALVDA ASVSSLMTTT EAIVVELPKD E----KEVPA 565
SEQ_ID_NO_1077  IMAAGIIDPT KVVRCCLEHA ASVAKTFLMS DCVVVEIKEP E----AAVAG 590
SEQ_ID_NO_1078  -MAAGIIDPT KVVRCCLEHA ASVAKTFLMS DCVVVEIKEP E----AAVAG 589
SEQ_ID_NO_1075  -LNAGVADPS RVARCALQSA VSIAGVVLTT QAILVDKYL- -----GSN-K 569
SEQ_ID_NO_1095  -IEKGVIDPK KVTRSGVQNS CSIAGMVLTT QAVITEIPKK KRAIGANAGP 565
SEQ_ID_NO_1055  -LDAGVIDPA KVTRNGLLNS VSIAGIMLTT QAVMVEKHKP SEIPGGMT-A 571
SEQ_ID_NO_1080  -VEAGVIDPA KVTRCALQNA ASVAGMVLTT QAIVVEKPSK K----APA-P 580
SEQ_ID_NO_1086  -VQAGVIDPA KVTRCALQNA ASVAGMVLTT QAIVVEKPKK K----ASA-A 574
SEQ_ID_NO_1085  -VEAGVIDPA KVTRCALQNA ASVAGMVLTT QAIVVEKPKK K----APA-A 575
SEQ_ID_NO_1097  -VEAGVIDPA KVTRCALQNA ASVAGMVLTT QAIVVEKPQK -----APA-A 576
SEQ_ID_NO_1054  -MEAGVIDPA KVTRCALQNA ASVAGMVLTT QAIVVEKPKP K----PQV-A 563
SEQ_ID_NO_1088  -IEAGVIDPA KVTRCALQNA ASVAGMVLTT QAIVVEKPKP K----APV-A 569
SEQ_ID_NO_1068  -FEAGVIDPA KVTRCALQNA ASVAGMVLTT QAIVVDKPKP K----APA-A 578
SEQ_ID_NO_1072  -LEAGVIDPA KVTRCALQNA ASVAGMVLTT QAIVVDKPKP K----APA-A 575
SEQ_ID_NO_1057  -LAAGVIDPA KVTRCALQNA ASVAGMVLTT QAIVVEKAKP K----APA-A 578
SEQ_ID_NO_1061  -MEAGVIDPA KVTRCALQNS ASVAGMVLTT QAIVVEKPKP K----TPA-A 578
SEQ_ID_NO_1076  -VESGVIDPA KVTRCALQNA ASVAGMVLTT QAIVVEKPKP K----AAV-A 579
SEQ_ID_NO_1092  -IESGVIDPA KVTRCALQNA ASVAGMVLTT QAIVVEKPKP R----APV-P 580
SEQ_ID_NO_1074  -VEAGVIDPA KVTRCALQNA ASVAGMVLTT QAIVVEKPKP K----APV-A 576
SEQ_ID_NO_1083  -VEAGVIDPA KVTRCALQNA ASVAGMVLTT QAIVVEKPKP K----APT-A 573
```

Figure 34 (continued)

| | | | | |
|---|---|---|---|---|
| SEQ_ID_NO_1058 | MGGGMGGMDY | ---------- | ------ | 575 |
| SEQ_ID_NO_1077 | NPMDNSGYGY | ---------- | ------ | 600 |
| SEQ_ID_NO_1078 | NPMDNSGYGY | ---------- | ------ | 599 |
| SEQ_ID_NO_1075 | NALTNGKVTV | AVSYSWGMMK | PMYYKA | 595 |
| SEQ_ID_NO_1095 | MADEEGNFSL | ---------- | ------ | 575 |
| SEQ_ID_NO_1055 | SGMPSG-MTI | ---------- | ------ | 580 |
| SEQ_ID_NO_1080 | AGMPQGMM-- | ---------- | ------ | 588 |
| SEQ_ID_NO_1086 | SGAPEGSLAM | ---------- | ------ | 584 |
| SEQ_ID_NO_1085 | AGAPEGSFAM | ---------- | ------ | 585 |
| SEQ_ID_NO_1097 | AAAP------ | ---------- | ------ | 580 |
| SEQ_ID_NO_1054 | -EPPEGALTV | ---------- | ------ | 572 |
| SEQ_ID_NO_1088 | -EPAEGTLTV | ---------- | ------ | 578 |
| SEQ_ID_NO_1068 | -AAPEG-LMV | ---------- | ------ | 586 |
| SEQ_ID_NO_1072 | -AAPEG-LMV | ---------- | ------ | 583 |
| SEQ_ID_NO_1057 | -AAPEG-LTI | ---------- | ------ | 586 |
| SEQ_ID_NO_1061 | -AATQGQYAV | ---------- | ------ | 587 |
| SEQ_ID_NO_1076 | -AAPQG-LTI | ---------- | ------ | 587 |
| SEQ_ID_NO_1092 | -GAPQG-LTV | ---------- | ------ | 588 |
| SEQ_ID_NO_1074 | -GAPQG-LTV | ---------- | ------ | 584 |
| SEQ_ID_NO_1083 | -AAPQG-LTI | ---------- | ------ | 581 |

Figure 35

```
SEQ_ID_NO_1106    MAELNVAPSP PPSTILTLED MLRKLPLPSD ETIRSPATTK MCKIVSHRSS    50
SEQ_ID_NO_1105    ---------- ---------- ---------- ---------- ---------M     1
SEQ_ID_NO_1108    ---------- ---------- ---------- ---------- ------MREY     4
SEQ_ID_NO_1109    --MAAVAPIA MPARVHHHHH HHRRALAASP AALAAAGNGL SATRRVRRSP    48
SEQ_ID_NO_1101    ---------- ------MPFA SSSSLIKRRP LL-------- ------RHAN    20
SEQ_ID_NO_1099    ---------- ---------- MTRHVILTSE E--------- ------RNSP    15
SEQ_ID_NO_1103    ---------- ---------- MTRHVILKSP LLVSSEESTM ------RNSP    24

SEQ_ID_NO_1106    PRHPTTKANK G------FQC AEVAGGTTAG CAALVCC-PC GIVGLLVLAT    93
SEQ_ID_NO_1105    TRQNQLQNRR R-------SV GEVAGNATAE CAAICCCVPC AVVDMVALAT    44
SEQ_ID_NO_1108    GRGHEEEEGE E--HEPQPGC GEGAGQAAAN CAAVCCCCPL ALLDVLLLVT    52
SEQ_ID_NO_1109    AVEMRRERER RRAREQQPRC GEVAGGTAAE CAAVFCCFPF AVVELVVLAA    98
SEQ_ID_NO_1101    SSGSSCCSGR F--------- GEIAGGTTAE CAAICCCCPC GLVNLLVLTI    61
SEQ_ID_NO_1099    PTTMIKHAER R-------KV GEVAGGAAAE CAAVWCCGPC AVVNLVVLAV    58
SEQ_ID_NO_1103    PSTTSLSKER R-------KV GEVAGGAAAE CAAVWCCCPC AVVNLMVLAV    67

SEQ_ID_NO_1106    VKLPAGLCRR ALSQKRRKRV KKR------- ------STTL RSRAMSFVSD   130
SEQ_ID_NO_1105    YKVPASLWKK AAINNRKKRL LKQ------- ---------- MKKDMKNFLE    77
SEQ_ID_NO_1108    VKLPAGVMRR VRRRRRRHRD RVS-----RK KRSAAAAAVE PASPSGSSGK    97
SEQ_ID_NO_1109    VRAPAALCRR AVRGGRRRRV RST-----KP KETGAMDIAS PRSLAAAAAK   143
SEQ_ID_NO_1101    YKIPAGICRR ALKRKQRKKL IKKGLFPPRG RGYGCGSCDD PELHIHPMAR   111
SEQ_ID_NO_1099    YRVPAAVCKK AWRQTKRQRF MRR-----RH GLLASAAA-- -ESTVHARLK   100
SEQ_ID_NO_1103    YKVPAAVCKK AWRRSKRRRF TRK-----RH GLLASATAEG SESTVHARLN   112

SEQ_ID_NO_1106    DEDFGVPSFV PRTPETWPSK SPSVEVAEK- EEEMW-AEFY SAGFWRSPSQ   178
SEQ_ID_NO_1105    HEKPGGP--G PETVVVGPTM EELLAQEELP EEDLW-ARFS VNGFWRSSSS   124
SEQ_ID_NO_1108    AMIGAAP--S PLEAEEEEAR GEAAAAAEL- EREIMSSRFY GAGFWRSVSS   144
SEQ_ID_NO_1109    ARKVDAD--F PAT----PKA EHLVDM---- EKEVW-ASFY GGGFWRSPSQ   182
SEQ_ID_NO_1101    VEDSLRE--F DGE-E-AVKK EE--AMLRL- EKEMW-ETFY GTGFWRSPSQ   153
SEQ_ID_NO_1099    EEDPTAE--I VFE-E-NVVN VELNDVVVL- EDEMF-ERFY GAGFWRSPSQ   144
SEQ_ID_NO_1103    EEDLTAE--I VFE-ECHVSG GELNDVVRL- ENEML-DRFY GAGFWRSPSQ   157
```

Figure 35 (continued)

| | | | | | | |
|---|---|---|---|---|---|---|
| SEQ_ID_NO_1106 | ---------- | KESN------ | ---------- | ---------- | --- | 182 |
| SEQ_ID_NO_1105 | -----QKHEP | DELQTGEN-- | ---------- | ---------- | -NR | 139 |
| SEQ_ID_NO_1108 | ---------- | GCSSSASMRY | Q--------- | ---------- | --- | 155 |
| SEQ_ID_NO_1109 | REDRRCIAAG | DGAAAAALFF | FSFTTVVGFL | AFLLPFLGKR | EDR | 225 |
| SEQ_ID_NO_1101 | RELPAKRSSP | RETPNARL-- | ---------- | ---------- | --- | 171 |
| SEQ_ID_NO_1099 | ---------- | RDTSSGSI-- | ---------- | ---------- | --- | 152 |
| SEQ_ID_NO_1103 | ---------- | KDTSSGSL-- | ---------- | ---------- | --- | 165 |

Figure 36

```
SEQ_ID_NO_1112    MAQNKMIVMV LLLSTFLVVA RSLWVPEEPS NADD-IRGAC IEECTKE-NK
SEQ_ID_NO_1113    MAQNKTIAVA LLLATLVAV- ----MGKEPE TLEETLRAGC KEECSEQKKK
SEQ_ID_NO_1114    MAQNKTIAVA LLLATLVAV- ----MGKEPE TLEEAVRAGC KEECSEQKKK

SEQ_ID_NO_1112    APGDKKTCEV LC-------- ---------- ---------- ---------T
SEQ_ID_NO_1113    APIDEKQCED FCFIKTKSIF EAHKGVKDLK ADRFIDFCNN ECNAVYKEDP
SEQ_ID_NO_1114    APIDEKQCED FCFIKTKSIF EAHKGVKDLK ADRFIDFCNN ECNAVYKEDP

SEQ_ID_NO_1112    KLTKKPSEEG KHD------- ---------- ----         74
SEQ_ID_NO_1113    ATSKKCAESC EADAKEAEVF LDKVVAYMQT MKQA         129
SEQ_ID_NO_1114    ATSKKCAESC EADAKEAEVF LDKVVAYIQT TKQA         129
```

Figure 37

| | | | | | | | |
|---|---|---|---|---|---|---|---|
| SEQ_ID_NO_1138 | M---KRSREA | EEEEEQAA-- | --GAELLLLL | SLSRGDKPA- | ---------- | | 32 |
| SEQ_ID_NO_1141 | M------TKH | PRDGEVIS-- | --LSLSLTLG | AAADSGERK- | ---------- | | 29 |
| SEQ_ID_NO_1143 | -MAMKR-MRS | EDIVGDKDSL | DDMAKCLMLL | S--HGGGLT- | ---------- | | 35 |
| SEQ_ID_NO_1120 | MLLSKVGQAD | HEILTNYR-- | --SAAAAAAA | A--TAGA--- | ---------- | | 31 |
| SEQ_ID_NO_1147 | MAKRERAAWE | VEAGAAAD-- | --TARLLMLL | A--QAQQQHL | LQQHAHHHHH | | 44 |
| SEQ_ID_NO_1132 | -----MAMKR | QRSNEGID-- | --YANCLMLL | S--CPQQ--- | ---------- | | 26 |
| SEQ_ID_NO_1134 | MSAMKR-SRE | DRQVEAAA-- | --MANCLMLL | S--KLNDKS- | ---------- | | 32 |
| SEQ_ID_NO_1136 | ---------- | ---------- | --MARILLLF | SGHHQHHAH- | ---------- | | 17 |
| SEQ_ID_NO_1145 | ---------- | ---------- | --MPMPMPVA | A--RGHR--- | ---------- | | 13 |
| SEQ_ID_NO_1144 | MVAI---SEI | KSTVETTA-- | --AANCLMLL | S--RVGQEN- | ---------- | | 30 |
| SEQ_ID_NO_1116 | MVAI---SEI | NPTVEAT--- | --AANCLMLL | S--RVGQK-- | ---------- | | 28 |
| SEQ_ID_NO_1123 | MVAI---SEI | KSTVDVT--- | --AANCLMLL | S--RVGQEN- | ---------- | | 29 |
| SEQ_ID_NO_1140 | -MTIKRSWED | DREVENLA-- | --MANCLMLL | S--RVGQS-- | ---------- | | 31 |
| SEQ_ID_NO_1133 | MVMINIPMKR | TREANDFDSI | TTMANCLMLL | SQNRSGEFI- | ---------- | | 39 |
| SEQ_ID_NO_1118 | -------MKR | GRDIDAMD-- | --MADCLMLL | S--RVGET-- | ---------- | | 25 |
| SEQ_ID_NO_1129 | -------MKR | GREESKLD-- | --MANCLMLL | T--KVGES-- | ---------- | | 25 |

| | | | | | | | |
|---|---|---|---|---|---|---|---|
| SEQ_ID_NO_1138 | ------TVRK | K---VRAAEG | ---VFECKLC | SRQFPTFQAL | GGHRTSHNRP | | 70 |
| SEQ_ID_NO_1141 | ------KPRR | GSSPAASGSG | ---DFVCKTC | SRAFPSFQAL | GGHRTSHLRG | | 70 |
| SEQ_ID_NO_1143 | ------TDTK | ----PKTCPH | PVDVFECKTC | NRQFSSFQAL | GGHRASHKRP | | 75 |
| SEQ_ID_NO_1120 | ---------- | ----GAGAGR | ---SFSCKTC | NKNFPSFQAL | GGHRASHKKP | | 64 |
| SEQ_ID_NO_1147 | HHHGVGVPPF | PAGRAAVHGR | ---VFECKTC | SRQFPTFQAL | GGHRASHKRP | | 91 |
| SEQ_ID_NO_1132 | ---------- | ----KSYENG | ---EYECKTC | NKKFSSFQAL | GGHRASHKRM | | 59 |
| SEQ_ID_NO_1134 | ------TSTT | TT--NQDHHN | ---DFECKTC | NKRFSSFQAL | GGHRASHKRP | | 71 |
| SEQ_ID_NO_1136 | ------YG-- | ----PSSPER | ---VFECKTC | NRRFPSFQAL | GGHRASHKKP | | 52 |
| SEQ_ID_NO_1145 | ---------- | ------APER | ---VFVCKTC | DRVFPSFQAL | GGHRASHKKP | | 44 |
| SEQ_ID_NO_1144 | ------VD-- | ----GGSAKR | ---VFTCKTC | LKEFHSFQAL | GGHRASHKKP | | 65 |
| SEQ_ID_NO_1116 | ---------- | ----GGDQKR | ---VFTCKTC | LKEFHSFQAL | GGHRASHKKP | | 61 |
| SEQ_ID_NO_1123 | ------VD-- | ----GGDQKR | ---VFTCKTC | LKQFHSFQAL | GGHRASHKKP | | 64 |
| SEQ_ID_NO_1140 | ---------- | ----GSTPDR | ---VFHCKTC | DKEFKSFQAL | GGHRASHKRP | | 64 |
| SEQ_ID_NO_1133 | ------DSTT | SNSSNLNSNR | ---VFECKTC | NRQFPSFQAL | GGHRASHKRP | | 80 |
| SEQ_ID_NO_1118 | ---------- | ----DRVAGR | ---VFACKTC | NKKFSSFQAL | GGHRASHKKP | | 58 |
| SEQ_ID_NO_1129 | ------ETNY | PISKGSDIG- | ---DFKCKTC | NRRFSSFQAL | GGHRASHKKP | | 65 |

Figure 37 (continued)

```
SEQ_ID_NO_1138   RVDRS----- -----TS--- ---------- ---------- --RRSVHQCS   85
SEQ_ID_NO_1141   RHGLA----L GLAAATAKET TKKVQEKPA- ---------- --AAATHECH   103
SEQ_ID_NO_1143   RLMGE----- -----EHKVD RTKLQSSGN- ---------- --KPKMHECS   102
SEQ_ID_NO_1120   KLKES----- -----T---- -GNLLKLPNS PS-------- --KPKTHQCS   89
SEQ_ID_NO_1147   RVLQQQQLQQ QQTVVADHAG QLCLGRQPLQ LPLPTTTTPQ QAKPRVHECP   141
SEQ_ID_NO_1132   KLAEG----- ---------- -EELKEQAKS LSLWN----- --KPKMHECS   86
SEQ_ID_NO_1134   KLLIG----- -----A---- -GEFLVQPS- ---------- --SKKMHECS   93
SEQ_ID_NO_1136   RLADG----- ---------- --AGAEPP-- ---------- --KPKVHGCS   71
SEQ_ID_NO_1145   RLDDG----- ---------- -GDL------ ---------- --KPKLHGCS   60
SEQ_ID_NO_1144   NNENL----- -----S---- -GLMKKTK-- ---------- --ASSSHPCP   86
SEQ_ID_NO_1116   NNNES----- ---------L SGLVKKAK-- ---------- --APSSHPCP   83
SEQ_ID_NO_1123   NNDAL----- -----SS--- -GLMKKV--- ---------- --KTSSHPCP   85
SEQ_ID_NO_1140   KTSDG----- ---------- -SEARTPP-- ---------- --KPKTHECP   84
SEQ_ID_NO_1133   RLGGD----- ---------- -LTLSQIPVA AA-------- --KPKTHECS   104
SEQ_ID_NO_1118   KLTVG----- -----DN--- -EGLAVSP-- ---K------ --KPKTHECS   81
SEQ_ID_NO_1129   KLMVT----- -----DL--- -SCHQELPNP TMKQ------ --QPRMHPCP   93

SEQ_ID_NO_1138   ICGVEFAMGQ ALGGHMRRHK PMAEDSKRSD PKK------- ----------   118
SEQ_ID_NO_1141   ICGQGFEMGQ ALGGHMRRHR EEAAAAAAAV H--------- ----------   134
SEQ_ID_NO_1143   LCGQKFSMGQ ALGGHMRRHR A--NEGLSSI MNPLDHA--- ------KVPM   141
SEQ_ID_NO_1120   ICGLEFPLGQ ALGGHMRRHR APNNVDTTST SSKDHELAVT QPPFLPAVPV   139
SEQ_ID_NO_1147   VCGLEFAVGQ ALGGHMRRHR AEAEAEATEA PSKVMMR--- --------PA   180
SEQ_ID_NO_1132   ICGMGFSLGQ ALGGHMRKHR AVINEGVSSI NQIIEKF--- --------PV   125
SEQ_ID_NO_1134   ICGMEFSLGQ ALGGHMRRHR AAIDEKSKAA TKAMMIP--- ---------V   131
SEQ_ID_NO_1136   ICGLEFAVGQ ALGGHMRRHR AVAAAGPGVG LGLSLGL--- --GLGPNEDG   116
SEQ_ID_NO_1145   VCGLEFAIGQ ALGGHMRRHR AMAAGGGGGV MPMTPPT--- ----AAAIKE   103
SEQ_ID_NO_1144   ICGVEFPMGQ ALGGHMRRHR NESG-GAGAL VTRELLP--- ----EAALMT   128
SEQ_ID_NO_1116   ICGVEFPMGQ ALGGHMRRHR NEIG-GGAAL VTRALLP--- ----EPTMTT   125
SEQ_ID_NO_1123   ICGVEFPMGQ ALGGHMRRHR NESGAAGGAL VTRALLP--- ----EPTVTT   128
SEQ_ID_NO_1140   VCGLEFAIGQ ALGGHMRRHR DVGNEK--SG RPVAARP--- ----------   119
SEQ_ID_NO_1133   ICGLEFAIGQ ALGGHMRRHR AAMSDSASGN SASPPRDDRT VVVKKSNIV-   153
SEQ_ID_NO_1118   ICGLEFAIGQ ALGGHMRRHR AALNDG---L VTRDLLP--- ---------E   116
SEQ_ID_NO_1129   ICGLEFAIGQ ALGGHMRKHR TAINDGLLCG KPSSSLS--- ------ILKE   134
```

Figure 38

```
SEQ_ID_NO_1162   MATKIFALLV LLALSASATT AVIIPQCSLA PTAAIIPRFL PPVSAIGFEH   50
SEQ_ID_NO_1163   MATKIFVLLA LLALSVSTTT AVIIPQCSLA PNAFIISQFL PPLTLVGFEH   49
SEQ_ID_NO_1161   MAAKIFAILA LLALSASVAT ATIIPQCSQ- -------QYL SPVTAARFEY   42
SEQ_ID_NO_1159   MATKIFSLLM LLALSACVAN ATIFPQCSQA PIASLLPPYL PSMIASVCEN   50
SEQ_ID_NO_1164   MAAKIFCFLM LLGLSASVAT ATIFPQCSQA PIASLLPPYL SPAVSSMCEN   50

SEQ_ID_NO_1162   PAVQAYRLQQ ALAASIL--- ----QQPLAQ LQQQSSAHLT IQTIAAQQ-Q   92
SEQ_ID_NO_1163   PALQAYRLQQ ALANSIL--- ----QQPFPQ LQQQSSAHLT VQTIAAQQQQ   92
SEQ_ID_NO_1161   PTIQSYRLQE AIAASILRSL ALTVQQPYAL LQQPSLMNLY LQRIAAQQLQ   92
SEQ_ID_NO_1159   PALQPYRLQQ AIAASNIPLS PLLFQQSPAL ----SLVQSL VQTIRAQQLQ   96
SEQ_ID_NO_1164   PIVQPYRIQQ AIATGILPLS PLFLQQPSAL LQQLPLVHLV AQNIRAQQLQ   100

SEQ_ID_NO_1162   QQFLPSLSQL AAANPTAYLQ QQLLASNPLA VANAIAYQHQ QQLQQLLPAL   142
SEQ_ID_NO_1163   QQFLPALSQL ALANPVAYLQ QQLLASNPLA LVNNAAYQ-Q QQLQQVLPVI   141
SEQ_ID_NO_1161   QQLLPTINQV VAANLAAYLQ Q--------- ---------- ---QQFLP-F   119
SEQ_ID_NO_1159   QLVLPVINQV ALANLSPYSQ Q--------- ---------- ---QQFLP-F   123
SEQ_ID_NO_1164   --------QL VLANLAAYSQ Q--------- ---------- ---HQFLP-F   119

SEQ_ID_NO_1162   SQLAVANPAA YLQ-SQLFPS NPLV-ANAAA YLQQQQLQQI LPVLSQLAVA   190
SEQ_ID_NO_1163   SQVAMANPAA YLQ-QQQLAY NPLVAANAAA YLQQQQLQQI LPALSQLALV   190
SEQ_ID_NO_1161   NQLAGVNPAA YLQAQQLLPF NQLV-RSPAA FLLQQQL--- LP-FHLQVVA   164
SEQ_ID_NO_1159   NQLSTLNPAA YLQ-QQLLPF SQLA----TA YSQQQQL--- LP-FNQLAAL   164
SEQ_ID_NO_1164   NQLAALNSAA YLQ-QQ-LPF SQLV----AA YP--RQF--- LP-FNQLAAL   157

SEQ_ID_NO_1162   DPNSYL-QQQ QLLPFNQVAV ANNAVYEQQH QLLQVNPLA- -----AAFLQ   233
SEQ_ID_NO_1163   NPAAYL-QQQ QLLPFNQLAV TNTAAYLQQQ QLLRVNPVVA ANPLAAAFLQ   239
SEQ_ID_NO_1161   NIAAFLQQQQ QLLPFYPQVV GNINAFLQQQ QLLPFYPQDV ANN--VAFLQ   212
SEQ_ID_NO_1159   NPAAYL-QQQ ILLPFSQLAA ANRASFLTQQ QLLPFYQQFA ANP--ATLLQ   211
SEQ_ID_NO_1164   NSAAYL-QQQ QLLPFSQLAD VSPAAFLTQQ QLLPFYLHAM PNA--GTLLQ   204

SEQ_ID_NO_1162   QQQRQLLPFN QMSLMNPALS WQQPIVGGVG F-   264
SEQ_ID_NO_1163   QQ--QLLPFN QISLMNPAFS WQQPIVGSAI F-   268
SEQ_ID_NO_1161   QQ--QLLPFN QLALTNPTTL LQQPTIGGAI F-   241
SEQ_ID_NO_1159   LQ--QLLPFV QLALTDRAAS YQQHIIGGAL F-   240
SEQ_ID_NO_1164   LQ--QLLPFN QLALTNSTVF YQQPIIGGAL FQ   234
```

Figure 39

```
SEQ_ID_NO_1167   MAK------- -NGINNSVAV GIAVQSDWDN RHFSSSLSLN VRRLFEFLLQ  42
SEQ_ID_NO_1182   MGR-----GG --GMGNPVNV GIAVQADWGN REFISNISLN VRRLFDFLLR  43
SEQ_ID_NO_1166   MGR-----GG --GMGNPVNV GIAVQADWEN REFISNISLN VRRLFDFLLR  43
SEQ_ID_NO_1183   MAR-----AG GHGMGNPVNV GIAVQADWEN REFISNISLN VRRLFDFLLR  45
SEQ_ID_NO_1173   MARAGGGGGG GGGITNAVNV GIAVQADWEN REFISHISLN IRRLFDFLIQ  50
SEQ_ID_NO_1169   MSR-----GG GVGITNAVNV GIAVQADWEN REFISNISIN VRRLFDFLIN  45
SEQ_ID_NO_1177   MAR-----AG --GITNAVNV GIAVQADWEN REFISHISLN VRRLFDFLVQ  43
SEQ_ID_NO_1180   MAR-----AG --GITNAVNV GIAVQADWEN REFISHISLN VRRLFDFLVQ  43
SEQ_ID_NO_1171   MAR-----AG --GITNAVNV GIAVQADWEN REFISHISLN VRRLFEFLLQ  43
SEQ_ID_NO_1175   MAK-----AG --GITNAVNV GIAVQADWEN REFISHISLN VRRLFEFLVQ  43

SEQ_ID_NO_1167   FESSTRSKLA TLNEKLTVLE RQLEFLEAQF STA-INPV-- --------  79
SEQ_ID_NO_1182   FEATTKSKLA SLNEKLDILE RKLEVLEVQV SSATTNPSVF N-------  84
SEQ_ID_NO_1166   FEATTKSKLA SLNEKLDILE RKLEVLEVQV GSATTNPSVF N-------  84
SEQ_ID_NO_1183   FEATTKSKLA SLNEKLDILE RKLEVLEVQV SSATTNPSVF N-------  86
SEQ_ID_NO_1173   FESTTKSKLS SLNLKLDTLE RRLQLLELQV STATSNPSLF TSTTTTTA  98
SEQ_ID_NO_1169   FEATTKSKLA SLNEKLDTLE RRLELLEVQV GTASANPSLF T-------  86
SEQ_ID_NO_1177   FEATTKSKLA SLNEKLDVLE RRLELLEVQV GNASANPSLF AT------  85
SEQ_ID_NO_1180   FEATTKSKLA SLNEKLDVLE RRLELLEVQV GNASANPSLF AT------  85
SEQ_ID_NO_1171   FEATTKSKLA SLNEKLDTLE RRLELLEVQV GTASANPSLF ST------  85
SEQ_ID_NO_1175   FESTTKSKLA SLNEKLDLLE RRLEMLEVQV STATANPSLF AT------  85
```

Figure 40

```
SEQ_ID_NO_1187   MFSWILRGCR  DECSATDQLK  Q---------  ---------A  RDVFVAKEAV   32
SEQ_ID_NO_1185   MFAWILRGCR  DECSASDQLK  Q---------  ---------A  HDVFKAKEVV   32
SEQ_ID_NO_1189   MFSWILRGCR  DECSASDQLK  Q---------  ---------A  RDVFMAKEAV   32
SEQ_ID_NO_1190   MFAWLLRGCR  DECSASDQLK  QGVVKEKNRC  WFWGAFSVNA  RDVFVAKEAV   50
SEQ_ID_NO_1191   MFAWLLRGCR  DECSASDQLK  Q---------  ---------A  RDVFVAKEAV   32

SEQ_ID_NO_1187   LQKKISQEME  RAKEFXKSGN  KQAAMQCLKR  KRYYESQMNQ  VGSVRLRIDT   82
SEQ_ID_NO_1185   LQKKISQEVE  RAKEFTKSGN  KQAAMQCLKR  KRYYESQMNQ  VGSVQLRINT   82
SEQ_ID_NO_1189   LQKKISQEME  RAKEFTKSGN  KQAAMQCLKR  KKYYESQMSQ  VGSVQLRINT   82
SEQ_ID_NO_1190   LQKKISQEME  RAKEFTKSGN  KQAAMQCLKR  KKYYESQMNQ  VGSVQLRINT  100
SEQ_ID_NO_1191   LQKKISQEME  RAKEFTKSGN  KQAAMQCLKR  KKYYESQMNQ  VGSVQLRINT   82

SEQ_ID_NO_1187   KEKMIADNMV  N---K   94
SEQ_ID_NO_1185   KERMIADHTG  N---K   94
SEQ_ID_NO_1189   KEKMIADHMG  N---K   94
SEQ_ID_NO_1190   KEKMIADHSG  NKEDK  115
SEQ_ID_NO_1191   KEKMIADHSG  NKEDK   97
```

Figure 41

```
SEQ_ID_NO_1204   -------MVK TRAAATPR-- ---------- -----PSGGG GAGAADITAG   26
SEQ_ID_NO_1203   MGEQSLSQPK PQPLSPFPSP PASAAL---- -----PPPAS ASASASASAA   41
SEQ_ID_NO_1205   MESPNPQQVN SMGDQSPLSP NLHPLS---- -----PSPSA AAAAAA----   37
SEQ_ID_NO_1196   MGEQTPSQPQ PQVQSQPPND SSTTTQAQVQ NQSGDPSNTS TAAVSTVTTA   50
SEQ_ID_NO_1202   MGEQTLGQAQ SLIEPQPL-- ---------- -----PAPSS TAVPDGATVD   33
SEQ_ID_NO_1194   ---MSLRKTL TAVNQSSL-- ---------- -----PPDSL ISAGNLTVSE   30
SEQ_ID_NO_1200   MGKPVTRSHS LLLHEPSS-- ---------- -----PPLS- ----------   22

SEQ_ID_NO_1204   ---------- ---------- ----KISFRS RKIVKSTPAK GKSVATTTTA   52
SEQ_ID_NO_1203   ---------- ---------S TSRTTSAAAS RPKKKVTN-P SPDRNPAKKP   71
SEQ_ID_NO_1205   ---------- ---------T PTPAAAAASS RSSRSKKPPH SSDPNQSKKP   68
SEQ_ID_NO_1196   CTAIVACGPT ELVNVPLPTS SPPSKIPSRP RKIRKLSPDL SFDPNASQQA  100
SEQ_ID_NO_1202   ---------S ELNNVPRPTT SPATKIPLRP RKIRKVSPDP STSESQTETP   74
SEQ_ID_NO_1194   ---------- --------VS GSSSRIRFRP RKIRKVSSDP SPRIIITASP   62
SEQ_ID_NO_1200   ---------- ---------T TTSSKISFQS RKIRKLSTNK TTTTTTAITS   53

SEQ_ID_NO_1204   ---------- -VLS------ ---------- ---PP----P LSSPGELAAA   68
SEQ_ID_NO_1203   ---------- -RLT------ ---------- ---FSIPGRP LSAVGEVGVA   91
SEQ_ID_NO_1205   ---------- -RLT------ ---------- ---LTVPGRP LSADGEVAAA   88
SEQ_ID_NO_1196   TTSSSTSLTE QRKTVGRTSK TKLSQHRALA VVAPRIIARS LSCEGEVETA  150
SEQ_ID_NO_1202   ---------- -KPAKTGGRN TTKAAPPRAL TVVPRIVARS LSCDGEVEIA  113
SEQ_ID_NO_1194   ---------- ---------- ---------- ---------P LSTKSTVDIA   73
SEQ_ID_NO_1200   ---------- -TSI------ ---------- ---PPL--KP LSHKGEIELA   71

SEQ_ID_NO_1204   LSHLRTADPL LSEVIASTGA PAFISSPSRP AFHSLAHSIL HQQLAPSAAA  118
SEQ_ID_NO_1203   IRYLRAADPA LAAVIDAH-E PPVFQCPHRP -FHSLVRSIL YQQLAFKAAA  139
SEQ_ID_NO_1205   IQHLRAADPA LATVIDAH-D PPAFQCPHRP -FHSLVRSIL YQQLAFKAAA  136
SEQ_ID_NO_1196   IRHLRDADPL LASLIDLH-P PPTFDTFHAP -FLALTRSIL YQQLAFKAGT  198
SEQ_ID_NO_1202   LRYLRNADPV LSPLIDIH-Q PPTFDNFHTP -FLALTRSIL YQQLAYKAGT  161
SEQ_ID_NO_1194   LRHLQSSDEL LGALITTHND PPVFDSSNTP -FLSLARSIL YQQLATKAAK  122
SEQ_ID_NO_1200   LDHLSKSDPL LAPLLNSH-E PPALNPCTSP -FLSLTKSIL FQQLATNAAK  119
```

Figure 41 (continued)

```
SEQ_ID_NO_1204   AIYARFLALI PAAADPDAAV VNPAAVLALS AADLRAIGVS ARKAAYLHDL   168
SEQ_ID_NO_1203   SVYSRFLALL ----G-GESC VAPDAVLALT PHQLRQIGVS PRKASYLHDL   184
SEQ_ID_NO_1205   SVYSRFLSLL ----G-GEHN VLPEAVLALT TQDLRQIGVS PRKASYLHDL   181
SEQ_ID_NO_1196   SIYTRFISLC ----G-GENG VVPETVLSLT SQQLRQIGVS GRKASYLHDL   243
SEQ_ID_NO_1202   SIYTRFIALC ----G-GENG VVPETVLALT PQQLRQIGVS GRKASYLHDL   206
SEQ_ID_NO_1194   CIYDRFISLF ----NGGEAG VFPESVISLS AVDLRKIGVS GRKASYLHDL   168
SEQ_ID_NO_1200   SIYTRFLTLC ----D-GESQ VNPDTVLSLS APKLREIGVS GRKASYLHDL   164

SEQ_ID_NO_1204   AGRFAAGELS ESAVAAMDEA ALLAELTKVK GVGEWTVHMF MIFSLHRPDV   218
SEQ_ID_NO_1203   ARKYASGILS DAAIVNMDDR SLAAMLTMVK GIGSWSVHMF MIFSLARPDV   234
SEQ_ID_NO_1205   ARKYASGILS DAAVVNMDDR SLAAMLTMVK GIGAWSVHMF MIFSLNRPDV   231
SEQ_ID_NO_1196   ARKYQTGILS DSAIVNMDDK SLFTMLTMVN GIGSWSVHMF MIFSLHRPDV   293
SEQ_ID_NO_1202   ARKYQNGILS DSAIVNMDDK SLLTMLTMVN GIGSWSVHMF MIFSLHRPDV   256
SEQ_ID_NO_1194   ADKYNNGVLS DELILKMSDE ELIDRLTLVK GIGVWTVHMF MIFSLHRPDV   218
SEQ_ID_NO_1200   AEKYRNGSLS DSSILEMNDD MLLNRLTEVK GIGVWSVHMF MLFSLHRPDV   214

SEQ_ID_NO_1204   LPSGDLGVRK GVQELYGLPA LPKPEEMAAL CERWRPYRSV GAWYMWRLME   268
SEQ_ID_NO_1203   LPSADLGVRK GVQMLYALED VPRPSQMDKL CERWRPYRSV GAWYMWRLIE   284
SEQ_ID_NO_1205   LPAADLGVRK GVQHLYGLDA VPRPSQMEKL CEQWRPYRSV GAWYMWRLIE   281
SEQ_ID_NO_1196   LPINDLGVRK GVQLLYNLEE LPRPSQMDQL CEKWRPYRSV ASWYLWRYVE   343
SEQ_ID_NO_1202   LPINDLGVRK GVQLLYNLED LPRPSQMDQL CDKWRPYRSV ASWYMWRFVE   306
SEQ_ID_NO_1194   LPVGDLGVRK GVKDLYGLKN LPGPLQMEQL CEKWRPYRSV GSWYMWRLIE   268
SEQ_ID_NO_1200   LPVGDLGVRK GVQSLYGLKD LPQALEMEQI CEKWKPYRSV GSWYMWRLME   264

SEQ_ID_NO_1204   SKGAAAKKAK SNAIATLPS- -------SC- ---------- ----------   289
SEQ_ID_NO_1203   SKVPQPAPAI PVGSLAFPS- ---------P DGQSMLQQQE QQQQQTVIQM   324
SEQ_ID_NO_1205   SKAPPPPPAI PVGPPALTE- -------HGD ELMLQQQQHQ QQQQQSVIQM   323
SEQ_ID_NO_1196   AKGAPSSAAA VAAGASLPP- ---------- ----LQQQEE PQQHQQQPPL   378
SEQ_ID_NO_1202   AKGTPSSAVA VATGAGLQQQ QHHQHHHQHQ QQEQQQQQQQ QQQHPPQPQL   356
SEQ_ID_NO_1194   SRKTK----- ---------- ---------- ---------- ----------   273
SEQ_ID_NO_1200   AKALANKAAK KA-------- ---------- ---------- ----------   276
```

Figure 41 (continued)

```
SEQ_ID_NO_1204    ---------- --------    289
SEQ_ID_NO_1203    IDPLQMLPGM G-------    335
SEQ_ID_NO_1205    IDPLQMLPGM G-------    334
SEQ_ID_NO_1196    MDPINSILNL G-ACAWGQ    395
SEQ_ID_NO_1202    LDPINSMFNL GAACAWGQ    374
SEQ_ID_NO_1194    ---------- --------    273
SEQ_ID_NO_1200    ---------- --------    276
```

Figure 42

| | | | | | | |
|---|---|---|---|---|---|---|
| SEQ_ID_NO_1241 | MFLVDWFYGV | LASLGLWQKD | AKILFLGLDN | AGKTTLLHML | KDERLVQHQP | 50 |
| SEQ_ID_NO_1229 | MFVLDWFYGV | LASLGLWQKE | AKILFLGLDN | AGKTTLLHML | KDERLVQHQP | 50 |
| SEQ_ID_NO_1249 | MFLWDWFYGV | LASLGLWQKE | AKILFLGLDN | AGKTTLLHML | KDERLVQHQP | 50 |
| SEQ_ID_NO_1264 | ---MGIVFTR | LFSSVFGNRE | ARILVLGLDN | AGKTTILYRL | QMGEVVSTIP | 47 |
| SEQ_ID_NO_1251 | ---MGIVFTR | LFSSVFGNRE | ARILVLGLDN | AGKTTILYRL | QMGEVVSTIP | 47 |
| SEQ_ID_NO_1265 | ---MGIVFTR | LFSSVFGNRE | ARILVLGLDN | AGKTTILYRL | QMGEVVSTIP | 47 |
| SEQ_ID_NO_1253 | ---MGIVFTK | LFSSVFGNKE | ARILVLGLDN | AGKTTILYRL | QMGEVVSTIP | 47 |
| SEQ_ID_NO_1210 | ---MGILFTR | MFSSVFGNKE | ARILVLGLDN | AGKTTILYRL | QMGEVVSTIP | 47 |
| SEQ_ID_NO_1267 | ---MGILFTR | MFSSVFGNKE | ARILVLGLDN | AGKTTILYRL | QMGEVVSTIP | 47 |
| SEQ_ID_NO_1213 | ---MGILFTK | MFSNLFGNRE | ARILVLGLDN | AGKTTILYRL | QMGEVVSTIP | 47 |
| SEQ_ID_NO_1218 | ---MGILFSK | MFSSVFGNKE | ARILVLGLDN | AGKTTILYRL | QMGEVVSTIP | 47 |
| SEQ_ID_NO_1232 | ---MGLVFTK | LFSSLFGNKE | ARILVLGLDN | AGKTTILYRL | QMGEVVSTIP | 47 |
| SEQ_ID_NO_1234 | ---MGLVFTR | LFSSVFGNKE | ARILVLGLDN | AGKTTILYRL | QMGEVVSTIP | 47 |
| SEQ_ID_NO_1272 | ---MGLSFTK | LFSRLFAKKE | MRILMVGLDA | AGKTTILYKL | KLGEIVTTIP | 47 |
| SEQ_ID_NO_1268 | ---MGITFAK | LFQRLFSKKE | MRILMVGLDA | AGKTTILYKL | KLGEIVTTIP | 47 |
| SEQ_ID_NO_1211 | ---MGLRFTK | ALSRLFGKKE | MRILMVGLDA | AGKTTILYKL | KLGEIVTTIP | 47 |
| SEQ_ID_NO_1216 | ---MGLSFTK | LLGRLFSEKE | MRILMVGLDA | AGKTTILYKL | KLGEIVTTIP | 47 |
| SEQ_ID_NO_1269 | ---MGLSFTK | LLGRLFSKKE | MRILMVGLDA | AGKTTILYKL | KLGEIVTTIP | 47 |
| SEQ_ID_NO_1239 | ---MGLSFTK | LFSRLFAKKE | MRILMVGLDA | AGKTTILYQL | KLGEIVTTIP | 47 |
| SEQ_ID_NO_1259 | ---MGLTFTK | LFSRLFAKKE | MRILMVGLDA | AGKTTILYKL | KLGEIVTTIP | 47 |
| SEQ_ID_NO_1233 | ---MGLTFTK | LFSRLFAKKE | MRILMVGLDA | AGKTTILYKL | KLGEIVTTIP | 47 |
| SEQ_ID_NO_1235 | ---MGLSFTK | LFSRLFAKKE | MRILMVGLDA | AGKTTILYKL | KLGEIVTTIP | 47 |
| SEQ_ID_NO_1243 | ---MGLSFTK | LFSRLFAKKE | MRILMVGLDA | AGKTTILYKL | KLGEIVTTIP | 47 |
| SEQ_ID_NO_1270 | ---MGLSFTK | LFSRLFAKKE | MRILMVGLDA | AGKTTILYKL | KLGEIVTTIP | 47 |
| SEQ_ID_NO_1242 | ---MGLSFGK | LFSRLFAKKE | MRILMVGLDA | AGKTTILYKL | KLGEIVTTIP | 47 |
| SEQ_ID_NO_1238 | ---MGLSFTK | LFSRLFAKKE | MRILMVGLDA | AGKTTILYKL | KLGEIVTTIP | 47 |
| SEQ_ID_NO_1236 | ---MGLSFTK | LFSRLFAKKE | MRILMVGLDA | AGKTTILYKL | KLGEIVTTIP | 47 |
| SEQ_ID_NO_1240 | ---MGLSFGK | LFSRLFAKKE | MRILMVGLDA | AGKTTILYKL | KLGEIVTTIP | 47 |

Figure 42 (continued)

```
SEQ_ID_NO_1241  T--------- ------QYPT SEELSIGNIK FKAFDLGGHQ IARRVWRDYY  85
SEQ_ID_NO_1229  T--------- ------QHPT SEELSIGKIK FKAFDLGGHQ IARRVWKDYY  85
SEQ_ID_NO_1249  T--------- ------QHPT SEELSIGKIK FKAFDLGGHQ IARRVWKDYY  85
SEQ_ID_NO_1264  SGFPAPDSLI FFLPFAIGFN VETVQYNNIK FQVWDLGGQT SIRPYWRCYF  97
SEQ_ID_NO_1251  T--------- ------IGFN VETVQYNNIK FQVWDLGGQT SIRPYWRCYF  82
SEQ_ID_NO_1265  T--------- ------IGFN VETVQYNNIK FQVWDLGGQT SIRPYWRCYF  82
SEQ_ID_NO_1253  T--------- ------IGFN VETVQYNNIK FQVWDLGGQT SIRPYWRCYF  82
SEQ_ID_NO_1210  T--------- ------IGFN VETVQYNNIK FQVWDLGGQT SIRPYWRCYF  82
SEQ_ID_NO_1267  T--------- ------IGFN VETVQYNNIK FQVWDLGGQT SIRPYWRCYF  82
SEQ_ID_NO_1213  T--------- ------IGFN VETVQYNNIK FQVWDLGGQT SIRPYWRCYF  82
SEQ_ID_NO_1218  T--------- ------IGFN VETVQYNNIK FQVWDLGGQT SIRPYWRCYF  82
SEQ_ID_NO_1232  T--------- ------IGFN VETVQYNNIK FQVWDLGGQT SIRPYWRCYF  82
SEQ_ID_NO_1234  T--------- ------IGFN VETVQYNNIK FQVWDLGGQT SIRPYWRCYF  82
SEQ_ID_NO_1272  T--------- ------IGFN VETVEYKNIS FTVWDVGGQD KIRPLWRHYF  82
SEQ_ID_NO_1268  T--------- ------IGFN VETVEYKNIS FTVWDVGGQD KIRPLWRHYF  82
SEQ_ID_NO_1211  T--------- ------IGFN VETVEYKNIS FTVWDVGGQD KIRPLWRHYF  82
SEQ_ID_NO_1216  T--------- ------IGFN VETVEYKNIS FTVWDVGGQD KIRPLWRHYF  82
SEQ_ID_NO_1269  T--------- ------IGFN VETVEYKNIS FTVWDVGGQD KIRPLWRHYF  82
SEQ_ID_NO_1239  T--------- ------IGFN VETVEYQYIS FTVWDVGGQD KIRPLWRHYF  82
SEQ_ID_NO_1259  T--------- ------IGFN VETVEYKNIS FTVWDVGGQD KIRPLWRHYF  82
SEQ_ID_NO_1233  T--------- ------IGFN VETVEYKNIS FTVWDVGGQD KIRPLWRHYF  82
SEQ_ID_NO_1235  T--------- ------IGFN VETVEYKNIS FTVWDVGGQD KIRPLWRHYF  82
SEQ_ID_NO_1243  T--------- ------IGFN VETVEYKNIS FTVWDVGGQD KIRPLWRHYF  82
SEQ_ID_NO_1270  T--------- ------IGFN VETVEYKNIS FTVWDVGGQD KIRPLWRHYF  82
SEQ_ID_NO_1242  T--------- ------IGFN VETVEYKNIS FTVWDVGGQD KIRPLWRHYF  82
SEQ_ID_NO_1238  T--------- ------IGFN VETVEYKNIS FTVWDVGGQD KIRPLWRHYF  82
SEQ_ID_NO_1236  T--------- ------IGFN VETVEYKNIS FTVWDVGGQD KIRPLWRHYF  82
SEQ_ID_NO_1240  T--------- ------IGFN VETVEYKNIS FTVWDVGGQD KIRPLWRHYF  82
```

Figure 42 (continued)

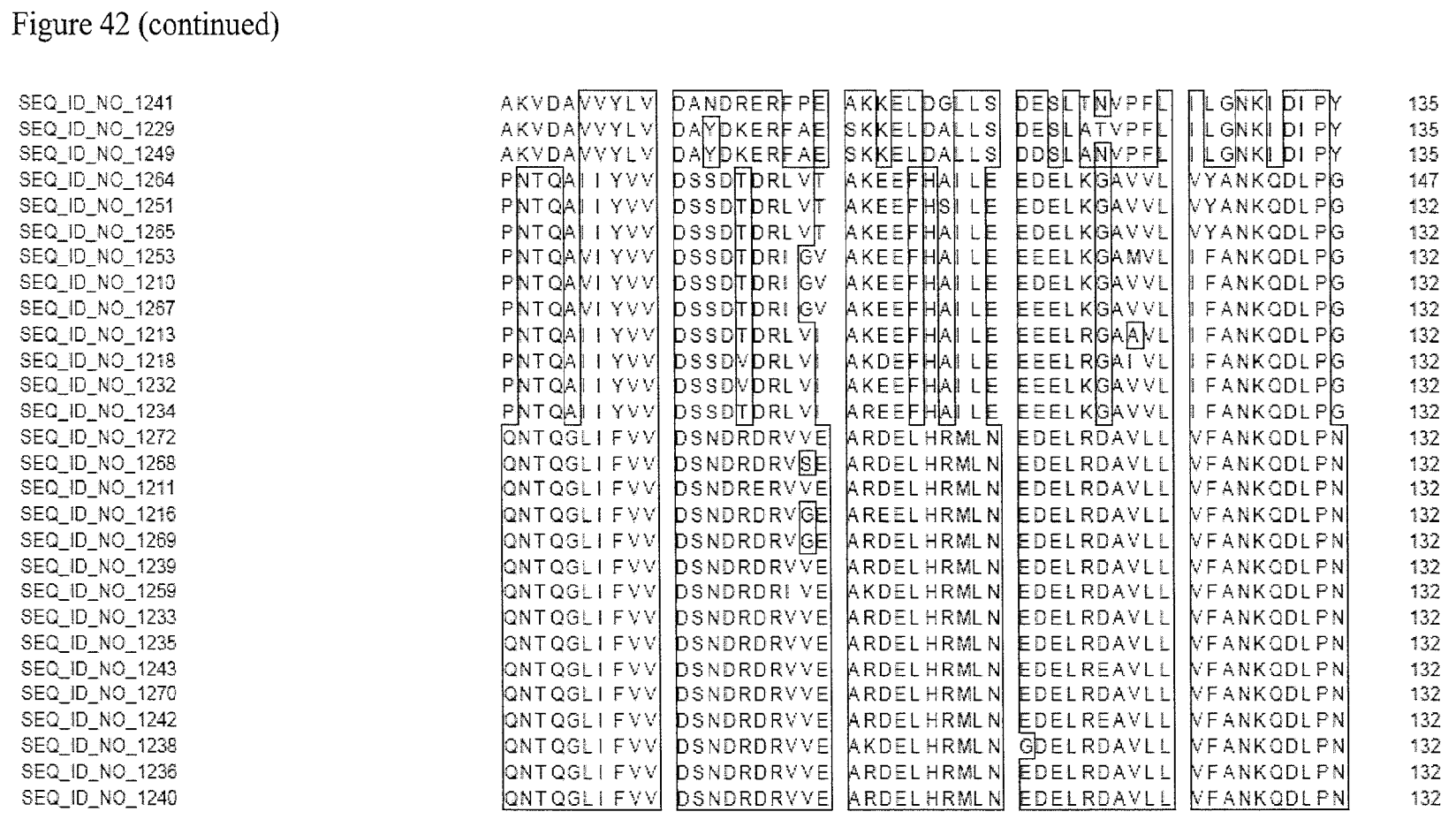

| | | | | | | |
|---|---|---|---|---|---|---|
| SEQ_ID_NO_1241 | AKVDAVVYLV | DANDRERFPE | AKKELDGLLS | DESLTNVPFL | ILGNKIDIPY | 135 |
| SEQ_ID_NO_1229 | AKVDAVVYLV | DAYDKERFAE | SKKELDALLS | DESLATVPFL | ILGNKIDIPY | 135 |
| SEQ_ID_NO_1249 | AKVDAVVYLV | DAYDKERFAE | SKKELDALLS | DDSLANVPFL | ILGNKIDIPY | 135 |
| SEQ_ID_NO_1264 | PNTQAIIYVV | DSSDTDRLVT | AKEEFHAILE | EDELKGAVVL | VYANKQDLPG | 147 |
| SEQ_ID_NO_1251 | PNTQAIIYVV | DSSDTDRLVT | AKEEFHSILE | EDELKGAVVL | VYANKQDLPG | 132 |
| SEQ_ID_NO_1265 | PNTQAIIYVV | DSSDTDRLVT | AKEEFHAILE | EDELKGAVVL | VYANKQDLPG | 132 |
| SEQ_ID_NO_1253 | PNTQAVIYVV | DSSDTDRIGV | AKEEFHAILE | EEELKGAMVL | IFANKQDLPG | 132 |
| SEQ_ID_NO_1210 | PNTQAVIYVV | DSSDTDRIGV | AKEEFHAILE | EDELKGAVVL | IFANKQDLPG | 132 |
| SEQ_ID_NO_1267 | PNTQAVIYVV | DSSDTDRIGV | AKEEFHAILE | EEELKGAVVL | IFANKQDLPG | 132 |
| SEQ_ID_NO_1213 | PNTQAIIYVV | DSSDTDRLVI | AKEEFHAILE | EEELRGAAVL | IFANKQDLPG | 132 |
| SEQ_ID_NO_1218 | PNTQAIIYVV | DSSDVDRLVI | AKDEFHAILE | EEELRGAIVL | IFANKQDLPG | 132 |
| SEQ_ID_NO_1232 | PNTQAIIYVV | DSSDVDRLVI | AKEEFHAILE | EEELKGAVVL | IFANKQDLPG | 132 |
| SEQ_ID_NO_1234 | PNTQAIIYVV | DSSDTDRLVI | AREEFHAILE | EEELKGAVVL | IFANKQDLPG | 132 |
| SEQ_ID_NO_1272 | QNTQGLIFVV | DSNDRDRVVE | ARDELHRMLN | EDELRDAVLL | VFANKQDLPN | 132 |
| SEQ_ID_NO_1268 | QNTQGLIFVV | DSNDRDRVSE | ARDELHRMLN | EDELRDAVLL | VFANKQDLPN | 132 |
| SEQ_ID_NO_1211 | QNTQGLIFVV | DSNDRERVVE | ARDELHRMLN | EDELRDAVLL | VFANKQDLPN | 132 |
| SEQ_ID_NO_1216 | QNTQGLIFVV | DSNDRDRVGE | AREELHRMLN | EDELRDAVLL | VFANKQDLPN | 132 |
| SEQ_ID_NO_1269 | QNTQGLIFVV | DSNDRDRVGE | ARDELHRMLN | EDELRDAVLL | VFANKQDLPN | 132 |
| SEQ_ID_NO_1239 | QNTQGLIFVV | DSNDRDRVVE | ARDELHRMLN | EDELRDAVLL | VFANKQDLPN | 132 |
| SEQ_ID_NO_1259 | QNTQGLIFVV | DSNDRDRIVE | AKDELHRMLN | EDELRDAVLL | VFANKQDLPN | 132 |
| SEQ_ID_NO_1233 | QNTQGLIFVV | DSNDRDRVVE | ARDELHRMLN | EDELRDAVLL | VFANKQDLPN | 132 |
| SEQ_ID_NO_1235 | QNTQGLIFVV | DSNDRDRVVE | ARDELHRMLN | EDELRDAVLL | VFANKQDLPN | 132 |
| SEQ_ID_NO_1243 | QNTQGLIFVV | DSNDRDRVVE | ARDELHRMLN | EDELREAVLL | VFANKQDLPN | 132 |
| SEQ_ID_NO_1270 | QNTQGLIFVV | DSNDRDRVVE | ARDELHRMLN | EDELRDAVLL | VFANKQDLPN | 132 |
| SEQ_ID_NO_1242 | QNTQGLIFVV | DSNDRDRVVE | ARDELHRMLN | EDELREAVLL | VFANKQDLPN | 132 |
| SEQ_ID_NO_1238 | QNTQGLIFVV | DSNDRDRVVE | AKDELHRMLN | GDELRDAVLL | VFANKQDLPN | 132 |
| SEQ_ID_NO_1236 | QNTQGLIFVV | DSNDRDRVVE | ARDELHRMLN | EDELRDAVLL | VFANKQDLPN | 132 |
| SEQ_ID_NO_1240 | QNTQGLIFVV | DSNDRDRVVE | ARDELHRMLN | EDELRDAVLL | VFANKQDLPN | 132 |

Figure 42 (continued)

| | | | | | | |
|---|---|---|---|---|---|---|
| SEQ_ID_NO_1241 | AASEDELRYH | LGLTGVTTGK | GNINLAGTNV | RP--IEVFMC | SIVRK--MGY | 181 |
| SEQ_ID_NO_1229 | AASEDELRYH | LGLSNFTTGK | GKVDLVGSNV | RP--LEVFMC | SIVRK--MGY | 181 |
| SEQ_ID_NO_1249 | AASEEELRYH | LGLSSFTTGK | GKVSLCDSNV | RP--LEVFMC | SVVRK--MGY | 181 |
| SEQ_ID_NO_1264 | ALDDAAITES | LELHKIKS-- | ---------- | RQ--WAIFKT | SAIKG--EGL | 181 |
| SEQ_ID_NO_1251 | ALDDAAITES | LELHKIKS-- | ---------- | RQ--WAIFKT | SAIKG--EGL | 166 |
| SEQ_ID_NO_1265 | ALDDAAITES | LELHKIKS-- | ---------- | RQ--WAIFKT | SAIKG--EGL | 166 |
| SEQ_ID_NO_1253 | ALDDAAVTEA | LELHKIKS-- | ---------- | RQ--WAIFKT | CAVKG--EGL | 166 |
| SEQ_ID_NO_1210 | ALDDAAVTEA | LELHKIKS-- | ---------- | RQ--WAIFKT | CAVKG--EGL | 166 |
| SEQ_ID_NO_1267 | ALDDAAVTEA | LELHKIKS-- | ---------- | RQ--WAIFKT | CAVKG--EGL | 166 |
| SEQ_ID_NO_1213 | ALDDAAVTES | LELHKIKN-- | ---------- | RQ--WAIFKT | SAIKG--EGL | 166 |
| SEQ_ID_NO_1218 | ALDDAAVTEA | LELHKIKN-- | ---------- | RQ--WAIFKT | SAIKG--EGL | 166 |
| SEQ_ID_NO_1232 | ALDDAAVTEA | LELHKIKN-- | ---------- | RQ--WAIFKT | SAIKG--EGL | 166 |
| SEQ_ID_NO_1234 | ALDDAAVTES | LELHKIKN-- | ---------- | RQ--WAIFKT | SAIKG--EGL | 166 |
| SEQ_ID_NO_1272 | AMNAAEITDK | LGLHSLRQ-- | ---------- | RPNLWGLINS | PKEVPLVANL | 170 |
| SEQ_ID_NO_1268 | AMSAAEITDK | LGLHSLRQ-- | ---------- | RH--WFIQST | CATSG--EGL | 166 |
| SEQ_ID_NO_1211 | AMNAAEITDK | LGLHSLRQ-- | ---------- | RH--WYIQST | CATSG--EGL | 166 |
| SEQ_ID_NO_1216 | AMNAAEITDK | LGLHSLRQ-- | ---------- | RH--WYIQST | CATSG--EGL | 166 |
| SEQ_ID_NO_1269 | AMNAAEITDK | LGLHSLRQ-- | ---------- | RH--WYIQST | CATSG--EGL | 166 |
| SEQ_ID_NO_1239 | AMNAAEITDK | HGLHSLRQ-- | ---------- | RH--WYIQST | CATSG--EGL | 166 |
| SEQ_ID_NO_1259 | AMNAAEITDK | LGLHSLRQ-- | ---------- | RH--WYIQST | CATSG--EGL | 166 |
| SEQ_ID_NO_1233 | AMNAAEITDK | LGLHSLRQ-- | ---------- | RH--WYIQST | CATSG--EGL | 166 |
| SEQ_ID_NO_1235 | AMNAAEITDK | LGLHSLRQ-- | ---------- | RH--WYIQST | CATSG--EGL | 166 |
| SEQ_ID_NO_1243 | AMNAAEITDK | LGLHSLRQ-- | ---------- | RH--WYIQST | CATSG--EGL | 166 |
| SEQ_ID_NO_1270 | AMNAAEITDK | LGLHSLRQ-- | ---------- | RH--WYIQST | CATSG--EGL | 166 |
| SEQ_ID_NO_1242 | AMNAAEITDK | LGLHSLRQ-- | ---------- | RH--WYIQST | CATSG--EGL | 166 |
| SEQ_ID_NO_1238 | AMNAAEITDK | LGLHSLRQ-- | ---------- | RH--WYIQST | CATSG--EGL | 166 |
| SEQ_ID_NO_1236 | AMNAAEITDK | LGLHSLRQ-- | ---------- | RH--WYIQST | CATSG--EGL | 166 |
| SEQ_ID_NO_1240 | AMNAAEITDK | LGLHSLRQ-- | ---------- | RH--WYIQST | CATSG--EGL | 166 |

Figure 42 (continued)

```
SEQ_ID_NO_1241   GEGFK----- ---------- ---------- -----WMSQY IK--------   193
SEQ_ID_NO_1229   GEGFK----- ---------- ---------- -----WLSQY IK--------   193
SEQ_ID_NO_1249   GDGFK----- ---------- ---------- -----WVSQY IN--------   193
SEQ_ID_NO_1264   FEGLDCSVLQ HIILQFLPDE CIWEYLMELT YKSLMYLHIE IKNRFVENDE   231
SEQ_ID_NO_1251   FEGLN----- ---------- ---------- -----WLSNA LKSGGS----   182
SEQ_ID_NO_1265   FEGLD----- ---------- ---------- -----WLSNA LKSKSS----   182
SEQ_ID_NO_1253   FEGLD----- ---------- ---------- -----WLSNT LKSGTG----   182
SEQ_ID_NO_1210   FEGLD----- ---------- ---------- -----WLSNT LKSGSG----   182
SEQ_ID_NO_1267   FEGLD----- ---------- ---------- -----WLSNT LKSGSG----   182
SEQ_ID_NO_1213   FEGLD----- ---------- ---------- -----WLSNT LKSGSG----   182
SEQ_ID_NO_1218   FEGLD----- ---------- ---------- -----WLSNT LKSGGG----   182
SEQ_ID_NO_1232   FEGLD----- ---------- ---------- -----WLSNT LKSGGG----   182
SEQ_ID_NO_1234   FEGLD----- ---------- ---------- -----WLSNT LKSGGG----   182
SEQ_ID_NO_1272   FLG------- ---------- ---------- -----WKGVL LIGGGPKNLG   188
SEQ_ID_NO_1268   YEGLD----- ---------- ---------- -----WLSSN ISQRA-----   181
SEQ_ID_NO_1211   YEGLD----- ---------- ---------- -----WLSNN LANKT-----   181
SEQ_ID_NO_1216   YEGLD----- ---------- ---------- -----WLSNN IASKA-----   181
SEQ_ID_NO_1269   YEGLD----- ---------- ---------- -----WLSNN ISSKA-----   181
SEQ_ID_NO_1239   YEGLD----- ---------- ---------- -----WLSNN IANKA-----   181
SEQ_ID_NO_1259   YEGLD----- ---------- ---------- -----WLSNN IASKA-----   181
SEQ_ID_NO_1233   YEGLD----- ---------- ---------- -----WLSNN IASKA-----   181
SEQ_ID_NO_1235   YEGLE----- ---------- ---------- -----WLSNN IASKA-----   181
SEQ_ID_NO_1243   YEGLD----- ---------- ---------- -----WLSNN IASKA-----   181
SEQ_ID_NO_1270   YEGLD----- ---------- ---------- -----WLSNN IASKG-----   181
SEQ_ID_NO_1242   YEGLD----- ---------- ---------- -----WLSNN ISNKA-----   181
SEQ_ID_NO_1238   YEGLD----- ---------- ---------- -----WLSNN IANKA-----   181
SEQ_ID_NO_1236   YEGLD----- ---------- ---------- -----WLSNN IANKA-----   181
SEQ_ID_NO_1240   YEGLD----- ---------- ---------- -----WLSNN IANKA-----   181
```

Figure 42 (continued)

| | | |
|---|---|---|
| SEQ_ID_NO_1241 | ---------- --- | 193 |
| SEQ_ID_NO_1229 | ---------- --- | 193 |
| SEQ_ID_NO_1249 | ---------- --- | 193 |
| SEQ_ID_NO_1264 | QTVRTLGHWW LYP | 244 |
| SEQ_ID_NO_1251 | ---------- --- | 182 |
| SEQ_ID_NO_1265 | ---------- --- | 182 |
| SEQ_ID_NO_1253 | ---------- --- | 182 |
| SEQ_ID_NO_1210 | ---------- --- | 182 |
| SEQ_ID_NO_1267 | ---------- --- | 182 |
| SEQ_ID_NO_1213 | ---------- --- | 182 |
| SEQ_ID_NO_1218 | ---------- --- | 182 |
| SEQ_ID_NO_1232 | ---------- --- | 182 |
| SEQ_ID_NO_1234 | ---------- --- | 182 |
| SEQ_ID_NO_1272 | LLSPKPK--- --- | 195 |
| SEQ_ID_NO_1268 | ---------- --- | 181 |
| SEQ_ID_NO_1211 | ---------- --- | 181 |
| SEQ_ID_NO_1216 | ---------- --- | 181 |
| SEQ_ID_NO_1269 | ---------- --- | 181 |
| SEQ_ID_NO_1239 | ---------- --- | 181 |
| SEQ_ID_NO_1259 | ---------- --- | 181 |
| SEQ_ID_NO_1233 | ---------- --- | 181 |
| SEQ_ID_NO_1235 | ---------- --- | 181 |
| SEQ_ID_NO_1243 | ---------- --- | 181 |
| SEQ_ID_NO_1270 | ---------- --- | 181 |
| SEQ_ID_NO_1242 | ---------- --- | 181 |
| SEQ_ID_NO_1238 | ---------- --- | 181 |
| SEQ_ID_NO_1236 | ---------- --- | 181 |
| SEQ_ID_NO_1240 | ---------- --- | 181 |

Figure 43

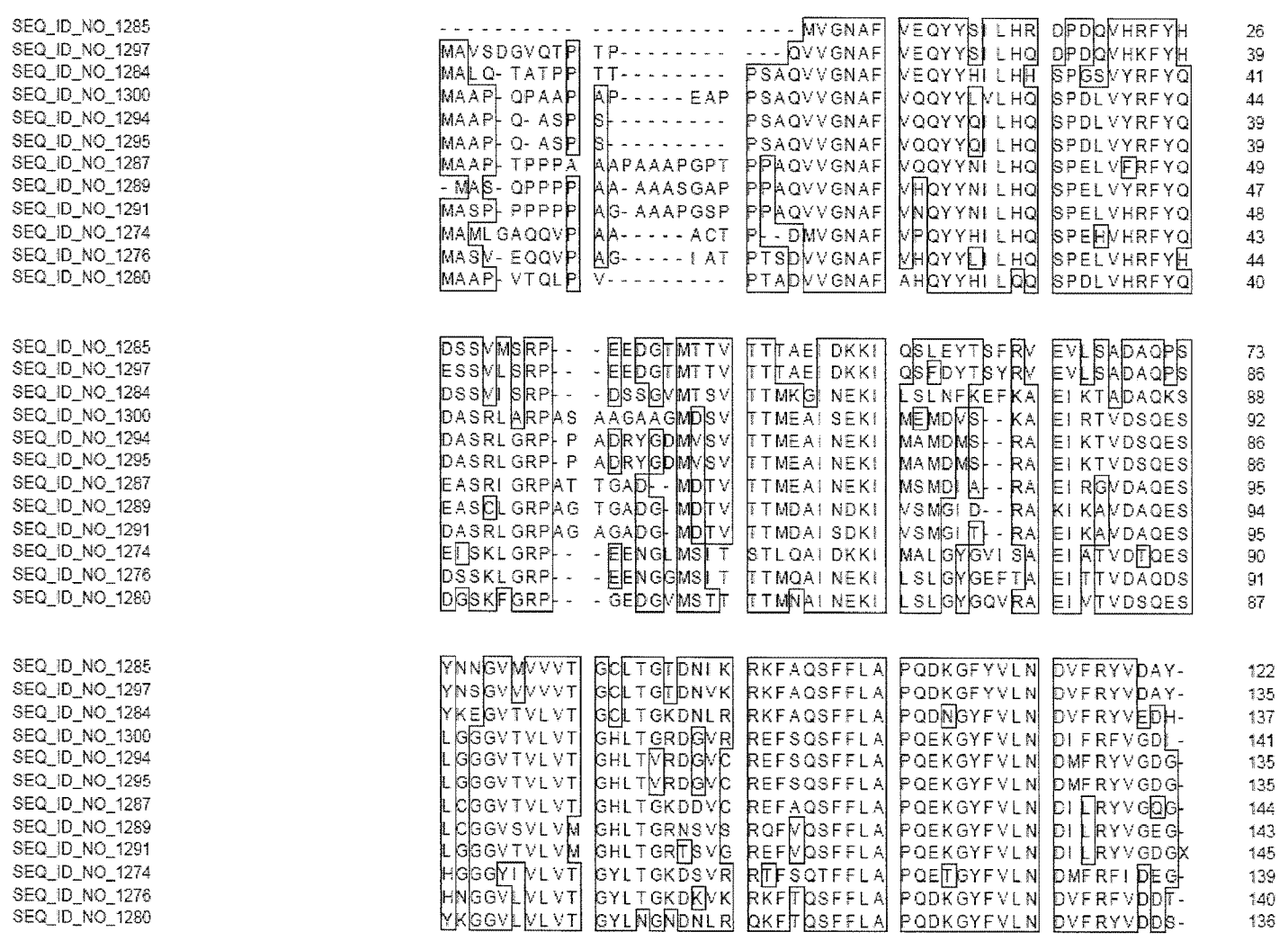

```
SEQ_ID_NO_1285  ----------  ----------  ----MVGNAF  VEQYYSI LHR  DPDQVHRFYH  26
SEQ_ID_NO_1297  MAVSDGVQTP  TP--------  ---QVVGNAF  VEQYYSI LHQ  DPDQVHKFYH  39
SEQ_ID_NO_1284  MALQ-TATPP  TT--------  PSAQVVGNAF  VEQYYHI LHH  SPGSVYRFYQ  41
SEQ_ID_NO_1300  MAAP-QPAAP  AP-----EAP  PSAQVVGNAF  VQQYYLVLHQ  SPDLVYRFYQ  44
SEQ_ID_NO_1294  MAAP-Q-ASP  S---------  PSAQVVGNAF  VQQYYQI LHQ  SPDLVYRFYQ  39
SEQ_ID_NO_1295  MAAP-Q-ASP  S---------  PSAQVVGNAF  VQQYYQI LHQ  SPDLVYRFYQ  39
SEQ_ID_NO_1287  MAAP-TPPPA  AAPAAAPGPT  PPAQVVGNAF  VQQYYNI LHQ  SPELVFRFYQ  49
SEQ_ID_NO_1289  -MAS-QPPPP  AA-AAASGAP  PPAQVVGNAF  VHQYYNI LHQ  SPELVYRFYQ  47
SEQ_ID_NO_1291  MASP-PPPPP  AG-AAAPGSP  PPAQVVGNAF  VNQYYNI LHQ  SPELVHRFYQ  48
SEQ_ID_NO_1274  MAMLGAQQVP  AA-----ACT  P--DMVGNAF  VPQYYHI LHQ  SPEHVHRFYQ  43
SEQ_ID_NO_1276  MASV-EQQVP  AG-----IAT  PTSDVVGNAF  VHQYYLI LHQ  SPELVHRFYH  44
SEQ_ID_NO_1280  MAAP-VTQLP  V---------  PTADVVGNAF  AHQYYHI LQQ  SPDLVHRFYQ  40

SEQ_ID_NO_1285  DSSVMSRP--  -EEDGTMTTV  TTTAEI DKKI  QSLEYTSFRV  EVLSADAQPS  73
SEQ_ID_NO_1297  ESSVLSRP--  -EEDGTMTTV  TTTAEI DKKI  QSFDYTSYRV  EVLSADAQPS  86
SEQ_ID_NO_1284  DSSVI SRP--  -DSSGVMTSV  TTMKGI NEKI  LSLNFKEFKA  EI KTADAQKS  88
SEQ_ID_NO_1300  DASRLARPAS  AAGAAGMDSV  TTMEAI SEKI  MEMDVS--KA  EI RTVDSQES  92
SEQ_ID_NO_1294  DASRLGRP-P  ADRYGDMVSV  TTMEAI NEKI  MAMDMS--RA  EI KTVDSQES  86
SEQ_ID_NO_1295  DASRLGRP-P  ADRYGDMVSV  TTMEAI NEKI  MAMDMS--RA  EI KTVDSQES  86
SEQ_ID_NO_1287  EASRI GRPAT  TGAD--MDTV  TTMEAI NEKI  MSMDI A--RA  EI RGVDAQES  95
SEQ_ID_NO_1289  EASCLGRPAG  TGADG-MDTV  TTMDAI NDKI  VSMGI D--RA  KI KAVDAQES  94
SEQ_ID_NO_1291  DASRLGRPAG  AGADG-MDTV  TTMDAI SDKI  VSMGI T--RA  EI KAVDAQES  95
SEQ_ID_NO_1274  EI SKLGRP--  -EENGLMSI T  STLQAI DKKI  MALGYGVI SA  EI ATVDTQES  90
SEQ_ID_NO_1276  DSSKLGRP--  -EENGGMSLT  TTMQAI NEKI  LSLGYGEFTA  EI TTVDAQDS  91
SEQ_ID_NO_1280  DGSKFGRP--  -GEDGVMSTT  TTMNAI NEKI  LSLGYGQVRA  EI VTVDSQES  87

SEQ_ID_NO_1285  YNNGVMVVVT  GCLTGTDNI K  RKFAQSFFLA  PQDKGFYVLN  DVFRYVDAY-  122
SEQ_ID_NO_1297  YNSGVVVVVT  GCLTGTDNVK  RKFAQSFFLA  PQDKGFYVLN  DVFRYVDAY-  135
SEQ_ID_NO_1284  YKEGVTVLVT  GCLTGKDNLR  RKFAQSFFLA  PQDNGYFVLN  DVFRYVEDH-  137
SEQ_ID_NO_1300  LGGGVTVLVT  GHLTGRDGVR  REFSQSFFLA  PQEKGYFVLN  DI FRFVGDL-  141
SEQ_ID_NO_1294  LGGGVTVLVT  GHLTVRDGVC  REFSQSFFLA  PQEKGYFVLN  DMFRYVGDG-  135
SEQ_ID_NO_1295  LGGGVTVLVT  GHLTVRDGVC  REFSQSFFLA  PQEKGYFVLN  DMFRYVGDG-  135
SEQ_ID_NO_1287  LCGGVTVLVT  GHLTGKDDVC  REFAQSFFLA  PQEKGYFVLN  DI LRYVGQG-  144
SEQ_ID_NO_1289  LCGGVSVLVM  GHLTGRNSVS  RQFVQSFFLA  PQEKGYFVLN  DI LRYVGEG-  143
SEQ_ID_NO_1291  LGGGVTVLVM  GHLTGRTSVG  REFVQSFFLA  PQEKGYFVLN  DI LRYVGDGX  145
SEQ_ID_NO_1274  HGGGYI VLVT  GYLTGKDSVR  RTFSQTFFLA  PQETGYFVLN  DMFRFI DEG-  139
SEQ_ID_NO_1276  HNGGVLVLVT  GYLTGKDKVK  RKFTQSFFLA  PQDKGYFVLN  DVFRFVDDT-  140
SEQ_ID_NO_1280  YKGGVLVLVT  GYLNGNDNLR  QKFTQSFFLA  PQDKGYFVLN  DVFRYVDDS-  136
```

Figure 43 (continued)

```
SEQ_ID_NO_1285   --------KS IDIESVPAND ADESAPSEAI ITPEPEPVHV PEVIPPTQTV   164
SEQ_ID_NO_1297   ---------K SVDIETVPAN DADESAPSEA FTPDPEPIHV A-------ED   169
SEQ_ID_NO_1284   --------EP SELPPVTGDG DSAAVTVTPE LEPSHVAD-- --------SC   169
SEQ_ID_NO_1300   --------PA PTAVEAQPEA DAVVPPVAAP LANGTATPAV EPAIPDDHDA   183
SEQ_ID_NO_1294   -------PTP AAAAAAAVEV QPEADAVAPP LANGTATAPL QPAAPDY-DG   177
SEQ_ID_NO_1295   ---------P TPAAAAAAEV QPEADAVAPP LANGTATAPL QPAAPDY-DA   175
SEQ_ID_NO_1287   --EADPSLPP PQQQPPAPEL DAVVAP-AAA LANGTVAP-- VETVPREQEA   189
SEQ_ID_NO_1289   ----GGDEGA EKQPAPEVAA DAEKTTSAPI LANGTVGGDA TTVPQ---DA   186
SEQ_ID_NO_1291   GEEGAGHPPP PPQQPVQETV TGAEAVPAPI LANGTVGG-D NETLPCEQDA   194
SEQ_ID_NO_1274   ---------- ----TVVHGN QIPVNNVQAP VNTYQDTAAA KEIPDDFVQE   175
SEQ_ID_NO_1276   ---------- ----KHQPGG QDPVNGFEAS LTHEQGHS-- ----------   164
SEQ_ID_NO_1280   ---------- ----THQNGN QEPASNFEAP VAPDQDTP-- ----------   160

SEQ_ID_NO_1285   IPTAQTVIPP TQTVIADTET IISKEVSLPL ENGKLSVT-- ----------   202
SEQ_ID_NO_1297   IPTIQPVIAD TDTNISK--- ----EVSLPL ENGKLSVT-- ----------   200
SEQ_ID_NO_1284   APEPTNSHVN KGQTVAE--- ----NAYELS NNHERQIPV- ----------   201
SEQ_ID_NO_1300   VPQQENHVVD RSPPQPEEED EA--EVYNPP PEEVV----- ----------   216
SEQ_ID_NO_1294   MPQEEPDVVE HAAVPPEEEE ----EVYNPP LEEVEGGAV- ----------   212
SEQ_ID_NO_1295   MPHEEPDVVE NVAVPPEEEE ----EVYNPP LEEVEGGAV- ----------   210
SEQ_ID_NO_1287   SPQPELDLSE SVPHTNEEED PKE-EVYNPP NDVEVPV--- ----------   225
SEQ_ID_NO_1289   SPQPECQVAE PALNPKEEVL NG--EVCNSL SDVEKPV--- ----------   221
SEQ_ID_NO_1291   SPQPEQPAAE SAPPTPEEED LYGEEVYNPP NDMEKPV--- ----------   231
SEQ_ID_NO_1274   KYVQENHAVK QTEVLSKSIN EPE-KVFTPS EDEQVSA--- ----------   211
SEQ_ID_NO_1276   -PVPENHIEQ PAA-LPEECN GP--EVYNSS ENGDGSIE-- ----------   198
SEQ_ID_NO_1280   -HTQETHISE PTAALSEEVI GG--EVYNPS ESGDVSVEVE EEESGDVSFE   207

SEQ_ID_NO_1285   ENVIPVNHVK ESSHHVKEPE QPTSIEKVAS NTQEDTPKKS FASIVNALKD   252
SEQ_ID_NO_1297   ENVIPVNHVK ESSHQEQMAS IEKV----PS NTQEDTPKKS FASIVSAYKD   246
SEQ_ID_NO_1284   ENEGNVESHF QSNGNDDSQA TELA-----S SAQDDAPKKS YASIVKVQKG   246
SEQ_ID_NO_1300   DEEQPVPEVI NEVPNNVAPV AATT---VAP VLQEEAPKKS YASIVKVMKE   263
SEQ_ID_NO_1294   EEEQSVPEVI NEVPNNVVPV VAPA---AAP VSHEEAPKKS YASIVKVMKE   259
SEQ_ID_NO_1295   EEEQSVPEVI NEVPNNVVPV VAPA---DAP VSHEEAPKKS YASIVKVMKE   257
SEQ_ID_NO_1287   VEETLVPEVI DEVPNNVAAS IPVS---APP VPHEEAPKKS YASIVKVMKA   272
SEQ_ID_NO_1289   AEETPVPDVI NEVPNNVAVA PPIS---SPP VPLKEAPKKS YASIVKVMKE   268
SEQ_ID_NO_1291   VQETPVAEVI NEVPNNVAVA APSS---SPS IPIEEAPKKS YASIVKVMKE   278
SEQ_ID_NO_1274   AEEVLVTETV NEAPIEVQKV GESD------ SRTGEIPKRS YASIVKVMKE   255
SEQ_ID_NO_1276   EEESPVAEVV DEIPDDSKMV SDSK------ PEMEELPKKS YASILKVLKE   242
SEQ_ID_NO_1280   EEEEPMPEVV DEIPPDSQLV ADSQVVVESS AKIEDTPKKS YASVVKVQKE   257
```

Figure 43 (continued)

```
SEQ_ID_NO_1285   NSAPFHL--- -RASPAKPAV HPP--RVHSV PAPEAPTPNM DIPLEKNN--   294
SEQ_ID_NO_1297   NSAPFLS--- -RTSPAKPAV QPP--RVHSV PAPEAPAPNM DIPSEKNN--   288
SEQ_ID_NO_1284   SSVPTKVYV- -PTNTLKSGP NKT--ESKVV ES-VESTEVP EAALESVSNP   291
SEQ_ID_NO_1300   VPLPA----- -PAPPTRPAP PKP--EKQS- -P-PAPTPVT DVPPFSSN-P   301
SEQ_ID_NO_1294   APVPAPIPAT RPAPAARPAP PKP--EKQSP AP-PAPAPVA DATPFSSN-A   305
SEQ_ID_NO_1295   APVPAPIPAT RPAPAARPAP PKP--EKQSP AP-PAPAPVA DATPFSSN-A   303
SEQ_ID_NO_1287   VLPPN----- -STVPYRPAP PKP--EKQA- -PAPAQSVAV DAPTFSPN-P   311
SEQ_ID_NO_1289   HRPLA----- -PAVPSRPAP PIT--EKQA- -S-PAPTPVT EAPAFSPN-P   306
SEQ_ID_NO_1291   YPPPA----- -PAVPSRPAP PKP--EKQA- -P-PAPSLVA DAPAFSPN-T   316
SEQ_ID_NO_1274   NAAPMSA--- -SRTPTKVEP KKQ--EDQAI HI-PLPTPLS EKSDSGANVA   298
SEQ_ID_NO_1276   NAVPVSAP-- -TQSPVKSAV KSQGHPRIAA PP-SAPMPAS DAQVSSNNVT   288
SEQ_ID_NO_1280   YTAPFSSP-- -TPSPLRSAP KIQ--EQVTA AV-SQP-PAA ESHVSSSNTF   300

SEQ_ID_NO_1285   ENAGR----- --AHAIFVAN LPMSATVEQL DRAFKKFGPI KRDGIQVRSN   337
SEQ_ID_NO_1297   ENGGR----- --AHAIFVAN LPMTATVEQL DRVFKKFGTI KRDGIQVRSN   331
SEQ_ID_NO_1284   ESSDAHE-EV E-GHSIYIRN LPLNVTVAQL ELEFKKFGPI KPGGIQVRNN   339
SEQ_ID_NO_1300   DNSNIQEPEV D-AHAIYVRN LPLNATETQL EDEFKKFGTI KQNGIQVRSN   350
SEQ_ID_NO_1294   ESSNTHEPEV D-AHAIYVRS LPLNATTTQL EDEFKKFGTI KPDGIQVRSH   354
SEQ_ID_NO_1295   ESSNTHEPEV D-AHAIYVRS LPLNATTTQL EDEFKKFGTI KPDGIQVRSH   352
SEQ_ID_NO_1287   ESSNIQDQEV D-ALAVYVKN LPLHATPSQL EEEFKRFGTI KHDGIQVRSH   360
SEQ_ID_NO_1289   QSGGFQDPEV D-AHAIYVRS LPLNATPQQL EEEFKRFGTI KHEGIQVRSN   355
SEQ_ID_NO_1291   QGGSFQDPEV D-AHAIYVRN LPLNATPQQL EEEFKRFGTI KHEGIQVRSN   365
SEQ_ID_NO_1274   VNENNQENER ALGPSIYLKG LPLDATPALL ENEFQKFGLI RTNGIQVRSQ   348
SEQ_ID_NO_1276   ENGNNQDAEA E-GPSIYVKG LPLNATPSML EVEFKKFGPI KSGGIQVRSQ   337
SEQ_ID_NO_1280   ENGNAQESE- E-GPSIYVKG LPLDATTTLL ENEFKKFGPI RNGGVQVRFQ   348

SEQ_ID_NO_1285   K--GSCFGFV EFESAASMQS ALEASPPVML DNRRLSIEER RGR-------   378
SEQ_ID_NO_1297   K--GSCFGFV EFESAASLQS ALEASPPVML DNRRLSIEER RGR-------   372
SEQ_ID_NO_1284   KQQGYCFGFV EFLSLNSMNS AIQAS-PVPI GGRQAVVEIK RTTTRVGSGI   388
SEQ_ID_NO_1300   KIQGFCYGFV EFEDSTSVQS AIEAS-PVTI GGRQCYVEEK RTP---GSR-   395
SEQ_ID_NO_1294   KIQGFCYGFV EFEEATAVQS AIEAS-PVMI GGRQCFVEEK RTP---GSR-   399
SEQ_ID_NO_1295   KIQGFCYGFV EFEEATAVQS AIEAS-PVMI GGRQCFVEEK RTP---GSR-   397
SEQ_ID_NO_1287   KIQGFCYGFI EFEDASSVQS ALAAS-PVTI DDRPCHVEEK RTP---GS--   404
SEQ_ID_NO_1289   KIQGFCYGFV EFEDASAVQA AIEAS-PVTI GERQCFVEEK RTT---GSRG   401
SEQ_ID_NO_1291   KIQGFCYGFV EFEDANAVQT AIEAS-PVMI SERQCYVEEK RTT---GSR-   410
SEQ_ID_NO_1274   K--GFCFGFV EFESASSMQS AIEAS-PVML NGHKVVVEEK RST---A---   389
SEQ_ID_NO_1276   K--GFCFGFV EFEMASSVQS AIEAS-PINI GGRKAVVEEK RST---S---   378
SEQ_ID_NO_1280   K--GFCFGFV EFEVASAVQS ALELIYLFLF T--------- ----------   377
```

Figure 43 (continued)

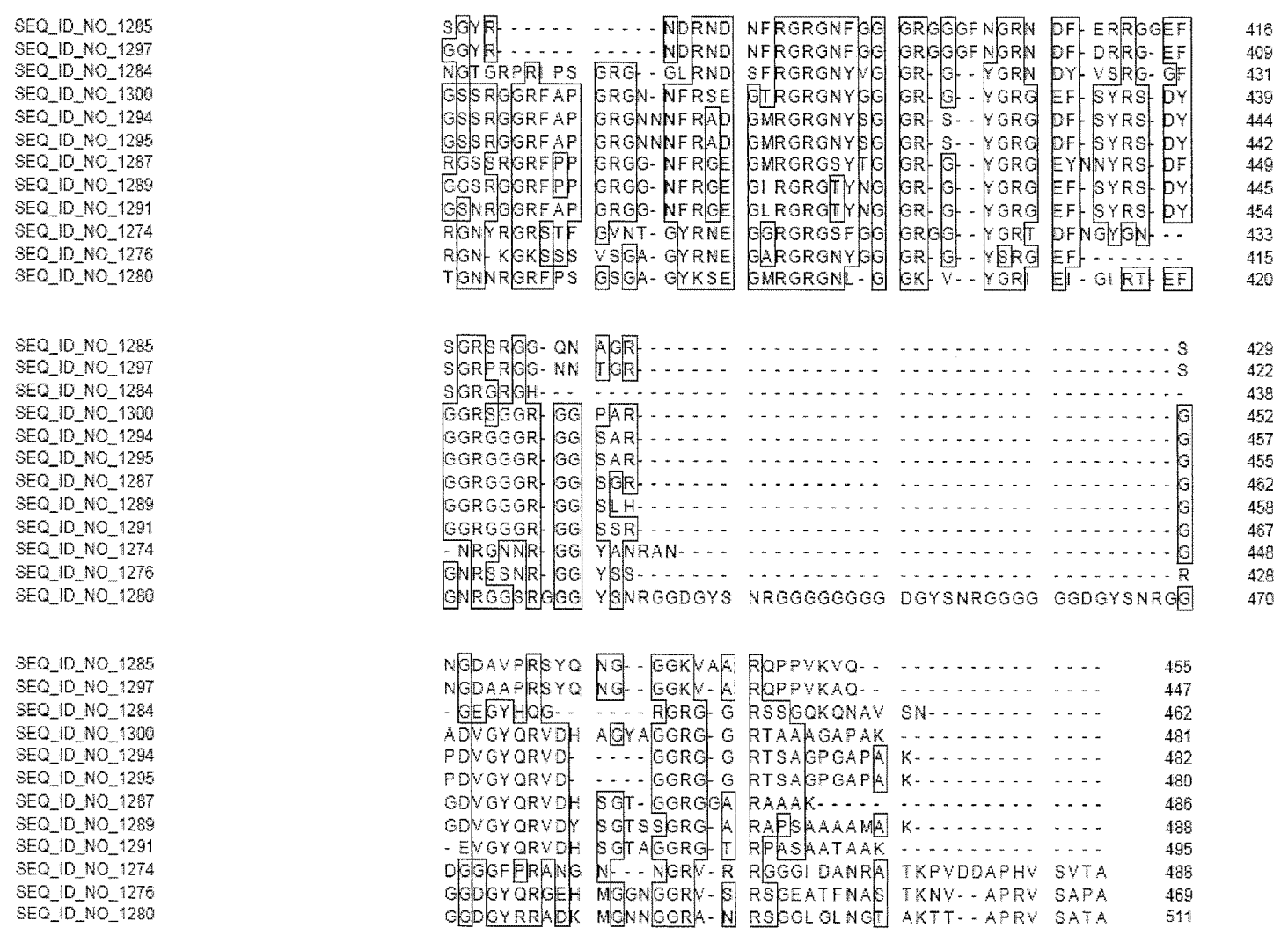

```
SEQ_ID_NO_1285   SGYR- - - - - -  - - - - - NDRND  NFRGRGNFGG  GRGGGFNGRN  DF- ERRGGEF   416
SEQ_ID_NO_1297   GGYR- - - - - -  - - - - - NDRND  NFRGRGNFGG  GRGGGFNGRN  DF- DRRG- EF   409
SEQ_ID_NO_1284   NGTGRPRLPS  GRG- - GLRND  SFRGRGNYVG  GR- G- - YGRN  DY- VSRG- GF   431
SEQ_ID_NO_1300   GSSRGGRFAP  GRGN- NFRSE  GTRGRGNYGG  GR- G- - YGRG  EF- SYRS- DY   439
SEQ_ID_NO_1294   GSSRGGRFAP  GRGNNNFRAD  GMRGRGNYSG  GR- S- - YGRG  DF- SYRS- DY   444
SEQ_ID_NO_1295   GSSRGGRFAP  GRGNNNFRAD  GMRGRGNYSG  GR- S- - YGRG  DF- SYRS- DY   442
SEQ_ID_NO_1287   RGSSRGRFPP  GRGG- NFRGE  GMRGRGSYTG  GR- G- - YGRG  EYNNYRS- DF   449
SEQ_ID_NO_1289   GGSRGGRFPP  GRGG- NFRGE  GIRGRGTYNG  GR- G- - YGRG  EF- SYRS- DY   445
SEQ_ID_NO_1291   GSNRGGRFAP  GRGG- NFRGE  GLRGRGTYNG  GR- G- - YGRG  EF- SYRS- DY   454
SEQ_ID_NO_1274   RGNYRGRSTF  GVNT- GYRNE  GGRGRGSFGG  GRGG- - YGRT  DFNGYGN- - -   433
SEQ_ID_NO_1276   RGN- KGKSSS  VSGA- GYRNE  GARGRGNYGG  GR- G- - YSRG  EF- - - - - - -   415
SEQ_ID_NO_1280   TGNNRGRFPS  GSGA- GYKSE  GMRGRGNL- G  GK- V- - YGRI  EI- GI RT- EF   420

SEQ_ID_NO_1285   SGRSRGG- QN  AGR- - - - - - -  - - - - - - - - - -  - - - - - - - - - -  - - - - - - - - - S   429
SEQ_ID_NO_1297   SGRPRGG- NN  TGR- - - - - - -  - - - - - - - - - -  - - - - - - - - - -  - - - - - - - - - S   422
SEQ_ID_NO_1284   SGRGRGH- - -  - - - - - - - - - -  - - - - - - - - - -  - - - - - - - - - -  - - - - - - - - - -   438
SEQ_ID_NO_1300   GGRSGGR- GG  PAR- - - - - - -  - - - - - - - - - -  - - - - - - - - - -  - - - - - - - - - G   452
SEQ_ID_NO_1294   GGRGGGR- GG  SAR- - - - - - -  - - - - - - - - - -  - - - - - - - - - -  - - - - - - - - - G   457
SEQ_ID_NO_1295   GGRGGGR- GG  SAR- - - - - - -  - - - - - - - - - -  - - - - - - - - - -  - - - - - - - - - G   455
SEQ_ID_NO_1287   GGRGGGR- GG  SGR- - - - - - -  - - - - - - - - - -  - - - - - - - - - -  - - - - - - - - - G   462
SEQ_ID_NO_1289   GGRGGGR- GG  SLH- - - - - - -  - - - - - - - - - -  - - - - - - - - - -  - - - - - - - - - G   458
SEQ_ID_NO_1291   GGRGGGR- GG  SSR- - - - - - -  - - - - - - - - - -  - - - - - - - - - -  - - - - - - - - - G   467
SEQ_ID_NO_1274   - NRGNNR- GG  YANRAN- - - -  - - - - - - - - - -  - - - - - - - - - -  - - - - - - - - - G   448
SEQ_ID_NO_1276   GNRSSNR- GG  YSS- - - - - - -  - - - - - - - - - -  - - - - - - - - - -  - - - - - - - - - R   428
SEQ_ID_NO_1280   GNRGGSRGGG  YSNRGGDGYS  NRGGGGGGGG  DGYSNRGGGG  GGDGYSNRGG   470

SEQ_ID_NO_1285   NGDAVPRSYQ  NG- - GGKVAA  RQPPVKVQ- -  - - - - - - - - - -  - - - -   455
SEQ_ID_NO_1297   NGDAAPRSYQ  NG- - GGKV- A  RQPPVKAQ- -  - - - - - - - - - -  - - - -   447
SEQ_ID_NO_1284   - GEGYHQG- -  - - - - RGRG- G  RSSGQKQNAV  SN- - - - - - - -  - - - -   462
SEQ_ID_NO_1300   ADVGYQRVDH  AGYAGGRG- G  RTAAAGAPAK  - - - - - - - - - -  - - - -   481
SEQ_ID_NO_1294   PDVGYQRVD-  - - - - GGRG- G  RTSAGPGAPA  K- - - - - - - - -  - - - -   482
SEQ_ID_NO_1295   PDVGYQRVD-  - - - - GGRG- G  RTSAGPGAPA  K- - - - - - - - -  - - - -   480
SEQ_ID_NO_1287   GDVGYQRVDH  SGT- GGRGGA  RAAAK- - - - -  - - - - - - - - - -  - - - -   486
SEQ_ID_NO_1289   GDVGYQRVDY  SGTSSGRG- A  RAPSAAAAMA  K- - - - - - - - -  - - - -   488
SEQ_ID_NO_1291   - EVGYQRVDH  SGTAGGRG- T  RPASAATAAK  - - - - - - - - - -  - - - -   495
SEQ_ID_NO_1274   DGGGFPRANG  N- - - NGRV- R  RGGGIDANRA  TKPVDDAPHV  SVTA   486
SEQ_ID_NO_1276   GGDGYQRGEH  MGGNGGRV- S  RSGEATFNAS  TKNV- - APRV  SAPA   469
SEQ_ID_NO_1280   GGDGYRRADK  MGNNGGRA- N  RSGGLGLNGT  AKTT- - APRV  SATA   511
```

Figure 44

| | | | | | | |
|---|---|---|---|---|---|---|
| SEQ_ID_NO_1327 | MVVTVAATG- | PDTAETLHST | TFASRYVRDQ | LPRYRMPENS | IPKEAAYQII | 49 |
| SEQ_ID_NO_1333 | MVVSVAATGA | GTDAEPVTST | FFASRYVRDP | LRRYRMPERS | IPREAAYQII | 50 |
| SEQ_ID_NO_1336 | MVVSVAATDS | DTAQPVQYST | FFASRYVRDP | LPRFRMPEQS | IPREAAYQII | 50 |
| SEQ_ID_NO_1319 | MVLTTTS--- | RDSEESLHCT | -FASRYVQEP | LPKFKMPKKS | MPKEAAYQIV | 47 |
| SEQ_ID_NO_1302 | MVLATN---- | SDSDEHLHST | -FASRYVRAV | VPRFKMPDHC | MPKDAAYQVI | 45 |
| SEQ_ID_NO_1311 | MVISTAA--- | TDSDENLYST | -FASRYVRTA | LPRFKMPENS | MPKDAAYQVI | 46 |
| SEQ_ID_NO_1317 | MVLTSTATHP | DEQDQSLNYT | -FASRYVREP | IPKFKMPEKS | IPKDAAYQII | 49 |
| SEQ_ID_NO_1305 | MLAAT----- | NPTEEHVHST | -FASRYVRAP | VPRFKMPEKS | IPKDAAYQVI | 44 |
| SEQ_ID_NO_1339 | MALSSA---- | TDSDGSIHST | -FASRYVQES | LPRFQIPSRS | IPKDAAYQII | 45 |
| SEQ_ID_NO_1318 | MVLSETA--- | THMDASVHST | -FASRYVRTS | LPRFKMGENS | IPKEAAYQII | 46 |
| SEQ_ID_NO_1331 | MVLSNTASSG | SESDLSIHST | -FASRYVRTS | LPRFKMPQES | IPKEAAYQII | 49 |
| SEQ_ID_NO_1313 | MVLSKTA--- | SESDVSIHST | -FASRYVRTS | LPRFEMPENS | IPKEAAYQII | 46 |
| SEQ_ID_NO_1303 | MVLSKTF--- | SESDESIHST | -FASRYVRNS | LPRFTMPENS | IPKEAAYQII | 46 |
| SEQ_ID_NO_1340 | MVLSKTA--- | SESDVSVHST | -FASRYVRAS | LPRFKMPENS | IPKEAAFQII | 46 |
| SEQ_ID_NO_1320 | MVLSKTA--- | SESDVSIHST | -FASRYVRTS | LPRFKMPENS | IPKEAAYQII | 46 |
| SEQ_ID_NO_1326 | MVLSKTV--- | SQSDVSIHST | -FASRYVRTS | LPRFKMPDNS | IPKEAAYQII | 46 |
| SEQ_ID_NO_1334 | MVLSKAV--- | SESDMSVHST | -FASRYVRAS | LPRYRMPENS | IPKEAAYQII | 46 |
| SEQ_ID_NO_1330 | MVLSHGV--- | GGSDESVHST | -FASRYVRTS | LPRYRMPEQS | IPKEAAYQII | 46 |

| | | | | | | |
|---|---|---|---|---|---|---|
| SEQ_ID_NO_1327 | SDELMLDGNP | RLNLASFVTT | WMEPECGKLI | MDSVNKNYVD | MDEYPVTTEL | 99 |
| SEQ_ID_NO_1333 | NDELMLDGNP | RLNLASFVTT | WMEPECDKLI | MGSINKNYVD | MDEYPVTTEL | 100 |
| SEQ_ID_NO_1336 | NDELMLDGNP | RLNLASFVTT | WMEPECDKLI | MDSVNKNYVD | MDEYPVTTEL | 100 |
| SEQ_ID_NO_1319 | NDELMLDGNP | RLNLASFVST | WMEPECDKLI | MSSINKNYVD | MDEYPVTTEL | 97 |
| SEQ_ID_NO_1302 | NDELMLDGNP | RLNLASFVTT | WMEPECDKLI | MDSVNKNYVD | MDEYPVTTEL | 95 |
| SEQ_ID_NO_1311 | NDELMLDGNP | RLNLASFVTT | WMEPECNDLI | MASINKNYVD | MDEYPVTTEL | 96 |
| SEQ_ID_NO_1317 | NDELMLDGAP | RLNLASFVTT | WMEPECDKLI | MASLNKNYVD | MDEYPVTTEL | 99 |
| SEQ_ID_NO_1305 | HDELMLDGNP | RLNLASFVTT | WMEPECDKLM | MAAINKNYVD | MDEYPVTTEL | 94 |
| SEQ_ID_NO_1339 | SDELMLDGNP | RLNLASFVTT | WMEPECDKLI | MQAINKNYVD | MDEYPVTTEL | 95 |
| SEQ_ID_NO_1318 | NDELMLDGNP | RLNLASFVTT | WMEPECDKLI | MASINKNYVD | MDEYPVTTEL | 96 |
| SEQ_ID_NO_1331 | NDELMLDGNP | RLNLASFVTT | WMEPECDKLI | MASINKNYVD | MDEYPVTTEL | 99 |
| SEQ_ID_NO_1313 | NDELMLDGNP | RLNLASFVTT | WMEPECDKLM | MESINKNYVD | MDEYPVTTEL | 96 |
| SEQ_ID_NO_1303 | NDELMLDGNP | RLNLASFVTT | WMEPECDKLM | MAAINKNYVD | MDEYPVTTEL | 96 |
| SEQ_ID_NO_1340 | NDELMLDGNP | RLNLASFVTT | WMEPECDKLI | IASINKNYVD | MDEYPVTTEL | 96 |
| SEQ_ID_NO_1320 | NDELMLDGNP | RLNLASFVTT | WMEPECNKLM | MDSINKNYVD | MDEYPVTTEL | 96 |
| SEQ_ID_NO_1326 | NDELMLDGNP | RLNLASFVTT | WMEPECDKLM | MDSINKNYVD | MDEYPVTTEL | 96 |
| SEQ_ID_NO_1334 | NDELMLDGNP | RLNLASFVTT | WMEPECDKLI | MAAINKNYVD | MDEYPVTTEL | 96 |
| SEQ_ID_NO_1330 | NDELMLDGNP | RLNLASFVTT | WMEPECDKLI | QASVNKNYVD | MDEYPVTTEL | 96 |

Figure 44 (continued)

```
SEQ_ID_NO_1327   QDRCVNMIAH LFNAPIGEDE TAIGVSTVGS SEAIMLAGLA FKRKWANKMK   149
SEQ_ID_NO_1333   QNRCVNMIAH LFNAPIKEDE TAVGVGTVGS SEAIMLAGLA FKRKWQNKRK   150
SEQ_ID_NO_1336   QNRCVNMIAH LFNAPIKEDE TAIGVGTVGS SEAIMLAGLA FKRKWQNKRK   150
SEQ_ID_NO_1319   QNRCVNMLAH LFHAPVGDDE TAVGVGTVGS SEAIMLAGLA FKRKWQSKRK   147
SEQ_ID_NO_1302   QNRCVNMIAN FFHAPVGEDE AAIGCGTVGS SEAIMLAGLA FKRKWQHRRK   145
SEQ_ID_NO_1311   QNRCVNIIAH LFNAPVGEKE TAVGVGTVGS SEAIMLAGLA FKRKWQNKRK   146
SEQ_ID_NO_1317   QNRCVNIIAN LFHAPISDDE TAVGVGTVGS SEAIMLAGLA FKRKWQTKRK   149
SEQ_ID_NO_1305   QNRCVNMIAN LFHAPVGEEE TAVGVGTVGS SEAIMLAGLA FKRRWQHKRK   144
SEQ_ID_NO_1339   QNRCVNIIAN LFNAPLGDGE EAVGVGTVGS SEAIMLAGLA FKRKWQNKRK   145
SEQ_ID_NO_1318   QNRCVNMIAH LFNAPLEDSE PAVGVGTVGS SEAIMLAGLA FKRKWQNRRK   146
SEQ_ID_NO_1331   QNRCVNMIAH LFNAPLGDSD T---VGTVGS SEAIMLAGLA FKRTWQNRRK   146
SEQ_ID_NO_1313   QNRCVNMIAR LFNAPLGDGE AAVGVGTVGS SEAIMLAGLA FKRQWQNKRK   146
SEQ_ID_NO_1303   QNRCVNIIAR LFNAPLEDSE TAVGVGTVGS SEAIMLAGLA FKRKWQNKRK   146
SEQ_ID_NO_1340   QNRCVNMIAH LFNAPLGDSE TAVGVGTVGS SEAIMLAGLA FKRKWQNKRK   146
SEQ_ID_NO_1320   QNRCVNMIAH LFNAPLGDGE TAVGVGTVGS SEAIMLAGLA FKRKWQNKMK   146
SEQ_ID_NO_1326   QNRCVNMIAH LFNAPLEDGE TAVGVGTVGS SEAIMLAGLA FKRKWQNKMK   146
SEQ_ID_NO_1334   QNRCVNMIAH LFHAPLGEDE TAVGVGTVGS SEAIMLAGLA FKRRWQNKRK   146
SEQ_ID_NO_1330   QNRCVNMIAH LFNAPLGDAE TAVGVGTVGS SEAIMLAGLA FKRRWQNKMK   146

SEQ_ID_NO_1327   EQGKPCDKPN IVTGANVQVC WEKFARYFEV ELKEVKLTEG YYVMDPKKAV   199
SEQ_ID_NO_1333   EQGKPYDKPN IVTGANVQVC WEKFARYFEV ELKEVKLSEG YYVMDPVKAV   200
SEQ_ID_NO_1336   EQGKPCDKPN IVTGANVQVC WEKFARYFEV ELKEVKLSEG YYVMDPVKAV   200
SEQ_ID_NO_1319   AEGKPFDKPN IVTGANVQVC WEKFARYFEV ELKEVKLKEG YYVMDPAKAV   197
SEQ_ID_NO_1302   AQGLPIDKPN IVTGANVQVC WEKFARYFEV ELKEVKLSED YYVMDPAKAV   195
SEQ_ID_NO_1311   AEGKFYDKPN IVTGANVQVC WEKFARYFEV ELKEVKLTEG YYVMDPVKAV   196
SEQ_ID_NO_1317   AEGKFYDKPN IVTGANVQVC WEKFARYFEV ELKEVKLKEG YYVMDPAKAV   199
SEQ_ID_NO_1305   TEGKPTDNPN IVTGANVQVC WEKFARYFEV GLKEVKLKEG YYVMDPEQAV   194
SEQ_ID_NO_1339   AEGKPYDKPN IVTGANVQVC WEKFARYFEV ELKEVKLKKD YYIMDPVKAV   195
SEQ_ID_NO_1318   SEGKSCENPN IVTGANVQVC WEKFARYFEV ELKEVKLRDG YYVMDPEKAA   196
SEQ_ID_NO_1331   AEGKPHDKPN IVTGANVQVC WEKFARYFEV ELKEVKLSEG YYVMDPQKAV   196
SEQ_ID_NO_1313   AQGLPYDKPN IVTGANVQVC WEKFARYFEV ELKEVKLREG YYVMDPEKAV   196
SEQ_ID_NO_1303   AEGKPFDKPN IVTGANVQVC WEKFARYFEV ELKEVKLSEG YYVMDPAKAV   196
SEQ_ID_NO_1340   AEGKPYDKPN IVTGANVQVC WEKFARYFEV ELKEVKLSDG YYVMDPEKAV   196
SEQ_ID_NO_1320   AQGKPCDKPN IVTGANVQVC WEKFARYFEV ELKEVKLSDG YYVMDPEKAV   196
SEQ_ID_NO_1326   AQGKPCDKPN IVTGANVQVC WEKFARYFEV ELKEVKLSEG YYVMDPEKAV   196
SEQ_ID_NO_1334   AEGKPFDKPN IITGANVQVC WEKFARYFEV ELKEVKLRDG YYVMDPEKAV   196
SEQ_ID_NO_1330   AAGKPCDKPN IVTGANVQVC WEKFARYFEV ELKEVKLSDG YYVMDPQKAV   196
```

Figure 44 (continued)

```
SEQ_ID_NO_1327   EMVDENTICV AAILGSTLTG EYEDVKLLND LLVEKNKETG WNVPIHVDAA   249
SEQ_ID_NO_1333   DMVDENTICV AAILGSTLTG EFEDVKQLND LLTEKNKETG WDVPIHVDAA   250
SEQ_ID_NO_1336   EMVDENTICV AAILGSTLTG EFEDVKLLNN LLTEKNKETG WDVPIHVDAA   250
SEQ_ID_NO_1319   EIVDENTICV AAILGSTLTG EFEDVKLLNE LLTKKNKETG WETPIHVDAA   247
SEQ_ID_NO_1302   EMVDENTICV AAILGSTLTG EFEDVKQLND LLAEKNAETG WETPIHVDAA   245
SEQ_ID_NO_1311   EMVDENTICV AAILGSTLTG EFEDVKLLND LLSKKNKETG WNTPIHVDAA   246
SEQ_ID_NO_1317   EMVDENTICV AAILGSTMTG EFEDVKLLDE LLTKKNNETG WDTPIHVDAA   249
SEQ_ID_NO_1305   ELVDENTICV AAILGSTLTG EFEDVKTLND LLMKKNEETG WGTPIHVDAA   244
SEQ_ID_NO_1339   EMVDENTICV AAILGSTYNG EFEDVKLVND LLIQKNKETG WDTPIHVDAA   245
SEQ_ID_NO_1318   EMVDENTICV AAILGSTLNG EFEDVKRLND LLVEKNAETG WDTPIHVDAA   246
SEQ_ID_NO_1331   DLVDENTICV AAILGSTLNG EFEDVKRLND LLIEKNKETG WDTPIHVDAA   246
SEQ_ID_NO_1313   EMVDENTICV AAILGSTLTG EFEDVKLLND LLVEKNKQTG WDTGIHVDAA   246
SEQ_ID_NO_1303   EMVDENTICV AAILGSTLNG EFEDVKLLND LLTEKNKETG WDTPIHVDAA   246
SEQ_ID_NO_1340   QMVDENTICV AAILGSTLNG EFEDVKLLND LLVEKNKSTG WDTPIHVDAA   246
SEQ_ID_NO_1320   EMVDENTICV AAILGSTLNG EFEDVKRLND LLIEKNKETG WDTPIHVDAA   246
SEQ_ID_NO_1326   EMVDENTICV AAILGSTLNG EFEDVKRLND LLVEKNKETG WDTPIHVDAA   246
SEQ_ID_NO_1334   DMVDENTICV AAILGSTLNG EFEDVKLLND LLDKKNKETG WETPIHVDAA   246
SEQ_ID_NO_1330   DMVDENTICV AAILGSTLNG EFEDVKLLND LLTKKNAETG WDTPIHVDAA   246

SEQ_ID_NO_1327   SGGFIAPFLQ PELEWDFRLP LVKSINVSGH KYGLVYPGVG WVIWRSKDDL   299
SEQ_ID_NO_1333   SGGFIAPFLY PELEWDFRLP LVKSINVSGH KYGLVYAGVG WVIWRSKKDL   300
SEQ_ID_NO_1336   SGGFIAPFLY PELEWDFRLP LVKSINVSGH KYGLVYPGVG WVIWRSKEDL   300
SEQ_ID_NO_1319   SGGFIAPFLW PDLEWDFRLP LVKSINVSGH KYGLVYAGVG WVIWRSKEDL   297
SEQ_ID_NO_1302   SGGFIAPFLY PDLEWDFRLP WVKSINVSGH KYGLVYAGVG WVVWRTKDDL   295
SEQ_ID_NO_1311   SGGFIAPFIW PDLEWDFRLP LVKSINVSGH KYGLVYAGVG WVVWRTKEDL   296
SEQ_ID_NO_1317   SGGFIAPFLY PDLEWDFRLP LVKSINVSCH KYGLVYPGVG WVVWRSKDDL   299
SEQ_ID_NO_1305   SGGFIAPFLY PDLEWDFRLP LVKSINVSGH KYGLVYAGVG WVVWRNKEDL   294
SEQ_ID_NO_1339   SGGFIAPFLY PELEWDFRLP LVKSINVSGH KYGLVYAGIG WVIWRAKQDL   295
SEQ_ID_NO_1318   SGGFIAPFLY PELVWDFRLS LVKSINVSGH KYGLVYAGIG WIIWRSKEDL   296
SEQ_ID_NO_1331   SGGFIAPFIY PELEWDFRLP LVKSINVSGH KYGLVYAGIG WVIWRNKEDL   296
SEQ_ID_NO_1313   SGGFIAPFLY PELEWDFRLP LVKSINVSGH KYGLVYAGIG WVVWRTKSDL   296
SEQ_ID_NO_1303   SGGFIAPFLY PELEWDFRLP LVKSINVSGH KYGLVYAGIG WVVWRNKEDL   296
SEQ_ID_NO_1340   SGGFIAPFIY PELEWDFRLP LVKSINVSGH KYGLVYAGIG WVIWRNKEDL   296
SEQ_ID_NO_1320   SGGFIAPFLY PELEWDFRLP LVKSINVSGH KYGLVYAGIG WAIWRNKEDL   296
SEQ_ID_NO_1326   SGGFIAPFIY PELEWDFRLP LVKSINVSGH KYGLVYAGIG WVVWRNKDDL   296
SEQ_ID_NO_1334   SGGFIAPFLY PELEWDFRLP WVKSINVSGH KYGLVYAGIG WCIWRNKEDL   296
SEQ_ID_NO_1330   SGGFIAPFLY PELEWDFRLP LVKSINVSGH KYGLVYAGIG WCIWRTKVDL   296
```

Figure 44 (continued)

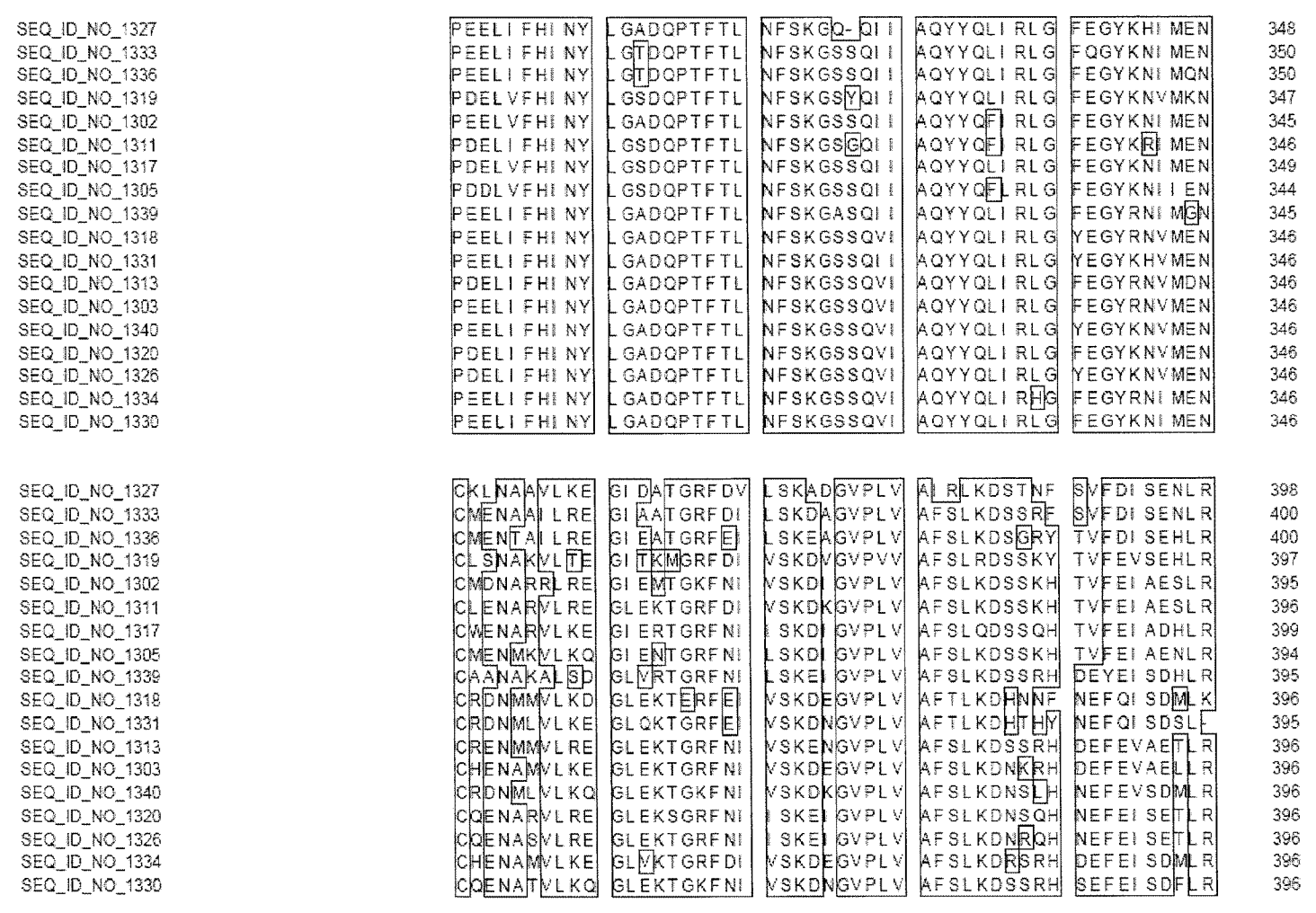

```
SEQ_ID_NO_1327   PEELIFHINY LGADQPTFTL NFSKGQ-QII AQYYQLIRLG FEGYKHIMEN  348
SEQ_ID_NO_1333   PEELIFHINY LGTDQPTFTL NFSKGSSQII AQYYQLIRLG FQGYKNIMEN  350
SEQ_ID_NO_1336   PEELIFHINY LGTDQPTFTL NFSKGSSQII AQYYQLIRLG FEGYKNIMQN  350
SEQ_ID_NO_1319   PDELVFHINY LGSDQPTFTL NFSKGSYQII AQYYQLIRLG FEGYKNVMKN  347
SEQ_ID_NO_1302   PEELVFHINY LGADQPTFTL NFSKGSSQII AQYYQFIRLG FEGYKNIMEN  345
SEQ_ID_NO_1311   PDELIFHINY LGSDQPTFTL NFSKGSGQII AQYYQFIRLG FEGYKRIMEN  346
SEQ_ID_NO_1317   PDELVFHINY LGSDQPTFTL NFSKGSSQII AQYYQLIRLG FEGYKNIMEN  349
SEQ_ID_NO_1305   PDDLVFHINY LGSDQPTFTL NFSKGSSQII AQYYQFLRLG FEGYKNIIEN  344
SEQ_ID_NO_1339   PEELIFHINY LGADQPTFTL NFSKGASQII AQYYQLIRLG FEGYRNIMGN  345
SEQ_ID_NO_1318   PEELIFHINY LGADQPTFTL NFSKGSSQVI AQYYQLIRLG YEGYRNVMEN  346
SEQ_ID_NO_1331   PEELIFHINY LGADQPTFTL NFSKGSSQII AQYYQLIRLG YEGYKHVMEN  346
SEQ_ID_NO_1313   PDELIFHINY LGADQPTFTL NFSKGSSQVI AQYYQLIRLG FEGYRNVMDN  346
SEQ_ID_NO_1303   PEELIFHINY LGADQPTFTL NFSKGSSQVI AQYYQLIRLG FEGYRNVMEN  346
SEQ_ID_NO_1340   PEELIFHINY LGADQPTFTL NFSKGSSQVI AQYYQLIRLG YEGYKNVMEN  346
SEQ_ID_NO_1320   PDELIFHINY LGADQPTFTL NFSKGSSQVI AQYYQLIRLG FEGYKNVMEN  346
SEQ_ID_NO_1326   PDELIFHINY LGADQPTFTL NFSKGSSQVI AQYYQLIRLG YEGYKNVMEN  346
SEQ_ID_NO_1334   PEELIFHINY LGADQPTFTL NFSKGSSQVI AQYYQLIRHG FEGYRNIMEN  346
SEQ_ID_NO_1330   PEELIFHINY LGADQPTFTL NFSKGSSQVI AQYYQLIRLG FEGYKNIMEN  346

SEQ_ID_NO_1327   CKLNAAVLKE GIDATGRFDV LSKADGVPLV AIRLKDSTNF SVFDISENLR  398
SEQ_ID_NO_1333   CMENAAILRE GIAATGRFDI LSKDAGVPLV AFSLKDSSRF SVFDISENLR  400
SEQ_ID_NO_1336   CMENTAILRE GIEATGRFEI LSKEAGVPLV AFSLKDSGRY TVFDISEHLR  400
SEQ_ID_NO_1319   CLSNAKVLTE GITKMGRFDI VSKDVGVPVV AFSLRDSSKY TVFEVSEHLR  397
SEQ_ID_NO_1302   CMDNARRLRE GIEMTGKFNI VSKDIGVPLV AFSLKDSSKH TVFEIAESLR  395
SEQ_ID_NO_1311   CLENARVLRE GLEKTGRFDI VSKDKGVPLV AFSLKDSSKH TVFEIAESLR  396
SEQ_ID_NO_1317   CWENARVLKE GIERTGRFNI ISKDIGVPLV AFSLQDSSQH TVFEIADHLR  399
SEQ_ID_NO_1305   CMENMKVLKQ GIENTGRFNI LSKDIGVPLV AFSLKDSSKH TVFEIAENLR  394
SEQ_ID_NO_1339   CAANAKALSD GLVRTGRFNI LSKEIGVPLV AFSLKDSSRH DEYEISDHLR  395
SEQ_ID_NO_1318   CRDNMMVLKD GLEKTERFEI VSKDEGVPLV AFTLKDHNNF NEFQISDMLK  396
SEQ_ID_NO_1331   CRDNMLVLKE GLQKTGRFEI VSKDNGVPLV AFTLKDHTHY NEFQISDSL   395
SEQ_ID_NO_1313   CRENMMVLRE GLEKTGRFNI VSKENGVPLV AFSLKDSSRH DEFEVAETLR  396
SEQ_ID_NO_1303   CHENAMVLKE GLEKTGRFNI VSKDEGVPLV AFSLKDNKRH DEFEVAELLR  396
SEQ_ID_NO_1340   CRDNMLVLKQ GLEKTGKFNI VSKDKGVPLV AFSLKDNSLH NEFEVSDMLR  396
SEQ_ID_NO_1320   CQENARVLRE GLEKSGRFNI ISKEIGVPLV AFSLKDNSQH NEFEISETLR  396
SEQ_ID_NO_1326   CQENASVLRE GLEKTGRFNI ISKEIGVPLV AFSLKDNRQH NEFEISETLR  396
SEQ_ID_NO_1334   CHENAMVLKE GLVKTGRFDI VSKDEGVPLV AFSLKDRSRH DEFEISDMLR  396
SEQ_ID_NO_1330   CQENATVLKQ GLEKTGKFNI VSKDNGVPLV AFSLKDSSRH SEFEISDFLR  396
```

Figure 44 (continued)

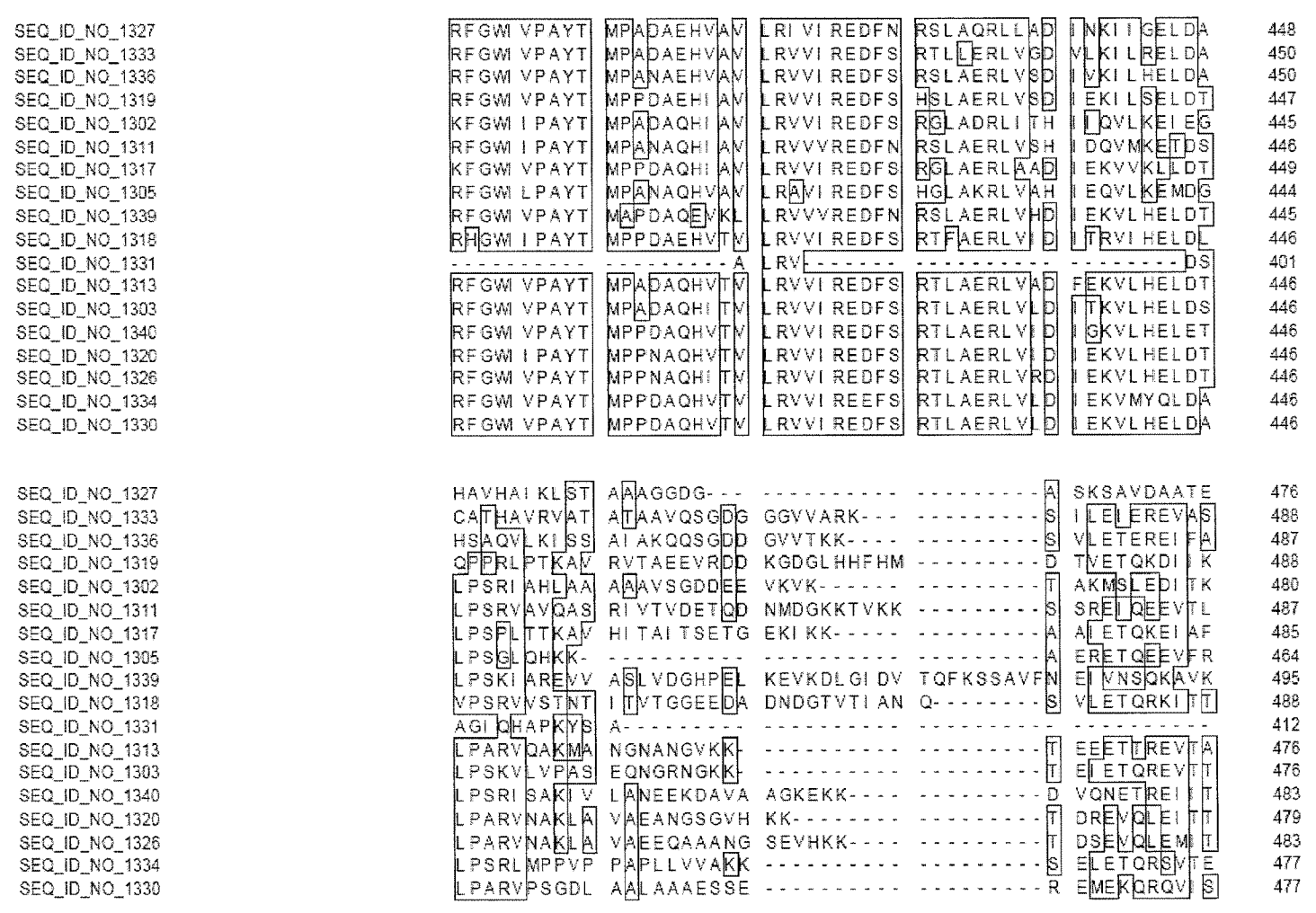

```
SEQ_ID_NO_1327   RFGWIVPAYT MPADAEHVAV LRIVIREDFN RSLAQRLLAD INKIIGELDA   448
SEQ_ID_NO_1333   RFGWIVPAYT MPADAEHVAV LRVVIREDFS RTLLERLVGD VLKILRELDA   450
SEQ_ID_NO_1336   RFGWIVPAYT MPANAEHVAV LRVVIREDFS RSLAERLVSD IVKILHELDA   450
SEQ_ID_NO_1319   RFGWIVPAYT MPPDAEHIAV LRVVIREDFS HSLAERLVSD IEKILSELDT   447
SEQ_ID_NO_1302   KFGWIIPAYT MPADAQHIAV LRVVIREDFS RGLADRLITH IIQVLKEIEG   445
SEQ_ID_NO_1311   RFGWIIPAYT MPANAQHIAV LRVVVREDFN RSLAERLVSH IDQVMKETDS   446
SEQ_ID_NO_1317   KFGWIVPAYT MPPDAQHIAV LRVVIREDFS RGLAERLAAD IEKVVKLLDT   449
SEQ_ID_NO_1305   RFGWILPAYT MPANAQHVAV LRAVIREDFS HGLAKRLVAH IEQVLKEMDG   444
SEQ_ID_NO_1339   RFGWIVPAYT MAPDAQEVKL LRVVVREDFN RSLAERLVHD IEKVLHELDT   445
SEQ_ID_NO_1318   RHGWIIPAYT MPPDAEHVTV LRVVIREDFS RTFAERLVID ITRVIHELDL   446
SEQ_ID_NO_1331   ---------- ---------A LRV------- ---------- --------DS   401
SEQ_ID_NO_1313   RFGWIVPAYT MPADAQHVTV LRVVIREDFS RTLAERLVAD FEKVLHELDT   446
SEQ_ID_NO_1303   RFGWIVPAYT MPADAQHITV LRVVIREDFS RTLAERLVLD ITKVLHELDS   446
SEQ_ID_NO_1340   RFGWIVPAYT MPPDAQHVTV LRVVIREDFS RTLAERLVID IGKVLHELET   446
SEQ_ID_NO_1320   RFGWIIPAYT MPPNAQHVTV LRVVIREDFS RTLAERLVID IEKVLHELDT   446
SEQ_ID_NO_1326   RFGWIVPAYT MPPNAQHITV LRVVIREDFS RTLAERLVRD IEKVLHELDT   446
SEQ_ID_NO_1334   RFGWIVPAYT MPPDAQHVTV LRVVIREEFS RTLAERLVLD IEKVMYQLDA   446
SEQ_ID_NO_1330   RFGWIVPAYT MPPDAQHVTV LRVVIREDFS RTLAERLVLD IEKVLHELDA   446

SEQ_ID_NO_1327   HAVHAIKLST AAAGGDG--- ---------- ---------A SKSAVDAATE   476
SEQ_ID_NO_1333   CATHAVRVAT ATAAVQSGDG GGVVARK--- ---------S ILELEREVAS   488
SEQ_ID_NO_1336   HSAQVLKISS AIAKQQSGDD GVVTKK---- ---------S VLETEREIFA   487
SEQ_ID_NO_1319   QPPRLPTKAV RVTAEEVRDD KGDGLHHFHM ---------D TVETQKDIIK   488
SEQ_ID_NO_1302   LPSRIAHLAA AAAVSGDDEE VKVK------ ---------T AKMSLEDITK   480
SEQ_ID_NO_1311   LPSRVAVQAS RIVTVDETQD NMDGKKTVKK ---------S SREIQEEVTL   487
SEQ_ID_NO_1317   LPSPLTTKAV HITAITSETG EKIKK----- ---------A AIETQKEIAF   485
SEQ_ID_NO_1305   LPSGLQHKK- ---------- ---------- ---------A ERETQEEVFR   464
SEQ_ID_NO_1339   LPSKIAREVV ASLVDGHPEL KEVKDLGIDV TQFKSSAVFN EIVNSQKAVK   495
SEQ_ID_NO_1318   VPSRVVSTNT ITVTGGEEDA DNDGTVTIAN Q--------S VLETQRKITT   488
SEQ_ID_NO_1331   AGIQHAPKYS A--------- ---------- ---------- ----------   412
SEQ_ID_NO_1313   LPARVQAKMA NGNANGVKK- ---------- ---------T EEETTREVTA   476
SEQ_ID_NO_1303   LPSKVLVPAS EQNGRNGKK- ---------- ---------T EIETQREVTT   476
SEQ_ID_NO_1340   LPSRISAKIV LANEEKDAVA AGKEKK---- ---------D VQNETREIIT   483
SEQ_ID_NO_1320   LPARVNAKLA VAEANGSGVH KK-------- ---------T DREVQLEITT   479
SEQ_ID_NO_1326   LPARVNAKLA VAEEQAAANG SEVHKK---- ---------T DSEVQLEMIT   483
SEQ_ID_NO_1334   LPSRLMPPVP PAPLLVVAKK ---------- ---------S ELETQRSVTE   477
SEQ_ID_NO_1330   LPARVPSGDL AALAAAESSE ---------- ---------R EMEKQRQVIS   477
```

Figure 44 (continued)

```
SEQ_ID_NO_1327    AFKDLAGK--  --KKAGVC--    490
SEQ_ID_NO_1333    RWRDAVSK--  --KKTGPC--    502
SEQ_ID_NO_1336    YWRDQVKK--  --KQTGIC--    501
SEQ_ID_NO_1319    HWRKIAGK--  --KTSGVC--    502
SEQ_ID_NO_1302    YWKRLVEH--  --KRNIVC--    494
SEQ_ID_NO_1311    YWRRLASE--  --KRTGAC--    501
SEQ_ID_NO_1317    YWKRLVDG--  --KRLGAC--    499
SEQ_ID_NO_1305    CWKRLVDR--  --KIAGVC--    478
SEQ_ID_NO_1339    AWKKFVAQ--  --KANRVC--    509
SEQ_ID_NO_1318    AWKKFVMNRK  --KTNGVC--    504
SEQ_ID_NO_1331    ----------  --RDRGPCSH    420
SEQ_ID_NO_1313    YWKKFVEAKK  -SNKNRIC--    493
SEQ_ID_NO_1303    YWRKFVSERK  ANNKNKIC--    494
SEQ_ID_NO_1340    AWRKLVVQRK  --KLNGVC--    499
SEQ_ID_NO_1320    AWKKFVADKK  K-KTNGVC--    496
SEQ_ID_NO_1326    AWKKFVEEKK  K-KTNRVC--    500
SEQ_ID_NO_1334    AWKKFVLAK-  --RTNGVC--    492
SEQ_ID_NO_1330    LWKRAVLAKK  --KTNGVC--    493
```

Figure 45

```
SEQ_ID_NO_1363   ---------- ---------- ---------- ---MSKTTNQ NRRPSFTSST   17
SEQ_ID_NO_1373   ---------- ---------- ---------- ---------- -------MVD   3
SEQ_ID_NO_1342   ---------- ---------- ---------- ---------- ----------   0
SEQ_ID_NO_1381   ---------- ---------- ---------- ---------- ----------   0
SEQ_ID_NO_1382   ---------- ---------- ---------- ---------- ----------   0
SEQ_ID_NO_1371   ---------- ---------- ---------- ---------- ----------   0
SEQ_ID_NO_1366   ---------- ---------- ---------- ---------- ---------M   1
SEQ_ID_NO_1370   ---------- ---------- ---------- ---------- ----------   0
SEQ_ID_NO_1346   ---------- ---------- ---------- ---------- ----------   0
SEQ_ID_NO_1372   ---------- ---------- ---------- ---------- ----------   0
SEQ_ID_NO_1374   ---------- ---------- ---------- ---------- --MKKQEKEA   8
SEQ_ID_NO_1355   ---------- ---------- ---------- ---------- ----------   0
SEQ_ID_NO_1364   ---------- ---------- ---------- ---------- ----------   0
SEQ_ID_NO_1378   MGSRHQVVQQ QNRGDVVPGA IKQKSMAVEK KNRRALGDIG NVV-TVRGVE   49
SEQ_ID_NO_1377   ---MNTNRAV LVPHRGEVGG KQKNGQADGR NNRRVLGDIG NLVTGAPVIE   47
SEQ_ID_NO_1379   MGSRAVVVPD QQPRGR--GG KQKNGQAEGR -NRRVLRDIG NLV-PVPTVE   46
SEQ_ID_NO_1380   ---------- ---------- ---------- ---MAGADEN HGAVKLANFR   17
SEQ_ID_NO_1383   ---------- ---------- ---------- ---------- ----------   0

SEQ_ID_NO_1363   ESSMRKRHGP SSSSSAVK-- PISNTAVMVA KKRAPLGNIT ----------   55
SEQ_ID_NO_1373   EENKVPATAA ASRGSNKR-- AFDSIAITNE NDPLQISERP ----------   41
SEQ_ID_NO_1342   ---------- ---------- ---------- ---------- ----------   0
SEQ_ID_NO_1381   -MADKENSTP ASAARLTRSS AAAGAQAKRS AAAGVADGGA ----------   39
SEQ_ID_NO_1382   -MADKENSTP ASAARLTRSS AAAGAQAKRS AAAGVADGGA ----------   39
SEQ_ID_NO_1371   ---------- ---------- -APSMTTPE- ---------- ----------   8
SEQ_ID_NO_1366   ATSENNSSAR PQREAKKR-- AAAAISQIHG N--------- ----------   30
SEQ_ID_NO_1370   MADQDNSTRR PQREAKKR-- AVAALCE--- ---------- ----------   25
SEQ_ID_NO_1346   -MAEQENCTR VTRAAKKR-- AAALASTEDQ ---------- ----------   27
SEQ_ID_NO_1372   -MADKENCIR VTRLAKKR-- AVEAMAASEQ Q--------- ----------   28
SEQ_ID_NO_1374   IMADLENCGR VTRLAKKR-- AAEAMASHQQ Q--------- ----------   37
SEQ_ID_NO_1355   MADEKENCVR MTRAATKRKA SMEAAIDKE- ---------- ----------   29
SEQ_ID_NO_1364   -MAENQNSTR MTRAAAKR-- KASVTDEN-- ---------- ----------   25
SEQ_ID_NO_1378   GKALPQVSRP ITRGFCAQLI ANAEAAAAEN NKNSLAVNAK GADGALPIKR   99
SEQ_ID_NO_1377   GKPKAQISRP ATRSFCAQLL ANAQAEKNKV KPLAEVVNKV ----------   87
SEQ_ID_NO_1379   EKPQNQISRP VTRSLCVQ-- PAAAAEKKNK KPLAEVVNGG GEVKAAAAAH   94
SEQ_ID_NO_1380   ETTNRRALKD IKNFVGAP-- SFPCAANKRQ LKEVVCGNND ----------   55
SEQ_ID_NO_1383   -MITGAQGVR QTRSKTTY-- EVPQQQQQQS FEW------- ----------   30
```

Figure 45 (continued)

```
SEQ_ID_NO_1363   -----NQRKD SRIFPNSSSA DSAHCPNKSA KLKLAAPTQP VCVNACETKS   100
SEQ_ID_NO_1373   -----YPANK KRVVLGELNN LGNV------ --IVSTQNSD LTETHESKRK   78
SEQ_ID_NO_1342   ------MGYL WRVRLSSFAA GAAT------ --ASAAGFFL LYKDHLLARA   36
SEQ_ID_NO_1381   -----PPAKR KRVALSDLPT LSNA------ --VVVAPRQP HHPVVIKPSS   76
SEQ_ID_NO_1382   -----PPAKR KRVALSDLPT LSNA------ --VVVAPRQP HHPVVIKPSS   76
SEQ_ID_NO_1371   ------PASK RRVVLGEISN NSSA------ --VSGNEDLL CREFEVPKCV   44
SEQ_ID_NO_1366   ------AAKK KRVVLGDVTN VSSS------ ---------- -----DVAVS   53
SEQ_ID_NO_1370   ------QRKR KRVALGDITN DVVS------ --ETEKLVSD SHSHTQKKKK   61
SEQ_ID_NO_1346   ------PLNK KRVVLGELPN LSNA------ --IVSS---- -NEPQKQKAK   58
SEQ_ID_NO_1372   ------RPSK KRVVLGELKN LSSN------ ---ISSIQTY DFSSGPQKQQ   63
SEQ_ID_NO_1374   ------HPSK KRVVLGEIQN FSNL------ --GVSQIKGL NTEPKKQPKS   73
SEQ_ID_NO_1355   ------RINK KRVVLGELPN LSNI------ ---------- ----KKSRKA   53
SEQ_ID_NO_1364   ------PVSK KRVVLGELPN NSNV------ ----PAPLIP LQERETQKPK   59
SEQ_ID_NO_1378   AVAR--VPVQ KKTVKSKPQE IIEISPDTEK KKAPVLEKEI TGEKSLKKKA   147
SEQ_ID_NO_1377   ------PAKK KASDKPAVQE AVIVISPDEE VKKKTIEKSP LSKRKAKKTG   131
SEQ_ID_NO_1379   KKHYDPPKPE TVIVISSDEE LESE------ --EKKKPVAV IARKSRVGSS   136
SEQ_ID_NO_1380   -----SVIPR RPITRQFAST LASK------ --SQQSHGET SNKHGQITGN   92
SEQ_ID_NO_1383   ------GRTS QRTSHGKPRR GSVM------ -------GGT MTTAGADVDM   61

SEQ_ID_NO_1363   TCEEEVVPIE RKAFSNLCIT PSSDTTTNVM SETENKEEKF MNIDNKDDAD   150
SEQ_ID_NO_1373   IKLRKTRNVV KETVELKTSA NSSPK----- ---------- --------DN   105
SEQ_ID_NO_1342   ADAESNSASY SPPLATADTA FSAPP----- ---------- RAVAP---AD   68
SEQ_ID_NO_1381   KQPEPAAEAA APSGGGGGSP VSSAST---- ---------- STASPSSGWD   112
SEQ_ID_NO_1382   KQPEPAAEAA APSGGGGGSP VSSAST---- ---------- STASPSSGWD   112
SEQ_ID_NO_1371   AQKKRKRGVK EDVGVDFGEK F--------- ---------- --------DD   67
SEQ_ID_NO_1366   VSKKPVQTHK NVKLEKPAAP VATPE----- ---------- ---KVEERHD   85
SEQ_ID_NO_1370   RNIAKSPVPE KL-------- ---------- ---------- --------ED   75
SEQ_ID_NO_1346   AKPKARKGAS TKKEGVLKED VDGNP----- ---------- --------ED   85
SEQ_ID_NO_1372   KNKNKRKAKE SLGFEVKEKK VEEAG----- ---------- IDVFSQS-DD   97
SEQ_ID_NO_1374   KQQQSKRKLK RAVTSKIDKE ELNVD----- ---------- -NVDANY-DD   106
SEQ_ID_NO_1355   TTKQKKKSVS IPTIETLNSD IDTRS----- ---------- --------DD   80
SEQ_ID_NO_1364   STLFAAKKQT KTPPIPQTVD FESGS----- ---------- --------SD   86
SEQ_ID_NO_1378   PTLTSTLTAR SKAASVVRTK PKEQI----- ---------- VDIDAADVNN   182
SEQ_ID_NO_1377   KTLTSTLTAR SKAACGLSNR PKNEI----- ---------- DDIDAADAAN   166
SEQ_ID_NO_1379   RTMTSILTAR SKALCGPTTK PKVPI----- ---------- ADIDAADVDN   171
SEQ_ID_NO_1380   EKHNPIIIDE DVPMVEESEE MEECELVEEI TMEDIVIDSA QDIDIGDVGN   142
SEQ_ID_NO_1383   RESYSTYLER SSAADVMTDA L--------- ---------- PDIDLYDHDN   92
```

Figure 45 (continued)

```
SEQ_ID_NO_1363   PQLYATFACD IYNHLRAAE- -AKKQPAVDY METVQKDVNS TMRGILVDWL   198
SEQ_ID_NO_1373   LQKCS-YGPL IYQHLHSLEV EERRRPLSNY MEKVQNNVIP SMRTVLVDWL   154
SEQ_ID_NO_1342   LQLSGSYASD IYTYLRSLEV DPQRRSRSDY IEAVQADVTA HMRSILVDWL   118
SEQ_ID_NO_1381   PQ----YASD IYTYLRSMEV EARRQSAADY IESVQVDVTA NMRAILVDWL   158
SEQ_ID_NO_1382   PQ----YASD IYTYLRSMEV EARRQSAADY IEAVQVDVTA NMRAILVDWL   158
SEQ_ID_NO_1371   PQMCSAYVSD VYEYLKQMEM ETKRRPMMNY IEQVQKDVTS NMRGVLVDWL   117
SEQ_ID_NO_1366   PQLCGPYVSD IYEYLRGMEV DPSKRPLMDY VQKIQRDVNA NMRGVLVDWL   135
SEQ_ID_NO_1370   PQLCEPYVSD IHDYLRNLEV DPSKRPLPDY IQKVQRDINA NMRGVLVDWL   125
SEQ_ID_NO_1346   PQMCAPYASD IYEYLHKMEV DPKRRPLPDY IEKVQKDVSP NMRGILVDWL   135
SEQ_ID_NO_1372   PQMCGAYVSD IYEYLHKMEM ETKRRPLPDY LDKVQKDVTA NMRGVLIDWL   147
SEQ_ID_NO_1374   PQMCSAYVSD IYDYLRKMEI EEKRRPLPDY LEKVQKDLSP NMRGVLVDWL   156
SEQ_ID_NO_1355   PQMCGPYVTS IFEYLRQLE- -VKSRPLVDY IEKIQKDVTS NMRGVLVDWL   128
SEQ_ID_NO_1364   PQMCGPFVAD ICAYLREMEG KLKQRPLHDY IEKVQSDLTP SMRGVLMDWL   136
SEQ_ID_NO_1378   DLAVVEYVED MYKFYKSAE- -NDSRPH-DY MD-SQPEINE KMRAILIDWL   228
SEQ_ID_NO_1377   HLAVVEYVED IYNFYKLTE- -DESRVN-NY ME-FQPELNH KMRAILVDWL   212
SEQ_ID_NO_1379   ELAVVEYVED IYKFYKLTE- -GESRVH-DY MD-SQPEINS KMRSILIDWL   217
SEQ_ID_NO_1380   PLAVVDYVDD IYNYYRRVE- -ASSCVHPDY MS-NQFDIND KMRAILIDWL   189
SEQ_ID_NO_1383   PLAVTQYVND IYQYWYKVE- -PDTRVSETY ML-IQGDINY KMRAILIDWL   139

SEQ_ID_NO_1363   VEVSEEYRLV PETLYLTVNY IDRYLSGNVI SRQKLQLLGV ACMMIAA-KY   247
SEQ_ID_NO_1373   VEVTEEYKLV SDTLYLAVSY IDRFLSSHVL AMEKLQLLGV SCMLVAS-KY   203
SEQ_ID_NO_1342   VEVAEEYKLV ADTLYLTISY VDRFLSVNAL GRDKLQLLGV ASMLIAA-KF   167
SEQ_ID_NO_1381   VEVADEYKLV ADTLYLAVSY LDRYLSAHPL RRNRLQLLGV GAMLIAA-KY   207
SEQ_ID_NO_1382   VEVADEYKLV ADTLYLAVSY LDRYLSAHPL RRNRLQLLGV GAMLIAA-KY   207
SEQ_ID_NO_1371   VEVSLEYKLL PETLYLAISY VDRYLSVNVL NRQKLQLLGV SSFLIAS-KY   166
SEQ_ID_NO_1366   VEVAEEYKLV SDTLYFSVAY IDRFLSLNIL SRQRLQLLGV ASMLIAS-KY   184
SEQ_ID_NO_1370   VEVAEEYKLV ADTLYFSVSY IDRFLSLNDL SRQKLQLLGV SSMLIAS-KY   174
SEQ_ID_NO_1346   VEVAEEYKLV SETLYLTVSY VDRFLSFNVL SRQRLQLLGV SSMLLAS-KY   184
SEQ_ID_NO_1372   VEVAEEYKLL PDTLYLTVSY IDRFLSMNAL SRQKLQLLGV SSMLIAS-KY   196
SEQ_ID_NO_1374   VEVAEEYKLL SDTLYLAVSY IDRFLSTNVI TRQKLQLLGV SSMLISA-KY   205
SEQ_ID_NO_1355   VEVAEEYKLL SDTLYLAVSY IDRFLSLKTV NKQRLQLLGV TSMLIAS-KY   177
SEQ_ID_NO_1364   VEVAEEYKLV SDTLYLTVSY VDRFLSAKPI NRQRLQLVGV SAMLIASRKY   186
SEQ_ID_NO_1378   VQVHYKFELS PETLYLTINI VDRYLASKTT SRRELQLLGM SSMLIAS-KY   277
SEQ_ID_NO_1377   IEVHRKFELM PESLYLTINI LDRFLSMKTV PRKELQLVGI SAMLIAC-KY   261
SEQ_ID_NO_1379   TEVHRKFELM PETLYLTINI VDRYLSMNAV PRRELQLVGI SSMLIAC-KY   266
SEQ_ID_NO_1380   VEVHYKFELM EETLYLTVNI IDRFLSRQAV VRKKLQLVGV TAMLLAC-KY   238
SEQ_ID_NO_1383   VEVHLKFKLM PETLFLTTNL IDRFLELKTV TRRNLQLVGV TAMLVAS-KY   188
```

Figure 45 (continued)

```
SEQ_ID_NO_1363   EEVCAPQVEE FCYITDNTYL KDEVLDMESA VLNYLKFEMS APTVKCFLRR   297
SEQ_ID_NO_1373   EEISPPHVED FCYITDNTYT REEVVNMERD LLSFLNFEIS SPTTITFLRI   253
SEQ_ID_NO_1342   EEISPPHPED FCYITDNTYT KEELLKMESD ILKLLKFELG NPTIKTFLRR   217
SEQ_ID_NO_1381   EEISPPHVED FCYITDNTYT RQEVVKMESD ILKLLEFEMG NPTIKTFLRR   257
SEQ_ID_NO_1382   EEISPPHVED FCYITDNTYT RQEVVKMESD ILKLLEFEMG NPTIKTFLRR   257
SEQ_ID_NO_1371   EEIKPKNVAD FVDITDNTYS QQEVVKMEAD LLKTLKFEMG SPTVKTFL-G   215
SEQ_ID_NO_1366   EEIKPPEVED FCYITDNTYS KEEVVNMEAE ILKALKFELG GPTVKTFLRR   234
SEQ_ID_NO_1370   EEIKPPEVED FCYITDNTYS KEEVLSMEAE ILKTLKFELG GPTIKTFLRR   224
SEQ_ID_NO_1346   EEINPPHVED FCYITDNTYT KEEVVKMEAD ILKSLKFEMG NPTIKTFLRR   234
SEQ_ID_NO_1372   EEISPPHVED FCYITDNTYK KEEVVKMEAD VLKFLKFEMG NPTIKTFLRR   246
SEQ_ID_NO_1374   EEISPPHVED FCYITDNTYT KEEVVKMEAD VLKTLNFEMG NPTVKTFLRR   255
SEQ_ID_NO_1355   EEITPPNVDD FCYITDNTYT KQEIVKMEAD ILLALQFELG NPTSNTFLRR   227
SEQ_ID_NO_1364   EEISPPKVED FVYITDNTFT RQDVVSMEAD ILLALQFELG CPTIKTFLRR   236
SEQ_ID_NO_1378   EEIWAPEVND LVCISDGSYS NEQVLRMEKK ILGALEWYLT VPTPYVFLVR   327
SEQ_ID_NO_1377   EEIWAPEVND FMHISDNVYT RDHILQMEKA ILGKLEWYLT VPTPYVFLVR   311
SEQ_ID_NO_1379   EEIWAPEVSD FIVISDNAYV REQILIMEKA ILGKLEWYLT VPTPYVFLVR   316
SEQ_ID_NO_1380   EEVSVPVVDD LVTISDRAYT RKEVLDMEKS IVKTLQFNTS VPTPFVFLRR   288
SEQ_ID_NO_1383   EEIWAPEVRD FVYISDRAYT RQQILEMEKQ MLNTLGFHLT VPTPYCFLNR   238

SEQ_ID_NO_1363   LF-SGCPRVH EAPCMQLECM ASYIAELSLL EY-TMLSHPP SLVAASAIFL   345
SEQ_ID_NO_1373   FL-KAAQDNL SFLTLQFEFL SCYLAELSLL DY-SCVRFLP SMTAASAIFL   301
SEQ_ID_NO_1342   FI-RSAHEDK KGSILLMEFL GSYLAELSLL DY-GCLRFLP SVVAASVMFV   265
SEQ_ID_NO_1381   FT-RSCQEDK KRSSLLLEFM GSYLAELSLL DY-SCLRFLP SVVAASVVFV   305
SEQ_ID_NO_1382   FT-RSCQEDK KRSSLLLEFM GSYLAELSLL DY-GCLRFLP SVVAASVVFV   305
SEQ_ID_NO_1371   FI-RAVQENP DVPKLKFEFL ANYLAELSLL DY-GCLEFVP SLIAASVTFL   263
SEQ_ID_NO_1366   FS-RVGQEGV DTSDLQFEFL SCYLAELSLL DY-NCIKFLP SLVAASVVFL   282
SEQ_ID_NO_1370   FITKVGQEGV DASELQFEFL CCYLAELSLL DY-NCVKFLP SMVAASVVFL   273
SEQ_ID_NO_1346   FT-RVALEDY KTSNLQLEFL GFYLAELSLL DY-NCVKFLP SLVAASVIFL   282
SEQ_ID_NO_1372   LT-RVVQDGD KNPNLQFEFL GYYLAELSLL DY-GCVKFLP SLIASSVIFL   294
SEQ_ID_NO_1374   FT-GVAQEDY KTPNLQLEFL GYYLAELSIL DY-SCVKYVP SLLAAAVVFL   303
SEQ_ID_NO_1355   FT-RVAQEDF EMSHLQMEFL CSYLSELSML DY-QSVKFLP STVAASAVFL   275
SEQ_ID_NO_1364   FT-RVAQEDF NESLLQIECL CCYLSELSLL DY-SCVKFLP SMLAASAVFL   284
SEQ_ID_NO_1378   FI-KASLPDS D----VEKNM VYFLAELGMM NYATIIMYCP SMIAAAAVYA   372
SEQ_ID_NO_1377   YI-KAAMPSD DQ---EIQNM AFFFAELGLM NYTTTISYCP SMLAASAVYA   357
SEQ_ID_NO_1379   FI-KASVPSN DHRE-EMENM VFFLAELGLM HYPTIILYCP SMIAASAVYA   364
SEQ_ID_NO_1380   FL-KAAGSEK K-----LELL SSFIIELSLV EY-QMLKFQP SLLAAAAIYT   331
SEQ_ID_NO_1383   FF-KAAGGDR Q-----FQLY ASYAVECALP EY-GMLKYSG STLAAAGVYI   281
```

Figure 45 (continued)

```
SEQ_ID_NO_1363   AKYTLDPTRR PWNSTLRHYT QYEAMELRGC VMDLQRLCSN AHV---STLP   392
SEQ_ID_NO_1373   SRFTVLPEVC PWTLALQQCT GYKPSELKDC VLVIHELQSS LME---ATGR   348
SEQ_ID_NO_1342   ARLTIDPNTN PWNTKLQKMT GYKVSELKDC IVAIHDLQLN RKC---PSLT   312
SEQ_ID_NO_1381   AKLNIDPYTN PWSKKMQKLT GYKVSELKDC ILAIHDLQLR KKC---SNLT   352
SEQ_ID_NO_1382   AKLNIDPYTN PWSKKMQKLT GYKVSELKDC ILAIHDLQLR KKC---SNLT   352
SEQ_ID_NO_1371   ARFTIRPNVN PWSIALQKCS GYKSKDLKEC VLLLHDLQMG RRG---GSLS   310
SEQ_ID_NO_1366   ARFMFSTKTH PWNSALHQLT RYKPADLKEC VLNLHDLYLS RRG---ASLQ   329
SEQ_ID_NO_1370   ARFMLNPKSR PWNSAICQFT SYKPADLKEC VLNMHDLYLG RKG---ATLQ   320
SEQ_ID_NO_1346   TRFLMRPKTN PWSSTLQQYT GYKAADLREC VLIIHDLYLS RRG---GGLQ   329
SEQ_ID_NO_1372   SRFTLQPKVH PWNSLLQHNS GYKPADLKEC VLIIHDLQLS KRG---SSLV   341
SEQ_ID_NO_1374   SRFTLQPNTH PWSLALQQYS GYKAADLKEC ILILHDLQLS RRG---GSLA   350
SEQ_ID_NO_1355   ARFIIRPKQH PWNVMLEEYT RYKAGDLKEC VAMIHDLYLS RKC---GALE   322
SEQ_ID_NO_1364   ARFIIRPKQR PWNQMLEEYT KYKASDLQQP VGIIHDLYLS RRG---NSLE   331
SEQ_ID_NO_1378   ARCTLNKMPI -WNETLRMHT GFSEVQLMDC AKLLIDFHGG STD---QKLQ   418
SEQ_ID_NO_1377   ARGTLNKGPL -WTPTLQHHT GYSEEQLMEC TKQLVSYHKG AAE---SKLK   403
SEQ_ID_NO_1379   ARCTLNSNPL -WTETLKHHT GYSEDQLGDC AKMLARFHSD GGGVEKSKLK   413
SEQ_ID_NO_1380   AQCSLKGFKF -WTRTCEQYT MYTEDQLLEC SKMMVGFHRN AGS---GKLT   377
SEQ_ID_NO_1383   AIRGLQTGS- -WNHTMEAHT RLSESEVYPC ACDMAELMRK APT---ATLT   326

SEQ_ID_NO_1363   AVRDKYSQHK YKFVAKKFCP SIIPPDFFK- ---NSLY-   425
SEQ_ID_NO_1373   ALREKYMNHK YKCVAALHPP -DIPSCFFD- ---DA---   378
SEQ_ID_NO_1342   AIRDKYKQHK FKCVSLILVP VVIPTSYFE- ---DLAE-   345
SEQ_ID_NO_1381   AIRDKYKQHK FKCVSTLLPP VDIPASYLQ- ---DLTE-   385
SEQ_ID_NO_1382   AIRDKYKQHK FKCVSTLLPP VDIPASYLQ- ---DLTE-   385
SEQ_ID_NO_1371   AVRDKYKKHK FKCVSTLSPA PEIPESIFN- ---DV---   341
SEQ_ID_NO_1366   AVREKYKQHK FKCVATTPSP PEIPLSFFEF EGQILRQL   367
SEQ_ID_NO_1370   AVRDKYKQHK FKCVATTPSP PEISLSFFEF RGADP---   355
SEQ_ID_NO_1346   AVREKYKQHK FKCVANMPSP PELPALYFE- ---EV---   360
SEQ_ID_NO_1372   AVRDKYKQHK FKCVSTLTAP PSIPDEFFE- ---DI---   372
SEQ_ID_NO_1374   AVRDKYKQHK FKCVSSLTSP VEIPASFFE- ---DMRQL   384
SEQ_ID_NO_1355   AIREKYKQHK FKCVATMPVS PELPLTVFE- ---DVNI-   355
SEQ_ID_NO_1364   AVRNKYKQHK FKCVATMPVS PELPQAFFE- ---DVTIR   365
SEQ_ID_NO_1378   GIYRKYSRLE KGAVALLPQP LLA------- --------   441
SEQ_ID_NO_1377   AIYRKFSSPD RGAVALFPPA RNLLPTTTT- ---TTTSS   437
SEQ_ID_NO_1379   AVYKKFSSSD RSSVALFPPA RSLLVL---- --------   440
SEQ_ID_NO_1380   GVHRKYSTSK FGFAGKSYPA LFLLDNRL-- --------   405
SEQ_ID_NO_1383   AVYKKYSSEK FMKIATLPVP HDLRL----- --------   351
```

Figure 46

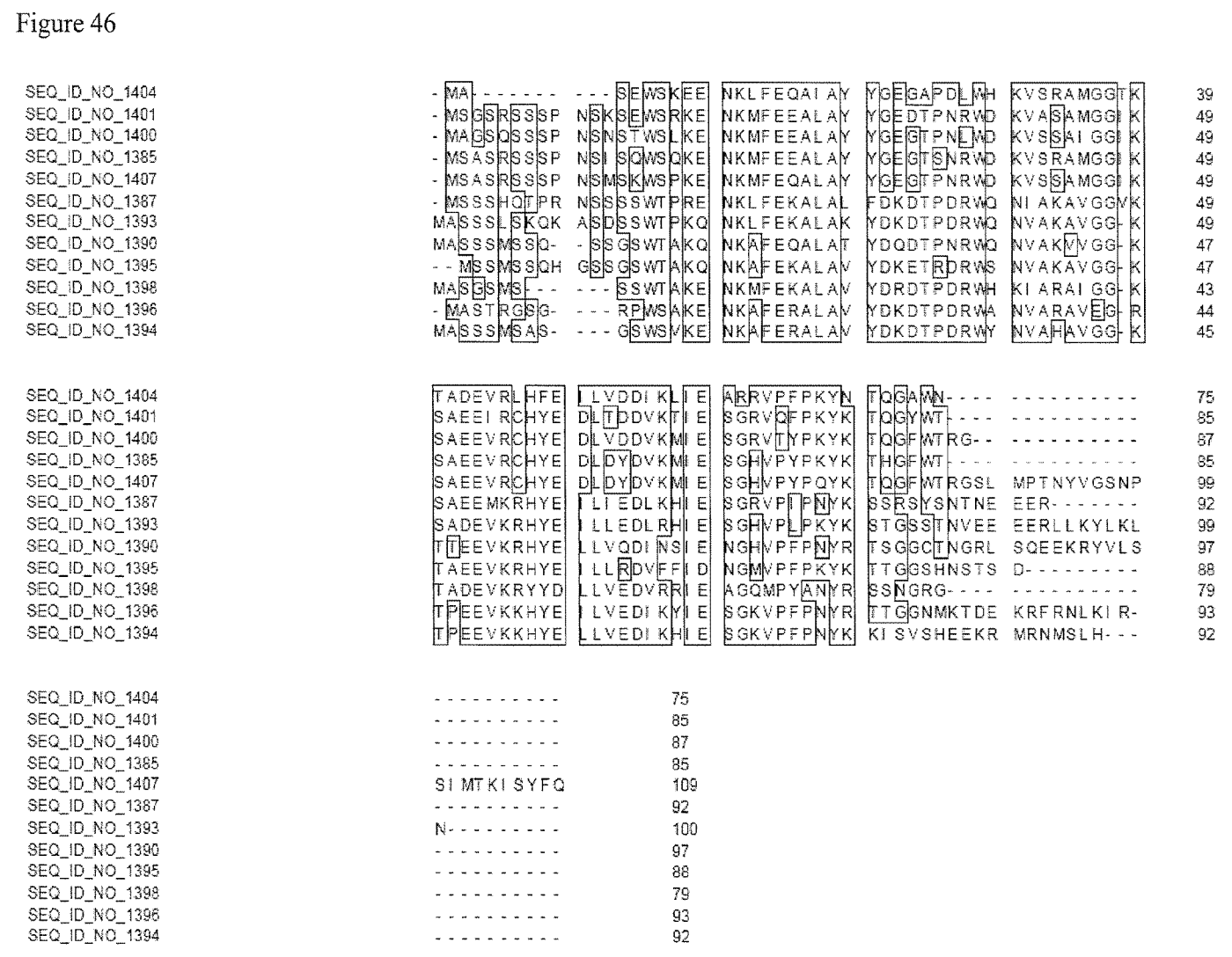

```
SEQ_ID_NO_1404   -MA------- ---SEWSKEE NKLFEQAIAY YGEGAPDLWH KVSRAMGGTK  39
SEQ_ID_NO_1401   -MSGSRSSSP NSKSEWSRKE NKMFEEALAY YGEDTPNRWD KVASAMGGIK  49
SEQ_ID_NO_1400   -MAGSQSSSP NSNSTWSLKE NKMFEEALAY YGEGTPNLWD KVSSAIGGIK  49
SEQ_ID_NO_1385   -MSASRSSSP NSISQWSQKE NKMFEEALAY YGEGTSNRWD KVSRAMGGIK  49
SEQ_ID_NO_1407   -MSASRSSSP NSMSKWSPKE NKMFEQALAY YGEGTPNRWD KVSSAMGGIK  49
SEQ_ID_NO_1387   -MSSSHQTPR NSSSSWTPRE NKLFEKALAL FDKDTPDRWQ NIAKAVGGVK  49
SEQ_ID_NO_1393   MASSSLSKQK ASDSSWTPKQ NKLFEKALAK YDKDTPDRWQ NVAKAVGG-K  49
SEQ_ID_NO_1390   MASSSMSSQ- -SSGSWTAKQ NKAFEQALAT YDQDTPNRWQ NVAKVVGG-K  47
SEQ_ID_NO_1395   --MSSMSSQH GSSGSWTAKQ NKAFEKALAV YDKETRDRWS NVAKAVGG-K  47
SEQ_ID_NO_1398   MASGSMS--- ---SSWTAKE NKMFEKALAV YDRDTPDRWH KIARAIGG-K  43
SEQ_ID_NO_1396   -MASTRGSG- ---RPWSAKE NKAFERALAV YDKDTPDRWA NVARAVEG-R  44
SEQ_ID_NO_1394   MASSSMSAS- ---GSWSVKE NKAFERALAV YDKDTPDRWY NVAHAVGG-K  45

SEQ_ID_NO_1404   TADEVRLHFE ILVDDIKLIE ARRVPFPKYN TQGAWN---- ----------  75
SEQ_ID_NO_1401   SAEEIRCHYE DLTDDVKTIE SGRVQFPKYK TQGYWT---- ----------  85
SEQ_ID_NO_1400   SAEEVRCHYE DLVDDVKMIE SGRVTYPKYK TQGFWTRG-- ----------  87
SEQ_ID_NO_1385   SAEEVRCHYE DLDYDVKMIE SGHVPYPKYK THGFWT---- ----------  85
SEQ_ID_NO_1407   SAEEVRCHYE DLDYDVKMIE SGHVPYPQYK TQGFWTRGSL MPTNYVGSNP  99
SEQ_ID_NO_1387   SAEEMKRHYE ILIEDLKHIE SGRVPIPNYK SSRSYSNTNE EER-------  92
SEQ_ID_NO_1393   SADEVKRHYE ILLEDLRHIE SGHVPLPKYK STGSSTNVEE EERLLKYLKL  99
SEQ_ID_NO_1390   TTEEVKRHYE LLVQDINSIE NGHVPFPNYR TSGGCTNGRL SQEEKRYVLS  97
SEQ_ID_NO_1395   TAEEVKRHYE ILLRDVFFID NGMVPFPKYK TTGGSHNSTS D---------  88
SEQ_ID_NO_1398   TADEVKRYYD LLVEDVRRIE AGQMPYANYR SSNGRG---- ----------  79
SEQ_ID_NO_1396   TPEEVKKHYE ILVEDIKYIE SGKVPFPNYR TTGGNMKTDE KRFRNLKIR-  93
SEQ_ID_NO_1394   TPEEVKKHYE LLVEDIKHIE SGKVPFPNYK KISVSHEEKR MRNMSLH---  92

SEQ_ID_NO_1404   ----------  75
SEQ_ID_NO_1401   ----------  85
SEQ_ID_NO_1400   ----------  87
SEQ_ID_NO_1385   ----------  85
SEQ_ID_NO_1407   SIMTKISYFQ  109
SEQ_ID_NO_1387   ----------  92
SEQ_ID_NO_1393   N---------  100
SEQ_ID_NO_1390   ----------  97
SEQ_ID_NO_1395   ----------  88
SEQ_ID_NO_1398   ----------  79
SEQ_ID_NO_1396   ----------  93
SEQ_ID_NO_1394   ----------  92
```

Figure 47

```
SEQ_ID_NO_1419   ---------- -----MSFYL F--------- ---------- --FLFITMPL   14
SEQ_ID_NO_1421   ---------- -----MAC-- F--------- ---------- --RSRSRAAA   12
SEQ_ID_NO_1409   ---------- -----MGQRR F--------- ---------- --EDERAALA   14
SEQ_ID_NO_1425   ---------- -----MADC- ---------- ---------- ---TTMRLAS   11
SEQ_ID_NO_1424   MEPWRWQICL VTPRSFLFQA FVRTGFRAMR VSSASSTPPP PAFAAAAWAV   50
SEQ_ID_NO_1413   ---------- -----MNRRF L--------- ---------- --FVLSSLSF   14
SEQ_ID_NO_1418   ---------- -----MRMEH I--------- ---------- --YKFQHWLF   14
SEQ_ID_NO_1415   MEGELKMRGG DLIRPGRFCI L--------- ---------- --SVATIISS   29

SEQ_ID_NO_1419   IVFCDF---- ---------- --EMPSGSST QIFHSFHE-- ----------   36
SEQ_ID_NO_1421   VVVVTM---- ---------- -LLLQACSEV SASSSPQF-- ----RKM---   38
SEQ_ID_NO_1409   TVASLL---- ---------- -LILTTAQAA AAAASGRH-- ----LSLPT-   42
SEQ_ID_NO_1425   SVTIIL---- ---------- -LLLVASQAL VVSGESSS-- ----SAM---   37
SEQ_ID_NO_1424   VLLAML---- -------RSD VALAAAASSN DDTGLSPLMP PPPPLAAPVP   89
SEQ_ID_NO_1413   AVLFLF---- ---------- LVALFSGQGK NINGSFGL-- ----KLLR--   42
SEQ_ID_NO_1418   FIGLGV---- ---------L LSLSLSVKAN DFEGSNDR-- ----RSIALK   45
SEQ_ID_NO_1415   LLAVFFEDIY HSSMHASSLV SLLLNPVQTQ SLTELFHL-- ----KAVSEI   73

SEQ_ID_NO_1419   -------DKN GSLTVSEKVE HAH------- ---------- ------YTPR   56
SEQ_ID_NO_1421   ---------- -LVSVNASSM SSS------- ---------- -GG-GGHSAE   58
SEQ_ID_NO_1409   --QKAAAARM NDTSSSDMQV ITP------- ---------- -APLAISTAA   72
SEQ_ID_NO_1425   --QSKTLNMN KLLNISED-- HSP------- ---------- -NG-GRHWMQ   64
SEQ_ID_NO_1424   AAVSPAPATP PAVLSPRKLL RPPGADVVGV GFVSGSGGGG GGGGGGDGVR   139
SEQ_ID_NO_1413   --LRINQGNH TLLTPHRKLL RTA------- ---------- -----LAEPN   68
SEQ_ID_NO_1418   A-RSFVSINE NRTALSRKLL LSP------- ---------- -DI--GDGTN   74
SEQ_ID_NO_1415   GSKKPVFYKE NNTNFARKLL QLP------- ---------- -DA---GSTN   102

SEQ_ID_NO_1419   KFWFHGSCTK -RDISISQSK GST--SGIPQ YLVQIVNTCV SG--------   95
SEQ_ID_NO_1421   PLE-LEECSK -DLLEVFQNN APSMAGGMPT YSVEITNTCI -D--------   97
SEQ_ID_NO_1409   RMG-PDGCSG -EDVAVYQSS ANPLPSGIPA YTVRIINVCS GG--------   112
SEQ_ID_NO_1425   RMQ-PDSCSE -QNVVVYQNN AEHLPSGIPT YSVEIINVCT -A--------   103
SEQ_ID_NO_1424   TRRVDDGCAG ADDIAIYQGR ATPLPSGVPA YTVDVMNRCA GGGGGGGDEE   189
SEQ_ID_NO_1413   RIW-GEKCSK -ADIVINQGP TAPLPSGIPT YTVEILNVCV SG--------   108
SEQ_ID_NO_1418   RIG--QDCSK -DDIVLFQGS TNPLPSGVPS YTVEIFNSCV SD--------   113
SEQ_ID_NO_1415   RIG--AACSK -DGIDIVQGS TAPLPNGIPS YTVQILNVCV SG--------   141
```

Figure 47 (continued)

```
SEQ_ID_NO_1419    CAPYDIHLHC GWFASARIIN PKLFKRLSYD DCLVHGGKPL TSNQIIRFTY   145
SEQ_ID_NO_1421    CAVCDVHIAC GDFASNDVID PDKFRRLGFN DCLVNGGGSI EPSFPVSFQY   147
SEQ_ID_NO_1409    CTVYDVHVSC GDFASTELVD PAKFQRVGFN DCVVKGGGAL EPSETVSFQY   162
SEQ_ID_NO_1425    CTVYDVHISC GEFASAELVD PSQFQRIGFN DCLVKGGGRL GPSEAVSFQY   153
SEQ_ID_NO_1424    CAIAGIHVRC GWFSSVSLVD PRVFRRLGHD DCLLNDGRPL LAGETVSFEY   239
SEQ_ID_NO_1413    CDISGIHLTC GWFSSARLIN PKIFKRLRYN DCLVNDGKPL INGGTLSFQY   158
SEQ_ID_NO_1418    CNIAEIHVSC GWFSSVRLVN PRVFRRLDYD DCLVNDGQPL GPGQSLSFQY   163
SEQ_ID_NO_1415    CSISNIHVSC GWFSSAKLIN PSVFRRIYYD DCLVNDGEPL GPGETLSFQY   191

SEQ_ID_NO_1419    SNSFMYPLAF KSARFC---- ---------- ---------- ---------   161
SEQ_ID_NO_1421    GNSFPYPMTV ASASCDCN-- ---------- ---------- ---------   165
SEQ_ID_NO_1409    SNSFSYHLSV ASVACR---- ---------- ---------- ---------   178
SEQ_ID_NO_1425    SNSFAYPLAV ANVACFHYSI VWASMIPCLP EHACHTASSV KGLGPRPHA   202
SEQ_ID_NO_1424    TNSFPYKLSV SVATCVVDPA AP-------- ---------- ---------   261
SEQ_ID_NO_1413    ANTFLYPLSV SRVVCS---- ---------- ---------- ---------   174
SEQ_ID_NO_1418    ANSFSYPLSV ASVSCF---- ---------- ---------- ---------   179
SEQ_ID_NO_1415    ANSFLYPLSV SSVACC---- ---------- ---------- ---------   207
```

Figure 48 (continued)

```
SEQ_ID_NO_1436   CLSDFADGEE IRVLPLCGHS FHVECIDKWL VSRSSCPXCR XILRPV---X  152
SEQ_ID_NO_1444   CLGEFADGEK VRVLPRCTHG FHVRCVDTWL LSHDSCPTCR ASVLDG----  158
SEQ_ID_NO_1452   CLGEFADGEK VRVLPRCAHG FHVRCVDTWL LSHDSCPTCR GTVLEAAAPG  170
SEQ_ID_NO_1428   CLGEFADGER VRVLPFCNHS FHMSCIDTWL VSHSSCPNCR HSLIEV----  153
SEQ_ID_NO_1430   CLGEFMGGEK VRVLPKCNHG FHVRCIDTWL LSHSSCPTCR QSLLDQA--T  174
SEQ_ID_NO_1432   CLGEFVDGEK VRVLPKCNHG FHVRCIDTWL LSHSSCPNCR HSLLEH---T  156
SEQ_ID_NO_1439   CLGEFEKGDR VRMLPKCNHG FHVRCIDTWL LSHSSCPNCR HSLLEK----  146
SEQ_ID_NO_1442   CLGEFADGEK VRVLPRCHHG FHVRCIDMWL ATHTSCPNCR ASLAED----  176
SEQ_ID_NO_1453   CLGDFADGDK VRVLPRCHHG FHVRCIDTWL AAHTSCPTCR DSILSV----  159
SEQ_ID_NO_1457   CLGDFADGDK VRVLPRCHHG FHVGCIDTWL AAHTSCPTCR DSILSV----  161

SEQ_ID_NO_1436   CDRCGHASXA GSQMKDHQHX QHXSQLTSXX XTFXP  187
SEQ_ID_NO_1444   --AKAATPAG GGSRWQGSEA AAIAVVIR-- -----  184
SEQ_ID_NO_1452   KDKAAASAPA GGSRRQGSEA AAIAVVIG-- -----  198
SEQ_ID_NO_1428   -------HVA GSE------- ---------- -----  159
SEQ_ID_NO_1430   SSSDGAVEIE NGIRPHGNSS GGQQADVPVP ADEVG  209
SEQ_ID_NO_1432   TDSGAAQEVT GAARPGENDP GRQARGWP-- -EHGG  188
SEQ_ID_NO_1439   ---PAAAPES GSGRRSEVVV VVEQAS---- -----  169
SEQ_ID_NO_1442   ----GAAAAN GGGR------ ---------- -----  186
SEQ_ID_NO_1453   -----HGVVA GGQT------ ---------- -----  168
SEQ_ID_NO_1457   -----HAGVT GGQT------ ---------- -----  170
```

Figure 49

```
SEQ_ID_NO_1473  ---------- ---MKLVWCP ETASQAFIAG VSALSDAEHG PAGSAG-VAE  36
SEQ_ID_NO_1474  ---------- ---------- -MASKAYIDG VRALAG--HD LAGAAADVAE  27
SEQ_ID_NO_1476  MAPPPPPAAQ VVRMKLVWCP EMASKAYIDG VRALAG--HD LAGAAADVAE  48
SEQ_ID_NO_1471  ---------- ---MKLAWSP ERASKAYIDT VQSCQV--FR ESG----VAE  31
SEQ_ID_NO_1463  ---------- ---MKLVWSP ETASDAYIDT VKSCKS--DK ESG----VAE  31
SEQ_ID_NO_1465  ---------- ---MKLVWTP DTALKAYVCT VKTCED--FK ESS----VAE  31

SEQ_ID_NO_1473  LVSAMVGGWN AQLVVEAPEV SAPDSATMSL ALAAAAGRTG GRYARVLPDE  86
SEQ_ID_NO_1474  LVSAMAGGWN ARLVVEAPDS AAPAAAATSL ALAAVARRTG GRYALVLPDR  77
SEQ_ID_NO_1476  LVSAMAGGWN ARLIVEAPDS AAPAAAATSL ALAAAARRTG GRYALVLPDR  98
SEQ_ID_NO_1471  FISAMAAGWN SQLIVETWSQ GGL--IATSV GLALARSHTC GRHVCVVPDE  79
SEQ_ID_NO_1463  FLSATAAGWN ARLIVETWSR GDP--ITTSV GLAVAATHTG GRHVCIVPDE  79
SEQ_ID_NO_1465  LLSAMAAGWN AKLIVESWSK AGP--IATSI GLAVAAKHTC GRHVCVVPDE  79

SEQ_ID_NO_1473  DA-------- ---------- -----DRAMA ELEGVDFLVV DARRRDGAAV  113
SEQ_ID_NO_1474  DAAAASAAET -------AEV VVGEADEAMA GLHGVDLLVV DARRRDAAAV  120
SEQ_ID_NO_1476  DAAAASAAET -------AEV VVGEADEAMA GLHGVDLLVV DARRRDAAAV  141
SEQ_ID_NO_1471  RARSEYAERM GEAGVT-AEI VVGEPEEVME GLVGVDFLVV DSRRKDFTRV  128
SEQ_ID_NO_1463  QSKLEYVLAM RGFVTTEVVV VGESVENTME EFPGVDFLVV DSKRREFVRT  129
SEQ_ID_NO_1465  GSRSEYVKAM HGAGMRETEV LVGEAEEVMA GLVGVDFLVA DCRRRDFVRV  129

SEQ_ID_NO_1473  LAAARPGPRG MVVV-RHGDE RRPGTKALEA SMAAGT--RV VRSVYLPVDK  160
SEQ_ID_NO_1474  LRAARPGARG MVVV-RHGDG RQRGAKDLAA SMAAGT--RV VRSVYLPIGK  167
SEQ_ID_NO_1476  LRAARPGARG MVVV-RHGDG RQRGAKDLAA SMAAGT--RV VRSVYLPIGK  188
SEQ_ID_NO_1471  LRLAKLSNKG AVLLCKNANS NSKG-FIWRS LVAKGSSRRV VRSAFLPVGK  177
SEQ_ID_NO_1463  LRFAKLSNKG AVLVCKNAMH RAISGFKWHD VLKRGT--RV VRSVFLPVGS  177
SEQ_ID_NO_1465  LRFAKLSHKG AVLACKNAFQ QSVSGFKWHG VLERGT--RV VKTAYLPVGQ  177

SEQ_ID_NO_1473  GVEVLHVGV- GKGPSLQCRR SRSASSRWIR HVDHKTGEEH LFRRP  204
SEQ_ID_NO_1474  GVEVLHVGV- GKGPSLQNHR DRRSTSRWIR HVDHDTGEEH VFRRQ  211
SEQ_ID_NO_1476  GVEVLHVGV- GKGPSLQNHR DRRSTSRWIR HVDHDTGEEH VFRRQ  232
SEQ_ID_NO_1471  GLDMAHVSAS GLG----N-- -NSSGHRWIK HVDQHSGDVH FIRR-  213
SEQ_ID_NO_1463  GLDIVHVGAT GRG------D SRNLRSRWIR HVDHLSGEEH LFRR-  215
SEQ_ID_NO_1465  GLDMAHIGSN GFG----DKR SRGGPSRWIK HIDRKSGEEH VFRE-  216
```

Figure 50

```
SEQ_ID_NO_1493  MTFLMPSPEV ---STAFAKI FSNPT-PRHK FLKSCAISKN DDEKVWSKTN  46
SEQ_ID_NO_1503  MAFLLPKLTT ---PSCKLPP S--PL-LKPQ LAQPVHGGGK IQGSVFGSVA  44
SEQ_ID_NO_1508  MAFLLPKLTT PSGPSCKLPP S--PL-LKPQ LAQPGHSGGK IQGSVSGAGA  47
SEQ_ID_NO_1501  MAFLLPKLTT ---PPCRSPP P--SP-LKPQ LGLPSHGGGR ----LHGAGS  40
SEQ_ID_NO_1504  MAFLLPKLTT ---PSCKSPP S--P--LKSQ LGLPGGGKLQ ---------P  34
SEQ_ID_NO_1505  MAFLLPKLTT ---PSCKSPP S--P--LKSQ LGLPGGGKLQ ---------P  34
SEQ_ID_NO_1495  MAFLLPNLS- ---PSLLINS KSFKDREKPV LYQTQTLPSH ----------  36
SEQ_ID_NO_1499  MAFLLPNLS- ---PSFLLQT GKSLK-EKPI STHSLSISSS -----SSSSN  40
SEQ_ID_NO_1491  MAFLLSNLSS ---PSIHLQT GKYPN-LKPI FSQSLSSSSS ---------V  37

SEQ_ID_NO_1493  ARVGVKDVGS TVSGLSQNLR LYVQFSAPVK -------RGS KSSKEEEEKQ  89
SEQ_ID_NO_1503  AQVAAPGHLS LLLLLSASQQ AAAP-AAKST ATKNR----- GKGGGDPQRS  88
SEQ_ID_NO_1508  AQVAAPGHLS LLLLLSAPQQ AADP-ASKST ATKNR----- GKGGGDPQRS  91
SEQ_ID_NO_1501  AQAAAPTHLN LPLLLSASQQ EA-P-TAKSA ETRNRAASGG GGGGGDPRRS  88
SEQ_ID_NO_1504  AQAVAPSHLN LLLLLGASQQ EAAAVPTPKS RSKNGGGRSG GGGGEDPRRS  84
SEQ_ID_NO_1505  AQAVAPSHLN LLLLLGASQQ EAAAVPTPKS RSKNGGGRSG GGGGEDPRRS  84
SEQ_ID_NO_1495  -YQTTTTTTS TTTKKPTNTN SSMPPPLQVK T------PPG AQDKEQHQRD  79
SEQ_ID_NO_1499  SYEFEEGSLS LLSLPVQAP- -----PAPGA QVKTM--PSE QDKHQQHGKD  82
SEQ_ID_NO_1491  SYEFVEENLS TLSLLSIQS- ---P-PLKDT QVQTR--HSS QDKHNNHDRD  80

SEQ_ID_NO_1493  DYYVNMGYAI RTLRKELPDI FYRELSFDIY RDDIVFKDPL NTFLGIDNYK  139
SEQ_ID_NO_1503  DFYLNLGTAV RTLRDDLPDV FVREPNYDIY REDITFVDPL NTFHGIDNYK  138
SEQ_ID_NO_1508  DFYLNLGTAV RTLRDDLPDV FDREPNYDIY REDITFVDPL NTFHGIDNYK  141
SEQ_ID_NO_1501  DFYLNLGAAV RALRDDLPAV FLREPNYDIY REDITFVDPL NTFHGIDNYK  138
SEQ_ID_NO_1504  DYYLNLGTAV RTLRDDLPAV FVREPNYDIY REDITFVDPL NTFHGIDNYK  134
SEQ_ID_NO_1505  DYYLNLGTAV RTLRDDLPAV FVREPNYDIY REDITFVDPL NTFHGIDNYK  134
SEQ_ID_NO_1495  EFYVNLGLAV RTLREDLPVL FTEDLNYDIY RDDITFIDPL NTFTGIDNYK  129
SEQ_ID_NO_1499  EFYINLGLAI RTLREDLPLL FSKDLNYDIY RDDITLVDPA NTFSGIENYK  132
SEQ_ID_NO_1491  EFYINLGVAV RTLREDLPLL FTRDLNYDIY RDDITFVDPM NTFTGMDNYK  130

SEQ_ID_NO_1493  SFFSAPRFHG RIFFKALWLD IVSVWQPMEN VIMVRWTIHG IPRVPWESHG  189
SEQ_ID_NO_1503  TIFWALRFHG RLLFREIGLD VSRIWQLTEN SIVVRWELWG TPRVPWESYG  188
SEQ_ID_NO_1508  TIFWALRFHG RLLFREIGLD VSRIWQLTET SIVVRWELWG TPRVPWESYG  191
SEQ_ID_NO_1501  TIFWALRFHG RLLFSEIGLD VSRIWQLTET SIVVRWELWG TPRVPWESYG  188
SEQ_ID_NO_1504  TIFWALRFHG RLLFREIGLD ISRIWQLTEN SIVVRWELWG TPRVPWESYG  184
SEQ_ID_NO_1505  TIFWALRFHG RLLFREIGLD ISRIWQLTEN SIVVRWELWG TPRVPWESYG  184
SEQ_ID_NO_1495  LIFWALRFHG KMLFREISLE VYRIWQPSEN VILIRWNLKG VPRVPWEAKG  179
SEQ_ID_NO_1499  LIFWALRFHG KILFRDXXXE XYRVWQPSEN MILIRWNXKG VPRVPWEAKG  182
SEQ_ID_NO_1491  IIFWALRFHG KILFRDISLE IFRVWQPSEN MILIRWNLKG VPRVPWEAKG  180
```

Figure 50 (continued)

```
SEQ_ID_NO_1493   RFDGTSEYKL DKKGKIYEHR VDNTALNSPP KF-HVLAVED LIRSVGCPST   238
SEQ_ID_NO_1503   CFSGTSRYKV DRNGKIYEHK VDNLALDFPR SVAKVGSIAD MV-VATP--S   235
SEQ_ID_NO_1508   CFSGTSRYKV DRNGKIYEHK VDNLALDFPR SVAKVGSIAD MV-VATP--S   238
SEQ_ID_NO_1501   CFSGTSRYKV DRNGKIYEHK VDNLALDFPR PAVKVSSITN LV-VAAYPPS   237
SEQ_ID_NO_1504   CFSGTSRYKV DRNGKIYEHK VDNLALDFPR PAAKVGSIAD IV-VATCPPS   233
SEQ_ID_NO_1505   CFSGTSRYKV DRNGKIYEHK VDNLALDFPR PAAKVGSIAD IV-VASCPPS   233
SEQ_ID_NO_1495   EFQGTSRYKL DRNGKIYEHK VDNLAFNFPQ QLKPAASVLD LV--AACPAS   227
SEQ_ID_NO_1499   EFQGTSRYKL DRNGKIYEHK VDNLAFNFPH QLKPATSVLD LV--TACPAS   230
SEQ_ID_NO_1491   EFQGTSRYKL DRNGKIYEHK VDNLAFNFPQ QLKPAASVLD LV-TASPASS   229

SEQ_ID_NO_1493   PRPTY----- ---------- ---------F EISSASPPEK NI-----IKP   259
SEQ_ID_NO_1503   PNLTF-WNVV G-TGDGCSWT KLYEAVLEAV EREEHSSTGI GVGALGPVGC   283
SEQ_ID_NO_1508   PNLTF-WNVV G-PGDGCSWT KLYEAVVEAV EREEHGSTGI GVGGL-PVPC   285
SEQ_ID_NO_1501   PNPTF-WDVV G-TGDGCSWT KLYRAVLETV EREGDIPAGI CMEGL--LTC   283
SEQ_ID_NO_1504   PNLTF-WDMV GSTGDGCSWA NLYQAVVETV EQEGNDPAGI AIEGL--LTC   280
SEQ_ID_NO_1505   PNLTF-WDMV GSTGDGCSWA NLYQAVVETV EREGNDPAGI AIEGL--LTC   280
SEQ_ID_NO_1495   PNPTFLWGPA D--VYSSSWV EFYRAVRETL DXEN---STN CFCKM--ATC   270
SEQ_ID_NO_1499   PNPTFMFGS- ---SYSSSWI EFYQAVQRTL DKQQDQI--V MQDRF--VIC   272
SEQ_ID_NO_1491   PNPTFFFSPV D--SYSSSWV KFYQAVRGTL ETEDMFVTTD CL----VTC   272

SEQ_ID_NO_1493   P---------   260
SEQ_ID_NO_1503   G----CGCSF   289
SEQ_ID_NO_1508   SFGCGCGSSF   295
SEQ_ID_NO_1501   S---------   284
SEQ_ID_NO_1504   S---------   281
SEQ_ID_NO_1505   S---------   281
SEQ_ID_NO_1495   S---------   271
SEQ_ID_NO_1499   L---------   273
SEQ_ID_NO_1491   S---------   273
```

Figure 51

```
SEQ_ID_NO_1520    MDSLPKLR-- ---------- -HPSPFPTPL SSSLSFRSLP PPHFPSSSFR    37
SEQ_ID_NO_1510    MESLGKLQLH HQPFHLSFTH TSSSTFPKNL -----FKSSI QPISS---LK    42
SEQ_ID_NO_1512    MESLTKLHCR LQPLHLSFNH QRPS-FAKPI SSSVSFRTS- ---SSSSPFK    45
SEQ_ID_NO_1516    MESVAKLHCR HQPFNLSLNP HRPS-FPKPI -ISLSFKTPP PSSSSPFKLS    48

SEQ_ID_NO_1520    LPSIRASSSP SQNDPAFRTP RNTPSLPPLL QTLTSFLSPL LETTCIMILA    86
SEQ_ID_NO_1510    SASIKASSSK FQNS---LTP LPK------- ST----PFRL FKSTCITLTT    78
SEQ_ID_NO_1512    LTSIRALSSS SSS----SVP LHQTPKPSLL QT----LAPL LKTTCITITA    87
SEQ_ID_NO_1516    STSIRASSSS SSR----LTP LN-------- KN----LGTI IKITSITLTA    82

SEQ_ID_NO_1520    AAAFFFMRFH HT-PAVLAAP LTSPAAETDT -----AFTQE EAERLLEERL    130
SEQ_ID_NO_1510    AAALLLANLH LKSPAIAAPI APPPSVESKE -----NVTLE EEERALDEHL    123
SEQ_ID_NO_1512    GAALLFMRFH QK-PALAATP TVTPTVEPAQ TDS--NVSLE DQEKTIEEHL    134
SEQ_ID_NO_1516    AAALFFTRLN IK-PAIASPL TASSTVDPTE ESSKENVSYE EQERALQDYL    131

SEQ_ID_NO_1520    STNPRDTEAL HALMEVKIKA RKMDEAFEVL NRLIELEPEE QEWPLLKANM    180
SEQ_ID_NO_1510    ITHPSDVDAL RSLMEVKIKS RKLTEAVEVI DRLIKLEPEE KEWPVLKANI    173
SEQ_ID_NO_1512    TQYPNDVEAL QSLMEVRIKS RKLPQAIEVI DRLIQLEPED TEWPMLRAQI    184
SEQ_ID_NO_1516    SQNPNDIEAL RSLMEVRIKS KKLVEAIEVV DRLIELEPNE DEWPLLKSQI    181

SEQ_ID_NO_1520    HIYNDDHASA RKLFEEILKK DPLRVEAFHG LVMATAQSNE PLKSLLKRVE    230
SEQ_ID_NO_1510    FTYSGDLDLA KTGFEEILAK DPLRVEAYHG LLMAYSDAGL DLKEVESRIE    223
SEQ_ID_NO_1512    HSYSGDFALA KNEFEEILAK DPVRVEAFHG LVMASSESGQ KLKELEKRIE    234
SEQ_ID_NO_1516    YTYSGDFESA KDGFEAILKK DPLRVEAYHG LVMANSESGG SLEVVLKRIE    231

SEQ_ID_NO_1520    EAIEVCKKQK KDSDVRDFRL LIAQIKVMEG DYTEALKAYQ ELVKEEPRDF    280
SEQ_ID_NO_1510    EAMLKCKKEN NQNDFRDFKL LVAQIRVIEG KHSEALKLYQ ELVKEEPRDF    273
SEQ_ID_NO_1512    GAMEKCKKEK KNKDFRDFKL LIAQIRVIEG DHLEALKVYE GLVKEEPRDF    284
SEQ_ID_NO_1516    SAMDKCKKEK KTSDLRDFKL LVAQVRVMEE KYLDALKVYE ELVKEEPRDF    281

SEQ_ID_NO_1520    RPYLCQGIIY TLLRKKDEAD KQFNKFRRLV PKDHPYKDYF EDNMFATKFF    330
SEQ_ID_NO_1510    RPYLCQGIIY TLLKKKDKAE EQFDNFRKLV PKNHPYREYF MDNMIATKLF    323
SEQ_ID_NO_1512    RPYLCMGIIY SLMKKKDEAE KHFEKVRKLV PRNHPYREYF VDNMVATKLF    334
SEQ_ID_NO_1516    RPYLCQGIIY TLLRKKDEAE KKFEQFKKLV PKNHPYREYL VDNMFATKFF    331
```

Figure 51 (continued)

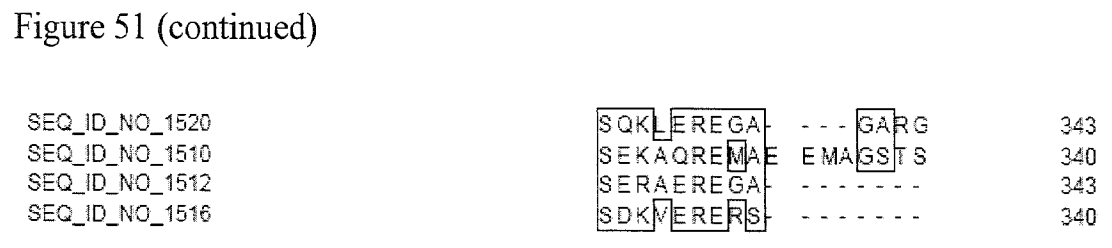

| | | |
|---|---|---|
| SEQ_ID_NO_1520 | SQKLEREGA- - - - GARG | 343 |
| SEQ_ID_NO_1510 | SEKAQREMAE EMAGSTS | 340 |
| SEQ_ID_NO_1512 | SERAEREGA- - - - - - - - | 343 |
| SEQ_ID_NO_1516 | SDKVERERS- - - - - - - - | 340 |

Figure 52 (continued)

```
SEQ_ID_NO_1525    ------GLKD FVRSNKY-EG KEEEGDAWSH SSSDLFELDS YRIGMGRYLK    319
SEQ_ID_NO_1535    ------GLKD YVRSSNIDEG KEEEDDVWSY SSSDLFELDH YRIGMGRYLK    318
SEQ_ID_NO_1527    ------SEFD FRGFHNYVAD DSDSDDE-SC TSSDLFELDH L-IGIGRYRE    356
SEQ_ID_NO_1534    YRNSGQGEFD FRGF--YDDD DEDDDDDVSC SSSDLFELDH L-IGAARYQE    366

SEQ_ID_NO_1525    ELPVYETTDF KTNQAIARSL LL    341
SEQ_ID_NO_1535    ELPVYETTDF KINQAIARGL LL    340
SEQ_ID_NO_1527    ELPVYETTNF KTNQAIANGF FP    378
SEQ_ID_NO_1534    ELPVYETTNL ETNKAIASGL CL    388
```

Figure 53

```
SEQ_ID_NO_1550    MDMNESSEKG ME----GNGS SGPGGGIPVE WQSQFS---G GGFS-A----   38
SEQ_ID_NO_1552    MYSGQQSDQC PS----ANS- ---------- ---------G REFSEA----   22
SEQ_ID_NO_1537    MLEGLVSQES LSLNS-MDMS VLER----LK WVQQQQQQLQ QVVSHS----   41
SEQ_ID_NO_1543    MLESLVSLES MSLSS-MDVS VLER----LK WLQQQ----Q QQVLST----   37
SEQ_ID_NO_1545    MLGYANPSGN LAVD--GDMT VLERQRARMK WQEEQEVFSG NSFNGV----   44
SEQ_ID_NO_1539    MLHC------ ------TDIT VLERQRACLK WQQEQQQQQQ VQLQQQEISY   38
SEQ_ID_NO_1548    MLHCLNTSGN LVGGIISDMT VLERQRARKK FQHEHEQD-Q QFFMVG----   45

SEQ_ID_NO_1550    HQHQQHPHMM DSFGSGMWS- --------AA SQHGAGFLAP VPGFLPPPGL   79
SEQ_ID_NO_1552    NRNTVTMHQK MGYNSG---- ---------- ---------- ------PYGF   42
SEQ_ID_NO_1537    SNNSPELLQI LQFHGSN--- --------ND ELLESSFSQF Q---MLGSGF   77
SEQ_ID_NO_1543    TNASPELLQF HGTN------ --------ND ELLQNTFSHF Q---MLRSGF   70
SEQ_ID_NO_1545    FSSSSSLHVP DSIMVAADS- ---------G CALAEVVAQA QPRSINKPSA   84
SEQ_ID_NO_1539    FTELTGVFQQ AGFHEGGLSE VVTRSVKPDP GLVDNGWNND H---VVGLGV   85
SEQ_ID_NO_1548    CDSALGEVVA NSMKPG---- ---------- ---------- ----------   61

SEQ_ID_NO_1550    GGHFPVDSG- -FIE----RA ARSSCFVGPG AGGGMMGAGA FGGAGDQQMG   123
SEQ_ID_NO_1552    GP---YNMG- -LEE----RP GLYQSSSGTF SQNIQM---- ---------S   70
SEQ_ID_NO_1537    GPNYNMGFGP PHES----IS RTSSCHMEPV DTMEVL---- ------LKTG   113
SEQ_ID_NO_1543    GPNYSMGFGP SHEAMDGCIS ITNSCQMDQA DTVGVM---- ------LKNS   110
SEQ_ID_NO_1545    AP------G- -LHANSSSIS RTFSCPPALV DPEPKPT--- ---------D   114
SEQ_ID_NO_1539    GPLYDNGSG- -FELNYGALS RISSCPPAAV AAVAAATVKG SESVVSDKIS   133
SEQ_ID_NO_1548    ------DLG- -FEN------ ---------- ---------- ----------   67

SEQ_ID_NO_1550    SAFGEGYLDH RRKEGGDKAE PELAGSGGVP SSEAAGGDCS SKGSDSKKRR   173
SEQ_ID_NO_1552    DEHSGGVKKR KGMD------ ---------- -------DCV AMLQNAGDQQ   97
SEQ_ID_NO_1537    EETRAVALKN KRKP------ ---------- -------EVK TREEQKTEKK   140
SEQ_ID_NO_1543    EENITISLKN KRKS------ ---------- -------EVK TREEEKTEKK   137
SEQ_ID_NO_1545    SSIGKDSFKK RKTD------ ---------- --KPHN-PKV VAENENKDKR   145
SEQ_ID_NO_1539    SGVGRESSKK RKVD------ ---------- --NKQNNSKV DAEEDTRDKR   165
SEQ_ID_NO_1548    ---VEETVKK RKAD------ ---------- ---------H KVDMKSKDKR   89
```

Figure 53 (continued)

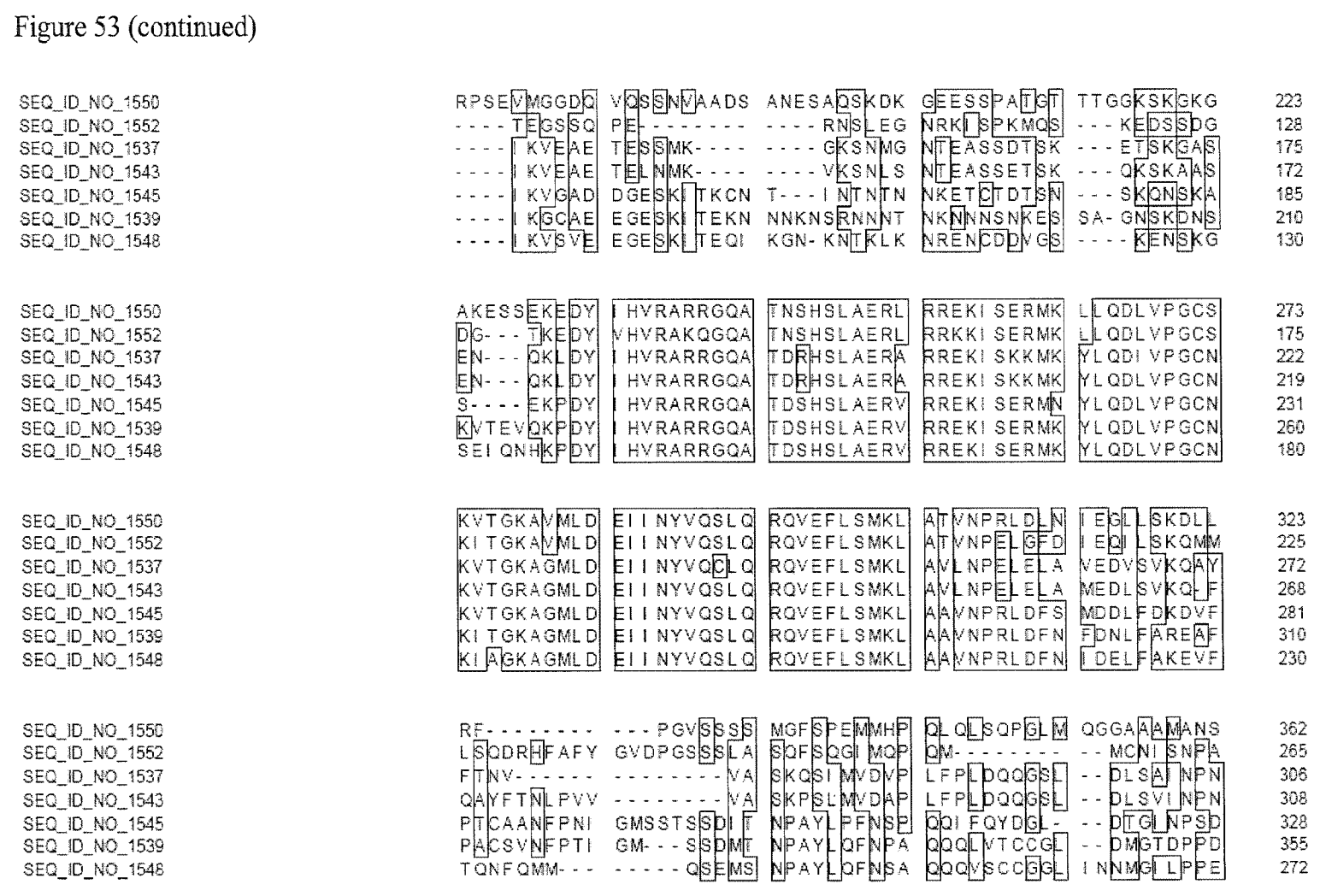

```
SEQ_ID_NO_1550   RPSEVMGGDQ VQSSNVAADS ANESAQSKDK GEESSPATGT TTGGKSKGKG   223
SEQ_ID_NO_1552   ----TEGSSQ PE-------- ----RNSLEG NRKISPKMQS ---KEDSSDG   128
SEQ_ID_NO_1537   ----IKVEAE TESSMK---- ----GKSNMG NTEASSDTSK ---ETSKGAS   175
SEQ_ID_NO_1543   ----IKVEAE TELNMK---- ----VKSNLS NTEASSETSK ---QKSKAAS   172
SEQ_ID_NO_1545   ----IKVGAD DGESKITKCN T---INTNTN NKETCTDTSN ---SKQNSKA   185
SEQ_ID_NO_1539   ----IKGCAE EGESKITEKN NNKNSRNNNT NKNNNSNKES SA-GNSKDNS   210
SEQ_ID_NO_1548   ----IKVSVE EGESKITEQI KGN-KNTKLK NRENCDDVGS ----KENSKG   130

SEQ_ID_NO_1550   AKESSEKEDY IHVRARRGQA TNSHSLAERL RREKISERMK LLQDLVPGCS   273
SEQ_ID_NO_1552   DG---TKEDY VHVRAKQGQA TNSHSLAERL RRKKISERMK LLQDLVPGCS   175
SEQ_ID_NO_1537   EN---QKLDY IHVRARRGQA TDRHSLAERA RREKISKKMK YLQDIVPGCN   222
SEQ_ID_NO_1543   EN---QKLDY IHVRARRGQA TDRHSLAERA RREKISKKMK YLQDLVPGCN   219
SEQ_ID_NO_1545   S----EKPDY IHVRARRGQA TDSHSLAERV RREKISERMN YLQDLVPGCN   231
SEQ_ID_NO_1539   KVTEVQKPDY IHVRARRGQA TDSHSLAERV RREKISERMK YLQDLVPGCN   260
SEQ_ID_NO_1548   SEIQNHKPDY IHVRARRGQA TDSHSLAERV RREKISERMK YLQDLVPGCN   180

SEQ_ID_NO_1550   KVTGKAVMLD EIINYVQSLQ RQVEFLSMKL ATVNPRLDLN IEGLLSKDLL   323
SEQ_ID_NO_1552   KITGKAVMLD EIINYVQSLQ RQVEFLSMKL ATVNPELGFD IEQILSKQMM   225
SEQ_ID_NO_1537   KVTGKAGMLD EIINYVQCLQ RQVEFLSMKL AVLNPELELA VEDVSVKQAY   272
SEQ_ID_NO_1543   KVTGRAGMLD EIINYVQSLQ RQVEFLSMKL AVLNPELELA MEDLSVKQLF   268
SEQ_ID_NO_1545   KVTGKAGMLD EIINYVQSLQ RQVEFLSMKL AAVNPRLDFS MDDLFDKDVF   281
SEQ_ID_NO_1539   KITGKAGMLD EIINYVQSLQ RQVEFLSMKL AAVNPRLDFN FDNLFAREAF   310
SEQ_ID_NO_1548   KIAGKAGMLD EIINYVQSLQ RQVEFLSMKL AAVNPRLDFN IDELFAKEVF   230

SEQ_ID_NO_1550   RF-------- ---PGVSSSS MGFSPEMMHP QLQLSQPGLM QGGAAAMANS   362
SEQ_ID_NO_1552   LSQDRHFAFY GVDPGSSSLA SQFSQGIMQP QM-------- --MCNISNPA   265
SEQ_ID_NO_1537   FTNV------ --------VA SKQSIMVDVP LFPLDQQGSL --DLSAINPN   306
SEQ_ID_NO_1543   QAYFTNLPVV --------VA SKPSLMVDAP LFPLDQQGSL --DLSVINPN   308
SEQ_ID_NO_1545   PTCAANFPNI GMSSTSSDIT NPAYLPFNSP QQIFQYDGL- --DTGLNPSD   328
SEQ_ID_NO_1539   PACSVNFPTI GM---SSDMT NPAYLQFNPA QQQLVTCCGL --DMGTDPPD   355
SEQ_ID_NO_1548   TQNFQMM--- -----QSEMS NPAYLQFNSA QQQVSCCGGL INNMGILPPE   272
```

Figure 53 (continued)

```
SEQ_ID_NO_1550    DVFRRIMQAQ ---------L GAKDGSHSQM AHALNGPFSD HVAQMAYPSM    403
SEQ_ID_NO_1552    DVLQGTIHDV ---------- ----STMNQI PAMWEG-LQN -LPQMNFNPG    299
SEQ_ID_NO_1537    QT-------- ---------- ----TSIEAP SGSWETQSQS -LYN------    327
SEQ_ID_NO_1543    QA-------- ---------- ----TTIEAP SASWETQSQS -LYN------    329
SEQ_ID_NO_1545    VGLRRTISAP VS--MPETYL QSSCFTQMLP SSTWEGDFQN -LCNFDVDQA    375
SEQ_ID_NO_1539    MGLKRTTSSP ES--IPETFL DSSCFTQAHP PPAWDADLQN -LYNVAFDQG    402
SEQ_ID_NO_1548    IGVRRNINAP ASASLPEIFL DPSCFTHILP SSTWEGDFQN -LHSVDFDQG    321

SEQ_ID_NO_1550    GSSHSHSQDL S--------I RPSQDAYQM    424
SEQ_ID_NO_1552    VAADSSANN- ---------- -SGSMKIEQ    316
SEQ_ID_NO_1537    ---------- ---------- -TSSLGFHY    335
SEQ_ID_NO_1543    ---------- ---------- -TSSLGFQY    337
SEQ_ID_NO_1545    RATSFPSQLL SGL------V EAGNLKMEM    398
SEQ_ID_NO_1539    RQTSFPTQPF TGKIKLSCSI EASNLKMEM    431
SEQ_ID_NO_1548    RSTSFPSQPF TGM------I EASNLKMEM    344
```

Figure 54 (continued)

```
SEQ_ID_NO_1571   AVEKKGEEDD KKEAEVEGKE EEEESKKEAE KEMEQEE--- ----------  150
SEQ_ID_NO_1567   AAEPAAEEPK AVVA------ ----AEAAAE EPAKEEPK-- ---AEEAKPA  188
SEQ_ID_NO_1572   PPEAGTEEPK AEASSEEAKT EEPKAEAAAD EPAKQESKAE AAPAEEAKPA  208
SEQ_ID_NO_1574   PPEAGTEEPK AEASSEEAKT EEPKAEAAAD EPAKEESKAE AAPAEEAKPA  211
SEQ_ID_NO_1555   KTEAEPEPVT ETVTVKVEET ITPHPAPETS LAPEADEKAA EPSTVVEKVA  211
SEQ_ID_NO_1563   ---------- ---------- ---------- ---------- ----------  107
SEQ_ID_NO_1575   AEEKKVEEVE KKEEEKGSSS EEPKTEAKIE AEPEAKKEET VLEVVEKIAT  216
SEQ_ID_NO_1554   ---------- ---------- ---------- ---------- ----------  145
SEQ_ID_NO_1565   ---------- ---------- ---------- ---------- ----------  78

SEQ_ID_NO_1571   ---------- ---------- ---------- --AGEAEKVA AAAEEKPAET  168
SEQ_ID_NO_1567   EPKKEEEAVV VAEE--GTKT ------AEPV EEAAAAATTT EQAAAPEPEA  230
SEQ_ID_NO_1572   EPEPEEKTVV VTEEEAATKT VEAIEETVVP AAAAPAAAAT EEAAAPEPEV  258
SEQ_ID_NO_1574   EPEPGGED-- ---------- ------RRGH RGRGGHQDGG SDRGNRRARC  243
SEQ_ID_NO_1555   VIDEDGAKTV EAIEESVVAV ------STPP PEESAPSKEE AEVEVEAAEA  255
SEQ_ID_NO_1563   ---------- ---------- ---------- ---------- ----------  107
SEQ_ID_NO_1575   STEEDGAKTV EAIQESIVSV ------TVTD GEQPVTETVG EAVAVAEVE-  259
SEQ_ID_NO_1554   ---------- ---------- ---------- ---------- ----------  145
SEQ_ID_NO_1565   ---------- ---------- ---------- ---------- ----------  78

SEQ_ID_NO_1571   AAVVVDKDIA LWGVPLLPSK GDE-ATDVVL LKFLRARDFK AGAAFEMLRR  217
SEQ_ID_NO_1567   E-AAAPEPVF IWGVPLV--- GDDERTDAVL LKFLRAREFK VKEAMAMLRS  276
SEQ_ID_NO_1572   QAAAAPEPVL IWGVPLV--- GDDERTDTVL LKFLRAREFK VKEAMAMLRS  305
SEQ_ID_NO_1574   CCACCRRHGG SRGAGTG--- GDDERTDTVL LKFLRAREFK VKEAMAMLRS  290
SEQ_ID_NO_1555   VPPPPPEEVF IWGIPLL--- GDE-RSDVIL LKFLRARDFK VKDAFTMIKN  301
SEQ_ID_NO_1563   ---------- ---------- ----KSDVIL LKFLRARDFK VKDAFTMLKS  133
SEQ_ID_NO_1575   VTPTTPEEVE IWGIPLL--- ADE-RSDVIL LKFLRARDFK VKEAYTMIKQ  305
SEQ_ID_NO_1554   ----TPEEVK IWGIPLL--- EDD-RSDVVL LKFLRAREFK VKDSFAMLKN  187
SEQ_ID_NO_1565   ------EEVS IWGVPLF--- KDD-RTDVIL LKFLRARELK VKDALVMFQN  118

SEQ_ID_NO_1571   TLRWRRDWPG FDADADADLP -EELAGACYL DGADREGHPV CYNALRVFAD  266
SEQ_ID_NO_1567   AVLWRKRF-G IESLLEADLA FPELEKVVFY RGADREGHPV CYNVYGEFQD  325
SEQ_ID_NO_1572   AVLWRKRF-G IESLLDADLA LPELDSVVFY RGADREGHPV CYNVYGEFQD  354
SEQ_ID_NO_1574   AVLWRKRF-G IESLLDADLA LPELDSVVFY RGADREGHPV CYNVYGEFQD  339
SEQ_ID_NO_1555   TVRWRKQF-D IEALLDEDLG -NQWDKVVFS HGVDREGHPV CYNVFGEFEN  349
SEQ_ID_NO_1563   TIRWRKEF-G IDELLEQDLG FDDLGKVVFM HGLDKEGHPV CYNVYGEFQN  182
SEQ_ID_NO_1575   TVIWRKEF-G IEALLQEDLG -TDWDKVVFT DGYDKEGHPV YYNVFGEFEN  353
SEQ_ID_NO_1554   TIKWRKEF-K IDELVEEDLV -DDLDKVVFM HGHDREGHPV CYNVYGEFQN  235
SEQ_ID_NO_1565   TLRWRKDF-N IDALLDEDLG -DHLEKVVFM HGHGREGHPV CYNVYGEFQN  166
```

Figure 54 (continued)

```
SEQ_ID_NO_1571  DAVYKKALGT EEGKARFLRW RVRAMERHV- AELDLKP-GG AASLLQVTDL  314
SEQ_ID_NO_1567  KEVYEKAFGD EEKRERFLKW RIQLLERGIL SQLDFAP-SG ICSMVQVTDL  374
SEQ_ID_NO_1572  KDLYEKAFGD EEKRERFLKW RIQLLERGIL SQLDFSP-SG ICSMVQVTDL  403
SEQ_ID_NO_1574  KDLYEKAFGD EEKRERFLKW RIQLLERGIL SQLDFSP-SG ICSMVQVTDL  388
SEQ_ID_NO_1555  KDLYQITFSD DEKSLKFLRW RVQFLEKSI- RKLDFSP-NG ISTIVQVNDL  397
SEQ_ID_NO_1563  KELYKNSFSD EEKRQRFLRW RIQFLEKSI- RTLDFSP-GG ISTIVQVNDL  230
SEQ_ID_NO_1575  KELYQNTFSD DEKRTKFIRW RIQSLEKSI- RKLDFTP-SG ISTIVQVNDL  401
SEQ_ID_NO_1554  KELYNKTFSD EEKRKHFLRT RIQFLERSI- RKLDFSS-GG VSTIFQVNDM  283
SEQ_ID_NO_1565  KDLYHKAFSS QDNRNKFLRW RIQLLERSI- RHLDFTPSSG INTIFQVNDL  215

SEQ_ID_NO_1571  KNSPGPAKKD FRVAVKQVLD LFQDNYPELV ARNILINVPF WYYAFSTLFY  364
SEQ_ID_NO_1567  KNSPPMLGKH -RAVTRQAVA LLQDNYPEFI AKKVFINVPW WYLAANKMMS  423
SEQ_ID_NO_1572  KNSPPMLGKH -RAVTRQAVA LLQDNYPEFI AKKVFINVPW WYLAANKMMS  452
SEQ_ID_NO_1574  KNSPPMLGKH -RAVTRQAVA LLQDNYPEFI AKKVFINVPW WYLAANKMMS  437
SEQ_ID_NO_1555  KNSPGLTKWE LRNATKRALQ LFQDNYPEFA AKQVFINVPW WYLAVNRMIS  447
SEQ_ID_NO_1563  KNSPGPAKRE LRQATRQALQ LLQDNYPEFV AKQIFINVPW WYLTVNRMIS  280
SEQ_ID_NO_1575  KNSPGLGKKE LRQATNKALQ LLQDNYPEFV AKQVFINVPW WYLAFSRFLS  451
SEQ_ID_NO_1554  KNSPGLGKKE LRSATKQAVE LLQDNYPEFV FKQAFINVPW WYLVFYTVIG  333
SEQ_ID_NO_1565  KNSPGPAKRE LRLATKQALQ LLQDNYPEFV AKQVFINVPW WYLAFYTMIN  265

SEQ_ID_NO_1571  PFLTQRTKSK FVLARPSKVT ETLLKYIPIE AIPVKYGGLK RDD---DTEF  411
SEQ_ID_NO_1567  PFLTQRTKSK FVFASQAKSP ETLFRYIAPE QVPVQFGGLF KED---DPDF  470
SEQ_ID_NO_1572  PFLTQRTKSK FIFASPAKSA ETLFRYIAPE QVPVQFGGLF KED---DPEF  499
SEQ_ID_NO_1574  PFLTQRTKSK FIFASPAKSA ETLFRYIAPE QVPVQFGGLF KED---DPEF  484
SEQ_ID_NO_1555  PFFTQRTKSK FVFAGPSKTA ETLFKYVTPE QVPVQYGGLS REG---EQEF  494
SEQ_ID_NO_1563  PFLTQRTRSK FVFVGPSKSA ETLIRYIAAE QIPVKYGGLS KDG-----EF  325
SEQ_ID_NO_1575  AFLTQRTKSK FVFAGPSKSA DTLFKYIAPE QVPVQYGGLS REG---EQEF  498
SEQ_ID_NO_1554  PFMTPRSKSK LVFAGPSRSA ETLFKYISPE QVPVQYGGLS VDPCDCNPDF  383
SEQ_ID_NO_1565  PFLTSRTKSK FVFAGPSKSP DTLFKYIFPE QVPVQYGGLS VDFCDCNPDF  315

SEQ_ID_NO_1571  SSADDGEVAE LTVKGSSTET IEIEAAEADA TLTWDLTVLG WEVNYKEEFV  461
SEQ_ID_NO_1567  TTSD--SVTE LTIKASSKET IEIPVTE-NS TIVWELRVLG WEVSHGAEFT  517
SEQ_ID_NO_1572  TTSD--AVTE LTIKPSSKET VEIPVTE-NS TIGWELRVLG WEVSYGAEFT  546
SEQ_ID_NO_1574  TTSD--AVTE LTIKPSSKET VEIPVTE-NS TIGWELRVLG WEVSYGAEFT  531
SEQ_ID_NO_1555  SIDD--PVTE VAIKAATKHT VEFPISE-PS LLVWELRVVG WDVSYGAEFL  541
SEQ_ID_NO_1563  GSAD--AVTE ITVKPAAKHT VEFPVTE-TC LLTWEVRVAG WDVSYSAEFV  372
SEQ_ID_NO_1575  TTAD--PATE VTIKPATKHA VEFPISE-KS TLVWEVRVVD WSVNYGAEFV  545
SEQ_ID_NO_1554  SLED--SASE ITVKPGTKQT VEIIIYE-KC ELVWEIRVTG WEVSYKAEFV  430
SEQ_ID_NO_1565  TMSD--PVTE IPIKPTTKQT VEIAIYE-KC IIVWELRVVG WEVSYNAEFK  362
```

Figure 54 (continued)

```
SEQ_ID_NO_1571    PADEGSYTII VRKGKKMGAG EEAV-RNSFR AGEPGKVVLT VENTSH-KKK    509
SEQ_ID_NO_1567    PDAEGAYTVI VQKTRKVPAN EEPIMKGSFK AGEAGKIVLT VSNAAS-KKK    566
SEQ_ID_NO_1572    PDAEGGYTVI VQKTRKVPAN EEPIMKGSFK VGEPGKIVLT INNPAS-KKK    595
SEQ_ID_NO_1574    PDAEGGYTVI VQKTRKVPAN EEPIMKGSFK VGEPGKIVLT INNPAS-KKK    580
SEQ_ID_NO_1555    PSAEGGYTVI VQKTAKLGPA DEPVISNSYR VGEAGKIVLT IDNLSSKKKK    591
SEQ_ID_NO_1563    PSAEDSYTVI IQKARKVAAT EEPVVCNSFK IGEPGKVVLT IDNSTSKKKK    422
SEQ_ID_NO_1575    PSAEDGYTVI IQKNRKVAPA DETIISNTFK IGEPGKVILT IDNQSS-KKK    594
SEQ_ID_NO_1554    PEEKDAYTVV IQKPRKMRPS DEPVLTHSFK VNELGKVLLT VDNPTS-KKK    479
SEQ_ID_NO_1565    PDVEDAYTVI IQKATKMSPT DEPVVSNSFK VVELGKLLLT IDNPTL-KKK    411

SEQ_ID_NO_1571    KVLFRHKSKS AFAKKC---- -    525
SEQ_ID_NO_1567    KLLYRSKVKC STGESVEADI P    587
SEQ_ID_NO_1572    KLLYRSKVKS TSESV----- -    610
SEQ_ID_NO_1574    KLLYRSKVKS TSESV----- -    595
SEQ_ID_NO_1555    ILLYRSKTKP ISD------- -    604
SEQ_ID_NO_1563    KLLYRLKTKP ASSD------ -    436
SEQ_ID_NO_1575    KLLYRSKTIP ISE------- -    607
SEQ_ID_NO_1554    KLVYRFNVKP L--------- -    490
SEQ_ID_NO_1565    RLLYRFKIKP YSD------- -    424
```

Figure 55 (continued)

| | | | | | | |
|---|---|---|---|---|---|---|
| SEQ_ID_NO_1578 | YPHNYGFVPK | TLCEDGDPLD | VLVLMQEPVV | PMCFLRAKPI | GVMQMLDQGE | 109 |
| SEQ_ID_NO_1607 | YPHNYGFIPR | TICEDSDPID | VLVLMQEPVL | TGSFLRARAI | GLMPMIDQGE | 140 |
| SEQ_ID_NO_1440 | YPHNYGFIPR | TLCEDGDPMD | VLVLMQEPVV | PGRFLRARAI | GLMPMIDQGE | 143 |
| SEQ_ID_NO_1648 | YPHNYGFIPR | TLCEDNDPLD | VLILMQEPVL | PGCFLR RAI | GLMPMIDQGE | 136 |
| SEQ_ID_NO_1651 | YPHNYGFIPR | SLCEDNDPMD | VLVLMQEPVL | PGAFLRARAI | GLMPMIDQGE | 147 |
| SEQ_ID_NO_1487 | YPHNYGFIPR | TLCEDNDPMD | VLVLMQEPVL | PGSFLRARAI | GLMPMIDQGE | 145 |
| SEQ_ID_NO_1040 | YPHNYGFIPR | TLCEDNDPMD | VLVLMQEPVI | PGSFLRARAI | GLMPMIDQGE | 138 |
| SEQ_ID_NO_1485 | YPHNYGFIPR | TLCEDNDPMD | VLVLMQEPVI | PGSFLRARAI | GLMPMIDQGE | 134 |
| SEQ_ID_NO_1580 | YPHNYGFIPR | TLCEDNDPLD | CLVIMQEPVL | PGCFLRARAL | GLMPMIDQGE | 136 |
| SEQ_ID_NO_1623 | YPQNYGFIPR | TLCEDNDPMD | VLVLMQEPVL | PGCFLRARAI | GLMPMIDQGE | 132 |
| SEQ_ID_NO_1622 | YPHNYGFIPR | TLCEDNDPID | VLVLMQEPVL | PGCFLRARAI | GLMPMIDQGE | 140 |
| SEQ_ID_NO_1041 | YPHNYGFIPR | TLCEDNDPLD | VLVLMQEPVL | PGCFLRARAI | GLMPMIDQGE | 136 |
| SEQ_ID_NO_1590 | YPHNYGFIPR | TLCEDNDPLD | VLVLMQEPVL | PGCFLRARAI | GLMPMIDQGE | 137 |
| SEQ_ID_NO_1577 | YPHNYGFVPR | TLCEDNDPID | VLVIMQEPVL | PGCFLRARAI | GLMPMIDQGE | 137 |
| SEQ_ID_NO_1611 | YPHNYGFIPR | TLCEDNDPLD | VLVIMQEPVL | PGCFLRARAI | GLMPMIDQGE | 135 |
| SEQ_ID_NO_1637 | YPHNYGFIPR | TLCEDNDPLD | VLVIMQEPVL | PGCFLRARAI | GLMPMIDQGE | 135 |
| SEQ_ID_NO_1627 | YPHNYGFIPR | TLCDDSDPID | VLVIMQEPVV | PGCFLRAKAI | GLMPMIDQGE | 149 |
| SEQ_ID_NO_1608 | YPHNYGFIPR | TLCEDNDPLG | CLDIMQEPVV | PGCFLRAKAI | GLMPMIDQGE | 149 |
| SEQ_ID_NO_1609 | YPHNYGFIPR | TICEDSDPMD | VLVIMQEPVL | PGCFLRAKAI | GLMPMIDQGE | 137 |

| | | | | | | |
|---|---|---|---|---|---|---|
| SEQ_ID_NO_1578 | RDDKLIAVHA | DDPEYKGFTD | ISQLPPHRLA | EIKRFFEDYK | KNEHKEVVVD | 159 |
| SEQ_ID_NO_1607 | KDDKIIAVCA | DDPEFRHYRD | IKELPPHRLA | EIRRFFEDYK | KNENKKVAVE | 190 |
| SEQ_ID_NO_1440 | KDDKIIAVCA | DDPEVRHYTD | INQLPPHRLA | EIRRFFEDYK | KNENKEVAVN | 193 |
| SEQ_ID_NO_1648 | KDDKIIAVCA | DDPEYRHYTD | IKQLAPHRLA | EIRRFFEDYK | KNENKEVAVN | 186 |
| SEQ_ID_NO_1651 | KDDKIIAVCA | DDPEYRHYND | ISELSPHRLQ | EIRRFFEDYK | KNENKEVAVN | 197 |
| SEQ_ID_NO_1487 | KDDKIIAVCA | DDPEYRHFNN | LSELSPHRLQ | EIRRFFEDYK | KNENKEVAVN | 195 |
| SEQ_ID_NO_1040 | KDDKIIAVCA | DDPEYRHYST | SVSLLP-RLQ | EIKR-LEDYK | KNENKEVAVD | 186 |
| SEQ_ID_NO_1485 | KDDKIIAVCA | DDPEYRHYND | IN-------- | ---------K | KNENKEVAVD | 167 |
| SEQ_ID_NO_1580 | KDDKIIAVCV | DDPEYKHYTD | IKDLPPHRLT | EIRRFFEDYK | KNENKEVAVD | 186 |
| SEQ_ID_NO_1623 | KDDKIIAVCA | DDPEYRHYTD | IKQLPPHRLA | EIRRFFEDYK | KNENKDVAVD | 182 |
| SEQ_ID_NO_1622 | KDDKIIAVCA | DDPEYKHFTD | YKELAPHRIM | EIRRFFEDYK | KNENKEVAVN | 190 |
| SEQ_ID_NO_1041 | KDDKIIAVCA | DDPEYKHYTD | IKELAPHRLS | EIRRFFEDYK | KNENKEVAVN | 186 |
| SEQ_ID_NO_1590 | KDDKIIAVCA | DDPEYKHYTD | IRELAPHRLS | EIRRFFEDYK | KNENKEVAVN | 187 |
| SEQ_ID_NO_1577 | KDDKIIAVCV | DDPEYKH TN | INELPPHRLS | EIRRFFEDYK | KNENKEVAVN | 187 |
| SEQ_ID_NO_1611 | KDDKIIAVCV | DDPEYKHYTD | IKELPPHRLS | EIRRFFEDYK | KNENKEVAVN | 185 |
| SEQ_ID_NO_1637 | KDDKIIAVCV | DDPEYKHYTD | IKELPPHRLT | EIRRFFEDYK | KNENKEVAVN | 185 |
| SEQ_ID_NO_1627 | ADDKIIAVCA | DDPEYRHFND | IKELPPHRLA | EIRRFFEDYK | KNENKEVAVN | 199 |
| SEQ_ID_NO_1608 | KDDQIIAVCA | DDPEYRHYND | IKELPPHRLA | EIRRFFEDYK | KNENKEVAVD | 199 |
| SEQ_ID_NO_1609 | KDDKIIAVCA | DDPEYRHYND | IKELPPHRLA | EIRRFFEDYK | KNENKEVEVH | 187 |

Figure 55 (continued)

| | | | | | | |
|---|---|---|---|---|---|---|
| SEQ_ID_NO_1578 | DFLGAEEAKK | VVKDSLNMYQ | EH | YVPRKLRN | VYE | 192 |
| SEQ_ID_NO_1607 | GFLPAQAAI D | AI KDSMDLYA | A- | YI KAGLQR | - - - | 219 |
| SEQ_ID_NO_1440 | EFLPAQIAHD | AI QHSMDLYA | E- | YI LQTLRR | - - - | 222 |
| SEQ_ID_NO_1648 | DFLPSATAHE | AI QYSMDLYA | E- | YI MMSLRR | - - - | 215 |
| SEQ_ID_NO_1651 | EFLPAEAARE | AI QYSMDLYG | Q- | YI MQTLRR | - - - | 226 |
| SEQ_ID_NO_1487 | DFLPAPTARE | AI QYSMDLYA | Q- | YI LQSLKR | - - - | 224 |
| SEQ_ID_NO_1040 | AFLPATTARE | AI QYSMDLYA | Q- | YI LQSLRQ | - - - | 215 |
| SEQ_ID_NO_1485 | AFLPANTARD | AI QYSMDLYA | Q- | YI LQSLRQ | - - - | 196 |
| SEQ_ID_NO_1580 | KFLPATAAVE | AVQYSMDLYA | E- | YI MQTLRR | - - - | 215 |
| SEQ_ID_NO_1623 | DFLPPNSAVN | AI QYSMDLYA | E- | YI LHSLRK | - - - | 211 |
| SEQ_ID_NO_1622 | DFLPPSTAVE | AI QYSMDLYA | E- | YI LHTLRR | - - - | 219 |
| SEQ_ID_NO_1041 | DFLPSNTAVE | AI QYSMDLYA | E- | YI LHTLRR | - - - | 215 |
| SEQ_ID_NO_1590 | DFLPSNSAVE | AI QYSMDLYA | E- | YI LHTLRR | - - - | 216 |
| SEQ_ID_NO_1577 | DFLQPGPAI E | AI QYSMDLYA | E- | YI LHTLRR | - - - | 216 |
| SEQ_ID_NO_1611 | DFLPNGPAVE | AI QYSMDLYA | E- | YI LHTLRR | - - - | 214 |
| SEQ_ID_NO_1637 | DFLPNGPAVE | AI QYSMDLYA | E- | YI LHTLRR | - - - | 214 |
| SEQ_ID_NO_1627 | DFLPSEDAYE | AI QHSMDLYA | T- | YI CEGLRR | - - - | 228 |
| SEQ_ID_NO_1608 | DFLPASTAFD | AI QHSMNLYA | D- | YI VESLRR | - - - | 228 |
| SEQ_ID_NO_1609 | DFLLATTAMR | AI KHSMTLYA | D- | YI VESLRR | - - - | 216 |

Figure 56

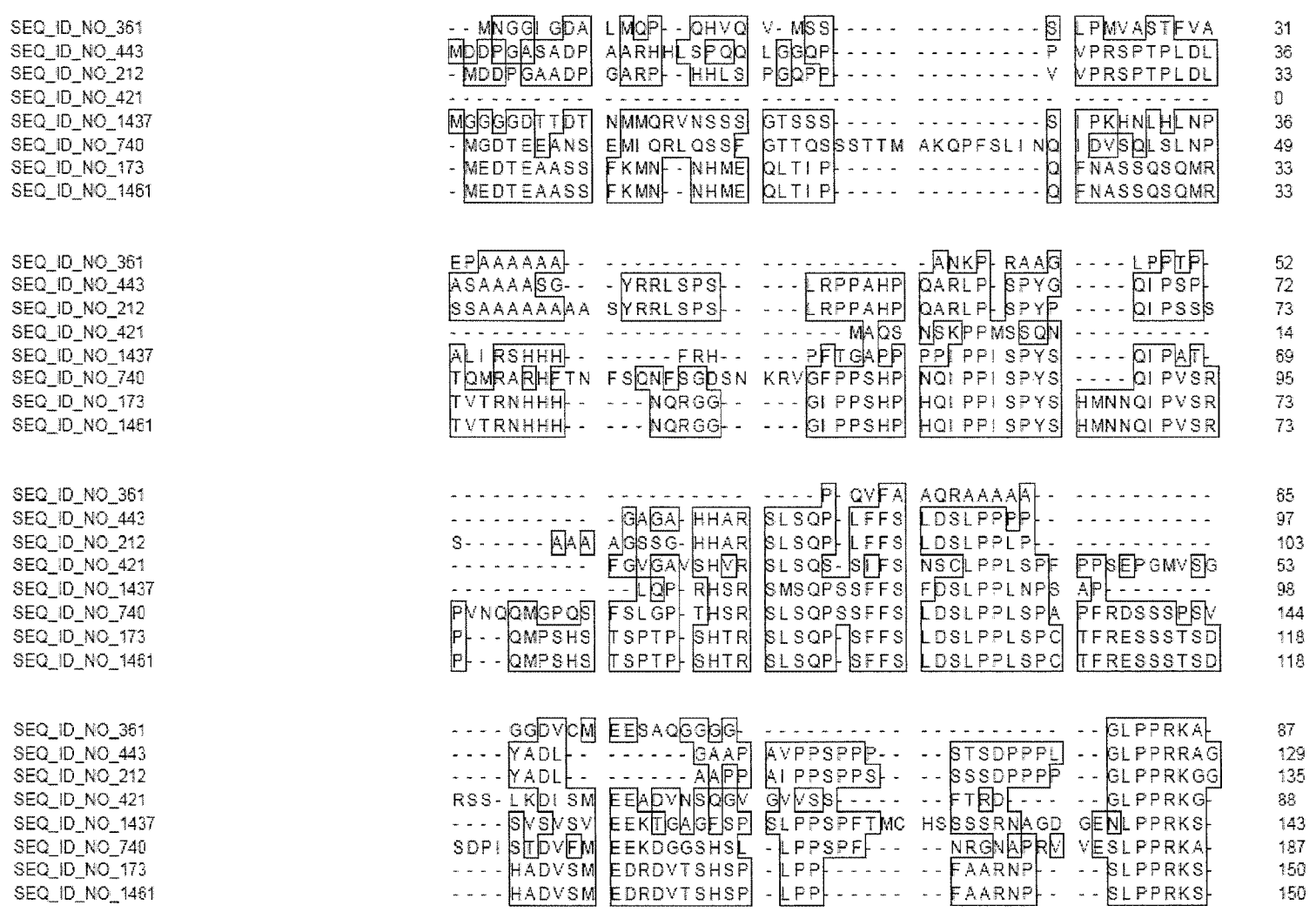

```
SEQ_ID_NO_361   --MNGGIGDA LMQP--QHVQ V-MSS----- ---------S LPMVASTFVA   31
SEQ_ID_NO_443   MDDPGASADP AARHHLSPQQ LGGQP----- ---------P VPRSPTPLDL   36
SEQ_ID_NO_212   -MDDPGAADP GARP--HHLS PGQPP----- ---------V VPRSPTPLDL   33
SEQ_ID_NO_421   ---------- ---------- ---------- ---------- ----------    0
SEQ_ID_NO_1437  MGGGGDTTDT NMMQRVNSSS GTSSS----- ---------S IPKHNLHLNP   36
SEQ_ID_NO_740   -MGDTEEANS EMIQRLQSSF GTTQSSSTTM AKQPFSLINQ IDVSQLSLNP   49
SEQ_ID_NO_173   -MEDTEAASS FKMN--NHME QLTIP----- ---------Q FNASSQSQMR   33
SEQ_ID_NO_1461  -MEDTEAASS FKMN--NHME QLTIP----- ---------Q FNASSQSQMR   33

SEQ_ID_NO_361   EPAAAAAA-- ---------- ---------- -ANKP-RAAG ----LPPTP-   52
SEQ_ID_NO_443   ASAAAASG-- -YRRLSPS-- ---LRPPAHP QARLP-SPYG ----QIPSP-   72
SEQ_ID_NO_212   SSAAAAAAAA SYRRLSPS-- ---LRPPAHP QARLP-SPYP ----QIPSSS   73
SEQ_ID_NO_421   ---------- ---------- ------MAQS NSKPPMSSQN ----------   14
SEQ_ID_NO_1437  ALIRSHHH-- -----FRH-- ---PFTGAPP PPIPPISPYS ----QIPAT-   69
SEQ_ID_NO_740   TQMRARHFTN FSQNFSGDSN KRVGFPPSHP NQIPPISPYS ----QIPVSR   95
SEQ_ID_NO_173   TVTRNHHH-- ---NQRGG-- ---GIPPSHP HQIPPISPYS HMNNQIPVSR   73
SEQ_ID_NO_1461  TVTRNHHH-- ---NQRGG-- ---GIPPSHP HQIPPISPYS HMNNQIPVSR   73

SEQ_ID_NO_361   ---------- ---------- ----P-QVFA AQRAAAAA-- ----------   65
SEQ_ID_NO_443   ---------- -GAGA-HHAR SLSQP-LFFS LDSLPPPP-- ----------   97
SEQ_ID_NO_212   S------AAA AGSSG-HHAR SLSQP-LFFS LDSLPPLP-- ----------  103
SEQ_ID_NO_421   ---------- FGVGAVSHVR SLSQS-SIFS NSCLPPLSPF PPSEPGMVSG   53
SEQ_ID_NO_1437  ---------- --LQP-RHSR SMSQPSSFFS FDSLPPLNPS AP--------   98
SEQ_ID_NO_740   PVNQQMGPQS FSLGP-THSR SLSQPSSFFS LDSLPPLSPA PFRDSSSPSV  144
SEQ_ID_NO_173   P---QMPSHS TSPTP-SHTR SLSQP-SFFS LDSLPPLSPC TFRESSSTSD  118
SEQ_ID_NO_1461  P---QMPSHS TSPTP-SHTR SLSQP-SFFS LDSLPPLSPC TFRESSSTSD  118

SEQ_ID_NO_361   ----GGDVCM EESAQGGGG- ---------- ---------- --GLPPRKA-   87
SEQ_ID_NO_443   ----YADL-- ------GAAP AVPPSPPP-- --STSDPPPL --GLPPRRAG  129
SEQ_ID_NO_212   ----YADL-- ------AAPP AIPPSPPS-- --SSSDPPPP --GLPPRKGG  135
SEQ_ID_NO_421   RSS-LKDISM EEADVNSQGV GVVSS----- --FTRD---- --GLPPRKG-   88
SEQ_ID_NO_1437  ----SVSVSV EEKTGAGFSP SLPPSPFTMC HSSSSRNAGD GENLPPRKS-  143
SEQ_ID_NO_740   SDPISTDVFM EEKDGGSHSL -LPPSPF--- --NRGNAPRV VESLPPRKA-  187
SEQ_ID_NO_173   ----HADVSM EDRDVTSHSP -LPP------ --FAARNP-- --SLPPRKS-  150
SEQ_ID_NO_1461  ----HADVSM EDRDVTSHSP -LPP------ --FAARNP-- --SLPPRKS-  150
```

Figure 56 (continued)

| | | | | | | | |
|---|---|---|---|---|---|---|---|
| SEQ_ID_NO_361 | HRRSSSDVPF | GYL------A | GQHQLLPP-- | ---------- | ---------- | 109 |
| SEQ_ID_NO_443 | HRRSQSDIPF | GFA------Q | LSPPLPPP-- | ---------- | ---------- | 151 |
| SEQ_ID_NO_212 | HRRSQSDIPF | GFS------H | LSPPLPPP-- | ---------- | ---------- | 157 |
| SEQ_ID_NO_421 | HRRSNSDVPL | GFSAMI---Q | SSPQLMPI-- | ---------- | ---------S | 114 |
| SEQ_ID_NO_1437 | HRRSNSDVTF | GFSSMMSQNQ | KSPPLSSLER | SISGEDT--- | --------SD | 182 |
| SEQ_ID_NO_740 | HRRSNSDIPF | GLANVL---Q | CSPPLIPS-R | GSSGLERSMS | GRENLGMAKP | 233 |
| SEQ_ID_NO_173 | HRRSNSDIPF | GFSTVL---Q | SSPPLIPL-R | GREGV----- | --------KP | 183 |
| SEQ_ID_NO_1461 | HRRSNSDIPF | GFSTVL---Q | SSPPLIPL-R | GREGV----- | --------KP | 183 |

| | | | | | | |
|---|---|---|---|---|---|---|
| SEQ_ID_NO_361 | -----KVEAG | W------GHL | GAGA----GG | AAAADDLFNA | YLNLDGLDGL | 144 |
| SEQ_ID_NO_443 | --APVKREVT | A------AAD | GCRSDGGGGD | DAALYDLVNA | YMDLDGLDPL | 193 |
| SEQ_ID_NO_212 | --APVKREAA | T------AAE | GCRSD---GD | DFALYDLVNS | YMDLDGMEAL | 196 |
| SEQ_ID_NO_421 | GQKVLGRAVS | LG-----DSN | GKIDERKPKG | E-VTDELLFS | YMNLENIETL | 158 |
| SEQ_ID_NO_1437 | WSNLVKKE-- | -------PRE | GFYKGRKPEV | EAAMDDVFTA | YMNLDNIDVL | 223 |
| SEQ_ID_NO_740 | AQSVKK---E | WERGGDSNAE | GMGERKS-EG | E-VVDDLFSA | YMNLDNIDVL | 278 |
| SEQ_ID_NO_173 | NSSVVKRETN | WEHG---NVE | GSGEKKSPEG | E-VVDDLFSA | YMNLDSEDTL | 229 |
| SEQ_ID_NO_1461 | NSSVVKRETN | WEHG---NVE | EK-KSLSPEG | E-VVDDLFSA | YMNLDNIDAI | 228 |

| | | | | | | |
|---|---|---|---|---|---|---|
| SEQ_ID_NO_361 | NSSDDRH-DE | GD-------- | SRGSSI-KTN | GADSSENESE | ECADDTRGGI | 184 |
| SEQ_ID_NO_443 | NSSEDRH-DD | RD-------- | SRASGTRAGS | AAESSENEAE | S--------- | 225 |
| SEQ_ID_NO_212 | NSSEERH-ED | RD-------- | SRASGTRTGS | VADSSENEAE | S--------- | 228 |
| SEQ_ID_NO_421 | NGSGTKD-RD | KD-------- | SIVSGT-KVT | GSESSNNEAE | SVMKGNNVS- | 197 |
| SEQ_ID_NO_1437 | NSFGGEDGKN | GNENVEEMES | SRGSGTKKTN | GGSSSDSEGD | SSASGNVK-- | 271 |
| SEQ_ID_NO_740 | NSSGTDD-KN | GNENREDLD- | SRASGT-KTN | GGDSSDNEAE | SSVNESGGNL | 325 |
| SEQ_ID_NO_173 | NSSGTDD-KN | GGENRDDLD- | SRACGT-KTN | GGDSSDNEAE | SSVNESGH-- | 274 |
| SEQ_ID_NO_1461 | NDDKNAATDD | ---------- | SRASGT-KTN | GGDSSDNEAE | SSVNESG--- | 264 |

| | | | | | | |
|---|---|---|---|---|---|---|
| SEQ_ID_NO_361 | RLWS-ADGGE | RREGVKRNAA | GEPATAPLAR | HARSLSMDS- | LIGKFNFTAG | 232 |
| SEQ_ID_NO_443 | ---------- | QSTSADRKDG | GK------SR | HCRSLSIDS- | FMGKLSFAAG | 258 |
| SEQ_ID_NO_212 | ---------- | HSTPVERKDG | GG-----KSR | HCRSLSVDS- | FIEKLNF--- | 259 |
| SEQ_ID_NO_421 | ------QPTN | LREGTKRSAD | AN---APAAR | HFRSLSMDS- | AIGNFHY--G | 237 |
| SEQ_ID_NO_1437 | -----VALSS | SSSGVKRRAG | GD---APTGR | HYRSVSMDSC | FMGKLNF--G | 312 |
| SEQ_ID_NO_740 | PRAGLSSSTE | KREGIKRSAG | GD---APTTR | HYRSVSMDS- | FMGKLNF--G | 370 |
| SEQ_ID_NO_173 | ------GGSE | KREGMKRSAG | GE---APTTR | HYRSVSMDS- | FIGKLNF--G | 313 |
| SEQ_ID_NO_1461 | ------DSMQ | RREGNKRSAG | GD---APTTR | HYRSVSMDS- | FIGKLNF--N | 303 |

Figure 56 (continued)

```
SEQ_ID_NO_361    TA-------- AAAGNGVALG PN-------- RFSLEFGSGE FTPSEMKKIM  266
SEQ_ID_NO_443    EESP-KLPLP SPGGSLTRSG SGSLEGGAVA LFNMEFTNGE FTDSEKKKIM  307
SEQ_ID_NO_212    DESP-KLPLP SPSGGLSRSG SGSLDGGAAS LFGAEFANGE FTEAEKKKIM  308
SEQ_ID_NO_421    DESP-NLP-T SLMMRSGQLS PSNSGNESSS KHNLDFGNSE FSEAEMKKIM  285
SEQ_ID_NO_1437   DESSLKLP-P SSSA---KVS PTNSGEGNSS AYSVEFGNSE FTAAEMKKIA  358
SEQ_ID_NO_740    NESP-KLP-P SPGTRPGQLS PTDSIDGN-- AFSLDFGNGE FSGAELKKIM  416
SEQ_ID_NO_173    DESP-KLP-P SPGQRGRLMS PAGGIDGNSA AFSLEFGSGE FSGPELKKIM  361
SEQ_ID_NO_1461   DESL-KMP-P SPGG---LMS PGNSGDGNNA AFSLEFGNGE FSGPELKKIM  348

SEQ_ID_NO_361    ADEKLAEMAL ADPKRVKRVL ANRQSAARSK ERKMRYIAEL EQKVQLLQSE  316
SEQ_ID_NO_443    ANERLAEIAL TDPKRVKRIL ANRQSAARSK ERKMRYIQEL EHKVQVLQTE  357
SEQ_ID_NO_212    ANERLAEIAL TDPKRVKRIL ANRQSAARSK ERKMRYIQEL EHKVQVLQTE  358
SEQ_ID_NO_421    ADERLAEIAV LDPKRAKRIL ANRLSAARSK ERKTRYISEL EHKVQKLQTE  335
SEQ_ID_NO_1437   ADEKLAEIVM ADPKRVKRIL ANRVSAARSK ERKTRYMAEL EHKVQTLQTE  408
SEQ_ID_NO_740    ANEKLAEIAL ADPKRAKRIL ANRQSAARSK ERKMRYISEL EHKVQTLQTE  466
SEQ_ID_NO_173    ANEKLAEIAL TDPKRAKRIL ANRQSAARSK ERKMRYISEL EHKVQTLQTE  411
SEQ_ID_NO_1461   ANEKLAEIAM ADPKRAKRIL ANRQSAARSK ERKMRYISEL EHKVQTLQTE  398

SEQ_ID_NO_361    ATNLSAQLTM MQRDSAGLAT QNNELKFRLH AMEQQAQLRD ALNEALTTEV  366
SEQ_ID_NO_443    ATTLSAQLTM LQRDSAGLAT QNNELKIRLQ AMEQQAQLRD ALNEALTAEV  407
SEQ_ID_NO_212    ATTLSAQLTM LQRDSTGLAT QNNELKIRLQ AMEQQAQLRD ALNEALTAEV  408
SEQ_ID_NO_421    TTTLSTQVTI LQKNFVEISS LNSELKFRIQ AMEQQAQLRD ALHEALTAEV  385
SEQ_ID_NO_1437   ATTLSAQLTH LQRDSMGLTN QNSELKFRLQ AMEQQAQLRD ALSEKLNEEV  458
SEQ_ID_NO_740    ATTLSAQLTL LQRDSVGLTN QNNELKFRIQ AMEQQAQLRD ALNEALTAEV  516
SEQ_ID_NO_173    ATTLSAQLTL LQRDSAGLTN QNSELKFRLQ SMEQQAKLRD ALNEALTAEV  461
SEQ_ID_NO_1461   ATTLSAQLTL LQRDSVGLTN QNSELKFRLQ SMEQQAKLRD ALNEALTAEV  448

SEQ_ID_NO_361    QRLKLATAEL GDSCSSSSLA QQLQLNAQNQ MFQL------ -------QQQ  403
SEQ_ID_NO_443    QRLKLATGEV T-DGRMPKGL QQQM---NSQ MLQL------ -------QQL  440
SEQ_ID_NO_212    QRLKLATGEI T-DGRMSKGL QQQM---NSQ LIQL------ ----------  438
SEQ_ID_NO_421    QRLKLAAGEH REEGRLPNNM TQQT-PVKHN IFQM------ ----------  418
SEQ_ID_NO_1437   QRLKLVIGEP NRRQSGSSSS ESKM-SLNPE MFQQ------ ---------L  492
SEQ_ID_NO_740    RRLKIATAEQ GGDSDPSKSM VQQQLSINPQ MYLQQPRPSQ LGMHQLQQQS  566
SEQ_ID_NO_173    QRLKIATAEL SSDSHGSSCL IPQH-SVNPL MFQQ------ -------QPP  497
SEQ_ID_NO_1461   QRLKIVTAEL NGESLPSNCM IPQH-SVNPM MFQQ------ ----------  481
```

Figure 56 (continued)

```
SEQ_ID_NO_361   QATQLPFYQL QQSQ------ ---------Q NGAAKNNESK E  429
SEQ_ID_NO_443   QVQQQAPQAQ QQGQ------ ---------- RQQQQQPQKS A  465
SEQ_ID_NO_212   --QQLQIQQQ QSSQ------ ---------- ----TTQQDR L  457
SEQ_ID_NO_421   --QRQQPSQM QQLS------ -------VGK ASAASATPAS A  444
SEQ_ID_NO_1437  SLSQLQHQQM QHSN------ --------QC STMKAKHTSN D  519
SEQ_ID_NO_740   SASQFNMHQR QRQQQQQQQQ QSSQPQPQQN GNTTPKPDSN Q  607
SEQ_ID_NO_173   SASQQNIHLQ QQQH------ -------RQN GNANSNSDLK Q  525
SEQ_ID_NO_1461  ---QHQHQQH QQQQ------ -------QQN GNANSKNELK Q  506
```

Figure 57

| | | | | | | |
|---|---|---|---|---|---|---|
| SEQ_ID_NO_97 | ----MGMKSP | NIAAFMLPLL | LILFTLSSQL | KVVESTGRKL | -AWGFSGTPI | 45 |
| SEQ_ID_NO_2013 | MKKKMGSKSP | NIGAFVLPLL | LILFTLSSQA | RLIESTGRKL | AAWGFGGAPI | 50 |
| SEQ_ID_NO_2015 | ----MGSKSP | NIAALVLPLL | LILFSLSSQA | RLVESSGRKL | AAWGFGGAPI | 46 |

| | | | | | | | |
|---|---|---|---|---|---|---|---|
| SEQ_ID_NO_97 | VYTPPSRSCG | TSPAVFTSKW | RRPRPCRLPP | GSYIPASDQS | P | 88 |
| SEQ_ID_NO_2013 | IWTPPSNSCG | ASPAVWYPKP | TKRGPCRGPP | GIGIPTSYQS | P | 91 |
| SEQ_ID_NO_2015 | IGTPSSNSCG | ASPAVWYPKP | TKPRPCRRTP | GIGIPTSHQS | P | 87 |

NUCLEOTIDE SEQUENCES AND CORRESPONDING POLYPEPTIDES CONFERRING IMPROVED NITROGEN USE EFFICIENCY CHARACTERISTICS IN PLANTS

This Application is a divisional application of U.S. patent application Ser. No. 14/164,064, filed Jan. 24, 2014, which is a divisional application of U.S. patent application Ser. No. 12/918,609, filed on Nov. 22, 2010, which is a 371 National Phase application of International Application No. PCT/US2009/034638, filed Feb. 20, 2009, which claims priority to U.S. Provisional Application No. 61/030,152, filed on Feb. 20, 2008; each of the entire contents of which are hereby incorporated by reference.

INCORPORATION-BY-REFERENCE OF SEQUENCE LISTING OR TABLE

The material in the accompanying sequence listing is hereby incorporated by reference in its entirety into this application. The accompanying file, named 2009_02_12_SequenceListing_2750_1699WO1.txt was created on Feb. 12, 2009 and is 6.27 MB. The file can be accessed using Microsoft Word on a computer that uses Windows OS.

TECHNICAL FIELD the present invention relates to methods and materials involved in tolerance of a plant to limiting exogenous nitrogen sources. For example, this document provides plants having increased low-nitrogen tolerance levels as well as materials and methods for making plants and plant products having increased low-nitrogen tolerance levels.

BACKGROUND

Nitrogen is often the rate-limiting element in plant growth, and all field crops have a fundamental dependence on exogenous nitrogen sources.

According to a recent study published in Field Crops Research (Volume 100, Issues 2-3, 1 Feb. 2007, Pages 210-217), Nitrogenous fertilizer, which is usually supplied as ammonium nitrate, potassium nitrate, or urea, typically accounts for 40% of the costs associated with crops, such as corn and wheat in intensive agriculture.

Improving nitrogen use efficiency of crop plants is an important goal towards reducing input costs and reducing the environmental consequences of intensive nitrogen fertilization on the environment. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively.

Plants have a number of means to cope with nutrient deficiencies, such as poor nitrogen availability. One important mechanism senses nitrogen availability in the soil and respond accordingly by modulating gene expression while a second mechanism is to sequester or store nitrogen in times of abundance to be used later. The nitrogen sensing mechanism relies on regulated gene expression and enables rapid physiological and metabolic responses to changes in the supply of inorganic nitrogen in the soil by adjusting nitrogen uptake, reduction, partitioning, remobilization and transport in response to changing environmental conditions. Nitrate acts as a signal to initiate a number of responses that serve to reprogram plant metabolism, physiology and development (Redinbaugh et al. (1991) *Physiol. Plant.* 82, 640-650.; Forde (2002) *Annual Review of Plant Biology* 53, 203-224). Nitrogen-inducible gene expression has been characterized for a number of genes in some detail. These include nitrate reductase, nitrite reductase, 6-phosphoglucante dehydrogenase, and nitrate and ammonium transporters (Redinbaugh et al. (1991) *Physiol. Plant.* 82, 640-650; Huber et al. (1994) *Plant Physiol* 106, 1667-1674; Hwang et al. (1997) *Plant Physiol.* 113, 853-862; Redinbaugh et al. (1998) *Plant Science* 134, 129-140; Gazzarrini et al. (1999) *Plant Cell* 11, 937-948; Glass et al. (2002) *J. Exp. Bot.* 53, 855-864; Okamoto et al. (2003) *Plant Cell Physiol.* 44, 304-317).

In the fields of agriculture and forestry, efforts are constantly being made to produce plants with an increased growth potential in order to feed the ever-increasing world population and to guarantee the supply of reproducible raw materials. There is a need for methods of increasing nitrogen use efficiency in plants, which leads to better growth potential and more biomass. This is done conventionally through plant breeding. The breeding process is, however, both time-consuming and labor-intensive. Furthermore, appropriate breeding programs must be performed for each relevant plant species. In addition, although great progresses that have been made about nitrogen utilization and the components involved in nitrogen use efficiency, such as nitrogen uptake, nitrogen assimilation and nitrogen partitioning or remobilization, much is still unknown about many of these complex interactions. Therefore, there is a continuing need for generally applicable processes that improve forest or agricultural plant growth to suit particular needs depending on specific environmental conditions. For example, genes that confer tolerance to growth on low nitrogen supply are valuable product prototypes for manipulating nitrogen use efficiency in plants (Good et al., 2004). One strategy to achieve such desirable traits involves genetic manipulation of plant characteristics through the introduction of exogenous nucleic acids conferring increased efficiency of nitrogen use by plants, which in turn should enable the production of higher yields with existing fertilizer inputs and/or enable existing yields of crops to be obtained with lower fertilizer input, or better yields on soils of poorer quality. Such approaches have the advantage of not usually being limited to one plant species, but instead being transferable among plant species. The present invention relates to a method for increasing growth potential, and/or increasing levels of nitrogen use efficiency in plants, characterized by expression of recombinant DNA molecules stably integrated into the plant genome

SUMMARY

The present invention provides methods and materials related to plants having modulated levels of low-nitrogen tolerance. For example, the present invention provides transgenic plants and plant cells having increased levels of low-nitrogen tolerance, nucleic acids (i.e. isolated polynucleotides), polypeptides encoded thereby used to generate transgenic plants and plant cells having increased levels of low-nitrogen tolerance, and methods for making plants and plant cells having increased levels of low-nitrogen tolerance. Such plants and plant cells can be grown under limiting exogenous nitrogen without stunted growth and diminished yields. Plants having increased low-nitrogen tolerance levels may be useful to produce biomass which may be converted to a liquid fuel or other chemicals and/or to produce food and feed on land that is currently marginally productive, resulting in an overall expansion of arable land.

Methods of producing a plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-57. The tissue has a difference in the level of low-nitrogen tolerance as compared to the corresponding level in tissue of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577. A plant and/or plant tissues produced from the plant cell has a difference in the level of low-nitrogen tolerance as compared to the corresponding level of low-nitrogen tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. A plant and/or plant tissues produced from the plant cell has a difference in the level of low-nitrogen tolerance as compared to the corresponding level low-nitrogen tolerance of a control plant that does not comprise the exogenous nucleic acid.

In another aspect, the invention provides a method of producing a plant, the method comprising growing a plant cell comprising an exogenous nucleic acid that is effective for downregulating an endogenous nucleic acid in the plant cell, wherein the endogenous nucleic acid encodes a polypeptide, and wherein the HMM bit score of the amino acid sequence of the polypeptide is greater than about 20, said HMM based on the amino acid sequences depicted in one of FIGS. 1-57

Methods of modulating the level of low-nitrogen tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-57. A plant and/or plant tissue produced from the plant cell has a difference in the level of low-nitrogen tolerance as compared to the corresponding level of low-nitrogen tolerance of a control plant that does not comprise the exogenous nucleic acid.

In certain embodiments, the HMM bit score of the amino acid sequence of the polypeptide is greater than about 40, using an HMM generated from the amino acid sequences depicted in one of FIGS. 1-57, wherein the polypeptide comprises a Pfam domain having 70 percent or greater sequence identity to a Pfam domain of any one of the polypeptides in the sequence listing.

In another aspect, a method comprises modulating the level of low-nitrogen tolerance in a plant by introducing into a plant cell an exogenous nucleic acid that comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

In another aspect, a method comprises modulating the level of low-nitrogen tolerance in a plant by introducing into a plant cell an exogenous nucleic acid, that comprises a regulatory region operably linked to a nucleotide sequence having 80 percent or greater sequence identity to a nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-57. The plant has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. A plant and/or plant tissue produced from the plant cell has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, or a fragment thereof. A plant and/or plant tissue of a plant produced from the plant cell has a difference in the level of low-nitrogen tolerance as compared to the corresponding level of low-nitrogen tolerance of a control plant that does not comprise the exogenous nucleic acid. A transgenic plant comprising such a plant cell is also provided.

Isolated nucleic acids are also provided. In one aspect, an isolated nucleic acid comprises a nucleotide sequence having 80% or greater sequence identity to the nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. In another aspect, an isolated nucleic acid comprises a nucleotide sequence encoding a polypeptide having 80% or greater sequence identity to the amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577.

In another aspect, methods of identifying a genetic polymorphism associated with variation in the level of low-nitrogen tolerance are provided. The methods include providing a population of plants, and determining whether one or more genetic polymorphisms in the population are genetically linked to the locus for a polypeptide selected from the group consisting of the polypeptides depicted in FIGS. 1-57, SEQ ID NO:556, SEQ ID NO:853, SEQ ID NO:1157, and functional homologs thereof, such as those in the Sequence Listing. The correlation between variation in the level of low-nitrogen tolerance in a tissue in plants of the population and the presence of the one or more genetic polymorphisms in plants of the population is measured, thereby permitting identification of whether or not the one or more genetic polymorphisms are associated with such variation.

In another aspect, the invention provides a method of making a plant line, said method comprising:

a) determining whether one or more genetic polymorphisms in a population of plants is associated with the locus for a polypeptide selected from the group consisting of the polypeptides depicted in FIGS. 1-57, SEQ ID NO: 556, SEQ ID NO: 853, and SEQ ID NO: 1157 and functional homologs thereof;

b) identifying one or more plants in said population in which the presence of at least one allele at said one or more genetic polymorphisms is associated with variation in a trait;

c) crossing each said one or more identified plants with itself or a different plant to produce seed;

d) crossing at least one progeny plant grown from said seed with itself or a different plant; and e) repeating steps c) and d) for an additional 0-5 generations to make said plant line, wherein said at least one allele is present in said plant line.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 and the other alignment figures provided herein were generated using the program MUSCLE version 3.52.

FIG. 5 is an alignment of ME02538 (SEQ ID NO:152) with homologous and/or orthologous amino acid sequences CeresClone:1843642 (SEQ ID NO:154), CeresAnnot:1459112 (SEQ ID NO:158), CeresClone:953633 (SEQ ID NO:162), and CeresClone:587957 (SEQ ID NO:164).

FIG. 6 is an alignment of ME02603 (SEQ ID NO:166) with homologous and/or orthologous amino acid sequences CeresClone:1857256 (SEQ ID NO:168), CeresAnnot:1442042 (SEQ ID NO:170), GI No. 89257469 (SEQ ID NO:174), CeresClone:389818 (SEQ ID NO:177), CeresClone:2019147 (SEQ ID NO:181), GI No. 125537720 (SEQ ID NO:182), GI No. 115443697 (SEQ ID NO:183), and GI No. 20340241 (SEQ ID NO:184).

FIG. 7 is an alignment of ME02613 (SEQ ID NO:186) with homologous and/or orthologous amino acid sequences CeresAnnot:1490274 (SEQ ID NO:188), CeresClone:873093 (SEQ ID NO:193), GI No. 6635384 (SEQ ID NO:194), CeresClone:663726 (SEQ ID NO:196), GI No.

92881411 (SEQ ID NO:197), CeresClone:686525 (SEQ ID NO:199), CeresClone:1524364 (SEQ ID NO:201), CeresClone:1742159 (SEQ ID NO:203), and GI No. 125543535 (SEQ ID NO:204).

FIG. 8 is an alignment of ME02801 (SEQ ID NO:208) with homologous and/or orthologous amino acid sequences CeresClone:981621 (SEQ ID NO:214) and CeresClone:564714 (SEQ ID NO:216).

Figure 9:
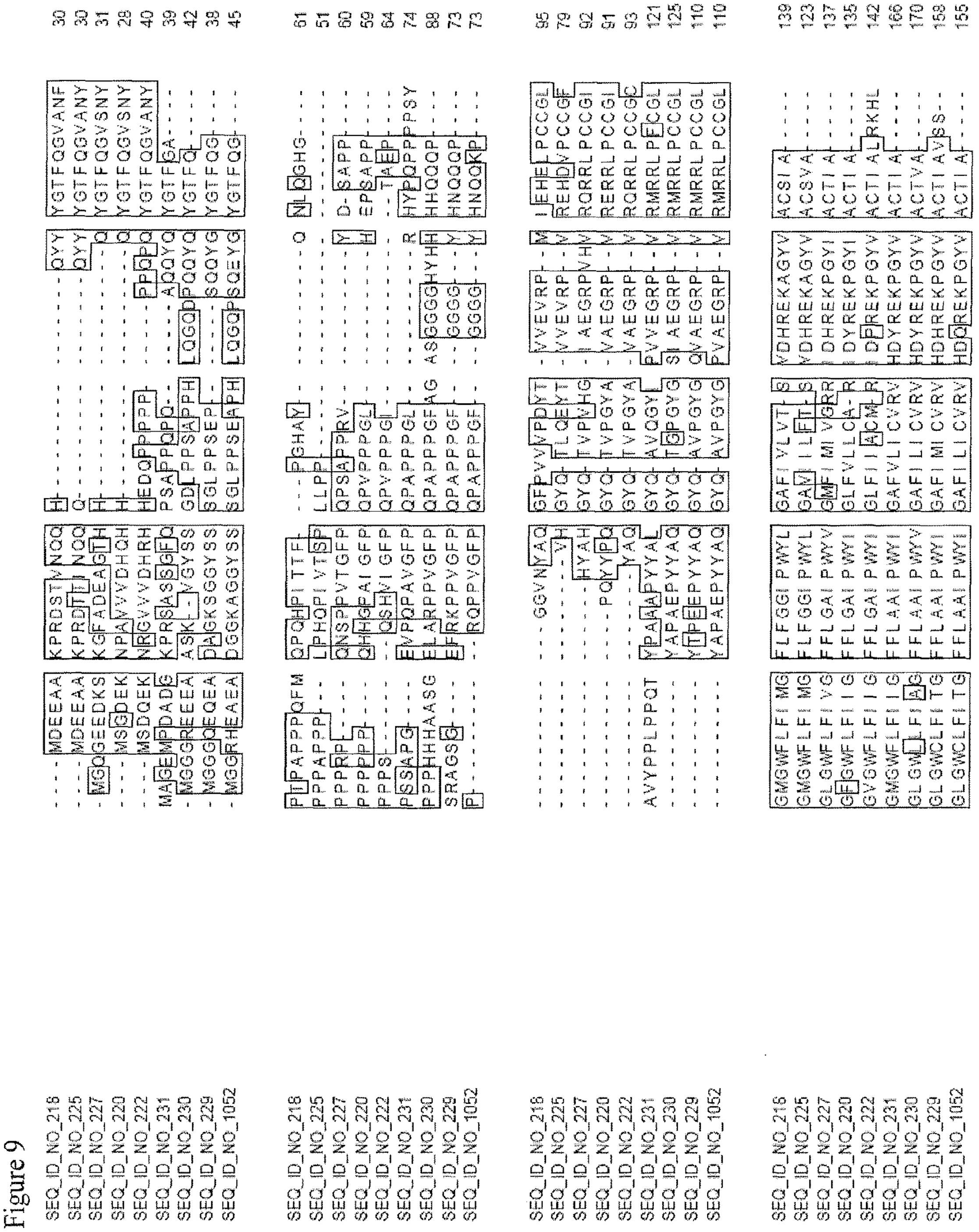

FIG. 9 is an alignment of ME03123 (SEQ ID NO:218) with homologous and/or orthologous amino acid sequences CeresClone:1899168 (SEQ ID NO:220), CeresAnnot:1494669 (SEQ ID NO:222), CeresClone:1017441 (SEQ ID NO:225), CeresClone:1065937 (SEQ ID NO:227), CeresClone:1822919 (SEQ ID NO:229), GI No. 125553329 (SEQ ID NO:230), GI No. 115439053 (SEQ ID NO:231), and CeresAnnot:6040744 (SEQ ID NO:1052).

FIG. 10 is an alignment of ME04204 (SEQ ID NO:234) with homologous and/or orthologous amino acid sequences CeresAnnot:1519952 (SEQ ID NO:236), CeresClone:234768 (SEQ ID NO:241), GI No. 108707052 (SEQ ID NO:242), and GI No. 55978030 (SEQ ID NO:244).

Figure 11:
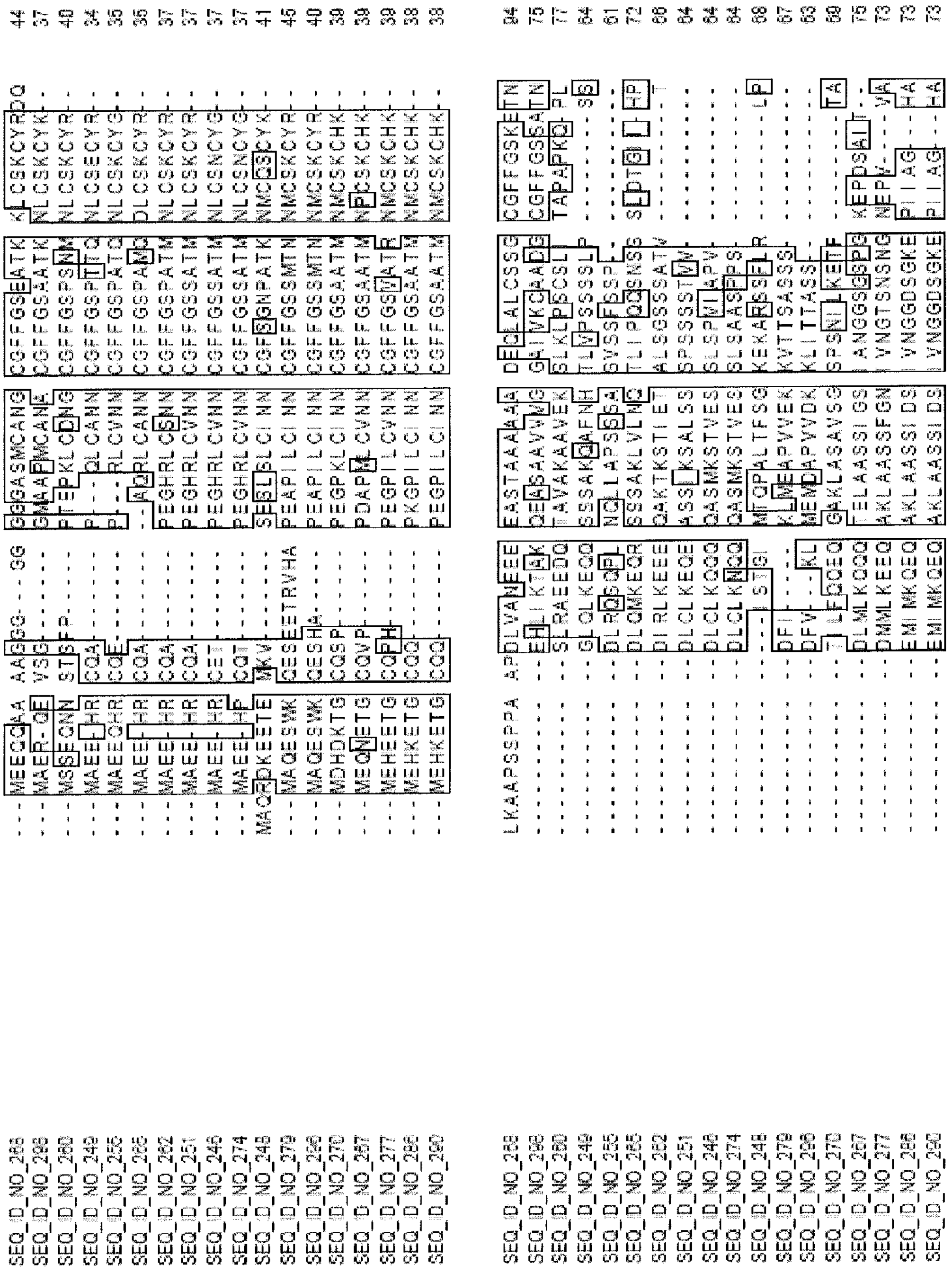
Figure 11:
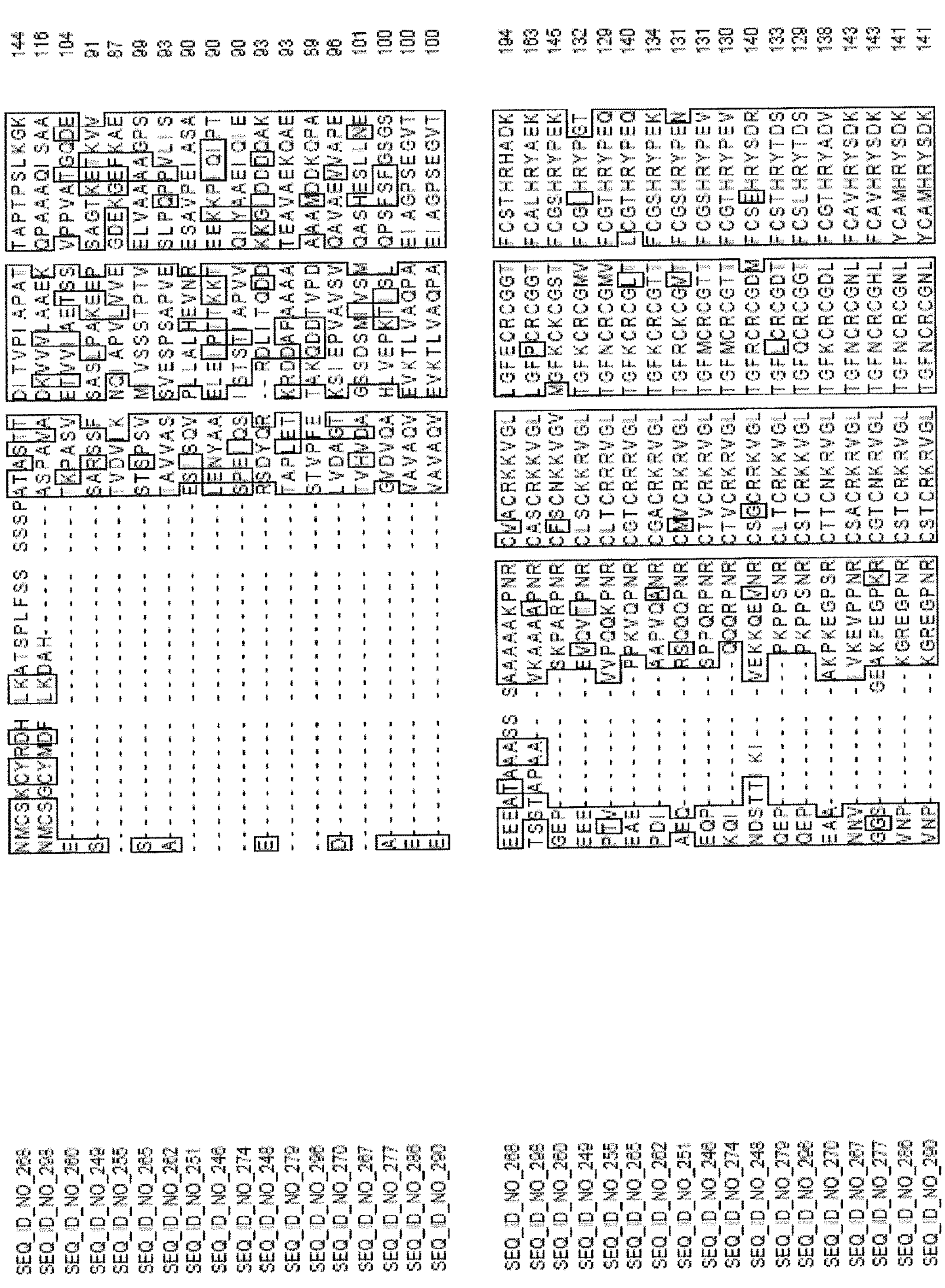

FIG. 11 s an alignment of ME04477 (SEQ ID NO:246) with homologous and/or orthologous amino acid sequences CeresClone:1620215 (SEQ ID NO:248), GI No. 38016527 (SEQ ID NO:249), CeresClone:1798756 (SEQ ID NO:251), CeresAnnot:1460527 (SEQ ID NO:255), GI No. 119720772 (SEQ ID NO:260), CeresClone:708446 (SEQ ID NO:262), GI No. 92896423 (SEQ ID NO:265), GI No. 113196593 (SEQ ID NO:267), GI No. 75133829 (SEQ ID NO:268), CeresClone:1030374 (SEQ ID NO:270), CeresClone:1387149 (SEQ ID NO:274), GI No. 5031281 (SEQ ID NO:277), CeresClone:1775820 (SEQ ID NO:279), GI No. 35187687 (SEQ ID NO:286), GI No. 115468934 (SEQ ID NO:290), GI No. 118424243 (SEQ ID NO:296), and CeresAnnot:6063957 (SEQ ID NO:298).

FIG. 12 is an alignment of ME04507 (SEQ ID NO:300) with homologous and/or orthologous amino acid sequences CeresAnnot:1513514 (SEQ ID NO:302), CeresClone:923483 (SEQ ID NO:310), CeresClone:304357 (SEQ ID NO:312), CeresClone:1902716 (SEQ ID NO:316), GI No. 116309713 (SEQ ID NO:319), GI No. 38345408 (SEQ ID NO:321), and CeresAnnot:6017635 (SEQ ID NO:325).

Figure 13:
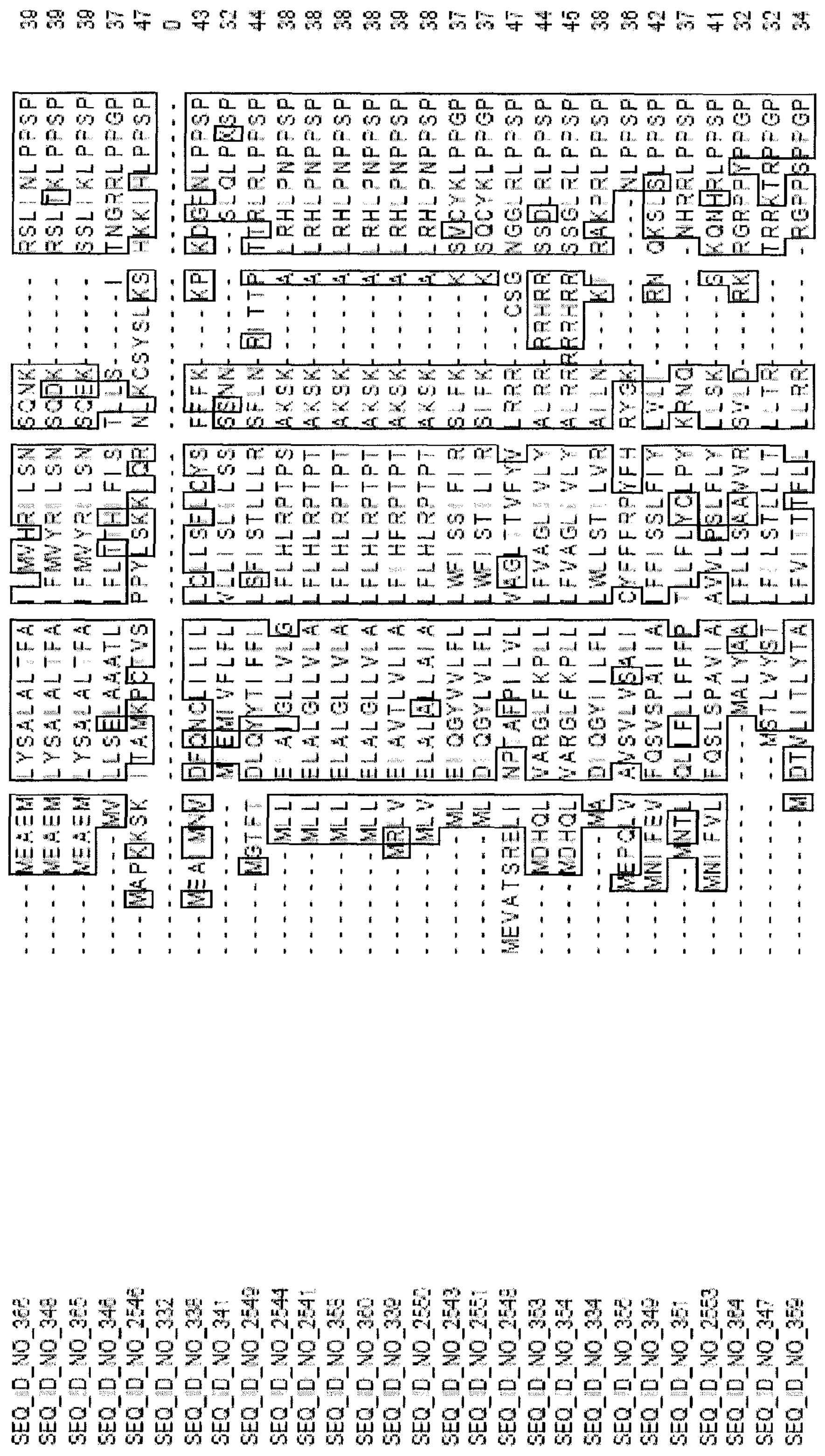
Figure 13:
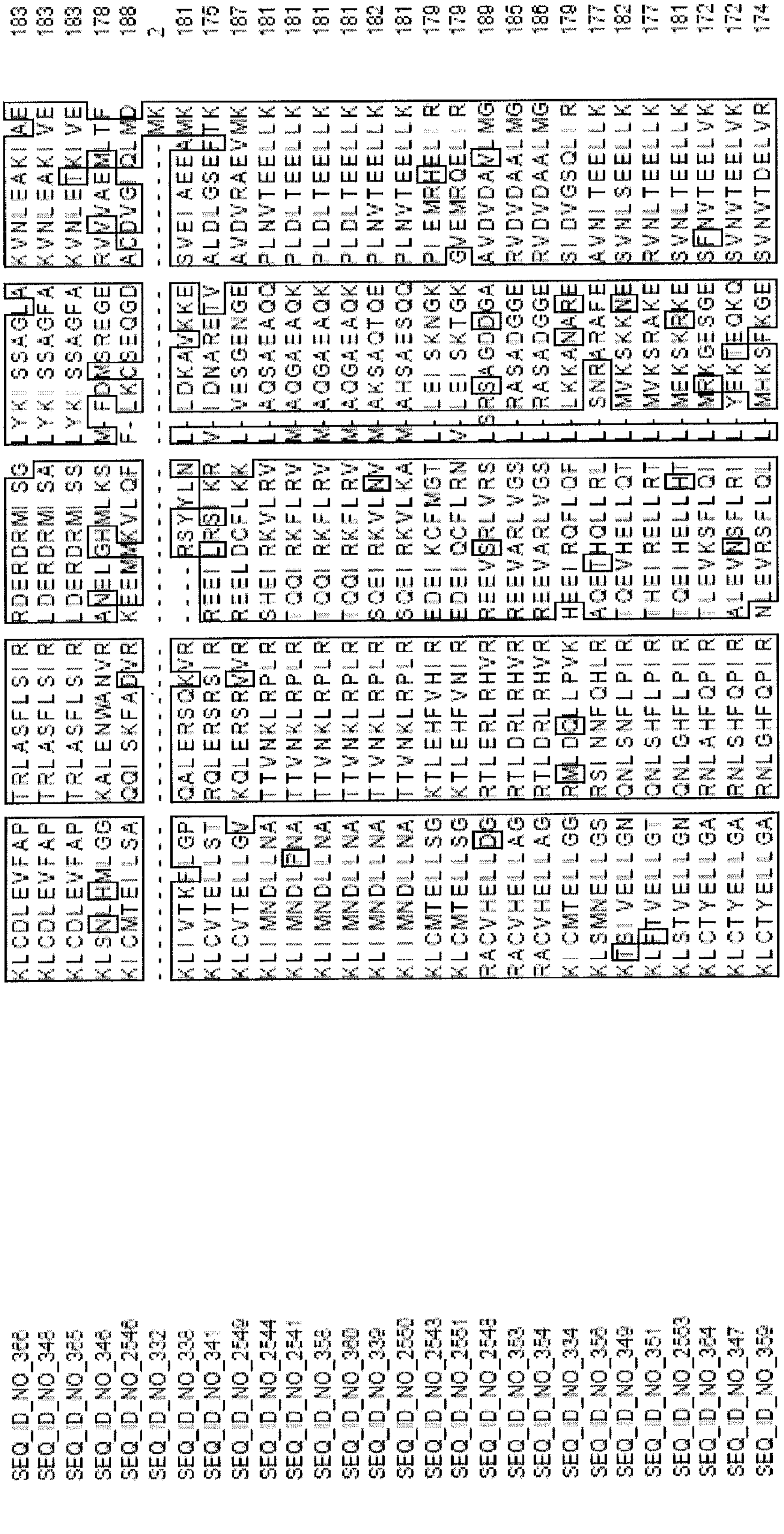
Figure 13:
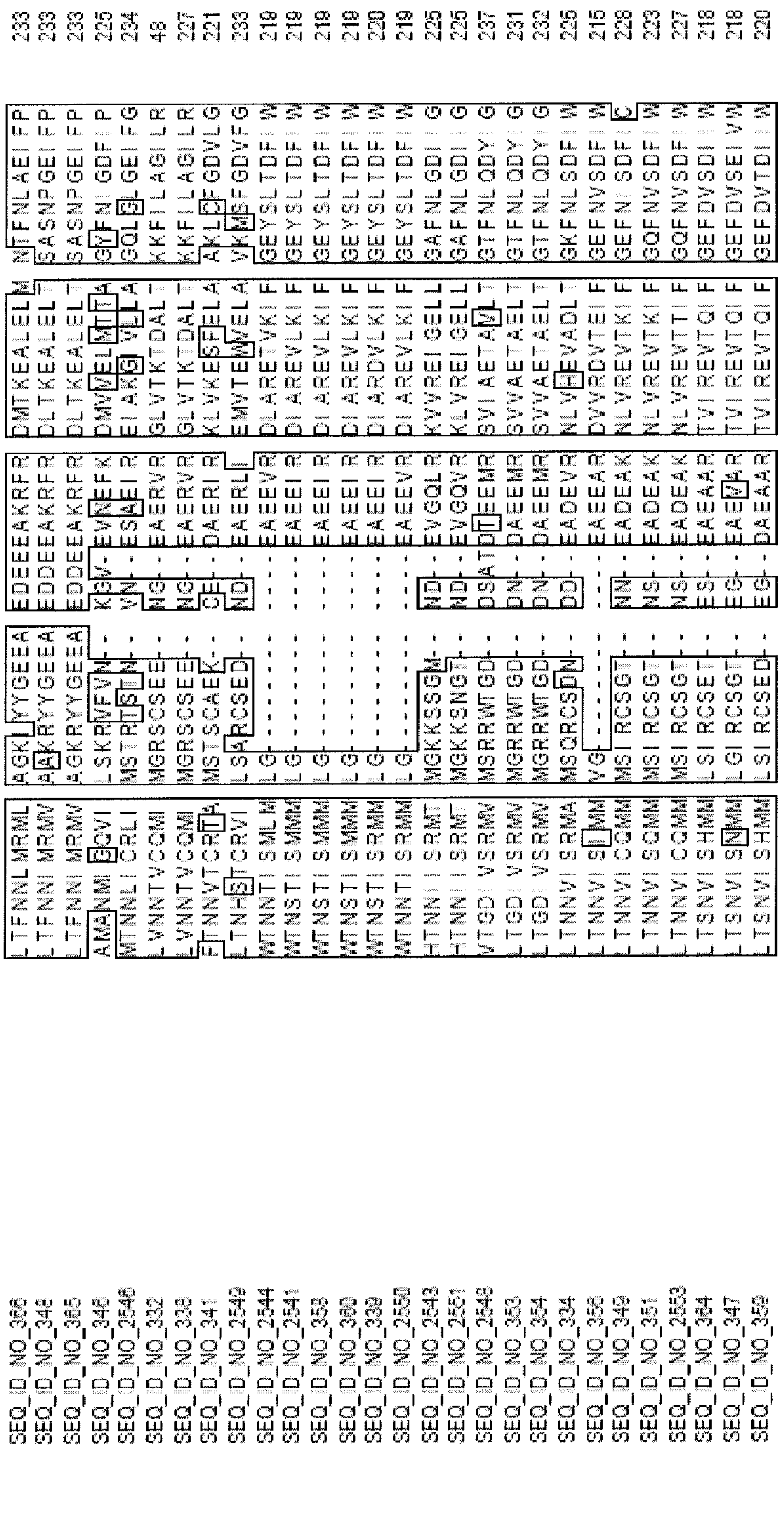
Figure 13:
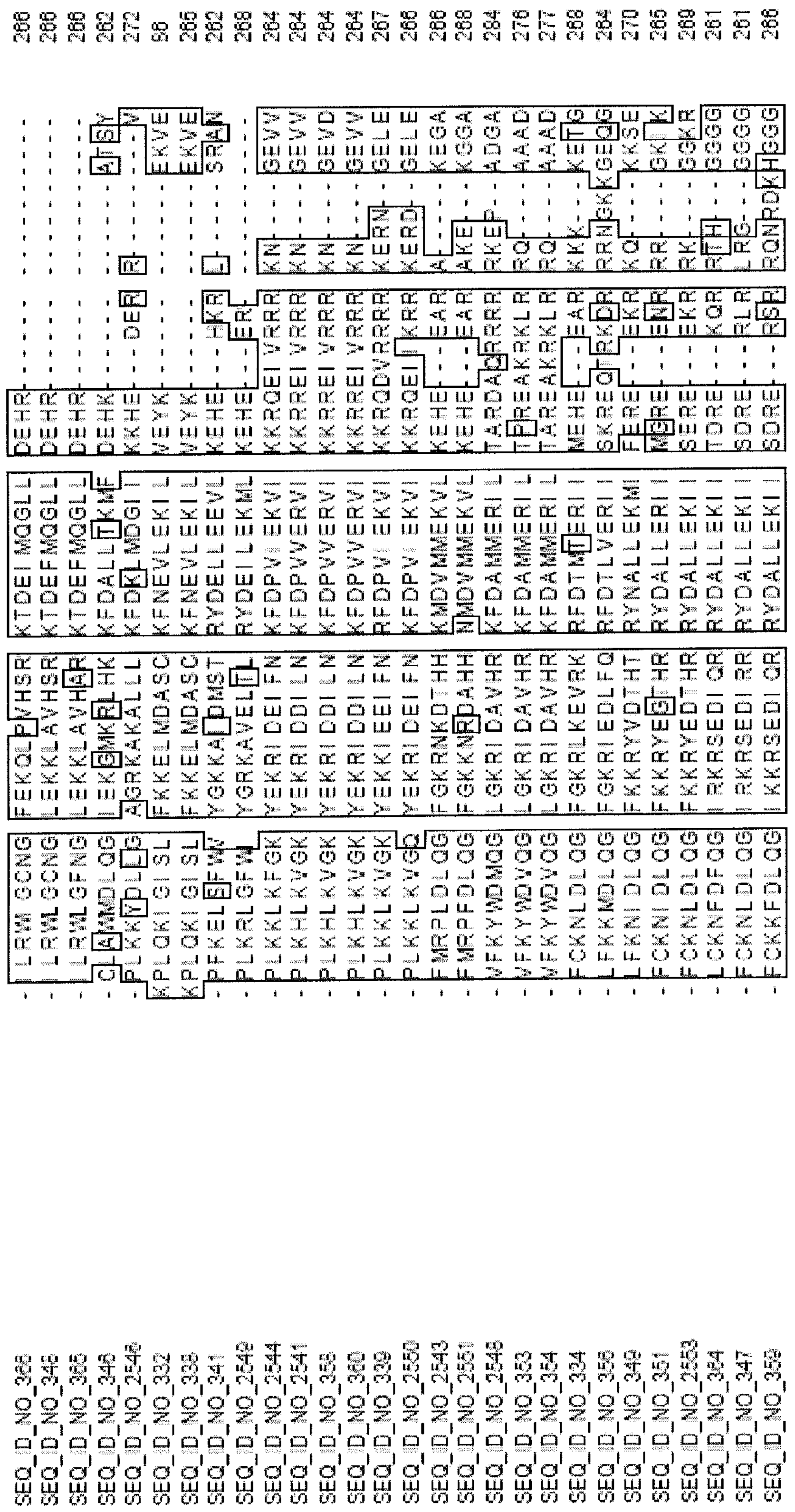
Figure 13:
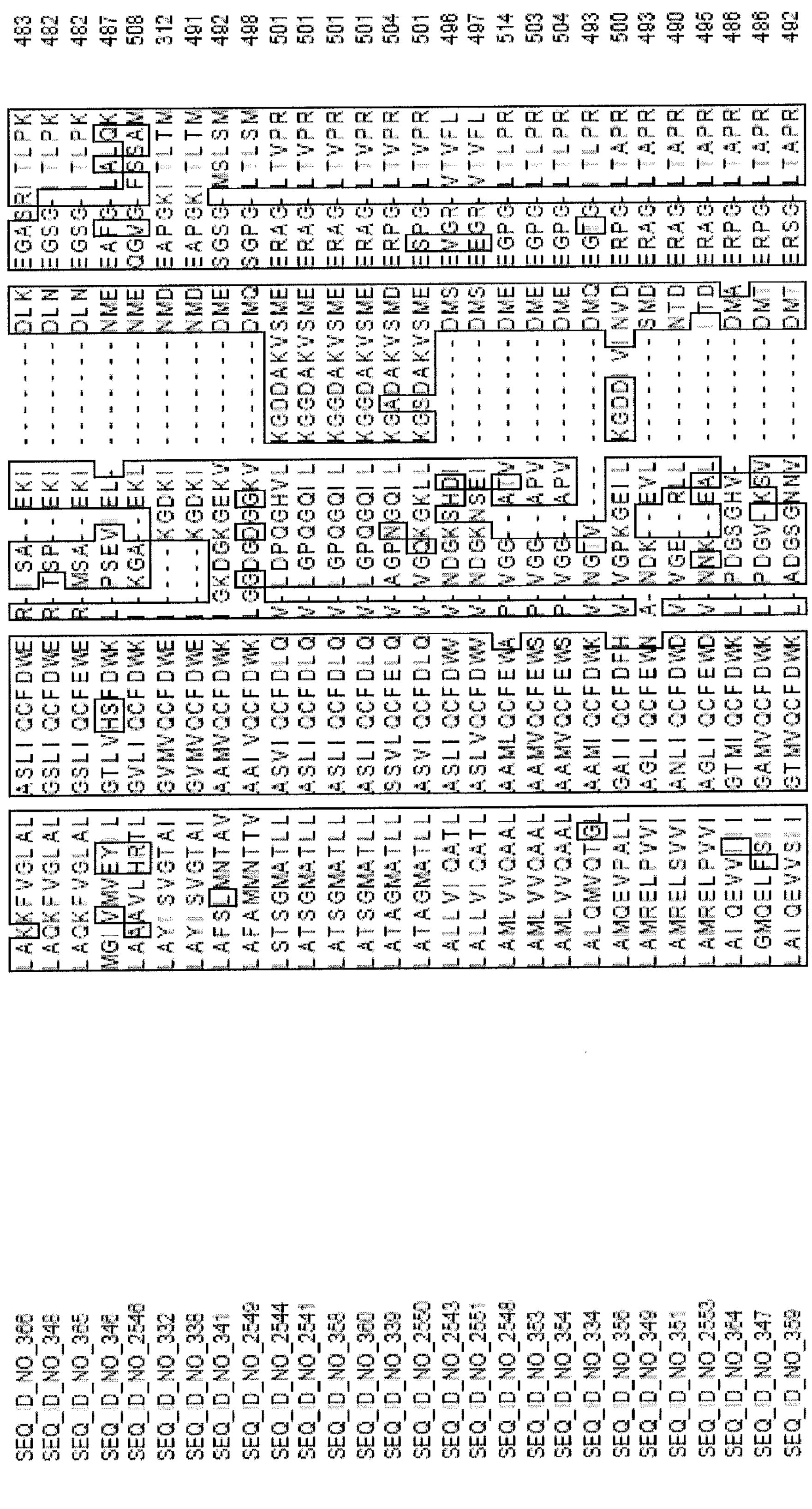

FIG. 13 is an alignment of ME04587 (SEQ ID NO:332) with homologous and/or orthologous amino acid sequences Ceres ANNOT ID no. 1474882 (SEQ ID NO:334), Ceres ANNOT ID no. 553243 (SEQ ID NO:338), Public GI ID no. 5514645 (SEQ ID NO:339), Ceres CLONE ID no. 464376 (SEQ ID NO:341), Public GI ID no. 1345643 (SEQ ID NO:346), Public GI ID no. 5832707 (SEQ ID NO:347), Public GI ID no. 81157968 (SEQ ID NO:348), Public GI ID no. 6118407 (SEQ ID NO:349), Public GI ID no. 5081817 (SEQ ID NO:351), Public GI ID no. 125556057 (SEQ ID NO:353), Public GI ID no. 115468946 (SEQ ID NO:354), Public GI ID no. 5915860 (SEQ ID NO:356), Public GI ID no. 6979544 (SEQ ID NO:358), Public GI ID no. 5832709 (SEQ ID NO:359), Public GI ID no. 6979542 (SEQ ID NO:360), Public GI ID no. 14278923 (SEQ ID NO:364), Public GI ID no. 81157970 (SEQ ID NO:365), Public GI ID no. 81157972 (SEQ ID NO:366), Public GI ID no. 169793907 (SEQ ID NO:2541), Public GI ID no. 84514153 (SEQ ID NO:2543), Public GI ID no. 184202209 (SEQ ID NO:2544), Ceres ANNOT ID no. 8459850 (SEQ ID NO:2546), Ceres ANNOT ID no. 8743452 (SEQ ID NO:2548), Public GI ID no. 157327290 (SEQ ID NO:2549), Public GI ID no. 148839039 (SEQ ID NO:2550), Public GI ID no. 197209782 (SEQ ID NO:2551), Public GI ID no. 171906244 (SEQ ID NO:2553).

Figure 14:
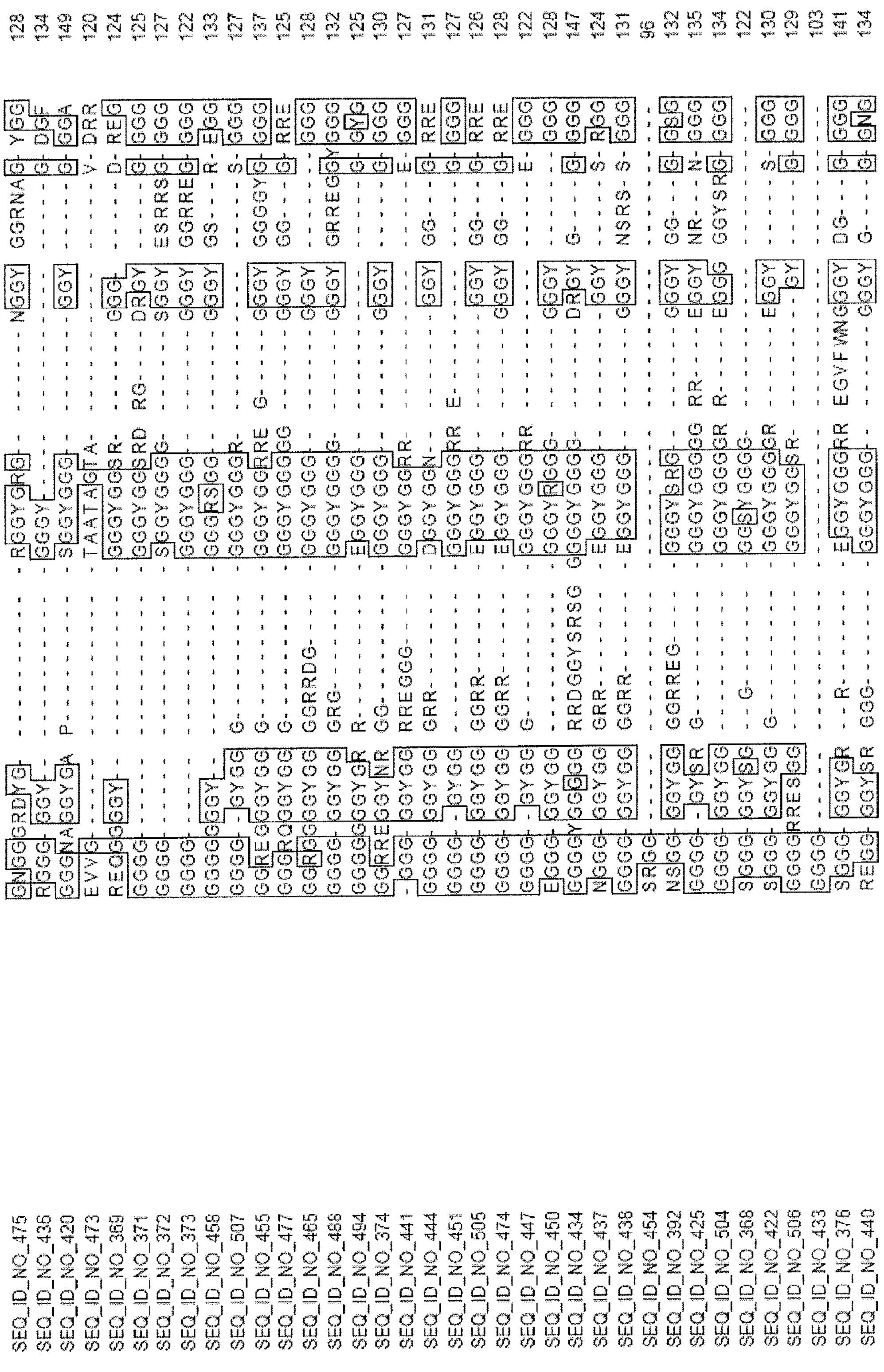

FIG. 14 is an alignment of ME04753 (SEQ ID NO:368) with homologous and/or orthologous amino acid sequences GI No. 21388658 (SEQ ID NO:369), GI No. 4704605 (SEQ ID NO:371), GI No. 90704785 (SEQ ID NO:372), GI No. 115529229 (SEQ ID NO:373), GI No. 20152613 (SEQ ID NO:374), CeresClone:1916226 (SEQ ID NO:376), CeresAnnot:1460836 (SEQ ID NO:392), GI No. 83032218 (SEQ ID NO:420), GI No. 1346180 (SEQ ID NO:422), CeresClone:621487 (SEQ ID NO:425), GI No. 6273331 (SEQ ID NO:433), GI No. 92874469 (SEQ ID NO:434), GI No. 1778374 (SEQ ID NO:436), GI No. 18076086 (SEQ ID NO:437), GI No. 2674201 (SEQ ID NO:438), GI No. 2267567 (SEQ ID NO:440), GI No. 544426 (SEQ ID NO:441), GI No. 6911144 (SEQ ID NO:444), GI No. 469071 (SEQ ID NO:447), GI No. 1934994 (SEQ ID NO:450), GI No. 82623423 (SEQ ID NO:451), GI No. 90265701 (SEQ ID NO:454), GI No. 544423 (SEQ ID NO:455), CeresClone:1320097 (SEQ ID NO:458), CeresClone:1469740 (SEQ ID NO:465), CeresClone:1740834 (SEQ ID NO:473), GI No. 2226370 (SEQ ID NO:474), GI No. 27527723 (SEQ ID NO:475), CeresClone:1762613 (SEQ ID NO:477), GI No. 125545195 (SEQ ID NO:488), GI No. 108710322 (SEQ ID NO:494), GI No. 34851124 (SEQ ID NO:504), GI No. 111162637 (SEQ ID NO:505), GI No. 7024451 (SEQ ID NO:506), and GI No. 1229138 (SEQ ID NO:507).

FIG. 15 is an alignment of ME04772 (SEQ ID NO:510) with homologous and/or orthologous amino acid sequences GI No. 38016521 (SEQ ID NO:511), CeresClone:1895044 (SEQ ID NO:513), CeresAnnot:1512198 (SEQ ID NO:517), CeresClone:682503 (SEQ ID NO:521), CeresClone:685324 (SEQ ID NO:523), CeresClone:1384414 (SEQ ID NO:525), CeresClone:1739919 (SEQ ID NO:527), CeresClone:2002832 (SEQ ID NO:529), GI No. 125531563 (SEQ ID NO:530), and GI No. 115478344 (SEQ ID NO:531).

Figure 16:
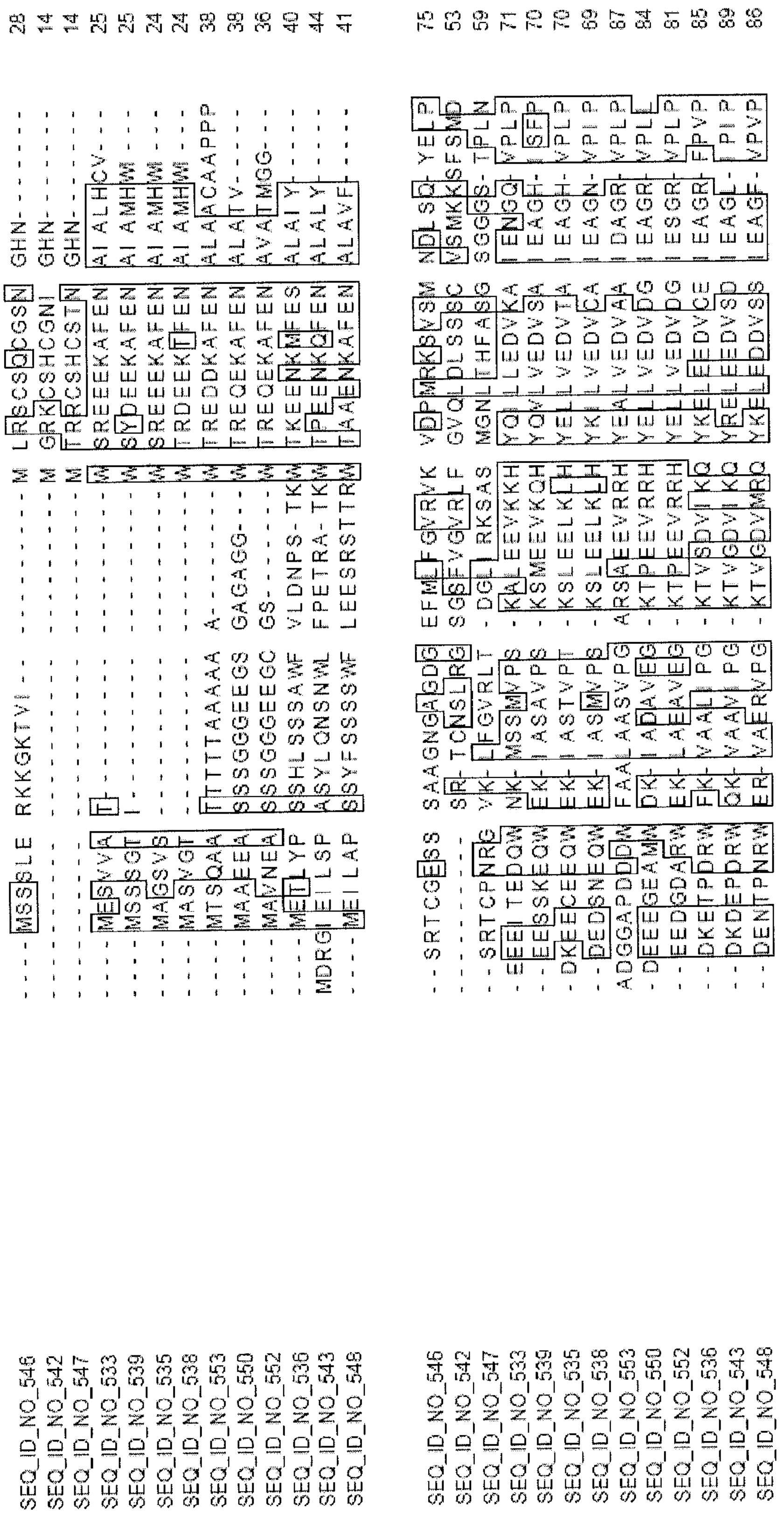

FIG. 16 is an alignment of ME04909 (SEQ ID NO:533) with homologous and/or orthologous amino acid sequences CeresClone:1839156 (SEQ ID NO:535), GI No. 56605378 (SEQ ID NO:536), CeresAnnot:1467946 (SEQ ID NO:538), GI No. 110931704 (SEQ ID NO:539), GI No. 92869601 (SEQ ID NO:542), GI No. 12005328 (SEQ ID NO:543), GI No. 119331596 (SEQ ID NO:546), GI No. 7705206 (SEQ ID NO:547), GI No. 18874263 (SEQ ID NO:548), CeresClone:753605 (SEQ ID NO:550), CeresClone:291733 (SEQ ID NO:552), and GI No. 21902114 (SEQ ID NO:553).

Figure 17:
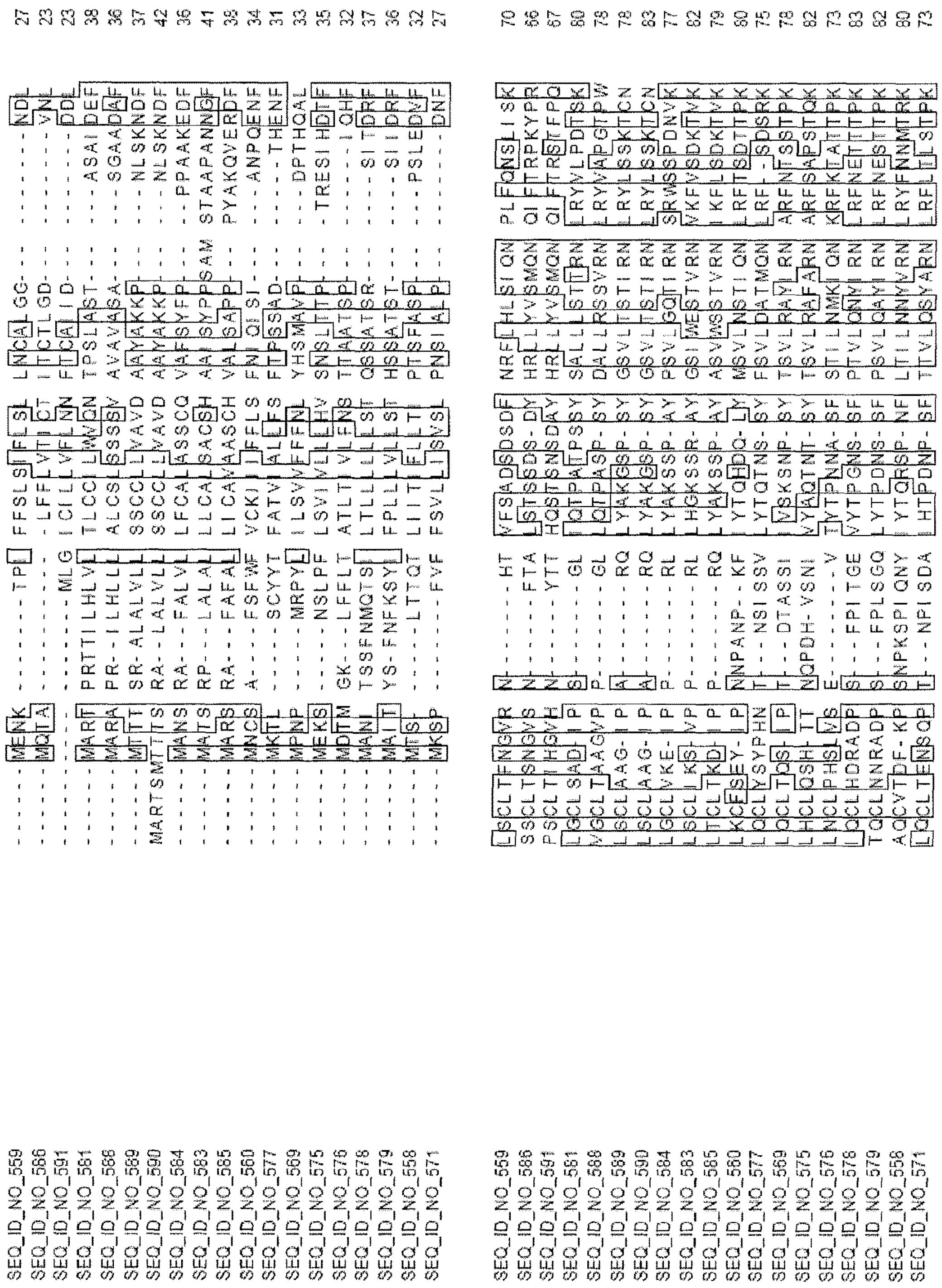
Figure 17:

FIG. 17 is an alignment of ME05194 (SEQ ID NO:558) with homologous and/or orthologous amino acid sequences GI No. 400972 (SEQ ID NO:559), GI No. 81158002 (SEQ ID NO:560), CeresClone:1834135 (SEQ ID NO:569), CeresAnnot:1467218 (SEQ ID NO:571), CeresClone:1104143 (SEQ ID NO:575), GI No. 87240745 (SEQ ID NO:576), GI No. 13161397 (SEQ ID NO:577), GI No. 18652400 (SEQ ID NO:578), GI No. 18652398 (SEQ ID NO:579), CeresClone:778892 (SEQ ID NO:581), CeresClone:222523 (SEQ ID NO:583), GI No. 82492267 (SEQ ID NO:584), GI No. 41393750 (SEQ ID NO:585), GI No. 4335857 (SEQ ID NO:586), CeresClone:1776394 (SEQ ID NO:588), GI No. 125555681 (SEQ ID NO:589), GI No. 115468460 (SEQ ID NO:590), and GI No. 51980210 (SEQ ID NO:591).

FIG. 18 is an alignment of ME05267 (SEQ ID NO:593) with homologous and/or orthologous amino acid sequences CeresAnnot:1511954 (SEQ ID NO:595), CeresClone:560687 (SEQ ID NO:599), CeresClone:579724 (SEQ ID NO:603), CeresClone:286197 (SEQ ID NO:605), and GI No. 115489090 (SEQ ID NO:610).

FIG. 19 is an alignment of ME05300 (SEQ ID NO:613) with homologous and/or orthologous amino acid sequences CeresAnnot:6431448 (SEQ ID NO:615), CeresClone:969084 (SEQ ID NO:620), CeresClone:471052 (SEQ ID NO:622), CeresClone:733048 (SEQ ID NO:624), CeresClone:1062332 (SEQ ID NO:626), CeresClone:1743166 (SEQ ID NO:634), CeresClone:1778589 (SEQ ID NO:638), GI No. 125548354 (SEQ ID NO:643), and GI No. 115458464 (SEQ ID NO:644).

FIG. 20 is an alignment of ME05341 (SEQ ID NO:646) with homologous and/or orthologous amino acid sequences CeresClone:1808421 (SEQ ID NO:648), CeresAnnot:1452653 (SEQ ID NO:656), CeresClone:1660955 (SEQ ID NO:660), CeresClone:1287179 (SEQ ID NO:668), CeresClone:1770929 (SEQ ID NO:676), GI No. 125542421 (SEQ ID NO:679), GI No. 115450741 (SEQ ID NO:681), and CeresAnnot:6063505 (SEQ ID NO:685).

FIG. 21 is an alignment of ME05392 (SEQ ID NO:687) with homologous and/or orthologous amino acid sequences CeresClone:1841531 (SEQ ID NO:689), CeresAnnot:1507382 (SEQ ID NO:691), CeresClone:978410 (SEQ ID NO:699), CeresClone:527314 (SEQ ID NO:703), GI No. 92893019 (SEQ ID NO:706), CeresClone:638935 (SEQ ID NO:708), CeresClone:1437744 (SEQ ID NO:712), CeresClone:1728293 (SEQ ID NO:718), GI No. 125526460 (SEQ ID NO:721), GI No. 115463325 (SEQ ID NO:724), and GI No. 40642817 (SEQ ID NO:728).

FIG. 22 is an alignment of ME05429 (SEQ ID NO:730) with homologous and/or orthologous amino acid sequences CeresAnnot:1539629 (SEQ ID NO:732), CeresClone:682471 (SEQ ID NO:735), CeresClone:729869 (SEQ ID NO:737), GI No. 115459766 (SEQ ID NO:738), and CeresAnnot: 6026765 (SEQ ID NO:742).

FIG. 23 is an alignment of ME05493 (SEQ ID NO:746) with homologous and/or orthologous amino acid sequences CeresAnnot:1455092 (SEQ ID NO:748), GI No. 15229284 (SEQ ID NO:751), CeresClone:961796 (SEQ ID NO:753), CeresClone:706956 (SEQ ID NO:755), GI No. 87162911 (SEQ ID NO:758), CeresClone:1061446 (SEQ ID NO:760), GI No. 125540686 (SEQ ID NO:761), GI No. 115447931 (SEQ ID NO:762), GI No. 20152976 (SEQ ID NO:763), and CeresAnnot:6007280 (SEQ ID NO:765).

FIG. 24 is an alignment of ME05885 (SEQ ID NO:769) with homologous and/or orthologous amino acid sequences CeresClone:1808741 (SEQ ID NO:771), CeresAnnot:1437729 (SEQ ID NO:773), CeresClone:952789 (SEQ ID NO:777), CeresClone:724313 (SEQ ID NO:779), CeresClone:791239 (SEQ ID NO:783), CeresClone:208975 (SEQ ID NO:785), CeresClone:1727075 (SEQ ID NO:789), and GI No. 115475611 (SEQ ID NO:790).

FIG. 25 is an alignment of ME07344 (SEQ ID NO:792) with homologous and/or orthologous amino acid sequences CeresClone:1843695 (SEQ ID NO:794), GI No. 56605376 (SEQ ID NO:799), CeresAnnot:1508502 (SEQ ID NO:801), CeresClone:1239229 (SEQ ID NO:805), GI No. 92893962 (SEQ ID NO:808), CeresClone:327364 (SEQ ID NO:810), CeresClone:1820378 (SEQ ID NO:816), GI No. 125524748 (SEQ ID NO:819), and GI No. 115435036 (SEQ ID NO:821).

FIG. 26 is an alignment of ME07859 (SEQ ID NO:824) with homologous amino acid sequence Fragment_of_Ceres ANNOT ID no. 6007357 (SEQ ID NO:826), Fragment_of_Ceres CLONE ID no. 771707 (SEQ ID NO:1708), and Fragment_of_Ceres CLONE ID no. 1790436 (SEQ ID NO:1713).

FIG. 27 is an alignment of ME08464 (SEQ ID NO:828) with homologous and/or orthologous amino acid sequences CeresAnnot:1499777 (SEQ ID NO:832), GI No. 22328730 (SEQ ID NO:837), GI No. 92886131 (SEQ ID NO:839), GI No. 559921 (SEQ ID NO:840), CeresClone:910787 (SEQ ID NO:842), CeresClone:1797432 (SEQ ID NO:844), GI No. 116310135 (SEQ ID NO:845), GI No. 38345464 (SEQ ID NO:847), and GI No. 90657544 (SEQ ID NO:850).

FIG. 28 is an alignment of ME11735 (SEQ ID NO:855) with homologous and/or orthologous amino acid sequences GI No. 35187445 (SEQ ID NO:856), CeresClone:1798230 (SEQ ID NO:858), CeresAnnot:1500963 (SEQ ID NO:862), CeresClone:567542 (SEQ ID NO:868), CeresClone:702251 (SEQ ID NO:870), CeresClone:1606777 (SEQ ID NO:876), CeresClone:1789146 (SEQ ID NO:878), GI No. 116309500 (SEQ ID NO:885), and GI No. 115446281 (SEQ ID NO:886).

Figure 29:
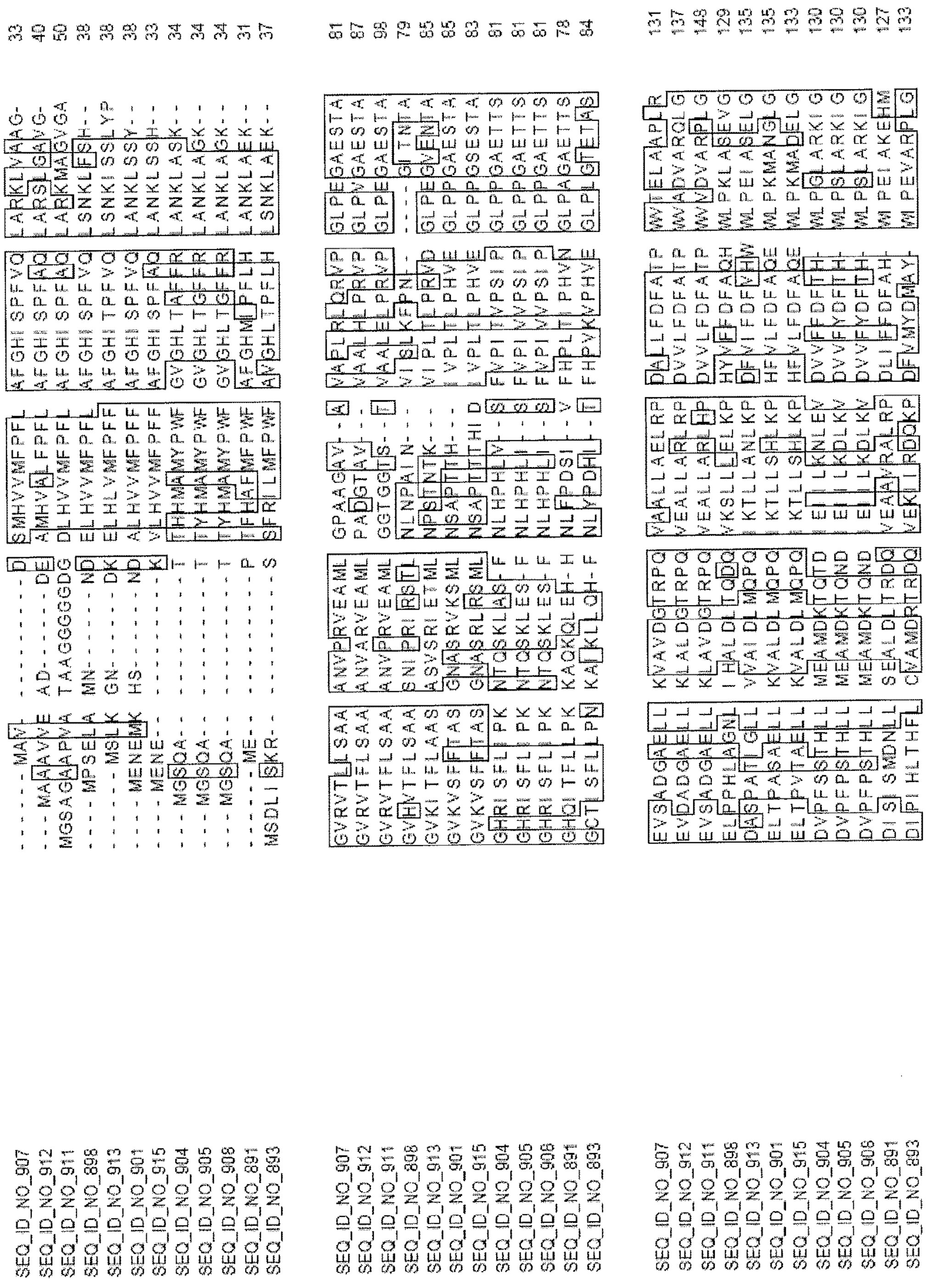
Figure 29:

FIG. 29 is an alignment of ME12910 (SEQ ID NO:891) with homologous and/or orthologous amino acid sequences CeresAnnot:1466353 (SEQ ID NO:893), CeresClone:519143 (SEQ ID NO:898), GI No. 2501497 (SEQ ID NO:901), GI No. 119394507 (SEQ ID NO:904), GI No. 62857206 (SEQ ID NO:905), CeresClone:766529 (SEQ ID NO:907), GI No. 62857204 (SEQ ID NO:908), GI No. 125534279 (SEQ ID NO:911), GI No. 115485437 (SEQ ID NO:912), GI No. 23955910 (SEQ ID NO:913), and GI No. 22759895 (SEQ ID NO:915).

Figure 30:
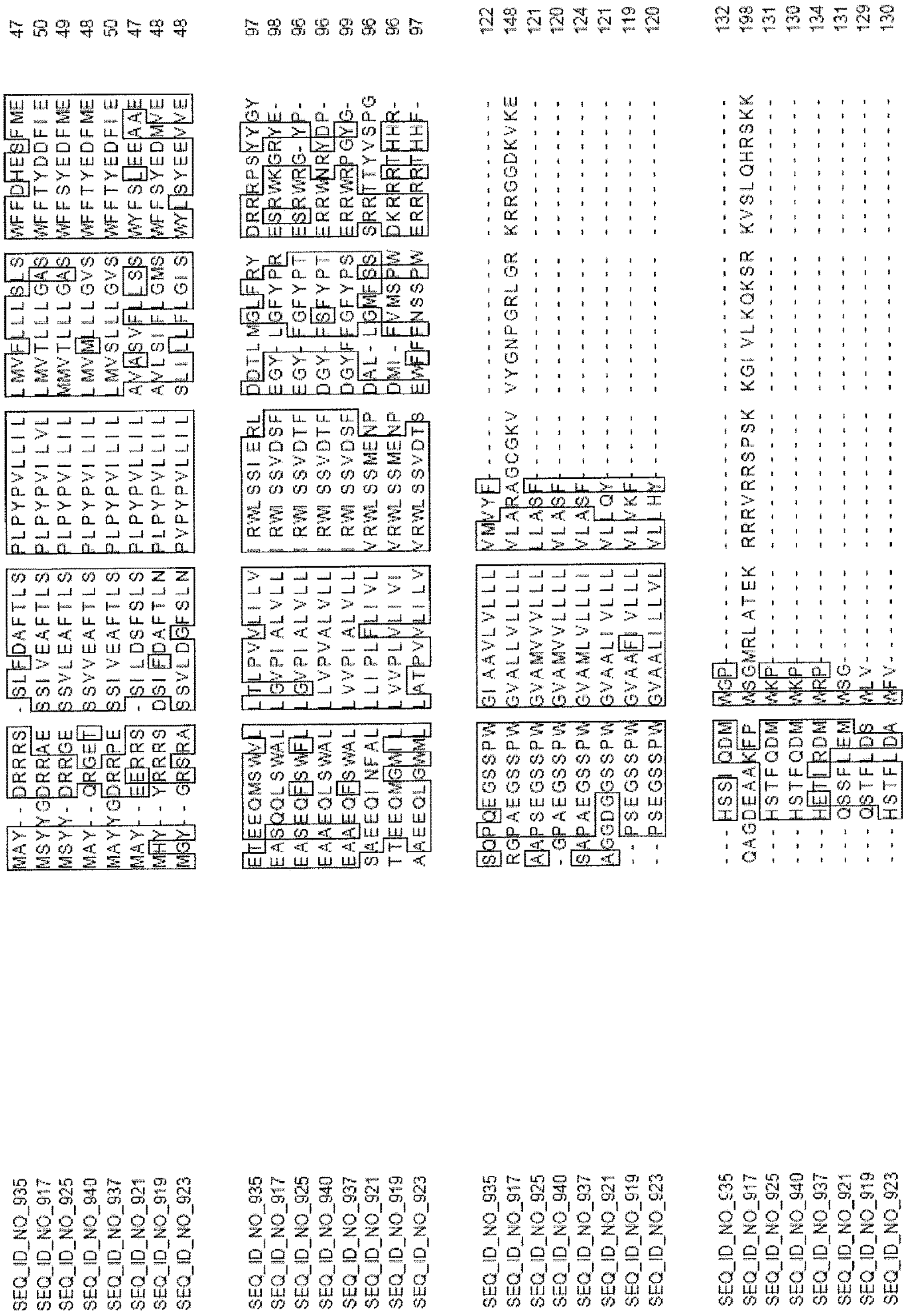

FIG. 30 is an alignment of ME12927 (SEQ ID NO:917) with homologous and/or orthologous amino acid sequences CeresAnnot:1503548 (SEQ ID NO:919), CeresClone:37778 (SEQ ID NO:921), CeresClone:681297 (SEQ ID NO:923), CeresClone:575835 (SEQ ID NO:925), CeresClone:1714750 (SEQ ID NO:935), CeresClone:1721907 (SEQ ID NO:937), and GI No. 115451923 (SEQ ID NO:940).

FIG. 31 is an alignment of ME12929 (SEQ ID NO:944) with homologous and/or orthologous amino acid sequences CeresAnnot:1447562 (SEQ ID NO:946), GI No. 98962139 (SEQ ID NO:947), CeresClone:641607 (SEQ ID NO:950), CeresClone:1715150 (SEQ ID NO:962), CeresClone:1873767 (SEQ ID NO:964), GI No. 115468306 (SEQ ID NO:967), and CeresAnnot:6059980 (SEQ ID NO:972).

FIG. 32 is an alignment of ME12954 (SEQ ID NO:976) with homologous and/or orthologous amino acid sequences CeresClone:957229 (SEQ ID NO:978) and CeresAnnot:1496202 (SEQ ID NO:980).

FIG. 33 is an alignment of ME12970 (SEQ ID NO:982) with homologous and/or orthologous amino acid sequences CeresClone:1935438 (SEQ ID NO:984), GI No. 117573664 (SEQ ID NO:985), GI No. 68349002 (SEQ ID NO:991), GI No. 68348998 (SEQ ID NO:992), CeresAnnot:1497170 (SEQ ID NO:995), GI No. 15221718 (SEQ ID NO:996), GI No. 3860331 (SEQ ID NO:1001), CeresClone:1075911 (SEQ ID NO:1003), GI No. 2920839 (SEQ ID NO:1008), CeresClone:698452 (SEQ ID NO:1011), CeresClone:2019456 (SEQ ID NO:1023), GI No. 90399071 (SEQ ID NO:1026), GI No. 115459588 (SEQ ID NO:1028), and GI No. 68349016 (SEQ ID NO:1032).

Figure 34:
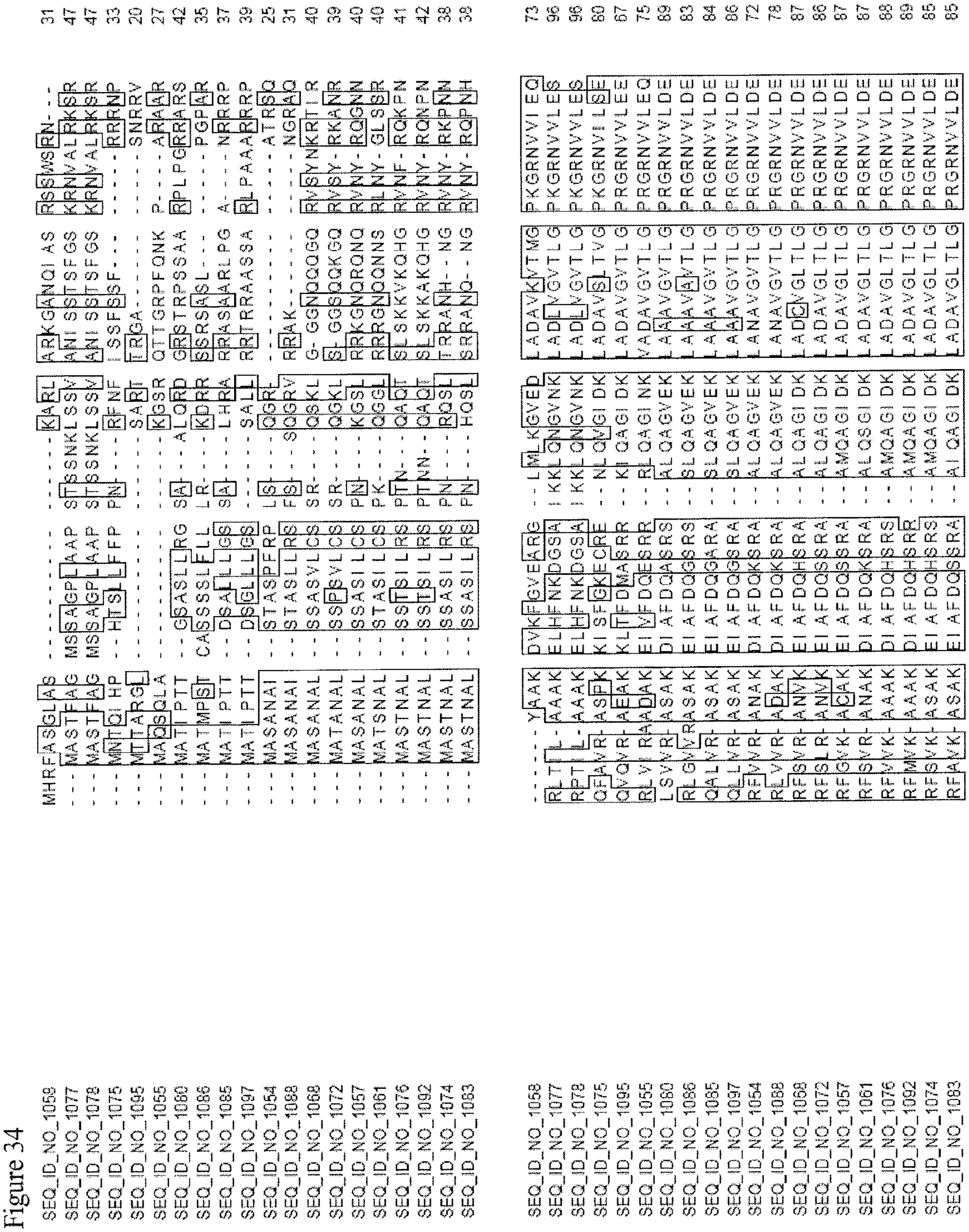

FIG. 34 is an alignment of ME13021 (SEQ ID NO:1054) with homologous and/or orthologous amino acid sequences GI No. 2493647 (SEQ ID NO:1055), CeresClone:1924252 (SEQ ID NO:1057), GI No. 461736 (SEQ ID NO:1058), CeresAnnot:1542060 (SEQ ID NO:1061), GI No. 15226314 (SEQ ID NO:1068), GI No. 464727 (SEQ ID NO:1072), CeresClone:480644 (SEQ ID NO:1074), GI No. 124301264 (SEQ ID NO:1075), GI No. 1710807 (SEQ ID NO:1076), GI No. 110349923 (SEQ ID NO:1077), GI No. 1762130 (SEQ ID NO:1078), CeresClone:706098 (SEQ ID NO:1080), GI No. 3790441 (SEQ ID NO:1083), CeresClone:1795282 (SEQ ID NO:1085), GI No. 125546535 (SEQ ID NO:1086), GI No. 115488160 (SEQ ID NO:1088), GI No. 84468456 (SEQ ID NO:1092), GI No. 116060917 (SEQ ID NO:1095), and CeresAnnot:6039555 (SEQ ID NO:1097).

FIG. 35 is an alignment of ME13064 (SEQ ID NO:1099) with homologous and/or orthologous amino acid sequences CeresAnnot:1528508 (SEQ ID NO:1101), CeresClone:9248 (SEQ ID NO:1103), GI No. 87240560 (SEQ ID NO:1105), GI No. 19453 (SEQ ID NO:1106), CeresClone:1795329 (SEQ ID NO:1108), and GI No. 108862979 (SEQ ID NO:1109).

FIG. 36 is an alignment of ME13071 (SEQ ID NO:1112) with homologous and/or orthologous amino acid sequences GI No. 125541485 (SEQ ID NO:1113), and GI No. 115449245 (SEQ ID NO:1114).

Figure 37:
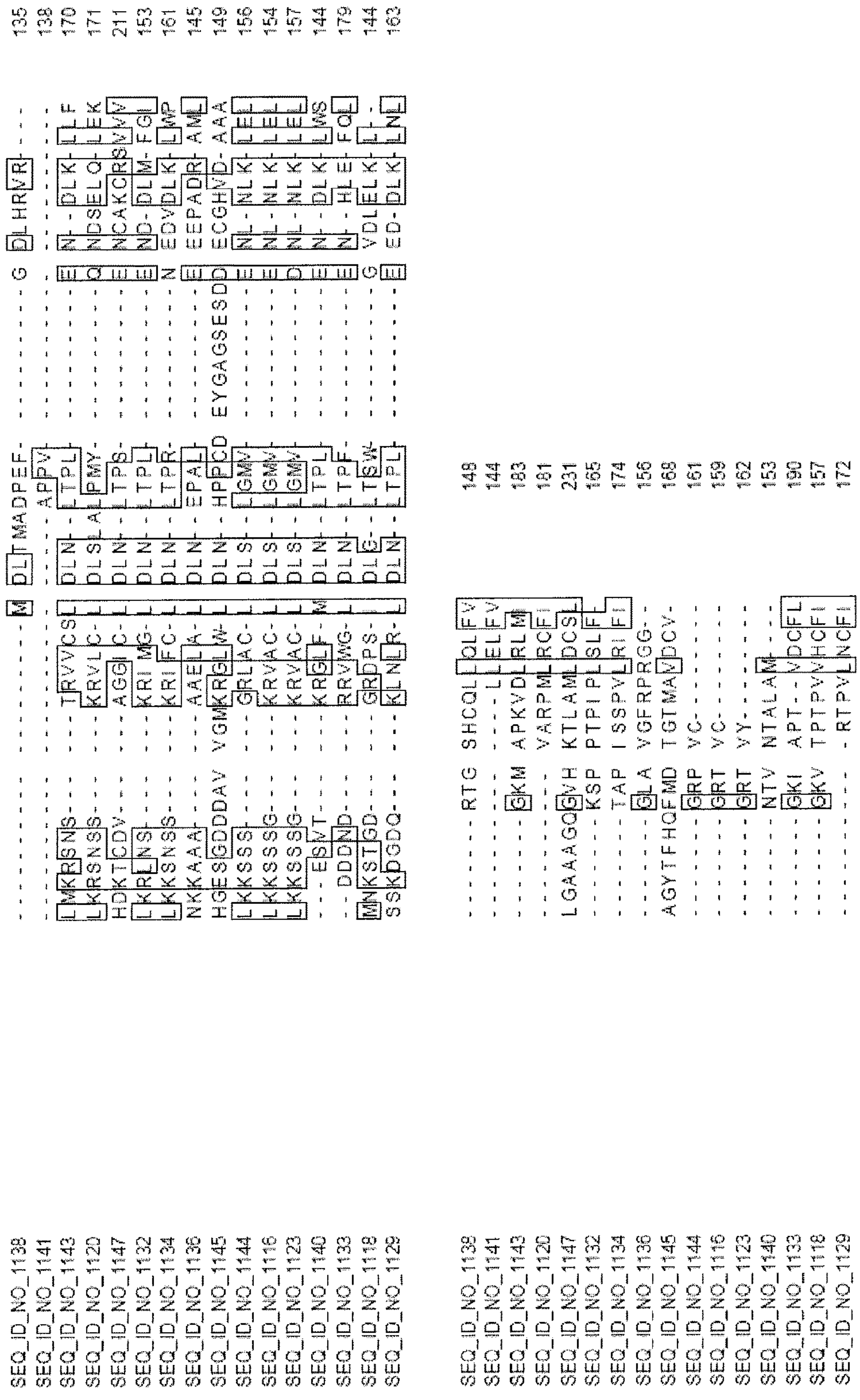

FIG. 37 is an alignment of ME13087 (SEQ ID NO:1116) with homologous and/or orthologous amino acid sequences CeresClone:100062822 (SEQ ID NO:1118), CeresAnnot:1440025 (SEQ ID NO:1120), GI No. 15238538 (SEQ ID NO:1123), GI No. 69111473 (SEQ ID NO:1129), GI No. 92873711 (SEQ ID NO:1132), GI No. 55734106 (SEQ ID NO:1133), GI No. 2346974 (SEQ ID NO:1134), CeresClone:569852 (SEQ ID NO:1136), CeresClone:1715326 (SEQ ID NO:1138), CeresClone:1608104 (SEQ ID NO:1140), GI No. 115456237 (SEQ ID NO:1141), GI No. 68655289 (SEQ ID NO:1143), GI No. 81022807 (SEQ ID NO:1144), GI No. 75706704 (SEQ ID NO:1145), and CeresAnnot:6016055 (SEQ ID NO:1147).

FIG. 38 is an alignment of ME13107 (SEQ ID NO:1159) with homologous and/or orthologous amino acid sequences CeresClone:1371824 (SEQ ID NO:1161), GI No. 22585 (SEQ ID NO:1162), GI No. 22208482 (SEQ ID NO:1163), and GI No. 16073 (SEQ ID NO:1164).

FIG. 39 is an alignment of ME13108 (SEQ ID NO:1166) with homologous and/or orthologous amino acid sequences GI No. 99109436 (SEQ ID NO:1167), CeresClone:1627939 (SEQ ID NO:1169), CeresClone:1840433 (SEQ ID NO:1171), CeresAnnot:1524198 (SEQ ID NO:1173), CeresClone:1650 (SEQ ID NO:1175), CeresClone:691979 (SEQ ID NO:1177), GI No. 92876897 (SEQ ID NO:1180), CeresClone:1774130 (SEQ ID NO:1182), and GI No. 115450018 (SEQ ID NO:1183).

FIG. 40 is an alignment of ME13110 (SEQ ID NO:1185) with homologous and/or orthologous amino acid sequences CeresClone:737317 (SEQ ID NO:1187), CeresClone:1880853 (SEQ ID NO:1189), GI No. 125558381 (SEQ ID NO:1190), and GI No. 115472157 (SEQ ID NO:1191).

FIG. 41 is an alignment of ME13125 (SEQ ID NO:1194) with homologous and/or orthologous amino acid sequences CeresClone:1938817 (SEQ ID NO:1196), CeresAnnot:1457245 (SEQ ID NO:1200), CeresClone:577910 (SEQ ID NO:1202), Public PUBLICCLONE ID no. 100736184 (SEQ ID NO:1203), GI No. 125553355 (SEQ ID NO:1204), and GI No. 5091600 (SEQ ID NO:1205).

FIG. 42 is an alignment of ME13149 (SEQ ID NO:1210) with homologous and/or orthologous amino acid sequences GI No. 1703374 (SEQ ID NO:1211), CeresClone:1846330 (SEQ ID NO:1213), GI No. 29124979 (SEQ ID NO:1216), CeresAnnot:1531725 (SEQ ID NO:1218), GI No. 3334321 (SEQ ID NO:1229), CeresClone:571410 (SEQ ID NO:1232), GI No. 39653273 (SEQ ID NO:1233), GI No. 92875403 (SEQ ID NO:1234), GI No. 11131026 (SEQ ID NO:1235), GI No. 77812440 (SEQ ID NO:1236), GI No. 89475524 (SEQ ID NO:1238), GI No. 3182919 (SEQ ID NO:1239), GI No. 7643794 (SEQ ID NO:1240), GI No. 1710851 (SEQ ID NO:1241), GI No. 115501471 (SEQ ID NO:1242), GI No. 77999251 (SEQ ID NO:1243), GI No. 3450893 (SEQ ID NO:1249), CeresClone:704589 (SEQ ID NO:1251), CeresClone:1384151 (SEQ ID NO:1253), CeresClone:1713894 (SEQ ID NO:1259), GI No. 125560752 (SEQ ID NO:1264), GI No. 115475543 (SEQ ID NO:1265), GI No. 3182922 (SEQ ID NO:1267), GI No. 145353078 (SEQ ID NO:1268), GI No. 11131023 (SEQ ID NO:1269), GI No. 47026845 (SEQ ID NO:1270), and GI No. 38353642 (SEQ ID NO:1272).

FIG. 43 is an alignment of ME13151 (SEQ ID NO:1274) with homologous and/or orthologous amino acid sequences CeresClone:1884601 (SEQ ID NO:1276), CeresAnnot:1445717 (SEQ ID NO:1280), CeresClone:527903 (SEQ ID NO:1284), GI No. 92891722 (SEQ ID NO:1285), CeresClone:790881 (SEQ ID NO:1287), CeresClone:299417 (SEQ ID NO:1289), CeresClone:1993894 (SEQ ID NO:1291), GI No. 125539547 (SEQ ID NO:1294), GI No. 48716424 (SEQ ID NO:1295), GI No. 84468278 (SEQ ID NO:1297), and CeresAnnot:6036303 (SEQ ID NO:1300).

FIG. 44 is an alignment of ME13153 (SEQ ID NO:1302) with homologous and/or orthologous amino acid sequences GI No. 70609690 (SEQ ID NO:1303), CeresClone:1927524 (SEQ ID NO:1305), CeresAnnot:1467310 (SEQ ID NO:1311), GI No. 45935270 (SEQ ID NO:1313), CeresClone:718446 (SEQ ID NO:1317), GI No. 92875133 (SEQ ID NO:1318), GI No. 1706318 (SEQ ID NO:1319), GI No. 3252856 (SEQ ID NO:1320), GI No. 1169238 (SEQ ID NO:1326), GI No. 31296711 (SEQ ID NO:1327), CeresClone:1468893 (SEQ ID NO:1330), GI No. 51587340 (SEQ ID NO:1331), CeresClone:1796201 (SEQ ID NO:1333), GI No. 125543034 (SEQ ID NO:1334), GI No. 115476804 (SEQ ID NO:1336), GI No. 75268060 (SEQ ID NO:1339), and GI No. 75268007 (SEQ ID NO:1340).

FIG. 45 is an alignment of ME13177 (SEQ ID NO:1342) with homologous and/or orthologous amino acid sequences CeresAnnot:1443786 (SEQ ID NO:1346), GI No. 15239172 (SEQ ID NO:1355), GI No. 562190 (SEQ ID NO:1363), GI No. 83032266 (SEQ ID NO:1364), CeresClone:602910 (SEQ ID NO:1366), GI No. 7242793 (SEQ ID NO:1370), GI No. 116167 (SEQ ID NO:1371), GI No. 2190259 (SEQ ID NO:1372), GI No. 5420278 (SEQ ID NO:1373), GI No. 1064931 (SEQ ID NO:1374), GI No. 6093215 (SEQ ID NO:1377), GI No. 461726 (SEQ ID NO:1378), GI No. 89111295 (SEQ ID NO:1379), GI No. 82949283 (SEQ ID NO:1380), GI No. 125537180 (SEQ ID NO:1381), GI No. 115489300 (SEQ ID NO:1382), and GI No. 55978000 (SEQ ID NO:1383).

FIG. 46 is an alignment of ME13200 (SEQ ID NO:1385) with homologous and/or orthologous amino acid sequences CeresAnnot:1503394 (SEQ ID NO:1387), GI No. 4914437 (SEQ ID NO:1390), CeresClone:638126 (SEQ ID NO:1393), GI No. 124360540 (SEQ ID NO:1394), GI No. 7981380 (SEQ ID NO:1395), GI No. 118137433 (SEQ ID NO:1396), CeresClone:1723374 (SEQ ID NO:1398), CeresClone:1785379 (SEQ ID NO:1400), GI No. 125553354 (SEQ ID NO:1401), GI No. 115471859 (SEQ ID NO:1404), and CeresAnnot:6040771 (SEQ ID NO:1407).

FIG. 47 is an alignment of ME13204 (SEQ ID NO:1409) with homologous and/or orthologous amino acid sequences CeresClone:1939206 (SEQ ID NO:1413), CeresAnnot:1453316 (SEQ ID NO:1415), GI No. 79319075 (SEQ ID NO:1418), GI No. 124359953 (SEQ ID NO:1419), CeresClone:891431 (SEQ ID NO:1421), GI No. 125536578 (SEQ ID NO:1424), and GI No. 20270065 (SEQ ID NO:1425).

Figure 48:
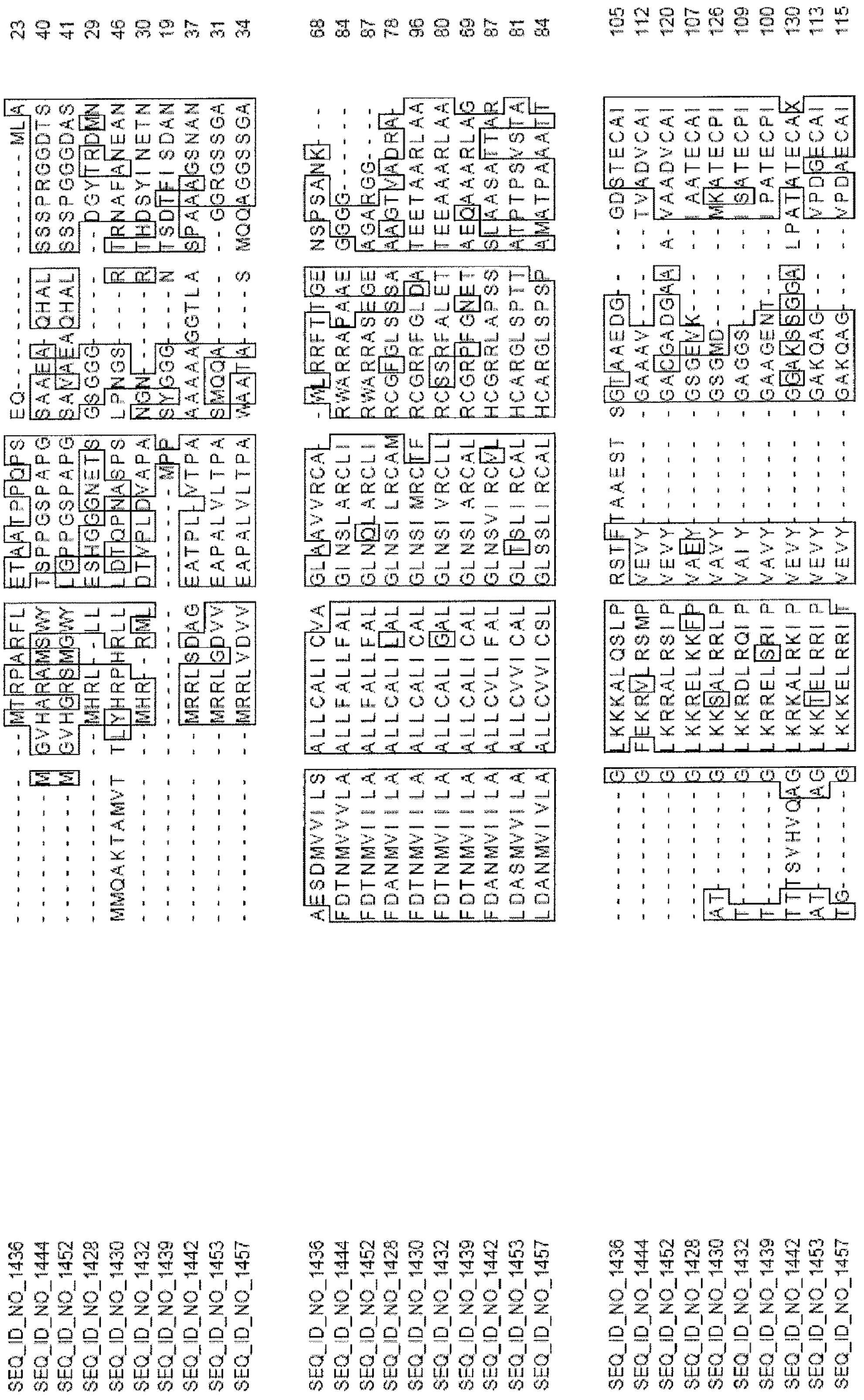

FIG. 48 is an alignment of ME14649 (SEQ ID NO:1428) with homologous and/or orthologous amino acid sequences CeresClone:1978733 (SEQ ID NO:1430), CeresAnnot:1476165 (SEQ ID NO:1432), CeresClone:871529 (SEQ ID NO:1436), CeresClone:1043344 (SEQ ID NO:1439), Ceres- Clone:786542 (SEQ ID NO:1442), CeresClone:346115 (SEQ ID NO:1444), CeresClone:1821683 (SEQ ID NO:1452), GI No. 125533171 (SEQ ID NO:1453), and GI No. 77553492 (SEQ ID NO:1457)

FIG. 49 is an alignment of ME16546 (SEQ ID NO:1463) with homologous and/or orthologous amino acid sequences CeresAnnot:1444102 (SEQ ID NO:1465), CeresClone: 582439 (SEQ ID NO:1471), CeresClone:579953 (SEQ ID NO:1473), GI No. 125539335 (SEQ ID NO:1474), and GI No. 115445987 (SEQ ID NO:1476).

FIG. 50 is an alignment of ME17567 (SEQ ID NO:1491) with homologous and/or orthologous amino acid sequences CeresClone:1895876 (SEQ ID NO:1493), CeresAnnot: 1464522 (SEQ ID NO:1495), CeresClone:968434 (SEQ ID NO:1499), CeresClone:686479 (SEQ ID NO:1501), CeresClone:1564962 (SEQ ID NO:1503), GI No. 125549699 (SEQ ID NO:1504), GI No. 125591612 (SEQ ID NO:1505), and CeresAnnot:6006969 (SEQ ID NO:1508).

FIG. 51 is an alignment of ME17932 (SEQ ID NO:1510) with homologous and/or orthologous amino acid sequences CeresClone:1842178 (SEQ ID NO:1512), CeresAnnot: 1475265 (SEQ ID NO:1516) and CeresClone:1044646 (SEQ ID NO:1520).

Figure 52:
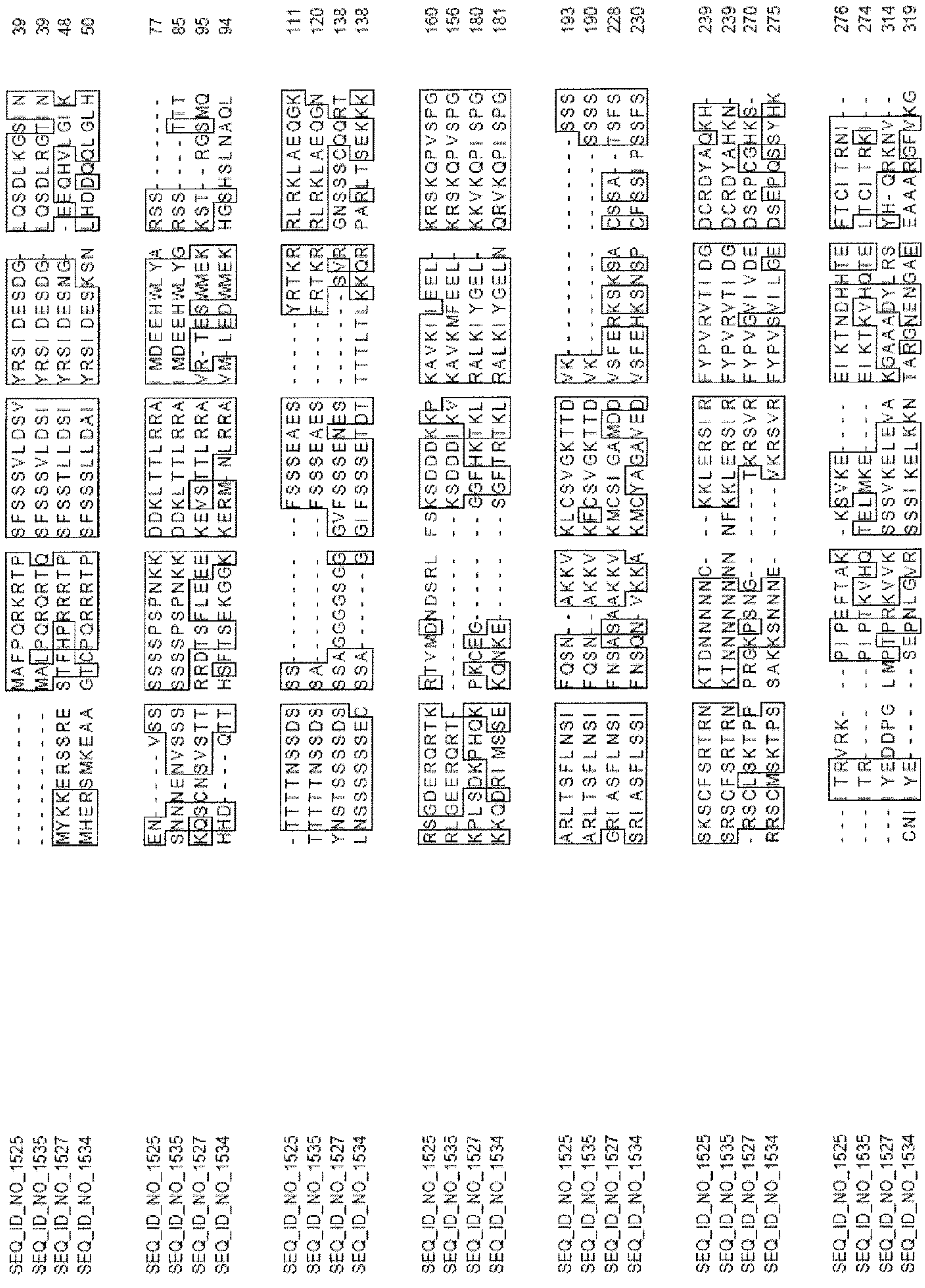

FIG. 52 is an alignment of ME17936 (SEQ ID NO:1525) with homologous and/or orthologous amino acid sequences CeresAnnot:1454324 (SEQ ID NO:1527), CeresClone: 1652842 (SEQ ID NO:1534), and GI No. 75214620 (SEQ ID NO:1535).

FIG. 53 is an alignment of ME18275 (SEQ ID NO:1537) with homologous and/or orthologous amino acid sequences CeresAnnot:1514086 (SEQ ID NO:1539), CeresClone: 1087909 (SEQ ID NO:1543), CeresClone:1359070 (SEQ ID NO:1545), GI No. 92880913 (SEQ ID NO:1548), CeresClone:932449 (SEQ ID NO:1550), and CeresClone: 1788695 (SEQ ID NO:1552).

Figure 54:
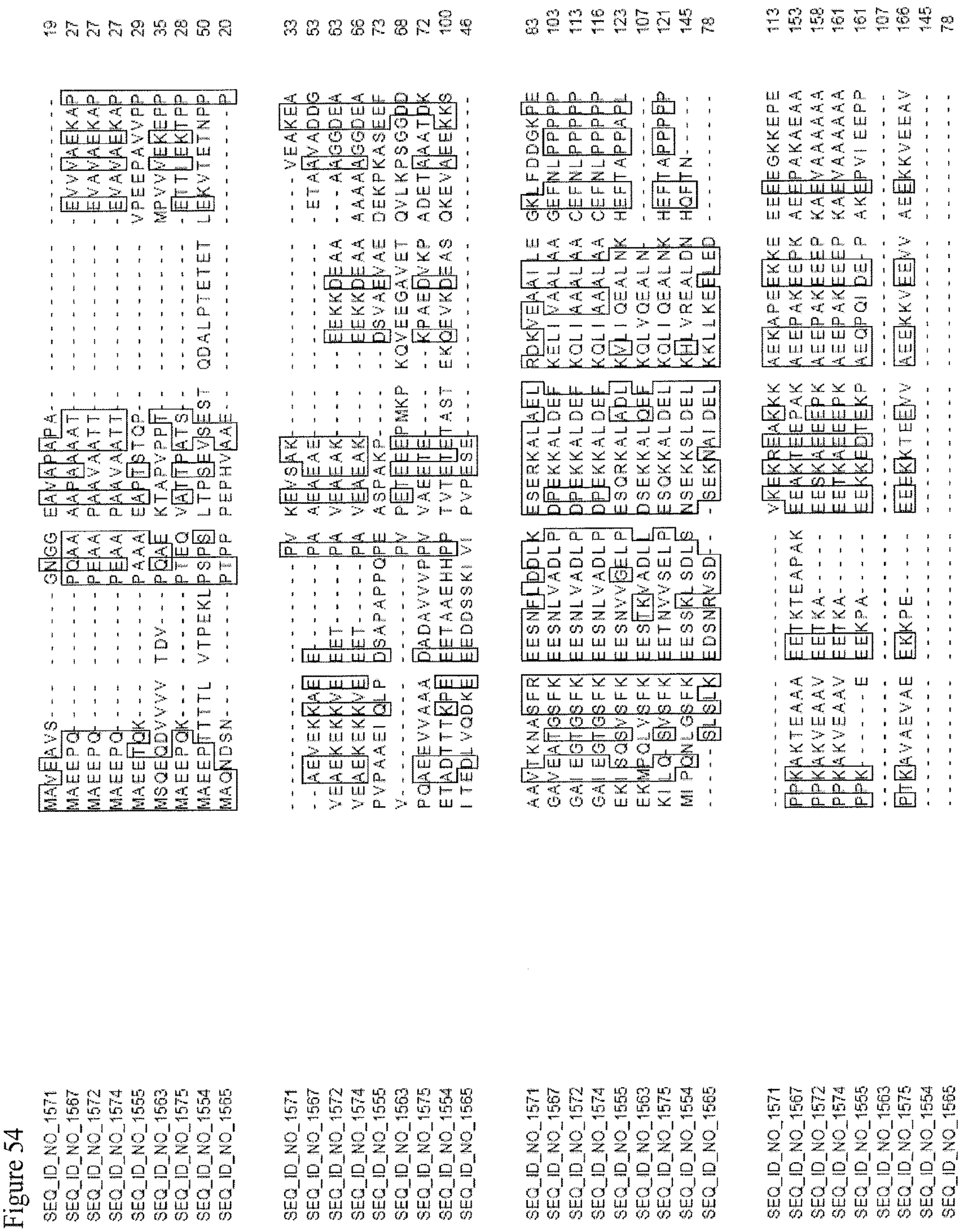

FIG. 54 is an alignment of ME18924 (SEQ ID NO:1554) with homologous and/or orthologous amino acid sequences GI No. 82469976 (SEQ ID NO:1555), CeresAnnot:1533704 (SEQ ID NO:1563), CeresClone:524404 (SEQ ID NO:1565), CeresClone:846541 (SEQ ID NO:1567), CeresClone:1769321 (SEQ ID NO:1571), GI No. 125528559 (SEQ ID NO:1572), GI No. 125572823 (SEQ ID NO:1574), and GI No. 84453208 (SEQ ID NO:1575).

Figure 55:
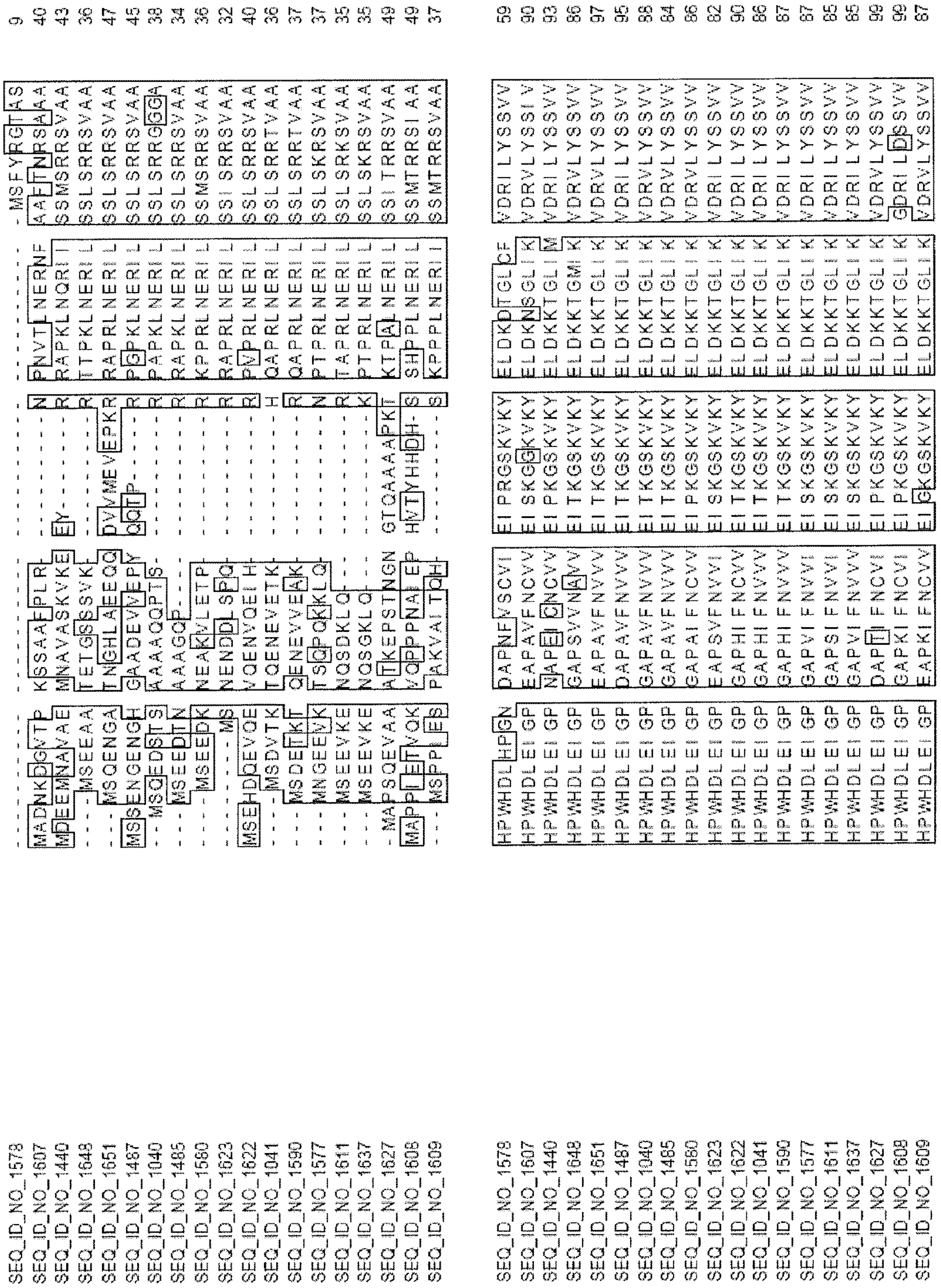

FIG. 55 is an alignment of ME19182 (SEQ ID NO:1577) with homologous and/or orthologous amino acid sequences GI No. 4033417 (SEQ ID NO:1040), GI No. 5669924 (SEQ ID NO:1041), GI No. 40642617 (SEQ ID NO:1440), GI No. 90399018 (SEQ ID NO:1485), GI No. 115464117 (SEQ ID NO:1487), GI No. 75164812 (SEQ ID NO:1578), CeresClone:1794223 (SEQ ID NO:1580), CeresAnnot:1471422 (SEQ ID NO:1590), CeresClone:968096 (SEQ ID NO:1607), GI No. 6752884 (SEQ ID NO:1608), GI No. 47775656 (SEQ ID NO:1609), CeresClone:1020799 (SEQ ID NO:1611), GI No. 87240865 (SEQ ID NO:1622), GI No. 2500047 (SEQ ID NO:1623), CeresClone:705340 (SEQ ID NO:1627), CeresClone:1430456 (SEQ ID NO:1637), GI No. 84619270 (SEQ ID NO:1648), and CeresClone: 1821143 (SEQ ID NO:1651).

FIG. 56 is an alignment of ME20628 (SEQ ID NO:1437) with homologous and/or orthologous amino acid sequences GI No. 113367236 (SEQ ID NO:173), GI No. 115477615 (SEQ ID NO:212), GI No. 125542223 (SEQ ID NO:361), GI No. 1838976 (SEQ ID NO:421), CeresClone:1547185 (SEQ ID NO:443), CeresAnnot:1450452 (SEQ ID NO:740), and GI No. 92870675 (SEQ ID NO:1461).

FIG. 57 is an alignment of ME01821 (SEQ ID NO:97) with homologous and/or orthologous amino acid sequences Public GI ID no. 167480754 (SEQ ID NO:2013) and Public GI ID no. 83830869 (SEQ ID NO:2015).

DETAILED DESCRIPTION

The invention provides methods and materials related to modulating low-nitrogen tolerance levels in plants. In some embodiments, the plants may also have modulated levels of low-nitrogen tolerance. The methods can include transforming a plant cell with a nucleic acid encoding a low nitrogen tolerance-modulating polypeptide, wherein expression of the polypeptide results in a modulated level of low-nitrogen tolerance. Plant cells produced using such methods can be grown to produce plants having an increased tolerance to conditions with limiting exogenous nitrogen sources. Such plants can be used for the production of higher yields and biomasses with existing fertilizer inputs, and/or enable existing yields and biomass of crops to be obtained with lower fertilizer input, or better yields and biomasses on soils of poorer quality.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Low Nitrogen Conditions" as used herein refers to nitrogen concentrations which lead to nitrogen deficiency symptoms such as pale green leaf color, chlorosis and reduced growth and vigor. Typically, low nitrogen conditions lead to a reduction of at least 20%, 25%, 30%, 35%, 40%, 45%, 50%, 60%, 70%, 80% or 90% in growth and/or vigor.

"Modulation" of the level of low-nitrogen tolerance refers to the change in the level of tolerance of a plant to limiting exogenous nitrogen sources that is observed as a result of expression of, or transcription from, an exogenous nucleic acid in a plant cell. The change in low-nitrogen tolerance level is measured by changes in plant size and greenness as well as greater photosynthesis efficiency, relative to the corresponding level in control plants in an environment with limiting nitrogen supply.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (-212 to -154) from the upstream region of the octopine synthase (ocs) gene. Fromm et al. (1989) *The Plant Cell,* 1:977-984.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include low nitrogen tolerance-modulating polypeptides. Low nitrogen tolerance-modulating polypeptides can be effective to modulate low-nitrogen tolerance levels when expressed in a plant or plant cell. Such polypeptides typically contain at least one domain indicative of low nitrogen tolerance-modulating polypeptides, as described in more detail herein. Low nitrogen tolerance-modulating polypeptides typically have an HMM bit score that is greater than 20, as described in more detail herein. In some embodiments, low nitrogen tolerance-modulating polypeptides have greater than 80% identity to SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, as described in more detail herein.

A. Domains Indicative of Low Nitrogen Tolerance-Modulating Polypeptides

A low nitrogen tolerance-modulating polypeptide can contain a P450 domain, which is characteristic of polypeptides belonging to the Cytochrome P450 superfamily. Cytochrome P450s are haem-thiolate proteins involved in the oxidative degradation of various compounds. They are particularly well known for their role in the degradation of environmental toxins and mutagens. In plants, these proteins are important for the biosynthesis of several compounds such as hormones, defensive compounds and fatty acids. Sequence conservation is relatively low within the family—there are only 3 absolutely conserved residues—but their general topography and structural fold are highly conserved. The conserved core is composed of a coil termed the 'meander', a four-helix bundle, helices J and K, and two sets of beta-sheets. These constitute the haem-binding loop, the proton-transfer groove and the conserved EXXR motif in helix K. While prokaryotic P450s are soluble proteins, most eukaryotic P450s are associated with microsomal membranes. Their general enzymatic function is to catalyse regiospecific and stereospecific oxidation of non-activated hydrocarbons at physiological temperatures. SEQ ID NO:3 and SEQ ID NO:332 set forth the amino acid sequence of *Arabidopsis* clones, identified herein as ME00919 (SEQ ID NO:3) and ME04587 (SEQ ID NO:332) respectively, that are predicted to encode polypeptides containing a Cytochrome P450 domain.

A low nitrogen tolerance-modulating polypeptide can contain a zf-Dof domain, which is conserved in several DNA-binding proteins of higher plants. Dof domain is a zinc finger DNA-binding domain that shows resemblance to the Cys2 zinc finger, although it has a longer putative loop where an extra Cys residue is typically conserved. The motif is also present in SEQ ID NO:49, which sets forth the amino acid sequence of an *Arabidopsis* clone, identified herein as Ceres ME01312 (SEQ ID NO:49), that is predicted to encode a polypeptide containing a zf-Dof domain.

A low nitrogen tolerance-modulating polypeptide can contain an Aminotran_3 domain characteristic of polypeptides belonging to the aminotransferase Class-III family. Aminotransferases share certain mechanistic features with other pyridoxalphosphate-dependent enzymes, such as the covalent binding of the pyridoxalphosphate group to a lysine residue. Class-III aminotransferases include acetylornithine aminotransferase, which catalyzes the transfer of an amino group from acetylornithine to alpha-ketoglutarate, yielding N-acetyl-glutamic-5-semi-aldehyde and glutamic acid; ornithine aminotransferase, which catalyzes the transfer of an amino group from ornithine to alpha-ketoglutarate, yielding glutamic-5-semi-aldehyde and glutamic acid; omega-amino acid-pyruvate aminotransferase, which catalyzes transamination between a variety of omega-amino acids, mono- and diamines, and pyruvate; 4-aminobutyrate aminotransferase; GABA transaminase, which catalyzes the transfer of an amino group from GABA to alpha-ketoglutarate, yielding succinate semialdehyde and glutamic acid; DAPA aminotransferase, a bacterial enzyme (bioA), which catalyzes an intermediate step in the biosynthesis of biotin, the transamination of 7-keto-8-aminopelargonic acid to form 7,8-diaminopelargonic acid; 2,2-dialkylglycine decarboxylase, a *Burkholderia cepacia* (*Pseudomonas cepacia*) enzyme (dgdA) that catalyzes the decarboxylating amino transfer of 2,2-dialkylglycine and pyruvate to dialkyl ketone, alanine and carbon dioxide; glutamate-1-semialdehyde aminotransferase (GSA); *Bacillus subtilis* aminotransferases yhxA and yodT; *Haemophilus influenzae* aminotransferase H10949; and *Caenorhabditis elegans* aminotransferase. On the basis of sequence similarity, these various enzymes can be grouped into subfamilies. The aminotran_3 domain is also present in SEQ ID NO:77, which set forth the amino acid sequences of *Arabidopsis* clone, identified herein as Ceres ME01463 (SEQ ID NO:77), that is predicted to encode polypeptides containing an aminotran_3 domain.

A low nitrogen tolerance-modulating polypeptide can contain a linker histone domain characteristic of polypeptides belonging to the linker histone H1 and H5 family. Linker histone H1 is an essential component of chromatin structure. H1 links nucleosomes into higher order structures. Histone H5 performs the same function as histone H1, and replaces H1 in certain cells. The structure of GH5, the globular domain of the linker histone H5 fold is similar to the DNA-binding domain of the catabolite gene activator protein, CAP, thus providing a possible model for the binding of GH5 to DNA. The domain is also present in SEQ ID NO:100, which sets forth the amino acid sequence of an *Arabidopsis* clone, identified herein as Ceres ME01910 (SEQ ID NO:100), that is predicted to encode a polypeptide containing a linker histone domain.

A low nitrogen tolerance-modulating polypeptide can contain a zf-C3HC4 domain, which is predicted to be characteristic of proteins belonging to the C3HC4 type zinc-finger (RING finger) protein family. The C3HC4 type zinc-finger (RING finger) is a cysteine-rich domain of approximately 40 to 60 residues that coordinates two zinc ions, and is probably involved in mediating protein-protein interactions. Members of the C3HC4 type zinc-finger (RING finger) protein family contain the loosely conserved sequence: C-X2-C-X(9-39)-C-X(1-3)-H-X(2-3)-C-X2-C-X(4-48)-C-X2-C where X is any amino acid. The domain is also present in SEQ ID NOs:166, 746, 976, 1428, which set forth the amino acid sequences of *Arabidopsis* clones, identified herein as Ceres ME02603 (SEQ ID NO:166), ME05493 (SEQ ID NO:746), ME12954 (SEQ ID NO:976), ME14649 (SEQ ID NO:1428) respectively, that are predicted to encode polypeptides containing a zf-C3HC4 domain.

A low nitrogen tolerance-modulating polypeptide can contain a Gal_Lectin domain characteristic of a galactose binding lectin domain protein. SEQ ID NO:208 sets forth the amino acid sequence of an *Arabidopsis* clone, identified herein as Ceres ME02801 (SEQ ID NO:208), that is predicted to encode a polypeptide containing a galactose binding lectin domain.

A low nitrogen tolerance-modulating polypeptide can contain a TRP 1 domain characteristic of tetratricopeptide repeat (TPR) domain protein. The tetratricopeptide repeat is a structural motif present in a wide range of proteins identified in various different organisms, ranging from bacteria to humans. It mediates protein-protein interactions and the assembly of multiprotein complexes. Sequence alignment of the TPR domains reveals a consensus sequence defined by a pattern of small and large amino acids. Proteins containing TPRs are involved in a variety of biological processes, such as cell cycle regulation, transcriptional control, mitochondrial and peroxisomal protein transport, neurogenesis and protein folding. The X-ray structure of a domain containing three TPRs from protein phosphatase 5 revealed that TPR adopts a helixturnhelix arrangement, with adjacent TPR motifs packing in a parallel fashion, resulting in a spiral of repeating anti-parallel alpha-helices. The two helices are denoted helix A and helix B. The packing angle between helix A and helix B is ~24° within a single TPR and generates a right-handed superhelical shape. Helix A interacts with helix B and with helix A' of the next TPR. Two protein surfaces are generated: the inner concave surface is contributed to mainly by residue on helices A, and the other surface presents residues from both helices A and B.

A low nitrogen tolerance-modulating polypeptide can contain a TRP_2 tetratricopeptide repeat domain, which is predicted to be characteristic of scaffold-proteins in multiprotein complexes. The TPR_2 domain consists of approximately 34-amino-acid motif with a loose consensus and is present, usually as multiple tandem repeats, in proteins with many cellular functions, including mitosis, transcription, protein transport, and development. Structural analysis of the TPR-2 domain demonstrates that it forms two α-helical regions separated by a turn, such that apposed bulky and small side chains form a "knob and hole" structure. In general, the hydrophobic surface of this structure mediates protein-protein interactions between TPR- and non-TPR-containing proteins.

SEQ ID NO:234 sets forth the amino acid sequence of *Arabidopsis* clone, identified herein as Ceres ME04204 (SEQ ID NO:234), that is predicted to encode a polypeptide containing a TRP_1 tetratricopeptide repeat domain and a TRP_2 tetratricopeptide repeat domain. SEQ ID NO:1510 sets forth the amino acid sequence of *Arabidopsis* clone, identified herein as Ceres ME17932 (SEQ ID NO:1510), that is predicted to encode a polypeptide containing a TRP_2 tetratricopeptide repeat domain.

A low nitrogen tolerance-modulating polypeptide can contain a zf-AN1 domain characteristic of polypeptides belonging to the AN1-like zinc finger domain protein family. The AN1-like zinc finger domain was first identified as a zinc finger at the C-terminus of An1 a ubiquitin-like protein in *Xenopus laevis*. The following pattern describes the zinc finger: C-X2-C-X(9-12)-C-X(1-2)-C-X4-C-X2-H-X5-H-X-C, where X can be any amino acid, and numbers in brackets indicate the number of residues.

A low nitrogen tolerance-modulating polypeptide can contain a zf-A20 domain, which is characteristic of A20-(an inhibitor of cell death)-like zinc fingers. In animals, A20-like zinc fingers are believed to mediate self-association in A20. These fingers also mediate IL-1-induced NF-kappa B activation. SEQ ID NO: 246 sets forth the amino acid sequence of *Arabidopsis* clone, identified herein as Ceres ME04477 (SEQ ID NO:246), that is predicted to encode a polypeptide containing an AN1-like zinc finger domain and zf-A20 domain.

A low nitrogen tolerance-modulating polypeptide can contain an Aa_trans domain, or transmembrane amino acid transporter domain, which is predicted to be characteristic of amino acid transporters and amino acid permeases. The domain is also present in SEQ ID NO:300, which sets forth the amino acid sequence of an *Arabidopsis* clone, identified herein as Ceres ME04507 (SEQ ID NO:300), that is predicted to encode a polypeptide containing an transmembrane amino acid transporter domain.

A low nitrogen tolerance-modulating polypeptide can contain an RNA recognition motif (as known as RRM_1, RRM, RBD, or RNP domain), which is characteristic of polypeptides belonging to the single strand RNA-binding protein superfamily. RRM proteins have a variety of RNA binding preferences and functions, and include heterogeneous nuclear ribonucleoproteins (hnRNPs), proteins implicated in regulation of alternative splicing, protein components of small nuclear ribonucleoproteins, and proteins that regulate RNA stability and translation. The RRM in heterodimeric splicing factor U2 snRNP auxiliary factor (U2AF) appears to have two RRM-like domains with specialized features for protein recognition. The motif also appears in a few single stranded DNA binding proteins. The typical RRM consists of four anti-parallel beta-strands and two alpha-helices arranged in a beta-alpha-beta-beta-alpha-beta fold with side chains that stack with RNA bases. Specificity of RNA binding is determined by multiple contacts with surrounding amino acids. A third helix is present during RNA binding in some cases. The motif is also present in SEQ ID NO:368 and SEQ ID NO:1274, which set forth the amino acid sequences of *Arabidopsis* clones, identified herein as Ceres ME04753 (SEQ ID NO:368) and ME13151 (SEQ ID NO:1274) respectively, that are predicted to encode polypeptides containing an RNA recognition motif.

A low nitrogen tolerance-modulating polypeptide can contain an NTF2 domain characteristic of a nuclear transport factor 2 (NTF2) polypeptide. NTF2 is a homodimer of approximately 14 kDa subunits which stimulates efficient nuclear import of a cargo protein. NTF2 binds to both RanGDP and FxFG repeat-containing nucleoporins. NTF2 binds to RanGDP sufficiently strongly for the complex to remain intact during transport through nucleopore complexes (NPCs), but the interaction between NTF2 and FxFG nucleoporins is much more transient, which would enable NTF2 to move through the NPC by hopping from one repeat to another. NTF2 folds into a cone with a deep hydrophobic cavity, the opening of which is surrounded by several negatively charged residues. RanGDP binds to NTF2 by inserting a conserved phenylalanine residue into the hydrophobic pocket of NTF2 and making electrostatic interactions with the conserved negatively charged residues that surround the cavity. A structurally similar domain appears in other nuclear import proteins. SEQ ID NO:1274, which sets forth the amino acid sequence of an *Arabidopsis* clone, identified herein as Ceres ME13151 (SEQ ID NO:1274), that is predicted to encode a polypeptide containing a NTF2 domain.

A low nitrogen tolerance-modulating polypeptide can contain a DUF1218 domain. SEQ ID NO:1274, which sets forth the amino acid sequence of an *Arabidopsis* clone, identified herein as Ceres ME04772 (SEQ ID NO:510), that is predicted to encode a polypeptide containing a DUF1218 domain.

A low nitrogen tolerance-modulating polypeptide can contain a Myb-like DNA-binding domain characteristic of polypeptides belonging to a protein family whose members contain the DNA binding domains from Myb proteins, as well as the SANT domain family. SEQ ID NO:533, which sets forth the amino acid sequence of an *Arabidopsis* clone, identified herein as Ceres ME04909 (SEQ ID NO:533), that is predicted to encode a polypeptide containing a Myb-like DNA-binding domain.

A low nitrogen tolerance-modulating polypeptide can contain a FAD_binding_4 domain. This domain is predicted to be characteristic of polypeptides belonging to a family of enzymes that use FAD (flavin adenine dinucleotide) as a co-factor, most of the enzymes are similar to oxygen oxidoreductase, containing a covalently bound FAD group which is attached to a histidine via an 8-alpha-(N3-histidyl)-riboflavin linkage.

A low nitrogen tolerance-modulating polypeptide can contain a BBE domain, which is predicted to be characteristic of a berberine bridge and berberine bridge-like enzyme. BBE enzymes are typically involved in the biosynthesis of numerous isoquinoline alkaloids. They catalyse the transformation of the N-methyl group of (S)-reticuline into the C-8 berberine bridge carbon of (S)-scoulerine. SEQ ID NO:558 sets forth the amino acid sequence of an *Arabidopsis* clone, identified herein as Ceres ME05194 (SEQ ID NO:558), that is predicted to encode a polypeptide containing an FAD_binding_4 domain and a BBE domain.

A low nitrogen tolerance-modulating polypeptide can contain a prefoldin (PFD) domain characteristic of polypeptides belonging to the prefoldin subunit family. Prefoldin (PFD) is a chaperone that typically interacts with type II chaperonins, hetero-oligomers lacking an obligate co-chaperonin that are found in eukaryotes (chaperonin-containing T-complex polypeptide-1 (CCT)) and archaea. Eukaryotic PFD can typically bind both actin and tubulin co-translationally. The chaperone can then delivers the target protein to CCT, interacting with the chaperonin through the tips of the coiled coils. SEQ ID NO:593 sets forth the amino acid sequence of an *Arabidopsis* clone, identified herein as Ceres ME05267 (SEQ ID NO:593), that is predicted to encode a polypeptide containing a prefoldin domain.

A low nitrogen tolerance-modulating polypeptide can contain an HR-lesion domain characteristic of polypeptides belonging to a family of plant proteins can be associated with the hypersensitive response (HR) pathway of defense against plant pathogens. The domain is also present in SEQ ID NO: 646, which sets forth the amino acid sequence of an *Arabidopsis* clone, identified herein as Ceres ME05341 (SEQ ID NO: 646), that is predicted to encode a polypeptide containing an HR-lesion domain.

A low nitrogen tolerance-modulating polypeptide can contain a DUF538 domain. SEQ ID NO:687 sets forth the amino acid sequence of an *Arabidopsis* clone, identified herein as Ceres ME05392 (SEQ ID NO:687), that is predicted to encode a polypeptide containing a DUF538 domain.

A low nitrogen tolerance-modulating polypeptide can contain a zinc finger C-x8-C-x5-C-x3-H type domain (zf-CCCH), which is characteristic of polypeptides belonging to the zinc finger protein superfamily. Members of zinc finger domains proteins are thought to be involved in DNA-binding, and exist as different types. Proteins containing zinc finger domains of the C-x8-C-x5-C-x3-H type include zinc finger proteins from eukaryotes involved in cell cycle or growth phase-related regulation. It has been shown that different CCCH zinc finger proteins interact with the 3' untranslated region of various mRNA. SEQ ID NO:792 sets forth the amino acid sequence of an *Arabidopsis* clone, identified herein as Ceres ME07344 (SEQ ID NO:792), that is predicted to encode a polypeptide containing a zf-CCCH domain.

A low nitrogen tolerance-modulating polypeptide can contain a DUF246 domain. SEQ ID NO:828 sets forth the amino acid sequence of an *Arabidopsis* clone, identified herein as Ceres ME08464 (SEQ ID NO:828), that is predicted to encode a polypeptide containing a DUF246 domain.

A low nitrogen tolerance-modulating polypeptide can contain a C2 domain. The C2 domain is a Ca2+-dependent membrane-targeting module found in many cellular proteins involved in signal transduction or membrane trafficking. C2 domains are unique among membrane targeting domains in that they typically show wide range of lipid selectivity for the major components of cell membranes, including phosphatidylserine and phosphatidylcholine. SEQ ID NO:982 sets forth the amino acid sequence of an *Arabidopsis* clone, identified herein as Ceres ME12970 (SEQ ID NO:982), that is predicted to encode a polypeptide containing an C2 domain.

A low nitrogen tolerance-modulating polypeptide can contain a Cpn60_TCP1 domain characteristic of polypeptides belonging to the TCP-1/cpn60 chaperonin family. This family includes members from the HSP60 chaperone family and the TCP-1 (T-complex protein) family. Chaperonins, a subfamily of molecular chaperones, are typically essential for the correct folding and assembly of polypeptides into oligomeric structures. Chaperonins are typically found in abundance in prokaryotes, chloroplasts and mitochondria. They are typically required for normal cell growth, and are stress-induced, acting to stabilize or protect disassembled polypeptides under heat-shock conditions. SEQ ID NO: 1054 sets forth the amino acid sequence of an *Arabidopsis* clone, identified herein as Ceres ME13021 (SEQ ID NO: 1054), that is predicted to encode a polypeptide containing a Cpn60_TCP1 domain.

A low nitrogen tolerance-modulating polypeptide can contain a zf-C2H2 domain characteristic of a C2H2 zinc finger domain polypeptide. Zinc finger domains are nucleic acid-binding protein structures composed of 25 to 30 amino-acid residues including 2 conserved Cys and 2 conserved His residues in a C-2-C-12-H-3-H type motif. The 12 residues separating the second Cys and the first His are mainly polar and basic, implicating this region in particular in nucleic acid binding. They have the ability to bind to both RNA and DNA, and it has been suggested that the zinc finger may thus represent the original nucleic acid binding protein. It has also been suggested that a Zn-centered domain could be used in a protein interaction, e.g. in protein kinase C. Many classes of zinc fingers are characterized according to the number and positions of the histidine and cysteine residues involved in the zinc atom coordination. In C2H2 zinc finger class, the first pair of zinc coordinating residues are cysteines, while the second pair are histidines. The motif is also present in SEQ ID NO:1116, which sets forth the amino acid sequence of an *Arabidopsis* clone, identified herein as Ceres ME13087 (SEQ ID NO:1116), that is predicted to encode a polypeptide containing a zf-C2H2 domain.

A low nitrogen tolerance-modulating polypeptide can contain a zein domain characteristic of polypeptides belonging to the zein family of seed storage proteins. SEQ ID NO:1159, which sets forth the amino acid sequence of an *Arabidopsis* clone, identified herein as Ceres ME13107 (SEQ ID NO: 1159), that is predicted to encode a polypeptide containing a zein domain.

A low nitrogen tolerance-modulating polypeptide can contain a snf7 domain characteristic of polypeptides belonging to a family of eukaryotic proteins related to yeast SNF7. SEQ ID NO:1185 sets forth the amino acid sequence of an *Arabidopsis* clone, identified herein as Ceres ME13110 (SEQ ID NO:1185), that is predicted to encode a polypeptide containing a snf7 domain.

A low nitrogen tolerance-modulating polypeptide can contain an HhH-GPD domain characteristic of polypeptides belonging to the HhH-GPD base excision DNA repair protein superfamily. Members of the HhH-GPD base excision DNA repair protein superfamily contain helix-hairpin-helix and Gly/Pro rich loop followed by a conserved aspartate. This domain is found in a diverse range of structurally related DNA repair proteins. The domain is also present in SEQ ID NO:1194 sets forth the amino acid sequence of an *Arabidopsis* clone, identified herein as Ceres ME13125 (SEQ ID NO:1194), that is predicted to encode a polypeptide containing an HhH-GPD domain.

A low nitrogen tolerance-modulating polypeptide can contain an Arf domain characteristic of polypeptides belonging to the ADP-ribosylation factor family. The small ADP ribosylation factor (Arf) GTP-binding proteins are major regulators of vesicle biogenesis in intracellular traffic. They are the founding members of a growing family that includes Arl (Arf-like), Arp (Arf-related proteins) and the remotely related Sar (Secretion-associated and Ras-related) proteins. Arf proteins cycle between inactive GDP-bound and active GTP-bound forms that bind selectively to effectors. The classical structural GDP/GTP switch is characterized by conformational changes at the so-called switch 1 and switch 2 regions, which bind tightly to the gamma-phosphate of GTP but poorly or not at all to the GDP nucleotide. Structural studies of Arf1 and Arf6 have revealed that although these proteins feature the switch 1 and 2 conformational changes, they depart from other small GTP-binding proteins in that they use an additional, unique switch to propagate structural information from one side of the protein to the other. The GDP/GTP structural cycles of human Arf1 and Arf6 feature a unique conformational change that affects the beta2beta3 strands connecting switch 1 and switch 2 (interswitch) and also the amphipathic helical N-terminus. SEQ ID NO: 1210 sets forth the amino acid sequence of an *Arabidopsis* clone, identified herein as Ceres ME13149 (SEQ ID NO:1210), that is predicted to encode a polypeptide containing an Arf domain.

A low nitrogen tolerance-modulating polypeptide can contain a Pyridoxal_deC domain characteristic of pyridoxal-dependent decarboxylase polypeptide. Pyridoxal-dependent decarboxylases typically share regions of sequence similarity, particularly in the vicinity of a conserved lysine residue, which provides the attachment site for the pyridoxal-phosphate (PLP) group. Pyridoxal phosphate is the active form of vitamin B6 (pyridoxine or pyridoxal). PLP is a versatile catalyst, acting as a coenzyme in a multitude of reactions, including decarboxylation, deamination and transamination. PLP-dependent enzymes, including pyridoxal-dependent decarboxylases, are involved in the biosynthesis of amino acids and amino acid-derived metabolites, but they are also found in the biosynthetic pathways of amino sugars and in the synthesis or catabolism of neurotransmitter. SEQ ID NO:1302 sets forth the amino acid sequence of an *Arabidopsis* clone, identified herein as Ceres ME13153 (SEQ ID NO:1302), that is predicted to encode a polypeptide containing a Pyridoxal_deC domain.

A low nitrogen tolerance-modulating polypeptide can contain a Cyclin_C domain, which is characteristic to the C-terminal domain of polypeptides belonging to the Cyclin family. Cyclins are eukaryotic proteins that play an active role in controlling nuclear cell division cycles, and regulate cyclin dependent kinases (CDKs). Cyclins, together with the p34 (cdc2) or cdk2 kinases, form the Maturation Promoting Factor (MPF). There are two main groups of cyclins, G1/S cyclins, which play a role in the control of the cell cycle at the G1/S (start) transition, and G2/M cyclins, which play a role in the control of the cell cycle at the G2/M (mitosis) transition. G2/M cyclins accumulate steadily during G2 and are abruptly destroyed as cells exit from mitosis (at the end of the M-phase). Cyclins typically contain two domains of similar all-alpha fold, of which this family corresponds with the C-terminal domain.

A low nitrogen tolerance-modulating polypeptide can contain a Cyclin_N domain, which defines the N-terminal domain of polypeptides belonging to the Cyclin family. SEQ ID NO: 1342 sets forth the amino acid sequence of an *Arabidopsis* clone, identified herein as Ceres ME13177 (SEQ ID NO: 1342), that is predicted to encode a polypeptide containing a Cyclin_C domain and a Cyclin_N domain A low nitrogen tolerance-modulating polypeptide can contain a DUF1442 domain. SEQ ID NO:1463, which sets forth the amino acid sequence of an *Arabidopsis* clone, identified herein as Ceres ME16546 (SEQ ID NO:1463), that is predicted to encode a polypeptide containing a DUF1442 domain.

A low nitrogen tolerance-modulating polypeptide can contain an HLH domain characteristic of polypeptides belonging to the Helix-loop-helix DNA-binding domain superfamily. Basic helix-loop-helix proteins (bHLH) are a group of eukaryotic transcription factors that can exert a determinative influence in a variety of developmental pathways. These transcription factors are characterized by a conserved bHLH domain that mediates specific dimerization. They can facilitate the conversion of inactive monomers to trans-activating dimers at appropriate stages of development. Members of this superfamily can be classified into discrete categories according to dimerization, DNA binding and expression characteristics. SEQ ID NO:1537 sets forth the amino acid sequence of an *Arabidopsis* clone, identified herein as Ceres ME18275 (SEQ ID NO:1537), that is predicted to encode a polypeptide containing an HLH domain.

A low nitrogen tolerance-modulating polypeptide can contain a CRAL_TRIO domain characteristic of the C-terminal of retinaldehyde/retinal-binding protein family. In animals, retinaldehyde/retinal-binding proteins may be functional components of the visual cycle. Cellular retinaldehyde-binding protein (CRALBP) may function as a substrate carrier protein that modulates interaction of these retinoids with visual cycle enzymes. The multidomain protein Trio can bind the LAR transmembrane tyrosine phosphatase, contains a protein kinase domain, and has separate rac-specific and rho-specific guanine nucleotide exchange factor domains. Trio is a multifunctional protein that can integrate and amplify signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes.

A low nitrogen tolerance-modulating polypeptide can contain a CRAL_TRIO_N which defines the N-terminal of retinaldehyde/retinal-binding protein family.

A low nitrogen tolerance-modulating polypeptide can contain an EMP24_GP25L domain characteristic of polypeptides belonging to the emp24/gp25L/p24 family/GOLD gene family. Members of this family are implicated in bringing cargo forward from the ER and binding to coat proteins by their cytoplasmic domains. This domain corresponds closely to the beta-strand rich GOLD domain. The GOLD domain is often found combined with lipid- or membrane-association domains. p24 proteins are major membrane components of COPI- and COPII-coated vesicles and are implicated in cargo selectivity of ER to Golgi transport. Multiple members of the p24 family are found in all eukaryotes, from yeast to mammals. Members of the p24 family are type I membrane proteins with a signal peptide at the amino terminus, a lumenal coiled-coil (extracytosolic) domain, a single transmembrane domain with conserved amino acids, and a short cytoplasmic tail. They may be grouped into at least three subfamilies based on primary sequence. One subfamily comprises yeast Emp24p and mammalian p24A. Another subfamily comprises yeast Erv25p and mammalian Tmp21, and the third subfamily comprises mammalian gp25L proteins. SEQ ID NO:1554 sets forth the amino acid sequence of an *Arabidopsis* clone, identified herein as Ceres ME18924 (SEQ ID NO:1554), that is predicted to encode a polypeptide containing a CRAL_TRIO domain, a CRAL_TRIO_N domain, and a EMP24_GP25L domain.

A low nitrogen tolerance-modulating polypeptide can contain a Pyrophosphatase domain, which is predicted to be characteristic of an inorganic pyrophosphatase (PPase). PPase is the enzyme responsible for the hydrolysis of pyrophosphate (PPi) which is formed principally as the product of the many biosynthetic reactions that utilize ATP. PPases may require the presence of divalent metal cations, with magnesium conferring the highest activity. Among other residues, a lysine has been postulated to be part of or close to the active site. The sequences of PPases share some regions of similarities, among which is a region that contains three conserved aspartates that are involved in the binding of cations. SEQ ID NO:1577 sets forth the amino acid sequence of an *Arabidopsis* clone, identified herein as Ceres ME19182 (SEQ ID NO:1577), that is predicted to encode a polypeptide containing a Pyrophosphatase domain.

A low nitrogen tolerance-modulating polypeptide can contain a bZIP_1 domain characteristic of polypeptides belonging to the superfamily of basic ZIP transcription factors. Members of the eukaryotic bZIP transcription factor superfamily contain a basic region mediating sequence-specific DNA-binding followed by a leucine zipper region required for dimerization. SEQ ID NO: 1437 sets forth the amino acid sequence of an *Arabidopsis* clone, identified herein as Ceres ME20628 (SEQ ID NO: 1437), that is predicted to encode a polypeptide containing a bZIP_1 domain.

B. Functional Homologs Identified by Reciprocal BLAST

In some embodiments, one or more functional homologs of a reference low nitrogen tolerance-modulating polypeptide defined by one or more of the Pfam descriptions indicated above are suitable for use as low nitrogen tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a low nitrogen tolerance-modulating polypeptide, or by combining domains from the coding sequences for different naturally-occurring low nitrogen tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of low nitrogen tolerance-modulating polypeptides. Sequence analysis can involve BLAST, Reciprocal BLAST, or PSI-BLAST analysis of nonredundant databases using a low nitrogen tolerance-modulating polypeptide amino acid sequence as the reference sequence. Amino acid sequence is, in some instances, deduced from the nucleotide sequence. Those polypeptides in the database that have greater than 20% sequence identity are candidates for further evaluation for suitability as a low nitrogen tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in low nitrogen tolerance-modulating polypeptides, e.g., conserved functional domains.

Conserved regions can be identified by locating a region within the primary amino acid sequence of a low nitrogen tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al. (1998) *Nucl. Acids Res.,* 26:320-322; Sonnhammer et al. (1997) *Proteins,* 28:405-420; and Bateman et al. (1999) *Nucl. Acids Res.,* 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 20% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1:
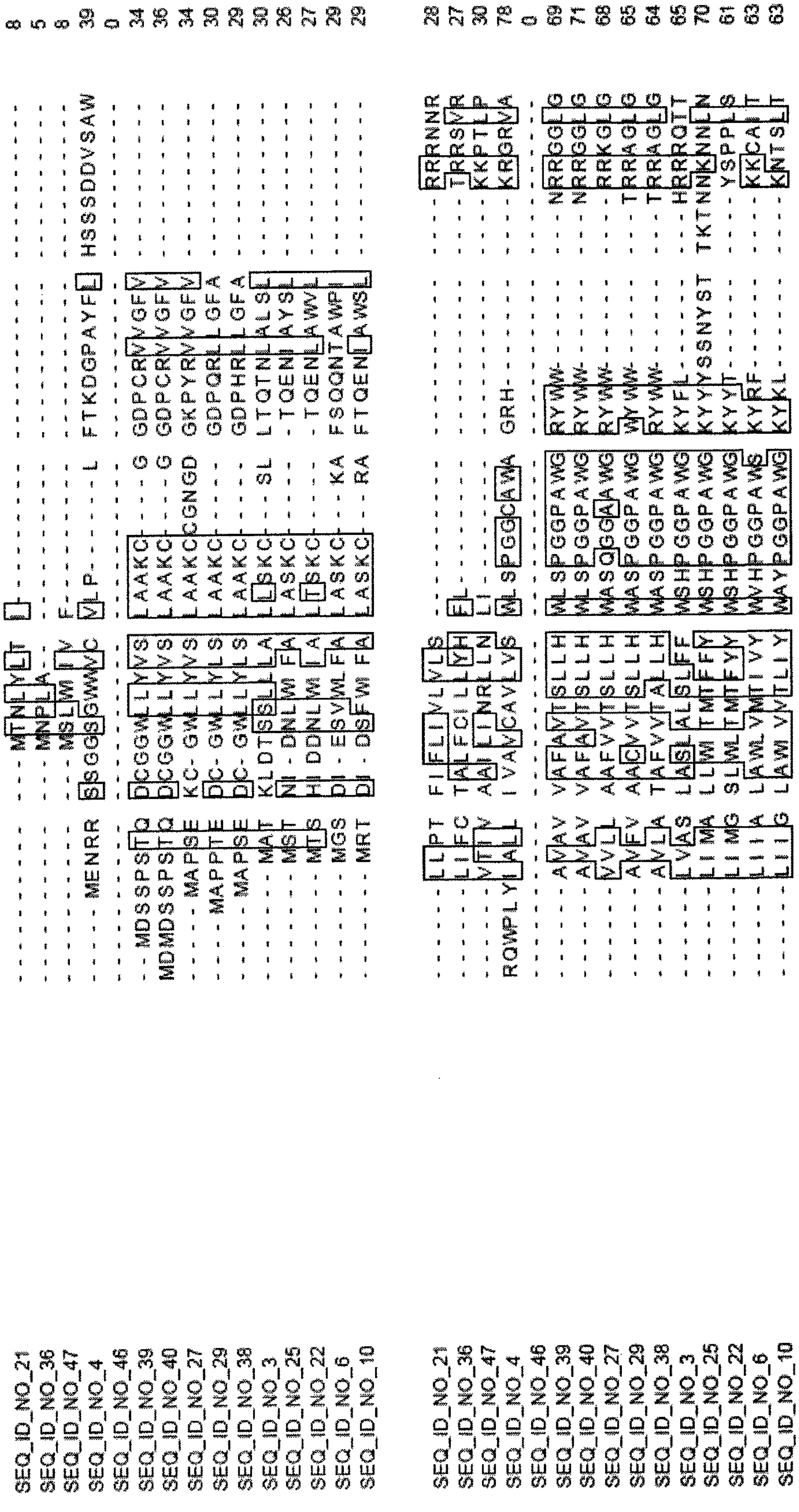
FIG. 1 is an alignment of Ceres SEEDLINE No. ME00919 (SEQ ID NO:3) with homologous and/or orthologous amino acid sequences GI No. 5921925 (SEQ ID NO:4), CeresClone:1929222 (SEQ ID NO:6), CeresAnnot:1471370 (SEQ ID NO:10), GI No. 84380741 (SEQ ID NO:21), GI No. 5921926 (SEQ ID NO:22), GI No. 84514161 (SEQ ID NO:25), CeresClone:779234 (SEQ ID NO:27), CeresClone:1600726 (SEQ ID NO:29), GI No. 78183420 (SEQ ID NO:36), CeresClone:1877346 (SEQ ID NO:38), GI No. 125562440 (SEQ ID NO:39), GI No. 115477665 (SEQ ID NO:40), GI No. 1173624 (SEQ ID NO:46), and GI No. 84468276 (SEQ ID NO:47). In all the alignment figures shown herein, a dash in an aligned sequence represents a gap, i.e., a lack of an amino acid at that position. Identical amino acids or conserved amino acid substitutions among aligned sequences are identified by boxes.

Examples of amino acid sequences of functional homologs of the polypeptide set forth in SEQ ID NO:3 are provided in FIG. 1 and in the Sequence Listing. Such functional homologs include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some cases, a functional homolog of SEQ ID NO:3 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Figure 2:
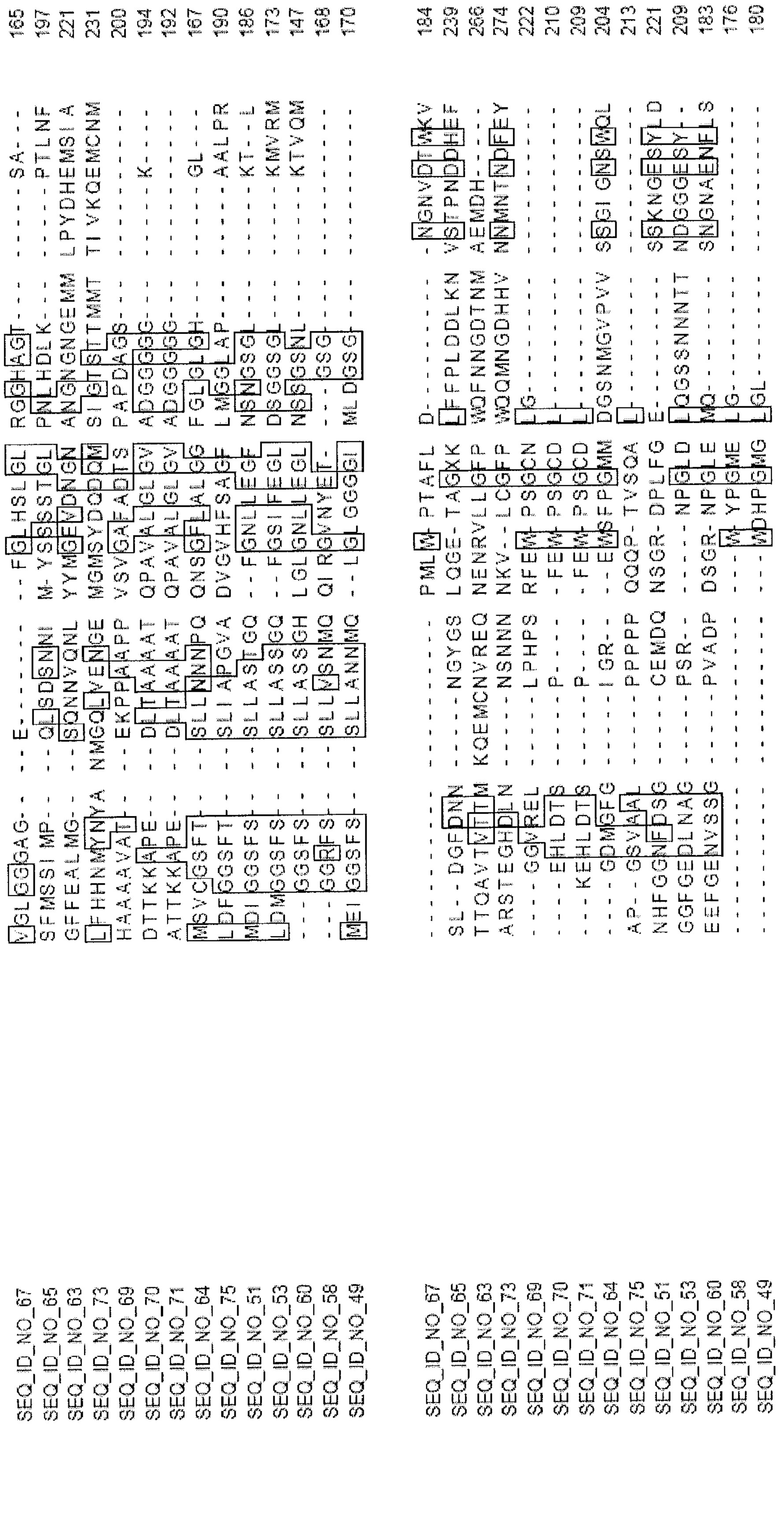
FIG. 2 is an alignment of ME01312 (SEQ ID NO:49) with homologous and/or orthologous amino acid sequences CeresClone:1869410 (SEQ ID NO:51), CeresAnnot:1540549 (SEQ ID NO:53), CeresClone:978708 (SEQ ID NO:58), CeresClone:1623097 (SEQ ID NO:60), GI No. 92873064 (SEQ ID NO:63), GI No. 37051131 (SEQ ID NO:64), GI No. 3341468 (SEQ ID NO:65), CeresClone:937560 (SEQ ID NO:67), CeresClone:456844 (SEQ ID NO:69), GI No. 125564100 (SEQ ID NO:70), GI No. 52077334 (SEQ ID NO:71), GI No. 113205234 (SEQ ID NO:73), and CeresAnnot:6100272 (SEQ ID NO:75).

Examples of amino acid sequences of functional homologs of the polypeptide set forth in SEQ ID NO:49 are provided in FIG. 2 and in the Sequence Listing. Such functional homologs include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75. In some cases, a functional homolog of SEQ ID NO:49 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49.

Figure 3:
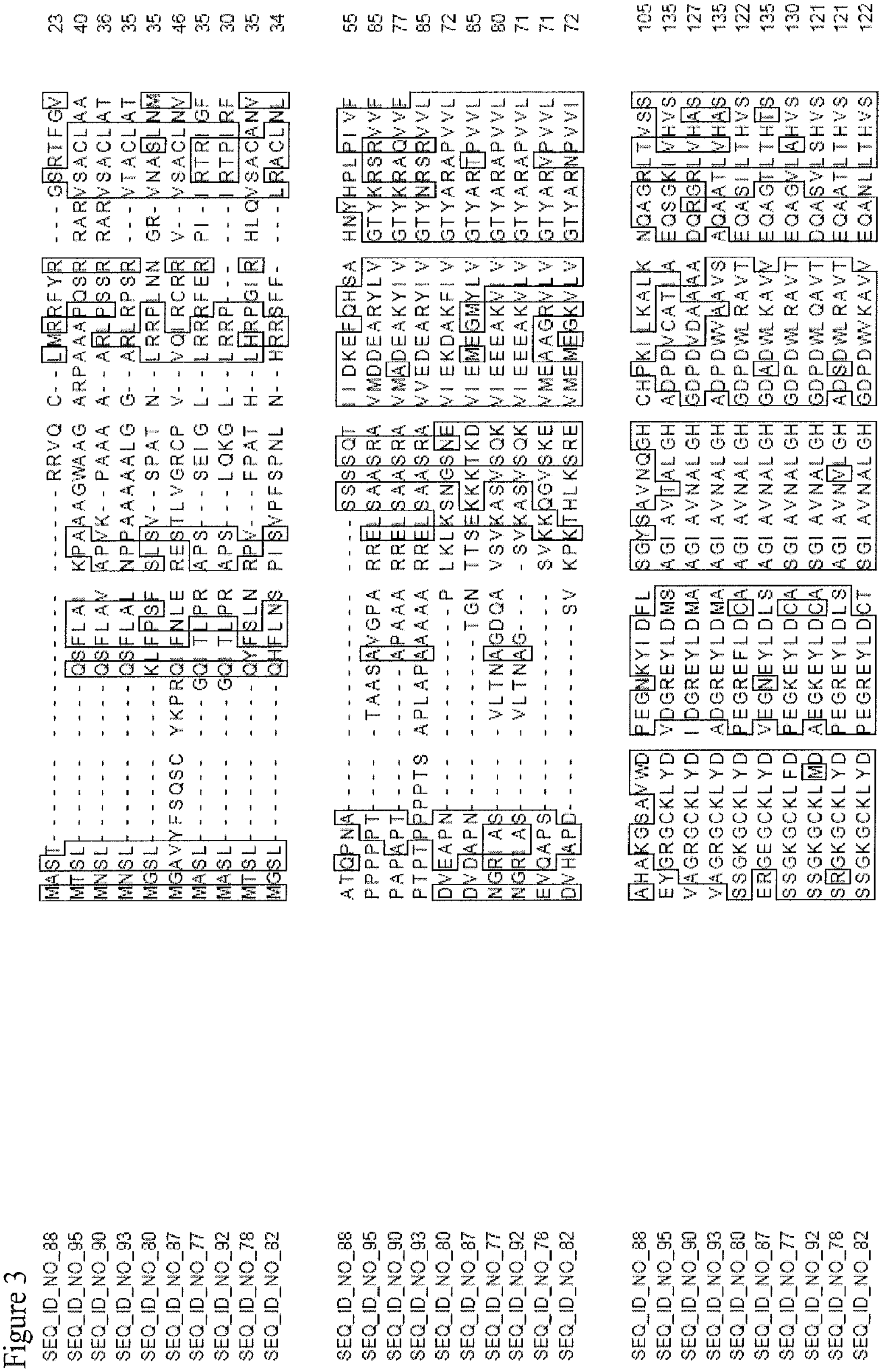
FIG. 3 is an alignment of ME01463 (SEQ ID NO:77) with homologous and/or orthologous amino acid sequences GI No. 2811029 (SEQ ID NO:78), CeresClone:1853284 (SEQ ID NO:80), CeresAnnot:1476446 (SEQ ID NO:82), CeresClone:527024 (SEQ ID NO:87), GI No. 27527063 (SEQ ID NO:88), CeresClone:913632 (SEQ ID NO:90), CeresClone:1386710 (SEQ ID NO:92), GI No. 115461885 (SEQ ID NO:93), and CeresAnnot:6054519 (SEQ ID NO:95)

Examples of amino acid sequences of functional homologs of the polypeptide set forth in SEQ ID NO:77 are provided in FIG. 3 and in the Sequence Listing. Such functional homologs include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and CeresAnnot: 839064 (SEQ ID NO:1479). In some cases, a functional homolog of SEQ ID NO:77 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77.

Figure 4:
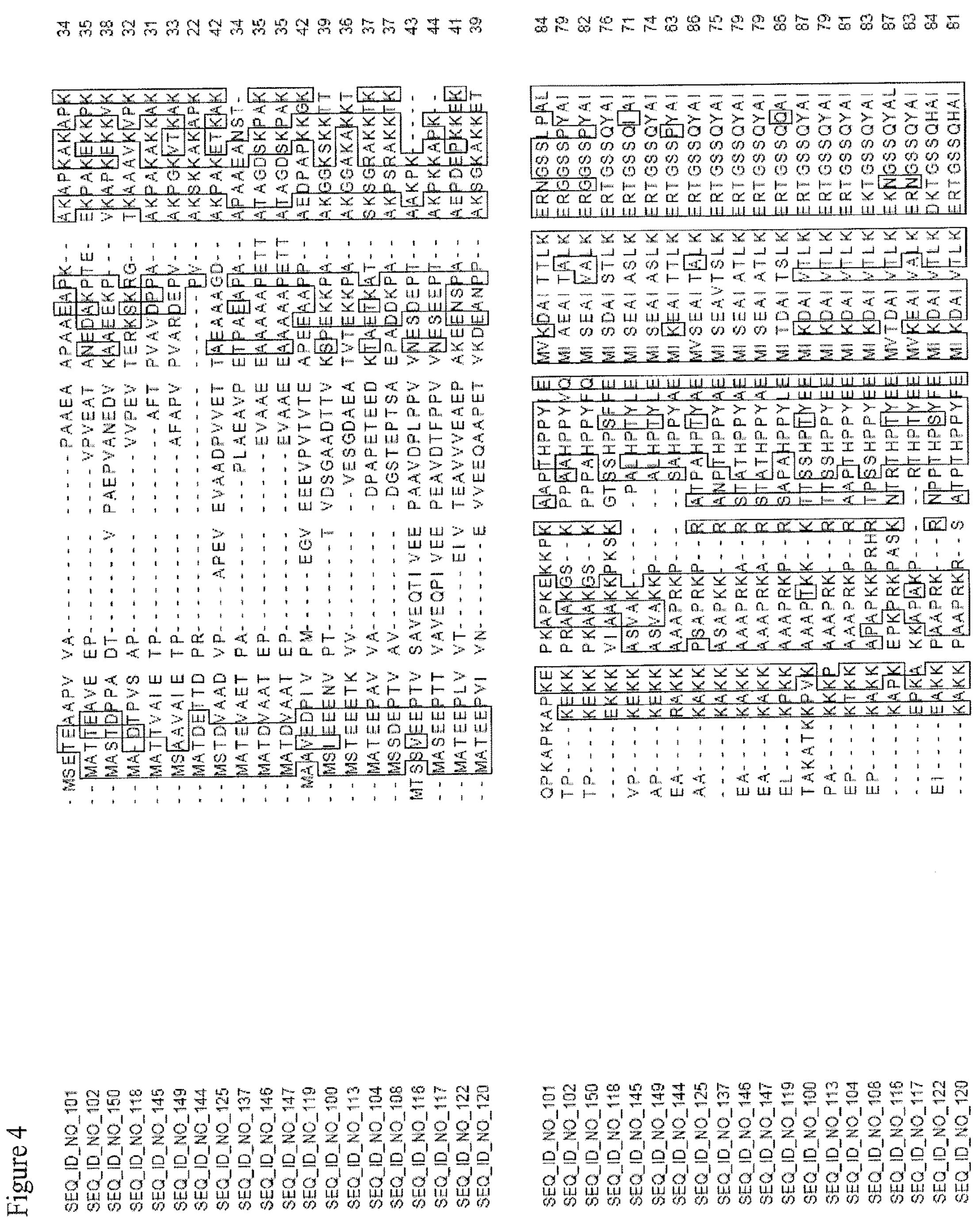
FIG. 4 is an alignment of ME01910 (SEQ ID NO:100) with homologous and/or orthologous amino acid sequences GI No. 585238 (SEQ ID NO:101), GI No. 90704789 (SEQ ID NO:102), CeresClone:1895729 (SEQ ID NO:104), CeresAnnot:1442808 (SEQ ID NO:108), CeresClone:1104700 (SEQ ID NO:113), GI No. 32966575 (SEQ ID NO:116), GI No. 4996567 (SEQ ID NO:117), GI No. 62286644 (SEQ ID NO:118), GI No. 2623960 (SEQ ID NO:119), GI No. 585241 (SEQ ID NO:120), GI No. 790929 (SEQ ID NO:122), CeresClone:579112 (SEQ ID NO:125), CeresClone:244199 (SEQ ID NO:137), CeresClone:1725848 (SEQ ID NO:144), GI No. 6474950 (SEQ ID NO:145), GI No. 125546057 (SEQ ID NO:146), GI No. 115455945 (SEQ ID NO:147), GI No. 2641211 (SEQ ID NO:149), and GI No. 30024108 (SEQ ID NO:150).
Figure 4:
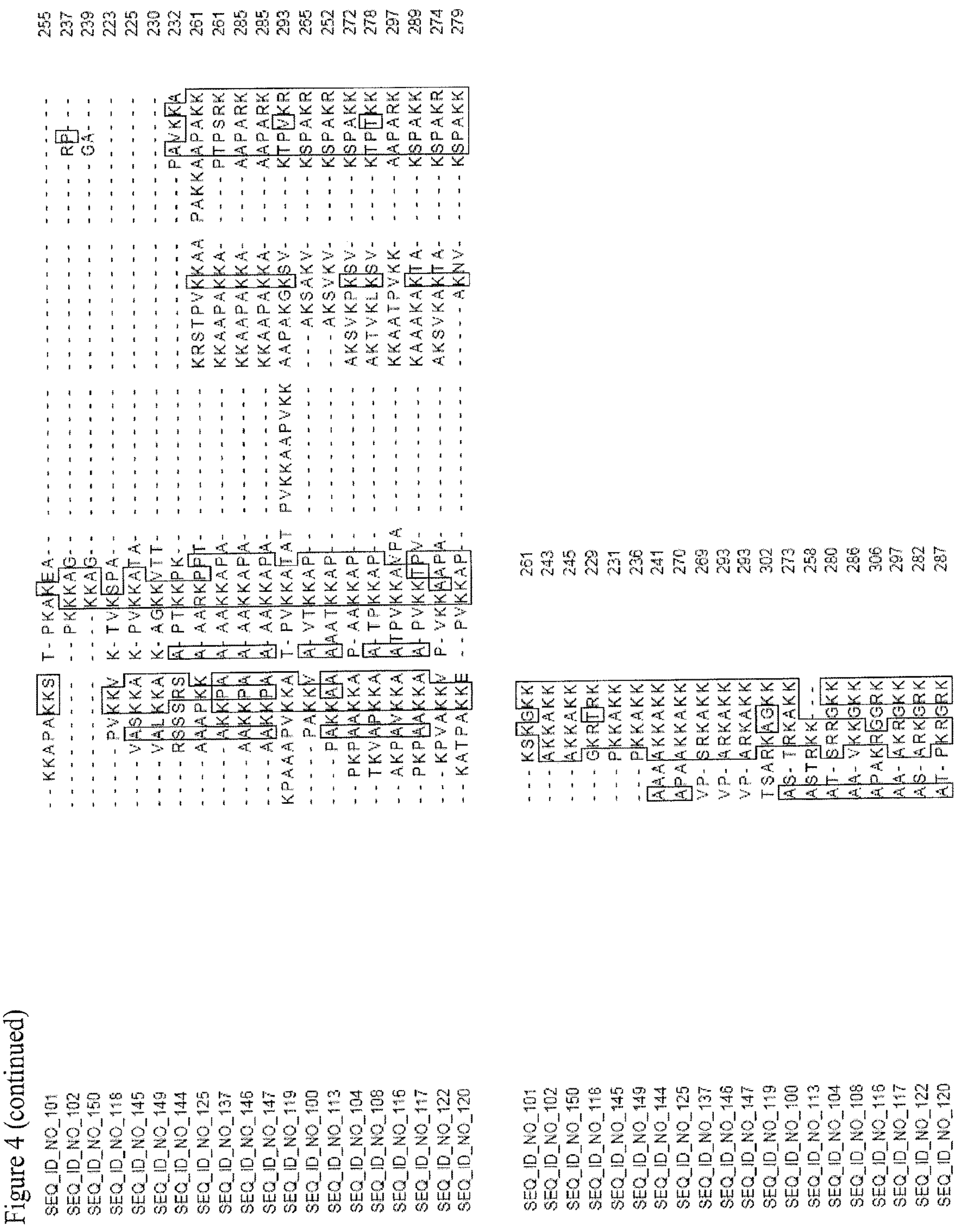

Examples of amino acid sequences of functional homologs of the polypeptide set forth in SEQ ID NO:100 are provided in FIG. 4 and in the Sequence Listing. Such functional homologs include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150. In some cases, a functional homolog of SEQ ID NO:100 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100.

Examples of amino acid sequences of functional homologs of the polypeptide set forth in SEQ ID NO:152 are provided in FIG. 5 and in the Sequence Listing. Such functional homologs include SEQ ID NO:154, SEQ ID NO:156, SEQ ID NO:158, SEQ ID NO:160, SEQ ID NO:162, and SEQ ID NO:164. In some cases, a functional homolog of SEQ ID NO:152 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152.

Examples of amino acid sequences of functional homologs of the polypeptide set forth in SEQ ID NO:166 are provided in FIG. 6 and in the Sequence Listing. Such functional homologs include SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184. In some cases, a functional homolog of SEQ ID NO:166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166.

Examples of amino acid sequences of functional homologs of the polypeptide set forth in SEQ ID NO:186 are provided in FIG. 7 and in the Sequence Listing. Such functional homologs include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206. In some cases, a functional homolog of SEQ ID NO:186 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186.

Examples of amino acid sequences of functional homologs of the polypeptide set forth in SEQ ID NO:208 are provided in FIG. 8 and in the Sequence Listing. Such functional homologs include SEQ ID NO:209, SEQ ID NO:210, SEQ ID NO:214, and SEQ ID NO:216. In some cases, a functional homolog of SEQ ID NO:208 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208.

Examples of amino acid sequences of functional homologs of the polypeptide set forth in SEQ ID NO:218 are provided in FIG. 9 and in the Sequence Listing. Such functional homologs include SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052. In some cases, a functional homolog of SEQ ID NO:218 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218.

Examples of amino acid sequences of functional homologs of the polypeptide set forth in SEQ ID NO:234 are provided in FIG. 10 and in the Sequence Listing. Such functional homologs include SEQ ID NO:236, SEQ ID NO:238, SEQ ID NO:239, SEQ ID NO:241, SEQ ID NO:242, SEQ ID NO:243, and SEQ ID NO:244. In some cases, a functional homolog of SEQ ID NO:234 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234.

Examples of amino acid sequences of functional homologs of the polypeptide set forth in SEQ ID NO:246 are provided in FIG. 11 and in the Sequence Listing. Such functional homologs include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298. In some cases, a functional homolog of SEQ ID NO:246 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246.

Examples of amino acid sequences of functional homologs of the polypeptide set forth in SEQ ID NO:300 are provided in FIG. 12 and in the Sequence Listing. Such functional homologs include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329. In some cases, a functional homolog of SEQ ID NO:300 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300.

Examples of amino acid sequences of functional homologs of the polypeptide set forth in SEQ ID NO:332 are provided in FIG. 13 and in the Sequence Listing. Such functional homologs include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553. In some cases, a functional homolog of SEQ ID NO:332 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332.

Examples of amino acid sequences of functional homologs of the polypeptide set forth in SEQ ID NO:368 are provided in FIG. 14 and in the Sequence Listing. Such functional homologs include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508. In some cases, a functional homolog of SEQ ID NO:368 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368.

Examples of amino acid sequences of functional homologs of the polypeptide set forth in SEQ ID NO:510 are provided in FIG. 15 and in the Sequence Listing. Such functional homologs include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531. In some cases, a functional homolog of SEQ ID NO:510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510.

Examples of amino acid sequences of functional homologs of the polypeptide set forth in SEQ ID NO:533 are provided in FIG. 16 and in the Sequence Listing. Such functional homologs include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554. In some cases, a functional homolog of SEQ ID NO:533 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533.

Examples of amino acid sequences of functional homologs of the polypeptide set forth in SEQ ID NO:558 are provided in FIG. 17 and in the Sequence Listing. Such functional homologs include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591. In some cases, a functional homolog of SEQ ID NO:558 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558.

Examples of amino acid sequences of functional homologs of the polypeptide set forth in SEQ ID NO:593 are provided in FIG. 18 and in the Sequence Listing. Such functional homologs include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611. In some cases, a functional homolog of SEQ ID NO:593 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593.

Examples of amino acid sequences of functional homologs of the polypeptide set forth in SEQ ID NO:613 are provided in FIG. 19 and in the Sequence Listing. Such functional homologs include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644. In some cases, a functional homolog of SEQ ID NO:613 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613.

Examples of amino acid sequences of functional homologs of the polypeptide set forth in SEQ ID NO:646 are provided in FIG. 20 and in the Sequence Listing. Such functional homologs include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685. In some cases, a functional homolog of SEQ ID NO:646 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646.

Examples of amino acid sequences of functional homologs of the polypeptide set forth in SEQ ID NO:687 are provided in FIG. 21 and in the Sequence Listing. Such functional homologs include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728. In some cases, a functional homolog of SEQ ID NO:687 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687.

Examples of amino acid sequences of functional homologs of the polypeptide set forth in SEQ ID NO:730 are provided in FIG. 22 and in the Sequence Listing. Such functional homologs include SEQ ID NO:732, SEQ ID NO:733, SEQ ID NO:735, SEQ ID NO:737, SEQ ID NO:738, and SEQ ID NO:742. In some cases, a functional homolog of SEQ ID NO:730 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730.

Examples of amino acid sequences of functional homologs of the polypeptide set forth in SEQ ID NO:746 are provided in FIG. 23 and in the Sequence Listing. Such functional homologs include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767. In some cases, a functional homolog of SEQ ID NO:746 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746.

Examples of amino acid sequences of functional homologs of the polypeptide set forth in SEQ ID NO:769 are provided in FIG. 24 and in the Sequence Listing. Such functional homologs include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790. In some cases, a functional homolog of SEQ ID NO:769 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769.

Examples of amino acid sequences of functional homologs of the polypeptide set forth in SEQ ID NO:792 are provided in FIG. 25 and in the Sequence Listing. Such functional homologs include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822. In some cases, a functional homolog of SEQ ID NO:792 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792.

Examples of amino acid sequences of functional homologs of the polypeptide set forth in SEQ ID NO:824 are provided in FIG. 26 and in the Sequence Listing. Such functional homologs include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716. In some cases, a functional homolog of SEQ ID NO:824 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824.

Examples of amino acid sequences of functional homologs of the polypeptide set forth in SEQ ID NO:828 are provided in FIG. 27 and in the Sequence Listing. Such functional homologs include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851. In some cases, a functional homolog of SEQ ID NO:828 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828.

Examples of amino acid sequences of functional homologs of the polypeptide set forth in SEQ ID NO:855 are provided in FIG. 28 and in the Sequence Listing. Such functional homologs include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889. In some cases, a functional homolog of SEQ ID NO:855 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855.

Examples of amino acid sequences of functional homologs of the polypeptide set forth in SEQ ID NO:891 are provided in FIG. 29 and in the Sequence Listing. Such functional homologs include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915. In some cases, a functional homolog of SEQ ID NO:891 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891.

Examples of amino acid sequences of functional homologs of the polypeptide set forth in SEQ ID NO:917 are provided in FIG. 30 and in the Sequence Listing. Such functional homologs include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940. In some cases, a functional homolog of SEQ ID NO:917 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917.

Examples of amino acid sequences of functional homologs of the polypeptide set forth in SEQ ID NO:944 are provided in FIG. 31 and in the Sequence Listing. Such functional homologs include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974. In some cases, a functional homolog of SEQ ID NO:944 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944.

Examples of amino acid sequences of functional homologs of the polypeptide set forth in SEQ ID NO:976 are provided in FIG. 32 and in the Sequence Listing. Such functional homologs include, but not limited to, SEQ ID NO:978 and SEQ ID NO:980. In some cases, a functional homolog of SEQ ID NO:976 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976.

Examples of amino acid sequences of functional homologs of the polypeptide set forth in SEQ ID NO:982 are provided in FIG. 33 and in the Sequence Listing. Such functional homologs include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033. In some cases, a functional homolog of SEQ ID NO:982 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982.

Examples of amino acid sequences of functional homologs of the polypeptide set forth in SEQ ID NO:1054 are provided in FIG. 34 and in the Sequence Listing. Such functional homologs include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097. In some cases, a functional homolog of SEQ ID NO:1054 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054.

Examples of amino acid sequences of functional homologs of the polypeptide set forth in SEQ ID NO:1099 are provided in FIG. 35 and in the Sequence Listing. Such functional homologs include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110. In some cases, a functional homolog of SEQ ID NO:1099 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099.

Examples of amino acid sequences of functional homologs of the polypeptide set forth in SEQ ID NO:1112 are provided in FIG. 36 and in the Sequence Listing. Such functional homologs include SEQ ID NO:1113 and SEQ ID NO:1114. In some cases, a functional homolog of SEQ ID NO:1112 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112.

Examples of amino acid sequences of functional homologs of the polypeptide set forth in SEQ ID NO:1116 are provided in FIG. 37 and in the Sequence Listing. Such functional homologs include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155. In some cases, a functional homolog of SEQ ID NO:1116 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116.

Examples of amino acid sequences of functional homologs of the polypeptide set forth in SEQ ID NO:1159 are provided in FIG. 38 and in the Sequence Listing. Such functional homologs include SEQ ID NO:1161, SEQ ID NO:1162, SEQ ID NO:1163, and SEQ ID NO:1164. In some cases, a functional homolog of SEQ ID NO:1159 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159.

Examples of amino acid sequences of functional homologs of the polypeptide set forth in SEQ ID NO:1166 are provided in FIG. 39 and in the Sequence Listing. Such functional homologs include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183. In some cases, a functional homolog of SEQ ID NO:1166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166.

Examples of amino acid sequences of functional homologs of the polypeptide set forth in SEQ ID NO:1185 are provided in FIG. 40 and in the Sequence Listing. Such functional homologs include SEQ ID NO:1187, SEQ ID NO:1189, SEQ ID NO:1190, SEQ ID NO:1191, and SEQ ID NO:1192. In some cases, a functional homolog of SEQ ID NO:1185 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185.

Examples of amino acid sequences of functional homologs of the polypeptide set forth in SEQ ID NO:1194 are provided in FIG. 41 and in the Sequence Listing. Such functional homologs include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208. In some cases, a functional homolog of SEQ ID NO:1194 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194.

Examples of amino acid sequences of functional homologs of the polypeptide set forth in SEQ ID NO:1210 are provided in FIG. 42 and in the Sequence Listing. Such functional homologs include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272. In some cases, a functional homolog of SEQ ID NO:1210 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210.

Examples of amino acid sequences of functional homologs of the polypeptide set forth in SEQ ID NO:1274 are provided in FIG. 43 and in the Sequence Listing. Such functional homologs include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300. In some cases, a functional homolog of SEQ ID NO:1274 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274.

Examples of amino acid sequences of functional homologs of the polypeptide set forth in SEQ ID NO:1302 are provided in FIG. 44 and in the Sequence Listing. Such functional homologs include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340. In some cases, a functional homolog of SEQ ID NO:1302 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302.

Examples of amino acid sequences of functional homologs of the polypeptide set forth in SEQ ID NO:1342 are provided in FIG. 45 and in the Sequence Listing. Such functional homologs include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383. In some cases, a functional homolog of SEQ ID NO:1342 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342.

Examples of amino acid sequences of functional homologs of the polypeptide set forth in SEQ ID NO:1385 are provided in FIG. 46 and in the Sequence Listing. Such functional homologs include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407. In some cases, a functional homolog of SEQ ID NO:1385 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385.

Examples of amino acid sequences of functional homologs of the polypeptide set forth in SEQ ID NO:1409 are provided in FIG. 47 and in the Sequence Listing. Such functional homologs include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426. In some cases, a functional homolog of SEQ ID NO:1409 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409.

Examples of amino acid sequences of functional homologs of the polypeptide set forth in SEQ ID NO:1428 are provided in FIG. 48 and in the Sequence Listing. Such functional homologs include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459. In some cases, a functional homolog of SEQ ID NO:1428 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428.

Examples of amino acid sequences of functional homologs of the polypeptide set forth in SEQ ID NO:1463 are provided in FIG. 49 and in the Sequence Listing. Such functional homologs include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477. In some cases, a functional homolog of SEQ ID NO:1463 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463.

Examples of amino acid sequences of functional homologs of the polypeptide set forth in SEQ ID NO:1491 are provided in FIG. 50 and in the Sequence Listing. Such functional homologs include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508. In some cases, a functional homolog of SEQ ID NO:1491 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491.

Examples of amino acid sequences of functional homologs of the polypeptide set forth in SEQ ID NO:1510 are provided in FIG. 51 and in the Sequence Listing. Such functional homologs include SEQ ID NO:1512, SEQ ID NO:1514, SEQ ID NO:1516, SEQ ID NO:1518, SEQ ID NO:1520, SEQ ID NO:1522, and SEQ ID NO:1523. In some cases, a functional homolog of SEQ ID NO:1510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510.

Examples of amino acid sequences of functional homologs of the polypeptide set forth in SEQ ID NO:1525 are provided in FIG. 52 and in the Sequence Listing. Such functional homologs include SEQ ID NO:1527, SEQ ID NO:1529, SEQ ID NO:1530, SEQ ID NO:1532, SEQ ID NO:1534, and SEQ ID NO:1535. In some cases, a functional homolog of SEQ ID NO:1525 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525.

Examples of amino acid sequences of functional homologs of the polypeptide set forth in SEQ ID NO:1537 are provided in FIG. 53 and in the Sequence Listing. Such functional homologs include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392. In some cases, a functional homolog of SEQ ID NO:1537 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537.

Examples of amino acid sequences of functional homologs of the polypeptide set forth in SEQ ID NO:1554 are provided in FIG. 54 and in the Sequence Listing. Such functional homologs include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575. In some cases, a functional homolog of SEQ ID NO:1554 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554.

Examples of amino acid sequences of functional homologs of the polypeptide set forth in SEQ ID NO:1577 are provided in FIG. 55 and in the Sequence Listing. Such functional homologs include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653. In some cases, a functional homolog of SEQ ID NO:1577 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577.

Examples of amino acid sequences of functional homologs of the polypeptide set forth in SEQ ID NO:1437 are provided in FIG. 56 and in the Sequence Listing. Such functional homologs include SEQ ID NO:173, SEQ ID NO:212, SEQ ID NO:361, SEQ ID NO:421, SEQ ID NO:443, SEQ ID NO:740, SEQ ID NO:744, SEQ ID NO:942, and SEQ ID NO:1461. In some cases, a functional homolog of SEQ ID NO:1437 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437.

Examples of amino acid sequences of functional homologs of the polypeptide set forth in SEQ ID NO:97 are provided in FIG. 57 and in the Sequence Listing. Such functional homologs include SEQ ID NO:2010, SEQ ID NO:2011, SEQ ID NO:2013, SEQ ID NO:2015, SEQ ID NO:2017. In some cases, a functional homolog of SEQ ID NO:97 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97.

The identification of conserved regions in a low nitrogen tolerance-modulating polypeptide facilitates production of variants of low nitrogen tolerance-modulating polypeptides. Variants of low nitrogen tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1-57 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful low nitrogen tolerance-modulating polypeptides include those that fit a Hidden Markov Model based on the polypeptides set forth in any one of FIGS. 1-57. A Hidden Markov Model (HMM) is a statistical model of a consensus sequence for a group of functional homologs. See, Durbin et al. (1998) *Biological Sequence Analysis: Probabilistic Models of Proteins and Nucleic Acids*, Cambridge University Press, Cambridge, UK. An HMM is generated by the program HMMER 2.3.2 with default program parameters, using the sequences of the group of functional homologs as input. The multiple sequence alignment is generated by ProbCons (Do et al. (2005) Genome Res., 15(2):330-40) version 1.11 using a set of default parameters: -c,—consistency REPS of 2; -ir,—iterative-refinement REPS of 100; -pre,—pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate low nitrogen tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The low nitrogen tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a low nitrogen tolerance-modulating polypeptide discussed below is about 50%, 60%, 70%, 80%, 90%, or 95% of the HMM bit score of a functional homolog provided the Sequence Listing of this application. In some embodiments, a low nitrogen tolerance-modulating polypeptide discussed below fits the indicated HMM with an HMM bit score greater than 20, and has a domain indicative of a low nitrogen tolerance-modulating polypeptide. In some embodiments, a low nitrogen tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-57.

Examples of polypeptides are shown in the sequence listing that have HMM bit scores greater than 800 when fitted to an HMM generated from the amino acid sequences set forth in FIG. 1 are identified in the Sequence Listing of this application. Such polypeptides include SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

Examples of polypeptides are shown in the sequence listing that have HMM bit scores greater than 150 when fitted to an HMM generated from the amino acid sequences set forth in FIG. 2 are identified in the Sequence Listing of this application. Such polypeptides include SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

Examples of polypeptides are shown in the sequence listing that have HMM bit scores greater than 540 when fitted to an HMM generated from the amino acid sequences set forth in FIG. 3 are identified in the Sequence Listing of this application. Such polypeptides include SEQ ID NO:77, SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and SEQ ID NO:1479.

Examples of polypeptides are shown in the sequence listing that have HMM bit scores greater than 210 when fitted to an HMM generated from the amino acid sequences set forth in FIG. 4 are identified in the Sequence Listing of this application. Such polypeptides include SEQ ID NO:100, SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

Examples of polypeptides are shown in the sequence listing that have HMM bit scores greater than 90 when fitted to an HMM generated from the amino acid sequences set forth in FIG. 5 are identified in the Sequence Listing of this application. Such polypeptides include SEQ ID NO:152, SEQ ID NO:154, SEQ ID NO:156, SEQ ID NO:158, SEQ ID NO:160, SEQ ID NO:162, and SEQ ID NO:164.

Examples of polypeptides are shown in the sequence listing that have HMM bit scores greater than 230 when fitted to an HMM generated from the amino acid sequences set forth in FIG. 6 are identified in the Sequence Listing of this application. Such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184.

Examples of polypeptides are shown in the sequence listing that have HMM bit scores greater than 90 when fitted to an HMM generated from the amino acid sequences set forth in FIG. 7 are identified in the Sequence Listing of this application. Such polypeptides include SEQ ID NO:186, SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

Examples of polypeptides are shown in the sequence listing that have HMM bit scores greater than 380 when fitted to an HMM generated from the amino acid sequences set forth in FIG. 8 are identified in the Sequence Listing of this application. Such polypeptides include SEQ ID NO:208, SEQ ID NO:209, SEQ ID NO:210, SEQ ID NO:214, and SEQ ID NO:216.

Examples of polypeptides are shown in the sequence listing that have HMM bit scores greater than 110 when fitted to an HMM generated from the amino acid sequences set forth in FIG. 9 are identified in the Sequence Listing of this application. Such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

Examples of polypeptides are shown in the sequence listing that have HMM bit scores greater than 220 when fitted to an HMM generated from the amino acid sequences set forth in FIG. 10 are identified in the Sequence Listing of this application. Such polypeptides include SEQ ID NO:234, SEQ ID NO:236, SEQ ID NO:238, SEQ ID NO:239, SEQ ID NO:241, SEQ ID NO:242, SEQ ID NO:243, and SEQ ID NO:244.

Examples of polypeptides are shown in the sequence listing that have HMM bit scores greater than 150 when fitted to an HMM generated from the amino acid sequences set forth in FIG. 11 are identified in the Sequence Listing of this application. Such polypeptides include SEQ ID NO:246, SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

Examples of polypeptides are shown in the sequence listing that have HMM bit scores greater than 950 when fitted to an HMM generated from the amino acid sequences set forth in FIG. 12 are identified in the Sequence Listing of this application. Such polypeptides include SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

Examples of polypeptides are shown in the sequence listing that have HMM bit scores greater than 460 when fitted to an HMM generated from the amino acid sequences set forth in FIG. 13 are identified in the Sequence Listing of this application. Such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

Examples of polypeptides are shown in the sequence listing that have HMM bit scores greater than 150 when fitted to an HMM generated from the amino acid sequences set forth in FIG. 14 are identified in the Sequence Listing of this application. Such polypeptides include SEQ ID NO:368, SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

Examples of polypeptides are shown in the sequence listing that have HMM bit scores greater than 410 when fitted to an HMM generated from the amino acid sequences set forth in FIG. 15 are identified in the Sequence Listing of this application. Such polypeptides include SEQ ID NO:510, SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

Examples of polypeptides are shown in the sequence listing that have HMM bit scores greater than 520 when fitted to an HMM generated from the amino acid sequences set forth in FIG. 16 are identified in the Sequence Listing of this application. Such polypeptides include SEQ ID NO:533, SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

Examples of polypeptides are shown in the sequence listing that have HMM bit scores greater than 1150 when fitted to an HMM generated from the amino acid sequences set forth in FIG. 17 are identified in the Sequence Listing of this application. Such polypeptides include SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

Examples of polypeptides are shown in the sequence listing that have HMM bit scores greater than 340 when fitted to an HMM generated from the amino acid sequences set forth in FIG. 18 are identified in the Sequence Listing of this application. Such polypeptides include SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

Examples of polypeptides are shown in the sequence listing that have HMM bit scores greater than 140 when fitted to an HMM generated from the amino acid sequences set forth in FIG. 19 are identified in the Sequence Listing of this application. Such polypeptides include SEQ ID NO:613, SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

Examples of polypeptides are shown in the sequence listing that have HMM bit scores greater than 250 when fitted to an HMM generated from the amino acid sequences set forth in FIG. 20 are identified in the Sequence Listing of this application. Such polypeptides include SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

Examples of polypeptides are shown in the sequence listing that have HMM bit scores greater than 170 when fitted to an HMM generated from the amino acid sequences set forth in FIG. 21 are identified in the Sequence Listing of this application. Such polypeptides include SEQ ID NO:687, SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

Examples of polypeptides are shown in the sequence listing that have HMM bit scores greater than 210 when fitted to an HMM generated from the amino acid sequences set forth in FIG. 22 are identified in the Sequence Listing of this application. Such polypeptides include SEQ ID NO:730, SEQ ID NO:732, SEQ ID NO:733, SEQ ID NO:735, SEQ ID NO:737, SEQ ID NO:738, and SEQ ID NO:742.

Examples of polypeptides are shown in the sequence listing that have HMM bit scores greater than 230 when fitted to an HMM generated from the amino acid sequences set forth in FIG. 23 are identified in the Sequence Listing of this application. Such polypeptides include SEQ ID NO:746, SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

Examples of polypeptides are shown in the sequence listing that have HMM bit scores greater than 180 when fitted to an HMM generated from the amino acid sequences set forth in FIG. 24 are identified in the Sequence Listing of this application. Such polypeptides include SEQ ID NO:769, SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

Examples of polypeptides are shown in the sequence listing that have HMM bit scores greater than 300 when fitted to an HMM generated from the amino acid sequences set forth in FIG. 25 are identified in the Sequence Listing of this application. Such polypeptides include SEQ ID NO:792, SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

Examples of polypeptides are shown in the sequence listing that have HMM bit scores greater than 190 when fitted to an HMM generated from the amino acid sequences set forth in FIG. 26 are identified in the Sequence Listing of this application. Such polypeptides include SEQ ID NO:824, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

Examples of polypeptides are shown in the sequence listing that have HMM bit scores greater than 630 when fitted to an HMM generated from the amino acid sequences set forth in FIG. 27 are identified in the Sequence Listing of this application. Such polypeptides include SEQ ID NO:828, SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

Examples of polypeptides are shown in the sequence listing that have HMM bit scores greater than 95 when fitted to an HMM generated from the amino acid sequences set forth in FIG. 28 are identified in the Sequence Listing of this application. Such polypeptides include SEQ ID NO:855, SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

Examples of polypeptides are shown in the sequence listing that have HMM bit scores greater than 850 when fitted to an HMM generated from the amino acid sequences set forth in FIG. 29 are identified in the Sequence Listing of this application. Such polypeptides include SEQ ID NO:891, SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

Examples of polypeptides are shown in the sequence listing that have HMM bit scores greater than 300 when fitted to an HMM generated from the amino acid sequences set forth in FIG. 30 are identified in the Sequence Listing of this application. Such polypeptides include SEQ ID NO:917, SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

Examples of polypeptides are shown in the sequence listing that have HMM bit scores greater than 60 when fitted to an HMM generated from the amino acid sequences set forth in FIG. 31 are identified in the Sequence Listing of this application. Such polypeptides include SEQ ID NO:944, SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

Examples of polypeptides are shown in the sequence listing that have HMM bit scores greater than 340 when fitted to an HMM generated from the amino acid sequences set forth in FIG. 32 are identified in the Sequence Listing of this application. Such polypeptides include SEQ ID NO:976, SEQ ID NO:978, and SEQ ID NO:980.

Examples of polypeptides are shown in the sequence listing that have HMM bit scores greater than 180 when fitted to an HMM generated from the amino acid sequences set forth in FIG. 33 are identified in the Sequence Listing of this application. Such polypeptides include SEQ ID NO:982, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

Examples of polypeptides are shown in the sequence listing that have HMM bit scores greater than 1060 when fitted to an HMM generated from the amino acid sequences set forth in FIG. 34 are identified in the Sequence Listing of this application. Such polypeptides include SEQ ID NO:1054, SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

Examples of polypeptides are shown in the sequence listing that have HMM bit scores greater than 260 when fitted to an HMM generated from the amino acid sequences set forth in FIG. 35 are identified in the Sequence Listing of this application. Such polypeptides include SEQ ID NO:1099, SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

Examples of polypeptides are shown in the sequence listing that have HMM bit scores greater than 150 when fitted to an HMM generated from the amino acid sequences set forth in FIG. 36 are identified in the Sequence Listing of this application. Such polypeptides include SEQ ID NO:1112, SEQ ID NO:1113, and SEQ ID NO:1114.

Examples of polypeptides are shown in the sequence listing that have HMM bit scores greater than 40 when fitted to an HMM generated from the amino acid sequences set forth in FIG. 37 are identified in the Sequence Listing of this application. Such polypeptides include SEQ ID NO:1116, SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

Examples of polypeptides are shown in the sequence listing that have HMM bit scores greater than 450 when fitted to an HMM generated from the amino acid sequences set forth in FIG. 38 are identified in the Sequence Listing of this application. Such polypeptides include SEQ ID NO:1159, SEQ ID NO:1161, SEQ ID NO:1162, SEQ ID NO:1163, and SEQ ID NO:1164.

Examples of polypeptides are shown in the sequence listing that have HMM bit scores greater than 160 when fitted to an HMM generated from the amino acid sequences set forth in FIG. 39 are identified in the Sequence Listing of this application. Such polypeptides include SEQ ID NO:1166, SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

Examples of polypeptides are shown in the sequence listing that have HMM bit scores greater than 180 when fitted to an HMM generated from the amino acid sequences set forth in FIG. 40 are identified in the Sequence Listing of this application. Such polypeptides include SEQ ID NO:1185, SEQ ID NO:1187, SEQ ID NO:1189, SEQ ID NO:1190, SEQ ID NO:1191, and SEQ ID NO:1192.

Examples of polypeptides are shown in the sequence listing that have HMM bit scores greater than 670 when fitted to an HMM generated from the amino acid sequences set forth in FIG. 41 are identified in the Sequence Listing of this application. Such polypeptides include SEQ ID NO:1194, SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

Examples of polypeptides are shown in the sequence listing that have HMM bit scores greater than 280 when fitted to an HMM generated from the amino acid sequences set forth in FIG. 42 are identified in the Sequence Listing of this application. Such polypeptides include SEQ ID NO:1210, SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

Examples of polypeptides are shown in the sequence listing that have HMM bit scores greater than 700 when fitted to an HMM generated from the amino acid sequences set forth in FIG. 43 are identified in the Sequence Listing of this application. Such polypeptides include SEQ ID NO:1274, SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

Examples of polypeptides are shown in the sequence listing that have HMM bit scores greater than 920 when fitted to an HMM generated from the amino acid sequences set forth in FIG. 44 are identified in the Sequence Listing of this application. Such polypeptides include SEQ ID NO:1302, SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

Examples of polypeptides are shown in the sequence listing that have HMM bit scores greater than 510 when fitted to an HMM generated from the amino acid sequences set forth in FIG. 45 are identified in the Sequence Listing of this application. Such polypeptides include SEQ ID NO:1342, SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

Examples of polypeptides are shown in the sequence listing that have HMM bit scores greater than 140 when fitted to an HMM generated from the amino acid sequences set forth in FIG. 46 are identified in the Sequence Listing of this application. Such polypeptides include SEQ ID NO:1385, SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

Examples of polypeptides are shown in the sequence listing that have HMM bit scores greater than 150 when fitted to an HMM generated from the amino acid sequences set forth in FIG. 47 are identified in the Sequence Listing of this application. Such polypeptides include SEQ ID NO:1409, SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, SEQ ID NO:1426.

Examples of polypeptides are shown in the sequence listing that have HMM bit scores greater than 190 when fitted to an HMM generated from the amino acid sequences set forth in FIG. 48 are identified in the Sequence Listing of this application. Such polypeptides include SEQ ID NO:1428, SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

Examples of polypeptides are shown in the sequence listing that have HMM bit scores greater than 450 when fitted to an HMM generated from the amino acid sequences set forth in FIG. 49 are identified in the Sequence Listing of this application. Such polypeptides include SEQ ID NO:1463, SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

Examples of polypeptides are shown in the sequence listing that have HMM bit scores greater than 580 when fitted to an HMM generated from the amino acid sequences set forth in FIG. 50 are identified in the Sequence Listing of this application. Such polypeptides include SEQ ID NO:1491, SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

Examples of polypeptides are shown in the sequence listing that have HMM bit scores greater than 100 when fitted to an HMM generated from the amino acid sequences set forth in FIG. 51 are identified in the Sequence Listing of this application. Such polypeptides include SEQ ID NO:1510, SEQ ID NO:1512, SEQ ID NO:1514, SEQ ID NO:1516, SEQ ID NO:1518, SEQ ID NO:1520, SEQ ID NO:1522, and SEQ ID NO:1523.

Examples of polypeptides are shown in the sequence listing that have HMM bit scores greater than 800 when fitted to an HMM generated from the amino acid sequences set forth in FIG. 52 are identified in the Sequence Listing of this application. Such polypeptides include SEQ ID NO:1525, SEQ ID NO:1527, SEQ ID NO:1529, SEQ ID NO:1530, SEQ ID NO:1532, SEQ ID NO:1534, and SEQ ID NO:1535.

Examples of polypeptides are shown in the sequence listing that have HMM bit scores greater than 490 when fitted to an HMM generated from the amino acid sequences set forth in FIG. 53 are identified in the Sequence Listing of this application. Such polypeptides include SEQ ID NO:1537, SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

Examples of polypeptides are shown in the sequence listing that have HMM bit scores greater than 690 when fitted to an HMM generated from the amino acid sequences set forth in FIG. 54 are identified in the Sequence Listing of this application. Such polypeptides include SEQ ID NO:1554, SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

Examples of polypeptides are shown in the sequence listing that have HMM bit scores greater than 380 when fitted to an HMM generated from the amino acid sequences set forth in FIG. 55 are identified in the Sequence Listing of this application. Such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1577, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653.

Examples of polypeptides are shown in the sequence listing that have HMM bit scores greater than 870 when fitted to an HMM generated from the amino acid sequences set forth in FIG. 56 are identified in the Sequence Listing of this application. Such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1437, and SEQ ID NO:1461.

Examples of polypeptides are shown in the sequence listing that have HMM bit scores greater than 140 when fitted to an HMM generated from the amino acid sequences set forth in FIG. 57 are identified in the Sequence Listing of this application. Such polypeptides include SEQ ID NO:97, SEQ ID NO:2010, SEQ ID NO:2011, SEQ ID NO:2013, SEQ ID NO:2015, and SEQ ID NO:2017.

D. Percent Identity

In some embodiments, a low nitrogen tolerance-modulating polypeptide has an amino acid sequence with at least 20% sequence identity, e.g., at least 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Polypeptides having such a percent sequence identity often have a domain indicative of a low nitrogen tolerance-modulating polypeptide and/or have an HMM bit score that is greater than 20, as discussed above. Amino acid sequences of low nitrogen tolerance-modulating polypeptides having at least 20% sequence identity to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577 are provided in FIGS. 1-57 and in the Sequence Listing.

"Percent sequence identity" refers to the degree of sequence identity between any given reference sequence, e.g., SEQ ID NO:3, and a candidate low nitrogen tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al. (2003) *Nucleic Acids Res.,* 31(13): 3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a low nitrogen tolerance-modulating polypeptide has an amino acid sequence with sequence similarity to the amino acid sequence set forth in SEQ ID NO:3, and preferably has at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3. Amino acid sequences of polypeptides having greater than 20% sequence identity to the polypeptide set forth in SEQ ID NO:3 are provided in FIG. 1 and in the Sequence Listing. Examples of such polypeptides include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

In some cases, a low nitrogen tolerance-modulating polypeptide has an amino acid sequence with sequence similarity to the amino acid sequence set forth in SEQ ID NO:49, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49. Amino acid sequences of polypeptides having greater than 45% sequence identity to the polypeptide set forth in SEQ ID NO:49 are provided in FIG. 2 and in the Sequence Listing. Examples of such polypeptides include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

In some cases, a low nitrogen tolerance-modulating polypeptide has an amino acid sequence with sequence similarity to the amino acid sequence set forth in SEQ ID NO:77, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77. Amino acid sequences of polypeptides having greater than 45% sequence identity to the polypeptide set forth in SEQ ID NO:77 are provided in FIG. 3 and in the Sequence Listing. Examples of such polypeptides include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, SEQ ID NO:1479.

In some cases, a low nitrogen tolerance-modulating polypeptide has an amino acid sequence with sequence similarity to the amino acid sequence set forth in SEQ ID NO:100, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100. Amino acid sequences of polypeptides having greater than 45% sequence identity to the polypeptide set forth in SEQ ID NO: 100 are provided in FIG. 4 and in the Sequence Listing. Examples of such polypeptides include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

In some cases, a low nitrogen tolerance-modulating polypeptide has an amino acid sequence with sequence similarity to the amino acid sequence set forth in SEQ ID NO:152, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152. Amino acid sequences of polypeptides having greater than 45% sequence identity to the polypeptide set forth in SEQ ID NO:152 are provided in FIG. 5 and in the Sequence Listing. Examples of such polypeptides include SEQ ID NO:154, SEQ ID NO:156, SEQ ID NO:158, SEQ ID NO:160, SEQ ID NO:162, and SEQ ID NO:164.

In some cases, a low nitrogen tolerance-modulating polypeptide has an amino acid sequence with sequence similarity to the amino acid sequence set forth in SEQ ID NO:166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166. Amino acid sequences of polypeptides having greater than 45% sequence identity to the polypeptide set forth in SEQ ID NO:166 are provided in FIG. 6 and in the Sequence Listing. Examples of such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, SEQ ID NO:184.

In some cases, a low nitrogen tolerance-modulating polypeptide has an amino acid sequence with sequence similarity to the amino acid sequence set forth in SEQ ID NO:186, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186. Amino acid sequences of polypeptides having greater than 45% sequence identity to the polypeptide set forth in SEQ ID NO:186 are provided in FIG. 7 and in the Sequence Listing. Examples of such polypeptides include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

In some cases, a low nitrogen tolerance-modulating polypeptide has an amino acid sequence with sequence similarity to the amino acid sequence set forth in SEQ ID NO:208, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208. Amino acid sequences of polypeptides having greater than 45% sequence identity to the polypeptide set forth in SEQ ID NO:208 are provided in FIG. 8 and in the Sequence Listing. Examples of such polypeptides include SEQ ID NO:209, SEQ ID NO:210, SEQ ID NO:214, and SEQ ID NO:216.

In some cases, a low nitrogen tolerance-modulating polypeptide has an amino acid sequence with sequence similarity to the amino acid sequence set forth in SEQ ID NO:218, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218. Amino acid sequences of polypeptides having greater than 45% sequence identity to the polypeptide set forth in SEQ ID NO:218 are provided in FIG. 9 and in the Sequence Listing. Examples of such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

In some cases, a low nitrogen tolerance-modulating polypeptide has an amino acid sequence with sequence similarity to the amino acid sequence set forth in SEQ ID NO:234, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234. Amino acid sequences of polypeptides having greater than 45% sequence identity to the polypeptide set forth in SEQ ID NO:234 are provided in FIG. 10 and in the Sequence Listing. Examples of such polypeptides include SEQ ID NO:236, SEQ ID NO:238, SEQ ID NO:239, SEQ ID NO:241, SEQ ID NO:242, SEQ ID NO:243, and SEQ ID NO:244.

In some cases, a low nitrogen tolerance-modulating polypeptide has an amino acid sequence with sequence similarity to the amino acid sequence set forth in SEQ ID NO:246, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246. Amino acid sequences of polypeptides having greater than 45% sequence identity to the polypeptide set forth in SEQ ID NO:246 are provided in FIG. 11 and in the Sequence Listing. Examples of such polypeptides include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

In some cases, a low nitrogen tolerance-modulating polypeptide has an amino acid sequence with sequence similarity to the amino acid sequence set forth in SEQ ID NO:300, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300. Amino acid sequences of polypeptides having greater than 45% sequence identity to the polypeptide set forth in SEQ ID NO:300 are provided in FIG. 12 and in the Sequence Listing. Examples of such polypeptides include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

In some cases, a low nitrogen tolerance-modulating polypeptide has an amino acid sequence with sequence similarity to the amino acid sequence set forth in SEQ ID NO:332, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332. Amino acid sequences of polypeptides having greater than 45% sequence identity to the polypeptide set forth in SEQ ID NO:332 are provided in FIG. 13 and in the Sequence Listing. Examples of such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

In some cases, a low nitrogen tolerance-modulating polypeptide has an amino acid sequence with sequence similarity to the amino acid sequence set forth in SEQ ID NO:368, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368. Amino acid sequences of polypeptides having greater than 45% sequence identity to the polypeptide set forth in SEQ ID NO:368 are provided in FIG. 14 and in the Sequence Listing. Examples of such polypeptides include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

In some cases, a low nitrogen tolerance-modulating polypeptide has an amino acid sequence with sequence similarity to the amino acid sequence set forth in SEQ ID NO:510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510. Amino acid sequences of polypeptides having greater than 45% sequence identity to the polypeptide set forth in SEQ ID NO:510 are provided in FIG. 15 and in the Sequence Listing. Examples of such polypeptides include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

In some cases, a low nitrogen tolerance-modulating polypeptide has an amino acid sequence with sequence similarity to the amino acid sequence set forth in SEQ ID NO:533, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533. Amino acid sequences of polypeptides having greater than 45% sequence identity to the polypeptide set forth in SEQ ID NO:533 are provided in FIG. 16 and in the Sequence Listing. Examples of such polypeptides include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

In some cases, a low nitrogen tolerance-modulating polypeptide has an amino acid sequence with sequence similarity to the amino acid sequence set forth in SEQ ID NO:558, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558. Amino acid sequences of polypeptides having greater than 45% sequence identity to the polypeptide set forth in SEQ ID NO:558 are provided in FIG. 17 and in the Sequence Listing. Examples of such polypeptides include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

In some cases, a low nitrogen tolerance-modulating polypeptide has an amino acid sequence with sequence similarity to the amino acid sequence set forth in SEQ ID NO:593, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593. Amino acid sequences of polypeptides having greater than 45% sequence identity to the polypeptide set forth in SEQ ID NO:593 are provided in FIG. 18 and in the Sequence Listing. Examples of such polypeptides include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

In some cases, a low nitrogen tolerance-modulating polypeptide has an amino acid sequence with sequence similarity to the amino acid sequence set forth in SEQ ID NO:613, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613. Amino acid sequences of polypeptides having greater than 45% sequence identity to the polypeptide set forth in SEQ ID NO:613 are provided in FIG. 19 and in the Sequence Listing. Examples of such polypeptides include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

In some cases, a low nitrogen tolerance-modulating polypeptide has an amino acid sequence with sequence similarity to the amino acid sequence set forth in SEQ ID NO:646, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646. Amino acid sequences of polypeptides having greater than 45% sequence identity to the polypeptide set forth in SEQ ID NO:646 are provided in FIG. 20 and in the Sequence Listing. Examples of such polypeptides include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

In some cases, a low nitrogen tolerance-modulating polypeptide has an amino acid sequence with sequence similarity to the amino acid sequence set forth in SEQ ID NO:687, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687. Amino acid sequences of polypeptides having greater than 45% sequence identity to the polypeptide set forth in SEQ ID NO:687 are provided in FIG. 21 and in the Sequence Listing. Examples of such polypeptides include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

In some cases, a low nitrogen tolerance-modulating polypeptide has an amino acid sequence with sequence similarity to the amino acid sequence set forth in SEQ ID NO:730, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730. Amino acid sequences of polypeptides having greater than 45% sequence identity to the polypeptide set forth in SEQ ID NO:730 are provided in FIG. 22 and in the Sequence Listing. Examples of such polypeptides include SEQ ID NO:732, SEQ ID NO:733, SEQ ID NO:735, SEQ ID NO:737, SEQ ID NO:738, and SEQ ID NO:742.

In some cases, a low nitrogen tolerance-modulating polypeptide has an amino acid sequence with sequence similarity to the amino acid sequence set forth in SEQ ID NO:746, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746. Amino acid sequences of polypeptides having greater than 45% sequence identity to the polypeptide set forth in SEQ ID NO:746 are provided in FIG. 23 and in the Sequence Listing. Examples of such polypeptides include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

In some cases, a low nitrogen tolerance-modulating polypeptide has an amino acid sequence with sequence similarity to the amino acid sequence set forth in SEQ ID NO:769, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769. Amino acid sequences of polypeptides having greater than 45% sequence identity to the polypeptide set forth in SEQ ID NO:769 are provided in FIG. 24 and in the Sequence Listing. Examples of such polypeptides include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

In some cases, a low nitrogen tolerance-modulating polypeptide has an amino acid sequence with sequence similarity to the amino acid sequence set forth in SEQ ID NO:792, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792. Amino acid sequences of polypeptides having greater than 20% sequence identity to the polypeptide set forth in SEQ ID NO:792 are provided in FIG. 25 and in the Sequence Listing. Examples of such polypeptides include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

In some cases, a low nitrogen tolerance-modulating polypeptide has an amino acid sequence with sequence similarity to the amino acid sequence set forth in SEQ ID NO:824, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824. Amino acid sequences of polypeptides having greater than 45% sequence identity to the polypeptide set forth in SEQ ID NO:824 are provided in FIG. 26 and in the Sequence Listing. Such polypeptides include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

In some cases, a low nitrogen tolerance-modulating polypeptide has an amino acid sequence with sequence similarity to the amino acid sequence set forth in SEQ ID NO:828, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828. Amino acid sequences of polypeptides having greater than 20% sequence identity to the polypeptide set forth in SEQ ID NO:828 are provided in FIG. 27 and in the Sequence Listing. Examples of such polypeptides include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

In some cases, a low nitrogen tolerance-modulating polypeptide has an amino acid sequence with sequence similarity to the amino acid sequence set forth in SEQ ID NO:855, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855. Amino acid sequences of polypeptides having greater than 20% sequence identity to the polypeptide set forth in SEQ ID NO:855 are provided in FIG. 28 and in the Sequence Listing. Examples of such polypeptides include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

In some cases, a low nitrogen tolerance-modulating polypeptide has an amino acid sequence with sequence similarity to the amino acid sequence set forth in SEQ ID NO:891, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891. Amino acid sequences of polypeptides having greater than 20% sequence identity to the polypeptide set forth in SEQ ID NO:891 are provided in FIG. 29 and in the Sequence Listing. Examples of such polypeptides include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

In some cases, a low nitrogen tolerance-modulating polypeptide has an amino acid sequence with sequence similarity to the amino acid sequence set forth in SEQ ID NO:917, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917. Amino acid sequences of polypeptides having greater than 20% sequence identity to the polypeptide set forth in SEQ ID NO:917 are provided in FIG. 30 and in the Sequence Listing. Examples of such polypeptides include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

In some cases, a low nitrogen tolerance-modulating polypeptide has an amino acid sequence with sequence similarity to the amino acid sequence set forth in SEQ ID NO:944, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944. Amino acid sequences of polypeptides having greater than 20% sequence identity to the polypeptide set forth in SEQ ID NO:944 are provided in FIG. 31 and in the Sequence Listing. Examples of such polypeptides include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

In some cases, a low nitrogen tolerance-modulating polypeptide has an amino acid sequence with sequence similarity to the amino acid sequence set forth in SEQ ID NO:976, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976. Amino acid sequences of polypeptides having greater than 45% sequence identity to the polypeptide set forth in SEQ ID NO:976 are provided in FIG. 32 and in the Sequence Listing. Examples of such polypeptides include SEQ ID NO:978 and SEQ ID NO:980.

In some cases, a low nitrogen tolerance-modulating polypeptide has an amino acid sequence with sequence similarity to the amino acid sequence set forth in SEQ ID NO:982, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982. Amino acid sequences of polypeptides having greater than 20% sequence identity to the polypeptide set forth in SEQ ID NO:982 are provided in FIG. 33 and in the Sequence Listing. Examples of such polypeptides include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

In some cases, a low nitrogen tolerance-modulating polypeptide has an amino acid sequence with sequence similarity to the amino acid sequence set forth in SEQ ID NO:1054, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054. Amino acid sequences of polypeptides having greater than 20% sequence identity to the polypeptide set forth in SEQ ID NO:1054 are provided in FIG. 34 and in the Sequence Listing. Examples of such polypeptides include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

In some cases, a low nitrogen tolerance-modulating polypeptide has an amino acid sequence with sequence similarity to the amino acid sequence set forth in SEQ ID NO:1099, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099. Amino acid sequences of polypeptides having greater than 20% sequence identity to the polypeptide set forth in SEQ ID NO:1099 are provided in FIG. 35 and in the Sequence Listing. Examples of such polypeptides include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

In some cases, a low nitrogen tolerance-modulating polypeptide has an amino acid sequence with sequence similarity to the amino acid sequence set forth in SEQ ID NO:1112, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112. Amino acid sequences of polypeptides having greater than 20% sequence identity to the polypeptide set forth in SEQ ID NO:1112 are provided in FIG. 36 and in the Sequence Listing. Examples of such polypeptides include SEQ ID NO:1113 and SEQ ID NO:1114.

In some cases, a low nitrogen tolerance-modulating polypeptide has an amino acid sequence with sequence similarity to the amino acid sequence set forth in SEQ ID NO:1116, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116. Amino acid sequences of polypeptides having greater than 20% sequence identity to the polypeptide set forth in SEQ ID NO:1116 are provided in FIG. 37 and in the Sequence Listing. Examples of such polypeptides include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

In some cases, a low nitrogen tolerance-modulating polypeptide has an amino acid sequence with sequence similarity to the amino acid sequence set forth in SEQ ID NO:1159, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159. Amino acid sequences of polypeptides having greater than 20% sequence identity to the polypeptide set forth in SEQ ID NO:1159 are provided in FIG. 38 and in the Sequence Listing. Examples of such polypeptides include SEQ ID NO:1161, SEQ ID NO:1162, SEQ ID NO:1163, and SEQ ID NO:1164.

In some cases, a low nitrogen tolerance-modulating polypeptide has an amino acid sequence with sequence similarity to the amino acid sequence set forth in SEQ ID NO:1166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166. Amino acid sequences of polypeptides having greater than 20% sequence identity to the polypeptide set forth in SEQ ID NO:1166 are provided in FIG. 39 and in the Sequence Listing. Examples of such polypeptides include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

In some cases, a low nitrogen tolerance-modulating polypeptide has an amino acid sequence with sequence similarity to the amino acid sequence set forth in SEQ ID NO:1185, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185. Amino acid sequences of polypeptides having greater than 20% sequence identity to the polypeptide set forth in SEQ ID NO:1185 are provided in FIG. 40 and in the Sequence Listing. Examples of such polypeptides include SEQ ID NO:1187, SEQ ID NO:1189, SEQ ID NO:1190, SEQ ID NO:1191, and SEQ ID NO:1192.

In some cases, a low nitrogen tolerance-modulating polypeptide has an amino acid sequence with sequence similarity to the amino acid sequence set forth in SEQ ID NO:1194, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194. Amino acid sequences of polypeptides having greater than 20% sequence identity to the polypeptide set forth in SEQ ID NO:1194 are provided in FIG. 41 and in the Sequence Listing. Examples of such polypeptides include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

In some cases, a low nitrogen tolerance-modulating polypeptide has an amino acid sequence with sequence similarity to the amino acid sequence set forth in SEQ ID NO:1210, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210. Amino acid sequences of polypeptides having greater than 20% sequence identity to the polypeptide set forth in SEQ ID NO:1210 are provided in FIG. 42 and in the Sequence Listing. Examples of such polypeptides include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

In some cases, a low nitrogen tolerance-modulating polypeptide has an amino acid sequence with sequence similarity to the amino acid sequence set forth in SEQ ID NO:1274, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274. Amino acid sequences of polypeptides having greater than 20% sequence identity to the polypeptide set forth in SEQ ID NO:1274 are provided in FIG. 43 and in the Sequence Listing. Examples of such polypeptides include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

In some cases, a low nitrogen tolerance-modulating polypeptide has an amino acid sequence with sequence similarity to the amino acid sequence set forth in SEQ ID NO:1302, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302. Amino acid sequences of polypeptides having greater than 20% sequence identity to the polypeptide set forth in SEQ ID NO:1302 are provided in FIG. 44 and in the Sequence Listing. Examples of such polypeptides include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

In some cases, a low nitrogen tolerance-modulating polypeptide has an amino acid sequence with sequence similarity to the amino acid sequence set forth in SEQ ID NO:1342, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342. Amino acid sequences of polypeptides having greater than 20% sequence identity to the polypeptide set forth in SEQ ID NO:1342 are provided in FIG. 45 and in the Sequence Listing. Examples of such polypeptides include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

In some cases, a low nitrogen tolerance-modulating polypeptide has an amino acid sequence with sequence similarity to the amino acid sequence set forth in SEQ ID NO:1385, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385. Amino acid sequences of polypeptides having greater than 20% sequence identity to the polypeptide set forth in SEQ ID NO:1385 are provided in FIG. 46 and in the Sequence Listing. Examples of such polypeptides include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

In some cases, a low nitrogen tolerance-modulating polypeptide has an amino acid sequence with sequence similarity to the amino acid sequence set forth in SEQ ID NO:1409, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409. Amino acid sequences of polypeptides having greater than 20% sequence identity to the polypeptide set forth in SEQ ID NO:1409 are provided in FIG. 47 and in the Sequence Listing. Examples of such polypeptides include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426.

In some cases, a low nitrogen tolerance-modulating polypeptide has an amino acid sequence with sequence similarity to the amino acid sequence set forth in SEQ ID NO:1428, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428. Amino acid sequences of polypeptides having greater than 20% sequence identity to the polypeptide set forth in SEQ ID NO:1428 are provided in FIG. 48 and in the Sequence Listing. Examples of such polypeptides include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

In some cases, a low nitrogen tolerance-modulating polypeptide has an amino acid sequence with sequence similarity to the amino acid sequence set forth in SEQ ID NO:1463, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463. Amino acid sequences of polypeptides having greater than 20% sequence identity to the polypeptide set forth in SEQ ID NO:1463 are provided in FIG. 49 and in the Sequence Listing. Examples of such polypeptides include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

In some cases, a low nitrogen tolerance-modulating polypeptide has an amino acid sequence with sequence similarity to the amino acid sequence set forth in SEQ ID NO:1491, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491. Amino acid sequences of polypeptides having greater than 20% sequence identity to the polypeptide set forth in SEQ ID NO:1491 are provided in FIG. 50 and in the Sequence Listing. Examples of such polypeptides include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

In some cases, a low nitrogen tolerance-modulating polypeptide has an amino acid sequence with sequence similarity to the amino acid sequence set forth in SEQ ID NO:1510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510. Amino acid sequences of polypeptides having greater than 20% sequence identity to the polypeptide set forth in SEQ ID NO:1510 are provided in FIG. 51 and in the Sequence Listing. Examples of such polypeptides include SEQ ID NO:1512, SEQ ID NO:1514, SEQ ID NO:1516, SEQ ID NO:1518, SEQ ID NO:1520, SEQ ID NO:1522, and SEQ ID NO:1523.

In some cases, a low nitrogen tolerance-modulating polypeptide has an amino acid sequence with sequence similarity to the amino acid sequence set forth in SEQ ID NO:1525, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525. Amino acid sequences of polypeptides having greater than 20% sequence identity to the polypeptide set forth in SEQ ID NO:1525 are provided in FIG. 52 and in the Sequence Listing. Examples of such polypeptides include SEQ ID NO:1527, SEQ ID NO:1529, SEQ ID NO:1530, SEQ ID NO:1532, SEQ ID NO:1534, and SEQ ID NO:1535.

In some cases, a low nitrogen tolerance-modulating polypeptide has an amino acid sequence with sequence similarity to the amino acid sequence set forth in SEQ ID NO:1537, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537. Amino acid sequences of polypeptides having greater than 20% sequence identity to the polypeptide set forth in SEQ ID NO:1537 are provided in FIG. 53 and in the Sequence Listing. Examples of such polypeptides include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

In some cases, a low nitrogen tolerance-modulating polypeptide has an amino acid sequence with sequence similarity to the amino acid sequence set forth in SEQ ID NO:1554, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554. Amino acid sequences of polypeptides having greater than 20% sequence identity to the polypeptide set forth in SEQ ID NO:1554 are provided in FIG. 54 and in the Sequence Listing. Examples of such polypeptides include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

In some cases, a low nitrogen tolerance-modulating polypeptide has an amino acid sequence with sequence similarity to the amino acid sequence set forth in SEQ ID NO:1577, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577. Amino acid sequences of polypeptides having greater than 20% sequence identity to the polypeptide set forth in SEQ ID NO:1577 are provided in FIG. 55 and in the Sequence Listing. Examples of such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, SEQ ID NO:1653.

In some cases, a low nitrogen tolerance-modulating polypeptide has an amino acid sequence with sequence similarity to the amino acid sequence set forth in SEQ ID NO:1437, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437. Amino acid sequences of polypeptides having greater than 20% sequence identity to the polypeptide set forth in SEQ ID NO:1437 are provided in FIG. 56 and in the Sequence Listing. Examples of such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1461.

In some cases, a low nitrogen tolerance-modulating polypeptide has an amino acid sequence with sequence similarity to the amino acid sequence set forth in SEQ ID NO:97, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97. Amino acid sequences of polypeptides having greater than 20% sequence identity to the polypeptide set forth in SEQ ID NO:1437 are provided in FIG. 57 and in the Sequence Listing. Examples of such polypeptides include SEQ ID NO:2010, SEQ ID NO:2011, SEQ ID NO:2013, SEQ ID NO:2015, and SEQ ID NO:2017

E. Other Sequences

It should be appreciated that a low nitrogen tolerance-modulating polypeptide can include additional amino acids that are not involved in low nitrogen tolerance-modulation, and thus such a polypeptide can be longer than would otherwise be the case. For example, a low nitrogen tolerance-modulating polypeptide can include a purification tag, a chloroplast transit peptide, a mitochondrial transit peptide, an amyloplast peptide, or a leader sequence added to the amino or carboxy terminus. In some embodiments, a low nitrogen tolerance-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate low-nitrogen tolerance levels when transcribed in a plant or plant cell. Such nucleic acids include, without limitation, those that encode a low nitrogen tolerance-modulating polypeptide and those that can be used to inhibit expression of low nitrogen tolerance-modulating polypeptide via a nucleic acid based method.

A. Nucleic Acids Encoding Low Nitrogen Tolerance-Modulating Polypeptides

Nucleic acids encoding low nitrogen tolerance-modulating polypeptides are described herein. Examples of such nucleic acids include SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576.

A low nitrogen tolerance-modulating nucleic acid can comprise the nucleotide sequence set forth in SEQ ID NO:1. Alternatively, a low nitrogen tolerance-modulating nucleic acid can be a variant of the nucleic acid having the nucleotide sequence set forth in SEQ ID NO:2. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:2.

A low nitrogen tolerance-modulating nucleic acid can comprise the nucleotide sequence set forth in SEQ ID NO: 48. Alternatively, a low nitrogen tolerance-modulating nucleic acid can be a variant of the nucleic acid having the nucleotide sequence set forth in SEQ ID NO: 48. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 48.

A low nitrogen tolerance-modulating nucleic acid can comprise the nucleotide sequence set forth in SEQ ID NO:76. Alternatively, a low nitrogen tolerance-modulating nucleic acid can be a variant of the nucleic acid having the nucleotide sequence set forth in SEQ ID NO:76. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:76.

A low nitrogen tolerance-modulating nucleic acid can comprise the nucleotide sequence set forth in SEQ ID NO:96. Alternatively, a low nitrogen tolerance-modulating nucleic acid can be a variant of the nucleic acid having the nucleotide sequence set forth in SEQ ID NO:96. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:96.

A low nitrogen tolerance-modulating nucleic acid can comprise the nucleotide sequence set forth in SEQ ID NO:99. Alternatively, a low nitrogen tolerance-modulating nucleic acid can be a variant of the nucleic acid having the nucleotide sequence set forth in SEQ ID NO:99. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:99.

A low nitrogen tolerance-modulating nucleic acid can comprise the nucleotide sequence set forth in SEQ ID NO:151. Alternatively, a low nitrogen tolerance-modulating nucleic acid can be a variant of the nucleic acid having the nucleotide sequence set forth in SEQ ID NO:151. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:151.

A low nitrogen tolerance-modulating nucleic acid can comprise the nucleotide sequence set forth in SEQ ID NO:165. Alternatively, a low nitrogen tolerance-modulating nucleic acid can be a variant of the nucleic acid having the nucleotide sequence set forth in SEQ ID NO:165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:165.

A low nitrogen tolerance-modulating nucleic acid can comprise the nucleotide sequence set forth in SEQ ID NO:175. Alternatively, a low nitrogen tolerance-modulating nucleic acid can be a variant of the nucleic acid having the nucleotide sequence set forth in SEQ ID NO:175. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:175.

A low nitrogen tolerance-modulating nucleic acid can comprise the nucleotide sequence set forth in SEQ ID NO:185. Alternatively, a low nitrogen tolerance-modulating nucleic acid can be a variant of the nucleic acid having the nucleotide sequence set forth in SEQ ID NO:185. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:185.

A low nitrogen tolerance-modulating nucleic acid can comprise the nucleotide sequence set forth in SEQ ID NO:207. Alternatively, a low nitrogen tolerance-modulating nucleic acid can be a variant of the nucleic acid having the nucleotide sequence set forth in SEQ ID NO:207. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:207.

A low nitrogen tolerance-modulating nucleic acid can comprise the nucleotide sequence set forth in SEQ ID NO:217. Alternatively, a low nitrogen tolerance-modulating nucleic acid can be a variant of the nucleic acid having the nucleotide sequence set forth in SEQ ID NO:217. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:217.

A low nitrogen tolerance-modulating nucleic acid can comprise the nucleotide sequence set forth in SEQ ID NO:233. Alternatively, a low nitrogen tolerance-modulating nucleic acid can be a variant of the nucleic acid having the nucleotide sequence set forth in SEQ ID NO:233. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:233.

A low nitrogen tolerance-modulating nucleic acid can comprise the nucleotide sequence set forth in SEQ ID NO:245. Alternatively, a low nitrogen tolerance-modulating nucleic acid can be a variant of the nucleic acid having the nucleotide sequence set forth in SEQ ID NO:245. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:245.

A low nitrogen tolerance-modulating nucleic acid can comprise the nucleotide sequence set forth in SEQ ID NO:299. Alternatively, a low nitrogen tolerance-modulating nucleic acid can be a variant of the nucleic acid having the nucleotide sequence set forth in SEQ ID NO:299. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:299.

A low nitrogen tolerance-modulating nucleic acid can comprise the nucleotide sequence set forth in SEQ ID NO:331. Alternatively, a low nitrogen tolerance-modulating nucleic acid can be a variant of the nucleic acid having the nucleotide sequence set forth in SEQ ID NO:331. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:331.

A low nitrogen tolerance-modulating nucleic acid can comprise the nucleotide sequence set forth in SEQ ID NO:367. Alternatively, a low nitrogen tolerance-modulating nucleic acid can be a variant of the nucleic acid having the nucleotide sequence set forth in SEQ ID NO:367. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:367.

A low nitrogen tolerance-modulating nucleic acid can comprise the nucleotide sequence set forth in SEQ ID NO:509. Alternatively, a low nitrogen tolerance-modulating nucleic acid can be a variant of the nucleic acid having the nucleotide sequence set forth in SEQ ID NO:509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:509.

A low nitrogen tolerance-modulating nucleic acid can comprise the nucleotide sequence set forth in SEQ ID NO:532. Alternatively, a low nitrogen tolerance-modulating nucleic acid can be a variant of the nucleic acid having the nucleotide sequence set forth in SEQ ID NO:532. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:532.

A low nitrogen tolerance-modulating nucleic acid can comprise the nucleotide sequence set forth in SEQ ID NO:555. Alternatively, a low nitrogen tolerance-modulating nucleic acid can be a variant of the nucleic acid having the nucleotide sequence set forth in SEQ ID NO:555. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:555.

A low nitrogen tolerance-modulating nucleic acid can comprise the nucleotide sequence set forth in SEQ ID NO:557. Alternatively, a low nitrogen tolerance-modulating nucleic acid can be a variant of the nucleic acid having the nucleotide sequence set forth in SEQ ID NO:557. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:557.

A low nitrogen tolerance-modulating nucleic acid can comprise the nucleotide sequence set forth in SEQ ID NO:592. Alternatively, a low nitrogen tolerance-modulating nucleic acid can be a variant of the nucleic acid having the nucleotide sequence set forth in SEQ ID NO:592. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:592.

A low nitrogen tolerance-modulating nucleic acid can comprise the nucleotide sequence set forth in SEQ ID NO:612. Alternatively, a low nitrogen tolerance-modulating nucleic acid can be a variant of the nucleic acid having the nucleotide sequence set forth in SEQ ID NO:612. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:612.

A low nitrogen tolerance-modulating nucleic acid can comprise the nucleotide sequence set forth in SEQ ID NO:645. Alternatively, a low nitrogen tolerance-modulating nucleic acid can be a variant of the nucleic acid having the nucleotide sequence set forth in SEQ ID NO:645. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:645.

A low nitrogen tolerance-modulating nucleic acid can comprise the nucleotide sequence set forth in SEQ ID NO:686. Alternatively, a low nitrogen tolerance-modulating nucleic acid can be a variant of the nucleic acid having the nucleotide sequence set forth in SEQ ID NO:686. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:686.

A low nitrogen tolerance-modulating nucleic acid can comprise the nucleotide sequence set forth in SEQ ID NO:729. Alternatively, a low nitrogen tolerance-modulating nucleic acid can be a variant of the nucleic acid having the nucleotide sequence set forth in SEQ ID NO:729. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:729.

A low nitrogen tolerance-modulating nucleic acid can comprise the nucleotide sequence set forth in SEQ ID NO:745. Alternatively, a low nitrogen tolerance-modulating nucleic acid can be a variant of the nucleic acid having the nucleotide sequence set forth in SEQ ID NO:745. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:745.

A low nitrogen tolerance-modulating nucleic acid can comprise the nucleotide sequence set forth in SEQ ID NO:768. Alternatively, a low nitrogen tolerance-modulating nucleic acid can be a variant of the nucleic acid having the nucleotide sequence set forth in SEQ ID NO:768. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:768.

A low nitrogen tolerance-modulating nucleic acid can comprise the nucleotide sequence set forth in SEQ ID NO:791. Alternatively, a low nitrogen tolerance-modulating nucleic acid can be a variant of the nucleic acid having the nucleotide sequence set forth in SEQ ID NO:791. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:791.

A low nitrogen tolerance-modulating nucleic acid can comprise the nucleotide sequence set forth in SEQ ID NO:823. Alternatively, a low nitrogen tolerance-modulating nucleic acid can be a variant of the nucleic acid having the nucleotide sequence set forth in SEQ ID NO:823. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:823.

A low nitrogen tolerance-modulating nucleic acid can comprise the nucleotide sequence set forth in SEQ ID NO:827. Alternatively, a low nitrogen tolerance-modulating nucleic acid can be a variant of the nucleic acid having the nucleotide sequence set forth in SEQ ID NO:827. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:827.

A low nitrogen tolerance-modulating nucleic acid can comprise the nucleotide sequence set forth in SEQ ID NO:852. Alternatively, a low nitrogen tolerance-modulating nucleic acid can be a variant of the nucleic acid having the nucleotide sequence set forth in SEQ ID NO:852. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:852.

A low nitrogen tolerance-modulating nucleic acid can comprise the nucleotide sequence set forth in SEQ ID NO:854. Alternatively, a low nitrogen tolerance-modulating nucleic acid can be a variant of the nucleic acid having the nucleotide sequence set forth in SEQ ID NO:854. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:854.

A low nitrogen tolerance-modulating nucleic acid can comprise the nucleotide sequence set forth in SEQ ID NO:890. Alternatively, a low nitrogen tolerance-modulating nucleic acid can be a variant of the nucleic acid having the nucleotide sequence set forth in SEQ ID NO:890. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:890.

A low nitrogen tolerance-modulating nucleic acid can comprise the nucleotide sequence set forth in SEQ ID NO:916. Alternatively, a low nitrogen tolerance-modulating nucleic acid can be a variant of the nucleic acid having the nucleotide sequence set forth in SEQ ID NO:916. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:916.

A low nitrogen tolerance-modulating nucleic acid can comprise the nucleotide sequence set forth in SEQ ID NO:943. Alternatively, a low nitrogen tolerance-modulating nucleic acid can be a variant of the nucleic acid having the nucleotide sequence set forth in SEQ ID NO:943. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:943.

A low nitrogen tolerance-modulating nucleic acid can comprise the nucleotide sequence set forth in SEQ ID NO:975. Alternatively, a low nitrogen tolerance-modulating nucleic acid can be a variant of the nucleic acid having the nucleotide sequence set forth in SEQ ID NO:975. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:975.

A low nitrogen tolerance-modulating nucleic acid can comprise the nucleotide sequence set forth in SEQ ID NO:981. Alternatively, a low nitrogen tolerance-modulating nucleic acid can be a variant of the nucleic acid having the nucleotide sequence set forth in SEQ ID NO:981. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:981.

A low nitrogen tolerance-modulating nucleic acid can comprise the nucleotide sequence set forth in SEQ ID NO: 1034. Alternatively, a low nitrogen tolerance-modulating nucleic acid can be a variant of the nucleic acid having the nucleotide sequence set forth in SEQ ID NO: 1034. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A low nitrogen tolerance-modulating nucleic acid can comprise the nucleotide sequence set forth in SEQ ID NO:1053. Alternatively, a low nitrogen tolerance-modulating nucleic acid can be a variant of the nucleic acid having the nucleotide sequence set forth in SEQ ID NO:1053. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1053.

A low nitrogen tolerance-modulating nucleic acid can comprise the nucleotide sequence set forth in SEQ ID NO:1098. Alternatively, a low nitrogen tolerance-modulating nucleic acid can be a variant of the nucleic acid having the nucleotide sequence set forth in SEQ ID NO:1098. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1098.

A low nitrogen tolerance-modulating nucleic acid can comprise the nucleotide sequence set forth in SEQ ID NO:1111. Alternatively, a low nitrogen tolerance-modulating nucleic acid can be a variant of the nucleic acid having the nucleotide sequence set forth in SEQ ID NO:1111. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1111.

A low nitrogen tolerance-modulating nucleic acid can comprise the nucleotide sequence set forth in SEQ ID NO:1115. Alternatively, a low nitrogen tolerance-modulating nucleic acid can be a variant of the nucleic acid having the nucleotide sequence set forth in SEQ ID NO:1115. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1115.

A low nitrogen tolerance-modulating nucleic acid can comprise the nucleotide sequence set forth in SEQ ID NO:1156. Alternatively, a low nitrogen tolerance-modulating nucleic acid can be a variant of the nucleic acid having the nucleotide sequence set forth in SEQ ID NO:1156. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1156.

A low nitrogen tolerance-modulating nucleic acid can comprise the nucleotide sequence set forth in SEQ ID NO:1158. Alternatively, a low nitrogen tolerance-modulating nucleic acid can be a variant of the nucleic acid having the nucleotide sequence set forth in SEQ ID NO:1158. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1158.

A low nitrogen tolerance-modulating nucleic acid can comprise the nucleotide sequence set forth in SEQ ID NO:1165. Alternatively, a low nitrogen tolerance-modulating nucleic acid can be a variant of the nucleic acid having the nucleotide sequence set forth in SEQ ID NO:1165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1165.

A low nitrogen tolerance-modulating nucleic acid can comprise the nucleotide sequence set forth in SEQ ID NO:1184. Alternatively, a low nitrogen tolerance-modulating nucleic acid can be a variant of the nucleic acid having the nucleotide sequence set forth in SEQ ID NO:1184. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1184.

A low nitrogen tolerance-modulating nucleic acid can comprise the nucleotide sequence set forth in SEQ ID NO:1193. Alternatively, a low nitrogen tolerance-modulating nucleic acid can be a variant of the nucleic acid having the nucleotide sequence set forth in SEQ ID NO:1193. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1193.

A low nitrogen tolerance-modulating nucleic acid can comprise the nucleotide sequence set forth in SEQ ID NO: 1209. Alternatively, a low nitrogen tolerance-modulating nucleic acid can be a variant of the nucleic acid having the nucleotide sequence set forth in SEQ ID NO: 1209. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1209.

A low nitrogen tolerance-modulating nucleic acid can comprise the nucleotide sequence set forth in SEQ ID NO:1273. Alternatively, a low nitrogen tolerance-modulating nucleic acid can be a variant of the nucleic acid having the nucleotide sequence set forth in SEQ ID NO:1273. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1273.

A low nitrogen tolerance-modulating nucleic acid can comprise the nucleotide sequence set forth in SEQ ID NO:1301. Alternatively, a low nitrogen tolerance-modulating nucleic acid can be a variant of the nucleic acid having the nucleotide sequence set forth in SEQ ID NO:1301. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1301.

A low nitrogen tolerance-modulating nucleic acid can comprise the nucleotide sequence set forth in SEQ ID NO:1341. Alternatively, a low nitrogen tolerance-modulating nucleic acid can be a variant of the nucleic acid having the nucleotide sequence set forth in SEQ ID NO:1341. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1341.

A low nitrogen tolerance-modulating nucleic acid can comprise the nucleotide sequence set forth in SEQ ID NO:1384. Alternatively, a low nitrogen tolerance-modulating nucleic acid can be a variant of the nucleic acid having the nucleotide sequence set forth in SEQ ID NO:1384. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1384.

A low nitrogen tolerance-modulating nucleic acid can comprise the nucleotide sequence set forth in SEQ ID NO:1408. Alternatively, a low nitrogen tolerance-modulating nucleic acid can be a variant of the nucleic acid having the nucleotide sequence set forth in SEQ ID NO:1408. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1408.

A low nitrogen tolerance-modulating nucleic acid can comprise the nucleotide sequence set forth in SEQ ID NO:1427. Alternatively, a low nitrogen tolerance-modulating nucleic acid can be a variant of the nucleic acid having the nucleotide sequence set forth in SEQ ID NO:1427. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1427.

A low nitrogen tolerance-modulating nucleic acid can comprise the nucleotide sequence set forth in SEQ ID NO:1462. Alternatively, a low nitrogen tolerance-modulating nucleic acid can be a variant of the nucleic acid having the nucleotide sequence set forth in SEQ ID NO:1462. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1462.

A low nitrogen tolerance-modulating nucleic acid can comprise the nucleotide sequence set forth in SEQ ID NO:1490. Alternatively, a low nitrogen tolerance-modulating nucleic acid can be a variant of the nucleic acid having the nucleotide sequence set forth in SEQ ID NO:1490. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1490.

A low nitrogen tolerance-modulating nucleic acid can comprise the nucleotide sequence set forth in SEQ ID NO:1509. Alternatively, a low nitrogen tolerance-modulating nucleic acid can be a variant of the nucleic acid having the nucleotide sequence set forth in SEQ ID NO:1509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1509.

A low nitrogen tolerance-modulating nucleic acid can comprise the nucleotide sequence set forth in SEQ ID NO:1524. Alternatively, a low nitrogen tolerance-modulating nucleic acid can be a variant of the nucleic acid having the nucleotide sequence set forth in SEQ ID NO:1524. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1524.

A low nitrogen tolerance-modulating nucleic acid can comprise the nucleotide sequence set forth in SEQ ID NO:1536. Alternatively, a low nitrogen tolerance-modulating nucleic acid can be a variant of the nucleic acid having the nucleotide sequence set forth in SEQ ID NO:1536. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1536.

A low nitrogen tolerance-modulating nucleic acid can comprise the nucleotide sequence set forth in SEQ ID NO:1553. Alternatively, a low nitrogen tolerance-modulating nucleic acid can be a variant of the nucleic acid having the nucleotide sequence set forth in SEQ ID NO:1553. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1553.

A low nitrogen tolerance-modulating nucleic acid can comprise the nucleotide sequence set forth in SEQ ID NO:1576. Alternatively, a low nitrogen tolerance-modulating nucleic acid can be a variant of the nucleic acid having the nucleotide sequence set forth in SEQ ID NO:1576. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1576.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Low Nitrogen Tolerance-Modulating Polypeptide A nucleic acid encoding one of the low nitrogen tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular low nitrogen tolerance-modulating polypeptide; i.e., for many amino acids, there is more than one nucleotide triplet that serves as the codon for the amino acid. Thus, codons in the coding sequence for a given low nitrogen tolerance-modulating polypeptide can be modified such that optimal expression in a particular plant species is obtained, using appropriate codon bias tables for that species.

In some cases, expression of a low nitrogen tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Low Nitrogen Tolerance-Modulating Polypeptide

Polynucleotides and recombinant constructs described herein can be used to inhibit expression of a low nitrogen tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding low nitrogen tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al. (1995) *Proc. Natl. Acad. Sci. USA,* 92(13):6175-6179; de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a low nitrogen tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the low nitrogen tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a low nitrogen tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the low nitrogen tolerance-modulating polypeptide. In other embodiments, one strand of the stem portion of a double stranded RNA comprises a sequence that is similar or identical to the sequence of an intron, or a fragment thereof, in the pre-mRNA encoding a low nitrogen tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a low nitrogen tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a low nitrogen tolerance-modulating polypeptide, or a fragment of such sequences. In some embodiments, the sense or antisense sequence is identical or complementary to a sequence of the regulatory region that drives transcription of the gene encoding a low nitrogen tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a low nitrogen tolerance-modulating polypeptide described herein. The sense sequence complementary to the antisense sequence can be a sequence present within the mRNA of the low nitrogen tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; Hyrup et al. (1996) *Bioorgan. Med. Chem.*, 4:5-23. In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate low-nitrogen tolerance levels. A recombinant nucleic acid construct can comprise a nucleic acid encoding a low nitrogen tolerance-modulating polypeptide as described herein, operably linked to a regulatory region suitable for expressing the low nitrogen tolerance-modulating polypeptide in the plant or cell. Thus, a nucleic acid can comprise a coding sequence that encodes any of the low nitrogen tolerance-modulating polypeptides as set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Examples of nucleic acids encoding low nitrogen tolerance-modulating polypeptides are set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576. The low nitrogen tolerance-modulating polypeptide encoded by a recombinant nucleic acid can be a native low nitrogen tolerance-modulating polypeptide, or can be heterologous to the cell. In some cases, the recombinant construct contains a nucleic acid that inhibits expression of a low nitrogen tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses.

Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al. (1989) *Plant Cell,* 1:855-866; Bustos et al. (1989) *Plant Cell,* 1:839-854; Green et al. (1988) *EMBO J.,* 7:4035-4044; Meier et al. (1991) *Plant Cell,* 3:309-316; and Zhang et al. (1996) *Plant Physiology,* 110:1069-1079.

Examples of various classes of regulatory regions are described below. Some of the regulatory regions indicated below as well as additional regulatory regions are described in more detail in U.S. patent application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA,* 86:7890-7894), root cell specific promoters reported by Conkling et al. (1990) *Plant Physiol.,* 93:1203-1211, and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al. (1989) *Plant Cell,*

1(9):839-853), the soybean trypsin inhibitor promoter (Riggs et al. (1989) *Plant Cell,* 1(6):609-621), the ACP promoter (Baerson et al. (1993) *Plant Mol. Biol.,* 22(2):255-267), the stearoyl-ACP desaturase promoter (Slocombe et al. (1994) *Plant Physiol.,* 104(4):167-176), the soybean α' subunit of β-conglycinin promoter (Chen et al. (1986) *Proc. Natl. Acad. Sci. USA,* 83:8560-8564), the oleosin promoter (Hong et al. (1997) *Plant Mol. Biol.,* 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.,* 13:5829-5842), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.,* 32:571-57; Conceicao (1994) *Plant,* 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics,* 142:1009-1020); maize Cat3 (see, GenBank No. L05934; Abler (1993) *Plant Mol. Biol.,* 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.,* 35:773-778), the Cab-1 promoter from wheat (Fejes et al. (1990) *Plant Mol. Biol.,* 15:921-932), the CAB-1 promoter from spinach (Lubberstedt et al. (1994) *Plant Physiol.,* 104:997-1006), the cab1R promoter from rice (Luan et al. (1992) *Plant Cell,* 4:971-981), the pyruvate orthophosphate dikinase (PPDK) promoter from corn (Matsuoka et al. (1993) *Proc. Natl. Acad. Sci. USA,* 90:9586-9590), the tobacco Lhcb1*2 promoter (Cerdan et al. (1997) *Plant Mol. Biol.,* 33:245-255), the *Arabidopsis thaliana* SUC2 sucrose-H+ symporter promoter (Truernit et al. (1995) *Planta,* 196:564-570), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner (1991) *Plant Cell,* 3(10):1051-1061), the *Commelina* yellow mottle virus (CoYMV) promoter (Medberry et al. (1992) *Plant Cell,* 4(2):185-192), and the rice tungro bacilliform virus (RTBV) promoter (Dai et al. (2004) *Proc. Natl. Acad. Sci. USA,* 101(2):687-692).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17:287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a low nitrogen tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low nitrogen tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a low nitrogen tolerance-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of low-nitrogen tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in low nitrogen tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea.*

Suitable species include *Panicum* spp. or hybrid thereof, *Sorghum* spp. or hybrid thereof, *sudangrass, Miscanthus* spp. or hybrid thereof, *Saccharum* spp. or hybrid thereof, *Erianthus* spp., *Populus* spp., *Andropogon gerardii* (big bluestem), *Pennisetum purpureum* (elephant grass)) or hybrid thereof (e.g., *Pennisetum purpureum*×*Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrid thereof, *Secale cereale* (rye), *Salix* spp. (willow), *Eucalyptus* spp. (*eucalyptus*), *Triticosecale* (*triticum*—wheat×rye), *Tripsicum dactyloides* (Eastern gammagrass), *Leymus cinereus* (basin wildrye), *Leymus condensatus* (giant wildrye) and bamboo.

In some embodiments, a suitable species can be a wild, weedy, or cultivated *sorghum* species such as, but not limited to, *Sorghum almum, Sorghum amplum, Sorghum angustum, Sorghum arundinaceum, Sorghum bicolor* (such as *bicolor, guinea, caudatum, kafir*, and *durra*), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum*×*almum, Sorghum*×*sudangrass* or *Sorghum*×*drummondii.*

Suitable species also include *Helianthus annuus* (sunflower), *Carthamus tinctorius* (safflower), *Jatropha curcas* (*jatropha*), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium.*

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (*petunia*) and *Poinsettia pulcherrima* (*poinsettia*).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (*sorghum, sudangrass*), *Miscanthus giganteus* (*miscanthus*), *Saccharum* sp. (energycane), *Populus balsamifera* (poplar), *Zea mays* (corn), *Glycine max* (soybean), *Brassica napus* (canola),

*Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp.× *Miscanthus* sp., *Panicum virgatum*×*Panicum amarum*, *Panicum virgatum*×*Panicum amarulum*, and *Pennisetum purpureum*×*Pennisetum typhoidum*).

D. Transgenic Plant Phenotypes

In some embodiments, a plant in which expression of a low nitrogen tolerance-modulating polypeptide is modulated can have increased levels of photosynthetic efficiency in seedlings. For example, a low nitrogen tolerance-modulating polypeptide described herein can be expressed in a transgenic plant, resulting in increased levels of photosynthetic efficiency in growth conditions with low nitrogen sources. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic in a corresponding control plant that does not express the transgene.

In some embodiments, a plant in which expression of a low nitrogen tolerance-modulating polypeptide is modulated can have increased or decreased levels of photosynthetic efficiency in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency in one or more green tissues. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic efficiency in a corresponding control plant that does not express the transgene.

Increases in photosynthetic efficiency in low-nitrogen growth conditions in such plants can provide improved plant growth in geographic locales where plant's intake of nitrogenous fertilizers is often insufficient. Decreases in photosynthetic efficiency, and hence less tolerance to low-nitrogen growth conditions in such plants can be useful for removing weeds and such from the environment, by applying to weeds and such. For example, a plant capable of inducing the decrease in photosynthetic efficiency can be prepared to apply for land improvements and such.

Typically, a difference in the level of photosynthetic efficiency in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the level of photosynthetic is statistically significant at $p<0.01$, $p<0.005$, or $p<0.001$. A statistically significant difference in, for example, the level of photosynthetic efficiency in a transgenic plant compared to the amount in cells of a control plant indicates that the recombinant nucleic acid present in the transgenic plant results in altered levels of photosynthetic efficiency.

In some embodiments, a plant in which expression of a low nitrogen tolerance-modulating polypeptide is modulated can have increased growth rates in seedlings. For example, a low nitrogen tolerance-modulating polypeptide described herein can be expressed in a transgenic plant, resulting in increased growth rate in growth conditions of limiting nitrogen sources. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased growth rates. The growth rate can be decreased by at least 2 percent, e.g., 2, 3, 4, 5, 10, 15, 20, 25, 30, 35, or more than 35 percent, as compared to the growth rate in a corresponding control plant that does not express the transgene. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a plant in which expression of a low nitrogen tolerance-modulating polypeptide is modulated can have increased or decreased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased levels of growth rate in one or more vegetative tissues. The growth rate can be decreased by at least 2 percent, e.g., 2, 3, 4, 5, 10, 15, 20, 25, 30, 35, or more than 35 percent, as compared to the growth rate in a corresponding control plant that does not express the transgene.

Increases in growth rate in low-nitrogen conditions in such plants can provide improved plant growth and initial establishment in geographic locales where plant's intake of nitrogenous fertilizers is often insufficient. Decreases in growth rate, and hence less tolerance to low-nitrogen growth conditions in such plants can be useful for engineering slow-growing plants, by applying to ornamentals and such. For example, a plant capable of inducing the decrease in growth rate can be prepared to apply for land improvements and such.

Typically, a difference in the growth rate of a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the growth rate is statistically significant at $p<0.01$, $p<0.005$, or $p<0.001$. A statistically significant difference in, for example, the growth rate of a transgenic plant compared to the growth rate of a control plant indicates that the recombinant nucleic acid present in the transgenic plant results in altered growth rates.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate photosynthetic efficiency and/or nitrogen content is useful in plant breeding, because genetic polymorphisms exhibiting a degree of linkage with loci for such polypeptides are more likely to be correlated with variation in a low-nitrogen tolerance trait. For example, genetic polymorphisms linked to the loci for such polypeptides are more likely to be useful in marker-assisted breeding programs to create lines having a desired modulation in the low-nitrogen tolerance trait.

Thus, one aspect of the invention includes methods of identifying whether one or more genetic polymorphisms are associated with variation in a low-nitrogen tolerance trait. Such methods involve determining whether genetic polymorphisms in a given population exhibit linkage with the locus for one of the polypeptides depicted in FIGS. 1-57, SEQ ID NO:556, SEQ ID NO:853, SEQ ID NO:1157 and/or a functional homolog thereof, such as, but not limited to those identified in the Sequence Listing of this application. The correlation is measured between variation in the low-nitrogen tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the low-nitrogen tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al. (1997) *Electrophoresis* 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany; Burr et al. (1998) *Genetics* 118: 519; and Gardiner, J. et al. (1993) *Genetics* 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the low-nitrogen tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought or limiting nitrogen sources. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the nitrogenous composition of the plant material. By providing higher yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. Examples

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* plants, CeresClone:29661 (SEQ ID NO:1), CeresClone:251343 (SEQ ID NO:48), CeresClone:19586 (SEQ ID NO:76), CeresClone:25136 (SEQ ID NO:96), CeresClone:1820 (SEQ ID NO:99), CeresClone: 13102 (SEQ ID NO:151), CeresClone:15457 (SEQ ID NO:165), Ceres Annot:859276 (SEQ ID NO:175), CeresClone:17883 (SEQ ID NO:185), CeresClone:251590 (SEQ ID NO:207), CeresClone:4898 (SEQ ID NO:217), CeresClone:148977 (SEQ ID NO:233), CeresClone:24255 (SEQ ID NO:245), CeresClone:38432 (SEQ ID NO:299), Ceres Annot:553243 (SEQ ID NO:331), CeresClone:1011900 (SEQ ID NO:367), CeresClone:5232 (SEQ ID NO:509), CeresClone:29302 (SEQ ID NO:532), CeresClone:93971 (SEQ ID NO:555), Ceres Annot:12669619_cDNA (SEQ ID NO:557), CeresClone:21608 (SEQ ID NO:592), CeresClone:2031 (SEQ ID NO:612), CeresClone:94503 (SEQ ID NO:645), CeresClone:21740 (SEQ ID NO:686), CeresClone:5609 (SEQ ID NO:729), CeresClone:3137 (SEQ ID NO:745), CeresClone:32430 (SEQ ID NO:768), CeresClone:101255 (SEQ ID NO:791), Ceres Annot:573161 (SEQ ID NO:854), Ceres Annot:552727 (SEQ ID NO:890), CeresClone:732 (SEQ ID NO:1193), CeresClone:2267 (SEQ ID NO:1209), CeresClone:39358 (SEQ ID NO:1273), CeresClone:115046 (SEQ ID NO:1301), Ceres Annot: 850581 (SEQ ID NO:1427), Ceres Annot:862321 (SEQ ID NO:1462), Ceres Annot:839064 (SEQ ID NO:1478), Ceres Annot:864666 (SEQ ID NO:1490), Ceres Annot:875012 (SEQ ID NO:1509), Ceres Annot:874016 (SEQ ID NO:1524), Ceres Annot:827304 (SEQ ID NO:1536), Ceres Annot:869192 (SEQ ID NO:1553), and Ceres Annot:876419 (SEQ ID NO:1576). The nucleic acid designated Ceres Clone: 968180 (SEQ ID NO:1115) was isolated from the species *Brassica napus*. The nucleic acid designated Ceres Clone: 1017441 (SEQ ID NO:224) was isolated from the species *Triticum aesticum*. The following is a list of nucleic acids that were isolated from *Zea mays* plants, CeresClone: 1387146 (SEQ ID NO:981), CeresClone:1408950 (SEQ ID NO:1098, CeresClone:208453 (SEQ ID NO:1111), CeresClone:208995 (SEQ ID NO:943), CeresClone:225681 (SEQ ID NO:975), CeresClone:239806 (SEQ ID NO:916), CeresClone:244306 (SEQ ID NO:1053), CeresClone:276809 (SEQ ID NO:823), CeresClone:324216 (SEQ ID NO:852), CeresClone:339439 (SEQ ID NO:1341), CeresClone: 424522 (SEQ ID NO:827), CeresClone:896483 (SEQ ID NO:1384), CeresClone:986438 (SEQ ID NO:1156), CeresClone:988083 (SEQ ID NO:1184), CeresClone:995409 (SEQ ID NO:1408), CeresClone:996227 (SEQ ID NO:1158), and CeresClone:996263 (SEQ ID NO:1165).

With the exception of Ceres Clone:29661 (SEQ ID NO:1), each isolated nucleic acid described above was cloned into a Ti plasmid vector, CRS338, containing a phosphinothricin acetyltransferase gene which confers FINALE™ resistance to transformed plants. Constructs were made using CRS338 that contained SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, each operably linked to a 35S promoter. Ceres Clone:29661 (SEQ ID NO:1) was cloned into a Ti plasmid vector, CRS 311, containing a phosphinothricin acetyltransferase gene, which confers FINALE™ resistance to transformed plants. SEQ ID NO:1 was operably linked to a p32449 promoter in the constructs made using the CRS 331 vector. Wild-type *Arabidopsis thaliana* ecotype Wassilewskija (Ws) plants were transformed separately with each construct. The transformations were performed essentially as described in Bechtold et al. (1993) *C.R. Acad. Sci. Paris*, 316:1194-1199.

Transgenic *Arabidopsis* lines containing SEQ ID NO:1, SEQ ID NO:48, SEQ ID NO:76, SEQ ID NO:96, SEQ ID NO:99, SEQ ID NO:151, SEQ ID NO:165, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:224, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1478, SEQ ID NO:1490, SEQ ID NO:1509, SEQ ID NO:1524, SEQ ID NO:1536, SEQ ID NO:1553, SEQ ID NO:1576, or SEQ ID NO:175 were designated ME00919, ME01312, ME01463, ME01821, ME01910, ME02538, ME02603, ME02613, ME02801, ME03123, ME04204, ME04477, ME04507, ME04587, ME04753, ME04772, ME04909, ME05033, ME05194, ME05267, ME05300, ME05341, ME05392, ME05429, ME05493, ME05885, ME07344, ME07859, ME08464, ME09939, ME11735, ME12910, ME12927, ME12929, ME12954, ME12970, ME13006, ME13021, ME13064, ME13071, ME13087, ME13106, ME13107, ME13108, ME13110, ME13125, ME13149, ME13151, ME13153, ME13177, ME13200, ME13204, ME14649, ME16546, ME17457, ME17567, ME17932, ME17936, ME18275, ME18924, ME19182, or ME20628, respectively. The presence of each vector containing a nucleic acid described above in the respective transgenic *Arabidopsis* line transformed with the vector was confirmed by FINALE™ resistance, PCR amplification from green leaf tissue extract, and/or sequencing of PCR products. As controls, wild-type *Arabidopsis* ecotype Ws plants were transformed with the empty vector, either CRS338 or CRS311.

Example 2—Screening for Transgenic Plants Tolerant to Low-Nitrogen Growth Conditions A low-nitrogen tolerance screen was carried out on seedlings in order to identify transgenic lines that showed increased photosynthesis efficiency or seedling size or greenness under limiting nitrogen conditions relative to the internal control plants. The media used for the low-nitrogen tolerance assay contained 0.5% sucrose, 0.5×MS without nitrogen media (PhytoTech), 0.05% MES Hydrate, and 0.8% Phytagar. In addition, for low ammonium nitrate assay, 240 μM NH4NO3 was used as nitrogen source. For low nitrate assay, nitrogen source was 300 μM KNO3. pH of the media was adjusted to pH 5.7 using 10N KOH. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 μEinsteins. The control plates were placed randomly within the set. Screen the seedlings daily starting at 14 days. In this screen, seedlings that were larger or greener relative to the internal controls on low nitrogen growth media were selected. As they were found each day, candidate seedlings were aseptically transplanted to standard MS germination plates for recovery. This intermediate recovery step was necessary before transplanting to soil to minimize the overall candidate mortality rate. The scoring and transplanting of candidates were continued until all remaining plants were small and yellowed from nitrogen stress. On the very last day of scoring, each plate was scanned for photosynthetic efficiency (Fv/Fm) on the chlorophyll fluorescence (CF) imager and scored as candidates and transplanted any extreme outliers on the high end of Fv/Fm scores. Fv/Fm ratio typically provides an estimate of the photosystem II (PSII) maximum efficiency within dark-adapted material where Fv is variable fluorescence, i.e. difference between minimum (Fo) and maximum (Fm) fluorescence signal, from dark-adapted material. This could be done visually by looking at the false color image for each seedling using the CF image analysis software (plants with high end Fv/Fm scores appear red). This step was typically done at ~24 days after germination. Seven days after being transferred to MS recovery plates, candidates were transplanted to soil (standard Sunshine:vermiculite 3:2 mix; Osmocote; Marathon). Five days after being transplanted to soil, candidates were sprayed with FINALE® [5 mL FINALE®/48 oz. water] to eliminate non-transgenics from the population. Two days after spraying with FINALE®, cauline leaf tissue of each candidate was collected for genomic DNA extraction, PCR, and sequencing to determine the identity of the transgene for each candidate.

Example 3—Validation Plate Assay

This assay was designed to validate transgenic lines that showed increased photosynthesis or size under limiting nitrogen conditions relative to the internal control. The media used for the low-nitrogen tolerance assay contained 0.5% sucrose, 0.5×MS without nitrogen media (PhytoTech), 0.05% MES Hydrate, and 0.8% Phytagar. pH of the media was adjusted to pH 5.7 using 10N KOH. In addition, for low ammonium nitrate assay, 240 μM $NH_4NO_3$ was used as nitrogen source. For low nitrate assay, nitrogen source was 300 μM $KNO_3$. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 μEinsteins. The control plates were placed randomly within the set. Plates were scanned every other day using the CF Imager (after 45 minute of dark-acclimation) and were completed after all wild-type plants have completely yellowed. After the plates were scanned on the last day, they were sprayed with FINALE® (10 mL FINALE® into 48 oz. full-strength MS liquid media). Two days after spraying, each plate was dark-acclimated for 45 minutes and scanned for Fv/Fm on the CF imager and scored for each of the plants at each time point. For each separate time point, the data for all the $T_2$ transgenic plants across an event was pooled and a one-tailed t-test was used to compare both the Fv/Fm ratios and rosette areas relative to the pooled non-transgenics across the same plate. Whenever possible, this process was repeated for the $T_3$ generation plants. A low nitrogen tolerant candidate was confirmed when the transgenic Fv/Fm ratio and/or rosette area was greater than the wild-type segregants with a p-value ≤0.05 in 2 or more events in both generations

Example 4—Validation Soil Assay

A Low, Medium, and High Nitrogen experiment on soil was carried out to assess phenotypic characteristics at a mature point in the life cycle of *Arabidopsis*, as compared to seedling screens. The lines to be tested were originally identified through superpool screens for low nitrate and low ammonium nitrate tolerance. These lines were later individually assayed as seedlings on low nitrate and low ammonium nitrate agar. For this assay, MetroMix200 soil was mixed with vermiculite and Marathon™ (MetroMix200: vermiculite 3:2 mix; Osmocote; Marathon) autoclaved and cooled before use. Experimental plants and controls were randomized across the flats. Prior to sowing seed, each flat was watered with 3 L filtered water. Flats with 24 wells were filled with the following 3:2 ratios of MetroMix200 to Thermorock vermiculite. At the beginning of the experiment no nitrogen was provided until 2 weeks after germination when ¼ Hoaglands supplemented with $KNO_3$ at 25 ppm, 250 ppm, and 1500 ppm were used to water the flats from beneath.

Seeds were stratified on soil and in the dark at 4° C. for 3 days. After the cold treatment, flats were transferred to the growth chamber. Plants were grown for approximately 5 weeks, or until full grown/mature. Plants were then dark-acclimated for one hour. Chlorophyll fluorescence images were taken using a CF-Imager (Technologica, UK) according to the manufacturer's protocol to measure the performance and efficiency of photosystem II: 1) Fv/Fm, maximum photosystem II efficiency 2) Fq'/Fm', operating efficiency and 3) non-photochemical quenching (NPQ).

One week after watering with ¼ Hoaglands supplemented with various $KNO_3$ concentrations, plant rosette area measurements were taken using the WhinRhizo imaging software (Reagent Instruments, Canada). The plants were then collected in manila envelopes, placed in a 125° C. drying oven for 1-2 days and weighed.

Example 5—Analysis of ME00919 Events

ME00919 contains Ceres Clone:29661 (At3g61880, SEQ ID NO:1) from *Arabidopsis thaliana*, which encodes a 534 amino acid cytochrome P450 protein. Evaluation of low-nitrogen tolerance for ME00919 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -03, showed significantly increased photosynthetic efficiency relative to the internal controls in both generations at p≤0.05 using a one-tailed t-test assuming unequal variance. A summary of photosynthetic efficiency of ME00919 seedlings on low ammonium nitrate-containing media are shown in Table 1. Events -01 and -03 segregated 15:1 and 3:1 (R:S), respectively, for FINALE™ resistance in the $T_2$ generation. ME00919 events were also tested for enhanced growth on the low ammonium nitrate media. No significant differences between the transgenics and the controls were observed.

TABLE 1 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME00919 | ME00919-01 ($T_2$) | 0.65641304 | 46 | 0.595818 | 11 | $2.48 \times 10^{-2}$ |
| ME00919 | ME00919-01 ($T_3$) | 0.66348780 | 41 | 0.595818 | 11 | $1.55 \times 10^{-2}$ |
| ME00919 | ME00919-03 ($T_2$) | 0.67212195 | 41 | 0.634026 | 38 | $3.35 \times 10^{-3}$ |
| ME00919 | ME00919-03 ($T_3$) | 0.69278947 | 19 | 0.634026 | 38 | $2.39 \times 10^{-5}$ |

Events -01 and -03 of ME00919 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 6—Analysis of ME01312 Events

ME01312 contains Ceres Clone:251343 (At3g21270, SEQ ID NO:48) from *Arabidopsis thaliana*, which encodes a 204 amino acid Dof zinc finger protein. Ceres Clone: 251343 shares approximately 40% amino acid identity to the corn Dof1 gene, which when overexpressed in *Arabidopsis*, has shown to confer tolerance to plants receiving low nitrogen stress (Yanagisawa et al., 2004). Evaluation of low-nitrogen tolerance for ME01312 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -11, showed significantly enhanced photosynthetic efficiency on either low nitrate or low ammonium nitrate-containing media after 16 and 17 days compared to the internal controls in both generations at p≤0.05 using a one-tailed t-test assuming unequal variance. Event -03 had a slightly greater p-value than 0.05 in the $T_3$ generation for the low nitrate screen, significant at p≤0.10. A summary of photosynthetic efficiency of ME01312 seedlings on either low nitrate or low ammonium nitrate-containing media is shown in Table 2. Events -03 and -11 segregated 3:1 (R:S), respectively, for FINALE™ resistance in the $T_2$ generation.

TABLE 2A

T-test comparison of photosynthetic efficiency between transgenic seedlings and pooled non-transgenic segregants after 16 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-03 ($T_2$) | 0.63 | 38 | 0.60 | 58 | 0.03 |
| ME01312 | ME01312-03 ($T_3$) | 0.63 | 38 | 0.60 | 58 | 0.07 |

TABLE 2A-continued

T-test comparison of photosynthetic efficiency between transgenic seedlings and pooled non-transgenic segregants after 16 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-11 ($T_2$) | 0.64 | 41 | 0.60 | 58 | 0.019 |
| ME01312 | ME01312-11 ($T_3$) | 0.64 | 47 | 0.60 | 58 | $9.89 \times 10^{-3}$ |

TABLE 2B

T-test comparison of photosynthetic efficiency between transgenic seedlings and pooled non-transgenic segregants after 17 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-03 ($T_2$) | 0.64 | 36 | 0.61 | 88 | $2.64 \times 10^{-3}$ |
| ME01312 | ME01312-03 ($T_3$) | 0.66 | 27 | 0.61 | 88 | $1.87 \times 10^{-5}$ |
| ME01312 | ME01312-11 ($T_2$) | 0.65 | 35 | 0.61 | 88 | $7.06 \times 10^{-4}$ |
| ME01312 | ME01312-11 ($T_3$) | 0.64 | 37 | 0.61 | 88 | 0.011 |

Events -03-11 of ME01312 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 7—Analysis of ME01463 Events

ME01463 contains Ceres Clone:19586 (At1g80600, SEQ ID NO:76) from *Arabidopsis thaliana*, which encodes a 457 acetylornithine aminotransferase, a member of the Class-III aminotransferase family. Evaluation of low-nitrogen tolerance for ME01463 in two generations was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -06, and -10, showed significantly increased photosynthetic efficiency on low ammonium nitrate containing-media relative to the internal controls in both generations at $p \leq 0.05$ using a one-tailed t-test assuming unequal variance. A summary of photosynthetic efficiency of ME01463 seedlings is shown in Table 3. Events -02, -06, and -10 segregated 2:1, 2:1 and 3:1 (R:S), respectively, for FINALE™ resistance in the $T_2$ generation. ME01463 events were also tested for enhanced growth on the low ammonium nitrate media. No significant differences between the transgenics and the controls were observed (data not shown).

TABLE 3

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01463 | ME01463-02 ($T_3$) | 0.6815 | 26 | 0.6376 | 122 | $2.47 \times 10^{-4}$ |
| ME01463 | ME01463-02 ($T_4$) | 0.6701 | 41 | 0.6376 | 122 | $1.57 \times 10^{-3}$ |
| ME01463 | ME01463-06 ($T_3$) | 0.6615 | 31 | 0.6376 | 122 | $2.37 \times 10^{-2}$ |
| ME01463 | ME01463-06 ($T_4$) | 0.6881 | 35 | 0.6376 | 122 | $5.85 \times 10^{-6}$ |
| ME01463 | ME01463-10 ($T_2$) | 0.6699 | 33 | 0.6376 | 122 | $2.25 \times 10^{-3}$ |
| ME01463 | ME01463-10 ($T_3$) | 0.6809 | 18 | 0.6376 | 122 | $4.60 \times 10^{-4}$ |

Events -02, -06, and -10 of ME01463 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 8—Analysis of ME01821 Events

ME01821 contains Ceres Clone:25136 (At1g65500, SEQ ID NO:96) from *Arabidopsis thaliana*, which encodes a 86 amino acid protein of unknown function. Evaluation of low-nitrogen tolerance for ME01821 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low nitrate-containing media relative to the internal controls in $T_2$ generation. Two events, -04 and -05, showed significantly increased photosynthetic efficiency on low ammonium nitrate-containing media relative to the internal controls in $T_2$ generation at $p \leq 0.05$ using a one-tailed t-test assuming unequal variance. A summary of photosynthetic efficiency of ME01821 seedlings is shown in Table 4.

TABLE 4A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01821 | ME01821-01 ($T_2$) | 0.6745 | 15 | 0.6520 | 33 | $3.76 \times 10^{-2}$ |
| ME01821 | ME01821-04 ($T_2$) | 0.6826 | 17 | 0.6614 | 14 | $2.76 \times 10^{-2}$ |
| ME01821 | ME01821-05 ($T_2$) | 0.6826 | 20 | 0.6614 | 14 | $3.74 \times 10^{-2}$ |

TABLE 4B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01821 | ME01821-04 ($T_2$) | 0.7422 | 13 | 0.7166 | 21 | $5.20 \times 10^{-3}$ |
| ME01821 | ME01821-05 ($T_2$) | 0.7426 | 19 | 0.7166 | 21 | $6.07 \times 10^{-3}$ |

A summary of the enhanced growth of ME01812 events on either low nitrate- or low ammonium nitrate-containing media is shown in Table 5. For two events -01 and -05, transgenic seedlings were found significantly larger than the pooled non-transgenic segregants after 14 days of growth on low nitrate-containing media (Table 5A). Transgenic seedlings of two events -02 and -05 were found significantly larger than the pooled non-transgenic segregants after 14 days of growth on low ammonium nitrate-containing media (Table 5B). In this study, the seedling area for transgenic plants within an event was compared to the seedling area for non-transgenic segregants pooled across the same line.

TABLE 5A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME01821 | ME01821-01 ($T_2$) | 0.0608 | 15 | 0.0555 | 33 | $3.97 \times 10^{-2}$ |
| ME01821 | ME01821-05 ($T_2$) | 0.0666 | 20 | 0.0530 | 14 | $3.05 \times 10^{-6}$ |

TABLE 5B

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME01821 | ME01821-02 ($T_2$) | 0.0750 | 19 | 0.0567 | 21 | $8.94 \times 10^{-5}$ |
| ME01821 | ME01821-05 ($T_2$) | 0.0680 | 19 | 0.0567 | 21 | $7.89 \times 10^{-3}$ |

Example 9—Analysis of ME01910 Events

ME01910 contains Ceres Clone:1820 (At2g30620, SEQ ID NO:99) from *Arabidopsis thaliana*, which encodes a 273 amino acid linker histone H1 and H5 family protein. Evaluation of low-nitrogen tolerance for ME01910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency relative to the internal controls in both generations at p≤0.05 using a one-tailed t-test assuming unequal variance. A summary of photosynthetic efficiency of ME01910 seedlings is shown in Table 6. Events -01 and -02 segregated 3:1 (R:S) for FINALE™ resistance in the $T_2$ generation. ME01910 events were also tested for enhanced growth on the low ammonium nitrate media. No significant differences between the transgenics and the controls were observed.

TABLE 6 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01910 | ME01910-01 ($T_2$) | 0.60433 | 39 | 0.56396 | 27 | $2.03 \times 10^{-2}$ |
| ME01910 | ME01910-01 ($T_3$) | 0.61274 | 31 | 0.56396 | 27 | $9.23 \times 10^{-3}$ |
| ME01910 | ME01910-02 ($T_2$) | 0.62705 | 37 | 0.58083 | 29 | $7.39 \times 10^{-3}$ |
| ME01910 | ME01910-02 ($T_3$) | 0.64146 | 24 | 0.58083 | 29 | $9.23 \times 10^{-4}$ |

Events -01 and -02 of ME01910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 10—Analysis of ME02538 Events

ME02538 contains Ceres Clone:13102 (At1g67920, SEQ ID NO:151) from *Arabidopsis thaliana*, which encodes a 67 amino acid protein of unknown function. Evaluation of low-nitrogen tolerance for ME02538 in $T_2$ generation was conducted under the same conditions as described in Example 2. In this study, the seedling photosynthetic efficiency was measured as Fv/Fm comparing transgenic plants within an event to non-transgenic segregants pooled across the same plate. Two events, -04 and -05, showed significantly increased photosynthetic efficiency relative to the internal controls in $T_2$ generation on both low nitrate-containing and ammonium nitrate-containing media at p≤0.05 using a one-tailed t-test assuming unequal variance. A summary of photosynthetic efficiency of ME01821 seedlings is shown in Table 7.

TABLE 7A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME02538 | ME02538-04 ($T_2$) | 0.6686 | 15 | 0.6171 | 24 | $1.92 \times 10^{-4}$ |
| ME02538 | ME02538-05 ($T_2$) | 0.6420 | 20 | 0.6171 | 24 | $4.84 \times 10^{-2}$ |

TABLE 7B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02538 | ME02538-04 ($T_2$) | 0.7345 | 13 | 0.7080 | 22 | $4.45 \times 10^{-3}$ |
| ME02538 | ME02538-05 ($T_2$) | 0.7356 | 20 | 0.7080 | 22 | $5.93 \times 10^{-3}$ |

ME02538 events were also tested for enhanced growth on the low ammonium nitrate media. A summary of the growth assay performed on ME01812 events is shown in Table 8. Transgenic seedlings of two events -01 and -02 were found significantly larger than the pooled non-transgenic segregants on both low nitrate-(Table 8A) and low ammonium nitrate-containing media (Table 8B).

TABLE 8A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME02538 | ME02538-01 ($T_2$) | 0.0655 | 16 | 0.0558 | 36 | $2.80 \times 10^{-4}$ |
| ME02538 | ME02538-02 ($T_2$) | 0.0651 | 13 | 0.0601 | 20 | $1.32 \times 10^{-2}$ |

TABLE 8B

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME02538 | ME02538-01 ($T_2$) | 0.0856 | 15 | 0.0737 | 39 | $8.60 \times 10^{-3}$ |
| ME02538 | ME02538-02 ($T_2$) | 0.0864 | 14 | 0.0776 | 22 | $3.13 \times 10^{-2}$ |

Example 11—Analysis of ME02603 Events

ME02603 contains Ceres Clone:15457 (At5g47610, SEQ ID NO:165) from *Arabidopsis thaliana*, which encodes a 166 amino acid zinc ion binding protein. Evaluation of low-nitrogen tolerance for ME02603 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME02603 seedlings is shown in Table 9.

Events -01 and -04 segregated 3:1 (R:S) for FINALE™ resistance in the $T_2$ generation. Transgenic plants of two events -01 and -04—were also tested for enhanced photosynthetic efficiency on the low nitrate media. No significant differences between the transgenics and the controls were observed.

TABLE 9

T-test comparison of photosynthetic efficiency between transgenic seedlings and pooled non-transgenic segregants after 17 days (21 days for the $T_2$ generation of ME02603- 01) of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02603 | ME02603-01 ($T_2$) | 0.61 | 10 | 0.54 | 32 | $9.00 \times 10^{-4}$ |
| ME02603 | ME02603-01 ($T_3$) | 0.67 | 28 | 0.65 | 62 | $6.11 \times 10^{-3}$ |
| ME02603 | ME02603-04 ($T_2$) | 0.69 | 25 | 0.65 | 62 | $4.45 \times 10^{-5}$ |
| ME02603 | ME02603-04 ($T_3$) | 0.68 | 24 | 0.65 | 62 | $7.53 \times 10^{-3}$ |

Events -01 and -04 of ME02603 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 12—Analysis of ME02613 Events

ME02613 contains Ceres Clone:17883 (At3g13910, SEQ ID NO:185) from *Arabidopsis thaliana*, which encodes a 102 amino acid protein of unknown function. Evaluation of low-nitrogen tolerance for ME02613 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. In $T_2$ generation, two events, -01 and -04, showed significantly increased photosynthetic efficiency on low nitrate containing-media relative to the internal controls in $T_2$ generation at p≤0.05 using a one-tailed t-test assuming unequal variance. Two events, -03 and -04, showed significantly increased photosynthetic efficiency on low ammonium nitrate containing-media relative to the internal controls in $T_2$ generation at p≤0.05 using a one-tailed t-test assuming unequal variance. A summary of photosynthetic efficiency of ME02613 seedlings is shown in Table 10.

TABLE 10A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-01 ($T_2$) | 0.6979 | 16 | 0.6630 | 21 | $1.45 \times 10^{-2}$ |
| ME02613 | ME02613-04 ($T_2$) | 0.7046 | 13 | 0.6630 | 21 | $5.73 \times 10^{-4}$ |

TABLE 10B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-03 ($T_2$) | 0.7270 | 9 | 0.7068 | 29 | $4.34 \times 10^{-2}$ |
| ME02613 | ME02613-04 ($T_2$) | 0.7485 | 15 | 0.7068 | 29 | $7.09 \times 10^{-5}$ |

A summary of the enhanced growth of ME02613 events on either low nitrate- or low ammonium nitrate-containing media is shown in Table 11. For two events -01 and -03, transgenic seedlings were found significantly larger than the pooled non-transgenic segregants after 14 days of growth on low nitrate-containing media (Table 11A). Transgenic seedlings of two events -02 and -03 were found significantly larger than the pooled non-transgenic segregants after 14 days of growth on low ammonium nitrate-containing media (Table 11B).

TABLE 11A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME02613 | ME02613-01 ($T_2$) | 0.05706 | 16 | 0.05259 | 31 | $4.71 \times 10^{-2}$ |
| ME02613 | ME02613-03 ($T_2$) | 0.06236 | 12 | 0.05789 | 29 | $2.39 \times 10^{-2}$ |

TABLE 1

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME02613 | ME02613-02 ($T_2$) | 0.08324 | 14 | 0.07018 | 29 | $2.72 \times 10^{-4}$ |
| ME02613 | ME02613-03 ($T_2$) | 0.08273 | 9 | 0.07018 | 29 | $1.41 \times 10^{-2}$ |

Example 13—Analysis of ME02801 Events

ME02801 contains Ceres Clone:251590 (At3g53080, SEQ ID NO:207) from *Arabidopsis thaliana*, which encodes a 155 amino acid protein of unknown function. Evaluation of low-nitrogen tolerance for ME02801 in $T_2$ and $T_3$ was conducted under the same conditions as described in Example 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME02801 seedlings is shown in Table 12. Events -02 and -04 segregated 3:1 (R:S) for FINALE™ resistance in the $T_2$ generation. ME02801 events were also tested for enhanced growth on the low nitrate media and enhanced photosynthetic efficiency and growth on low ammonium nitrate media. No significant differences between the transgenics and the controls were observed.

TABLE 12 t-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME02801 | ME02801-02 ($T_2$) | 0.536385 | 39 | 0.465903 | 113 | $5.49 \times 10^{-7}$ |
| ME02801 | ME02801-02 ($T_3$) | 0.536465 | 43 | 0.465903 | 113 | $5.11 \times 10^{-7}$ |
| ME02801 | ME02801-04 ($T_2$) | 0.532419 | 31 | 0.465903 | 113 | $1.28 \times 10^{-5}$ |
| ME02801 | ME02801-04 ($T_3$) | 0.510406 | 32 | 0.465903 | 113 | $1.74 \times 10^{-2}$ |

Events -02 and -04 of ME02801 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 14—Analysis of ME03123 Events

ME03123 contains Ceres Clone:4898 (At1g29970, SEQ ID NO:217) from *Arabidopsis thaliana*, which encodes a 158 amino acid protein of unknown function. Evaluation of low-nitrogen tolerance for ME03123 in $T_2$ and/or $T_3$ was conducted under the same conditions as described in Examples 2 and 3. In this study, the seedling photosynthetic efficiency was measured as Fv/Fm comparing transgenic plants within an event to non-transgenic segregants pooled across the same plate. A summary of photosynthetic efficiency of ME03123 seedlings is shown in Table 13. Two events, -01 and -10, showed significantly increased photosynthetic efficiency on low nitrate- or low ammonium nitrate-containing media relative to the internal controls in $T_2$ or $T_3$ generation at $p \leq 0.05$ using a one-tailed t-test assuming unequal variance.

TABLE 13A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME03123 | ME03123-01 ($T_2$) | 0.6282 | 15 | 0.5732 | 26 | $6.60 \times 10^{-5}$ |
| ME03123 | ME03123-10 ($T_3$) | 0.6069 | 12 | 0.5732 | 26 | $1.05 \times 10^{-2}$ |

TABLE 13B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME03123 | ME03123-01 ($T_2$) | 0.6736 | 17 | 0.6315 | 16 | $1.74 \times 10^{-2}$ |
| ME03123 | ME03123-10 ($T_3$) | 0.6699 | 20 | 0.6315 | 16 | $1.60 \times 10^{-2}$ |

ME03123 events were also tested for enhanced growth on the low ammonium nitrate media. In this assay, transgenic seedlings of ME03123-02 and ME03123-04 ($T_2$) were significantly larger than the pooled non-transgenic segregants after 14 days of growth on low nitrate (Table 14).

TABLE 14

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME03123 | ME03123-02 ($T_2$) | 0.07235 | 19 | 0.05623 | 20 | $1.41 \times 10^{-6}$ |
| ME03123 | ME03123-04 ($T_3$) | 0.06571 | 7 | 0.05729 | 41 | $7.74 \times 10^{-3}$ |

Example 15—Analysis of ME04204 Events

ME04204 contains Ceres Clone:148977 (At1g78770, SEQ ID NO:233) from *Arabidopsis thaliana*, which encodes a 159 amino acid anaphase promoting complex/cyclosome subunit protein. However, it is also possible that this is natural variant transcript produced by the plant, because multiple annotations for locus At1g78770 were found in public domain. Evaluation of low-nitrogen tolerance for ME04204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency relative to the internal controls in both generations at p≤0.05 using a one-tailed t-test assuming unequal variance. A summary of photosynthetic efficiency of ME04204 seedlings is shown in Table 15. Events -01 and -05 segregated 3:1 (R:S) for FINALE™ resistance in the $T_2$ generation. ME04204 events were also tested for enhanced growth on the low nitrate media. No significant differences between the transgenics and the controls were observed.

TABLE 15

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events -01 and -05 of ME04204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 16—Analysis of ME04477 Events

ME04477 contains Ceres Clone:24255 (At2g36320, SEQ ID NO:245) from *Arabidopsis thaliana*, which encodes a 161 amino acid DNA binding/zinc ion binding protein. Evaluation of low-nitrogen tolerance for ME04477 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME04477 seedlings is shown in Table 16. Events -01 and -05 segregated 3:1 (R:S) for FINALE™ resistance in the $T_2$ generation. ME04477 events were also tested for enhanced growth on the low nitrate media. No significant differences between the transgenics and the controls were observed.

TABLE 16

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |

TABLE 16-continued

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events -01 and -05 of ME04477 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 17—Analysis of ME04507 Events

ME04507 contains Ceres Clone:38432 (At4g38250, SEQ ID NO:299) from *Arabidopsis thaliana*, which encodes a 436 amino acid transmembrane amino acid transporter protein. Evaluation of low-nitrogen tolerance for ME04507 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME04507 seedlings is shown in Table 17. Events -03 and -04 segregated 15:1 and 3:1 (R:S), respectively, for FINALE™ resistance in the $T_2$ generation. ME04507 events were also tested for enhanced growth on the low nitrate media. No significant differences between the transgenics and the controls were observed.

TABLE 17

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04507 | ME04507-03 ($T_2$) | 0.57753 | 40 | 0.53084 | 103 | $4.90 \times 10^{-4}$ |
| ME04507 | ME04507-03 ($T_3$) | 0.56318 | 39 | 0.53084 | 103 | $2.64 \times 10^{-2}$ |
| ME04507 | ME04507-04 ($T_2$) | 0.57708 | 38 | 0.53084 | 103 | $6.12 \times 10^{-3}$ |
| ME04507 | ME04507-04 ($T_3$) | 0.57277 | 22 | 0.53084 | 103 | $2.35 \times 10^{-2}$ |

Events -03 and -04 of ME04507 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 18—Analysis of ME04587 Events

ME04587 contains Ceres Annot: 553243 (At2g27010, SEQ TD NO:331) from *Arabidopsis thaliana*, which encodes a 516 amino acid cytochrome P450 protein. Evaluation of low-nitrogen tolerance for ME04587 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME04587 seedlings is shown in Table 18. In $T_2$ generation, events -01 and -02 segregated 1:1 and 47:1 respectively (R:S) for FINALE™ resistance. These two events segregated 2:1 and 7:1 respectively (R:S) for FINALE® resistance in the $T_3$ generation.

TABLE 18

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME04587 | ME04587-01 ($T_2$) | 0.6424 | 10 | 0.5437 | 30 | $2.48 \times 10^{-3}$ |
| ME04587 | ME04587-01 ($T_3$) | 0.6165 | 25 | 0.5437 | 30 | $1.24 \times 10^{-2}$ |
| ME04587 | ME04587-02 ($T_2$) | 0.6022 | 47 | 0.5437 | 30 | $3.08 \times 10^{-2}$ |
| ME04587 | ME04587-02 ($T_3$) | 0.6310 | 43 | 0.5437 | 30 | $3.68 \times 10^{-3}$ |

ME04587 events were also tested for enhanced growth on the low ammonium nitrate media. In addition, these events were tested on low nitrate media for increased seedling area and photosynthetic efficiency. No statistically significant differences between the transgenics and the controls were observed.

Events -01 and -02 of ME04587 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 19—Analysis of ME04753 Events

ME04753 contains Ceres Clone:1011900 (At2g21660, SEQ ID NO:367) from *Arabidopsis thaliana*, which encodes a 130 amino acid glycine-rich RNA binding protein. Evaluation of low-nitrogen tolerance for ME04753 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low nitrate-containing media relative to the internal controls in both generations at $p \leq 0.05$ using a one-tailed t-test assuming unequal variance. A summary of photosynthetic efficiency of ME04753 seedlings is shown in Table 19. Events -01 and -02 segregated 3:1 and 2:1 respectively (R:S) for FINALE™ resistance in the $T_2$ generation. ME04753 events were also tested for enhanced growth on the low nitrate media. No significant differences between the transgenics and the controls were observed.

TABLE 19

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04753 | ME04753-01 ($T_2$) | 0.49323 | 39 | 0.45917 | 66 | $3.17 \times 10^{-2}$ |
| ME04753 | ME04753-01 ($T_3$) | 0.50942 | 26 | 0.45917 | 66 | $1.80 \times 10^{-2}$ |
| ME04753 | ME04753-02 ($T_2$) | 0.49856 | 34 | 0.45917 | 66 | $2.43 \times 10^{-2}$ |
| ME04753 | ME04753-02 ($T_3$) | 0.51274 | 27 | 0.45917 | 66 | $1.15 \times 10^{-2}$ |

Events -01 and -02 of ME04753 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 20—Analysis of ME04772 Events

ME04772 contains Ceres Clone:5232 (At1g13380, SEQ ID NO:509) from *Arabidopsis thaliana*, which encodes a 188 amino acid protein of unknown function. Evaluation of low-nitrogen tolerance for ME04772 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME04772 seedlings is shown in Table 20. Events -02 and -04 segregated 2:1 and 3:1 respectively (R:S) for FINALE™ resistance in the $T_2$ generation. ME04772 events were also tested for enhanced growth on the low nitrate media. No significant differences between the transgenics and the controls were observed.

TABLE 20

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04772 | ME04772-02 ($T_2$) | 0.53708 | 25 | 0.46204 | 53 | $3.36 \times 10^{-5}$ |
| ME04772 | ME04772-02 ($T_3$) | 0.53121 | 34 | 0.46204 | 53 | $1.27 \times 10^{-4}$ |
| ME04772 | ME04772-04 ($T_2$) | 0.52921 | 34 | 0.46204 | 53 | $3.71 \times 10^{-4}$ |
| ME04772 | ME04772-04 ($T_3$) | 0.50272 | 36 | 0.46204 | 53 | $2.73 \times 10^{-2}$ |

Events -02 and -04 of ME04772 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 21—Analysis of ME04772 Events

ME04909 contains Ceres Clone:29302 (At1g49010, SEQ ID NO:532) from *Arabidopsis thaliana*, which encodes a 314 amino acid Myb-like DNA-binding domain protein. Evaluation of low-nitrogen tolerance for ME04909 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at $p \leq 0.05$ using a one-tailed t-test assuming unequal variance. A summary of photosynthetic efficiency of ME04909 seedlings is shown in Table 21. Events -01 and -03 segregated 15:1 (R:S) for FINALE™ resistance in the $T_2$ generation. ME04909 events were also tested for enhanced growth on the low nitrate media. No significant differences between the transgenics and the controls were observed.

TABLE 21 t-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04909 | ME04909-01 ($T_2$) | 0.587774 | 31 | 0.550342 | 111 | $1.36 \times 10^{-2}$ |
| ME04909 | ME04909-01 ($T_3$) | 0.607452 | 31 | 0.550342 | 111 | $1.28 \times 10^{-3}$ |
| ME04909 | ME04909-03 ($T_2$) | 0.581537 | 41 | 0.550342 | 111 | $1.8 \times 10^{-2}$ |
| ME04909 | ME04909-03 ($T_3$) | 0.609806 | 31 | 0.550342 | 111 | $4.3 \times 10^{-5}$ |

Events -01 and -03 of ME04909 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 22—Analysis of ME05033 Events

ME05033 contains Ceres Clone:93971 (At4g19095, SEQ ID NO:555) from *Arabidopsis thaliana*, which encodes a 188 amino acid protein of unknown function. Evaluation of low-nitrogen tolerance for ME05033 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME05033 seedlings is shown in Table 22. Events -03 and -05 segregated 15:1 and 2:1 respectively (R:S) for FINALE™ resistance in the $T_2$ generation. ME05033 events were also tested for enhanced growth on the low nitrate media. No significant differences between the transgenics and the controls were observed.

TABLE 22

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME05033 | ME05033-03 ($T_2$) | 0.65717 | 46 | 0.62621 | 132 | $9.20 \times 10^{-3}$ |
| ME05033 | ME05033-03 ($T_3$) | 0.64956 | 39 | 0.62621 | 132 | $4.52 \times 10^{-3}$ |
| ME05033 | ME05033-05 ($T_2$) | 0.64448 | 29 | 0.62621 | 132 | $3.46 \times 10^{-2}$ |
| ME05033 | ME05033-05 ($T_3$) | 0.65537 | 30 | 0.62621 | 132 | $2.38 \times 10^{-4}$ |

Events -03 and -05 of ME05033 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 23—Analysis of ME05194 Events

ME05194 contains Ceres cDNA:12669619 (At1g30710, SEQ ID NO:557) from *Arabidopsis thaliana*, which encodes a 531 amino acid electron carrier protein. Evaluation of low-nitrogen tolerance for ME05194 in $T_2$ and $T_3$ was conducted under the same conditions as described in Examples 2 and 3. Two events, -03 and -05, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 23. Events -03 and -05 segregated 1:1 (R:S) for FINALE™ resistance in the $T_2$ generation. ME05194 events were also tested for increased photosynthetic efficiency on the low nitrate media. No significant differences between the transgenics and the controls were observed.

TABLE 23 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05194 | ME05194-03 ($T_2$) | 0.051216 | 38 | 0.040874 | 82 | $2.54 \times 10^{-5}$ |
| ME05194 | ME05194-03 ($T_3$) | 0.047042 | 45 | 0.040874 | 82 | $2.61 \times 10^{-2}$ |
| ME05194 | ME05194-05 ($T_2$) | 0.048746 | 26 | 0.040874 | 82 | $6.15 \times 10^{-3}$ |
| ME05194 | ME05194-05 ($T_3$) | 0.048457 | 14 | 0.040874 | 82 | $3.03 \times 10^{-2}$ |

Events -03 and -05 of ME05194 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 24—Analysis of ME05267 Events

ME05267 contains Ceres Clone:21608 (At5g49510, SEQ ID NO:592) from *Arabidopsis thaliana*, which encodes a 195 amino acid von Hippel-Lindau binding protein. Evaluation of low-nitrogen tolerance for ME05267 in $T_2$ and $T_3$ was conducted under the same conditions as described in Examples 2 and 3. Two events, -01 and -04, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 24. Events -01 and -04 segregated 15:1 (R:S) for FINALE™ resistance in the $T_2$ generation. ME05267 events were also tested for increased photosynthetic efficiency on the low nitrate media. No significant differences between the transgenics and the controls were observed.

TABLE 24 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05267 | ME05267-01 ($T_2$) | 0.053263 | 46 | 0.0450197 | 122 | $4.4 \times 10^{-5}$ |
| ME05267 | ME05267-01 ($T_3$) | 0.051135 | 26 | 0.0450197 | 122 | $5.0 \times 10^{-2}$ |
| ME05267 | ME05267-04 ($T_2$) | 0.049977 | 44 | 0.0450197 | 122 | $6.4 \times 10^{-3}$ |
| ME05267 | ME05267-04 ($T_3$) | 0.053084 | 38 | 0.0450197 | 122 | $8.4 \times 10^{-4}$ |

Events -01 and -04 of ME05267 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 25—Analysis of ME05300 Events

ME05300 contains Ceres Clone:2031 (At1g72020, SEQ ID NO:612) from *Arabidopsis thaliana*, which encodes a 97 amino acid protein of unknown function. Evaluation of low-nitrogen tolerance for ME05300 in $T_2$ generation was conducted under the same conditions as described in Examples 2 and 3. A summary of photosynthetic efficiency of ME05300 seedlings is shown in Table 25. Two events, -04 and -05, showed significantly increased photosynthetic efficiency on low nitrate- and low ammonium nitrate-containing media relative to the internal controls in $T_2$ generation at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. In addition, two events, -01 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low nitrate and low ammonium nitrate growth conditions of ME05300 seedlings is shown in Table 26.

TABLE 25A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME05300 | ME05300-04 ($T_2$) | 0.6867 | 7 | 0.6488 | 27 | $1.65 \times 10^{-2}$ |
| ME05300 | ME05300-05 ($T_2$) | 0.6839 | 16 | 0.6488 | 27 | $2.50 \times 10^{-3}$ |

TABLE 25B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05300 | ME05300-04 ($T_2$) | 0.6767 | 6 | 0.6323 | 32 | $1.68 \times 10^{-2}$ |
| ME05300 | ME05300-05 ($T_2$) | 0.6934 | 11 | 0.6323 | 32 | $7.04 \times 10^{-4}$ |

TABLE 26A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05300 | ME05300-01 ($T_2$) | 0.0737 | 18 | 0.0588 | 21 | $3.80 \times 10^{-3}$ |
| ME05300 | ME05300-05 ($T_2$) | 0.0655 | 16 | 0.0570 | 27 | $1.59 \times 10^{-2}$ |

TABLE 26B

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME05300 | ME05300-01 ($T_2$) | 0.0987 | 17 | 0.0776 | 29 | $3.89 \times 10^{-3}$ |
| ME05300 | ME05300-05 ($T_2$) | 0.1082 | 11 | 0.0776 | 29 | $1.57 \times 10^{-3}$ |

Example 26—Analysis of ME05341 Events

ME05341 contains Ceres Clone:94503 (At4g14420, SEQ ID NO:645) from *Arabidopsis thaliana*, which encodes a 158 amino acid elicitor-like protein. Evaluation of low-nitrogen tolerance for ME05341 in $T_2$ and $T_3$ was conducted under the same conditions as described in Examples 2 and 3. Two events, -01 and -02, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of photosynthetic efficiency of ME05341 seedlings is shown in Table 27. Events -01 and -02 segregated 15:1 (R:S) for FINALE™ resistance in the $T_2$ generation. ME05341 events were also tested for increased photosynthetic efficiency on the low nitrate media. No significant differences between the transgenics and the controls were observed.

TABLE 27 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05341 | ME05341-01 ($T_2$) | 0.06253 | 46 | 0.04988 | 143 | $4.17 \times 10^{-10}$ |
| ME05341 | ME05341-01 ($T_3$) | 0.05876 | 38 | 0.04988 | 143 | $4.13 \times 10^{-4}$ |
| ME05341 | ME05341-02 ($T_2$) | 0.06152 | 46 | 0.04988 | 143 | $2.91 \times 10^{-7}$ |
| ME05341 | ME05341-02 ($T_3$) | 0.05572 | 48 | 0.04988 | 143 | $2.90 \times 10^{-3}$ |

Events -01 and -02 of ME05341 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 27—Analysis of ME05392 Events

ME05392 contains Ceres Clone:21740 (At5g01610, SEQ ID NO:686) from *Arabidopsis thaliana*, which encodes a 170 amino acid protein of unknown function. Evaluation of low-nitrogen tolerance for ME05392 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at p≤0.05 using a one-tailed t-test assuming unequal variance. A summary of photosynthetic efficiency of ME05392 seedlings is shown in Table 20. Events -01 and -03 segregated 2:1 (R:S) for FINALE™ resistance in the $T_2$ generation. ME05392 events were also tested for enhanced growth on the low nitrate media. No significant differences between the transgenics and the controls were observed.

TABLE 28

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME05392 | ME05392-01 ($T_2$) | 0.61759 | 32 | 0.60093 | 107 | $3.70 \times 10^{-2}$ |
| ME05392 | ME05392-01 ($T_3$) | 0.63388 | 40 | 0.60093 | 107 | $5.05 \times 10^{-5}$ |
| ME05392 | ME05392-03 ($T_2$) | 0.64335 | 23 | 0.60093 | 107 | $5.81 \times 10^{-5}$ |
| ME05392 | ME05392-03 ($T_3$) | 0.63397 | 36 | 0.60093 | 107 | $4.30 \times 10^{-5}$ |

Events -01 and -03 of ME05392 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 28—Analysis of ME05429 Events

ME05429 contains Ceres Clone:5609 (At3g60480, SEQ ID NO:729) from *Arabidopsis thaliana*, which encodes a 188 amino acid protein of unknown function. Evaluation of low-nitrogen tolerance for ME05429 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -06 and -08, showed significantly increased photosynthetic efficiency on low ammonium nitrate-containing media relative to the internal controls in both generations at p≤0.05 using a one-tailed t-test assuming unequal variance. A summary of photosynthetic efficiency of ME05429 seedlings is shown in Table 29. Events -06 and -08 segregated 3:1 and 2:1 respectively (R:S) for FINALE™ resistance in the $T_2$ generation. ME05429 events were tested for enhanced growth on the low ammonium nitrate media. In addition, these events were also tested for enhanced growth and photosynthetic efficiency on low nitrate media. No significant differences between the transgenics and the controls were observed.

TABLE 29 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05429 | ME05429-06 ($T_2$) | 0.62521 | 28 | 0.59991 | 78 | $2.85 \times 10^{-2}$ |
| ME05429 | ME05429-06 ($T_3$) | 0.63031 | 39 | 0.59991 | 78 | $8.49 \times 10^{-3}$ |
| ME05429 | ME05429-08 ($T_2$) | 0.64526 | 23 | 0.59991 | 78 | $1.67 \times 10^{-3}$ |

TABLE 29-continued t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05429 | ME05429-08 ($T_3$) | 0.65076 | 17 | 0.59991 | 78 | $2.76 \times 10^{-4}$ |

Events -06 and -08 of ME05429 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 29—Analysis of ME05493 Events

ME05493 contains Ceres Clone:3137 (At3g43430, SEQ ID NO:745) from *Arabidopsis thaliana*, which encodes a 169 amino acid zinc finger family protein. Evaluation of low-nitrogen tolerance for ME05493 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME05493 seedlings is shown in Table 30. Events -01 and -05 segregated 15:1 (R:S) for FINALE™ resistance in the $T_2$ generation. ME05493 events were also tested for enhanced growth on the low nitrate media. No significant differences between the transgenics and the controls were observed.

TABLE 30 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p- value |
| ME05493 | ME05493-01 ($T_2$) | 0.64121 | 32 | 0.61097 | 92 | $1.13 \times 10^{-3}$ |
| ME05493 | ME05493-01 ($T_3$) | 0.64250 | 46 | 0.61097 | 92 | $3.03 \times 10^{-4}$ |
| ME05493 | ME05493-05 ($T_2$) | 0.62865 | 43 | 0.61097 | 92 | $1.75 \times 10^{-2}$ |
| ME05493 | ME05493-05 ($T_3$) | 0.63936 | 42 | 0.61097 | 92 | $1.21 \times 10^{-4}$ |

Events -01 and -05 of ME05493 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 30—Analysis of ME05885 Events

ME05885 contains Ceres Clone:32430 (At1g16170, SEQ ID NO:768) from *Arabidopsis thaliana*, which encodes a 92 amino acid protein of unknown function. Evaluation of low-nitrogen tolerance for ME05885 in $T_3$ generation was conducted under the same conditions as described in Examples 2 and 3. A summary of photosynthetic efficiency of ME05885 seedlings is shown in Table 31. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media and low ammonium nitrate-containing media relative to the internal controls in $T_3$ generation at $p \leq 0.05$ using a one-tailed t-test assuming unequal variance.

TABLE 31A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME05885 | ME05885-01 ($T_3$) | 0.6759 | 12 | 0.6533 | 28 | $4.32 \times 10^{-2}$ |
| ME05885 | ME05885-05 ($T_3$) | 0.6831 | 7 | 0.6530 | 52 | $3.68 \times 10^{-6}$ |

TABLE 31B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05885 | ME05885-01 ($T_3$) | 0.6490 | 13 | 0.6135 | 30 | $3.06 \times 10^{-2}$ |
| ME05885 | ME05885-05 ($T_3$) | 0.6810 | 9 | 0.6133 | 43 | $6.77 \times 10^{-5}$ |

ME05885 events were also tested for enhanced growth on the low nitrate and low ammonium nitrate media. A summary of enhanced growth under low nitrate and low ammonium nitrate growth conditions of ME05885 seedlings in $T_3$ generation is shown in Table 32. Two events, -03 and -05, showed significantly enhanced growth on low nitrate-containing media. Two events, -02 and -05, showed significantly enhanced growth on low ammonium nitrate-containing media relative to the internal controls at $p \leq 0.05$ using a one-tailed t-test assuming unequal variance. In this study, the seedling area for transgenic plants within an event was compared to the seedling area for non-transgenic segregants pooled across the same line.

TABLE 32A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05885 | ME05885-03 ($T_3$) | 0.06245 | 6 | 0.05286 | 14 | $1.42 \times 10^{-2}$ |
| ME05885 | ME05885-05 ($T_3$) | 0.05893 | 7 | 0.04725 | 12 | $5.61 \times 10^{-3}$ |

TABLE 32B

T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME05885 | ME05885-02 ($T_3$) | 0.0744 | 14 | 0.05595 | 6 | $3.28 \times 10^{-5}$ |
| ME05885 | ME05885-05 ($T_3$) | 0.0753 | 9 | 0.06179 | 11 | $5.08 \times 10^{-3}$ |

Example 31—Analysis of ME07344 Events

ME07344 contains Ceres Clone:101255 (At2g19810, SEQ ID NO:791) from *Arabidopsis thaliana*, which encodes a 359 amino acid CCCH-type zinc finger protein. Evaluation of low-nitrogen tolerance for ME07344 in $T_2$ and $T_3$ was conducted under the same conditions as described in Example 4. In this study, the $4^{th}$ true leaf from each plant was collected on day 38 and analyzed on the CF imager for its Fv/Fm value. Transgenic plants within an event were compared to all non-transgenic plants, including the non-transgenic segregants and external controls. Two events, -02 and -03, showed significantly increased photosynthetic efficiency relative to the internal controls in both generations at p≤0.05 using a one-tailed t-test assuming unequal variance. A summary of photosynthetic efficiency of ME07344 seedlings is shown in Table 33. Events -02 and -03 segregated 3:1 (R:S) for FINALE™ resistance in the $T_2$ generation. ME07344 events were also tested for enhanced growth on the low nitrate media. No significant differences between the transgenics and the controls were observed.

TABLE 33

T-test comparison of photosynthetic efficiency between transgenic plants and non-transgenic controls after 38 days of growth on nitrogen-depleted soil.

| | | Transgenic | | Non-Transgenic Controls | | t-test |
|---|---|---|---|---|---|---|
| Line | Events | Fv/Fm | n | Fv/Fm | n | p-value |
| ME07344 | ME07344-02 ($T_2$) | 0.752 | 17 | 0.729 | 50 | $2.86 \times 10^{-4}$ |
| ME07344 | ME07344-02 ($T_3$) | 0.750 | 16 | 0.729 | 50 | $1.11 \times 10^{-4}$ |
| ME07344 | ME07344-03 ($T_2$) | 0.741 | 13 | 0.729 | 50 | 0.018 |
| ME07344 | ME07344-03 ($T_3$) | 0.754 | 17 | 0.729 | 50 | $4.62 \times 10^{-6}$ |

Events -02 and -03 of ME07344 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 32—Analysis of ME07859 Events

ME07859 contains Ceres Clone:276809 (SEQ ID NO:823) from *Zea mays*, which encodes a 135 amino acid sterol desaturase protein. Evaluation of low-nitrogen tolerance for ME07859 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME07859 seedlings is shown in Table 34. Events -02 and -04 segregated 1:1 and 2:1 respectively (R:S) for FINALE™ resistance in the $T_2$ generation. ME07859 events were also tested for enhanced growth on the low nitrate media as well as for enhanced growth and photosynthetic efficiency on low ammonium nitrate media. No significant differences between the transgenics and the controls were observed.

TABLE 34 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME07859 | ME07859-02 ($T_2$) | 0.6598 | 24 | 0.6378 | 127 | 0.03 |
| ME07859 | ME07859-02 ($T_3$) | 0.6825 | 14 | 0.6378 | 127 | $1.3 \times 10^{-3}$ |
| ME07859 | ME07859-04 ($T_2$) | 0.6539 | 33 | 0.6378 | 127 | 0.05 |
| ME07859 | ME07859-04 ($T_3$) | 0.6601 | 17 | 0.6378 | 127 | 0.05 |

Events -02 and -04 of ME07859 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 33—Analysis of ME08464 Events

ME08464 contains Ceres Clone:424522 (SEQ ID NO:827) from *Zea mays*, which encodes a 500 amino acid unknown protein. Evaluation of low-nitrogen tolerance for ME08464 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME07859 seedlings is shown in Table 35. Events -02 and -03 segregated 3:1 (R:S) for FINALE™ resistance in the $T_2$ generation. ME08464 events were also tested for increased photosynthetic efficiency on the low nitrate media. No significant differences between the transgenics and the controls were observed.

TABLE 35

T-test comparison of photosynthetic efficiency between transgenic seedlings and pooled non-transgenic segregants after 15 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME08464 | ME08464-02 ($T_2$) | 0.65 | 41 | 0.62 | 40 | 0.015 |
| ME08464 | ME08464-02 ($T_3$) | 0.67 | 32 | 0.62 | 40 | $2.32 \times 10^{-4}$ |
| ME08464 | ME08464-03 ($T_2$) | 0.65 | 43 | 0.62 | 40 | 0.013 |
| ME08464 | ME08464-03 ($T_3$) | 0.65 | 42 | 0.62 | 40 | $6.85 \times 10^{-3}$ |

Events -02 and -03 of ME08464 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 34—Analysis of ME09939 Events

ME09939 contains Ceres Clone:324216 (SEQ ID NO:852) from *Zea mays*, which encodes a 38 amino acid protein of unknown function. Evaluation of low-nitrogen tolerance for ME09939 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME09939 seedlings is shown in Table 36. Events -04 and -05 segregated 15:1 and 3:1 respectively (R:S) for FINALE™ resistance in the $T_2$ generation. ME09939 events were also tested for enhanced growth on the low ammonium nitrate media. No significant differences between the transgenics and the controls were observed.

TABLE 36

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME09939 | ME09939-04 ($T_2$) | 0.49285 | 40 | 0.38571 | 7 | 0.05 |
| ME09939 | ME09939-04 ($T_3$) | 0.50697 | 34 | 0.38571 | 7 | $3.50 \times 10^{-2}$ |
| ME09939 | ME09939-05 ($T_2$) | 0.53487 | 39 | 0.47492 | 24 | $1.19 \times 10^{-2}$ |
| ME09939 | ME09939-05 ($T_3$) | 0.55341 | 32 | 0.47492 | 24 | $1.82 \times 10^{-3}$ |

Events -04 and -05 of ME09939 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 35—Analysis of ME11735 Events

ME11735 contains Ceres Annot:573161 (At5g43260, SEQ ID NO:854) from *Arabidopsis thaliana*, which encodes a 97 amino acid DnaJ-related chaperone protein. Evaluation of low-nitrogen tolerance for ME11735 in $T_2$ and $T_3$ was conducted under the same conditions as described in Example 2 and 3. A summary of the enhanced growth of ME11735 events on low nitrate-containing media is shown in Table 37. In this study, the seedling area for transgenic plants within an event was compared to the seedling area for non-transgenic segregants pooled across the same line. Two events, -04 and -05, were found significantly larger than the pooled non-transgenic segregants after 14 days of growth on low nitrate-containing media relative to the internal controls in both generations at $p \leq 0.05$ using a one-tailed t-test assuming unequal variance. ME11735 events were also tested for increased photosynthetic efficiency on the low nitrate media. No significant differences between the transgenics and the controls were observed. Events -04 and -05 segregated 40:1 and 4:1 respectively (R:S) for FINALE™ resistance in the $T_2$ generation.

TABLE 37 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME11735 | ME11735-04 ($T_2$) | 0.05820 | 41 | 0.04994 | 127 | $5.91 \times 10^{-5}$ |
| ME11735 | ME11735-04 ($T_3$) | 0.05553 | 42 | 0.04994 | 127 | $1.26 \times 10^{-2}$ |
| ME11735 | ME11735-05 ($T_2$) | 0.05788 | 37 | 0.04994 | 127 | $1.59 \times 10^{-3}$ |
| ME11735 | ME11735-05 ($T_3$) | 0.06011 | 13 | 0.04994 | 127 | $1.64 \times 10^{-2}$ |

Events -04 and -05 of ME11735 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 36—Analysis of ME12910 Events

ME12910 contains Ceres Annot:552727 (At2g22930, SEQ ID NO:890) from *Arabidopsis thaliana*, which encodes a 442 amino acid UDP-glucoronosyl and UDP-glucosyl transferase family protein. Evaluation of low-nitrogen tolerance for ME12910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME12910 seedlings is shown in Table 38. ME12910 events were also tested for enhanced growth on the low ammonium nitrate media. No significant differences between the transgenics and the controls were observed.

TABLE 38 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12910 | ME12910-03 ($T_2$) | 0.5851 | 39 | 0.5191 | 29 | $1.54 \times 10^{-3}$ |
| ME12910 | ME12910-03 ($T_3$) | 0.5861 | 22 | 0.5191 | 29 | $2.17 \times 10^{-3}$ |
| ME12910 | ME12910-05 ($T_2$) | 0.5523 | 44 | 0.4251 | 7 | $1.23 \times 10^{-2}$ |
| ME12910 | ME12910-05 ($T_3$) | 0.5600 | 42 | 0.4251 | 7 | $9.62 \times 10^{-3}$ |

Events -03 and -05 segregated 3:1 and 15:1 respectively (R:S) for FINALE™ resistance in the $T_2$ generation.

Events -03 and -05 of ME12910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 37—Analysis of ME12927 Events

ME12927 contains Ceres Clone:239806 (SEQ ID NO:916) from *Zea mays*, which encodes a 201 amino acid lipoprotein amino terminal region. Evaluation of low-nitrogen tolerance for ME12927 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -03 and -05, showed significantly increased photosynthetic efficiency on low ammonium nitrate-containing media relative to the internal controls in both generations at p≤0.05, using a one-tailed t-test assuming unequal variance. A summary of photosynthetic efficiency of ME12927 seedlings is shown in Table 39.

TABLE 39 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12927 | ME12927-02 ($T_2$) | 0.60843 | 44 | 0.47813 | 8 | $4.88 \times 10^{-3}$ |
| ME12927 | ME12927-02 ($T_3$) | 0.60867 | 36 | 0.47813 | 8 | $5.23 \times 10^{-3}$ |
| ME12927 | ME12927-03 ($T_2$) | 0.61906 | 32 | 0.57929 | 38 | $8.96 \times 10^{-3}$ |
| ME12927 | ME12927-03 ($T_3$) | 0.63437 | 19 | 0.57929 | 38 | $5.35 \times 10^{-4}$ |
| ME12927 | ME12927-05 ($T_2$) | 0.60581 | 43 | 0.53982 | 22 | $7.26 \times 10^{-3}$ |
| ME12927 | ME12927-05 ($T_3$) | 0.63145 | 29 | 0.53982 | 22 | $5.83 \times 10^{-4}$ |

ME12927 events were also tested for enhanced growth on the low ammonium nitrate media. A summary of the enhanced growth of ME11735 events on low ammonium nitrate-containing media is shown in Table 40. In this study, the seedling area for transgenic plants within an event was compared to the seedling area for non-transgenic segregants pooled across the same line. Three events, -02, -03 and -05, were found significantly larger than the pooled non-transgenic segregants after 18 days of growth on low ammonium nitrate-containing media relative to the internal controls in both generations at p≤0.05, using a one-tailed t-test assuming unequal variance.

TABLE 40 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME12927 | ME12927-02 ($T_2$) | 0.066920 | 44 | 0.056585 | 117 | $1.65 \times 10^{-4}$ |
| ME12927 | ME12927-02 ($T_3$) | 0.062119 | 36 | 0.056585 | 117 | $3.51 \times 10^{-2}$ |
| ME12927 | ME12927-03 ($T_2$) | 0.068972 | 32 | 0.056585 | 117 | $1.18 \times 10^{-5}$ |
| ME12927 | ME12927-03 ($T_3$) | 0.063716 | 19 | 0.056585 | 117 | $1.98 \times 10^{-2}$ |
| ME12927 | ME12927-05 ($T_2$) | 0.069972 | 43 | 0.056585 | 117 | $4.25 \times 10^{-6}$ |
| ME12927 | ME12927-05 ($T_3$) | 0.064014 | 29 | 0.056585 | 117 | $8.49 \times 10^{-3}$ |

Events 02, -03 and -05 segregated 15:1, 2:1 and 15:1 respectively (R:S) for FINALE™ resistance in the $T_2$ generation.

Events 02, -03 and -05 of ME12927 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in $T_1$ generation.

Example 38—Analysis of ME12929 Events

ME12929 contains Ceres Clone:208995 (SEQ ID NO:943) from *Zea mays*, which encodes a 94 amino acid protein of unknown function. Evaluation of low-nitrogen tolerance for ME12929 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME12929 seedlings is shown in Table 41. ME12929 events were also tested for enhanced growth on the low ammonium nitrate media. No significant differences between the transgenics and the controls were observed. Events -03 and -04 segregated 1:1 and 3:1 respectively (R:S) for FINALE™ resistance in the $T_2$ generation.

Events -03 and -04 of ME12929 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

TABLE 41 t-test comparison of seedling photosynthetic efficiency between transgenic seedlings and pooled non-transgenic segregants after 14 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12929 | ME12929-03 ($T_2$) | 0.6410 | 33 | 0.5736 | 24 | $9.44 \times 10^{-4}$ |
| ME12929 | ME12929-03 ($T_3$) | 0.6610 | 41 | 0.5736 | 24 | $4.38 \times 10^{-5}$ |
| ME12929 | ME12929-04 ($T_2$) | 0.6544 | 47 | 0.5790 | 9 | $3.68 \times 10^{-2}$ |
| ME12929 | ME12929-04 ($T_3$) | 0.6663 | 43 | 0.5790 | 9 | $2.15 \times 10^{-2}$ |

Example 39—Analysis of ME12954 Events

ME12954 contains Ceres Clone:225681 (SEQ ID NO:975) from *Zea mays*, which encodes a 286 amino acid protein of unknown function. Evaluation of low-nitrogen tolerance for ME12954 in $T_2$ and $T_3$ was conducted under the same conditions as described in Examples 2 and 3. Two events, -04 and -05, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12954 seedlings is shown in Table 42.

TABLE 42 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12954 | ME12954-04 ($T_2$) | 0.6236 | 40 | 0.5973 | 152 | $6.61 \times 10^{-3}$ |
| ME12954 | ME12954-04 ($T_3$) | 0.6200 | 39 | 0.5973 | 152 | $1.97 \times 10^{-2}$ |
| ME12954 | ME12954-05 ($T_2$) | 0.6280 | 45 | 0.5973 | 152 | $1.79 \times 10^{-2}$ |
| ME12954 | ME12954-05 ($T_3$) | 0.6315 | 35 | 0.5973 | 152 | $2.85 \times 10^{-2}$ |

ME12954 events were also tested for enhanced growth on the low ammonium nitrate media. A summary of the enhanced growth of ME12954 events on low ammonium nitrate-containing media is shown in Table 43. In this study, the seedling area for transgenic plants within an event was compared to the seedling area for non-transgenic segregants pooled across the same line. Two events, -02 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 43 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME12954 | ME12954-02 ($T_2$) | 0.06883 | 31 | 0.05579 | 152 | $1.86 \times 10^{-5}$ |
| ME12954 | ME12954-02 ($T_3$) | 0.06604 | 26 | 0.05579 | 152 | $1.48 \times 10^{-3}$ |
| ME12954 | ME12954-04 ($T_2$) | 0.06469 | 40 | 0.05579 | 152 | $1.95 \times 10^{-4}$ |
| ME12954 | ME12954-04 ($T_3$) | 0.06301 | 39 | 0.05579 | 152 | $3.32 \times 10^{-3}$ |

Events -02, -04 and -05 segregated 2:1, 3:1 and 15:1 respectively (R:S) for FINALE™ resistance in the T2 generation.

Events -02, -04 and -05 of ME12954 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 40—Analysis of ME12970 Events

ME12970 contains Ceres Clone:1387146 (SEQ ID NO:981) from *Zea mays*, which encodes a 147 amino acid C2 domain-containing protein. Evaluation of low-nitrogen tolerance for ME12970 in $T_2$ and $T_3$ was conducted under the same conditions as described in Examples 2 and 3. Two events, -02 and -03, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12970 seedlings is shown in Table 44. ME12970 events were also tested for enhanced growth on the low ammonium nitrate media. No significant differences between the transgenics and the controls were observed.

TABLE 44 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12970 | ME12970-02 ($T_2$) | 0.55136 | 44 | 0.52401 | 108 | $3.78 \times 10^{-2}$ |
| ME12970 | ME12970-02 ($T_3$) | 0.58305 | 43 | 0.52401 | 108 | $1.89 \times 10^{-5}$ |
| ME12970 | ME12970-03 ($T_2$) | 0.58759 | 37 | 0.52401 | 108 | $2.14 \times 10^{-6}$ |
| ME12970 | ME12970-03 ($T_3$) | 0.59131 | 29 | 0.52401 | 108 | $3.05 \times 10^{-6}$ |

Events -02 and -03 segregated 15:1 and 3:1 respectively (R:S) for FINALE™ resistance in the T2 generation.

Events -02 and -03 of ME12970 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 41—Analysis of ME13006 Events

ME13006 contains Ceres Clone:1017441 (SEQ ID NO:224) from *Triticum aestivum*, which encodes a 143 amino acid polypeptide, predicted to be a homolog of Ceres Clone:4898 (ME03123, SEQ ID NO:217). Evaluation of low-nitrogen tolerance for ME13006 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13006 seedlings is shown in Table 45. ME13006 events were also tested for enhanced growth on the low nitrate media. No significant differences between the transgenics and the controls were observed.

TABLE 45 t-test comparison of seedling area between transgenic seedlings and pooled non-transgenic segregants after 14 days of growth on low ammonium nitrate.

| | | Transgenic | | Pooled Non-Transgenics | | t-test |
|---|---|---|---|---|---|---|
| Line | Events | Area | n | Area | n | p-value |
| ME13006 | ME13006-01 ($T_2$) | 0.0777 | 42 | 0.0648 | 7 | $3.29 \times 10^{-2}$ |
| ME13006 | ME13006-01 ($T_3$) | 0.0660 | 28 | 0.0540 | 19 | $1.49 \times 10^{-3}$ |
| ME13006 | ME13006-03 ($T_2$) | 0.0706 | 21 | 0.0601 | 29 | $4.83 \times 10^{-3}$ |
| ME13006 | ME13006-03 ($T_3$) | 0.0758 | 14 | 0.0617 | 33 | $2.60 \times 10^{-3}$ |

Events -01 and -03 segregated 3:1 and 1:1 respectively (R:S) for FINALE™ resistance in the $T_2$ generation.

Events -01 and -03 of ME13006 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 42—Analysis of ME13021 Events

ME13021 contains Ceres Clone:244306 (SEQ ID NO:1053) from *Zea mays*, which encodes a 572 amino acid TCP-1/cpn60 chaperonin family protein. Evaluation of low-nitrogen tolerance for ME13021 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13021 seedlings is shown in Table 46. ME13021 events were also tested for enhanced growth on the low ammonium nitrate media. No significant differences between the transgenics and the controls were observed.

TABLE 46 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13021 | ME13021-04 ($T_2$) | 0.56697 | 39 | 0.49440 | 10 | $2.47 \times 10^{-2}$ |
| ME13021 | ME13021-04 ($T_3$) | 0.59916 | 37 | 0.48685 | 13 | $1.54 \times 10^{-3}$ |
| ME13021 | ME13021-05 ($T_2$) | 0.60575 | 32 | 0.50344 | 18 | $6.05 \times 10^{-4}$ |
| ME13021 | ME13021-05 ($T_3$) | 0.64400 | 23 | 0.55638 | 26 | $3.86 \times 10^{-6}$ |

Events -04 and -05 segregated 3:1 and 2:1 respectively (R:S) for FINALE™ resistance in the T2 generation.

Events -04 and -05 of ME13021 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 43—Analysis of ME13064 Events

ME13064 contains Ceres Clone:1408950 (SEQ ID NO:1098) from *Zea mays*, which encodes a 152 amino acid protein of unknown function. Evaluation of low-nitrogen tolerance for ME13064 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13064 seedlings is shown in Table 47. ME13064 events were also tested for enhanced growth on the low ammonium nitrate media. No significant differences between the transgenics and the controls were observed.

TABLE 47 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13064 | ME13064-03 ($T_2$) | 0.59444 | 27 | 0.54793 | 28 | $5.84 \times 10^{-3}$ |
| ME13064 | ME13064-03 ($T_3$) | 0.59676 | 29 | 0.54793 | 28 | $1.25 \times 10^{-2}$ |
| ME13064 | ME13064-04 ($T_2$) | 0.58577 | 31 | 0.51053 | 40 | $2.05 \times 10^{-3}$ |
| ME13064 | ME13064-04 ($T_3$) | 0.59128 | 25 | 0.51053 | 40 | $8.93 \times 10^{-4}$ |

Events -03 and -04 segregated 2:1 (R:S) for FINALE™ resistance in the T2 generation.

Events -03 and -04 of ME13064 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 44—Analysis of ME13071 Events

ME13071 contains Ceres Clone:208453 (SEQ ID NO:1111) from *Zea mays*, which encodes a 74 amino acid protein of unknown function. Evaluation of low-nitrogen tolerance for ME13071 in $T_2$ and $T_3$ was conducted under the same conditions as described in Examples 2 and 3. Two events, -03 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 48. ME13071 events were also tested for photosynthetic efficiency on the low ammonium nitrate media. No significant differences between the transgenics and the controls were observed.

TABLE 48 t-test comparison of seedling area between transgenic seedlings and pooled non- transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13071 | ME13071-03 ($T_2$) | 0.06694 | 26 | 0.05915 | 19 | $3.55 \times 10^{-3}$ |
| ME13071 | ME13071-03 ($T_3$) | 0.07787 | 24 | 0.07040 | 22 | $3.65 \times 10^{-2}$ |
| ME13071 | ME13071-05 ($T_2$) | 0.06232 | 32 | 0.05491 | 16 | $2.07 \times 10^{-3}$ |
| ME13071 | ME13071-05 ($T_3$) | 0.06335 | 22 | 0.05626 | 28 | $1.09 \times 10^{-2}$ |

Events -03 and -05 segregated 1:1 and 2:1 respectively (R:S) for FINALE™ resistance in the T2 generation.

Events -03 and -05 of ME13071 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 45—Analysis of ME13087 Events

ME13087 contains Ceres Clone:968180 (SEQ ID NO:1115) from *Brassica napus*, which encodes a 159 amino acid zinc finger protein. Evaluation of low-nitrogen tolerance for ME13087 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13087 seedlings is shown in Table 49. ME13087 events were also tested for enhanced growth on the low ammonium nitrate media. No significant differences between the transgenics and the controls were observed.

TABLE 49 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13087 | ME13087-01 ($T_2$) | 0.59761 | 23 | 0.56163 | 38 | $9.61 \times 10^{-3}$ |
| ME13087 | ME13087-01 ($T_3$) | 0.61247 | 15 | 0.56163 | 38 | $5.99 \times 10^{-4}$ |
| ME13087 | ME13087-02 ($T_2$) | 0.63400 | 39 | 0.58532 | 34 | $9.30 \times 10^{-3}$ |
| ME13087 | ME13087-02 ($T_3$) | 0.63442 | 26 | 0.58532 | 34 | $1.22 \times 10^{-2}$ |
| ME13087 | ME13087-03 ($T_2$) | 0.61429 | 38 | 0.55533 | 24 | $5.04 \times 10^{-3}$ |
| ME13087 | ME13087-03 ($T_3$) | 0.62283 | 35 | 0.55533 | 24 | $3.31 \times 10^{-3}$ |
| ME13087 | ME13087-04 ($T_2$) | 0.62714 | 28 | 0.60068 | 56 | $3.02 \times 10^{-2}$ |
| ME13087 | ME13087-04 ($T_3$) | 0.64543 | 7 | 0.60068 | 56 | $9.04 \times 10^{-3}$ |

Events -01, -02, -03 and -04 segregated 2:1, 3:1, 3:1 and 2:1 respectively (R:S) for FINALE™ resistance in the T2 generation.

Events -01, -02, -03 and -04 of ME13087 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 46—Analysis of ME13106 Events

ME13106 contains Ceres Clone:986438 (SEQ ID NO:1156) from *Zea mays*, which encodes a 188 amino acid protein of unknown function. Evaluation of low-nitrogen tolerance for ME13106 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13106 seedlings is shown in Table 50. ME13106 events were also tested for enhanced growth on the low ammonium nitrate media. No significant differences between the transgenics and the controls were observed.

TABLE 50 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13106 | ME13106-03 ($T_2$) | 0.62726 | 27 | 0.58600 | 43 | $1.50 \times 10^{-2}$ |
| ME13106 | ME13106-03 ($T_3$) | 0.65163 | 30 | 0.58600 | 43 | $1.69 \times 10^{-4}$ |
| ME13106 | ME13106-04 ($T_2$) | 0.60836 | 36 | 0.55876 | 25 | $2.62 \times 10^{-2}$ |
| ME13106 | ME13106-04 ($T_3$) | 0.64250 | 38 | 0.55876 | 25 | $5.01 \times 10^{-4}$ |

Events -03 and -04 segregated 1:1 and 3:1 respectively (R:S) for FINALE™ resistance in the $T_2$ generation.

Events -03 and -04 of ME13106 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 47—Analysis of ME13107 Events

ME13107 contains Ceres Clone:996227 (SEQ ID NO:1158) from *Zea mays*, which encodes a 240 amino acid zein seed storage protein. Evaluation of low-nitrogen tolerance for ME13107 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13107 seedlings is shown in Table 51.

TABLE 51 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13107 | ME13107-02 ($T_2$) | 0.63122 | 37 | 0.56643 | 21 | $1.07 \times 10^{-2}$ |
| ME13107 | ME13107-02 ($T_3$) | 0.63848 | 29 | 0.56643 | 21 | $6.03 \times 10^{-3}$ |
| ME13107 | ME13107-04 ($T_2$) | 0.62948 | 27 | 0.55918 | 50 | $2.07 \times 10^{-5}$ |
| ME13107 | ME13107-04 ($T_3$) | 0.63019 | 21 | 0.55918 | 50 | $6.72 \times 10^{-5}$ |
| ME13107 | ME13107-05 ($T_2$) | 0.61952 | 29 | 0.54440 | 48 | $7.85 \times 10^{-5}$ |
| ME13107 | ME13107-05 ($T_3$) | 0.62185 | 20 | 0.54440 | 48 | $4.02 \times 10^{-5}$ |

ME13107 events were also tested for enhanced growth on the low ammonium nitrate media. Two events, -02 and -04, showed significantly enhanced growth on low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 52.

TABLE 2 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13107 | ME13107-02 ($T_2$) | 0.07738 | 37 | 0.06919 | 203 | $3.63 \times 10^{-2}$ |
| ME13107 | ME13107-02 ($T_3$) | 0.07688 | 29 | 0.06919 | 203 | $4.60 \times 10^{-2}$ |
| ME13107 | ME13107-04 ($T_2$) | 0.07514 | 27 | 0.06919 | 203 | $3.18 \times 10^{-2}$ |
| ME13107 | ME13107-04 ($T_3$) | 0.07585 | 21 | 0.06919 | 203 | $2.27 \times 10^{-2}$ |

Events -02, -04 and -05 segregated 3:1, 1:1 and 2:1 respectively (R:S) for FINALE™ resistance in the $T_2$ generation.

Events -02, -04 and -05 of ME13107 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 48—Analysis of ME13108 Events

ME13108 contains Ceres Clone:996263 (SEQ ID NO:1165) from *Zea mays*, which encodes an 84 amino acid BRICK1 protein. Evaluation of low-nitrogen tolerance for ME13108 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13108 seedlings is shown in Table 53. ME13108 events were also tested for enhanced growth on the low ammonium nitrate media. No significant differences between the transgenics and the controls were observed.

TABLE 53 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13108 | ME13108-01 ($T_2$) | 0.56703 | 36 | 0.53932 | 195 | $1.97 \times 10^{-2}$ |
| ME13108 | ME13108-01 ($T_3$) | 0.59250 | 26 | 0.53932 | 195 | $3.64 \times 10^{-4}$ |
| ME13108 | ME13108-04 ($T_2$) | 0.60032 | 37 | 0.53932 | 195 | $3.37 \times 10^{-7}$ |
| ME13108 | ME13108-04 ($T_3$) | 0.60463 | 30 | 0.53932 | 195 | $4.10 \times 10^{-5}$ |

TABLE 53-continued t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13108 | ME13108-05 ($T_2$) | 0.60727 | 30 | 0.53932 | 195 | $4.97 \times 10^{-9}$ |
| ME13108 | ME13108-05 ($T_3$) | 0.61850 | 32 | 0.53932 | 195 | $2.35 \times 10^{-9}$ |

Events -01, -04 and -05 segregated 3:1 (R:S) for FINALE™ resistance in the $T_2$ generation.

Events -01, -04 and -05 of ME13108 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 49—Analysis of ME13110 Events

ME13110 contains Ceres Clone:988083 (SEQ ID NO:1184) from *Zea mays*, which encodes a 188 amino acid protein of unknown function. Evaluation of low-nitrogen tolerance for ME13110 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -03, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13110 seedlings is shown in Table 54. ME13110 events were also tested for enhanced growth on the low ammonium nitrate media. No significant differences between the transgenics and the controls were observed.

TABLE 54 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13110 | ME13110-03 ($T_2$) | 0.5721 | 34 | 0.3948 | 16 | $8.92 \times 10^{-3}$ |
| ME13110 | ME13110-03 ($T_3$) | 0.5773 | 24 | 0.4583 | 26 | $4.58 \times 10^{-4}$ |
| ME13110 | ME13110-04 ($T_2$) | 0.5651 | 35 | 0.4243 | 15 | $4.34 \times 10^{-2}$ |
| ME13110 | ME13110-04 ($T_3$) | 0.6000 | 10 | 0.4594 | 40 | $3.29 \times 10^{-3}$ |
| ME13110 | ME13110-05 ($T_2$) | 0.5143 | 28 | 0.3809 | 22 | $2.24 \times 10^{-2}$ |
| ME13110 | ME13110-05 ($T_3$) | 0.5278 | 28 | 0.3688 | 21 | $1.28 \times 10^{-2}$ |

Events -03, -04 and -05 segregated 3:1, 1:1 and 3:1 respectively (R:S) for FINALE™ resistance in the $T_2$ generation.

Events -03, -04 and -05 of ME13110 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 50—Analysis of ME13125 Events

ME13125 contains Ceres Clone:732 (At3g50880, SEQ TD NO:1193) from *Arabidopsis thaliana*, which encodes a 188 amino acid protein of unknown function. Evaluation of low-nitrogen tolerance for ME13125 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13125 seedlings is shown in Table 55. ME13125 events were also tested for enhanced growth on the low ammonium nitrate media. No significant differences between the transgenics and the controls were observed.

TABLE 55 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13125 | ME13125-01 ($T_2$) | 0.61129 | 42 | 0.53829 | 125 | $4.82 \times 10^{-7}$ |
| ME13125 | ME13125-01 ($T_3$) | 0.61929 | 38 | 0.53829 | 125 | $1.96 \times 10^{-7}$ |
| ME13125 | ME13125-03 ($T_2$) | 0.63360 | 45 | 0.53829 | 125 | $3.05 \times 10^{-13}$ |
| ME13125 | ME13125-03 ($T_3$) | 0.62218 | 44 | 0.53829 | 125 | $3.81 \times 10^{-9}$ |
| ME13125 | ME13125-05 ($T_2$) | 0.61565 | 31 | 0.53829 | 125 | $4.12 \times 10^{-8}$ |
| ME13125 | ME13125-05 ($T_3$) | 0.58469 | 16 | 0.53829 | 125 | 0.05 |

Events -01, -03 and -05 segregated 3:1, 15:1 and 2:1 respectively (R:S) for FINALE™ resistance in the $T_2$ generation.

Events -01, -03 and -05 of ME13125 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 51—Analysis of ME13149 Events

ME13149 contains Ceres Clone:2267 (At2g24765, SEQ ID NO:1209) from *Arabidopsis thaliana*, which encodes a 182 amino acid ADP-ribosylation factor 3 protein. Evaluation of low-nitrogen tolerance for ME13149 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13149 seedlings is shown in Table 56. ME13149 events were also tested for enhanced growth on the low ammonium nitrate media. No significant differences between the transgenics and the controls were observed.

TABLE 56 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13149 | ME13149-02 ($T_2$) | 0.55623 | 30 | 0.51138 | 55 | $2.29 \times 10^{-2}$ |
| ME13149 | ME13149-02 ($T_3$) | 0.54818 | 17 | 0.51138 | 55 | $4.56 \times 10^{-2}$ |
| ME13149 | ME13149-03 ($T_2$) | 0.55998 | 42 | 0.51138 | 55 | $5.11 \times 10^{-3}$ |
| ME13149 | ME13149-03 ($T_3$) | 0.58450 | 24 | 0.51138 | 55 | $2.77 \times 10^{-4}$ |

Events -02 and -03 segregated 2:1 and 15:1 respectively (R:S) for FINALE™ resistance in the $T_2$ generation.

Events -02 and -03 of ME13149 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 52—Analysis of ME13151 Events

ME13151 contains Ceres Clone:39358 (At3g25150, SEQ ID NO:1273) from *Arabidopsis thaliana*, which encodes a 488 amino acid nuclear transport factor 2 (NTF2) domain protein. Evaluation of low-nitrogen tolerance for ME13151 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13151 seedlings is shown in Table 57. ME13151 events were also tested for enhanced growth on the low ammonium nitrate media. No significant differences between the transgenics and the controls were observed.

TABLE 57

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13151 | ME13151-01 ($T_2$) | 0.62593 | 44 | 0.53141 | 17 | $8.58 \times 10^{-4}$ |
| ME13151 | ME13151-01 ($T_3$) | 0.59936 | 33 | 0.53141 | 17 | $1.21 \times 10^{-2}$ |
| ME13151 | ME13151-02 ($T_2$) | 0.59879 | 39 | 0.46956 | 16 | $3.08 \times 10^{-5}$ |
| ME13151 | ME13151-02 ($T_3$) | 0.59566 | 32 | 0.46956 | 16 | $4.28 \times 10^{-5}$ |

Events -01 and -02 segregated 9:1 and 6:1 respectively (R:S) for FINALE™ resistance in the T2 generation.

Events -01 and -02 of ME13151 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 53—Analysis of ME13153 Events

ME13153 contains Ceres Clone:115046 (At3g17760, SEQ ID NO:1301) from *Arabidopsis thaliana*, which encodes a 494 amino acid glutamate decarboxylase. Evaluation of low-nitrogen tolerance for ME13153 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13153 seedlings is shown in Table 58. ME13153 events were also tested for increased photosynthetic efficiency on the low nitrate media. No significant differences between the transgenics and the controls were observed.

TABLE 58

T-test comparison of seedling photosynthetic efficiency between transgenic seedlings and non-transgenic segregants after 14 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13153 | ME13153-03 ($T_2$) | 0.62 | 34 | 0.56 | 16 | $3.0 \times 10^{-2}$ |
| ME13153 | ME13153-03 ($T_3$) | 0.60 | 19 | 0.54 | 22 | $2.9 \times 10^{-2}$ |
| ME13153 | ME13153-04 ($T_2$) | 0.57 | 32 | 0.50 | 18 | $4.3 \times 10^{-2}$ |
| ME13153 | ME13153-04 ($T_3$) | 0.61 | 24 | 0.55 | 24 | $2.1 \times 10^{-2}$ |

Events -03 and -04 segregated 3:1 (R:S) for FINALE™ resistance in the $T_2$ generation.

Events -03 and -04 of ME13153 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting. Events -03 and -04 yielded slightly less seed per plant compared to the controls, but these differences are not significant at p≤0.10.

Example 54—Analysis of ME13177 Events

ME13177 contains Ceres Clone:339439 (SEQ ID NO:1341) from *Zea mays*, which encodes a 345 amino acid cyclin C-terminal domain protein. Evaluation of low-nitrogen tolerance for ME13177 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13177 seedlings is shown in Table 59. ME13177 events were also tested for enhanced growth on the low ammonium nitrate media. No significant differences between the transgenics and the controls were observed.

TABLE 59 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13177 | ME13177-01 ($T_2$) | 0.6315 | 32 | 0.6112 | 175 | $2.43 \times 10^{-2}$ |
| ME13177 | ME13177-01 ($T_3$) | 0.6407 | 29 | 0.6112 | 175 | $7.33 \times 10^{-3}$ |
| ME13177 | ME13177-02 ($T_2$) | 0.6400 | 41 | 0.6112 | 175 | $1.23 \times 10^{-3}$ |
| ME13177 | ME13177-02 ($T_3$) | 0.6499 | 20 | 0.6112 | 175 | $6.47 \times 10^{-3}$ |

Events -01 and -02 segregated 2:1 and 3:1 respectively (R:S) for FINALE™ resistance in the $T_2$ generation.

Events -01 and -02 of ME13177 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 55—Analysis of ME13200 Events

ME13200 contains Ceres Clone:896483 (SEQ ID NO:1384) from *Zea mays*, which encodes an 85 amino acid myb family transcription factor. Evaluation of low-nitrogen tolerance for ME13200 in $T_2$ and $T_3$ was conducted under the same conditions as described in Examples 2 and 3. A summary of the enhanced growth of ME13200 events on low ammonium nitrate-containing media is shown in Table 60. In this study, the seedling area for transgenic plants within an event was compared to the seedling area for non-transgenic segregants pooled across the same line. Two events, -03 and -04, were found significantly larger than the pooled non-transgenic segregants after 18 days of growth on low ammonium nitrate-containing media relative to the internal controls in both generations at p≤0.05 using a one-tailed t-test assuming unequal variance. ME13200 events were also tested for increased photosynthetic efficiency on the low ammonium nitrate media as well as for enhanced photosynthesis and growth on low nitrate media. No significant differences between the transgenics and the controls were observed.

TABLE 60 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME13200 | ME13200-03 ($T_2$) | 0.07366 | 43 | 0.06342 | 35 | $4.09 \times 10^{-4}$ |
| ME13200 | ME13200-03 ($T_3$) | 0.08193 | 34 | 0.06342 | 35 | $2.37 \times 10^{-5}$ |
| ME13200 | ME13200-04 ($T_2$) | 0.07377 | 48 | 0.06342 | 35 | $4.87 \times 10^{-4}$ |
| ME13200 | ME13200-04 ($T_3$) | 0.07530 | 47 | 0.06342 | 35 | $1.88 \times 10^{-4}$ |

Events -03 and -04 segregated 3:1 and 15:1 respectively respectively (R:S) for FINALE™ resistance in the $T_2$ generation.

Events -03 and -04 of ME13200 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 56—Analysis of ME13204 Events

ME13204 contains Ceres Clone:995409 (SEQ TD NO:1408) from *Zea mays*, which encodes a 178 amino acid protein of unknown function. Evaluation of low-nitrogen tolerance for ME13204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME13204 seedlings is shown in Table 61. ME13204 events were also tested for enhanced growth on the low nitrate media as well as for enhanced growth and photosynthetic efficiency on low ammonium nitrate media. No significant differences between the transgenics and the controls were observed.

TABLE 61

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME13204 | ME13204-01 ($T_2$) | 0.5874 | 45 | 0.5354 | 46 | $1.41 \times 10^{-2}$ |
| ME13204 | ME13204-01 ($T_3$) | 0.5932 | 36 | 0.5354 | 46 | $9.85 \times 10^{-3}$ |
| ME13204 | ME13204-05 ($T_2$) | 0.5855 | 34 | 0.5354 | 46 | $2.00 \times 10^{-2}$ |
| ME13204 | ME13204-05 ($T_3$) | 0.5998 | 20 | 0.5354 | 46 | $5.58 \times 10^{-3}$ |

Events -01 and -05 segregated 9:1 and 3:1 respectively (R:S) for FINALE™ resistance in the $T_2$ generation.

Events -01 and -05 of ME13204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 57—Analysis of ME14649 Events

ME14649 contains Ceres Annot:850581 (At5g01880, SEQ ID NO:1427) from *Arabidopsis thaliana*, which encodes a 159 amino acid zinc finger protein. Evaluation of low-nitrogen tolerance for ME14649 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME14649 seedlings is shown in Table 62. ME14649 events were also tested for enhanced growth on the low ammonium nitrate media. No significant differences between the transgenics and the controls were observed.

TABLE 62 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME14649 | ME14649-02 ($T_2$) | 0.59789 | 35 | 0.54533 | 30 | $1.54 \times 10^{-4}$ |
| ME14649 | ME14649-02 ($T_3$) | 0.58154 | 26 | 0.54533 | 30 | $3.42 \times 10^{-2}$ |

TABLE 62-continued t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME14649 | ME14649-03 ($T_2$) | 0.61875 | 28 | 0.56539 | 33 | $2.03 \times 10^{-3}$ |
| ME14649 | ME14649-03 ($T_3$) | 0.62630 | 27 | 0.56539 | 33 | $9.18 \times 10^{-4}$ |

Events -02 and -03 segregated 3:1 and 2:1 respectively (R:S) for FINALE™ resistance in the $T_2$ generation.

Events -02 and -03 of ME14649 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 58—Analysis of ME16546 Events

ME16546 contains Ceres Annot:862321 (At2g45360, SEQ ID NO:1462) from *Arabidopsis thaliana*, which encodes a 215 amino acid protein of unknown function. Evaluation of low-nitrogen tolerance for ME16546 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME16546 seedlings is shown in Table 63. ME16546 events were also tested for enhanced growth on the low ammonium nitrate media. No significant differences between the transgenics and the controls were observed.

TABLE 63 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME16546 | ME16546-04 ($T_2$) | 0.59891 | 33 | 0.56124 | 130 | $2.21 \times 10^{-4}$ |
| ME16546 | ME16546-04 ($T_3$) | 0.57924 | 41 | 0.56124 | 130 | $3.77 \times 10^{-2}$ |
| ME16546 | ME16546-05 ($T_2$) | 0.58861 | 36 | 0.56124 | 130 | $7.17 \times 10^{-3}$ |
| ME16546 | ME16546-05 ($T_3$) | 0.61763 | 27 | 0.56124 | 130 | $3.25 \times 10^{-6}$ |

Events -04 and -05 segregated 2:1 and 3:1 respectively (R:S) for FINALE™ resistance in the $T_2$ generation.

Events -04 and -05 of ME16546 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 59—Analysis of ME17457 Events

ME17457 contains Ceres Annot:839064 (At1g80600, SEQ ID NO:1478) from *Arabidopsis thaliana*, which encodes a 457 acetylornithine aminotransferase, a member of the Class-III aminotransferase family. This is a homolog of Ceres Clone:19586 (ME01463, SEQ ID NO:76). Evaluation of low-nitrogen tolerance for ME17457 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -02, -03, -05 and -06, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME17457 seedlings is shown in Table 64. ME17457 events were also tested for enhanced growth on the low ammonium nitrate media. No significant differences between the transgenics and the controls were observed.

TABLE 64 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME17457 | ME17457-02 ($T_2$) | 0.60800 | 21 | 0.50878 | 46 | $6.99 \times 10^{-4}$ |
| ME17457 | ME17457-02 ($T_3$) | 0.59539 | 18 | 0.50878 | 46 | $9.02 \times 10^{-3}$ |
| ME17457 | ME17457-03 ($T_2$) | 0.55164 | 11 | 0.49673 | 45 | $3.45 \times 10^{-2}$ |
| ME17457 | ME17457-03 ($T_3$) | 0.57356 | 18 | 0.49673 | 45 | $2.49 \times 10^{-3}$ |
| ME17457 | ME17457-05 ($T_2$) | 0.52928 | 18 | 0.42672 | 32 | $2.23 \times 10^{-3}$ |
| ME17457 | ME17457-05 ($T_3$) | 0.56660 | 25 | 0.42672 | 32 | $5.97 \times 10^{-5}$ |
| ME17457 | ME17457-06 ($T_2$) | 0.54088 | 33 | 0.47350 | 30 | $3.59 \times 10^{-4}$ |
| ME17457 | ME17457-06 ($T_3$) | 0.52210 | 21 | 0.47350 | 30 | $2.03 \times 10^{-2}$ |

Events -02, -03 and -05 segregated 1:1, and Event -06 segregated 3:1 (R:S) for FINALE™ resistance in the $T_2$ generation.

Events -02, -03, -05 and -06 of ME17457 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 60—Analysis of ME17567 Events

ME17567 contains Ceres Annot:864666 (At1g16320, SEQ ID NO:1490) from *Arabidopsis thaliana*, which encodes a 273 amino acid protein of unknown function. Evaluation of low-nitrogen tolerance for ME17567 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low nitrate-containing media relative to the internal controls in both generations at p≤0.05 using a one-tailed t-test assuming unequal variance. A summary of photosynthetic efficiency of ME17567 seedlings is shown in Table 65. ME17567 events were also tested for enhanced growth on the low nitrate media as well as enhanced photosynthetic efficiency and growth on low ammonium nitrate media. No significant differences between the transgenics and the controls were observed.

TABLE 65 t-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME17567 | ME17567-01 ($T_2$) | 0.605455 | 33 | 0.474791 | 67 | $9.69 \times 10^{-10}$ |
| ME17567 | ME17567-01 ($T_3$) | 0.6244 | 20 | 0.474791 | 67 | $6.79 \times 10^{-13}$ |
| ME17567 | ME17567-04 ($T_2$) | 0.57727 | 37 | 0.474791 | 67 | $1.22 \times 10^{-7}$ |
| ME17567 | ME17567-04 ($T_3$) | 0.615143 | 35 | 0.474791 | 67 | $5.95 \times 10^{-13}$ |

Events -01 and -04 segregated 2:1 and 3:1 respectively (R:S) for FINALE™ resistance in the $T_2$ generation.

Events -01 and -04 of ME17567 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 61—Analysis of ME17932 Events

ME17932 contains Ceres Annot:875012 (At3g53560, SEQ ID NO:1509) from *Arabidopsis thaliana*, which encodes a 340 amino acid chloroplast lumen common family protein. Evaluation of low-nitrogen tolerance for ME17932 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME17932 seedlings is shown in Table 66. ME17932 events were also tested for enhanced growth on the low ammonium nitrate media. No significant differences between the transgenics and the controls were observed.

TABLE 66 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME17932 | ME17932-01 ($T_2$) | 0.6292 | 36 | 0.6094 | 194 | 0.050 |
| ME17932 | ME17932-01 ($T_3$) | 0.6640 | 22 | 0.6094 | 194 | $2.82 \times 10^{-6}$ |
| ME17932 | ME17932-02 ($T_2$) | 0.6351 | 32 | 0.6094 | 194 | $1.05 \times 10^{-2}$ |
| ME17932 | ME17932-02 ($T_3$) | 0.6373 | 20 | 0.6094 | 194 | $2.82 \times 10^{-2}$ |
| ME17932 | ME17932-03 ($T_2$) | 0.6504 | 45 | 0.6094 | 194 | $1.80 \times 10^{-5}$ |
| ME17932 | ME17932-03 ($T_3$) | 0.6708 | 20 | 0.6094 | 194 | $8.38 \times 10^{-4}$ |
| ME17932 | ME17932-05 ($T_2$) | 0.6349 | 24 | 0.6094 | 194 | $3.23 \times 10^{-2}$ |
| ME17932 | ME17932-05 ($T_3$) | 0.6615 | 11 | 0.6094 | 194 | $1.16 \times 10^{-3}$ |

Events -01, -02, -03 and -05 segregated 3:1, 2:1, 15:1 and 1:1 respectively (R:S) for FINALE™ resistance in the $T_2$ generation.

Events -01, -02, -03 and -05 of ME17932 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 62—Analysis of ME17936 Events

ME17936 contains Ceres Annot:874016 (At3g42800, SEQ ID NO:1524) from *Arabidopsis thaliana*, which encodes a 341 amino acid protein of unknown function. Evaluation of low-nitrogen tolerance for ME17936 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME17936 seedlings is shown in Table 67. ME17936 events were also tested for for enhanced growth on the low nitrate media as well as for increased photosynthetic efficiency and enhanced growth on low ammonium nitrate media. No significant differences between the transgenics and the controls were observed.

TABLE 67 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME17936 | ME17936-01 ($T_2$) | 0.64778 | 36 | 0.61762 | 39 | $4.68 \times 10^{-3}$ |
| ME17936 | ME17936-01 ($T_3$) | 0.66081 | 21 | 0.61762 | 39 | $4.33 \times 10^{-5}$ |
| ME17936 | ME17936-05 ($T_2$) | 0.63189 | 35 | 0.61444 | 50 | $2.73 \times 10^{-2}$ |
| ME17936 | ME17936-05 ($T_3$) | 0.64257 | 14 | 0.61444 | 50 | $2.56 \times 10^{-2}$ |

Events -01 and -05 segregated 3:1 (R:S) for FINALE™ resistance in the $T_2$ generation.

Events -01 and -05 of ME17936 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 63—Analysis of ME18275 Events

ME18275 contains Ceres Annot:827304 (At2g18300, SEQ ID NO:1536) from *Arabidopsis thaliana*, which encodes a 335 amino acid helix-loop-helix DNA-binding domain. Evaluation of low-nitrogen tolerance for ME18275 in $T_2$ and $T_3$ was conducted under the same conditions as described in Examples 2 and 3. A summary of the enhanced growth of ME18275 events on low nitrate-containing media is shown in Table 68. In this study, the seedling area for transgenic plants within an event was compared to the seedling area for non-transgenic segregants pooled across the same line. Three events, -01, -02 and -03, were found significantly larger than the pooled non-transgenic segregants after 14 days of growth on low nitrate-containing media relative to the internal controls in both generations at p≤0.05, using a one-tailed t-test assuming unequal variance. ME18275 events were also tested for photosynthetic efficiency on the low nitrate media as well as for increased photosynthetic efficiency and enhanced growth on low ammonium nitrate media. No significant differences between the transgenics and the controls were observed.

TABLE 68 t-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME18275 | ME18275-01 ($T_2$) | 0.09574 | 40 | 0.05961 | 10 | $3.24 \times 10^{-10}$ |
| ME18275 | ME18275-01 ($T_3$) | 0.07807 | 32 | 0.05142 | 15 | $3.71 \times 10^{-4}$ |
| ME18275 | ME18275-02 ($T_2$) | 0.11903 | 33 | 0.05884 | 16 | $6.21 \times 10^{-14}$ |
| ME18275 | ME18275-02 ($T_3$) | 0.08552 | 22 | 0.04208 | 24 | $2.82 \times 10^{-5}$ |
| ME18275 | ME18275-03 ($T_2$) | 0.10281 | 39 | 0.06789 | 9 | $9.48 \times 10^{-8}$ |
| ME18275 | ME18275-03 ($T_3$) | 0.09136 | 20 | 0.05646 | 26 | $9.46 \times 10^{-4}$ |

Events -01, -02 and -03 segregated 3:1 (R:S) for FINALE™ resistance in the $T_2$ generation.

Events -01, -02 and -03 of ME18275 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 64—Analysis of ME18924 Events

ME18924 contains Ceres Annot:869192 (At1g72160, SEQ ID NO:1553) from *Arabidopsis thaliana*, which encodes a 490 amino acid emp24/gp25L/p24 family protein. Evaluation of low-nitrogen tolerance for ME18924 in $T_2$ and $T_3$ was conducted under the same conditions as described in Examples 2 and 3. A summary of photosynthetic efficiency of ME18924 seedlings is shown in Table 69. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05, using a one-tailed t-test assuming unequal variance.

TABLE 69 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME18924 | ME18924-02 ($T_2$) | 0.6515 | 46 | 0.6223 | 138 | $6.43 \times 10^{-3}$ |
| ME18924 | ME18924-02 ($T_3$) | 0.6639 | 45 | 0.6223 | 138 | $1.52 \times 10^{-4}$ |
| ME18924 | ME18924-04 ($T_2$) | 0.6489 | 33 | 0.6223 | 138 | $2.72 \times 10^{-3}$ |
| ME18924 | ME18924-04 ($T_3$) | 0.6517 | 21 | 0.6223 | 138 | $1.58 \times 10^{-2}$ |
| ME18924 | ME18924-05 ($T_2$) | 0.6602 | 35 | 0.6223 | 138 | $5.55 \times 10^{-5}$ |

TABLE 69-continued t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME18924 | ME18924-05 ($T_3$) | 0.6488 | 31 | 0.6223 | 138 | $4.25 \times 10^{-2}$ |

ME18924 events were also tested for enhanced growth on the low ammonium nitrate media. A summary of the enhanced growth of ME18924 events on low nitrate-containing media is shown in Table 70. In this study, the seedling area for transgenic plants within an event was compared to the seedling area for non-transgenic segregants pooled across the same line. Two events, -01 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 70 t-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME18924 | ME18924-01 ($T_2$) | 0.06881 | 37 | 0.06311 | 138 | $1.31 \times 10^{-2}$ |
| ME18924 | ME18924-01 ($T_3$) | 0.07164 | 34 | 0.06311 | 138 | $7.43 \times 10^{-3}$ |
| ME18924 | ME18924-04 ($T_2$) | 0.08401 | 33 | 0.06311 | 138 | $5.64 \times 10^{-8}$ |
| ME18924 | ME18924-04 ($T_3$) | 0.07365 | 21 | 0.06311 | 138 | $3.82 \times 10^{-2}$ |

Events -01, -02, -04 and -05 segregated 3:1, 15:1, 2:1 and 2:1 respectively (R:S) for FINALE™ resistance in the $T_2$ generation.

Events -01, -02, -04 and -05 of ME18924 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 65—Analysis of ME19182 Events

ME19182 contains Ceres Annot:876419 (At4g01480, SEQ ID NO:1576) from *Arabidopsis thaliana*, which encodes a 216 amino acid inorganic pyrophosphatase protein. Evaluation of low-nitrogen tolerance for ME19182 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME19182 seedlings is shown in Table 71. ME19182 events were also tested for enhanced growth on the low ammonium nitrate media. No significant differences between the transgenics and the controls were observed.

TABLE 71 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME19182 | ME19182-01 ($T_2$) | 0.64938 | 24 | 0.61988 | 154 | $2.47 \times 10^{-2}$ |
| ME19182 | ME19182-01 ($T_3$) | 0.65546 | 13 | 0.61988 | 154 | $1.08 \times 10^{-2}$ |
| ME19182 | ME19182-03 ($T_2$) | 0.64797 | 37 | 0.61988 | 154 | $3.84 \times 10^{-3}$ |
| ME19182 | ME19182-03 ($T_3$) | 0.65388 | 26 | 0.61988 | 154 | $3.15 \times 10^{-3}$ |

Events -01 and -03 segregated 2:1 and 3:1 respectively (R:S) for FINALE™ resistance in the T2 generation.

Events -01 and -03 of ME19182 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 66—Analysis of ME20628 Events

ME20628 contains Ceres Annot:859276 (At2g21230, SEQ ID NO:175) from *Arabidopsis thaliana*, which encodes a 188 amino acid protein of unknown function. Evaluation of low-nitrogen tolerance for ME20628 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME20628 seedlings is shown in Table 72. ME20628 events were also tested for enhanced growth on the low nitrate media as well as for increased photosynthetic efficiency and enhanced growth on low ammonium nitrate media. No significant differences between the transgenics and the controls were observed.

TABLE 72 t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME20628 | ME20628-03 ($T_2$) | 0.62771 | 42 | 0.58957 | 7 | $9.94 \times 10^{-3}$ |
| ME20628 | ME20628-03 ($T_3$) | 0.64375 | 20 | 0.61914 | 28 | $2.97 \times 10^{-2}$ |

TABLE 72-continued t-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME20628 | ME20628-04 ($T_2$) | 0.62439 | 38 | 0.59667 | 12 | $4.78 \times 10^{-2}$ |
| ME20628 | ME20628-04 ($T_3$) | 0.64768 | 22 | 0.61360 | 25 | $9.93 \times 10^{-4}$ |

Events -03 and -04 segregated 3:1 (R:S) for FINALE™ resistance in the $T_2$ generation.

Events -03 and -04 of ME20628 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 67—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al. (1998) *Proc. Natl. Acad. Sci. USA,* 95:6239-6244) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e−5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:49, SEQ ID NO:77, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1463, SEQ ID NO:1491, SEQ ID NO:1510, SEQ ID NO:1525, SEQ ID NO:1537, SEQ ID NO:1554, SEQ ID NO:1577, and SEQ ID NO:1437 are shown in FIGS. 1-57, respectively. Additional exemplary homologs are correlated to certain Figures in the Sequence Listing.

Example 68—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-57, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10138492B2). An electronic copy of the "Sequence Listing" will also be available from the USPTO upon request and payment of the fee set forth in 37 CFR 1.19(b)(3).

What is claimed is:

1. A method of producing a plant, said method comprising (a) growing a plant cell comprising an exogenous nucleic acid, said exogenous nucleic acid comprising a regulatory region operably linked to a nucleotide sequence, said nucleotide sequence comprising 95 percent or greater sequence identity to the nucleotide sequence of SEQ ID NO:48, or wherein said nucleotide sequence encodes a polypeptide comprising 95 percent or greater sequence identity to the amino acid sequence of SEQ ID NO:49;

(b) growing a plant from said plant cell; and (c) selecting for a plant comprising an increased level of low-nitrogen tolerance as compared to the corresponding level of low-nitrogen tolerance of a control plant that does not comprise said nucleic acid.

2. The method of claim 1, wherein said nucleotide sequence encodes a polypeptide sequence comprising 95 percent or greater sequence identity to the amino acid sequence of SEQ ID NO:49.

3. The method of claim 1, wherein the nucleotide sequence comprises 95 percent or greater sequence identity to the nucleotide sequence of SEQ ID NO:48.

4. The method of claim 1, wherein said nucleotide sequence comprises the nucleotide sequence of SEQ ID NO:48, or wherein said nucleotide encodes a polypeptide comprising the amino acid sequence of SEQ ID NO:49.

5. A method of modulating the level of low-nitrogen tolerance in a plant, said method comprising (a) introducing into a plant cell an exogenous nucleic acid, said exogenous nucleic acid comprising a regulatory region operably linked to a nucleotide sequence, said nucleotide sequence comprising 95 percent or greater sequence identity to the nucleotide sequence of SEQ ID NO:48, or wherein said nucleotide sequence encodes a polypeptide comprising 95 percent or greater sequence identity to the amino acid sequence of SEQ ID NO:49;

(b) growing a plant from said plant cell; and (c) selecting for a plant that comprises an increased level of low-nitrogen tolerance as compared to the corresponding level of low nitrogen tolerance of a control plant that does not comprise said nucleic acid.

6. The method of claim 5, wherein said nucleotide sequence encodes a polypeptide comprising 95 percent or greater sequence identity to the amino acid sequence of SEQ ID NO:49.

7. The method of claim 5, wherein said nucleotide sequence comprises 95 percent or greater sequence identity to the nucleotide sequence of SEQ ID NO:48.

8. The method of claim 5, wherein said nucleotide sequence comprises the nucleotide sequence of SEQ ID NO:48, or wherein said nucleotide encodes a polypeptide comprising the amino acid sequence of SEQ ID NO:49.

9. A plant cell comprising an exogenous nucleic acid, said exogenous nucleic acid comprising a regulatory region operably linked to a nucleotide sequence, said nucleotide sequence comprising 95 percent or greater sequence identity to the nucleotide sequence of SEQ ID NO:48, or wherein said nucleotide sequence encodes a polypeptide comprising 95 percent or greater sequence identity to the amino acid sequence of SEQ ID NO:49 and wherein a plant produced from said plant cell has an increase in the level of low-nitrogen tolerance as compared to the corresponding level of low-nitrogen tolerance of a control plant that does not comprise said nucleic acid.

10. The plant cell of claim 9, wherein said nucleotide sequence encodes a polypeptide comprising 95 percent or greater sequence identity to the amino acid sequence of SEQ ID NO:49.

11. The plant cell of claim 9, wherein said nucleotide sequence comprises 95 percent or greater sequence identity to the nucleotide sequence of SEQ ID NO:48.

12. A transgenic plant comprising the plant cell of claim 9, wherein the transgenic plant comprises an increased level of low-nitrogen tolerance as compared to the corresponding level of low-nitrogen tolerance of a control plant that does not comprise said nucleic acid.

13. The transgenic plant of claim 12, wherein said plant is a member of a species selected from the group consisting of *Panicum virgatum* (switchgrass), *Sorghum bicolor* (*sorghum, sudangrass*), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

14. The transgenic plant of claim 12, wherein said nucleotide sequence encodes a polypeptide comprising 95 percent or greater sequence identity to the amino acid sequence of SEQ ID NO:49.

15. A product comprising plant tissue from a transgenic plant according to claim 13.

* * * * *